(12) United States Patent
Karrer et al.

(10) Patent No.: US 8,491,899 B2
(45) Date of Patent: Jul. 23, 2013

(54) IMMUNOSUPPRESSIVE POLYPEPTIDES AND NUCLEIC ACIDS

(75) Inventors: Erik E Karrer, Mountain View, CA (US); Madan M. Paidhungat, San Francisco, CA (US); Steven H Bass, Hillsborough, CA (US); Margaret Neighbors, San Jose, CA (US); Juha Punnonen, Belmont, CA (US); Steven J. Chapin, San Francisco, CA (US)

(73) Assignee: Perseid Therapeutics LLC, Redwood City, CA (US)

( * ) Notice: Subject to any disclaimer, the term of this patent is extended or adjusted under 35 U.S.C. 154(b) by 249 days.

(21) Appl. No.: 13/045,335

(22) Filed: Mar. 10, 2011

(65) Prior Publication Data

US 2011/0177071 A1 Jul. 21, 2011

Related U.S. Application Data

(62) Division of application No. 12/763,902, filed on Apr. 20, 2010, now Pat. No. 8,071,095, which is a division of application No. 12/251,960, filed on Oct. 15, 2008, now Pat. No. 7,794,718.

(60) Provisional application No. 60/984,631, filed on Nov. 1, 2007, provisional application No. 61/051,215, filed on May 7, 2008.

(51) Int. Cl.
*A61K 39/00* (2006.01)
*C07K 14/00* (2006.01)

(52) U.S. Cl.
USPC ...... 424/134.1; 424/192.1; 514/3.9; 514/18.7

(58) Field of Classification Search
None
See application file for complete search history.

(56) References Cited

U.S. PATENT DOCUMENTS

| | | | |
|---|---|---|---|
| 5,116,964 A | 5/1992 | Capon et al. | |
| 5,155,027 A | 10/1992 | Sledziewski et al. | |
| 5,336,603 A | 8/1994 | Capon et al. | |
| 5,428,130 A | 6/1995 | Capon et al. | |
| 5,434,131 A | 7/1995 | Linsley et al. | |
| 5,455,165 A | 10/1995 | Capon et al. | |
| 5,514,582 A | 5/1996 | Capon et al. | |
| 5,565,335 A | 10/1996 | Capon et al. | |
| 5,637,481 A | 6/1997 | Ledbetter et al. | |
| 5,770,197 A | 6/1998 | Linsley et al. | |
| 5,773,253 A | 6/1998 | Linsley et al. | |
| 5,843,725 A | 12/1998 | Sledziewski et al. | |
| 5,844,095 A | 12/1998 | Linsley et al. | |
| 5,851,795 A | 12/1998 | Linsley et al. | |
| 5,885,579 A | 3/1999 | Linsley et al. | |
| 5,885,796 A | 3/1999 | Linsley et al. | |
| 5,916,560 A | 6/1999 | Larsen et al. | |
| 5,993,800 A | 11/1999 | Linsley et al. | |
| 6,018,026 A | 1/2000 | Sledziewski et al. | |
| 6,090,914 A | 7/2000 | Linsley et al. | |
| 6,117,655 A | 9/2000 | Capon et al. | |
| 6,132,992 A | 10/2000 | Ledbetter et al. | |
| 6,291,212 B1 | 9/2001 | Sledziewski et al. | |
| 6,291,646 B1 | 9/2001 | Sledziewski et al. | |
| 6,300,099 B1 | 10/2001 | Sledziewski et al. | |
| 6,323,323 B1 | 11/2001 | Sledziewski et al. | |
| 6,406,697 B1 | 6/2002 | Capon et al. | |
| 6,444,792 B1 | 9/2002 | Gray et al. | |
| 6,482,919 B2 | 11/2002 | Ledbetter et al. | |
| 6,521,419 B1 | 2/2003 | Koduri et al. | |
| 6,623,940 B1 | 9/2003 | Ledbetter et al. | |
| 6,685,941 B1 | 2/2004 | Thompson et al. | |
| 6,710,169 B2 | 3/2004 | Capon et al. | |
| 6,750,334 B1 | 6/2004 | Gray et al. | |
| 6,800,457 B2 | 10/2004 | Koduri et al. | |
| 7,041,634 B2 | 5/2006 | Weber et al. | |
| 7,070,776 B1 | 7/2006 | Linsley et al. | |
| 7,094,874 B2 | 8/2006 | Peach et al. | |
| 7,105,166 B1 | 9/2006 | Linsley et al. | |
| 7,307,064 B2 | 12/2007 | Rusnak | |
| 7,332,303 B2 | 2/2008 | Schilling et al. | |
| 7,794,718 B2 * | 9/2010 | Karrer et al. | 424/134.1 |
| 8,071,095 B2 * | 12/2011 | Karrer et al. | 424/134.1 |
| 8,268,587 B2 * | 9/2012 | Karrer et al. | 435/69.1 |
| 8,283,447 B2 * | 10/2012 | Karrer et al. | 530/350 |
| 8,318,176 B2 * | 11/2012 | Karrer et al. | 424/185.1 |
| 2003/0083246 A1 | 5/2003 | Cohen et al. | |
| 2003/0219876 A1 | 11/2003 | Ledbetter et al. | |
| 2004/0022787 A1 | 2/2004 | Cohen et al. | |
| 2004/0151725 A1 | 8/2004 | Gray et al. | |
| 2004/0185046 A1 | 9/2004 | Thompson et al. | |
| 2005/0154189 A1 * | 7/2005 | Punnonen et al. | 530/350 |
| 2005/0196402 A1 | 9/2005 | Gray et al. | |

(Continued)

FOREIGN PATENT DOCUMENTS

EP 0314317 A1 5/1989
EP 0325224 A2 7/1989

(Continued)

OTHER PUBLICATIONS

Vaughan et al., J Immunology 165: 3175-3181, 2000.*
Webster's II New Riverside University Dictionary, p. 933, 1984.*
June 1, 2010 Amendments filed in EP Application No. 08844441.9, Filed Jun. 1, 2010 with the EPO, Perseid Therapeutics LLC.
Brunet JF, et al. A new member of the immunoglobulin superfamily—CTLA-4. Nature 1987; 328(6127):267-270.
Harper K, et al. CTLA-4 and CD28 activated lymphocyte molecules are closely related in both mouse and human as to sequence, message expression, gene structure, and chromosomal location. J. Immunol. 1991; 147 (3):1037-1044.
Morton PA, et al. Differential effects of CTLA-4 substitutions on the binding of human CD80 (B7-1) and CD86 (B7-2). J. Immunol. 1996; 156(3):1047-1054.

(Continued)

*Primary Examiner* — Phuong Huynh
(74) *Attorney, Agent, or Firm* — Sharon M. Fujita

(57) ABSTRACT

The invention provides immunosuppressive polypeptides and nucleic acids encoding such polypeptides. In one aspect, the invention provides mutant CTLA-4 polypeptides and nucleic acids encoding mutant CTLA-4 polypeptides. Compositions and methods for utilizing such polypeptides and nucleic acids are also provided.

**21 Cla

U.S. PATENT DOCUMENTS

| | | | |
|---|---|---|---|
| 2005/0214313 A1 | 9/2005 | Peach et al. | |
| 2006/0269566 A1* | 11/2006 | Punnonen et al. | 424/192.1 |
| 2008/0070280 A1 | 3/2008 | Schilling | |
| 2008/0160022 A1 | 7/2008 | Larsen | |
| 2009/0258031 A1* | 10/2009 | Karrer et al. | 424/185.1 |
| 2010/0260759 A1* | 10/2010 | Karrer et al. | 424/134.1 |
| 2010/0261660 A1* | 10/2010 | Punnonen et al. | 514/21.2 |
| 2011/0129875 A1* | 6/2011 | Karrer et al. | 435/69.6 |
| 2011/0130546 A1* | 6/2011 | Karrer et al. | 530/387.3 |
| 2011/0159542 A1* | 6/2011 | Karrer et al. | 435/69.7 |
| 2011/0166324 A1* | 7/2011 | Karrer et al. | 530/350 |
| 2011/0182898 A1* | 7/2011 | Karrer et al. | 424/134.1 |

FOREIGN PATENT DOCUMENTS

| | | |
|---|---|---|
| EP | 0610046 A2 | 8/1994 |
| EP | 0613944 A2 | 9/1994 |
| EP | 0757099 A2 | 2/1997 |
| EP | 0832971 A1 | 4/1998 |
| EP | 1666498 A2 | 6/2006 |
| WO | WO8902922 A1 | 4/1989 |
| WO | WO9108298 A2 | 6/1991 |
| WO | WO9300431 A1 | 1/1993 |
| WO | WO9319767 A1 | 10/1993 |
| WO | WO9639514 A1 | 12/1996 |
| WO | WO9711607 A1 | 4/1997 |
| WO | WO9728267 A1 | 8/1997 |
| WO | WO9734633 A1 | 9/1997 |
| WO | WO9947558 A2 | 9/1999 |
| WO | WO0017337 A1 | 3/2000 |
| WO | WO0037504 A2 | 6/2000 |
| WO | WO0192337 A2 | 12/2001 |
| WO | WO0202638 A2 | 1/2002 |
| WO | WO 2005/017148 A1 | 2/2005 |
| WO | WO2006108035 A1 | 10/2006 |
| WO | WO2008047150 A2 | 4/2008 |
| WO | WO 2009/058564 A2 | 5/2009 |

OTHER PUBLICATIONS

Nuttall SD, et al. Design and expression of soluble CTLA-4 variable domain as a scaffold for the display of functional polypeptides. Proteins 1999; 36(2):217-227.

Ostrov DA, et al. Structure of murine CTLA-4 and its role in modulating T cell responsiveness. Science 2000; 290(5492):816-819.

Peach, RJ, et al. Complementarity determining region 1 (CDR1)- and CDR3-analogous regions in CTLA-4 and CD28 determine the binding to B7-1. J. Exp. Med. 1994; 180(6):2049-2058.

Schwartz JC, et al. Structural basis for co-stimulation by the human CTLA-4/B7-2 complex. Nature 2001; 410 (6828):604-608.

Sorensen P, et al. Identification of protein-protein interfaces implicated in CD80-CD28 costimulatory signaling. J. Immunol. 2004; 172(11):6803-6809.

Stamper CC, et al. Crystal structure of the B7-1/CTLA-4 complex that inhibits human immune responses. Nature 2001; 410(6828):608-611.

Truneh A, et al. Differential recognition by CD28 of its cognate counter receptors CD80 (B7.1) and B70 (B7.2): analysis by site directed mutagenesis. Mol Immunol. 1996; 33(3):321-334.

Vaughan AN, et al. Porcine CTLA4-Ig lacks a MYPPPY motif, binds inefficiently to human B7 and specifically suppresses human CD4+ T cell responses costimulated by pig but not human B7. J. Immunol. 2000; 165 (6):3175-3181.

Villinger F, et al. Cloning, sequencing, and homology analysis of nonhuman primate Fas/Fas-ligand and co-stimulatory molecules. Immunogenetics 2001; 53(4):315-328.

* cited by examiner

Figure 2A

| ...FCSG | VIHVT............HFPDN | GVT | PKSCD............LSPGK |
|---|---|---|---|
| Signal (1 – 34) | Human CD80 ECD (35 – 242) | Linker (243-245) | Human IgG1 Fc (246-476) |

Figure 2B

| ...LSGA | APLKI............EDPQPPP | GVT | PKSCD............LSPGK |
|---|---|---|---|
| Signal (1 – 23) | Human CD86 ECD (24 – 243) | Linker (244-246) | Human IgG1 Fc (247-477) |

Figure 2C

| ...FCKA | MHVAQ............CPDSD | Q | EPKSS............LSPGK |
|---|---|---|---|
| Signal (1 – 37) | LEA29Y ECD (38 – 161) | Linker (162) | Modified human IgG1 Fc (163-394) |

Figure 2D

| ...FCKA | MHVAQ............CPDSD | ERKCC............LSPGK |
|---|---|---|
| Signal (1 – 37) | Human CTLA4 ECD (38 – 161) | Human IgG2 Fc (162-389) |

```
               *        20         *        40         *        60
hCTLA4ECD  : MHVAQPAVVLASSRGIASFVCEYASPGKATEVRVTVLRQADSQVTEVCAATYMMGNELTFLDDSI     : 65
LEA29YECD  : ...............................Y.............................PS     : 65
D3-1       : ............................................N.I......G....M...K.D...PS    : 65
D3-2       : ............................................N.I...........M...K.D...PS    : 65
D3-3       : .........................................E..N.............M...K.D...PS    : 65
D3-4       : .........................................E..N.I......G....M...K.D...PS    : 65
D3-5       : .........................................E..N.I...........M...K.D...PS    : 65
D3-6       : .........................................E..N.I......G....M.....D...PS    : 65
D3-7       : .........................................E..N.I......G....M...K.....PS    : 65
D3-8       : .........................................E..N.I...........M...K.....S     : 65
D3-9       : .........................................E..N.I......G....M...K.D...P.    : 65
D3-11      : .........................................E..N.I......G....M...K.D...PS    : 65
D3-12      : .........................................E..N.I...........M...K.D...PS    : 65
D3-14      : .........................................E..N.I......G....M...K.D...PS    : 65
D3-15      : .........................................E..N.I......G....M...K.D...PS    : 65
D3-16      : .........................................E..N.I...........M...K.D...PS    : 65
D3-17      : .........................................E..N.I......G....M...K.D...PS    : 65
D3-19      : .........................................E..N.I...........M...K.D...PS    : 65
D3-20      : .........................................E..N.I...........M...K.....PS    : 65
D3-21      : .........................................E..N.I......G....M...K.....PS    : 65
D3-22      : .........................................E..N.I...........M...K.....PS    : 65
D3-23      : .........................................E..N.I......G....M...K.D...PS    : 65
D3-24      : .........................................E..N.I......G....M...K.D...PS    : 65
D3-25      : .........................................E..N.I...........M...K.....PS    : 65
D3-26      : ..............................................N.I.........M...K.....PS    : 65
D3-27      : .........................................E..N.............M...K.....PS    : 65
D3-28      : .........................................E..N.I...........M...K.D...PS    : 65
D3-29      : .........................................E..N.I...........M...K.D...P.    : 65
D3-30      : .........................................E..N.I...........M...K.D...PS    : 65
D3-31      : .........................................E..N.I...........M...KED...PS    : 65
```

Figure 12A

| | | 20 | | 40 | | 60 | |
|---|---|---|---|---|---|---|---|
| hCTLA4ECD | : | MHVAQPAVVLASSRGIASFVCEYASPGKATEVRVTVLRQADSQVTEVCAATYMMGNELTFLDDSI | : | | | | 65 |
| LEA29YECD | : | ................................Y..............................L......EI | : | | | | 65 |
| D3-32 | : | ..............................E.....N.I........K.............M...K.D...PS | : | | | | 65 |
| D3-33 | : | ..............................E.....N.I........K.............M...KED..PS | : | | | | 65 |
| D3-34 | : | ....................................N..........................M...K....P. | : | | | | 65 |
| D3-39 | : | ..............................E.....N..........................M...K...PS | : | | | | 65 |
| D3-50 | : | ....................................N..........................M...K...P. | : | | | | 65 |
| D3-52 | : | ..............................E.....N..........................M...K.D..P. | : | | | | 65 |
| D3-53 | : | ....................................N.I.......G................M...K.D..PS | : | | | | 65 |
| D3-54 | : | ..............................E.....N..........................M...KE...P. | : | | | | 65 |
| D3-55 | : | ....................................N..........................M...KE..PS | : | | | | 65 |
| D3-56 | : | ....................................N.I........................M...KE..P. | : | | | | 65 |
| D3-57 | : | ..............................E.....N.I........................M...KED..PS | : | | | | 65 |
| D3-58 | : | ....................................N..........................M...KED..P. | : | | | | 65 |
| D3-59 | : | ..............................E.....N..........................M...KE..PS | : | | | | 65 |
| D3-60 | : | ....................................N.I........................M...KE..P. | : | | | | 65 |
| D3-61 | : | ..............................E.....N.I........................M...KE..PS | : | | | | 65 |
| D3-62 | : | ....................................N..........................M...KED..PS | : | | | | 65 |
| D3-63 | : | .....................................I.........................M...KE...P. | : | | | | 65 |
| D3-64 | : | ......................................N.........................M....E...P. | : | | | | 65 |
| D3-65 | : | ..............................E.....N..........................M...K....PS | : | | | | 65 |
| D3-66 | : | ....................................N..........................M...K.D..P. | : | | | | 65 |
| D3-68 | : | ..............................E.....N.I........................M...K.D..PS | : | | | | 65 |
| D3-69 | : | ..............................E.....N.I........................M...K.D..P. | : | | | | 65 |
| D3-70 | : | ..............................E.....N.I........................M...K.D..PS | : | | | | 65 |
| D3-71 | : | ..............................E.....N..........................M...K....PS | : | | | | 65 |
| D3-72 | : | ....................................N.I........................M...K....P. | : | | | | 65 |
| D3-73 | : | ..............................E.....N..........................M...K....P. | : | | | | 65 |
| D3-74 | : | ....................................N.I........................M...K....P. | : | | | | 65 |
| D3-75 | : | ..............................E.....N..........................M...KE..PS | : | | | | 65 |
| D3-76 | : | ......................................N.........................M...KED..P. | : | | | | 65 |

```
              *        20         *        40         *        60
hCTLA4ECD : MHVAQPAVVLASSRGIASFVCEYASPGKATEVRVTVLRQADSQVTEVCAATYMMGNELTFLDDSI : 65
LEA29YECD : ............................Y...............................PF. : 65
D1        : ....................E..H...I..N.............M..K.D..........PF. : 65
D1T       : ....................E..H..N.I..N.............M..K.D..........PF. : 65
D2        : ....................E..H..N.I..N.............M..K.D..........PF. : 65
D3        : ....................E...N.I...G.............M..K.D..........PS. : 65
D4        : ....................S...D.I...S.............M..E.D..........PT. : 65
D5        : ........................I....................D..............P.. : 65
D6        : ........................I....................D..............P.. : 65
D20       : ....................E..H..I....................M..ED.........P.. : 65
D21       : ....................SA.HN.D.I..K.S...........M..EED.........PT. : 65
D23       : ....................SA.HN.A.I..K.G...........M..KED.........PS. : 65
D24       : ....................E...N.I..K.G.............M..KED.........PS. : 65
D26       : ....................EA.H..N...E.G.............M..VED.........PS. : 65
D27       : ....................E...N...E.G.............M..VED.........PS. : 65
D28       : ....................EA.H..N...G..............M..ED..........PS. : 65
D29       : ....................EA.H..D.I..K..............M..ED..........PS. : 65
D31       : ....................EA.HN.D.I...G.............M..VED.........K.. : 65
```

```
                     *          80          *         100          *         120
hCTLA4ECD  : CTGTSSGNQVNLTIQGLRAMDTGLYICKVELMYPPPYYLGIGNGTQIYVIDPEPCPDSD :    124
LEA29YECD  : ..............................E............................ :    124
D3-1       : .....F...............A...................................... :    124
D3-2       : .....F...............A.......................F.............. :    124
D3-3       : .....F...............A.......................F.............. :    124
D3-4       : .....F...............A.......................F.............. :    124
D3-5       : .....F...............A.......................F.............. :    124
D3-6       : .....F...............A.......................F.............. :    124
D3-7       : .....F...............A.......................F.............. :    124
D3-8       : .....F...............A.......................F.............. :    124
D3-9       : .....F...............A.......................F.............. :    124
D3-11      : .....F...............A.......................F.............. :    124
D3-12      : .....F...............A.......................F.............. :    124
D3-14      : .....F...............A.......................F.............. :    124
D3-15      : .....F...............................................F...... :    124
D3-16      : .....F....................................................... :    124
D3-17      : .....F...............A.......................F.............. :    124
D3-19      : .....F....................................................... :    124
D3-20      : .....F....................................................... :    124
D3-21      : .....F...............A.......................F.............. :    124
D3-22      : .....F.......................................F.............. :    124
D3-23      : .....F...............A.......................F.............. :    124
D3-24      : .....F....................................................... :    124
D3-25      : .....F...............A.......................F.............. :    124
D3-26      : .....F....................................................... :    124
D3-27      : .....F....................................................... :    124
D3-28      : .....F....................................................... :    124
D3-29      : .....F....................................................... :    124
D3-30      : .....F....................................................... :    124
D3-31      : .....F...............A....................................... :    124
```

```
                     *        80         *        100        *       120
hCTLA4ECD  : CTGTSSGNQVNLTIQGLRAMDTGLYICKVELMYPPPYYLGIGNGTQIYVIDPEPCPDSD : 124
LEA29YECD  : ............................................E............ : 124
D1         : ...........F...........A.................................. : 124
D1T        : ...........F...........A................M................. : 124
D2         : ...........F...........A..................F............... : 124
D3         : ...........F...........A................................. : 124
D4         : ...........F...........V...................F............... : 124
D5         : ...........F.............................................. : 124
D6         : ...........F.............................................. : 124
D20        : ...........F.............................................. : 124
D21        : ...........F...........V................F................. : 124
D23        : ...........F...........A................L................. : 124
D24        : ...........F...........A................L................. : 124
D26        : ...........F...........A.................................. : 124
D27        : ...........F...........A................L................. : 124
D28        : ...........F...........A................L................. : 124
D29        : ...........F...........A................L................. : 124
D31        : ...........F.............................L................ : 124
```

Figure 12F

BLOSUM62 SUBSTITUTION MATRIX

|   | A | R | N | D | C | Q | E | G | H | I | L | K | M | F | P | S | T | W | Y | V | B | Z | X | * |
|---|---|---|---|---|---|---|---|---|---|---|---|---|---|---|---|---|---|---|---|---|---|---|---|---|
| A | 4 | -1 | -2 | -2 | 0 | -1 | -1 | 0 | -2 | -1 | -1 | -1 | -1 | -2 | -1 | 1 | 0 | -3 | -2 | 0 | -2 | -1 | 0 | -4 |
| R | -1 | 5 | 0 | -2 | -3 | 1 | 0 | -2 | 0 | -3 | -2 | 2 | -1 | -3 | -2 | -1 | -1 | -3 | -2 | -3 | -1 | 0 | -1 | -4 |
| N | -2 | 0 | 6 | 1 | -3 | 0 | 0 | 0 | 1 | -3 | -3 | 0 | -2 | -3 | -2 | 1 | 0 | -4 | -2 | -3 | 3 | 0 | -1 | -4 |
| D | -2 | -2 | 1 | 6 | -3 | 0 | 2 | -1 | -1 | -3 | -4 | -1 | -3 | -3 | -1 | 0 | -1 | -4 | -3 | -3 | 4 | 1 | -1 | -4 |
| C | 0 | -3 | -3 | -3 | 9 | -3 | -4 | -3 | -3 | -1 | -1 | -3 | -1 | -2 | -3 | -1 | -1 | -2 | -2 | -1 | -3 | -3 | -2 | -4 |
| Q | -1 | 1 | 0 | 0 | -3 | 5 | 2 | -2 | 0 | -3 | -2 | 1 | 0 | -3 | -1 | 0 | -1 | -2 | -1 | -2 | 0 | 3 | -1 | -4 |
| E | -1 | 0 | 0 | 2 | -4 | 2 | 5 | -2 | 0 | -3 | -3 | 1 | -2 | -3 | -1 | 0 | -1 | -3 | -2 | -2 | 1 | 4 | -1 | -4 |
| G | 0 | -2 | 0 | -1 | -3 | -2 | -2 | 6 | -2 | -4 | -4 | -2 | -3 | -3 | -2 | 0 | -2 | -2 | -3 | -3 | -1 | -2 | -1 | -4 |
| H | -2 | 0 | 1 | -1 | -3 | 0 | 0 | -2 | 8 | -3 | -3 | -1 | -2 | -1 | -2 | -1 | -2 | -2 | 2 | -3 | 0 | 0 | -1 | -4 |
| I | -1 | -3 | -3 | -3 | -1 | -3 | -3 | -4 | -3 | 4 | 2 | -3 | 1 | 0 | -3 | -2 | -1 | -3 | -1 | 3 | -3 | -3 | -1 | -4 |
| L | -1 | -2 | -3 | -4 | -1 | -2 | -3 | -4 | -3 | 2 | 4 | -2 | 2 | 0 | -3 | -2 | -1 | -2 | -1 | 1 | -4 | -3 | -1 | -4 |
| K | -1 | 2 | 0 | -1 | -3 | 1 | 1 | -2 | -1 | -3 | -2 | 5 | -1 | -3 | -1 | 0 | -1 | -3 | -2 | -2 | 0 | 1 | -1 | -4 |
| M | -1 | -1 | -2 | -3 | -1 | 0 | -2 | -3 | -2 | 1 | 2 | -1 | 5 | 0 | -2 | -1 | -1 | -1 | -1 | 1 | -3 | -1 | -1 | -4 |
| F | -2 | -3 | -3 | -3 | -2 | -3 | -3 | -3 | -1 | 0 | 0 | -3 | 0 | 6 | -4 | -2 | -2 | 1 | 3 | -1 | -3 | -3 | -1 | -4 |
| P | -1 | -2 | -2 | -1 | -3 | -1 | -1 | -2 | -2 | -3 | -3 | -1 | -2 | -4 | 7 | -1 | -1 | -4 | -3 | -2 | -2 | -1 | -2 | -4 |
| S | 1 | -1 | 1 | 0 | -1 | 0 | 0 | 0 | -1 | -2 | -2 | 0 | -1 | -2 | -1 | 4 | 1 | -3 | -2 | -2 | 0 | 0 | 0 | -4 |
| T | 0 | -1 | 0 | -1 | -1 | -1 | -1 | -2 | -2 | -1 | -1 | -1 | -1 | -2 | -1 | 1 | 5 | -2 | -2 | 0 | -1 | -1 | 0 | -4 |
| W | -3 | -3 | -4 | -4 | -2 | -2 | -3 | -2 | -2 | -3 | -2 | -3 | -1 | 1 | -4 | -3 | -2 | 11 | 2 | -3 | -4 | -3 | -2 | -4 |
| Y | -2 | -2 | -2 | -3 | -2 | -1 | -2 | -3 | 2 | -1 | -1 | -2 | -1 | 3 | -3 | -2 | -2 | 2 | 7 | -1 | -3 | -2 | -1 | -4 |
| V | 0 | -3 | -3 | -3 | -1 | -2 | -2 | -3 | -3 | 3 | 1 | -2 | 1 | -1 | -2 | -2 | 0 | -3 | -1 | 4 | -3 | -2 | -1 | -4 |
| B | -2 | -1 | 3 | 4 | -3 | 0 | 1 | -1 | 0 | -3 | -4 | 0 | -3 | -3 | -2 | 0 | -1 | -4 | -3 | -3 | 4 | 1 | -1 | -4 |
| Z | -1 | 0 | 0 | 1 | -3 | 3 | 4 | -2 | 0 | -3 | -3 | 1 | -1 | -3 | -1 | 0 | -1 | -3 | -2 | -2 | 1 | 4 | -1 | -4 |
| X | 0 | -1 | -1 | -1 | -2 | -1 | -1 | -1 | -1 | -1 | -1 | -1 | -1 | -1 | -2 | 0 | 0 | -2 | -1 | -1 | -1 | -1 | -1 | -4 |
| * | -4 | -4 | -4 | -4 | -4 | -4 | -4 | -4 | -4 | -4 | -4 | -4 | -4 | -4 | -4 | -4 | -4 | -4 | -4 | -4 | -4 | -4 | -4 | 1 |

(upper: amino acids 39-53 of hCTLA-4 ECD)
(lower: amino acids 40-54 of D3)

```
 Q   A   D   S   Q   V   T   E   V   C   A   A   T   Y   M
 A   G   S   Q   V   T   E   V   C   A   M   T   Y   M   K
-1   0   0   0  -2   0  -1  -2  -1   0  -1   0  -2  -1  -1
```
                                                                    = −12

B.

(upper: amino acids 39-53 of hCTLA-4 ECD)
(lower: amino acids 41-55 of D3)

```
 Q   A   D   S   Q   V   T   E   V   C   A   A   T   Y   M
     A   G   S   Q   V   T   E   V   C   A   M   T   Y   M   K
     4  -1   4   5   4   5   5   4   9   4  -1   5   7   5
```
                                                                    = 59

C.

(upper: amino acids 39-53 of hCTLA-4 ECD)
(lower: amino acids 41-55 of D3, with amino acids 49-50 deleted)

```
 Q   A   D   S   Q   V   T   E   V   C   A   A   T   Y   M
     A   G   S   Q   V   T   E   V   C           T   Y   M   K
     4  -1   4   5   4   5   5   4   9           0  -2  -1  -2
```
                                                                    = 34

D.

(upper: amino acids 39-53 of hCTLA-4 ECD)
(lower: amino acids 41-55 of D3, with amino acids 49-50 deleted)

IMMUNOSUPPRESSIVE POLYPEPTIDES AND NUCLEIC ACIDS

CROSS-REFERENCES TO RELATED APPLICATIONS

This application is a divisional of U.S. patent application Ser. No. 12/763,902 filed on Apr. 20, 2010, now U.S. Pat. No. 8,071,095, issued Dec. 6, 2011 which is a divisional of U.S. patent application Ser. No. 12/251,960, filed Oct. 15, 2008, now U.S. Pat. No. 7,794,718, issued Sep. 14, 2010, which in turn claims priority to and benefit of U.S. Provisional Patent Application Ser. No. 60/984,631, filed on Nov. 1, 2007, and U.S. Provisional Patent Application Ser. No. 61/051,215, filed on May 7, 2008, the disclosure of each of which is incorporated herein by reference in its entirety for all purposes.

COPYRIGHT NOTIFICATION

Pursuant to 37 C.F.R. 1.71(e), Applicants note that a portion of this disclosure contains material which is subject to copyright protection. The copyright owner has no objection to the facsimile reproduction by anyone of the patent document or patent disclosure, as it appears in the Patent and Trademark Office patent file or records, but otherwise reserves all copyright rights whatsoever.

FIELD OF THE INVENTION

This invention relates generally to novel polypeptides that bind CD80 and/or CD86, nucleic acid encoding such polypeptides, and methods of making and using such polypeptides and nucleic acids.

BACKGROUND OF THE INVENTION

T cells play a major role in the initiation and regulation of immune responses. For complete activation of T cells to occur, at least two distinct signaling events are required. A first signal is produced by the interaction of T cell receptors (TCR) expressed on T cells with specific antigens (Ag) presented in the context of major histocompatibility complex (MHC) molecules expressed on antigen-presenting cells (APCs). A second (co-stimulation) signal results from the interaction between co-stimulatory ligands expressed on APCs and their corresponding receptors expressed on T cells. A dominant co-stimulation pathway involves the interaction between the CD80 (B7-1 or B7.1) and CD86 (B7-2 or B7.2) ligands expressed on APCs with CD28 and CTLA-4 (also known as CD152) expressed mainly on T cells. CTLA-4 (cytotoxic T-lymphocyte antigen 4) and CD28 serve as receptors for the CD80 and CD86 ligands.

Positive signaling is mediated through the CD28 receptor. Binding of the CD80 and/or CD86 ligand(s) to CD28 lowers the threshold of T cell activation by promoting the formation of immunological synapses (Viola A. et al., *Science* 283:680-682 (1999)). Additionally, CD28 co-stimulation activates or enhances the production of factors central to T cell proliferation and survival, such as interleukin-2 (IL-2), NF-κB, and Bcl-XL (Norton S. D. et at., J. Immunol. 149:1556-1561 (1992); Vella A. T. et al., J. Immunol. 158: 4714-4720 (1997)). In vivo, CD28-deficient mice are severely immunocompromised and show poor antigen-specific T cell responses (Green, J. M. et al., Immunity 1:501-508 (1994)). T cell anergy or tolerance may result when T cells are activated in the absence of the costimulatory signal.

Negative signaling is mediated through the CTLA-4 receptor. The CD80 and CD86 ligands each bind with high avidity to CTLA-4 and counterbalance immunoproliferative responses derived from CD28 signaling. Potential mechanisms of CTLA-4 signaling include competitive binding of co-stimulatory molecules CD80/CD86 (Masteller, E. M. et al., J. Immunol. 164:5319 (2000)), inhibition of TCR signaling by induction of phosphatases to the immunosynapse (Lee K. M. et al., Science 282:2263 (1998)), and disruption of the immunological synapse (Pentcheva-Hoang T. et al., Immunity 21:401 (2004); Chikuma S. et al., J. Exp. Med. 197:129 (2003); Schneider H. et al., Science 313: 1972 (2006)). In vivo, CTLA-4 deficient mice show profound autoimmune phenotypes characterized by massive tissue infiltration and organ destruction (Waterhouse P. et al., Science 270:985 (1995)).

Therapeutic agents designed to antagonize the CD80/CD86 co-stimulation pathway, such as soluble human CTLA-4-Ig, hold promise for the treatment of autoimmune diseases and disorders. The present invention provides advantageous molecules having improved abilities to modulate or suppress signaling through the CD80/CD86 co-stimulation pathway and methods of using such molecules for selected and differential manipulation of T cell responses. Such molecules are of beneficial use in a variety of applications as discussed in detail below.

SUMMARY OF THE INVENTION

In a first aspect, the invention provides an isolated or recombinant CTLA-4 polypeptide comprising a polypeptide sequence which differs from the polypeptide sequence of the extracellular domain of human CTLA-4 shown in SEQ ID NO:159 in up to 15 amino acid residues, wherein the isolated or recombinant CTLA-4 polypeptide has an ability to bind CD80 or CD86 or an extracellular domain of either and/or has an ability to suppress or inhibit an immune response.

A polypeptide according to the first aspect of the invention may have at least 90% sequence identity, or at least 95%, at least 96%, at least 97%, at least 98%, or at least 99% sequence identity, to the polypeptide sequence of SEQ ID NO:36. A polypeptide according to the first aspect of the invention may comprise the polypeptide sequence of SEQ ID NO:36.

A polypeptide according to the first aspect of the invention may have at least 90% sequence identity, or at least 95%, at least 96%, at least 97%, at least 98%, or at least 99% sequence identity, to the polypeptide sequence of SEQ ID NO:50. A polypeptide according to the first aspect of the invention may comprise the polypeptide sequence of SEQ ID NO:50.

A polypeptide according to the first aspect of the invention may have an ability to bind human CD80 or human CD86 or an extracellular domain of either.

A polypeptide according to the first aspect of the invention may comprise a polypeptide sequence that is 124 amino acid residues in length.

A polypeptide according to the first aspect of the invention may comprise one amino acid substitution at an amino acid position selected from the group consisting of amino acid positions corresponding to position 50, 54, 55, 56, 64, 65, 70, or 85 relative to SEQ ID NO:159.

A polypeptide according to the first aspect of the invention may comprise two, three, or four amino acid substitutions at amino acid positions selected from the group consisting of amino acid positions corresponding to position 50, 54, 55, 56, 64, 65, 70, or 85 relative to SEQ ID NO:159.

A polypeptide of the first aspect of the invention may comprise an amino acid substitution at position 70 relative to SEQ ID NO:159, such as the substitution S70F. A polypeptide of the first aspect of the invention may comprise an amino acid substitution at position 104 relative to SEQ ID NO:159, such as the substitution L104E.

A polypeptide of the first aspect of the invention may comprise an amino acid substitution at position 30 relative to SEQ ID NO:159, such as the substitution T30N/D/A or the substitution T30N.

A polypeptide of the first aspect of the invention may comprise an amino acid substitution at position 64 relative to SEQ ID NO:159, such as the substitution S64P.

A polypeptide of the first aspect of the invention may comprise an amino acid substitution at position 50 relative to SEQ ID NO:159, such as the substitution A50M.

A polypeptide of the first aspect of the invention may comprise an amino acid substitution at position 54 relative to SEQ ID NO:159, such as the substitution M54K/V or the substitution M54K.

A polypeptide of the first aspect of the invention may comprise an amino acid substitution at position 65 relative to SEQ ID NO:159, such as the substitution I65S.

A polypeptide of the first aspect of the invention may comprise an amino acid substitution at position 56 relative to SEQ ID NO:159, such as the substitution N56D.

A polypeptide of the first aspect of the invention may comprise an amino acid substitution at position 55 relative to SEQ ID NO:159, such as the substitution G55E.

A polypeptide of the first aspect of the invention may comprise an amino acid substitution at positions 85 relative to SEQ ID NO:159, such as the substitution M85A.

A polypeptide of the first aspect of the invention may comprise an amino acid substitution at position 24 relative to SEQ ID NO:159, such as the substitution A24E/S or the substitution A24E.

A polypeptide of the first aspect of the invention may have a binding affinity for CD86 or an extracellular domain thereof that is about equal to or greater than the binding affinity of a monomeric human CTLA-4 extracellular domain for CD86 or CD86 extracellular domain.

A polypeptide of the first aspect of the invention may have a binding affinity for CD80 or an extracellular domain thereof that is greater than the binding affinity of a monomeric human CTLA-4 extracellular domain for CD80 or CD80 extracellular domain.

A polypeptide of the first aspect of the invention may have an ability to suppress an immune response.

A polypeptide of the first aspect of the invention may have an ability to inhibit T cell activation or T cell proliferation.

In a second aspect, the invention provides an isolated or recombinant polypeptide multimer comprising at least two polypeptides of the first aspect of the invention.

In a third aspect, the invention provides an isolated or recombinant fusion protein comprising (a) a polypeptide according to the first aspect of the invention, and (b) a second polypeptide, wherein the second polypeptide is an Ig Fc polypeptide, and wherein the fusion protein has an ability to bind CD80 and/or CD86 or an extracellular domain of either or both, and/or an ability to modulate or regulate an immune response.

In a fourth aspect, the invention provides an isolated or recombinant dimeric fusion protein comprising two monomeric fusion proteins according to the third aspect of the invention.

In a fifth aspect, the invention provides an isolated or recombinant nucleic acid comprising a nucleotide sequence that encodes a polypeptide of the first aspect of the invention, a multimer of the second aspect of the invention, a fusion protein of the third aspect of the invention, or a dimeric fusion protein of the fourth aspect of the invention.

In a sixth aspect, the invention provides a vector comprising a nucleic acid of the fifth aspect of the invention.

In a seventh aspect, the invention provides an isolated or recombinant host cell comprising a polypeptide of the first aspect of the invention, a multimer of the second aspect of the invention, a fusion protein of the third aspect of the invention, a dimeric fusion protein of the fourth aspect of the invention, a nucleic acid of the fifth aspect of the invention, and/or a vector of the sixth aspect of the invention.

In an eighth aspect, the invention provides a pharmaceutical composition comprising a pharmaceutically acceptable excipient, pharmaceutically acceptable carrier, or pharmaceutically acceptable diluent and one or more of the following: a polypeptide of the first aspect of the invention, a multimer of the second aspect of the invention, a fusion protein of the third aspect of the invention, a dimeric fusion protein of the fourth aspect of the invention, a nucleic acid of the fifth aspect of the invention, a vector of the sixth aspect of the invention, and/or a host cell of the seventh aspect of the invention.

In a ninth aspect, the invention provides a method for suppressing an immune response, said method comprising contacting a B7-positive cell with an effective amount of at least one of: a polypeptide of the first aspect of the invention, a multimer of the second aspect of the invention, a fusion protein of the third aspect of the invention, a dimeric fusion protein of the fourth aspect of the invention, a nucleic acid of the fifth aspect of the invention, a vector of the sixth aspect of the invention, and/or a host cell of the seventh aspect of the invention, to suppress an immune response, wherein an immune response is thereby suppressed.

In a tenth aspect, the invention provides a polypeptide of the first aspect of the invention, a multimer of the second aspect of the invention, a fusion protein of the third aspect of the invention, a dimeric fusion protein of the fourth aspect of the invention, a nucleic acid of the fifth aspect of the invention, a vector of the sixth aspect of the invention, and/or a host cell of the seventh aspect of the invention, for use in suppressing an immune response.

In an eleventh aspect, the invention provides the use of a polypeptide of the first aspect of the invention, a multimer of the second aspect of the invention, a fusion protein of the third aspect of the invention, a dimeric fusion protein of the fourth aspect of the invention, a nucleic acid of the fifth aspect of the invention, a vector of the sixth aspect of the invention, and/or a host cell of the seventh aspect of the invention, in the manufacture of a medicament for suppressing an immune response.

In a twelfth aspect, the invention provides a conjugate comprising a polypeptide of the first aspect of the invention, a multimer of the second aspect of the invention, a fusion protein of the third aspect of the invention, or a dimeric fusion protein of the fourth aspect of the invention, and a non-polypeptide moiety covalently attached to such polypeptide, multimer, fusion protein, or dimeric fusion protein, wherein said conjugate has an ability to suppress an immune response.

Other aspects of the invention are described below.

In another aspect, the invention provides an isolated or recombinant polypeptide comprising a polypeptide sequence having at least 95%, 96%, 97%, 98%, 99%, or 100% sequence identity to at least one polypeptide sequence selected from the group consisting of SEQ ID NOS:1-73, wherein the polypeptide binds CD80 or CD86 or an extracellular domain (ECD) of either, and/or has an ability to suppress or inhibit an immune response.

In another aspect, the invention provides an isolated or recombinant polypeptide comprising a polypeptide sequence having at least 95%, 96%, 97%, 98%, 99%, or 100% sequence identity to at least one polypeptide sequence selected from the group consisting of SEQ ID NOS:1-73, wherein the polypeptide has a binding affinity for a human CD86 extracellular domain or human CD80 extracellular domain that is about equal to or greater than the binding affinity of a human CTLA-4 extracellular domain for the human CD86 extracellular domain or human CD80 extracellular domain, respectively, and wherein the polypeptide optionally has an ability to suppress an immune response. Some such polypeptides have a binding affinity for the human CD86 extracellular domain that is greater than the binding affinity of the human CTLA-4 extracellular domain for the human CD86 extracellular domain. Some such polypeptides have a binding affinity for the human CD80 extracellular domain that is greater than the binding affinity of the human CTLA-4 extracellular domain for the human CD80 extracellular domain.

In another aspect, the invention provides an isolated or recombinant mutant CTLA-4 polypeptide comprising a polypeptide sequence which (a) differs from the polypeptide sequence of the extracellular domain of human CTLA-4 shown in SEQ ID NO:159 in no more than 10, 9, 8, 7, or 6 amino acid residues (e.g., no more than 1, 2, 3, 4, 5, 6, 7, 8, 9, or 10 amino acid residues), and (b) comprises at least one amino acid substitution at an amino acid position corresponding to position 50, 54, 55, 56, 64, 65, 70, or 85 relative to SEQ ID NO:159, wherein the mutant CTLA-4 polypeptide has an ability to bind CD80 or CD86 or an extracellular domain of either, and/or has an ability to suppress or inhibit an immune response.

In another aspect, the invention provides an isolated or recombinant polypeptide which comprises a polypeptide sequence comprising (i) at least 95%, 96%, 97%, 98%, 99%, or 100% sequence identity to a polypeptide sequence selected from the group consisting of SEQ ID NOS:1-73 and (ii) a phenylalanine residue at an amino acid position corresponding to position 70 of said polypeptide sequence selected from the group consisting of SEQ ID NO:1-73, wherein the polypeptide has an ability to bind CD80 and/or CD86 or an extracellular domain of either or both, and/or has an ability to suppress or inhibit an immune response.

In another aspect, the invention provides an isolated or recombinant mutant CTLA-4 polypeptide that binds CD80 and/or CD86 and/or an extracellular domain of either or both, and/or is capable of suppressing an immune response, wherein said polypeptide comprises a polypeptide sequence which (a) differs from the polypeptide sequence of human CTLA-4 extracellular domain polypeptide shown in SEQ ID NO:159 in no more than 10, 9, 8, 7, or 6 amino acid residues (e.g., no more than 1, 2, 3, 4, 5, 6, 7, 8, 9, or 10 amino acid residues), and (b) comprises at least one amino acid substitution, wherein said at least amino acid substitution comprises S70F, wherein amino acid residue positions are numbered according to SEQ ID NO:159.

In another aspect, the invention provides an isolated or recombinant mutant CTLA-4 polypeptide comprising a polypeptide sequence which (a) differs from the polypeptide sequence of the extracellular domain of human CTLA-4 shown in SEQ ID NO:159 in no more than 11, 10, 9, 8, 7, or 6 amino acid residues (e.g., no more than 1, 2, 3, 4, 5, 6, 7, 8, 9, 10, or 11 amino acid residues), and (b) comprises at least one amino acid substitution at an amino acid residue position corresponding to position 24, 30, 32, 50, 54, 55, 56, 64, 65, 70, or 85 relative to SEQ ID NO:159, wherein the mutant CTLA-4 polypeptide has an ability to bind CD80 or CD86 or an extracellular domain of either, and/or has an ability to suppress or inhibit an immune response.

In another aspect, the invention provides an isolated or recombinant polypeptide comprising a polypeptide sequence which (a) differs from the polypeptide sequence shown in SEQ ID NO:31 in no more than 10, 9, 8, 7, or 6 amino acid residues (e.g., no more than 1, 2, 3, 4, 5, 6, 7, 8, 9, or 10 amino acid residues), and (b) comprises at least one of the following: a methionine residue at a position corresponding to position 50 of SEQ ID NO:31, a lysine residue at a position corresponding to position 54 of SEQ ID NO:31, a glutamic acid residue at a position corresponding to position 55 of SEQ ID NO:31, a proline residue at a position corresponding to position 64 of SEQ ID NO:31, a serine residue at a position corresponding to position 65 of SEQ ID NO:31, a phenylalanine residue at a position corresponding to position 70 of SEQ ID NO:31, wherein amino acid residue positions are numbered according to SEQ ID NO:31, and the polypeptide binds CD80 and/or CD86 and/or an ECD of either or both, and/or inhibits an immune response.

In another aspect, the invention provides an isolated or recombinant fusion protein dimer comprising two monomeric fusion proteins linked via at least one disulfide bond formed between two cysteine residues present in each monomeric mutant fusion protein, wherein each monomeric fusion protein comprises (a) a polypeptide comprising a polypeptide sequence having at least 95%, 96%, 97%, 98%, 99%, or 100% identity to at least one polypeptide sequence selected from the group consisting of SEQ ID NOS:1-73 and (b) an Ig Fc polypeptide, wherein the fusion protein dimer has an ability to bind CD80 and/or CD86, and/or CD80-Ig and/or CD86-Ig, and/or has an ability to inhibit or suppress an immune response.

In another aspect, the invention provides an isolated or recombinant fusion protein dimer comprising two monomeric fusion proteins, each such monomeric fusion protein comprising a polypeptide sequence having at least 95%, 96%, 97%, 98%, 99%, or 100% sequence identity to at least one polypeptide sequence selected from the group consisting of SEQ ID NOS:74-79, 197-200, 205-214, and 219-222, wherein the polypeptide binds CD80 and/or CD86 and/or an extracellular domain thereof and/or suppresses an immune response, or a complementary polynucleotide sequence thereof.

In another aspect, the invention provides an isolated or recombinant fusion protein dimer comprising two monomeric fusion proteins, wherein each monomeric fusion protein comprises: (1) a polypeptide comprising a polypeptide sequence which differs from a polypeptide sequence selected from the group consisting of SEQ ID NOS:1-73 in no more than 10, 9, 8, 7, or 6 amino acid residues (e.g., no more than 1, 2, 3, 4, 5, 6, 7, 8, 9, or 10 amino acid residues), and wherein the amino acid residue in the polypeptide sequence at position 41, 50, 54, 55, 56, 64, 65, 70, or 85 is identical to the amino acid residue at the corresponding position of said selected polypeptide sequence, and (2) an Ig Fc polypeptide, wherein the fusion protein dimer binds CD80 and/or CD86, and/or inhibits an immune response.

In another aspect, the invention provides an isolated or recombinant fusion protein dimer comprising two monomeric fusion proteins, wherein each monomeric fusion protein comprises: (1) a mutant CTLA-4 extracellular domain polypeptide comprising a polypeptide sequence which (i) differs from the polypeptide sequence of the extracellular domain of human CTLA-4 shown in SEQ ID NO:159 in no more than 10, 9, 8, 7, or 6 amino acid residues (e.g., no more than 1, 2, 3, 4, 5, 6, 7, 8, 9, or 10 amino acid residues), and (ii)

comprises at least one amino acid substitution at an amino acid position corresponding to position 50, 54, 55, 56, 64, 65, 70, or 85 relative to the polypeptide sequence of SEQ ID NO:159; and (2) an Ig Fc polypeptide, wherein the fusion protein dimer binds CD80 and/or CD86, and/or suppresses or inhibits an immune response. Some such fusion protein dimers comprise one or more substitutions at amino acid positions relative to SEQ ID NO:159 selected from the group consisting of A50M, M54K, G55E, N56D, S64P, I65S, and S70F; and (2) an Ig Fc polypeptide, which Ig Fc polypeptide optionally is IgG2 Fc polypeptide, wherein the mutant CTLA-4-Ig dimer binds hCD80 and/or hCD86, and/or suppresses or inhibits an immune response.

In another aspect, the invention provides an isolated or recombinant polypeptide comprising a polypeptide sequence having at least 95%, 96%, 97%, 98%, 99%, or 100% sequence identity to a polypeptide sequence selected from the group consisting of SEQ ID NO:26, SEQ ID NO:36, SEQ ID NO:38, SEQ ID NO:50, and SEQ ID NO:56, wherein the polypeptide (i) binds CD80 and/or CD86 or an extracellular domain of either or both, and/or (ii) suppresses an immune response.

In another aspect, the invention provides an isolated or recombinant polypeptide comprising a polypeptide sequence having at least 95%, 96%, 97%, 98%, 99%, or 100% sequence identity to a polypeptide sequence selected from the group consisting of SEQ ID NOS:74-79, 197-200, 205-214, and 219-222, wherein the polypeptide (i) binds CD80 and/or CD86 or an extracellular domain of either or both, (ii) binds a CD80-Ig fusion protein and/or CD86-Ig fusion protein, and/or (iii) suppresses an immune response.

Also provided is an isolated or recombinant fusion protein dimer comprising two monomeric fusion proteins linked via at least one disulfide bond formed between two cysteine residues present in each monomeric mutant fusion protein, wherein each monomeric fusion protein comprises (a) a polypeptide comprising a polypeptide sequence having at least 95% identity to at least one polypeptide sequence selected from the group consisting of SEQ ID NO:79, SEQ ID NO:197, SEQ ID NO:198, SEQ ID NO:199, and SEQ ID NO:200 and (b) an Ig Fc polypeptide, wherein the fusion protein dimer has (i) an ability to bind CD80 and/or CD86 and/or an extracellular domain of CD80 and/or CD86, (ii) an ability to bind CD80-Ig and/or CD86-Ig, and/or (iii) has an ability to inhibit or suppress an immune response.

In another aspect, the invention provides an isolated or recombinant nucleic acid comprising a polynucleotide sequence that encodes a polypeptide comprising a polypeptide sequence having at least 95%, 96%, 97%, 98%, 99% or 100% sequence identity to at least one polypeptide sequence selected from the group consisting of SEQ ID NOS:1-79, 197-200, 205-214, and 219-222, wherein the polypeptide binds CD80 and/or CD86 and/or an extracellular domain of either or both, and/or has an ability to suppress an immune response, or a complementary polynucleotide sequence thereof.

In another aspect, the invention provides an isolated or recombinant nucleic acid comprising a polynucleotide sequence that encodes a fusion protein comprising a polypeptide sequence having at least 95%, 96%, 97%, 98%, 99% or 100% sequence identity to at least one polypeptide sequence selected from the group consisting of SEQ ID NOS: 74-79, 197-200, 205-214, and 219-222, wherein the polypeptide binds CD80 and/or CD86 and/or an extracellular domain thereof and/or suppresses an immune response, or a complementary polynucleotide sequence thereof.

In another aspect, the invention provides an isolated of recombinant nucleic acid comprising: (a) a polynucleotide sequence having at least 95%, 96%, 97%, 98%, 99% or 100% sequence identity to at least one polynucleotide sequence selected from the group consisting of SEQ ID NOS:80-158, 201-204, 223, and 224; (b) a complementary polynucleotide sequence of (a); or (c) a fragment of any polynucleotide sequence of (a) or (b), wherein the nucleic acid encodes a polypeptide that binds CD80 and/or CD86 and/or an extracellular domain of either or both, and/or has an ability to suppress or inhibit an immune response.

In another aspect, the invention provides an isolated or recombinant nucleic acid comprising a polynucleotide sequence which encodes a polypeptide which comprises a polypeptide sequence (a) which differs from a polypeptide sequence selected from the group consisting of SEQ ID NOS: 1-73 in no more than 10, 9, 8, 7, or 6 amino acid residues (e.g., no more than 1, 2, 3, 4, 5, 6, 7, 8, 9, or 10 amino acid residues), and (b) wherein the amino acid residue in the polypeptide sequence at position 41, 50, 54, 55, 56, 64, 65, 70, or 85 is identical to the amino acid residue at the corresponding position of said polypeptide sequence selected from the group consisting of SEQ ID NOS:1-73, wherein the polypeptide binds CD80 and/or CD86 and/or an extracellular domain of either or both, and/or inhibits an immune response, or a complementary polynucleotide sequence thereof.

In another aspect, the invention provides an isolated or recombinant nucleic acid comprising a polynucleotide sequence which encodes a polypeptide comprising a polypeptide sequence which (a) differs from the polypeptide sequence of the extracellular domain of human CTLA-4 shown in SEQ ID NO:159 in no more than 10, 9, 8, 7, or 6 amino acid residues (e.g., no more than 1, 2, 3, 4, 5, 6, 7, 8, 9, or 10 amino acid residues), and (b) comprises at least one amino acid substitution at an amino acid position corresponding to position 50, 54, 55, 56, 64, 65, 70, or 85 relative to SEQ ID NO:159, wherein said polypeptide has an ability to bind CD80 and/or CD86 and/or an extracellular domain of either, and/or has an ability to suppress or inhibit an immune response, or a complementary polynucleotide sequence thereof.

In another aspect, the invention provides an isolated or recombinant nucleic acid comprising a polynucleotide sequence which encodes a polypeptide comprising a polypeptide sequence having (i) at least 95%, 96%, 97%, 98%, 99%, or 100% identity to a polypeptide sequence selected from the group consisting of SEQ ID NOS:1-73 and (ii) a phenylalanine residue at an amino acid position corresponding to position 70 of said polypeptide sequence selected from the group consisting of SEQ ID NO:1-73, wherein the polypeptide binds hCD80 and/or hCD86 or an ECD thereof and/or inhibits an immune response, wherein said amino acid substitution optionally comprises S70F, or a complementary polynucleotide sequence thereof.

In another aspect, the invention provides an isolated or recombinant nucleic acid comprising a polynucleotide sequence which encodes a recombinant polypeptide dimer comprising two polypeptides, wherein each such polypeptide comprises a polypeptide sequence having at least 95%, 96%, 97%, 98%, 99%, or 100% identity to a sequence selected from the group consisting of SEQ ID NOS:1-73, wherein the dimer binds hCD80 and/or hCD86 and/or inhibits an immune response, or a complementary polynucleotide sequence thereof.

In another aspect, the invention provides an isolated or recombinant nucleic acid comprising a polynucleotide sequence which encodes a fusion protein comprising (a) a polypeptide comprising a polypeptide sequence that has at least 95%, 96%, 97%, 98%, 99%, or 100% identity to at least one polypeptide sequence selected from the group consisting of SEQ ID NOS:1-73, and (b) an Ig polypeptide, wherein the fusion protein binds CD80 and/or CD86, and/or has an ability to suppress an immune response, or a complementary polynucleotide sequence thereof.

In another aspect, the invention provides an isolated or recombinant nucleic acid comprising a polynucleotide sequence which encodes a polypeptide comprising a polypeptide sequence which (a) differs from the polypeptide sequence shown in SEQ ID NO:31 in no more than 10, 9, 8, 7, or 6 amino acid residues (e.g., no more than 1, 2, 3, 4, 5, 6, 7, 8, 9, or 10 amino acid residues), and (b) comprises at least one of the following: a methionine residue at a position corresponding to position 50 of SEQ ID NO:31, a lysine residue at a position corresponding to position 54 of SEQ ID NO:31, a glutamic acid residue at a position corresponding to position 55 of SEQ ID NO:31, a proline residue at a position corresponding to position 64 of SEQ ID NO:31, a serine residue at a position corresponding to position 65 of SEQ ID NO:31, a phenylalanine residue at a position corresponding to position 70 of SEQ ID NO:31, wherein amino acid residue positions are numbered according to SEQ ID NO:31, and wherein the polypeptide binds CD80 and/or CD86, and/or inhibits an immune response, or a complementary polynucleotide sequence thereof.

In another aspect, the invention provides an expression vector comprising: (i) a first polynucleotide sequence that encodes a first polypeptide comprising a polypeptide sequence having at least 95%, 96%, 97%, 98%, 99%, or 100% identity to at least one polypeptide sequence selected from the group consisting of SEQ ID NOS:1-73, wherein said first polypeptide binds human CD86 and/or human CD80 and/or an extracellular domain of either or both, and/or suppresses an immune response, and (ii) a second polynucleotide sequence that encodes a second polypeptide comprising a hinge region, a CH2 domain, and a CH3 domain of an immunoglobulin (Ig) polypeptide, which Ig polypeptide is optionally human IgG2 Fc polypeptide.

In another aspect, the invention provides an isolated or recombinant host cell transfected with a nucleic acid encoding a fusion protein, the nucleic acid comprising: (i) a first nucleotide sequence encoding a first polypeptide comprising a polypeptide sequence having at least 95%, 96%, 97%, 98%, 99%, or 100% identity to at least one polypeptide sequence selected from the group consisting of SEQ ID NOS:1-73, wherein said first polypeptide has an ability to bind human CD86 and/or human CD80 and/or an extracellular domain of either or both, and/or has an ability to suppress an immune response; and (ii) a second nucleotide sequence encoding a second polypeptide comprising a hinge region, a CH2 domain, and a CH3 domain of an immunoglobulin (Ig) polypeptide, which Ig polypeptide is optionally human IgG2 Fc polypeptide, wherein the host cell is capable of expressing the fusion protein.

In another aspect, the invention provides a method of suppressing an immune response, said method comprising contacting a B7-positive cell with an effective amount of at least one polypeptide, conjugate, nucleic acid, vector, or cell of the invention to suppress an immune response, wherein an immune response is thereby suppressed.

In another aspect, the invention provides a method of modulating the interaction of T cells expressing CD28 and/or CTLA-4 with B7-positive cells, the method comprising contacting B7-positive cells with an effective amount of at least one polypeptide, conjugate, nucleic acid, vector, or cell of the invention to modulate the interaction of B7-positive cells with CD28-positive T cells and/or CTLA-4-positive T cells, wherein the interaction of B7-positive cells with CD28-positive T cells and/or CTLA-4-positive T cells is modulated.

In another aspect, the invention provides a method of inhibiting the interaction of CD28-positive T cells and/or CTLA-4-positive T cells with B7-positive cells, the method comprising contacting B7-positive cells with an effective amount of at least one polypeptide, conjugate, nucleic acid, vector, or cell of the invention, wherein the interaction of CD28-positive T cells and/or CTLA-4-positive T cells with B7-positive cells is inhibited.

In another aspect, the invention provides a method of inhibiting the interaction of CD28-positive T cells with B7-positive cells in a subject, said method comprising administering to a subject an effective amount of at least one polypeptide, conjugate, nucleic acid, vector, or cell of the invention, wherein the interaction of endogenous CD28-positive T cells with endogenous B7-positive cells in the subject is inhibited.

In another aspect, the invention provides a method of treating a subject having an immune system disease or disorder modulated by interaction of endogenous T cells with endogenous cells expressing CD80 and/or CD86, said method comprising administering to a subject in need of such treatment a therapeutically effective amount of at least one polypeptide, conjugate, nucleic acid, vector, or cell of the invention, wherein interaction(s) between endogenous T cells and endogenous cells expressing said CD80 and/or said CD86 is inhibited, thereby treating the immune system disease or disorder in the subject.

In another aspect, the invention provides a method of inhibiting rejection of a tissue or organ transplant from a donor by a recipient subject, the method comprising administering to the recipient subject in need thereof a therapeutically effective amount of at least one polypeptide, conjugate, nucleic acid, vector, or cell of the invention, thereby inhibiting rejection of the tissue or organ transplant by the recipient subject.

In another aspect, the invention provides a method of making a fusion protein, the method comprising: (1) culturing a host cell transformed with a nucleic acid in a culture medium, wherein the nucleic acid comprises (i) a first nucleotide sequence that encodes a polypeptide having at least 95%, 96%, 97%, 98%, 99%, or 100% identity to a polypeptide sequence of any of SEQ ID NOS:1-73, which polypeptide binds CD86 and/or CD80, and/or an extracellular domain of either CD86 or CD80, and (ii) a second nucleotide sequence encoding an Ig polypeptide comprising a hinge region, CH2 domain, and CH3 domain, whereby the nucleic acid is expressed and a fusion protein is produced; and (2) recovering the fusion protein.

Also provided is a method of producing a polypeptide comprising introducing into a population of cells a nucleic acid of the invention, wherein the nucleic acid is operatively linked to a regulatory sequence effective to produce the polypeptide encoded by the nucleic acid; culturing the cells in a culture medium to produce the polypeptide; and isolating the polypeptide from the cells or culture medium.

Also provided are compositions which comprise a molecule of the invention (e.g., mutant CTLA-4 molecule) and an excipient, carrier, or diluent. Also included are pharmaceutical compositions comprising a molecule of the invention and a pharmaceutically acceptable and an excipient, carrier, or diluent.

Additional aspects of the invention are described below.

BRIEF DESCRIPTION OF THE FIGURES

In FIG. 1, each mutant CTLA-4-Ig fusion protein comprises a mutant CTLA-4 ECD polypeptide of the invention fused at its C-terminus to the N-terminus of a human IgG2 (hIgG2) Fc polypeptide.

FIGS. 2A-2D are schematic diagrams of exemplary hCD80-Ig, hCD86-Ig, LEA29Y-Ig, and hCTLA-4-IgG2 fusion proteins, respectively. The signal peptide, extracellular domain (ECD), linker (if any), and Ig Fc domain of each fusion protein are shown schematically. The amino acid residues present at the junctions between the signal peptide, ECD, linker (if any), and Ig Fc are also shown. The signal peptide of each fusion protein is typically cleaved during processing and thus the secreted (mature) fusion protein typically does not contain the signal peptide sequence. FIG. 2D presents a schematic diagram of a human CTLA-4-IgG2 ("hCTLA-4-IgG2") fusion protein comprising a human CTLA-4 extracellular domain ("hCTLA-4 ECD") covalently fused at its C-terminus to the N-terminus of a human IgG2 polypeptide. The predicted polypeptide sequence of this hCTLA-4-IgG2 fusion protein is shown in SEQ ID NO:161 and comprises the following segments: hCTLA-4 signal peptide (amino acid residues 1-37), hCTLA-4 ECD polypeptide (amino acid residues 38-161), and human IgG2 Fc polypeptide (amino acid residues 162-389). No linker (e.g., no amino acid residue(s)) is included between the C-terminus of the hCTLA-4 ECD polypeptide and the N-terminus of the human IgG2 Fc. The human IgG2 Fc polypeptide comprises a hinge, CH2 domain, and CH3 domain of human IgG2. In FIG. 2D, the amino acid residues at the junctions between these various segments are shown. Specifically, the last four amino acid residues of the signal peptide, the first five and last five amino acid residues of the hCTLA-4 ECD polypeptide, and the first five and last five amino acid residues of the human IgG2 Fc polypeptide are shown.

The signal peptide is typically cleaved during processing and thus the secreted fusion protein (mature fusion protein) of hCTLA-4-IgG2 does not typically contain the signal peptide sequence. The polypeptide sequence of the mature or secreted form of this hCTLA-4-IgG2 fusion protein is shown in SEQ ID NO:162. The sequence of the hCTLA-4 ECD polypeptide comprises amino acid residues 1-124 of SEQ ID NO:162, and the sequence of human IgG2 Fc polypeptide comprises amino acid residues 125-352 of SEQ ID NO:162. In another aspect, this mature hCTLA-4 Ig fusion protein does not include the C-terminal lysine (K) residue and thus comprises amino acid residues 1-351 of SEQ ID NO:162.

The mature hCTLA-4-IgG2 fusion protein, which has a total of 352 amino acids, comprises amino acid residues 38-389 of the polypeptide sequence of the full-length WT hCTLA-4 protein shown in SEQ ID NO:160, and begins with the amino acid sequence: methionine-histidine-valine-alanine. If desired, the amino acids of the mature form can be numbered beginning with the Met of the Met-His-Val-Ala sequence, designating Met as the first residue (e.g., the ECD comprises amino acid residues numbered 1-124), as in SEQ ID NO:162. A mature hCTLA-4IgG2 dimer is the form of the fusion protein typically used in the assays of the Examples described infra, unless stated otherwise. A DNA sequence encoding the hCTLA-4-IgG2 fusion protein, which comprises the hCTLA-4 ECD fused to the hIgG2 Fc polypeptide, is shown in SEQ ID NO:163.

Figure 3:
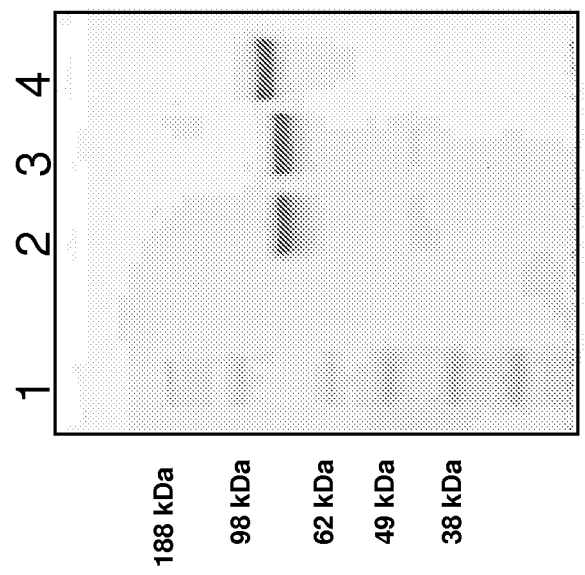

FIG. 3 represents SDS/PAGE analyses of the following proteins: molecular weight markers of various mass (kilodaltons (kDa) (lane 1); an exemplary mutant CTLA-4-Ig fusion protein of the invention based on clone D3 (i.e., D3-IgG2) (lane 2); an exemplary mutant CTLA-4-Ig fusion protein based on clone D4 (i.e., D4-IgG2) (lane 3); and the Orencia® (Abatacept) fusion protein (lane 4) (Bristol-Myers Squibb Co., Princeton, N.J.).

Figure 4:
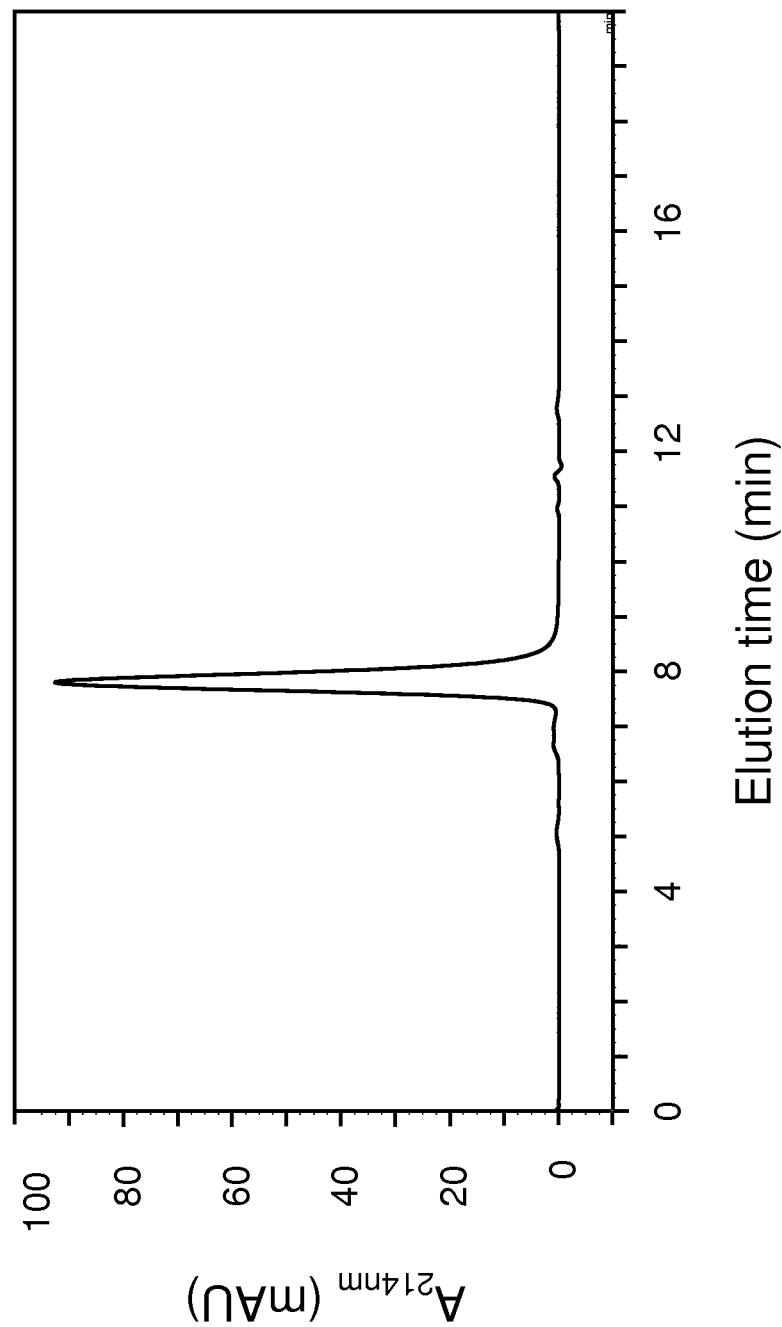

FIG. 4 presents an elution profile of an exemplary mutant CTLA-4-Ig fusion protein of the invention (i.e., D3-IgG2) from SEC analysis, demonstrating that mutant CTLA-4-Ig fusion proteins of the invention are homogenous in size when purified from transiently-transfected COS cells.

Figure 5:
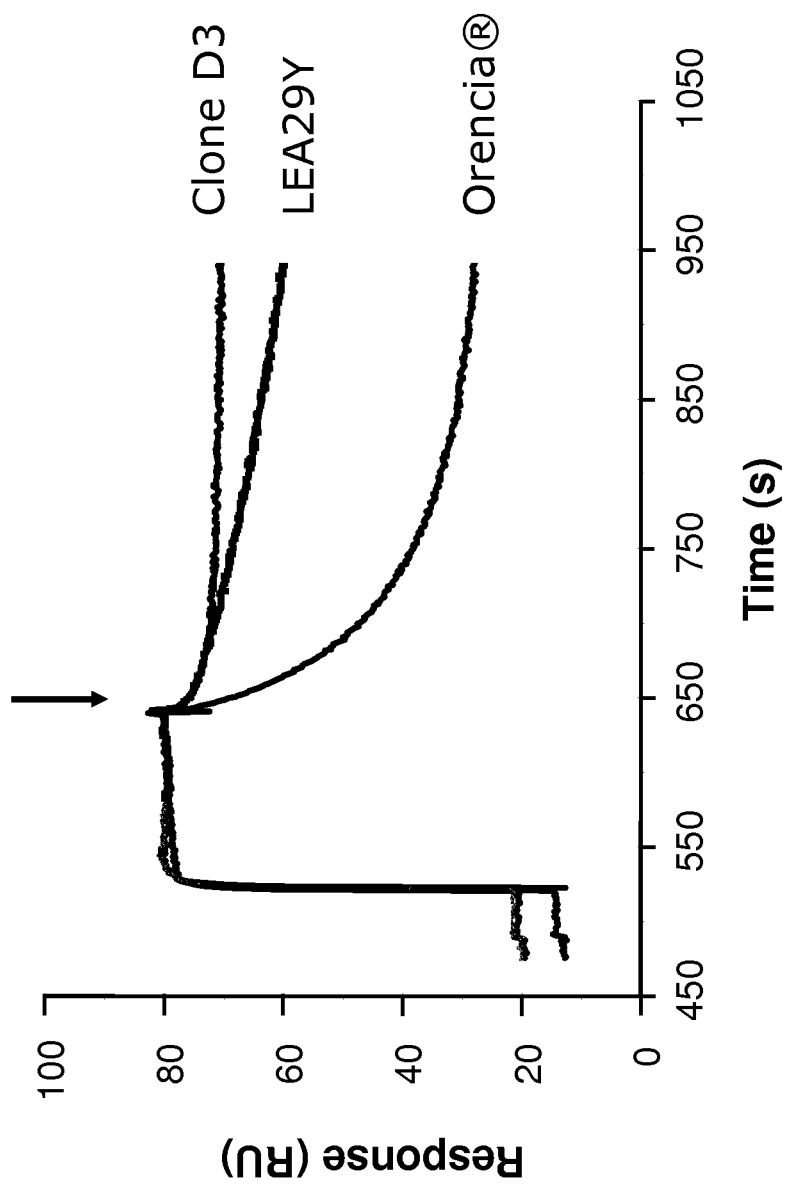

FIG. 5 shows a typical Biacore™ analysis of the binding of the following fusion proteins to hCD86-Ig: Orencia® fusion protein, LEA29Y-Ig, and D3-IgG2. The dissociation phase of the analysis begins at the time marked by the arrow. The Orencia® fusion protein, which is composed of the wild-type human CTLA-4 ECD polypeptide fused to a mutant IgG1 Fc domain polypeptide, effectively serves as a wild-type human CTLA-4-Ig control. A mutant CTLA-4-Ig fusion protein of the invention, such as D3-IgG2, which has a higher avidity binding to CD86-Ig than the Orencia® fusion protein has a slower rate of dissociation from CD86-Ig than the Orencia® protein.

Figure 6:
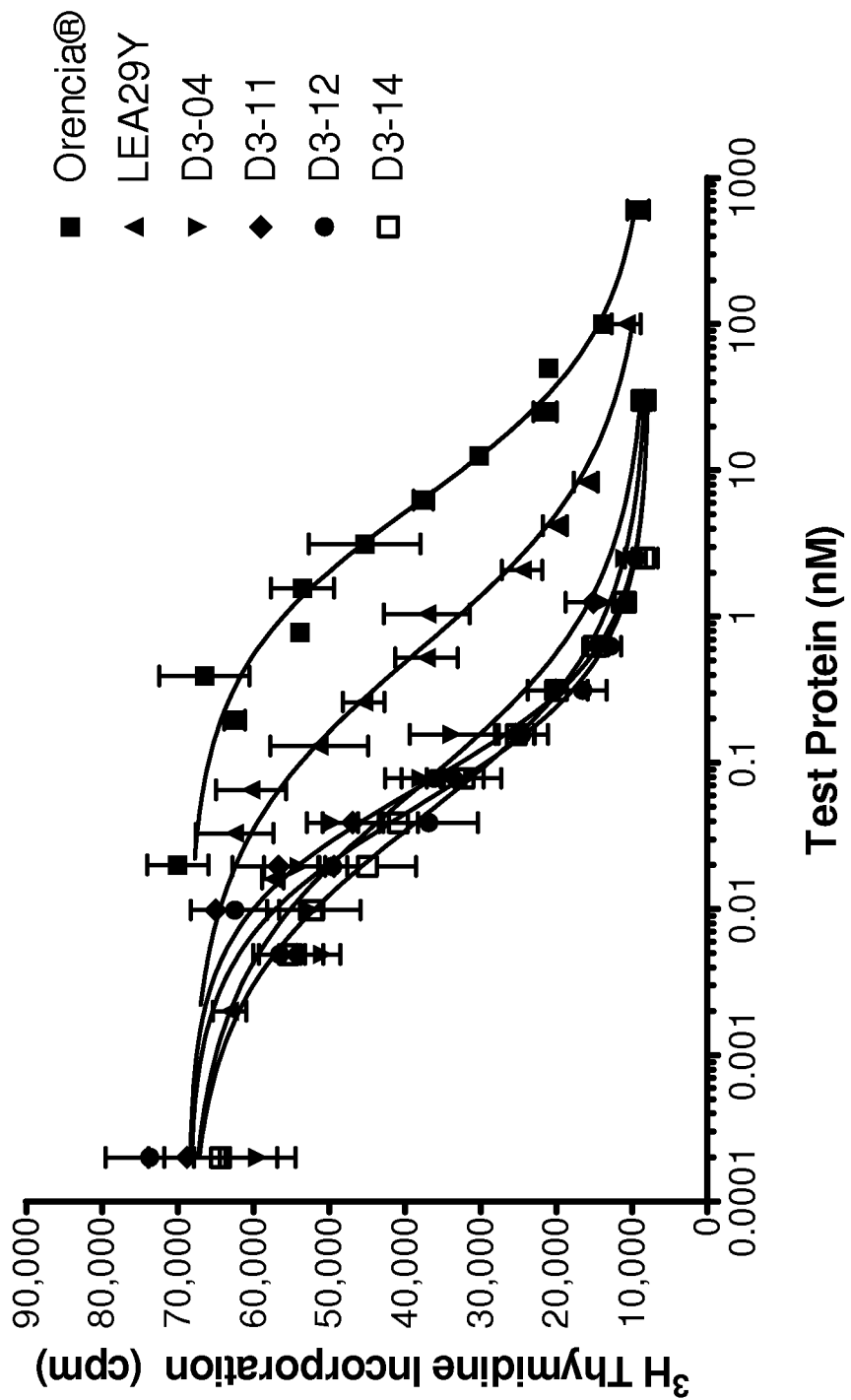

FIG. 6 is a graphical representation of the results of PBMC proliferation inhibition assays (with anti-CD3 antibody stimulation) involving exemplary mutant CTLA-4-Ig fusion proteins of the invention (D3-04-IgG2, D3-11-IgG2, D3-12-IgG2, D3-14-IgG2). These assays show that mutant CTLA-4-Ig fusion proteins of the invention are significantly more potent than Orencia® and LEA29Y-Ig in inhibiting T cell proliferation in vitro.

Figure 7:
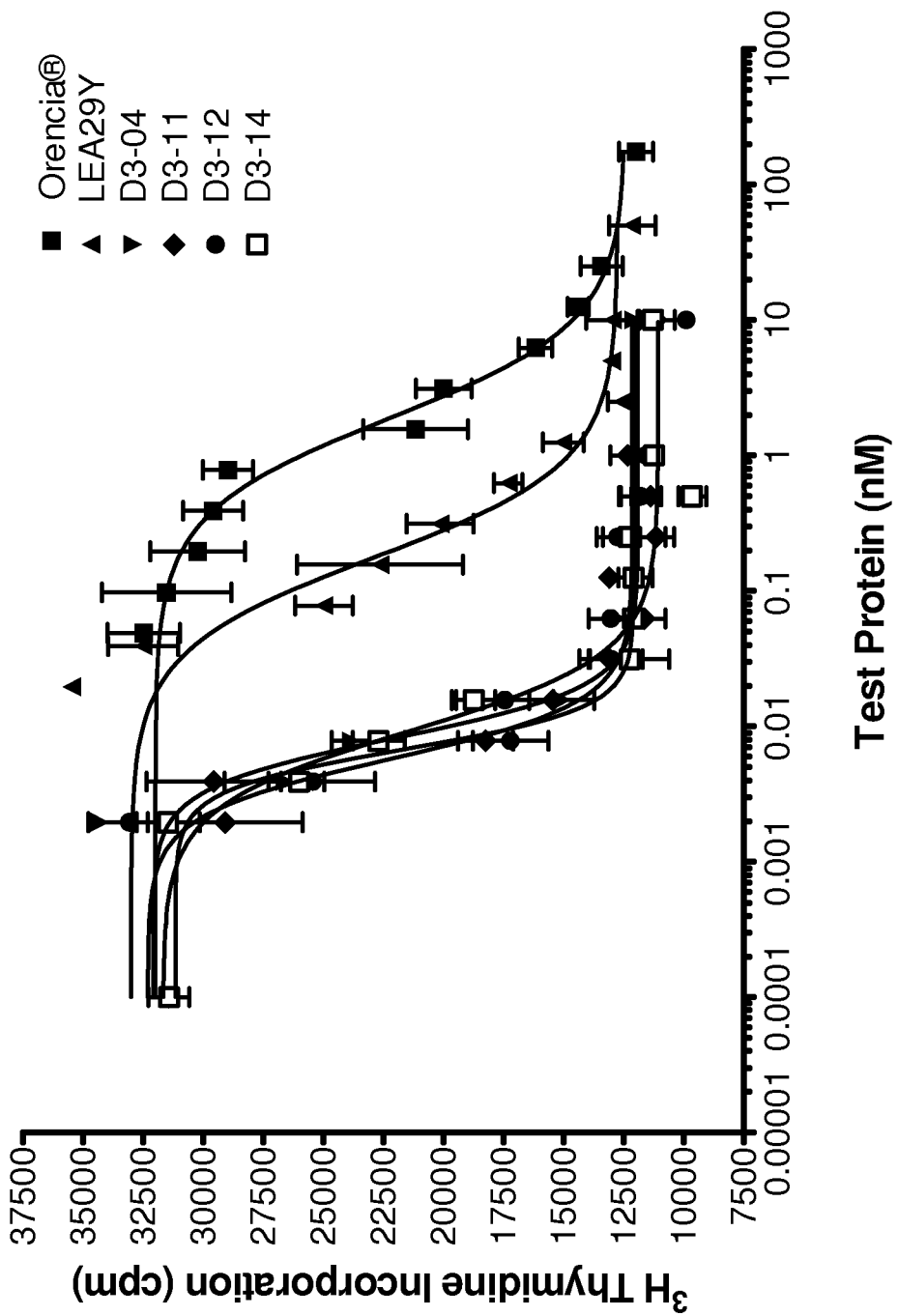

FIG. 7 is a graphical representation of CD4+ T cell proliferation inhibition assays (with anti-CD3 stimulation and hB7.2-dependent costimulation) involving an exemplary set of mutant CTLA-4-Ig fusion proteins of the invention. The Orencia® and LEA29Y-Ig fusion proteins were included as controls for comparison.

Figure 8:
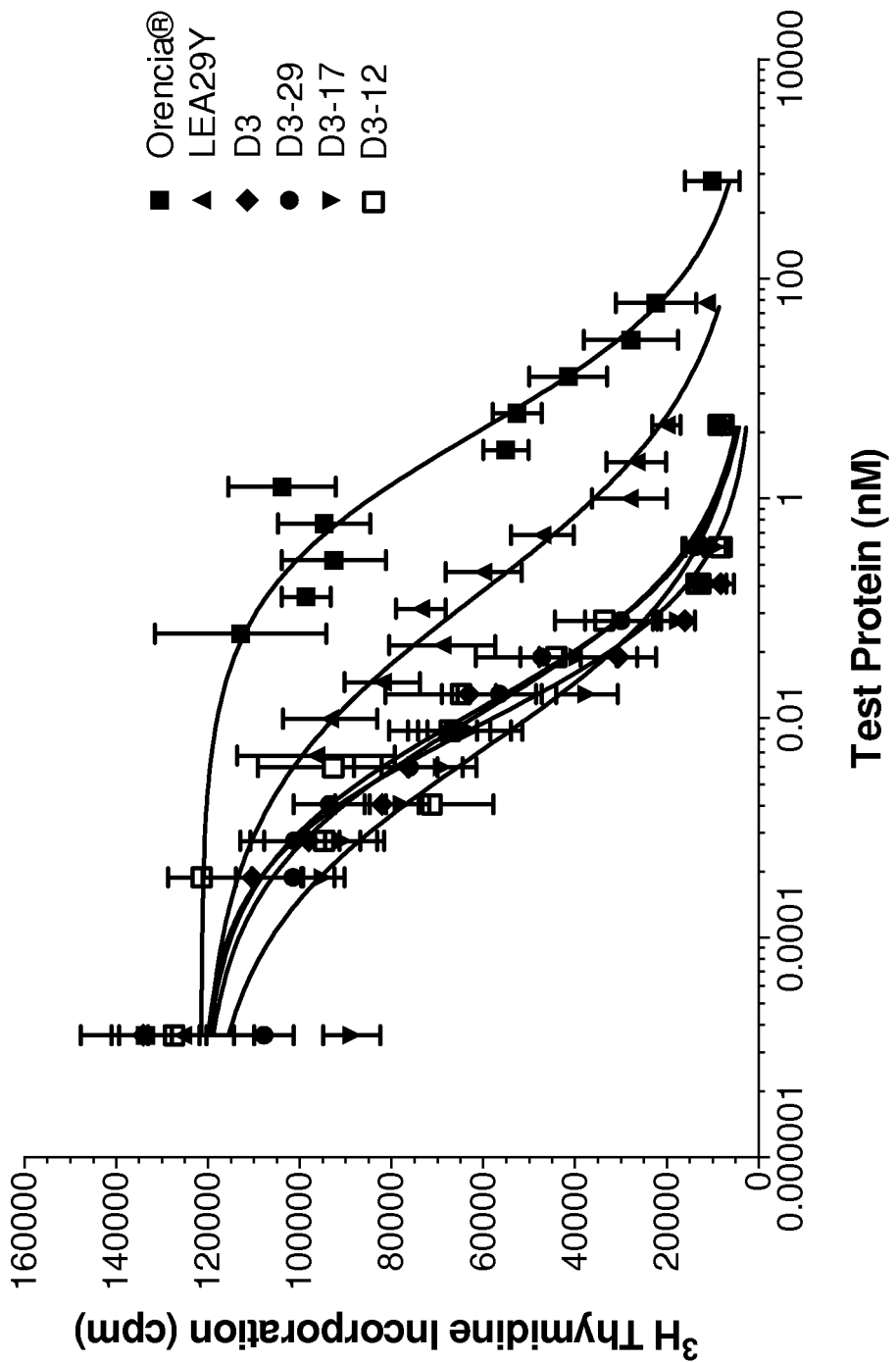

FIG. 8 is a graphical representation of PBMC proliferation inhibition assays (with PPD antigen stimulation) involving an exemplary set of mutant CTLA-4-Ig fusion proteins of the invention. Orencia® and LEA29Y-Ig were included as controls for comparison.

Figure 9:
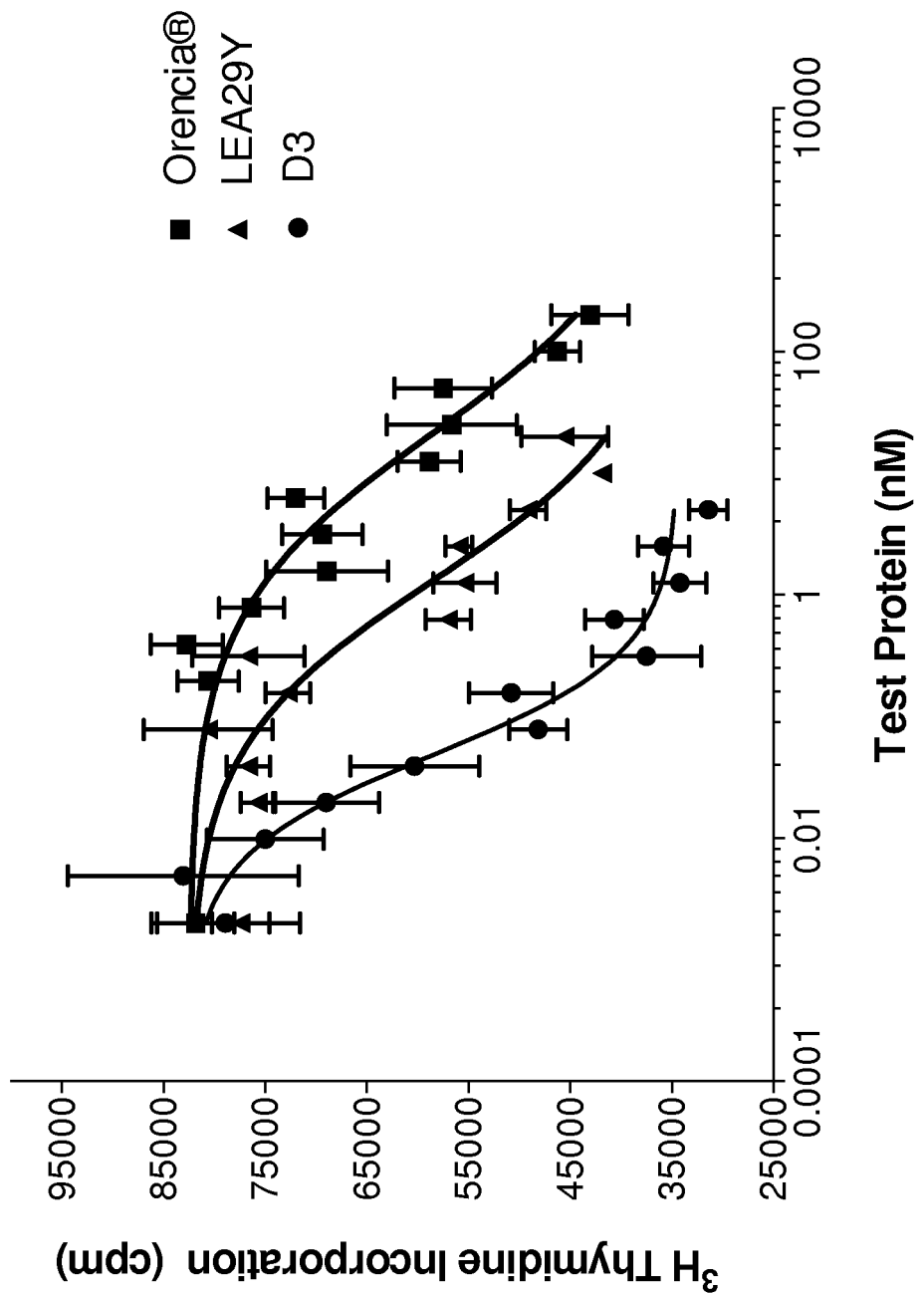

FIG. 9 is a graphical representation of one-way mixed lymphocyte reaction (MLR) proliferation inhibition assays involving an exemplary mutant CTLA-4-Ig fusion protein of the invention—D3-IgG2. The Orencia® and LEA29Y-Ig fusion proteins were included as controls for comparison.

Figure 10:
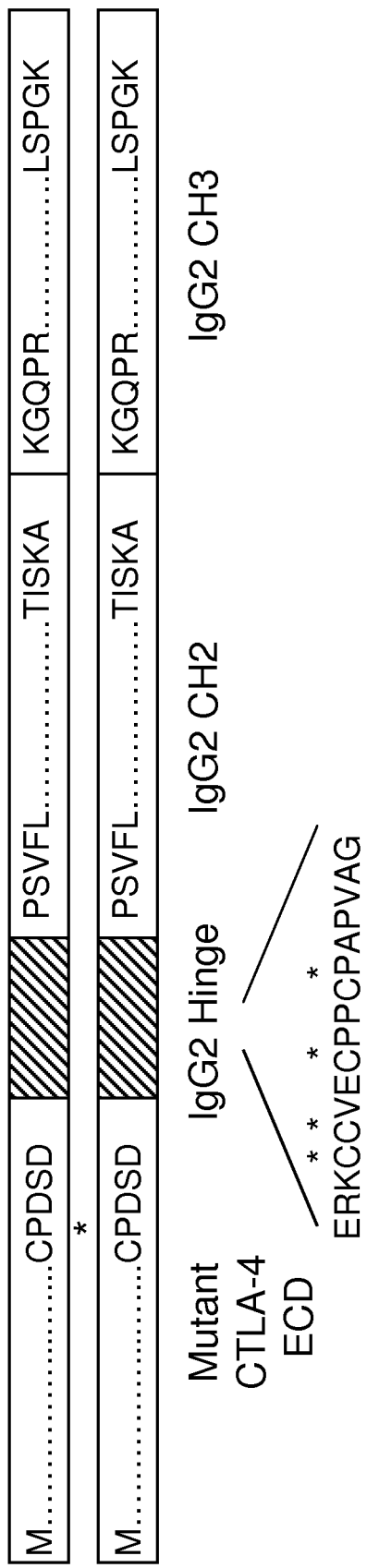

FIG. 10 is a schematic diagram showing the structure of an exemplary mutant CTLA-4-Ig fusion protein of the invention. Two identical monomeric mutant CTLA-4-Ig fusion proteins are shown schematically, each comprising a mature mutant CTLA-4 ECD fused at its C-terminus to the N-terminus of a human IgG2 Fc polypeptide. Each human IgG2 polypeptide includes an IgG2 hinge, CH2 domain, and CH3 domain. Exemplary amino acid residues present at the junctions between the ECD and Ig Fc polypeptides are also shown. The amino acid residues at the junctions between these components may differ depending upon the mutant CTLA-4 ECD polypeptide sequence and/or Ig polypeptide sequence. The dimeric fusion protein results from the formation of at least one disulfide bond between cysteine residues at analogous positions in the two monomers. The cysteine (C) residues potentially involved in forming disulfide bonds between the two monomers are marked with asterisks. The signal peptide of each monomeric fusion protein is typically cleaved during processing and thus the secreted (mature) fusion protein typically does not include the signal peptide sequence.

Figure 11:
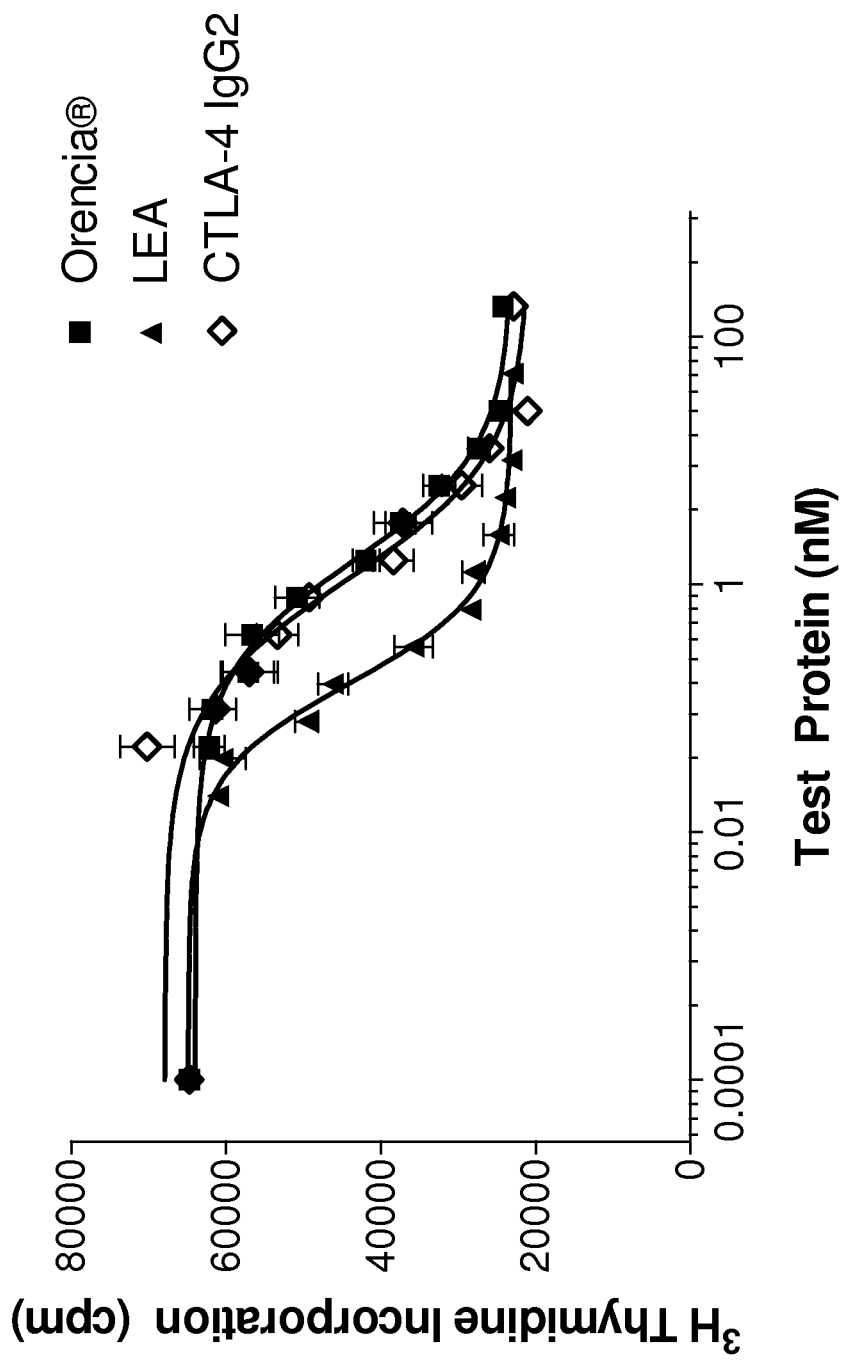

FIG. 11 is a graphical representation of CD4+ T cell proliferation assays (with anti-CD3 stimulation and hB7.2-dependent costimulation) involving hCTLA-4-IgG2, Orencia® and LEA29Y-Ig fusion proteins.

Figure 12E:
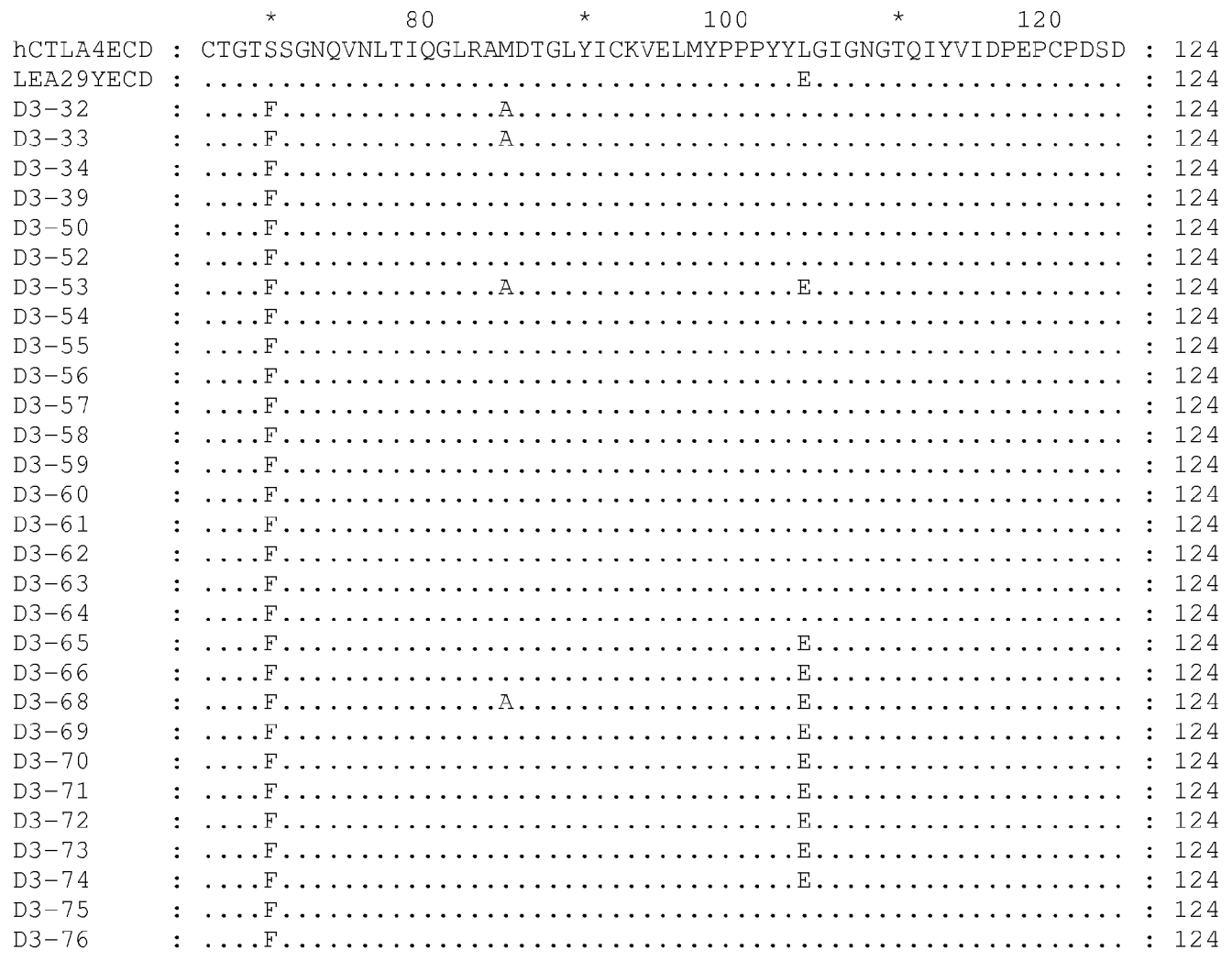

FIGS. 12A-12F present an alignment of the polypeptide sequence of the wild-type human CTLA-4 extracellular domain (designated in the figure as "hCTLA4ECD"), the polypeptide sequence of the LEA29Y polypeptide (designated in the figure as "LEA29YECD"), and the polypeptide sequences of exemplary mutant CTLA-4 ECD polypeptides of the invention. The clone names of these mutant CTLA-4 ECD polypeptides of the invention are indicated at the left. Amino acid residues that are identical to those in the wild-type human CTLA-4 ECD are indicated with a period (.).

FIG. 13 presents a BLOSUM62 matrix.

FIGS. 14A-14D show exemplary alignments and alignment scores determined by manual calculation for two amino acid sequences.

Figure 15A:
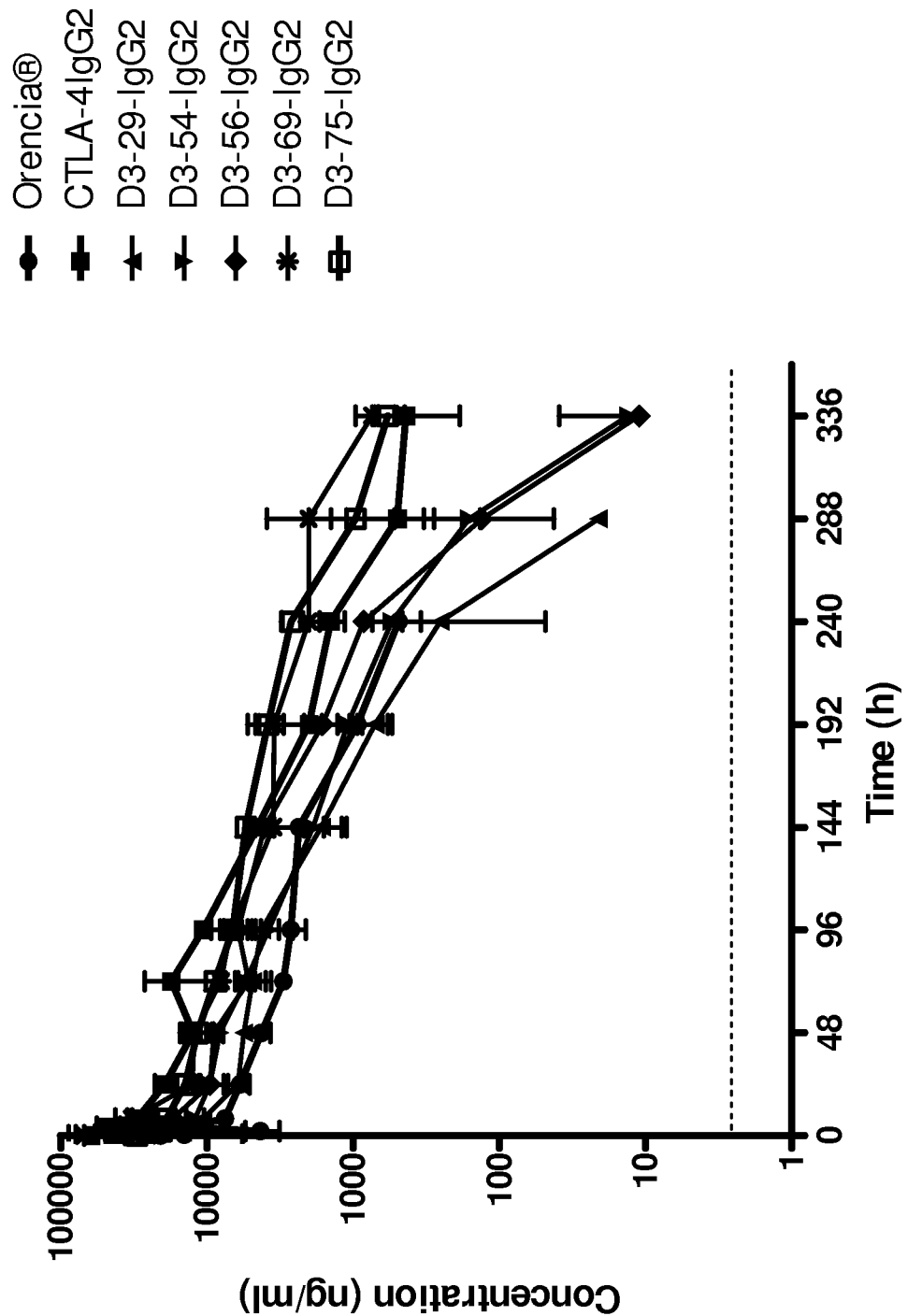
Figure 15B:
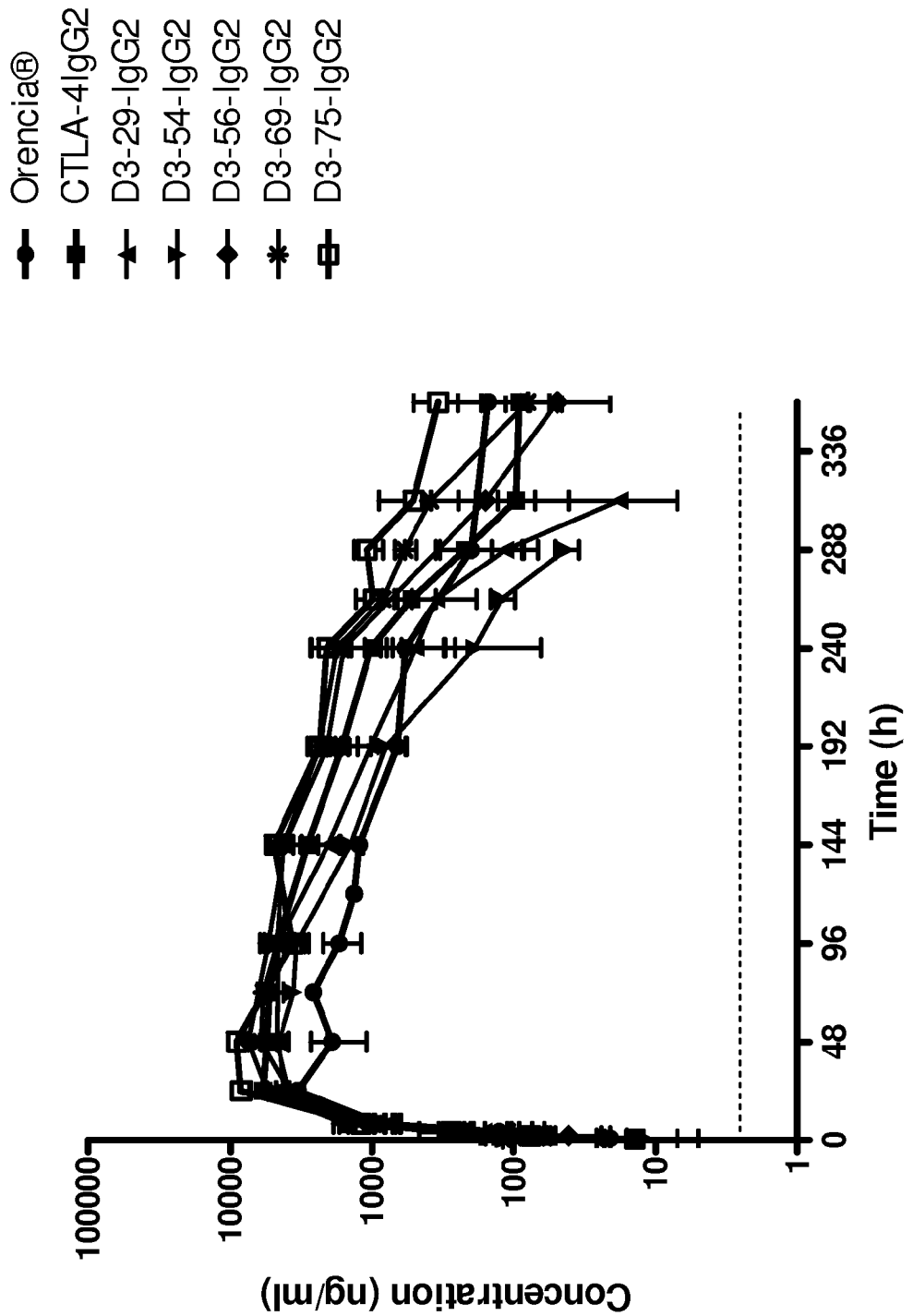

FIGS. 15A-15B show pharmacokinetic (PK) profiles for Orencia® fusion protein, human CTLA-4-IgG2, and representative mutant CTLA-4-IgG2 fusion proteins of the invention administered at 1 mg/kg as a single (A) intravenous (IV) bolus or (B) subcutaneous (SC) injection in rats.

DETAILED DESCRIPTION OF THE INVENTION

Definitions

It is also to be understood that the terminology used herein is for the purpose of describing particular embodiments only and is not intended to be limiting. Unless defined otherwise, all technical and scientific terms used herein have the same meaning as commonly understood by one of ordinary skill in the art to which the invention pertains.

The terms "nucleic acid" and "polynucleotide" are used interchangeably to refer to a polymer of nucleic acid residues (e.g., deoxyribonucleotides or ribonucleotides) in either single- or double-stranded form. Unless specifically limited, the terms encompass nucleic acids containing known analogues of natural nucleotides that have similar binding properties as the reference nucleic acid and are metabolized in a manner similar to naturally-occurring nucleotides. Unless otherwise indicated, a particular nucleic acid sequence also implicitly encompasses conservatively modified variants thereof (e.g., degenerate codon substitutions) and complementary nucleotide sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605 2608 (1985); and Cassol et al. (1992); Rossolini et al., Mol. Cell. Probes 8:91 98 (1994)). The term nucleic acid or polynucleotide is used interchangeably with cDNA or mRNA encoded by a gene.

The term "gene" broadly refers to any nucleic acid segment (e.g., DNA) associated with a biological function. A gene may include a coding sequence and/or regulatory sequence required for their expression. A gene may also include non-expressed DNA nucleic acid segment(s) that, e.g., form recognition sequences for other protein(s) (e.g., promoter, enhancer, or other regulatory region). A gene can be obtained from a variety of sources, including cloning from a source of interest or synthesizing from known or predicted sequence information, and may include one or more sequences designed to have desired parameters.

The terms "polypeptide," "peptide," and "protein" are used interchangeably to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers. As used herein, the terms encompass amino acid chains of any length, including full-length proteins (i.e., antigens), wherein the amino acid residues are linked by covalent peptide bonds.

Numbering of a given amino acid polymer or nucleic acid polymer "corresponds to" or is "relative to" the numbering of a selected amino acid polymer or nucleic acid polymer when the position of any given polymer component (e.g., amino acid, nucleotide, also referred to generically as a "residue") is designated by reference to the same or an equivalent position in the selected amino acid or nucleic acid polymer, rather than by the actual numerical position of the component in the given polymer. Thus, for example, the numbering of a given amino acid position in a given polypeptide sequence corresponds to the same or equivalent amino acid position in a selected polypeptide sequence used as a reference sequence.

An "equivalent position" (for example, an "equivalent amino acid position" or "equivalent nucleic acid position" or "equivalent residue position") is defined herein as a position (such as an amino acid position or nucleic acid position or residue position) of a test polypeptide (or test polynucleotide) sequence which aligns with a corresponding position of a reference polypeptide (or reference polynucleotide) sequence, when aligned (preferably optimally aligned) using an alignment algorithm as described herein. The equivalent amino acid position of the test polypeptide sequence need not have the same numerical position number as the corresponding position of the test polypeptide. Likewise, the equivalent nucleic acid position of the test polynucleotide sequence need not have the same numerical position number as the corresponding position of the test polynucleotide.

A "mutant" polypeptide comprises a polypeptide sequence that differs in one or more amino acid residues from the polypeptide sequence of a parent or reference polypeptide (such as, e.g., a wild-type (WT) polypeptide sequence). In one aspect, a mutant polypeptide comprises a polypeptide sequence which differs from the polypeptide sequence of a parent or reference polypeptide in from about 1%, 2%, 3%, 4%, 5%, 6%, 7%, 8%, 9%, 10%, 11%, 12%, 13%, 14%, 15%, 20%, 30% 40%, 50% or more of the total number of residues of the parent or reference polypeptide sequence. In another aspect, a mutant polypeptide comprises a polypeptide sequence that has at least about 50%, 60%, 70%, 80%, 85%, 86%, 87%, 88%, 89%, 90%, 91%, 92%, 93%, 94%, 95%, 96%, 97%, 98%, or 99% sequence identity to the polypeptide sequence of a parent or reference polypeptide. In another aspect, a mutant polypeptide comprises a polypeptide sequence that differs from the polypeptide sequence of a parent or reference polypeptide in from 1 to 100 or more amino acid residues (e.g., 1, 2, 3, 4, 5, 6, 7, 8, 9, 10, 11, 12, 13, 14, 15, 16, 17, 18, 19, 20 or more amino acid residues). A mutant polypeptide may comprise a polypeptide sequence that differs from the polypeptide sequence of a parent or reference polypeptide by, e.g., the deletion, addition, or substitution of one or more amino acid residues (e.g., 1, 2, 3, 4, 5, 6, 7, 8, 9, 10, 11, 12, 13, 14, 15, 16, 17, 18, 19, 20 or more amino acid residues) of the parent or reference polypeptide, or any combination of such deletion(s), addition(s), and/or substitution(s). The reference or parent polypeptide may itself be a mutant polypeptide.

A "mutant" nucleic acid comprises a nucleotide sequence that differs in one or more nucleic acid residues from the nucleotide sequence of a parent or reference nucleic acid (such as a WT nucleic acid). In one aspect, a mutant nucleic acid comprises a nucleotide sequence which differs from the nucleotide sequence of a parent or reference nucleic acid in from about 1%, 2%, 3%, 4%, 5%, 6%, 7%, 8%, 9%, 10%, 11%, 12%, 13%, 14%, 15%, 20%, 30% 40%, 50% or more of the total number of residues of the parent or reference nucleotide sequence. In another aspect, a mutant nucleic acid comprises a nucleotide sequence that has at least about 50%, 60%, 70%, 80%, 85%, 86%, 87%, 88%, 89%, 90%, 91%, 92%, 93%, 94%, 95%, 96%, 97%, 98%, or 99% sequence identity to the nucleotide sequence of a parent or reference nucleic acid. In another aspect, a mutant nucleic acid comprises a nucleotide sequence that differs from the nucleotide sequence of a parent or reference nucleic acid in from 1 to 100 or more nucleotide residues (e.g., 1, 2, 3, 4, 5, 6, 7, 8, 9, 10, 11, 12, 13, 14, 15, 16, 17, 18, 19, 20 or more nucleotide residues). A mutant nucleic acid may comprise a nucleotide sequence that differs from that of a parent or reference nucleic acid by, e.g., the deletion, addition, or substitution of one or more nucleotide residues (e.g., 1, 2, 3, 4, 5, 6, 7, 8, 9, 10, 11, 12, 13, 14, 15, 16, 17, 18, 19, 20 or more nucleotide residues) of the parent or reference nucleic acid, or any combination of such deletion(s), addition(s), and/or substitution(s). A mutation in a nucleic acid may also result from an alternative splicing or truncation of nucleotides or errors in processing or cleavage of nucleotides. The reference or parent nucleic acid may itself be a mutant nucleic acid.

"Naturally occurring" as applied to an object means the object is found in nature as distinct from being artificially produced by man. "Non-naturally occurring" as applied to an object means the object is not naturally occurring (i.e., that the object cannot be found in nature). For example, a non-naturally occurring polypeptide refers to a polypeptide that has been prepared by man, such as, for example, by being synthesized in vitro or prepared artificially.

A "subsequence" or "fragment" of a sequence of interest is any portion of the entire sequence, up to but not including the entire sequence of interest.

A nucleic acid, protein or other component is "isolated" when it is partially or completely separated from components with which it is normally associated (other proteins, nucleic acids, cells, synthetic reagents, etc.). On a molar basis, an isolated species is more abundant than other species in a composition. For example, an isolated species may comprise at least about 50%, 70%, 80%, 85%, 90%, 91%, 92%, 93%, 94%, 95%, 96%, 97%, 98%, 99%, or 100% (on a molar basis) of all macromolecular species present. Preferably, the species of interest is purified to essential homogeneity (i.e., contaminant species cannot be detected in the composition by conventional detection methods). Purity and homogeneity can be determined using a number of techniques well known in the art, such as agarose or polyacrylamide gel electrophoresis of a protein or nucleic acid sample, followed by visualization upon staining. If desired, a high-resolution technique, such as high performance liquid chromatography (HPLC) or a similar means can be utilized for purification of the material.

The term "purified" as applied to nucleic acids or polypeptides generally denotes a nucleic acid or polypeptide that is essentially free from other components as determined by analytical techniques well known in the art (e.g., a purified polypeptide or polynucleotide forms a discrete band in an electrophoretic gel, chromatographic eluate, and/or a media subjected to density gradient centrifugation). For example, a nucleic acid or polypeptide that gives rise to essentially one band in an electrophoretic gel is "purified." A purified nucleic acid or polypeptide is at least about 50% pure, usually at least about 75%, 80%, 85%, 90%, 91%, 92%, 93%, 94%, 95%, 96%, 97%, 98%, 99%, 99.5%, 99.6%, 99.7%, 99.8% or more pure (e.g., percent by weight on a molar basis).

In a related sense, the invention provides methods of enriching compositions for one or more molecules of the invention, such as one or more polypeptides or polynucleotides of the invention. A composition is enriched for a molecule when there is a substantial increase in the concentration of the molecule after application of a purification or enrichment technique. A substantially pure polypeptide or polynucleotide will typically comprise at least about 55%, 60%, 70%, 80%, 85%, 90%, 91%, 92%, 93%, 94%, 95%, 96%, 97%, 98, 99%, 99.5% or more by weight (on a molar basis) of all macromolecular species in a particular composition.

A nucleic acid or polypeptide is "recombinant" when it is artificial or engineered, or derived from an artificial or engineered protein or nucleic acid.

The term "recombinant" when used with reference to a cell typically indicates that the cell replicates a heterologous nucleic acid or expresses a polypeptide encoded by a heterologous nucleic acid. Recombinant cells can comprise genes that are not found within the native (non-recombinant) form of the cell. Recombinant cells also include those that comprise genes that are found in the native form of the cell, but are modified and re-introduced into the cell by artificial means. The term also encompasses cells that comprise a nucleic acid endogenous to the cell that has been modified without removing the nucleic acid from the cell; such modifications include those obtained by gene replacement, site-specific mutation, and related techniques known to those of ordinary skill in the art. Recombinant DNA technology includes techniques for the production of recombinant DNA in vitro and transfer of the recombinant DNA into cells where it may be expressed or propagated, thereby producing a recombinant polypeptide.

A "recombinant expression cassette" or simply an "expression cassette" is a nucleic acid construct, generated recombinantly or synthetically, with nucleic acid elements that are capable of effecting expression of a structural gene in hosts compatible with such sequences. Expression cassettes include at least promoters and optionally transcription termination signals. Typically, the recombinant expression cassette includes a nucleic acid to be transcribed (e.g., a nucleic acid encoding a desired polypeptide) and a promoter. Additional factors necessary or helpful in effecting expression may also be used as described herein. For example, an expression cassette can also include nucleotide sequences that encode a signal sequence that directs secretion of an expressed protein from the host cell. Transcription termination signals, enhancers, and other nucleic acid sequences that influence gene expression, can also be included in an expression cassette.

An "exogenous" nucleic acid," "exogenous DNA segment," "heterologous sequence," or "heterologous nucleic acid," as used herein, is one that originates from a source foreign to the particular host cell, or, if from the same source, is modified from its original form. Thus, a heterologous gene in a host cell includes a gene that is endogenous to the particular host cell, but has been modified. Modification of a heterologous sequence in the applications described herein typically occurs through the use of directed molecular evolution methods. Thus, the terms refer to a DNA segment which is foreign or heterologous to the cell, or homologous to the cell but in a position within the host cell nucleic acid in which the element is not ordinarily found. Exogenous nucleic acids or exogenous DNA are expressed to yield exogenous polypeptides.

A "vector" may be any agent that is able to deliver or maintain a nucleic acid in a host cell and includes, for example, but is not limited to, plasmids (e.g., DNA plasmids), naked nucleic acids, viral vectors, viruses, nucleic acids complexed with one or more polypeptide or other molecules, as well as nucleic acids immobilized onto solid phase particles. Vectors are described in detail below. A vector can be useful as an agent for delivering or maintaining an exogenous gene and/or protein in a host cell. A vector may be capable of transducing, transfecting, or transforming a cell, thereby causing the cell to replicate or express nucleic acids and/or proteins other than those native to the cell or in a manner not native to the cell. A vector may include materials to aid in achieving entry of a nucleic acid into the cell, such as a viral particle, liposome, protein coating, or the like. Any method of transferring a nucleic acid into the cell may be used; unless otherwise indicated, the term vector does not imply any particular method of delivering a nucleic acid into a cell or imply that any particular cell type is the subject of transduction. The present invention is not limited to any specific vector for delivery or maintenance of any nucleic acid of the invention, including, e.g., a nucleic acid encoding a mutant CTLA-4 polypeptide of the invention or a fragment thereof (e.g., mutant CTLA-4 ECD) that binds CD80 and/or CD86 or a fragment thereof (e.g., a CD80 ECD or CD86 ECD).

The term "expression vector" typically refers to a nucleic acid construct or sequence, generated recombinantly or synthetically, with a series of specific nucleic acid elements that permit transcription of a particular nucleic acid in a host cell. The expression vector typically includes a nucleic acid to be transcribed operably linked to a promoter. The term "expression" includes any step involved in the production of the polypeptide including, but not limited to, transcription, post-transcriptional modification, translation, post-translational modification, and/or secretion.

A "signal peptide" is a peptide (or amino acid) sequence that typically precedes a polypeptide of interest and is translated in conjunction with the polypeptide and directs or facilitates the polypeptide to the secretory system. A signal peptide is typically covalently attached or fused to the amino terminus of the polypeptide of interest and facilitates secretion of the polypeptide of interest from a host cell. The signal peptide is typically cleaved from the polypeptide of interest following translation.

The term "encoding" refers to the ability of a nucleotide sequence to code for one or more amino acids. The term does not require a start or stop codon. An amino acid sequence can be encoded in any one of six different reading frames provided by a polynucleotide sequence and its complement.

The term "control sequence" is defined herein to include all components, which are necessary or advantageous for the expression of a polypeptide of the present invention. Each control sequence may be native or foreign to the nucleotide sequence encoding the polypeptide. Such control sequences include, but are not limited to, a leader, polyadenylation sequence, propeptide sequence, promoter, signal peptide sequence, and transcription terminator. At a minimum, a control sequence includes a promoter, and transcriptional and translational stop signals. The control sequences may be provided with linkers for the purpose of introducing specific restriction sites facilitating ligation of the control sequences with the coding region of the nucleotide sequence encoding a polypeptide.

The term "coding sequence" refers to a nucleotide sequence that directly specifies the amino acid sequence of its protein product. The boundaries of the coding sequence are generally determined by an open reading frame (ORF), which may begin with the ATG start codon.

A nucleic acid is "operably linked" with another nucleic acid sequence when it is placed into a functional relationship with another nucleic acid sequence. For instance, a promoter or enhancer is operably linked to a coding sequence if it directs transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

A "host cell" is any cell that is susceptible to transformation with a nucleic acid.

"Substantially the entire length of a polynucleotide sequence" or "substantially the entire length of a polypeptide sequence" refers to at least about 50%, 60%, 70%, 75%, 80%, 85%, 86%, 87%, 88%, 89%, 90%, 91%, 92%, 93%, 94%, 95%, 96%, 97%, 98%, 99%, 99.5% or more of the length of a polynucleotide sequence or polypeptide sequence, respectively.

An "antigen" refers to a substance that reacts with the product(s) of an immune response stimulated by a specific immunogen. See, e.g., JULIUS CRUSE ET AL., ATLAS OF IMMUNOLOGY 60 (1999); RICHARD COICO ET AL., IMMUNOLOGY: A SHORT COURSE 27-30 (5$^{th}$ ed. 2003). An immune response may comprise a humoral response and/or a cell-mediated immune response (e.g., cytotoxic T lymphocytes (CTLs)). Products of an immune response may include antibodies and/or CTLs. Antigens are typically macromolecules (e.g., polypeptides, nucleic acids, complex carbohydrates, phospholipids, polysaccharides) that are foreign to the host; that portion of the antigen known as the antigenic determinant reacts with (e.g., binds to) the product(s) of the immune response, such as an antibody or a specific T cell receptor on a T lymphocyte. An antigen may, but not necessarily, induce an immune response as well as react with the product(s) of the immune response. "Antigenicity" refers the state or property of being antigenic—i.e., having the properties of an antigen. Specificity of an antigen may be shown in the relation of an antigen to its antibody or vice versa; an antigen typically reacts in a highly specific fashion with its corresponding antibody and not with the same degree of specificity with other antibodies evoked by the immunogen. An "antigenic amount" is an amount of an antigen that detectably reacts with the product(s) of an immune response stimulated by a specific immunogen.

An "immunogen" is a substance that is capable of inducing an immune response rather than immunological tolerance. See, e.g., JULIUS CRUSE ET AL., supra at 60-61; RICHARD COICO, supra at 27-30. Immunogens also reacts with (e.g., bind) the product(s) of the induced immune response that has or have been specifically induced against them. Thus, all immunogens are antigens. "Immunogenicity" refers the state or property of being immunogenic—i.e., having the properties of an immunogen. An "immunogenic amount" is an amount of an immunogen that is effective to induce a detectable an immune response. An immunogen may elicit a strong immune response in a subject, such as at least partial or complete protective immunity to at least one pathogen.

An "immunomodulator" or "immunomodulatory" molecule, such as an immunomodulatory polypeptide or nucleic acid, modulates an immune response. By "modulation" or "modulating" an immune response is intended that the immune response is altered. For example, "modulation" of or "modulating" an immune response in a subject generally means that an immune response is stimulated, induced, inhibited, decreased, suppressed, increased, enhanced, or otherwise altered in the subject. Such modulation of an immune response can be assessed by means known to those skilled in the art, including those described below. An "immunosuppressor" or "immunosuppressant" is a molecule, such as a polypeptide or nucleic acid, which suppresses an immune response.

As used herein, an "antibody" (abbreviated "Ab") refers to an immunoglobulin protein (abbreviated "Ig"), whether natural or wholly or partially synthetically produced. The term includes all derivatives thereof that maintain specific binding ability to an antigen. The term also covers any protein having a binding domain that is homologous or largely homologous to an immunoglobulin binding domain. Such proteins may be derived from natural sources, or partly or wholly synthetically produced. An antibody may be monoclonal or polyclonal. An antibody may be a member of any immunoglobulin class, including any of the five human classes: IgA (which includes subclasses IgA1 and IgA2), IgD, IgE, IgG (which includes subclasses IgG1, IgG2, IgG3, and IgG4), and IgM. Antibodies comprise paired heavy and light polypeptide chains, and each such chain is composed of individual immunoglobulin domains. Each chain includes a constant (C) region and a variable (V) region. A typical antibody structural unit comprises a tetramer. Each tetramer is composed of two identical pairs of polypeptide chains, each pair having one "light" (about 25 kDa) and one "heavy" chain (about 50-70 kDa). Heavy chains exist in five major types ($\gamma$, $\mu$, $\delta$, $\alpha$, and $\epsilon$) depending on the antibody class and contain about 450-600 amino acid residues. Light chains are of two major types ($\lambda$ and $\kappa$) and contain about 230 amino acid residues. As an example, an IgG antibody is a tetrameric protein comprising two heavy chains and two light chains. Each IgG heavy chain contains four immunoglobulin domains linked in the following order from the N-terminus to the C-terminus: $V_H$-$C_H$1-$C_H$2-$C_H$3 (also sometimes abbreviated as VH-CH1-CH2-CH3). These abbreviations refer to the heavy chain variable domain, heavy chain constant domain 1, heavy chain constant domain 2, and heavy chain constant domain 3), respectively. A heavy chain may also be referred to by antibody class, such as, e.g., C$\gamma$1, which represents the first constant domain of the gamma ($\gamma$) heavy chain of IgG antibody. Each IgG light chain comprises two immunoglobulin domains linked in the following order from N- to C-terminus: $V_H$-$C_L$, wherein $V_H$ and $C_L$ refer to the light chain variable domain and light chain constant domain, respectively.

The variable region of an antibody, which typically comprises about 100 to 110 or more amino acids at the N-terminus of each polypeptide chain, includes the antigen binding determinants and thus is primarily responsible for antigen recognition and specificity. The greatest degree of amino acid sequence variability between antibodies is found in the variable region. Most sequence variability occurs in the complementarity determining regions (CDRs) located in the variable region. There are a total of six CDRs, three CDRs in each heavy chain and three CDRs in each light chain, which together form the antigen-binding site. The heavy chain CDRs are designated as $V_H$CDR1, $V_H$CDR2, and $V_H$CDR3 while the light chain CDRs are designated as $V_L$ CDR1, $V_L$ CDR2, and $V_L$ CDR3. The region located outside the CDRs is termed the framework (FR) region. Framework regions of different antibodies may vary in amino acid residues, but the degree of amino acid variability is not nearly as great as that which exists between the variable regions of different antibodies. In many instances, the framework regions provide a stable or constant scaffold for the amino acid diversity presented by the CDRs.

The term "antibody fragment" refers to any derivative of an antibody that is less than full-length. Examples of antibody fragments include, but are not limited to, e.g., the antigen binding fragment (Fab) containing $V_H$-$C_H$1 and $V_H$-$C_L$, the variable fragment (Fv) containing $V_H$ and $V_L$, the single chain variable fragment (scFv) containing $V_H$ and $V_L$ linked together in one chain, as well as other V region fragments, such as Fab', F(ab)$_2$, F(ab')$_2$, dsFv diabody, Fc, and Fd polypeptide fragments. See Scott, T. A. and Mercer, E. I., CONCISE ENCYCLOPEDIA: BIOCHEMISTRY AND MOLECULAR BIOLOGY (de Gruyter, 3d ed. 1997), and Watson, J. D. et al., RECOMBINANT DNA (2d ed. 1992) (hereinafter "Watson").

An antibody fragment may be produced by any means known in the art. For instance, the antibody fragment may be enzymatically or chemically produced by fragmentation of an intact antibody or it may be recombinantly produced from a gene encoding the partial antibody sequence. For example, fragments of antibodies can be produced by digestion with a peptidase. For example, pepsin digests an antibody below the disulfide linkages in the hinge region to produce F(ab')$_2$, a dimer of a Fab fragment which itself is a light chain joined to $V_H$-$C_H$1 by a disulfide bond. The F(ab')$_2$ may be reduced under mild conditions to break the disulfide linkage in the hinge region thereby converting the (Fab')$_2$ dimer into an Fab' monomer. The Fab' monomer is essentially a Fab fragment with part of the hinge region. See FUNDAMENTAL IMMUNOLOGY, W. E. Paul, ed., Raven Press, N.Y. (1993) for a more detailed description of antibodies and antibody fragments. While various antibody fragments are defined in terms of the digestion of an intact antibody, one of skill will appreciate that such Fab' fragments may be synthesized de novo either chemically or by utilizing recombinant DNA methodology. Thus, the term also includes antibody fragments either produced by the modification of whole antibodies or synthesized de novo using recombinant DNA methodologies.

Alternatively, the antibody fragment may be wholly or partially synthetically produced. The antibody fragment may optionally be a single chain antibody fragment. Alternatively, the fragment may comprise multiple chains that are linked together, for instance, by disulfide linkages. The fragment may also optionally be a multimolecular complex. A functional antibody fragment will typically comprise at least about 50 amino acids and more typically will comprise at least about 200 amino acids.

An Fc region or domain of an immunoglobulin or antibody molecule (also termed an Ig Fc polypeptide or Fc polypeptide) corresponds largely to the constant region of the immunoglobulin heavy chain, and is responsible for various functions, including the antibody's effector function(s). For example, the Ig Fc region of IgG molecule comprises the immunoglobulin domains CH2 and CH3 and the N-terminal hinge region leading into CH2. The hinge region is a portion of the heavy chain between Fc and CH1 containing the inter-heavy chain disulfide binds and gives flexibility to the antibody molecule. The constant domains of the Fc region interact with cells of the immune system. Fc receptors are proteins that bind the Fc region of antibodies. One significant family of Fc receptors for the IgG antibody class includes the Fc gamma receptors (Fc$\gamma$R). The binding of antibodies to Fc receptors on cells mediates a number of antibody functions. Different IgG subclasses exhibit different affinities for Fc gamma receptors. In general, IgG1 and IgG3 bind to the receptors with a greater affinity than IgG2 and IgG4. Fc receptors are expressed on a variety of cells, including, e.g., B cells, monocytes, dendritic cells, neutrophils, and certain lymphocytes. Binding of an Ig Fc to its receptor brings these effector cells to sites of the bound antigen, resulting ultimately in signaling and immune responses, including B cell activation, inflammatory responses, cytotoxic responses, and phagocytic responses.

An Ig Fc fusion is a molecule comprising one or more polypeptides (or one or more small molecules) operably linked to an Fc region of an immunoglobulin or antibody. See, e.g., Chamow et al., 1996, Trends Biotechnol. 14:52-60. Accordingly, an Ig Fc fusion protein is a molecule comprising one or more polypeptides operably linked to an Ig Fc region. An Ig Fc fusion protein may comprise, for example, the Fc region of an antibody (which facilitates effector functions and pharmacokinetics) and the binding region or binding domain of a receptor protein or ligand protein or other protein or fragment thereof. The binding region or binding domain mediates recognition of the target receptor or ligand (comparable to that of antibody variable region of an antibody for an antigen). An Ig Fc region may be linked indirectly or directly to one or more polypeptides or small molecules (fusion partners). Various linkers known in the art and as described in greater detail below can be used to link an Ig Fc to a fusion partner to generate an Ig Fc fusion. An Ig Fc fusion protein typically comprises an Ig Fc region covalently linked directly or indirectly to at least one polypeptide, which polypeptide typically binds a target ligand or receptor.

Monoclonal or polyclonal antibodies can be prepared any technique known in the art can be used (see, e.g., Kohler & Milstein, Nature 256:495 497 (1975); Kozbor et al., Immunology Today 4: 72 (1983); Cole et al., pp. 77 96 in Monoclonal Antibodies and Cancer Therapy (1985)). Techniques for the production of single chain antibodies (U.S. Pat. No. 4,946,778) can be adapted to produce antibodies to polypeptides of the invention. In addition, transgenic mice or other organisms, including mammals, may be used to express humanized antibodies. Phage display technology can be used to identify antibodies and heteromeric Fab fragments that specifically bind to selected antigens (see, e.g., McCafferty et al., Nature 348:552 554 (1990); Marks et al., Biotechnology 10:779 783 (1992)).

The term "epitope" refers to an antigenic determinant capable of specific binding to a part of an antibody. Epitopes usually consist of chemically active surface groupings of molecules such as amino acids or sugar side chains and usually have specific 3-dimensional structural characteristics, as well as specific charge characteristics. Conformational and nonconformational epitopes are distinguished in that the binding to the former but not the latter is lost in the presence of denaturing solvents.

A "specific binding affinity" between two molecules, e.g., a ligand and a receptor, means a preferential binding of one molecule for another. The binding of molecules is typically considered specific if the equilibrium binding association constant (e.g., $K_A$) is about $1 \times 10^2 \, M^{-1}$ to about $1 \times 10^{13} \, M^{-1}$ or greater, including about $10^4$ to $10^{13} \, M^{-1}$, about $10^6$ to $10^{12} \, M^{-1}$, about $10^8 \, M^{-1}$ to $10^{11} \, M^{-1}$ or about $10^8$ to $10^{10} \, M^{-1}$. Values of $K_A$ for the binding interaction between an antigen and an antibody typically range from about $10^5 \, M^{-1}$ to about $10^{12} \, M^{-1}$, usually about $10^7 \, M^{-1}$ to about $10^{11} \, M^{-1}$, and often about $10^8 \, M^{-1}$ to about $10^{10} \, M^{-1}$. $K_A$ ($M^{-1}$) is determined by calculating $k_a/k_d$, where $k_a$ is the association rate constant and $k_d$ is the disassociation rate constant. The units of $k_a$ and $k_d$ are $M^{-1} \, s^{-1}$ and $s^{-1}$, respectively. The equilibrium dissociation constant, $K_D$, is the reciprocal of $K_A$. $K_D = k_d/k_a$. For the reaction A+B<=>AB (representing a single ligand binding to a single protein of interest (e.g., receptor)), $K_D$ is equal to ([A]·[B])/[AB]. Non-limiting examples of well-known techniques for measuring binding affinities and/or avidities of molecules include, e.g., Biacore™ technology (GE Healthcare) as discussed elsewhere herein, isothermal titration microcalorimetry (MicroCal LLC, Northampton, Mass. USA), ELISA, and fluorescence activated cell sorting (FACS) methods. For example, FACS or other sorting methods may be used to select for populations of molecules (such as for example, cell surface-displayed ligands) that specifically bind to the associated binding pair member (such as a receptor, e.g., a soluble receptor). Ligand-receptor complexes may be detected and sorted e.g., by fluorescence (e.g., by reacting the complex with a fluorescent antibody that recognizes the complex). Molecules of interest that bind an associated binding pair member (e.g., receptor) are pooled and re-sorted in the presence of lower concentrations of receptor. By performing multiple rounds sorting in the presence of decreasing concentrations of receptor (an exemplary concentration range being on the order of $10^{-6}$ M down to $10^{-13}$ M, i.e., 1 micromolar (μM) down to 1 nanomolar (nM), or less (e.g., $10^{-11}$ M or $10^{-12}$M), depending on the nature of the ligand-receptor interaction), populations of the molecule of interest exhibiting specific binding affinity for the receptor may be isolated.

The phrase "specifically (or selectively) binds" to an antibody or "specifically (or selectively) immunoreactive with," when referring to a protein, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Usually, a specific or selective reaction will be at least twice background signal or noise and more typically more than 10 to 100 times background.

The term "cytokine" includes, e.g., but is not limited to, interleukins, interferons (IFN), chemokines, hematopoietic growth factors, tumor necrosis factors (TNF), and transforming growth factors. In general, these are small molecular weight proteins that regulate maturation, activation, proliferation, and differentiation of cells of the immune system.

The term "screening" describes, in general, a process that identifies optimal molecules of the present invention, such as, e.g., including polypeptides of the invention, and related fusion proteins comprising the same, and nucleic acids encoding all such molecules. Several properties of the respective molecules can be used in selection and screening, for example, an ability of a respective molecule to induce or alter a desired immune response in a test system or in an in vitro, ex vivo, or in vivo application. "Selection" is a form of screening in which identification and physical separation are achieved simultaneously by expression of a selection marker, which, in some genetic circumstances, allows cells expressing the marker to survive while other cells die (or vice versa). Screening markers include, for example, luciferase, beta-galactosidase and green fluorescent protein, reaction substrates, and the like. Selection markers include drug and toxin resistance genes, and the like. Another mode of selection involves physical sorting based on a detectable event, such as binding of a ligand to a receptor, reaction of a substrate with an enzyme, or any other physical process which can generate a detectable signal either directly (e.g., by utilizing a chromogenic substrate or ligand) or indirectly (e.g., by reacting with a chromogenic secondary antibody). Selection by physical sorting can be accomplished by a variety of methods, including, but not limited to, e.g., FACS in whole cell or microdroplet formats.

Because of limitations in studying primary immune responses in vitro, in vivo studies are particularly useful screening methods. In some such studies, a polynucleotide or polypeptide of the invention is first introduced to a test subject (e.g., a mammal, such as an animal), and an induced immune response is subsequently studied by analyzing the type of immune response in the immunized animal (e.g., antibody production in the immunized animal's serum, proliferation of T cells), or by studying the quality or strength of the induced immune response in the immunized animal (e.g., induced antibody titer level).

The term "subject" as used herein includes, but is not limited to, an organism or animal, including mammals and non-mammals. A mammal includes, e.g., but is not limited to, a human, non-human primate (e.g., baboon, orangutan, monkey, gorilla), mouse, dog, pig, cow, goat, cat, rabbit, rat, guinea pig, hamster, horse, sheep, or other non-human mammal. A non-mammal includes, e.g., but is not limited to, a non-mammalian invertebrate and non-mammalian vertebrate, such as a bird (e.g., a chicken or duck) or a fish.

The term "pharmaceutical composition" refers to a composition suitable for pharmaceutical use in a subject, including an animal or human. A pharmaceutical composition typically comprises an effective amount of an active agent and a carrier, excipient, or diluent. The carrier, excipient, or diluent is typically a pharmaceutically acceptable carrier, excipient or diluent, respectively.

The term "effective amount" refers to a dosage (or dose) or amount of a substance sufficient to produce a desired result. The desired result may comprise an objective or subjective improvement in the recipient of the dosage or amount. For example, the desired result may comprise a measurable, detectable or testable induction, promotion, enhancement or modulation of an immune response in a subject to whom a dosage or amount of a particular antigen or immunogen (or composition thereof) has been administered. A dosage (or dose) or amount of an immunogen sufficient to produce such result can be described as an "immunogenic" dosage (or dose) or amount.

A "prophylactic treatment" is a treatment administered to a subject who does not display signs or symptoms of, or displays only early signs or symptoms of, a disease, pathology, or disorder, such that treatment is administered for the purpose of preventing or decreasing the risk of developing the disease, pathology, or disorder. A prophylactic treatment functions as a preventative treatment against a disease, pathology, or disorder, or as a treatment that inhibits or reduces further development or enhancement of a disease, pathology or disorder. A "prophylactic activity" is an activity of an agent that, when administered to a subject who does not display signs or symptoms of, or who displays only early signs or symptoms of, a pathology, disease, or disorder, prevents or decreases the risk of the subject developing the pathology, disease, or disorder. A "prophylactically useful" agent (e.g., nucleic acid or polypeptide) refers to an agent that is useful in preventing development of a disease, pathology, or disorder, or useful in inhibiting or reducing further development or enhancement of a disease, pathology or disorder.

A "therapeutic treatment" is a treatment administered to a subject who displays symptoms or signs of pathology, disease, or disorder, in which treatment is administered to the subject for the purpose of diminishing or eliminating those signs or symptoms. A "therapeutic activity" is an activity of an agent that eliminates or diminishes signs or symptoms of pathology, disease or disorder when administered to a subject suffering from such signs or symptoms. A "therapeutically useful" agent means the agent is useful in decreasing, treating, or eliminating signs or symptoms of a disease, pathology, or disorder.

Generally, the nomenclature used herein and many of the laboratory procedures in cell culture, molecular genetics, molecular biology, nucleic acid chemistry, and protein chemistry described below are well known and commonly employed by those of ordinary skill in the art. Standard techniques, such as described in Sambrook et al., Molecular Cloning—A Laboratory Manual (2nd Ed.), Vols. 1-3, Cold Spring Harbor Laboratory, Cold Spring Harbor, N.Y., 1989 (hereinafter "Sambrook") and CURRENT PROTOCOLS IN MOLECULAR BIOLOGY, F. M. Ausubel et al., eds., Current Protocols, a joint venture between Greene Publishing Associates, Inc. and John Wiley & Sons, Inc. (1994, supplemented through 1999) (hereinafter "Ausubel"), are used for recombinant nucleic acid methods, nucleic acid synthesis, cell culture methods, and transgene incorporation, e.g., electroporation, injection, gene gun, impressing through the skin, and lipofection. Generally, oligonucleotide synthesis and purification steps are performed according to specifications. The techniques and procedures are generally performed according to conventional methods in the art and various general references that are provided throughout this document. The procedures therein are believed to be well known to those of ordinary skill in the art and are provided for the convenience of the reader.

Various additional terms are defined or otherwise characterized herein.

Molecules and Methods of the Invention

The present invention provides molecules and methods for treating diseases, disorders, and conditions of the immune system, including, e.g., those in which modulation of the immune system (e.g., T-cell dependent immune responses) is desirable. Molecules of the invention (e.g., polypeptides of the invention, conjugates of the invention, soluble fusion proteins of the invention, nucleic acids encoding such polypeptides or fusion proteins) are useful for the treatment of immune system diseases, disorders, and conditions in which immunosuppression is desirable, including, e.g., but not limited to, the treatment of autoimmune diseases, disorders, and conditions, immunoproliferative diseases, graft-related disorders, and treatment methods involving tissue, cell, organ, or graft transplantation from a donor to a recipient where suppression of an immune response in the recipient against the donor tissue, cell, organ, or graft is desirable.

In one aspect, the invention provides novel mutant CTLA-4 molecules having improved properties compared to a CTLA-4 molecule, such as the wild-type human CTLA-4 polypeptide ("hCTLA-4") or a fragment thereof that binds CD80 and/or CD86, such as the extracellular domain of human CTLA-4 ("hCTLA-4 ECD"). As discussed in greater detail below, a variety of mutagenesis and screening strategies were used to make and identify novel mutant CTLA-4 molecules that bind CD80 and/or CD86. In particular, such strategies were used to make and identify CTLA-4 mutant molecules having improved binding avidities for CD80 (B7-1) and/or CD86 (B7-2), as compared to human CTLA-4 ("hCTLA-4"), and/or having improved binding affinities for CD80 and/or CD86, as compared to the hCTLA-4 ECD. Mutant CTLA-4 molecules of the invention that bind endogenous CD80 and/or CD86 ligands expressed on antigen-presenting cells effectively inhibit or block the interaction of these ligands with the endogenous CD28 receptor, which is expressed on the surface of T cells. As a result, the costimulatory signal critical for T cell activation provided by the interaction of the T cell surface receptor CD28 with the B7 molecules (i.e., CD80 and CD86) is inhibited or blocked. Such T cells are not optimally activated and have reduced capacities for proliferation.

In instances where signaling between a CD80 or CD86 ligand and a CD28 receptor is blocked, T cells are not optimally stimulated to become active and thus are not optimally induced to proliferate. Similarly, in instances where the signaling between a CD80 or CD86 ligand and a CD28 receptor is inhibited, activation and proliferation of T cells is inhibited. In one aspect, the invention provides mutant CTLA-4 molecules that function as antagonists to CTLA-4 signaling. In another aspect, the invention provides mutant CTLA-4 molecules that function as antagonists to CD28 signaling, thereby suppressing or blocking T cell-dependent immune responses; such molecules function as immunosuppressive agents. In yet another aspect, the invention provides mutant CTLA-4 molecules that bind both CD80 and CD86, but which have higher binding avidity for CD86 than for CD80, and therefore inhibit CD86-dependent costimulation to a greater extent than CD80-dependent costimulation. All such mutant CTLA-4 molecules of the invention are expected to be useful for the treatment of diseases, disorders, or conditions in which immunosuppression is desirable or would be of benefit.

A human CTLA-4-Ig fusion protein and a specific mutant CTLA-4-Ig fusion protein—both developed by Bristol-Myers Squibb Co. (Princeton, N.J.)—have been shown to be effective in treating certain immune-related diseases or conditions. The Orencia® fusion protein (also known as Abatacept ("ABA")) (Bristol-Myers Squibb Co. (Princeton, N.J.)) is a soluble recombinant dimeric fusion protein consisting of two identical monomeric immunoglobulin (Ig) fusion proteins covalently linked together by a disulfide bond formed between a cysteine residue present in each monomeric fusion protein. ORENCIA is a registered trademark of Bristol-Myers Squibb Company. Each monomeric Ig fusion protein of the Orencia® dimer consists of the extracellular domain of human CTLA-4 (SEQ ID NO:159) fused at its C-terminus to the N-terminus of a specific mutant IgG1 Fc polypeptide (SEQ ID NO:186). The complete polypeptide sequence of each such monomeric fusion protein is shown in SEQ ID NO:164. The Orencia® dimer is produced in a mammalian expression system and has an apparent molecule weight of 92 kDa. It is believed that the two monomeric Ig fusion proteins of the Orencia® dimer are covalently linked together by a single disulfide bond formed between the cysteine residue at position 120 of each hCTLA-4-mutant IgG1 monomer and that no disulfide bonds are formed between the two mutant IgG1 Fc polypeptides.

The Orencia® dimer is a selective costimulation modulator that inhibits T cell activation by binding to CD80 and CD86 and thus blocking interaction with CD28. The Orencia® dimer is currently approved for the treatment of human adults suffering from moderate to severe rheumatoid arthritis (RA). Additional information about the Orencia® dimer and its clinical indications and effectiveness is provided on the worldwide web at orencia.com and bms.com.

As noted above, each fusion protein monomer of the Orencia® dimer contains a human CTLA-4 extracellular domain. Human CTLA-4 is a membrane protein that is transiently expressed on T cells. The full-length protein sequence of WT full-length hCTLA-4 is shown in SEQ ID NO:160, and a nucleic acid sequence encoding WT full-length hCTLA-4 is shown in SEQ ID NO:194. Human CTLA-4 includes a signal peptide (SP), extracellular domain (ECD), transmembrane domain (TD), and cytoplasmic domain (CD, covalently linked together in that order (e.g., the C-terminus of the SP is covalently linked to the N-terminus of the ECD, the C-terminus of the ECD is covalently linked to the N-terminus of the TD, and the C-terminus of the TD is covalently linked to the N-terminus of the CD). The WT hCTLA-4 ECD polypeptide typically comprises residues 38-161 of the full-length hCTLA-4 protein sequence (SEQ ID NO:160) and typically is 124 amino acid residues in length. This hCTLA-4 ECD polypeptide sequence is shown in SEQ ID NO:159. The signal peptide (SP) of the full-length hCTLA-4 protein, which typically comprises amino acid residues 1-35 or 1-37 of SEQ ID NO:160, is cleaved during processing. See, e.g., Harper et al., J. Immunol. 147(3):1037-1044 (1991). The human CTLA-4 signal peptide sequence comprising amino acid residues 1-35 or 1-37 of the hCTLA-4 protein is shown in SEQ ID NO:182 or SEQ ID NO:216, respectively. Whether the signal peptide sequence is that shown in SEQ ID NO:182 or SEQ ID NO:216, when the signal peptide is cleaved, the mature hCTLA-4 protein typically begins with the methionine residue at amino acid position 38 of the full-length hCTLA-4 protein sequence shown in SEQ ID NO:160. Thus, even if the hCTLA-4 signal peptide sequence is that of SEQ ID NO:182, which comprises amino acid residues 1-35 of the hCTLA-4 protein, the resulting mature secreted hCTLA-4 protein begins with the methionine that is at position 38 of the full-length hCTLA-4 protein. The lysine (K) and alanine (A) residues at positions 36 and 37, respectively, of the full-length hCTLA-4 protein are not present in the mature hCTLA-4 protein and are believed to be cleaved from the mature hCTLA-4 protein during processing. The amino acid residues of the mature hCTLA-4 protein sequence thus are typically numbered beginning with the methionine residue present at position 38 of the full-length hCTLA-4 protein as the first amino acid (i.e., occupying position 1); accordingly, the histidine residue occupies amino acid position 2 in the mature hCTLA-4 protein, etc. Each monomer of the Orencia® dimer includes the hCTLA-4 ECD polypeptide sequence shown in SEQ ID NO:159. In the full-length WT hCTLA-4 protein, the signal peptide comprises amino acid residues 1-37, the extracellular domain (ECD) comprises amino acid residues 38-161, the transmembrane domain (TD) comprises amino acid residues 162-182, and the cytoplasmic domain (CD) comprises amino acid residues 183-223 of SEQ ID NO:160. The mature domain (MD) of the hCTLA-4 protein typically comprises amino acid residues 36-223, or in some instances, amino acid residues 37-223 or 38-223 of SEQ ID NO:160.

The nucleic acid of SEQ ID NO:194 comprises a nucleic acid sequence encoding signal peptide sequence (nucleotide residues 1-111), a nucleic acid sequence encoding hCTLA-4 ECD (nucleotide residues 112-483), a nucleic acid sequence encoding the hCTLA-4 transmembrane and cytoplasmic domains (nucleotide residues 484-669); the last 3 C-terminal nucleotides are the TGA stop codon.

Belatacept (also known as "LEA29Y-Ig," "LEA-Ig," or "A29YL104E-Ig") (Bristol-Myers Squibb Co. (Princeton, N.J.)) is a soluble recombinant dimeric protein composed of two identical Ig fusion proteins covalently linked together by a disulfide bond formed between a cysteine residue in each monomeric fusion protein. Each monomeric fusion protein is composed of a mutant CTLA-4 extracellular domain polypeptide fused at its C-terminus to the N-terminus of a specific mutant IgG1 polypeptide. The polypeptide sequence of the mutant CTLA-4 ECD differs from the polypeptide sequence of WT human CTLA-4 ECD by two mutations, specifically a substitution of a tyrosine for the alanine at position 29 (abbreviated as the substitution A29Y) and a substitution of a glutamine for the leucine at position 104 (abbreviated as the substitution L104E), wherein amino acid residues in the human CTLA-4 ECD are numbered with the methionine at the N-terminus representing the amino acid at position 1. Each monomer of Belatacept includes the mutant IgG1 Fc polypeptide sequence shown in SEQ ID NO:186; this mutant IgG1 Fc polypeptide is identical to the mutant IgG1 Fc polypeptide included in the Orencia® fusion protein. Belatacept monomeric fusion protein thus differs from each Orencia® monomeric fusion protein by two amino acids. The polypeptide sequence of each such monomeric fusion protein in Belatacept is shown in SEQ ID NO:166. The name "LEA29Y-Ig" thus reflects the fact that each monomeric fusion protein of the Belatacept dimer is composed of a mutant CTLA-4 ECD which differs from the human CTLA-4 ECD polypeptide sequence by two the mutations L104E and A29Y. Belatacept has been shown to bind CD86 about 4 times more avidly and to bind CD80 about 2 times more avidly than the Orencia® dimer (Larson et al., Amer. J. Transplant. 5:443-453, 444 (2005). Belatacept has been shown to be up to about 10 times more potent than the Orencia® dimer in inhibiting T cell activation in vitro and to have improved in vivo immunosuppressive potency compared to the Orencia® protein as shown by its increased ability to inhibit T cell-dependent antibody responses and its improved prolongation of renal allograft survival in clinical trials involving non-human primates. Id. Additional information about Belatacept and its clinical indications and effectiveness is provided on the worldwide web at bms.com.

In one aspect, the invention provides mutant CTLA-4 molecules, including novel soluble recombinant mutant CTLA-4-Ig fusion proteins described herein, which have a binding avidity for CD86 that is greater than the binding avidity of the Orencia® dimer (dimeric hCTLA-4-Ig) for CD86. The invention also provides mutant CTLA-4 molecules, including novel soluble recombinant dimeric mutant CTLA-4-Ig fusion proteins, which have a binding avidity for CD80 that is about equal to or greater than the binding avidity of the Orencia® dimer for CD80. In yet another aspect, the invention provides mutant CTLA-4 molecules, including novel soluble recombinant mutant CTLA-4-Ig fusion proteins, which have a greater ability to suppress one or more immune responses (e.g., T cell-dependent immune responses) than Orencia® (Abatacept). Mutant CTLA-4 molecules of the invention having one or more improved properties compared to the Orencia® dimer are expected to more potent and thus more effective, useful, and advantageous than the Orencia® dimer in treating diseases, disorders, or conditions in which immunosuppression is desirable, including those diseases, disorders, or conditions for which the Orencia® dimer is approved and/or has been shown to provide clinical benefit, such as autoimmune diseases, including, e.g., rheumatoid arthritis and psoriasis.

In another aspect, the invention provides mutant CTLA-4 molecules, including novel soluble recombinant mutant CTLA-4-Ig fusion proteins described herein, which have a binding avidity for CD86 that is greater than the binding avidity of Belatacept (LEA29Y-Ig) for CD86. The invention also provides mutant CTLA-4 molecules, including novel soluble recombinant mutant CTLA-4-Ig fusion proteins described herein, which have a binding avidity for CD86 that is greater than the binding avidity of Belatacept for CD86. In another aspect, the invention provides mutant CTLA-4 molecules, including novel soluble recombinant mutant CTLA-4-Ig fusion proteins described herein, which have a greater ability to suppress one or more immune responses (e.g., T cell-dependent immune responses) than Belatacept. Mutant CTLA-4 molecules of the invention having one or more improved properties compared to Belatacept are expected to more potent than Belatacept and thus more effective, useful, and advantageous than Belatacept in treating diseases, disorders, or conditions in which immunosuppression is desirable, including those diseases, disorders, or conditions for which the Belatacept fusion protein has been shown to provide clinical benefit, such as renal allograft survival in non-human primates.

The safety, tolerability, pharmacokinetics, immunogenicity, and clinical efficacy of a molecule of the invention, such as a mutant CTLA-4 molecule of the invention, (e.g., mutant CTLA-4 ECD polypeptide or soluble mutant CTLA-4-Ig fusion protein as described in detail below) in a subject having an immune disease or disorder (e.g., rheumatoid arthritis, multiple sclerosis, psoriasis, etc.) to whom a particular dose of the molecule is administered in a particular manner (e.g., parenteral, intravenous, or subcutaneous administration) can be determined using methodologies comparable to those employed in clinical trials for Orencia® involving similar subjects. See, e.g., the worldwide website addresses at bms.com and orencia.com. For example, the degree to which a mutant CTLA-4 molecule of the invention (e.g., soluble mutant CTLA-4-Ig) is effective in reducing in subjects having rheumatoid arthritis (RA) the progression of joint damage, in alleviating the signs and symptoms of RA, including pain reduction, can be evaluated using methodologies similar to those employed in the Orencia® clinical trials involving RA patients.

The safety, tolerability, pharmacokinetics, immunogenicity, and clinical efficacy of a molecule of the invention (e.g., mutant CTLA-4 ECD polypeptide or soluble mutant CTLA-4-Ig fusion protein as described in detail below) in a subject in which immunosuppression is desirable (e.g., a subject undergoing tissue, cell, organ, or graft transplantation from a donor) and to whom a particular dose of the molecule is administered in a particular manner (e.g., parenteral, intravenous, or subcutaneous administration) can be determined using methodologies comparable to those employed in clinical trials for Belatacept involving similar subjects. See, e.g., the worldwide website address bms.com. For example, the degree to which a mutant CTLA-4 molecule of the invention (e.g., soluble mutant CTLA-4-Ig) is effective in reducing in kidney or renal transplant rejection in a recipient patient undergoing kidney or renal transplantation can be evaluated using methodologies similar to those employed in the Belatacept clinical trial involving patients undergoing kidney or renal transplantation.

Molecules and methods of the invention and other aspects of the invention are discussed in additional detail below.

Polypeptides of the Invention

The present invention provides novel polypeptides, collectively referred to as "polypeptides of the invention." The term "polypeptides of the invention" is intended to include variants and/or derivatives of the polypeptide sequences disclosed herein. Polypeptides of the invention include recombinant non-naturally occurring or mutant CTLA-4 polypeptides that bind CD80 and/or CD86 and/or that inhibit or suppress immune responses. Polypeptides of the invention include recombinant fusion proteins comprising a mutant CTLA-4 polypeptide of the invention, and include monomeric and dimer forms of such fusion proteins. Polypeptides of the invention include multimers comprising one or more mutant CTLA-4 polypeptides of the invention. The invention also includes conjugates comprising one or more mutant CTLA-4 polypeptides of the invention. Some polypeptides of the invention are soluble polypeptides. For example, as described in more detail below, the invention includes soluble fusion proteins comprising a mutant CTLA-4 ECD polypeptide linked to a different polypeptide (such as, e.g., an immunoglobulin polypeptide, such as, e.g., an Ig Fc polypeptide) that enhances solubility of the mutant CTLA-4 ECD polypeptide.

As discussed in greater detail below, in one aspect of the invention, a variety of mutagenesis and screening strategies were used to make and identify novel polypeptides that bind CD80 and/or CD86. In particular, such strategies were used to make and identify novel polypeptides having improved abilities to bind CD80 and/or CD86, including novel mutant CTLA-4 polypeptides having improved binding affinities or avidities for CD80 and/or CD86. Polypeptides of the invention that bind CD80 and/or CD86 ligands expressed on antigen-presenting cells interfere with or block the interaction of these ligands with the CD28 receptors expressed on T cells. As a result, the T cell costimulatory signal provided by the interaction of the T cell surface receptor CD28 with the B7 molecules (i.e., CD80 and CD86) is inhibited or blocked. Such polypeptides are believed useful in the prophylactic and therapeutic treatment of diseases, disorders, and conditions in which modulation of the immune system (e.g., T cell responses) is of benefit.

Mutant CTLA-4 Polypeptides

In one aspect, the invention provides isolated or recombinant polypeptides which each comprise a polypeptide sequence that has at least 75%, 80%, 85%, 86%, 87%, 88%, 89%, 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, or 100% sequence identity to at least one polypeptide sequence selected from the group consisting of SEQ ID NOS:1-73 (e.g., SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:18, SEQ ID NO:19, SEQ ID NO:20, SEQ ID NO:21, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:35, SEQ ID NO:36, SEQ ID NO:37, SEQ ID NO:38, SEQ ID NO:39, SEQ ID NO:40, SEQ ID NO:41, SEQ ID NO:42, SEQ ID NO:43, SEQ ID NO:44, SEQ ID NO:45, SEQ ID NO:46, SEQ ID NO:47, SEQ ID NO:48, SEQ ID NO:49, SEQ ID NO:50, SEQ ID NO:51, SEQ ID NO:52, SEQ ID NO:53, SEQ ID NO:54, SEQ ID NO:55, SEQ ID NO:56, SEQ ID NO:57, SEQ ID NO:58, SEQ ID NO:59, SEQ ID NO:60, SEQ ID NO:61, SEQ ID NO:62, SEQ ID NO:63, SEQ ID NO:64, SEQ ID NO:65, SEQ ID NO:66, SEQ ID NO:67, SEQ ID NO:68, SEQ ID NO:69, SEQ ID NO:70, SEQ ID NO:71, SEQ ID NO:72, and SEQ ID NO:73), wherein the polypeptide binds CD80 and/or CD86 or a polypeptide fragment of CD80 and/or CD86 (or an ECD of either or both), and/or modulate or regulate an immune response. Some such polypeptides, such as each of those set forth in SEQ ID NOS:1-73, are described as secreted or mature mutant CTLA-4 ECD polypeptides. The mutant CTLA-4 ECD polypeptides set forth in each of SEQ ID NO:1-73 do not include a signal peptide; it has been cleaved during processing, thereby producing the mature or secreted polypeptide. A polypeptide fragment of CD80 may comprise, e.g., an extracellular domain polypeptide of a CD80 polypeptide, such as, e.g., human CD80 ECD polypeptide ("hCD80 ECD"). A polypeptide fragment of CD86 may comprise, e.g., an extracellular domain polypeptide of a CD86 polypeptide, such as, e.g., human CD86 ECD polypeptide ("hCD86 ECD"). Some such polypeptides bind a mammalian CD80 and/or CD86 or polypeptide fragment thereof, such as, e.g., a mammalian CD80 or CD86 ECD. Some such polypeptides bind WT human CD80 ("hCD80") and/or WT human CD86 ("hCD86") or a polypeptide fragment thereof, such as, e.g., hCD80 ECD or hCD86 ECD. In some such methods, at least one immune response is suppressed or inhibited.

Some such polypeptides have a binding affinity or avidity for hCD80 or a fragment thereof (e.g., hCD80 ECD) that is at least about equal to or greater than the binding affinity or avidity of the hCTLA-4 ECD polypeptide for hCD80 or a fragment thereof, respectively. The predicted full-length hCD80 polypeptide sequence, which includes a signal peptide, ECD, transmembrane domain, and cytoplasmic domain covalently linked together in that order, is set forth in SEQ ID NO:195. The signal peptide comprises amino acid residues 1-34, the ECD comprises amino acid residues 35-242, the transmembrane domain comprises amino acid residues 243-263, and the cytoplasmic domain comprises amino acid residues 264-288 of SEQ ID NO:195. The polypeptide sequence of the hCD80 ECD is shown in SEQ ID NO:174. The nucleic acid sequence shown in SEQ ID NO:173 encodes the WT human CD80 signal peptide (at N-terminus) and human CD80 ECD.

Some such polypeptides have a binding affinity or avidity for hCD86 or a fragment thereof (e.g., hCD86 ECD) that is at least about equal to or greater than the binding affinity or avidity of the hCTLA-4 ECD polypeptide for hCD86 or a fragment thereof (e.g., ECD), respectively. The predicted full-length hCD86 polypeptide sequence, which includes a signal peptide, ECD, transmembrane domain, and cytoplasmic domain covalently linked together in that order, is set forth in SEQ ID NO:175, and an exemplary nucleic acid encoding the predicted full-length hCD86 polypeptide sequence is shown in SEQ ID NO:176. The polypeptide sequence of the hCD86 ECD is shown in SEQ ID NO:180. Some such polypeptides have a binding affinity or avidity for hCD86 that is at least about equal to or greater than the binding affinity or avidity of the LEA29Y ECD polypeptide having the sequence set forth in SEQ ID NO:168 for hCD86. Exemplary polypeptides of the invention that have binding affinities or binding avidities for hCD86 or hCD86 ECD that are at least equal to or greater than those of hCTLA-4 ECD and LEA29Y ECD (also termed "A29YL104E" or "L104EA29Y" ECD) for hCD86 or hCD86 ECD, respectively, include, e.g., but are not limited to, those comprising a polypeptide sequence having at least 95%, 96%, 97%, 98%, 99% or 100% sequence identity to the sequence of any of SEQ ID NOS:4, 10-12, 15, 17, 24, 26, 28, 35, and 61. See, e.g., Table 5 in Example 4. The data presented in Table 5 reflect a monomeric interaction between a representative CTLA-4-Ig and monomeric CD86 ECD. The term LEA29Y (or A29YL104E or L104EA29Y), if not otherwise indicated, refers to LEA29Y ECD (or A29YL104E or L104EA29Y ECD).

Some such polypeptides comprise a polypeptide sequence having an amino acid length about equal to the amino acid length of the human CTLA-4 extracellular domain. Such polypeptides may be described as mutant CTLA-4 ECD polypeptides. Some such mutant CTLA-4 ECD polypeptides comprise a polypeptide sequence that is about 110 amino acids to about 138 amino acid residues, about 112 to about 136 amino acid residues, about 114 to about 134 amino acid residues, about 116 to about 132 amino acid residues, about 118 to about 130 amino acid residues, about 119 to about 129 amino acid residues, about 120 to about 128 amino acid residues, about 121 to about 127 amino acid residues, about 122 to about 126 amino acid residues, about 123 to about 125 amino acid residues in length. Some such mutant CTLA-4

ECD polypeptides comprise a sequence that is 124 amino acid residues in length. Exemplary polypeptides include, e.g., but are not limited to, a polypeptide comprising a polypeptide sequence having at least 90%, 91%, 92%, 93%, 94%, 95%, 96%, 97%, 98%, 99% or 100% sequence identity to at least one polypeptide sequence selected from the group consisting of SEQ ID NOS:1-73, wherein such polypeptide binds CD80 and/or CD86 (or an ECD of either or both).

Some such polypeptides described above, including, e.g., those isolated or recombinant polypeptides which each comprising a polypeptide sequence having at least 75%, 80%, 85%, 86%, 87%, 88%, 89%, 90%, 91%, 92%, 93%, 94%, 95%, 96%, 97%, 98%, 99%, 99.5%, or 100% sequence identity to at least one polypeptide sequence selected from the group of SEQ ID NOS:1-73 and which bind CD80 and/or CD86 and/or an ECD thereof, have an ability to modulate or regulate an immune response. One or more of a variety of immune responses may be modulated or regulated by such polypeptides of the invention, including, but not limited to, e.g., T cell activation or proliferation, cytokine synthesis or production (e.g., production of TNF-α, IFN-γ, IL-2, etc.), induction of various activation markers (e.g., CD25, IL-2 receptor, etc.), synthesis or production of inflammatory molecules, inflammation, joint swelling, joint tenderness, pain, stiffness, serum levels of C-reactive protein, anti-collagen antibody production, and/or T cell-dependent antibody response(s)). In some instances, such a polypeptide has a greater ability to suppress or inhibit at least one such immune response than hCTLA-4 or hCTLA-4 ECD.

For example, some such polypeptides are capable of inhibiting T cell activation or T cell proliferation in in vitro assays. Examples 4-9 set forth below, for example, demonstrate the ability of representative fusion proteins of the invention comprising a representative mutant CTLA-4 ECD polypeptide sequence, such as those described herein, to inhibit T cell proliferation in vitro. Some such polypeptides are capable of inhibiting or suppressing an immune response in a subject in vivo, such as through the administration of a therapeutically or prophylactically effective amount of at least one such polypeptide to a subject needing immunosuppressive therapy. Some such polypeptides are expected to be useful in a variety of applications, including, e.g., but not limited to, prophylactic and/or therapeutic methods for treating immune system diseases, disorders, and conditions in which immunomodulation is desirable, as discussed in greater detail infra. Such polypeptides are expected to be useful in prophylactic and/or therapeutic methods for inhibiting or suppressing an immune response in a subject (e.g., in the in vivo treatment of immune system diseases or disorders of mammals, such as e.g., humans, in which immunoinhibition or immunosuppression is desirable), methods for inhibiting rejection of a tissue or organ transplant from a donor by a recipient (e.g., by a mammal, such as, e.g., a human), and other methods described elsewhere herein.

Additionally or alternatively, some such polypeptides have an ability to suppress or inhibit an immune response that is at least about equal to or greater than the ability of hCTLA-4 or hCTLA-4 ECD to suppress or inhibit one or more types of immune responses. For example, some such polypeptides have an ability to inhibit T cell activation or proliferation in in vitro and/or in vivo assays and/or applications, such as those described above and in greater detail below, which is at least about equal to or greater than the ability of hCTLA-4 or hCTLA-4 ECD to inhibit T cell activation or proliferation in such applications. Additionally, some such polypeptides have an ability to inhibit or suppress an immune response (e.g., T cell activation or proliferation, cytokine production, T cell-dependent antibody response) that is greater than the ability of a LEA29Y polypeptide—a specific mutant CTLA-4 ECD comprising the polypeptide sequence shown in SEQ ID NO:168—to inhibit or suppress an immune response. Examples 4-9 set forth below, for example, compare the ability of representative fusion proteins of the invention comprising a mutant CTLA-4 ECD polypeptide sequence of the invention to inhibit T cell proliferation in vitro relative to the ability of a fusion protein comprising the hCTLA-4 ECD or LEA29Y polypeptide to inhibit T cell proliferation in vitro. Such molecules are expected to be of beneficial use in a variety of therapeutic applications, including treatment of autoimmune diseases and disorders, and prophylactic and therapeutic methods for inhibiting rejection of organ, cell, or tissue graft transplantation.

Some such polypeptides may differ from one another by, e.g., an amino acid deletion, addition and/or substitution. An amino acid substitution may be a conservative or non-conservative substitution. See, e.g., the section entitled "Sequence Variation."

In another aspect, the invention also provides isolated or recombinant polypeptides which each comprise a polypeptide sequence having at least 95%, 96%, 97%, 98%, 99%, or 100% sequence identity to at least one polypeptide sequence selected from the group consisting of SEQ ID NOS:1-73, wherein the polypeptide binds a monomeric hCD80 or monomeric hCD86 or an ECD of either or both. Some such polypeptides have (1) a binding affinity for monomeric hCD86 that is about equal to or greater than the binding affinity of monomeric hCTLA-4 or an LEA29Y polypeptide for monomeric hCD86 or an ECD thereof, and (2) a binding affinity for monomeric hCD80 that is about equal to or greater than the binding affinity of monomeric hCTLA-4 for monomeric hCD80. The LEA29Y polypeptide comprises the polypeptide sequence of SEQ ID NO:168. Further, some such polypeptides have a greater ability to suppress one or more immune responses described herein (e.g., T cell activation/proliferation, cytokine synthesis/production, induction of activation markers, production of inflammatory molecules, inflammation, anti-collagen Ab production, T cell-dependent Ab response) than monomeric hCTLA-4, monomeric hCTLA-4 ECD, or LEA29Y polypeptide.

The invention also provides isolated or recombinant polypeptides which each comprise a polypeptide sequence having at least 95%, 96%, 97%, 98%, 99%, or 100% sequence identity to at least one polypeptide sequence selected from the group consisting of SEQ ID NOS:1-73, wherein the polypeptide has a binding affinity for a hCD86 ECD or hCD80 ECD that is about equal to or greater than the binding affinity of a hCTLA-4 ECD for the hCD86 ECD or hCD80 ECD, respectively. Some such polypeptides have a binding affinity for the hCD86 ECD that is greater than the binding affinity of the hCTLA-4 ECD (SEQ ID NO:159) or the LEA29Y polypeptide (SEQ ID NO:168) for the hCD86 ECD. Some such polypeptides have a binding affinity for the hCD80 ECD that is greater than the binding affinity of the hCTLA-4 ECD for the hCD80 ECD. Some such polypeptides have an ability to suppress an immune response, in some instances, a greater ability to suppress one or more immune responses, including those described above and throughout, than the hCTLA-4 ECD or the LEA29Y polypeptide.

In another aspect, the invention provides an isolated or recombinant CTLA-4 polypeptide variant comprising a polypeptide sequence which (a) which differs from a polypeptide sequence of human CTLA-4 ECD shown in SEQ ID NO:159 in no more than 15 amino acid residues, no more than 14 amino acid residues, no more than 13 amino acid residues, no more than 12 amino acid residues, no more than 11 amino acid residues, no more than 10 amino acid residues, no more than 9 amino acid residues, no more than 8 amino acid residues, no more than 7 amino acid residues, no more than 6 amino acid residues, no more than 5 amino acid residues (e.g., no more than 1, 2, 3, 4, 5, 6, 7, 8, 9, 10, 11, 12, 13, or 14 amino acid residues), and (b) wherein the amino acid residue at position 24, 30, 32, 39, 41, 50, 54, 55, 56, 64, 65, 70, 85, 104 or 106 of the hCTLA-4 ECD polypeptide sequence (SEQ ID NO:159) is substituted with a different amino acid residue in the CTLA-4 polypeptide variant sequence, wherein amino acid residue positions of the CTLA-4 polypeptide variant are numbered according to SEQ ID NO:159, and wherein the CTLA-4 polypeptide variant has an ability to bind CD80 or CD86 or an extracellular domain or fragment of either, and/or has an ability to suppress or inhibit an immune response. Some such variants comprise one or more (e.g., one, two, three, four, five, six, seven, eight, nine, ten, eleven, twelve, thirteen, fourteen or fifteen) amino acid substitutions selected from the group consisting of A24E, A24S, S25A, G27H, K28N, T30N, T30D, T30A, V32I, Q39K, Q39E, D41G, D41N, D41S, A50M, A50G, M54K, M54E, M54V, G55E, G55K, N56D, D63K, S64P, I65S, I65F, I65T, S70F, M85A, M85V, M85A, L104E, L104D, and I106M, I106F, and I106L.

In another aspect, the invention provides an isolated or recombinant mutant CTLA-4 polypeptide comprising a polypeptide sequence which (a) differs from the polypeptide sequence of the extracellular domain of human CTLA-4 shown in SEQ ID NO:159 in no more than 12 amino acid residues (e.g., no more than 2, 3, 4, 5, 6, 7, 8, 9, 10, 11, or 12 amino acid residues), and (b) comprises two, three, four, five, six, seven, eight, nine, ten, eleven, or 12 amino acid substitutions selected from the group consisting of amino acid positions corresponding to amino acid positions 24, 30, 32, 50, 54, 55, 56, 64, 65, 70, and 104 of SEQ ID NO:159, wherein amino acid positions of the mutant CTLA-4 polypeptide are numbered according to SEQ ID NO:159, and wherein the mutant CTLA-4 polypeptide has an ability to bind CD80 or CD86 or an extracellular domain or fragment of either, and/or has an ability to suppress or inhibit an immune response. Exemplary amino acid substitutions in these positions include, but are not limited to, conservative amino acid substitutions of the amino acid residues present in WT hCTLA-4 ECD and/or A24S/E (that is, A24S or A24E), T30N/D/A (that is, T30N or T30D or T30A), V32I/L/M/V, A50M/G, M54E/V/K, G55E/K/R, N56D/A, S64P/M/C, I65S/T/F/V, S70F/Y/W, L104E/M, or any combination of substitutions thereof.

In another aspect, the invention provides isolated or recombinant polypeptides (e.g., mutant CTLA-4 ECD polypeptides) which each comprise a polypeptide sequence (a) which differs from a polypeptide sequence selected from the group consisting of SEQ ID NOS:1-73 in no more than 14, 13, 12, 11, 10, 9, 8, 7, 6, 5, 4, 3, 2, or 1 amino acid residue(s), and (b) wherein the amino acid residue in the polypeptide sequence at amino acid residue position 41, 50, 54, 55, 56, 64, 65, 70, or 85 is identical to the amino acid residue at the corresponding position of said selected polypeptide sequence (e.g., a polypeptide selected from SEQ ID NOS:1-73), wherein the polypeptide binds CD80 and/or CD86 and/or an extracellular domain of either or both, and/or inhibits an immune response(s). In some instances, the polypeptide differs from the selected polypeptide (e.g., selected from SEQ ID NOS:1-73) in no more than 10, 9, 8, 7, or 6 amino acid residues (e.g., no more than 1, 2, 3, 4, 5, 6, 7, 8, 9, or 10 amino acid residues), but the amino acid occupying one or more of amino acid residue positions 41, 50, 54, 55, 56, 64, 65, 70, and 85 is identical to the amino acid residue included at that position in the selected polypeptide sequence (e.g., one selected from SEQ NOS: 1-73) and is not deleted or substituted with another amino acid. Some such polypeptides comprise a polypeptide sequence which differs from the selected polypeptide sequence in no more than 10, 9, 8, 7, or 6 amino acid residues (e.g., no more than 1, 2, 3, 4, 5, 6, 7, 8, 9, or 10 amino acid residues) and which includes amino acid residues at one or more of amino acid residue positions 24, 30, 32, 41, 50, 54, 55, 56, 64, 65, 70, 85, 104 and 106 that are identical to the amino acid residues at the corresponding positions in the selected polypeptide sequence. Such polypeptides can differ from the selected polypeptide sequence by amino acid deletion(s), addition(s), and/or amino acid substitution(s) at a position(s) that are not specified as having an amino acid identical to that of the selected sequence. Such polypeptides having a binding affinity or avidity for hCD86 or a fragment thereof (e.g., hCD86 ECD) that is at least about equal to or greater than the binding affinity or avidity of the hCTLA-4 ECD or LEA29Y polypeptide for hCD86 or a fragment thereof (e.g., ECD), respectively, are included. Some such polypeptides have a binding affinity or avidity for hCD80 or a fragment thereof (e.g., hCD80 ECD) that is at least about equal to or greater than the binding affinity or avidity of the hCTLA-4 ECD polypeptide for hCD80 or a fragment thereof, respectively. Some such polypeptides comprise a polypeptide sequence having a length about equal to the amino acid length of the hCTLA-4 ECD, e.g., 118-130, 119-129, 120-128, 121-127, 122-126, 123-125, or 124 amino acid residues in length.

Some such polypeptides are capable of suppressing one or more of a variety of immune responses, including, e.g., T cell activation, T cell proliferation, cytokine synthesis or production (e.g., production of TNF-$\alpha$, IFN-$\gamma$, IL-2), induction of activation markers (e.g., CD25, IL-2 receptor), inflammation, production of inflammatory molecules, anti-collagen Ab production, and/or T cell-dependent Ab response(s)). Some such polypeptides have a greater ability to inhibit one or more such immune responses than hCTLA-4, hCTLA-4 ECD polypeptide, or LEA29Y polypeptide. For example, some such polypeptides are capable of inhibiting T cell activation or T cell proliferation in in vitro assays. Examples 4-9, e.g., compare the ability of representative fusion proteins of the invention comprising a mutant CTLA-4 ECD polypeptide sequence of the invention to inhibit T cell proliferation in vitro relative to the ability of a fusion protein comprising the hCTLA-4 ECD or LEA29Y polypeptide to do so. Some such polypeptides are capable of inhibiting or suppressing an immune response in a subject in vivo, such as through the administration of a therapeutically or prophylactically effective amount of at least one such polypeptide to a subject needing immunosuppressive therapy. Such polypeptides are expected to be useful in a variety of applications, including, e.g., but not limited to, prophylactic and/or therapeutic methods for treating immune system diseases, disorders, and conditions in which suppression of an immune response is desirable, including, e.g., prophylactic and/or therapeutic methods for treating autoimmune diseases and disorders, methods for inhibiting rejection of a tissue or organ transplant from a donor by a recipient (e.g., by a mammal, such as, e.g., a human), and other methods described elsewhere herein.

In another aspect, the invention provides isolated or recombinant polypeptides (e.g., mutant CTLA-4 ECD polypeptides) which each comprise a polypeptide sequence which (a) differs from the polypeptide sequence of the extracellular domain of human CTLA-4 shown in SEQ ID NO:159 in no more than 10 amino acid residues, no more than 9 amino acid residues, no more than 8 amino acid residues, no more than 7, amino acid residues, no more than 6 amino acid residues, no more than 5 amino acid residues, no more than 4 amino acid residues, no more than 3 amino acid residues, no more than 2 amino acid residues, or no more than 1 amino acid residue (e.g., no more than 1, 2, 3, 4, 5, 6, 7, 8, 9, or 10 amino acid residues), and (b) comprises at least one amino acid substitution at an amino acid residue position corresponding to position 50, 54, 55, 56, 64, 65, 70, or 85 relative to the polypeptide sequence of SEQ ID NO:159, wherein the polypeptide binds hCD80 and/or hCD86 and/or an ECD of either or both, and/or inhibits an immune response (e.g., T cell activation or proliferation, cytokine synthesis or production (e.g., production of TNF-α, IFN-γ, IL-2), induction of activation markers (e.g., CD25, IL-2 receptor), inflammation, production of inflammatory molecules, anti-collagen Ab production, and/or T cell-dependent Ab response), such as in in vitro and/or in vivo methods and/or assays as described in greater detail below. Some such polypeptides comprise a polypeptide sequence that is 124 amino acid residues in length. Some such polypeptides comprise 2, 3, 4, 5, or 6 amino acid substitutions at positions relative to the polypeptide sequence set forth in SEQ ID NO:159 selected from the group consisting of amino acid residue position 50, 54, 55, 56, 64, 65, 70, and 85. Some such polypeptides further comprise an amino acid substitution at an amino acid residue position corresponding to position 104 and/or 30 relative to SEQ ID NO:159. Some such polypeptides comprise at least one amino acid substitution relative to SEQ ID NO:159 at position 70 (optionally S70F), position 64 (optionally S64P), position 50 (optionally A50M/G, e.g., A50M, A50G), position 54 (optionally M54K/V, e.g., M54K), position 65 (optionally I65S), position 56 (optionally N56D), position 55 (optionally G55E/K, e.g., G55E, G55K), position 85 (optionally M85A), and/or position 24 (optionally A24E/S, e.g., A24E). Any such polypeptide may further comprise an amino acid substitution relative to SEQ ID NO:159 at position 104 (optionally L104E/D, e.g., L104E), position 30 (optionally T30N/D/A, e.g., T30N, T30D, or T30A), and/or position 32 (optionally V32I). In some instances, the polypeptide comprises one or more substitutions at amino acid positions relative to SEQ ID NO:159 selected from the group consisting of A50M, M54K, G55E, N56D, S64P, I65S, and S70F. Some such polypeptides exhibit a binding affinity for CD86 (e.g., hCD86) or CD86 ECD (e.g., hCD86 ECD) that is about equal to or greater than the binding affinity of a monomeric hCTLA-4 ECD for CD86 or CD86 ECD, respectively. Some such polypeptides exhibit a binding affinity for CD80 (e.g., hCD80) or CD80 ECD (e.g., hCD80 ECD) that is greater than the binding affinity of a monomeric hCTLA-4 ECD for CD80 or CD80 ECD, respectively.

Some such polypeptides have an ability to suppress or inhibit one or more immune responses (e.g., T cell activation or proliferation, cytokine production, etc.), such as in vitro and/or in vivo. Some such polypeptides inhibit one or more such immune responses to a greater degree than hCTLA-4, hCTLA-4 ECD, or LEA29Y polypeptide. Such polypeptides are expected to be of beneficial use in a variety of therapeutic applications, including prophylactic and/or therapeutic methods for treating autoimmune diseases and disorders, or prophylactic and/or therapeutic methods for inhibiting organ, cell, or tissue graft transplantation rejection.

In another aspect, the invention provides isolated or recombinant polypeptides (e.g., mutant CTLA-4 ECD polypeptides) which each comprise a polypeptide sequence which (a) differs from the polypeptide sequence of the extracellular domain of human CTLA-4 shown in SEQ ID NO:159 in no more than 6 amino acid residues (e.g., no more than 1, 2, 3, 4, 5, or 6 amino acid residues), and (b) comprises one or more substitutions at amino acid positions relative to SEQ ID NO:159 selected from the group consisting of A50M, M54K, G55E, N56D, S64P, I65S, and S70F, wherein the polypeptide binds hCD80 and/or hCD86 or an extracellular domain of either or both, and/or inhibits an immune response (e.g., T cell activation or proliferation, cytokine synthesis or production, induction of activation markers, production of inflammatory molecules, inflammation, joint swelling or tenderness, pain, stiffness, serum levels of C-reactive protein, anti-collagen Ab production, and/or T cell-dependent Ab response, etc.) in in vitro assays and/or in vivo methods. Such polypeptides are expected to be useful in treating a subject suffering from a disease, disorder, or condition in which immunosuppressive therapy would be of benefit, including, e.g., therapeutic and prophylactic methods for treating autoimmune diseases and disorders, and prophylactic and therapeutic methods for inhibiting organ, cell, or tissue graft transplantation.

The invention also includes an isolated or recombinant polypeptide which comprises a polypeptide sequence comprising (i) at least 95%, 96%, 97%, 98%, 99%, or 100% sequence identity to any polypeptide sequence selected from the group consisting of SEQ ID NOS:1-73 and (ii) a phenylalanine residue at an amino acid position corresponding to position 70 of said polypeptide sequence selected from the group consisting of SEQ ID NO:1-73, wherein the polypeptide binds hCD80 and/or hCD86 or an extracellular domain thereof and/or inhibits an immune response (e.g., T cell activation or proliferation, cytokine synthesis or production, induction of activation markers, production of inflammatory molecules, inflammation, joint or tenderness, pain, stiffness, serum levels of C-reactive protein, anti-collagen Ab production, and/or T cell-dependent Ab response, etc.) in in vitro assays and/or in vivo methods. Some such polypeptides comprise one or more of the following relative to the selected sequence: a glutamic acid residue at an amino acid position corresponding to position 24; an asparagine residue at an amino acid position corresponding to position 30; an isoleucine residue at an amino acid position corresponding to position 32; a methionine residue at an amino acid position corresponding to position 50; a lysine residue at an amino acid position corresponding to position 54; a glutamic acid residue at an amino acid position corresponding to position 55; an aspartic acid residue at an amino acid position corresponding to position 56; a proline residue at an amino acid position corresponding to position 64; a serine residue at an amino acid position corresponding to position 65; and a glutamic acid residue at an amino acid position corresponding to position 104. Such polypeptides are expected to be of beneficial use in a variety of applications, including methods for treating autoimmune diseases and disorders, and methods for inhibiting organ, cell or tissue graft transplantation.

For example, in one non-limiting aspect, the invention includes an isolated or recombinant polypeptide (e.g., mutant CTLA-4 ECD) which comprises a polypeptide sequence comprising (i) at least 95%, 96%, 97%, 98%, 99%, or 100% identity to the polypeptide sequence of SEQ ID NO:24 and (ii) a phenylalanine residue at an amino acid position corresponding to position 70 of the polypeptide sequence of SEQ ID NO:24, wherein the polypeptide binds hCD80 and/or hCD86 and/or an ECD of either or both, and/or inhibits an immune response in vitro and/or in vivo. The polypeptide may comprise at least one of the following relative to SEQ ID NO:24: a glutamic acid residue at position 24; an asparagine residue at position 30; an isoleucine residue at position 32; a methionine residue at position 50; a lysine residue at position 54; a glutamic acid residue at position 55; an aspartic acid residue at position 56; a proline residue at position 64; a serine residue at position 65; and a glutamic acid residue at position 104.

The invention also includes an isolated or recombinant polypeptide (e.g., mutant CTLA-4 ECD polypeptide) that binds hCD80 and/or hCD86 (and/or an ECD of either or both) and/or inhibits an immune response (as described above), e.g., in vitro and/or in vivo, wherein the polypeptide comprises a polypeptide sequence which (a) differs from the polypeptide sequence of human CTLA-4 ECD polypeptide shown in SEQ ID NO:159 in no more than 6 amino acid residues, and (b) comprises at least one amino acid substitution, wherein said at least amino acid substitution comprises S70F, wherein amino acid residue positions are numbered according to SEQ ID NO:159. The polypeptide may further comprise at least one amino acid substitution selected from the group consisting of A24E, T30N, V32I, D41G, A50M, M54K, G55E, N56D, S64P, I65S, M85A, L104E, and I106F. Such polypeptides believed useful in a variety of applications, including methods for treating autoimmune diseases and disorders, and methods for inhibiting organ, cell, tissue, or graft transplantation.

The invention also includes an isolated or recombinant polypeptide comprising a polypeptide sequence which (a) differs from the polypeptide sequence shown in SEQ ID NO:31 in no more than 6 amino acid residues, and (b) comprises at least one of the following: a methionine residue at a position corresponding to position 50 of SEQ ID NO:31, a lysine residue at a position corresponding to position 54 of SEQ ID NO:31, a glutamic acid residue at a position corresponding to position 55 of SEQ ID NO:31, a proline residue at a position corresponding to position 64 of SEQ ID NO:31, a serine residue at a position corresponding to position 65 of SEQ ID NO:31, a phenylalanine residue at a position corresponding to position 70 of SEQ ID NO:31, wherein amino acid residue positions are numbered according to SEQ ID NO:31, and the polypeptide binds CD80 and/or CD86 and/or an ECD of either or both, and/or inhibits an immune response as described above in vitro and/or in vivo. The polypeptide may comprise a glutamic acid residue at a position corresponding to position 104, an asparagine acid residue at a position corresponding to position 30, and/or an isoleucine residue at a position corresponding to position 32 of SEQ ID NO:31. Such polypeptides believed useful in a variety of applications, including methods for treating rheumatic diseases and disorders, and methods for inhibiting organ, cell or tissue graft transplantation.

In another aspect, the invention provides an isolated or recombinant polypeptide which comprises a polypeptide sequence comprising (i) at least 95%, 96%, 97%, 98%, or 99% sequence identity to a polypeptide sequence selected from the group consisting of SEQ ID NOS:36-46 and 55, and (ii) a glutamic acid residue at an amino acid position 55 of said selected polypeptide sequence, wherein the polypeptide binds CD80 and/or CD86 or an extracellular domain of either or both and/or suppresses an immune response. Immune responses that can be suppressed include, e.g., T cell activation or proliferation, cytokine synthesis or production (e.g., production of TNF-α, IFN-γ, IL-2), induction of activation markers (e.g., CD25, IL-2 receptor), inflammation, production of inflammatory molecules, anti-collagen Ab production, and/or T cell-dependent Ab response). Such polypeptide sequence may further comprise a phenylalanine residue at amino acid position 70. Such polypeptide sequence may further comprise a proline residue at position 64 and/or an asparagine residue at position 30. Such polypeptide sequence may further comprise a methionine residue at position 50 and/or a lysine residue at position 54.

In another aspect, the invention provides an isolated or recombinant polypeptide which comprises a polypeptide sequence comprising (i) at least 95%, 96%, 97%, 98%, or 99% sequence identity to a polypeptide sequence selected from the group consisting of SEQ ID NOS:28, 30, 36-46, 55-57, and 65-73, and (ii) a glutamic acid residue at an amino acid position 55 of said selected polypeptide sequence, wherein the polypeptide binds CD80 and/or CD86 or an extracellular domain of either or both and/or suppresses an immune response, such as T cell activation or proliferation, cytokine synthesis or production (e.g., production of TNF-α, IFN-γ, IL-2), induction of activation markers (e.g., CD25, IL-2 receptor), inflammation, production of inflammatory molecules, anti-collagen Ab production, and/or T cell-dependent Ab response. Such polypeptide sequence may further comprise a phenylalanine residue at amino acid position 70. Such polypeptide sequence may further comprise a proline residue at position 64 and/or an asparagine residue at position 30. Such polypeptide sequence may further comprise a methionine residue at position 50 and/or a lysine residue at position 54.

Any polypeptide of the invention described above may further include a peptide that facilitates secretion of said polypeptide. Thus, in one aspect, the invention provides an isolated or recombinant polypeptide comprising (a) any polypeptide as described above (e.g., a mutant CTLA-4 ECD described above), and (b) a peptide that facilitates secretion of the expressed polypeptide from a host cell. The peptide is optionally a signal peptide. The C-terminus of the signal peptide is typically covalently linked to the N-terminus of the polypeptide. The signal peptide may comprise an amino acid sequence having at least 90%, 91%, 92%, 93%, 94%, 95%, 96%, 97%, 98%, 99%, or 100% sequence identity to the amino acid sequence of SEQ ID NO:182 or SEQ ID NO:216. The signal peptide may comprise an amino acid sequence having at least 90%, 91%, 92%, 93%, 94%, 95%, 96%, 97%, 98%, 99%, or 100% identity to an amino acid sequence comprising amino acid residues 1-35, 1-36, or 1-37 of SEQ ID NO:160.

Any polypeptide of the invention described above may further comprise a transmembrane domain and/or cytoplasmic domain. Thus, in one aspect, the invention provides an isolated or recombinant polypeptide comprising (a) any polypeptide of the invention described above (e.g., a mutant CTLA-4 ECD described above), and (b) a transmembrane domain. Such protein may optionally further comprise a signal peptide as described above, wherein the C-terminus of the signal peptide is covalently linked to the N-terminus of the polypeptide of the invention. The C-terminus of the signal peptide is typically covalently linked to the N-terminus of the transmembrane domain. The C-terminus of the transmembrane domain is typically covalently linked to the N-terminus of the cytoplasmic domain. In some instances, the transmembrane domain comprises an amino acid sequence having at least 90%, 91%, 92%, 93%, 94%, 95%, 96%, 97%, 98%, 99%, or 100% identity to an amino acid sequence comprising amino acid residues 162-182 of SEQ ID NO:160. In some instances, the cytoplasmic domain comprises an amino acid sequence having at least 90%, 91%, 92%, 93%, 94%, 95%, 96%, 97%, 98%, 99%, or 100% identity to an amino acid sequence comprising amino acid residues 183-223 of SEQ ID NO:160. Any of the above-described polypeptides may comprise one or more of the amino acid residues that are glycosylated or pegylated.

The invention also includes isolated or recombinant polypeptide multimers comprising two or more polypeptides, wherein at least one of the polypeptides of the multimer is a mutant CTLA-4 polypeptide of the invention as described herein (e.g., a mutant CTLA-4 ECD or mutant CTLA-4-Ig). Such a multimer comprises at least one polypeptide of the invention and may further comprise at least one additional polypeptide that need not be a polypeptide of the invention. For example, the multimer may comprise at least one polypeptide of the invention and at least one other polypeptide which may be, e.g., a wild-type polypeptide (e.g., hCTLA-4 ECD or hCTLA-4-Ig) and/or at least other mutant polypeptide (such as a mutant polypeptide that is not a polypeptide of the invention). Some or all of the polypeptides in the multimer (or multimeric polypeptide) may be identical to one another, or, in some instances, all polypeptides in the multimer may be different from one another. In some instances, the polypeptide multimer is a dimer comprising two polypeptides of the invention, which optionally may be identical polypeptides (i.e., homodimer) or different polypeptides (i.e., heterodimer). In some instances, the polypeptide multimer is a tetramer comprising four polypeptides of the invention. The tetramer can comprise four identical polypeptides (i.e., homotetramer) or any combination of four polypeptides of the invention such that at least one polypeptide is not identical to the other three polypeptides (i.e., heterotetramer). The invention also includes a tetramer comprising four identical WT CTLA-4 ECD polypeptides (e.g., hCTLA-4 ECD) or four identical WT CTLA-4-Ig (e.g., hCTLA-4-Ig). In some instances, the multimer is capable of binding CD80 and/or CD86 (or an ECD of either or both) and/or suppressing or inhibiting an immune response in in vitro and/or in vivo methods (e.g., T cell proliferation or activation, cytokine production, etc.). Some such multimers have a greater ability to suppress or inhibit an immune response in vitro and/or in vivo than hCTLA-4 or hCTLA-4-Ig (e.g., hCTLA-4-IgG2 or Orencia® protein). The polypeptides of the multimers may be linked together, such as by covalent linkages, such as via disulfide bonds between one or more cysteine residues in the one or more polypeptides.

Some such tetramers of the invention comprise a structure schematically similar to that of an antibody, but in which the variable domains of the antibody are each replaced with any mutant CTLA-4 ECD polypeptide of the invention described herein. The heavy chain of an antibody comprises a heavy chain variable domain ($V_H$) fused to an immunoglobulin (Ig) CH1 domain (e.g., IgG2 CH1), which is fused to a hinge. The hinge is fused to an Ig CH2 domain (e.g., IgG2 CH2), which is fused to an Ig CH3 domain (e.g., IgG2 CH3). The light chain of an antibody comprises a light chain variable domain ($V_L$) fused to an Ig C kappa ($C_\kappa$) or C lambda ($C_\lambda$) domain. Two heavy chains and two light chains are covalently linked together by one or more disulfide bonds formed via cysteine residues in the heavy and light chains. The invention includes a mutant CTLA-4 tetramer in which each of the variable domains of the heavy and light chains is replaced with a mutant CTLA-4 ECD polypeptide of the invention. Thus, such tetramer comprises two light chains and two heavy chains. Each light chain comprises a mutant CTLA-4 ECD polypeptide fused to an Ig $C_\kappa$ or $C_\lambda$ domain. Each heavy chain comprises a mutant CTLA-4 ECD fused to an Ig CH1 domain (e.g., IgG2 CH1), which is fused to a hinge. The hinge is fused to an Ig CH2 domain (e.g., IgG2 CH2), which is fused to an Ig CH3 domain (e.g., IgG2 CH3). The two heavy chains and two light chains are covalently linked together by one or more disulfide bonds formed via cysteine residues in the heavy and light chains. Such tetramer may be described as a CTLA-4-Ig tetramer. Methods for constructing such CTLA-4-Ig tetramer are known and would be understood by those of ordinary skill in the art. A tetrameric CD4-Ig construct, which comprises a CD4 polypeptide and which neutralizes primary HIV type 1 isolates, is described in Allaway, G. P. et al., AIDS Res. Hum. Retroviruses 11(5):533-9 (1995). The tetramer can comprise four identical four mutant CTLA-4 ECD polypeptides or any combination of four mutant CTLA-4 ECD polypeptides of the invention such that at least one mutant CTLA-4 ECD is not identical to the other three mutant CTLA-4 ECD polypeptides. Some such tetramers are capable of binding CD80 and/CD86 with a higher binding avidity than hCTLA-4 (or hCTLA-4-Ig). Some such tetramers are capable of suppressing or inhibiting an immune response; in some instances, such a tetramer has a greater ability to suppress or inhibit an immune response in in vitro assays or in vivo applications (e.g., T cell proliferation or activation, cytokine production, etc) than hCTLA-4 or hCTLA-4-Ig (e.g., hCTLA-4-IgG2 or Orencia®). Multimers of the invention are expected to be of beneficial use in a variety of applications, including methods for treating autoimmune diseases and disorders, and methods for inhibiting organ, cell, or tissue graft transplantation.

The invention also includes an isolated or recombinant conjugate multimers comprising two or more conjugates, wherein at least one of the conjugates is a conjugate of the invention which comprises a mutant CTLA-4 polypeptide of the invention (e.g., a mutant CTLA-4 ECD or mutant CTLA-4-Ig). Some or all of the conjugates in the multimer may be identical to one another, or all conjugates in the multimer may be different from one another. In some instances, the conjugate multimer is a dimer comprising two conjugates or a tetramer comprising four conjugates of the invention. Some such conjugate multimers are capable of binding CD80 and/ CD86 (or an ECD of either or both) and/or suppressing or inhibiting an immune response in vitro and/or in vivo. Conjugate molecules in multimers may be linked together, such as by covalent linkages, such as via disulfide bonds between one or more cysteine residues in the one or more conjugates.

The invention includes an isolated or recombinant polypeptide dimer comprising any two polypeptides of the invention described above (e.g., mutant CTLA-4 ECD described above), wherein the dimer has a binding avidity for human CD86 or an extracellular domain thereof that is about equal to or greater than the binding avidity of a dimer comprising two human CTLA-4 extracellular domains for human CD86 or an extracellular domain thereof, respectively.

The invention includes isolated or recombinant polypeptide dimers comprising two polypeptides of the invention described above (e.g., mutant CTLA-4 ECD described above), wherein the dimer has a binding avidity for hCD80 or an ECD thereof that is about equal to or greater than the binding avidity of a dimer comprising two hCTLA-4 ECD polypeptides (SEQ ID NO:159) for hCD80 or an ECD thereof, respectively. For example, in a non-limiting aspect, the dimer may comprise two polypeptides, wherein each polypeptide comprises a polypeptide sequence having at least 95%, 96%, 97%, 98%, 99%, or 100% identity to a sequence selected from the group consisting of SEQ ID NOS:1-73, and each polypeptide binds hCD80 and/or hCD86 and/or inhibits an immune response. In another non-limiting aspect, the dimer may comprise two polypeptides, wherein each polypeptide differs from the polypeptide sequence of the hCTLA-4 ECD (SEQ ID NO:159) in no more than 6 amino acid residues and comprises at least one substitution at an amino acid position relative to SEQ ID NO:159 selected from the group consisting of A50M, M54K, G55E, N56D, S64P, I65S, and S70F; and which polypeptide optionally further comprises the substitution L104E, and each polypeptide binds hCD80 and/or hCD86 and/or inhibits an immune response.

In some instances, the dimer has a binding avidity for hCD80 or an ECD thereof that is about equal to or greater than the binding avidity of a dimer comprising two hCTLA-4 ECD polypeptides for hCD80 or an ECD thereof, respectively. In some instances, the dimer has a binding avidity for hCD86 or an ECD thereof that is greater than the binding avidity of a dimer comprising two LEA29Y polypeptides for hCD86 or an ECD thereof, respectively, wherein each LEA29Y polypeptide comprises the polypeptide sequence shown in SEQ ID NO:168. In some instances, the dimer dissociates from binding hCD86 or an ECD thereof at a rate that is less than the rate at which a dimer comprising two hCTLA-4 ECD polypeptides dissociates from binding hCD86 or an ECD thereof, respectively. In some instances, the dimer dissociates from binding hCD86 or an ECD thereof at a rate that is less than the rate at which a dimer comprising two LEA29Y polypeptides dissociates from binding hCD86 or an ECD thereof, respectively, wherein each LEA29Y polypeptide comprises the polypeptide sequence shown in SEQ ID NO:168.

In some instances, the dimer associates with hCD86 or an ECD thereof at a rate that is greater than the rate at which a dimer comprising two hCTLA-4 ECD polypeptides associates with hCD86 or an ECD thereof, respectively. In some instances, the dimer associates with hCD86 or an ECD thereof at a rate that is greater than the rate at which a dimer comprising two LEA29Y polypeptides associates with hCD86 or an ECD thereof, respectively, wherein each LEA29Y polypeptide comprises the polypeptide sequence shown in SEQ ID NO:168.

In some instances, such dimer comprising a mutant CTLA-4 ECD has a greater ability to suppress an immune response (e.g., T cell activation or proliferation, cytokine production, etc.) than a dimer comprising two human CTLA-4 extracellular domains or two LEA29Y polypeptides.

Some such dimers have a CD86 equilibrium dissociation constant ($K_D$) that is less than the CD86 equilibrium dissociation constant ($K_D$) of a dimer comprising two hCTLA-4 ECD polypeptides or two LEA29Y polypeptides. Some such dimers have a CD86 equilibrium dissociation constant ($K_D$) that is less than the CD86 equilibrium dissociation constant ($K_D$) of a dimer comprising two LEA29Y polypeptides, each LEA29Y polypeptide comprising the polypeptide sequence set forth in SEQ ID NO:168.

Some such multimers comprising at least two polypeptides of the invention (e.g., a dimer comprising two mutant CTLA-4 ECD polypeptides of the invention) have an enhanced ability to suppress an immune response compared to a multimer of full-length hCTLA-4 of the same valency (i.e., a multimer comprising the same number of full-length CTLA-4 polypeptides). Some such multimers comprising at least two polypeptides of the invention have an enhanced ability to suppress an immune response compared to a multimer of hCTLA-4 ECCD of the same valency (i.e., a multimer comprising the same number of hCTLA-4 ECD polypeptides).

Any polypeptide of the invention described above may further comprise an additional polypeptide sequence that enhances solubility, such as an immunoglobulin (Ig) polypeptide sequence, thereby forming, e.g., a soluble fusion protein, as discussed in greater detail infra. Each polypeptide of a polypeptide multimer may further comprise an additional polypeptide sequence that enhances solubility, such as an Ig polypeptide sequence, thereby forming, e.g., a soluble fusion protein. Thus, for example, each polypeptide of a dimer comprising two or more polypeptides of the invention, as described above, may further comprise an additional polypeptide sequence that enhances solubility, such as an Ig polypeptide sequence, thereby forming, e.g., a soluble fusion protein.

Such polypeptides and dimers of the invention are expected to be of beneficial use in a variety of applications, including methods for treating autoimmune diseases and disorders, and methods for inhibiting organ, cell, or tissue graft transplantation.

As discussed previously, the mature hCTLA-4 protein sequence typically begins with the methionine residue at amino acid position 38 of the full-length hCTLA-4 protein sequence shown in SEQ ID NO:160, and the amino acid residues of the mature hCTLA-4 protein sequence are typically numbered beginning with this methionine residue as the first amino acid (i.e., occupying amino acid position 1).

Some mutant CTLA-4 polypeptides of the invention (including monomeric and dimeric fusion proteins and multimeric polypeptides) include at least one amino acid substitution at an amino acid position corresponding to an amino acid position in the mature hCTLA-4 protein sequence that is outside the classical hCTLA-4/hB7-2 binding interface (see, e.g., Schwartz et al., Nature 410:604-608 (2001)), including, but not limited to, for example, any of amino acid positions 24, 41, 54, 55, 56, 64, 65, 70, and 85. In general, one of ordinary skill in the art would not have predicted that an amino acid substitution at any of the above-mentioned positions (24, 41, 54, 55, 56, 64, 65, 70, and/or 85) or any combination of one or more substitutions selected from the group of positions 24, 41, 54, 55, 56, 64, 65, 70, and 85 would have an ability to enhance the binding affinity or avidity of hCTLA-4 for hB7-2, would have an enhanced ability to inhibit the interaction of CD28-positive with B7-2-positive cells, or would provide a greater ability to suppress or inhibit an immune response than, e.g., hCTLA-4 ECD or hCTLA-4-Ig (e.g., T cell activation or proliferation, cytokine synthesis or production, induction of activation markers, synthesis or production of inflammatory molecules, anti-collagen antibody production, T cell-dependent antibody response, and the like). Further, one of ordinary skill in the art would not have predicted that a particular amino acid substitution(s) or combination of particular amino acid substitutions described herein at any of the above-mentioned positions (24, 41, 54, 55, 56, 64, 65, 70, and/or 85) or any combination of such positions would have ability to enhance the binding affinity or avidity of hCTLA-4 for hB7-2, have an enhanced ability to inhibit the interaction of CD28-positive with B7-2-positive cells, or provide a greater ability to suppress or inhibit an immune response than, e.g., hCTLA-4 ECD or hCTLA-4-Ig.

Mutant CTLA-4 Fusion Proteins

The invention also provides novel isolated and recombinant fusion proteins which comprise a first polypeptide that is at least one of the polypeptides of the invention described above and throughout (such as a mutant CTLA-4 polypeptide of the invention, such as, e.g., a mutant CTLA-4 ECD polypeptide) linked or fused to a second polypeptide, thereby forming a fusion protein. The second polypeptide typically facilitates secretion or expression of the first polypeptide. Exemplary mutant CTLA-4 ECD polypeptides include those comprising sequences identified as SEQ ID NOS:1-73. The invention includes fusion proteins comprising immunoglobulin (Ig) domains, such as Ig Fc domains, fused or attached to biological active moieties of the invention, such as mutant CTLA-4 polypeptides of the invention. Fusion proteins of the invention are believed useful as prophylactic and/or therapeutic agents for the prophylactic and/or therapeutic treatment of a variety of immune system diseases and disorders and conditions in immunomodulation and/or immunosuppression is of benefit, in diagnostic assays, and for the preparation of medicaments or agents having immunomodulating and/or immunosuppressive activities or properties as discussed in greater detail elsewhere herein.

Fusion proteins of the invention comprising a mutant CTLA-4 polypeptide and an Ig polypeptide (e.g., Ig Fc) are typically termed mutant CTLA-4-Ig fusion proteins. Any of the fusion proteins of the invention, including monomeric and dimeric fusion proteins of the invention described in greater detail below and in the Examples, may comprise as Ig polypeptide, such as, e.g., an Ig Fc polypeptide, as described herein and elsewhere above and below. The second polypeptide may be linked directly to the first polypeptide. For example, the N-terminus of the second polypeptide (e.g., an Ig polypeptide, such as an Ig Fc polypeptide) may be covalently fused directly to the C-terminus of the first polypeptide of the invention (e.g., mutant CTLA-4 ECD polypeptide). Alternatively, the second polypeptide may be linked indirectly to the first polypeptide, such as where a linker amino acid sequence comprising 1, 2, 3, 4, 5, 6, 7, 8, 9, or 10 or more amino acid residues is included between the first and second polypeptides. In instances in which a linker is included, the N-terminus of the amino acid linker sequence is typically covalently fused to the C-terminus of the first polypeptide (e.g., mutant CTLA-4 ECD), and the N-terminus of the second polypeptide (e.g., an Ig polypeptide, such as an Ig Fc) is typically covalently fused to the C-terminus of the amino acid linker sequence.

In some instances, the second polypeptide comprises at least a portion of an Ig polypeptide, such as, e.g., one or more domains of an Ig heavy chain constant region. The second polypeptide may comprise as a hinge region, CH2 domain, and CH3 domain of an Ig polypeptide. In some instances, the second polypeptide comprises an Fc domain of a WT Ig polypeptide (i.e., WT Ig Fc polypeptide), such as, e.g., an Fc domain of a WT human Ig polypeptide (i.e., WT human Ig Fc polypeptide). As discussed elsewhere, the Ig polypeptide may be from various species, including, e.g., mammal, e.g., human, mouse, non-human primate (e.g., monkey, gorilla), cat, dog, horse, etc., and can be from various classes (e.g., IgG, IgM, IgE, etc.) and subclasses (e.g., for IgG include IgG1, IgG2, IgG4, etc.), and may comprise an Fc domain or portion of any such Ig polypeptide. The amino acid and nucleic acid sequences of Ig polypeptides of such various species are known in the art.

In one aspect, the invention provides novel isolated or recombinant fusion proteins which each comprise an isolated or recombinant mutant CTLA-4 polypeptide of the invention described above (e.g., mutant CTLA-4 ECD) covalently linked or fused, either directly or indirectly (via an amino acid linker sequence), at its C-terminus to the N-terminus of an Ig Fc polypeptide, i.e., the Fc domain of an Ig polypeptide. Any of the fusion proteins of the invention, including monomeric and dimeric mutant CTLA-4-Ig fusion proteins of the invention described in greater detail below and in the Examples, may comprise as Ig Fc polypeptide as described herein and elsewhere above and below. An Ig Fc polypeptide typically comprises the hinge region, CH2 domain and CH3 domain of the Ig polypeptide. The Ig Fc polypeptide may be derived from various species, including, e.g., human, mouse, primate, etc., and may comprise a wild-type Ig Fc polypeptide (e.g., WT IgG1, IgG2, or IgG4). Exemplary human IgG Fc polypeptides include, e.g., but are not limited to, human IgG1, human IgG2, human IgG4, etc. The polypeptide sequence of exemplary human IgG1 Fc is set forth in SEQ ID NO:185. The polypeptide sequences of exemplary human IgG2 Fc polypeptides are set forth in SEQ ID NOS:184 and 218, respectively. Alternatively, the Ig Fc polypeptide may comprise a mutant Ig polypeptide. For example, a mutant IgG1 Fc in which one or more cysteine residues have been substituted with another amino acid (e.g., a serine residue), thereby eliminating one or more disulfide bonds formed between two Ig chains, or in which one or more proline residues is substituted with another amino acid (e.g., proline) to reduce effector function (reduced Fc receptor binding), may be included in a mutant CTLA-4-Ig fusion protein. The polypeptide sequence of an exemplary mutant IgG1 Fc polypeptide is shown in SEQ ID NO:186. The invention includes an isolated or recombinant fusion protein, such as a mutant CTLA-4-Ig dimer or mutant CTLA-4-Ig monomer, which comprises at least one recombinant mutant CTLA-4 polypeptide described above linked at its C-terminus to the N-terminus of a recombinant Ig Fc polypeptide comprising an amino acid sequence having at least 95%, 96%, 97%, 98%, 99%, or 100% identity to an amino acid sequence selected from the group consisting of SEQ ID NOS:184 (human IgG2 Fc polypeptide), 185 (human IgG1 Fc polypeptide), 186 (mutant IgG1 Fc polypeptide), and 218 (human IgG2 Fc polypeptide without C-terminal lysine (K) residue).

In one aspect, the predicted polypeptide sequence of a mutant CTLA-4-Ig fusion protein of the invention comprises the following segments: a signal peptide sequence which facilitates secretion of the fusion protein (e.g., hCTLA-4 signal peptide (SEQ ID NO:182 or SEQ ID NO:216)); a mutant CTLA-4 ECD polypeptide, which mutant CTLA-4 ECD polypeptide typically, but not necessarily, comprises from about 118 to 130 amino acid residues, and usually about 124 amino acid residues in length; and an Ig Fc polypeptide. Exemplary mutant CTLA-4 ECD polypeptides include those described above and below. In some instances, no amino acid linker sequence is included between the C-terminus of the mutant CTLA-4 ECD polypeptide and the N-terminus of the human Ig Fc polypeptide; that is, the C-terminus of a mutant CTLA-4 ECD polypeptide is covalently fused directly to the N-terminus of the Ig Fc polypeptide in the mutant CTLA-4-Ig fusion protein. If desired, however, a mutant CTLA-4-Ig may include a linker (e.g., one or more amino acid residues) between the C-terminus of the mutant CTLA-4 ECD polypeptide and the N-terminus of the human Ig Fc polypeptide. The signal peptide of a predicted monomeric mutant CTLA-4-Ig fusion protein of the invention is typically cleaved from the N-terminus of the mutant CTLA-4 Ig fusion protein during processing and thus the mature or secreted form of a mutant CTLA-4-Ig fusion protein of the invention does not usually include a signal peptide sequence. A fusion protein dimer comprising two such monomeric mutant CTLA-4-Ig fusion proteins is typically formed during cellular processing by the creation of covalent disulfide bonds between (1) cysteine residues in the mutant CTLA-4 ECD and IgG2 Fc of one such monomeric fusion protein and (2) cysteine residues in the mutant CTLA-4 ECD and IgG2 Fc of the second (typically, but not necessarily identical) monomeric fusion protein.

The invention includes dimeric fusion proteins (also termed fusion protein dimer) which each comprise two monomeric fusion proteins of the invention. The dimer may comprise two identical or different monomeric fusion proteins. The dimeric fusion protein is formed by a linkage(s) between the two monomeric fusion proteins. A dimeric fusion protein comprising two such monomeric fusion proteins is typically formed during cellular processing by the generation of covalent disulfide bonds between cysteine residues in one monomeric fusion protein and cysteine residues in the second monomeric fusion protein. Thus, in some instances, a mutant CTLA-4-Ig fusion protein of the invention is expressed as a dimer comprising two monomeric fusion proteins of the invention.

In one aspect, the invention provides an isolated or recombinant dimeric mutant CTLA-4-Ig fusion protein comprising two monomeric fusion proteins, wherein each monomeric fusion protein comprises a mutant CTLA-4 ECD polypeptide of the invention, as described in detail above and further below, fused at its C-terminus to an Ig Fc polypeptide. The dimer is formed during cellular processing by the generation of covalent disulfide bonds between cysteine residues in the mutant CTLA-4 ECD and Ig Fc of one monomeric fusion protein and cysteine residues in the mutant CTLA-4 ECD and Ig Fc of the second monomeric fusion protein. The two monomeric fusion proteins typically, but not necessarily, comprise identical sequences. The secreted or mature form of a mutant CTLA-4-Ig fusion protein does not include a signal peptide, as the signal peptide is typically cleaved from the N-terminus of the protein during processing. The predicted mutant CTLA-4-Ig fusion includes a signal peptide, the C-terminus of which is typically covalently linked to the N-terminus of the mutant CTLA-4-Ig protein. The N-terminus of each monomer of a mature mutant CTLA-4-Ig fusion protein typically comprises a methionine (M).

As a non-limiting example, the invention provides dimeric fusion proteins comprising two monomeric CTLA-4-Ig fusion proteins, wherein each monomeric mutant CTLA-4-Ig fusion protein comprises a mutant CTLA-4 ECD polypeptide linked at its C-terminus to the N-terminus of an Ig Fc polypeptide, wherein the mutant CTLA-4 ECD polypeptide comprises a polypeptide sequence selected from any of SEQ ID NOS:1-73. In some such dimeric fusion proteins, the two monomeric fusion proteins are covalently linked together by a covalent disulfide bond formed during cellular processing between a cysteine residue at position 120 in each CTLA-4 mutant ECD polypeptide sequence. Alternatively, or in addition, the two monomeric fusion proteins are covalently linked together by a covalent disulfide bond formed between one or more cysteine residues in the Ig Fc polypeptide of the first monomeric fusion protein and one or more cysteine residues in the Ig Fc polypeptide of the second monomeric fusion protein. The monomeric fusion proteins may be linked together by multiple disulfide bonds (e.g., one, two, three, four, or more disulfide bonds) formed during cellular processing between cysteine residues present in their respective Ig Fc polypeptides. In some instances, each monomeric fusion protein is comprised of the same Ig Fc polypeptide (e.g., human IgG2 Fc, as shown in, e.g., SEQ ID NO:184 or 218), and covalent disulfide bond(s) may be generated during cellular processing between cysteine residues at equivalent positions in each Ig Fc polypeptide.

An exemplary mutant CTLA-4 ECD polypeptide is the D3-12 mutant CTLA-4 ECD polypeptide comprising the polypeptide sequence of SEQ ID NO:11. An exemplary mutant CTLA-4-Ig fusion protein of the invention is the D3-12 mutant CTLA-4 ECD polypeptide covalently linked or fused directly (no linker) at its C-terminus to the N-terminus of the human IgG2 Fc polypeptide shown in SEQ ID NO:218, thereby forming the D3-12-IgG2 fusion protein shown in SEQ ID NO:205, or covalently linked or fused directly (no linker) at its C-terminus to the N-terminus of the human IgG2 Fc polypeptide shown in SEQ ID NO:184, thereby forming the D3-12-IgG2 fusion protein shown in SEQ ID NO:74. The sequence of SEQ ID NO:74 differs from that of SEQ ID NO:205 by one residue—i.e., an additional lysine residue is present at the C-terminus of SEQ ID NO:74. We have found experimentally by liquid chromatography mass spectrometry (LCMS) analysis, or the like, that a mature CTLA-4-Ig fusion protein made in CHO cells by transfecting an expression vector comprising a nucleotide sequence encoding a mutant CTLA-4 ECD, such as, e.g., the D3-12 ECD polypeptide sequence shown in SEQ ID NO:11, and the hIgG2 Fc polypeptide shown in SEQ ID NO:184 does not typically include the predicted C-terminal lysine (K) residue, as would be expected based on the hIgG2 Fc sequence shown in SEQ ID NO:184.

For example, the nucleotide sequence of SEQ ID NO:153 encodes the hCTLA-4 signal peptide and D3-12-IgG2 fusion protein and includes the stop codon TAA at its C-terminus. The codon AAA, which codes for a lysine residue, immediately precedes the stop codon TAA in the sequence of SEQ ID NO:153. The predicted polypeptide sequence of a mature D3-12-IgG2 fusion protein produced by transfecting an expression vector comprising the nucleotide sequence of SEQ ID NO:153 into CHO cells is shown in SEQ ID NO:74. The signal peptide is absent in the mature form of the D3-12-IgG2 fusion protein, as it has been cleaved during processing to form the mature fusion protein. However, we have found, based on LCMS analysis, that in such instance the mature D3-12-IgG2 does not typically include the predicted C-terminal lysine residue, as would be expected based on the nucleotide sequence of SEQ ID NO:153. Rather, the resulting mature D3-12-IgG2 polypeptide sequence produced by such method is that shown in SEQ ID NO:205. The C-terminal lysine of the IgG2 Fc polypeptide is believed to be cleaved during processing or prior to secretion.

It is believed that production of D3-12-IgG2 protein using another mammalian cell line by transfection of such vector comprising the nucleotide sequence of SEQ ID NO:153 into such mammalian cell (e.g., COS cells and the like) would produce a similar D3-12-IgG2 fusion protein lacking the predicted C-terminal lysine residue by virtue of analogous processing or secretion machinery.

The dimeric D3-12-IgG2 fusion protein comprises two such D3-12-IgG2 monomers linked together by one or more disulfide bonds formed during cellular processing by the generation of covalent disulfide bonds between cysteine residues. D3-12-IgG2 and other fusion proteins of the invention can be made, e.g., by using methods set forth in Example 3. For example, a nucleic acid sequence encoding a D3-12 polypeptide (e.g., SEQ ID NO:90) can be cloned into the IgG2 Fc fusion vector, mammalian cells can be transfected with the vector, and the resultant fusion protein can be expressed (typically in dimeric form), purified, and evaluated as described in Example 3.

Another exemplary mutant CTLA-4 ECD polypeptide is the D3-54 mutant CTLA-4 ECD polypeptide comprising the polypeptide sequence of SEQ ID NO:36, and an exemplary mutant CTLA-4-Ig fusion protein comprises the D3-54 mutant CTLA-4 ECD polypeptide covalently linked or fused directly (no linker) at its C-terminus to the N-terminus of the hIgG2 Fc polypeptide shown in SEQ ID NO:218 (without the C-terminal lysine), thereby forming the D3-54-IgG2 fusion protein shown in SEQ ID NO:211, or covalently linked or fused directly (no linker) at its C-terminus to the N-terminus of the hIgG2 Fc polypeptide shown in SEQ ID NO:184 (with the C-terminal lysine), thereby forming the D3-54-IgG2 fusion protein shown in SEQ ID NO:197. As discussed above, experimental analysis indicates that the mature D3-54-IgG2 fusion protein made in CHO cells does not typically include the predicted C-terminal lysine residue. The C-terminal lysine of hIgG2 Fc is believed to be cleaved during processing or prior to secretion, resulting in the D3-54-IgG2 fusion protein sequence shown in SEQ ID NO:211. Further, as noted above, D3-29-IgG2 can be made by using methods of Example 3. The dimeric D3-54-IgG2 fusion protein comprises two D3-54-IgG2 monomers linked together by one or more disulfide bonds formed during cellular processing by the generation of covalent disulfide bonds between cysteine residues. The nucleic acid sequence shown in SEQ ID NO:201 encodes the fusion proteins shown in SEQ ID NOS: 197 and 211.

Other fusion proteins of the invention can similarly comprise a mutant CTLA-4 ECD polypeptide linked or fused to hIgG2 (SEQ ID NO:218 or 184). Exemplary mature mutant CTLA-4-IgG2 fusion proteins of the invention include, e.g., the polypeptide sequences of each of SEQ ID NOS:74-79, 197-200, 205-214, and 219-222. Each of the polypeptide sequences of SEQ ID NOS:74-79, 197-200, 220, and 222 includes a C-terminal lysine residue; this C-terminal lysine residue is typically cleaved during processing or prior to secretion, resulting in the polypeptide sequences without the C-terminal lysine shown in SEQ ID NOS:205-210, 211-214, 219, and 221, respectively.

FIG. 10 is a schematic diagram showing an exemplary configuration or structure of an exemplary mutant CTLA-4-IgG2 fusion protein of the invention. Two identical monomeric mutant CTLA-4-IgG2 fusion proteins are shown schematically, each comprising a mature mutant CTLA-4 ECD polypeptide covalently linked at its C-terminus to the N-terminus of a human IgG2 Fc polypeptide. Each human IgG2 polypeptide includes a human IgG2 hinge, CH2 domain, and CH3 domain. Exemplary amino acid residues present at the junctions between the ECD and Ig Fc polypeptides are also shown. The amino acid residues at the junctions between these components may differ depending upon the mutant CTLA-4 ECD polypeptide sequence and/or Ig polypeptide sequence. This dimeric mutant CTLA-4-IgG2 fusion protein results from the formation of at least one disulfide bond between cysteine residues at analogous positions in the two mutant CTLA-4-IgG2 fusion protein monomers. The cysteine (C) residues potentially involved in forming disulfide bonds between the two monomers are marked with asterisks. The signal peptide of each monomeric fusion protein is typically cleaved during processing and thus the secreted (mature) fusion protein typically does not include the signal peptide sequence. The polypeptide sequence of the human IgG2 polypeptide, which comprises the hinge, CH2 domain, and CH3 domain of human IgG2, is shown in SEQ ID NO:184. In an alternative aspect, the polypeptide sequence of the human IgG2 polypeptide, which comprises the hinge, CH2 domain, and CH3 domain of human IgG2, is shown in SEQ ID NO:218; in this instance, the IgG2 polypeptide does not include the C-terminal lysine (K) residue, as compared to the sequence of SEQ ID NO:184.

The properties of mutant CTLA-4-Ig fusion proteins of the invention, described in detail elsewhere, may be compared to the properties of one or more reference Ig fusion proteins, such as, e.g., hCTLA-4-IgG1, hCTLA-4-IgG2, Orencia® fusion protein, and LEA29Y-Ig. Properties that may be compared include, e.g., ability to bind CD80 and/or CD86 (and/or CD80-Ig and/or CD86-Ig), and/or ability to inhibit or suppress an immune response (e.g., T cell activation or proliferation, cytokine production, etc.). The mature hCTLA-4-IgG1 fusion protein typically exists in solution as a hCTLA-4-IgG1 fusion protein dimer comprising two identical monomeric hCTLA-4-IgG1 proteins, each monomeric hCTLA-4-IgG1 fusion protein comprising a hCTLA-4 ECD polypeptide (SEQ ID NO:159) linked to an IgG1 Fc polypeptide. The mature hCTLA-4-IgG2 fusion protein typically exists in solution as an hCTLA-4-IgG2 fusion protein dimer comprising two identical monomeric hCTLA-4-IgG2 proteins, each monomeric hCTLA-4-IgG2 fusion protein (SEQ ID NO:162) comprising an hCTLA-4 ECD polypeptide (SEQ ID NO:159) linked to an IgG2 Fc polypeptide. The mature Orencia® fusion protein is a fusion protein dimer comprising two identical monomeric Orencia® fusion proteins, each monomeric fusion protein (SEQ ID NO:164) comprising a hCTLA-4 ECD polypeptide (SEQ ID NO:159) linked to a specific mutant IgG1 polypeptide (SEQ ID NO:186). The mature LEA29Y-Ig fusion protein typically exists in solution as a LEA29Y-Ig fusion protein dimer comprising two identical monomeric LEA29Y-Ig fusion proteins, each monomeric LEA29Y-Ig fusion protein (SEQ ID NO:166) comprising a specific mutant CTLA-4 ECD polypeptide (SEQ ID NO:168) linked to a specific mutant IgG1 polypeptide (SEQ ID NO:186). It is believed that the two fusion protein monomers of the Orencia® dimer are covalently linked together by a single disulfide bond formed between the cysteine residue at position 120 of each hCTLA-4-mutant IgG1 monomer and that no disulfide bonds are formed between the two mutant IgG1 Fc polypeptides.

Some mutant CTLA-4 fusion proteins bind CD80 (e.g., hCD80) and/or CD86 (e.g., hCD86). Some such mutant CTLA-4-Ig fusion proteins bind a CD80-Ig fusion protein and/or a CD86-Ig fusion protein. Exemplary CD80-Ig fusion proteins include the hCD80-mIg fusion protein (SEQ ID NO:225), which comprises a human CD80 ECD linked to a murine Ig Fc polypeptide; and the hCD80-hIgG1 fusion protein (SEQ ID NO:171), which comprises the sequence of hCD80 ECD linked to human IgG1 Fc polypeptide. Exemplary CD86-Ig fusion proteins include the hCD86-mIg fusion protein (SEQ ID NO:226), which comprises an hCD86 ECD (SEQ ID NO:180) linked to a murine Ig Fc polypeptide; and the mature hCD86-hIgG1 fusion protein (SEQ ID NO:178), which comprises the sequence of hCD86 ECD (SEQ ID NO:180) linked to the human IgG1 Fc polypeptide (SEQ ID NO:185). Exemplary nucleic acid sequences encoding hCD86-mIg and hCD80-mIg fusion proteins are shown in SEQ ID NOS:227 and 228, respectively.

In one aspect, the invention provides an isolated or recombinant fusion protein comprising (a) a polypeptide comprising a polypeptide sequence that has at least 80%, 85%, 90%, 91%, 92%, 93%, 94%, 95%, 96%, 97%, 98%, 99%, 99.5%, or 100% sequence identity to at least one polypeptide sequence selected from the group consisting of SEQ ID NOS:1-73, and (b) an Ig Fc polypeptide (e.g., hIgG2 Fc), wherein the fusion protein binds CD80 and/or CD86, and/or CD80-Ig and/or CD86-Ig fusion protein, and/or exhibits an ability to inhibit or suppress an immune response. The Ig Fc polypeptide may comprise a polypeptide sequence having at least 95%, 96%, 97%, 98%, 99%, or 100% identity to a polypeptide sequence selected from the group of SEQ ID NO:184, 185, 186, and 218. In some instances, the C-terminus of the polypeptide of (a) is covalently linked to the N-terminus of the Ig Fc polypeptide of (b). Some such mutant CTLA-4-Ig fusion proteins bind a mammalian CD80 and/or CD86 (e.g., hCD80 and/or hCD86), and/or a CD80-Ig and/or CD86-Ig fusion protein. A CD80-Ig may comprise, e.g., a human CD80 ECD linked to an Ig Fc (e.g., hCD80-Ig). In one embodiment, an hCD80-Ig is a human CD80 ECD linked to a human Ig Fc (hCD80-hIg); in another embodiment, an hCD80-Ig is a human CD80 ECD linked to a murine Ig Fc (hCD80-mIg). In one embodiment, an hCD86-Ig is a human CD86 ECD linked to a human Ig Fc (hCD86-hIg); in another embodiment, an hCD86-Ig is a human CD86 ECD linked to a murine Ig Fc (hCD86-mIg). Some such fusion proteins have an ability to inhibit or suppress one or more of a variety of immune responses, such as, e.g., T cell activation, T cell proliferation, cytokine synthesis or production (e.g., production of TNF-α, IFN-γ, IL-2), induction of activation markers (e.g., CD25, IL-2 receptor) or inflammatory molecules, inflammation, anti-collagen Ab production, and/or T cell-dependent Ab response(s) in in vitro and/or in vivo assays and/or methods. Such fusion proteins are expected to be of beneficial use in a variety of applications, including methods for treating immune system diseases and disorders (e.g., autoimmune diseases), and methods for inhibiting organ, cell, or tissue graft transplantation, as discussed below.

In another aspect, the invention provides an isolated or recombinant mutant CTLA-4-Ig fusion protein dimer comprising two monomeric mutant CTLA-4-Ig fusion proteins linked via at least one disulfide bond formed between two cysteine residues present in each monomeric mutant CTLA-4-Ig fusion protein. Each mutant CTLA-4-Ig fusion protein monomer comprises: (a) a mutant CTLA-4 ECD polypeptide comprising a polypeptide sequence having at least 90%, 91%, 92%, 93%, 94%, 95%, 96%, 97%, 98%, 99%, 99.5%, or 100% sequence identity to at least one polypeptide sequence selected from the group consisting of SEQ ID NOS:1-73, and (b) an Ig Fc polypeptide (e.g., hIgG2 Fc), wherein the fusion protein dimer binds CD80 and/or CD86, and/or CD80-Ig and/or CD86-Ig, and/or exhibits an ability to inhibit or suppress an immune response. In some instances, the C-terminus of the polypeptide of (a) is covalently linked or fused to the N-terminus of the Ig Fc polypeptide of (b). The Ig Fc polypeptide may comprise a polypeptide sequence having at least 95%, 96%, 97%, 98%, 99%, or 100% identity to a polypeptide sequence selected from the group consisting of SEQ ID NO:184-186 and 218. In some instances, the fusion protein dimer is formed by a covalent disulfide bond between a cysteine residue at amino acid position 120 of each mutant CTLA-4 ECD polypeptide sequence, or at an amino acid position corresponding to position 120 in each mutant CTLA-4 ECD polypeptide sequence relative to the hCTLA-4 ECD polypeptide sequence shown in SEQ ID NO:159. Some such fusion protein dimers have an ability to inhibit or suppress one or more of a variety of immune responses, such as, e.g., T cell activation, T cell proliferation, cytokine synthesis or production (e.g., production of TNF-α, IFN-γ, IL-2), induction of activation markers (e.g., CD25, IL-2 receptor) or inflammatory molecules, inflammation, anti-collagen Ab production, and/or T cell-dependent Ab response(s) in in vitro and/or in vivo assays and/or methods. Such fusion protein dimers are expected to be of beneficial use in a variety of applications, including methods for treating immune system diseases and disorders (e.g., autoimmune diseases), and methods for inhibiting organ, cell, or tissue graft transplantation, as discussed below.

Some such mutant CTLA-4-Ig fusion protein monomers have binding affinities for hCD86 or hCD86 ECD that are at least equal to or greater than those of hCTLA-4 ECD and LEA29 for hCD86 or hCD86 ECD, respectively. See, e.g., Table 5 in Example 4. The mutant CTLA-4 ECD polypeptide present in some such dimeric and monomeric fusion proteins comprises a polypeptide sequence having an amino acid length about equal to the amino acid length of the hCTLA-4 ECD. For example, some such mutant CTLA-4 ECD polypeptides comprise a polypeptide sequence that is about 110 to 138, 112 to 136, 114 to 134, 116 to 132, 118 to 130, 119 to 129, 120 to 128, 121 to 127, 122 to 126, or 123 to 125 amino acid residues in length. Some such mutant CTLA-4 ECD polypeptides comprise a sequence of 124 amino acid residues. Exemplary mutant CTLA-4 ECD polypeptides include, e.g., but are not limited to, those comprising a polypeptide sequence having at least 95%, 96%, 97%, 98%, 99% or 100% sequence identity to at least one polypeptide sequence selected from the group consisting of SEQ ID NOS:1-73, wherein such mutant CTLA-4 ECD polypeptide binds CD80 and/or CD86 (or an ECD of either or both), and/or has an ability to inhibit an immune response.

Some such mutant CTLA-4-Ig fusion protein dimers have a binding avidity for hCD86 and/or hCD86-Ig that is at least about equal to or greater than the binding avidity of a hCTLA-4-Ig fusion protein dimer (e.g., hCTLA-4-IgG2 or hCTLA-4-IgG1 dimer), Orencia® dimer, and/or LEA29Y-Ig dimer for hCD86 and/or hCD86-Ig, respectively. Some such fusion protein dimers have a binding avidity for hCD86 and/or hCD86-mIg that is 2-10 times (2×-10×), 5-10 times (5×-10×), 10-20 times (10×-20×), 20-40 times (20×-40×), or more than 40 times (>40×) greater than the binding avidity of Orencia® dimer for hCD86 and/or hCD86-mIg. See, e.g., exemplary dimeric fusion proteins of the invention in Table 3 below. Alternatively or additionally, some such fusion protein dimers have a binding avidity for hCD80 and/or hCD80-Ig that is at least about equal to or greater than the binding avidity of a hCTLA-4-Ig dimer (e.g., hCTLA-4-IgG2 or hCTLA-4-IgG1 dimer), Orencia® dimer, and/or LEA29Y-Ig dimer for hCD80 and/or hCD80-Ig, respectively. Some such fusion protein dimers have a binding avidity for hCD80 and/or hCD80-mIg that is 0.5-2 times (0.5×-2×), 2-4 times (2×-4×), or more than 2 times (>2×) greater than the binding avidity of Orencia® dimer for hCD86 and/or hCD86-mIg. See, e.g., exemplary dimeric fusion proteins of the invention in Table 4 below.

Some such mutant CTLA-4-Ig fusion protein dimers dissociate from binding hCD86 and/or hCD86-Ig at a rate that is less than the rate at which a hCTLA-4-Ig dimer (e.g., hCTLA-4-IgG2 or hCTLA-4-IgG1 dimer), Orencia® dimer, and/or LEA29Y-Ig dimer dissociates from binding hCD86 and/or hCD86-Ig, respectively. Some such fusion proteins associate with or bind to hCD86 and/or hCD86-Ig at a rate that is at least equal to or greater than the rate at which an hCTLA-4-Ig dimer (e.g., hCTLA-4-IgG2 or hCTLA-4-IgG1 dimer), Orencia® dimer, and/or LEA29Y-Ig dimer associates with hCD86 and/or hCD86-Ig, respectively. For some such fusion protein dimers, the equilibrium dissociation constant ($K_D$) for the binding reaction between CD86 (or CD86-Ig) and the fusion protein dimer of the invention is less than the equilibrium dissociation constant ($K_D$) for the binding reaction between CD86 (or CD86-Ig) and an hCTLA-4-Ig dimer (e.g., hCTLA-4-IgG2 or hCTLA-4-IgG1 dimer), Orencia® dimer, and/or LEA29Y-Ig dimer. See, e.g., exemplary fusion protein dimers of the invention in Table 3. For some such fusion protein dimers, the equilibrium dissociation constant ($K_D$) for the binding reaction between CD80 (or CD80-Ig) and the fusion protein dimer of the invention is about equal to or less than the equilibrium dissociation constant ($K_D$) for the binding reaction between CD80 (or CD80-Ig) and a hCTLA-4-Ig dimer (e.g., hCTLA-4-IgG2 or hCTLA-4-IgG1 dimer), Orencia® dimer, or LEA29Y-Ig dimer. See, e.g., exemplary fusion protein dimers of the invention in Table 4.

Some such mutant CTLA-4-Ig fusion protein dimers have an ability to inhibit or suppress an immune response (e.g., inhibit T cell activation or proliferation, inhibit cytokine production, etc.) that is at least about equal to or greater than the ability of a hCTLA-4-Ig dimer (e.g., hCTLA-4-IgG2 or hCTLA-4-IgG1 dimer), Orencia® dimer, and/or LEA29Y-Ig dimer to inhibit or suppress said immune response, respectively. For example, some such fusion protein dimers are capable of inhibiting T cell activation or T cell proliferation in in vitro assays. Examples 4-9 set forth below, for example, demonstrate the ability of representative fusion protein dimers of the invention comprising a representative mutant CTLA-4 ECD polypeptide sequence to inhibit T cell proliferation in vitro. Some such dimers are capable of inhibiting or suppressing an immune response in a subject in vivo, such as through the administration of a therapeutically or prophylactically effective amount of at least one such dimer to a subject needing immunosuppressive therapy. Some such fusion protein dimers are expected to be useful in a variety of applications, including, e.g., but not limited to, in prophylactic and/or therapeutic methods for inhibiting or suppressing an immune response in a subject suffering from an immune system disease or disorder in which immunosuppression is desirable (e.g., autoimmune diseases) and methods for inhibiting rejection of a tissue, cell, or organ transplant from a donor by a recipient.

Some such dimers have varied abilities to modulate or suppress signaling through CD28, since they have different comparative binding avidities for CD80 and CD86. Such dimers are useful in applications in which differential manipulation of T cell responses is desirable, including therapeutic and prophylactic methods for treating immune system diseases and disorders, such as, e.g., immunodeficiency diseases and disorders (e.g., RA, MS, psoriasis, etc.). Exemplary dimeric fusion proteins comprising polypeptides of the invention having some of the above-described differential CD80/CD86 binding avidities and immunoinhibitory properties are shown in Example 4.

Some such mutant CTLA-4-Ig dimers have an ability to suppress or inhibit an immune response that is at least about equal to or greater than the ability of the hCTLA-4 protein or a hCTLA-4-Ig dimer to suppress or inhibit one or more types of immune responses. For example, some such dimers have an ability to inhibit T cell activation or proliferation in in vitro and/or in vivo assays and/or applications, such as those described above and below, which is at least about equal to or greater than the ability of the hCTLA-4 protein or a hCTLA-4-Ig dimer (e.g., Orencia®, hCTLA-4-IgG2 dimer, or hCTLA-4-IgG1 dimer) to inhibit T cell activation or proliferation in such applications. Additionally, some such dimers have an ability to inhibit or suppress an immune response (e.g., T cell activation or proliferation, cytokine production, T cell-dependent antibody response) that is greater than the ability of a LEA29Y-Ig dimer to inhibit or suppress an immune response. Examples 4-9, e.g., compare the ability of representative dimeric fusion proteins of the invention comprising a mutant CTLA-4 ECD polypeptide sequence of the invention to inhibit T cell proliferation in vitro relative to the ability of dimeric hCTLA-4-IgG2, Orencia®, and LEAY29-Ig to inhibit T cell proliferation in vitro. See, e.g., Tables 6-9 below. Some such dimers have both an ability to bind hCD80 and/or hCD86 (or hCD80-Ig and/or hCD86-Ig) and an ability to inhibit or suppress an immune response in an in vitro and/or in vivo assays and/or applications, such as those described above and in greater detail below (e.g., an in vivo method in which in a therapeutically or prophylactically effective amount of at least one such dimer is administered). Some such dimers have a binding avidity for hCD80 and/or hCD86 (or hCD80-Ig and/or hCD86-Ig) that is at least about equal to or greater than the binding avidity of hCTLA-4 protein, a dimeric hCTLA-4-Ig (e.g., hCTLA-4-IgG2, Orencia®) or dimeric LEA29Y-Ig for hCD80 and/or hCD86 (or hCD80-Ig and/or hCD86-Ig), respectively, and an ability to inhibit an immune response that is at least equal to or greater than the ability of hCTLA-4 protein, a dimeric hCTLA-4-Ig (e.g., hCTLA-4-IgG2, Orencia®) or dimeric LEA29Y-Ig to inhibit an immune response. Such mutant CTLA-4-Ig fusion protein dimers are expected to be useful in a variety of applications, including, e.g., prophylactic and/or therapeutic methods for treating immune system diseases, disorders, and conditions, as discussed in greater detail infra.

In another aspect, the invention provides an isolated or recombinant fusion protein dimer (e.g., mutant CTLA-4-Ig fusion protein dimer) comprising two identical monomeric fusion proteins (e.g., two monomeric mutant CTLA-4-Ig fusion proteins), wherein each such monomeric fusion protein comprises a polypeptide sequence having at least 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, or 100% identity to a polypeptide sequence selected from the group consisting of SEQ ID NOS:74-79, 197-200, 205-214, and 219-222, wherein the dimer binds CD80 and/or CD86 (and/or a CD80-Ig and/or CD86-Ig, such as hCD80-mIg and/or hCD86-mIg, respectively), and/or has an ability to inhibit an immune response, including those described above and further below. Each of the polypeptide sequences set forth in SEQ ID NOS:74-79, 197-200, 205-214, and 219-222 is a mature mutant CTLA-4 ECD fused at its C-terminus to the N-terminus of an IgG2 Fc polypeptide, and each such sequence may be termed a mutant CTLA-4-Ig fusion protein. The polypeptide sequence of each of SEQ ID NOS:74-79, 197-200, 220, and 222 is identical to SEQ ID NOS:205-214, 219, and 221, except that each of SEQ ID NOS:74-79, 197-200, 220, and 222 includes a lysine at the C-terminus.

In another aspect, the invention provides an isolated or recombinant fusion protein monomer comprising a polypeptide sequence having at least 90%, 90.5%, 91%, 91.5%, 92%, 92.5%, 93%, 93.5%, 94%, 94.5%, 95%, 95.5%, 96%, 96.5%, 97%, 97.5%, 98%, 98.5%, 99%, 99.5%, or 100% identity to a polypeptide sequence comprising amino acid residues 1-351 of any of SEQ ID NOS:74-79, 197-200, 205-214, and 219-222, wherein the fusion protein binds CD80 and/or CD86 (and/or a CD80-Ig and/or CD86-Ig, such as hCD80-mIg and/or hCD86-mIg, respectively), and/or has an ability to inhibit an immune response, including those described above and further below.

In another aspect, the invention provides an isolated or recombinant fusion protein dimer comprising two identical monomeric fusion proteins, wherein each such monomeric fusion protein comprises a polypeptide sequence having at least 90%, 91%, 92%, 93%, 94%, 95%, 96%, 97%, 98%, 99% or 100% identity to a polypeptide sequence comprising amino acid residues 1-351 of any of SEQ ID NOS:74-79, 197-200, 205-214, and 219-222, wherein said fusion protein dimer protein binds CD80 and/or CD86 (and/or a CD80-Ig and/or CD86-Ig, such as hCD80-mIg and/or hCD86-mIg, respectively), and/or has an ability to inhibit an immune response, including those described above and further below.

Also provided is a mutant monomeric CTLA-4-Ig fusion protein comprising a polypeptide sequence having at least 90%, 91%, 92%, 93%, 94%, 95%, 96%, 97%, 98%, 99% or 100% identity to a polypeptide sequence selected from the group consisting of SEQ ID NOS:74-79, 197-200, 205-214, and 219-222, wherein said monomeric fusion protein binds CD80 and/or CD86 (and/or a CD80-Ig and/or CD86-Ig, such as hCD80-mIg and/or hCD86-mIg, respectively), and/or has an ability to inhibit an immune response. Some such fusion protein monomers and dimers have an ability to inhibit or suppress one or more immune responses, including, e.g., T cell activation or proliferation, cytokine synthesis or production (e.g., production of TNF-α, IFN-γ, IL-2), induction of activation markers (e.g., CD25, IL-2 receptor), inflammation, anti-collagen Ab production, and/or T cell-dependent Ab response(s)) in in vitro and/or in vivo assays and/or methods (e.g., in vivo in a subject suffering from a disease, disorder, or condition in which immunosuppressive therapy would be of benefit and to whom a therapeutically effective amount of such dimeric fusion protein is administered as discussed in greater detail below). Such fusion protein monomers and dimers are expected to be useful in a variety of applications, including therapeutic and/or prophylactic methods for treating immune system diseases, including those discussed below.

In another aspect, the invention provides an isolated or recombinant fusion protein dimer (e.g., mutant CTLA-4-Ig fusion protein dimer) comprising two monomeric fusion proteins (e.g., monomeric mutant CTLA-4-Ig fusion protein), wherein each such monomeric fusion protein comprises: (1) a polypeptide (e.g., mutant CTLA-4 extracellular domain polypeptide) which comprises a polypeptide sequence which differs from a polypeptide sequence selected from the group consisting of SEQ ID NOS:1-73 in no more than 6 amino acid residues (e.g., no more than 1, 2, 3, 4, 5, or 6 amino acid residues), and wherein the amino acid residue in the polypeptide sequence at position 41, 50, 54, 55, 56, 64, 65, 70, or 85 is identical to the amino acid residue at the corresponding position of said selected polypeptide sequence (e.g., a polypeptide selected from SEQ ID NOS:1-73), and (2) an Ig Fc polypeptide (e.g., IgG2 Fc), wherein the fusion protein dimer binds CD80 and/or CD86 (and/or CD80-Ig and/or CD86-Ig), and/or inhibits an immune response (e.g., T cell activation or proliferation, cytokine production, induction of activation markers or inflammatory molecules, anti-collagen Ab production, T cell-dependent Ab responses, etc.) in in vitro and/or in vivo assays and/or methods as discussed in detail below. The invention also includes an isolated or recombinant monomeric fusion protein as described above which binds CD80 and/or CD86 (and/or CD80-Ig and/or CD86-Ig) and/or induces an immune response in vitro or in vivo. In the fusion protein dimer, the two monomeric fusion proteins (e.g., mutant CTLA-4-Ig monomer) are optionally covalently linked together by one or more disulfide bonds via cysteine residues in each monomer, and the two monomers are typically identical to one another. In some instances, the mutant CTLA-4 ECD polypeptide in such fusion protein dimer or monomer differs from the selected polypeptide (e.g., selected from SEQ ID NOS:1-73) in no more than 6 amino acid residues, but the amino acid occupying position 41, 50, 54, 55, 56, 64, 65, 70, or 85 is identical to the amino acid residue included at that position in the selected polypeptide sequence; that is, an amino acid residue at such position cannot be deleted or substituted. Some such mutant CTLA-4 ECD polypeptides in such a fusion protein comprise a polypeptide sequence which differs from the selected polypeptide sequence by no more than 6 amino acid residues and which includes amino acid residues at positions 24, 30, 32, 41, 50, 54, 55, 56, 64, 65, 70, 85, 104 and 106 that are identical to the amino acid residues at the corresponding positions in the selected polypeptide sequence. Such mutant CTLA-4 ECD polypeptide can differ from the selected polypeptide sequence by amino acid deletion(s), addition(s), and/or amino acid substitution(s). An amino acid substitution may be a conservative or non-conservative substitution. See, e.g., the "Sequence Variation" section. Some such dimeric fusion proteins have a binding avidity for hCD86 or hCD86-Ig that is at least about equal to or greater than the binding avidity of hCTLA-4, dimeric hCTLA-4-Ig, dimeric LEA29Y-Ig, or Orencia® protein for hCD86 or hCD86-Ig, respectively. Some such monomeric fusion proteins have a binding affinity or avidity for hCD86, hCD86-Ig, or hCD86 ECD that is at least about equal to or greater than the binding affinity or avidity of the monomeric hCTLA-4, monomeric hCTLA-4-Ig, or monomeric LEA29Y-Ig for hCD86, hCD86-Ig, or hCD86 ECD, respectively. Alternatively or additionally, some such dimeric fusion proteins have a binding avidity for hCD80 or hCD80-Ig that is at least about equal to or greater than the avidity of hCTLA-4 or hCTLA-4-Ig for hCD80, respectively. Alternatively or additionally, some such monomeric fusion proteins have a binding affinity or avidity for hCD80, hCD80-Ig, or hCD80 ECD that is at least about equal to or greater than the binding affinity or avidity of monomeric hCTLA-4 or monomeric hCTLA-4-Ig for hCD80, hCD80-Ig, or hCD80 ECD, respectively. In some instances, the mutant CTLA-4 ECD polypeptide in such fusion protein dimer or monomer comprises a polypeptide sequence having a length about equal to the amino acid length of the hCTLA-4 ECD, e.g., from about 118-130, 119-129, 120-128, 121-127, 122-126, 123-125, or 124 amino acid residues in length. The N-terminus of the Ig Fc polypeptide (e.g., IgG2 Fc, IgG1 Fc, IgG4 Fc, or a mutant IgG Fc that reduces effector function or Fc receptor binding) may be covalently linked or fused directly or indirectly (via a linker comprising, e.g., from 1-10 amino acid residues) to the C-terminus of the mutant CTLA-4 ECD polypeptide. The Ig Fc polypeptide may comprise a polypeptide sequence having at least 95%, 96%, 97%, 98%, 99%, or 100% sequence identity to a polypeptide sequence selected from the group consisting of SEQ ID NOS:184-186 and 218, e.g., any of SEQ ID NO:184, 185, 186, and 218.

Some such mutant CTLA-4-Ig fusion protein dimers and monomers are capable of suppressing one or more of a variety of immune responses, including, e.g., T cell activation, T cell proliferation, cytokine synthesis or production (e.g., production of TNF-α, IFN-γ, IL-2), induction of activation markers (e.g., CD25, IL-2 receptor) or inflammatory molecules, inflammation, anti-collagen Ab production, and/or T cell-dependent Ab response(s). Some such mutant CTLA-4-Ig dimers have a greater ability to inhibit one or more such immune responses than hCTLA-4, dimeric hCTLA-4-Ig, or dimeric LEA29Y-Ig. Examples 4-9, e.g., provide data comparing the ability of representative dimeric fusion proteins of the invention comprising a mutant CTLA-4 ECD polypeptide of the invention to inhibit T cell proliferation in vitro relative to the ability of a dimeric hCTLA-4-Ig or dimeric LEA29Y-Ig to do so. Some such mutant CTLA-4-Ig monomers have a greater ability to inhibit one or more such immune responses than monomeric hCTLA-4, monomeric hCTLA-4-Ig, or monomeric LEA29Y-Ig. Some such monomers and dimers are capable of inhibiting or suppressing an immune response in a subject in vivo, such as through the administration of a therapeutically or prophylactically effective amount of at least one such polypeptide to a subject needing immunosuppressive therapy. Such fusion proteins are expected to be of beneficial use in a variety of applications, including methods for treating a disease, disorder, or condition in which immunosuppressive therapy would be of benefit, such as prophylactic and/or therapeutic methods for treating autoimmune diseases and disorders, and methods for inhibiting organ, cell, or tissue graft transplantation.

In another aspect, the invention provides an isolated or recombinant protein dimer (e.g., mutant CTLA-4-Ig fusion protein dimer) comprising two monomeric fusion proteins (e.g., two monomeric mutant CTLA-4-Ig fusion proteins), wherein each such monomeric fusion protein comprises: (1)

a mutant CTLA-4 extracellular domain (ECD) polypeptide comprising a polypeptide sequence which (a) differs from a polypeptide sequence selected from the group consisting of SEQ ID NOS:1-73 in no more than 6 amino acid residues (e.g., no more than 1, 2, 3, 4, 5, or 6 amino acid residues), and (b) comprises at least one amino acid substitution at an amino acid position corresponding to position 50, 54, 55, 56, 64, 65, 70, or 85 relative to the polypeptide sequence of SEQ ID NO:159; and (2) an Ig Fc polypeptide, wherein the fusion protein dimer binds CD80 and/or CD86 (and/or CD80-Ig and/or CD86-Ig), and/or inhibits an immune response (e.g., T cell activation or proliferation, cytokine production, induction of activation markers, inflammation, anti-collagen antibody production, T cell-dependent antibody response, etc.) in in vitro and/or in vivo assays and/or methods as described in greater detail below. The invention also includes an isolated or recombinant monomeric fusion protein, as described above, which binds CD80 and/or CD86 (and/or CD80-Ig and/or CD86-Ig) and/or induces an immune response in vitro or in vivo. In some instances, CD80 is hCD80 and CD86 is hCD86. In the fusion protein dimer, the two monomeric fusion proteins (e.g., mutant CTLA-4-Ig monomer) are optionally covalently linked together by one or more disulfide bonds via cysteine residues in each monomer, and the two monomers are typically identical to one another. The N-terminus of the Ig Fc polypeptide (e.g., IgG2 Fc, IgG1 Fc, IgG4 Fc, or a mutant IgG Fc that reduces effector function or Fc receptor binding) may be covalently linked or fused directly or indirectly (via a linker comprising, e.g., from 1-10 amino acid residues) to the C-terminus of the mutant CTLA-4 ECD polypeptide. The Ig Fc polypeptide may comprise a polypeptide sequence having at least 95%, 96%, 97%, 98%, 99%, or 100% sequence identity to a polypeptide sequence selected from the group consisting of SEQ ID NOS:184-186 and 218.

Some such fusion protein dimers or monomers comprise a mutant CTLA-4 ECD polypeptide which comprises a polypeptide sequence having a length about equal to the amino acid length of the hCTLA-4 ECD, e.g., 118-130, 119-129, 120-128, 121-127, 122-126, or 123-125 amino acid residues in length. Some such mutant CTLA-4 ECD polypeptides in such fusion protein dimer or monomer comprise a polypeptide sequence that is 124 amino acid residues in length. Some such mutant CTLA-4-ECD polypeptides comprise 2, 3, 4, 5, or 6 amino acid substitutions at positions relative to the sequence set forth in SEQ ID NO:159 selected from the group consisting of position 50, 54, 55, 56, 64, 65, 70, and 85. Some such mutant CTLA-4 ECD polypeptides further comprise an amino acid substitution at a position corresponding to position 104 and/or 30 relative to SEQ ID NO:159. Some such mutant CTLA-4 ECD polypeptides comprise at least one amino acid substitution relative to SEQ ID NO:159 at position 70 (optionally S70F), position 64 (optionally S64P), position 50 (optionally A50M), position 54 (optionally M54K/V, e.g., M54K), position 65 (optionally I65S), position 56 (optionally N56D), position 55 (optionally G55E), position 85 (optionally M85A), and/or position 24 (optionally A24E/S, e.g., A24E). Any such mutant CTLA-4 ECD polypeptide may further comprise an amino acid substitution relative to SEQ ID NO:159 at position 104 (optionally L104E/D, e.g., L104E), position 30 (optionally T30N/D/A, e.g., T30N, T30D, or T30A), and/or position 32 (optionally V32I). Some such mutant CTLA-4 ECD polypeptides comprise at least one substitution at an amino acid position relative to SEQ ID NO:159 selected from the group consisting of A50M, M54K, G55E, N56D, S64P, I65S, and S70F. Some such mutant CTLA-4 ECD polypeptides comprise 2, 3, 4, 5, or 6 substitutions at amino acid positions relative to SEQ ID NO:159 selected from the group consisting of A50M, M54K, G55E, N56D, S64P, I65S, and S70F.

Some such mutant CTLA-4-Ig dimers exhibit a binding avidity for CD86 (e.g., hCD86) or dimeric CD86-Ig (e.g., hCD86-Ig) that is about equal to or greater than the binding avidity of hCTLA-4 protein, dimeric hCTLA-4-Ig (e.g., CTLA-4-IgG1 or CTLA-4-IgG2), Orencia® protein, or dimeric LEA29Y-Ig for CD86 or dimeric CD86-Ig, respectively. Some such dimers have a binding avidity for CD80 (e.g., hCD80) or dimeric CD80-Ig (e.g., hCD80-Ig) that is greater than the binding avidity of hCTLA-4, a dimeric hCTLA-4-Ig, Orencia® protein, and/or dimeric LEAY29-Ig for CD80 or dimeric CD80-Ig, respectively.

Some such mutant CTLA-4-Ig monomers exhibit a binding affinity or avidity for CD86 (e.g., hCD86) or CD86-Ig (e.g., hCD86-Ig) that is about equal to or greater than the binding affinity or avidity of monomeric hCTLA-4, monomeric hCTLA-4-Ig, or monomeric LEA29Y-Ig for CD86 or CD86-Ig, respectively. Some such monomers have a binding affinity or avidity for CD80 (e.g., hCD80) or CD80-Ig (e.g., hCD80-Ig) that is greater than the binding affinity or avidity of monomeric hCTLA-4 or monomeric hCTLA-4-Ig (e.g., monomeric CTLA-4-IgG1 or CTLA-4-IgG2) for CD80 or dimeric CD80-Ig, respectively.

Some such mutant CTLA-4-Ig dimers and monomers have an ability to suppress or inhibit one or more immune responses, including those described above and throughout (e.g., T cell activation or proliferation, cytokine production, induction of activation markers, inflammation, anti-collagen antibody production, T cell-dependent antibody responses), in in vitro and/or in vivo assays and/or methods (e.g., in vivo in a subject suffering from a disease, disorder, or condition in which immunosuppressive therapy would be of benefit and to whom a therapeutically effective amount of at least one such mutant CTLA-4-Ig dimer is administered). Some such mutant CTLA-4-Ig dimers inhibit one or more such immune responses to a greater degree than hCTLA-4, a dimeric hCTLA-4-Ig (e.g., dimeric CTLA-4-IgG1 or CTLA-4-IgG2), Orencia® protein, and/or dimeric LEAY29-Ig. Some such mutant CTLA-4-Ig monomers inhibit one or more such immune responses to a greater degree than monomeric hCTLA-4, monomeric hCTLA-4-Ig, and/or monomeric LEAY29-Ig. Such mutant CTLA-4-Ig dimers and monomers are expected to be of beneficial use in a variety of applications, including methods for treating autoimmune diseases and disorders, and methods for inhibiting organ, cell, or tissue graft transplantation.

In another aspect, the invention provides an isolated or recombinant fusion protein dimer (e.g., mutant CTLA-4-Ig fusion protein dimer) comprising two monomeric fusion proteins (e.g., monomeric mutant CTLA-4-Ig fusion protein), wherein each such monomeric fusion protein comprises: (1) a polypeptide (e.g., mutant CTLA-4 extracellular domain) comprising a polypeptide sequence which (i) has at least 95%, 96%, 97%, 98%, 99%, or 100% sequence identity to any polypeptide sequence selected from the group consisting of SEQ ID NOS:1-73 and (ii) includes a phenylalanine residue at an amino acid position corresponding to position 70 of said polypeptide sequence selected from the group consisting of SEQ ID NO:1-73; and (2) an Ig Fc polypeptide (e.g., IgG2 Fc, IgG1 Fc, IgG4 Fc, or a mutant IgG Fc that reduces effector function or Fc receptor binding), wherein the fusion protein dimer binds CD80 (e.g., hCD80) and/or CD86 (e.g., hCD86) (and/or CD80-Ig, e.g., hDC80-Ig, and/or CD86-Ig, e.g., hCD86-Ig), and/or has an ability to inhibit an immune response in vitro or in vivo. The invention also includes an isolated or recombinant monomeric fusion protein as described above which binds CD80 (e.g., hCD80) and/or CD86 (e.g., hCD86) (and/or CD80-Ig, e.g., hDC80-Ig, and/or CD86-Ig, e.g., hCD86-Ig) and/or induces an immune response in vitro or in vivo. In some instances, the Ig Fc polypeptide comprises a sequence having at least 95%, 96%, 97%, 98%, 99%, or 100% sequence identity to a polypeptide sequence selected from the group consisting of SEQ ID NOS: 184-186 and 218. The N-terminus of the Ig Fc polypeptide may be covalently linked or fused directly or indirectly (via a linker comprising, e.g., from 1-10 amino acids) to the C-terminus of the mutant CTLA-4 ECD polypeptide.

In some such mutant CTL-4-Ig dimers or monomers, the mutant CTLA-4 ECD polypeptide comprises one or more of the following relative to said selected polypeptide sequence: a glutamic acid residue at an amino acid position corresponding to position 24; an asparagine residue at an amino acid position corresponding to position 30; an isoleucine residue at an amino acid position corresponding to position 32; a methionine residue at an amino acid position corresponding to position 50; a lysine residue at an amino acid position corresponding to position 54; a glutamic acid residue at an amino acid position corresponding to position 55; an aspartic acid residue at an amino acid position corresponding to position 56; a proline residue at an amino acid position corresponding to position 64; a serine residue at an amino acid position corresponding to position 65; and a glutamic acid residue at an amino acid position corresponding to position 104. For example, some such mutant CTLA-4 ECD polypeptides in such mutant CTLA-4-Ig dimers or monomers comprise a polypeptide sequence comprising (i) at least 95%, 96%, 97%, 98%, 99%, or 100% sequence identity to the polypeptide sequence of SEQ ID NO:24 and (ii) a phenylalanine residue at an amino acid position corresponding to position 70 of the polypeptide sequence of SEQ ID NO:24, wherein the fusion protein dimer binds hCD80 and/or hCD86 (and/or hCD80-Ig and/or hCD86-Ig), and/or inhibits an immune response in in vitro and/or in vivo assays and/or methods. Some such mutant CTLA-4 ECD polypeptides in such mutant CTLA-4-Ig dimers or monomers comprises one or more of the following relative to SEQ ID NO:24: a glutamic acid residue at position 24; an asparagine residue at position 30; an isoleucine residue at position 32; a methionine residue at position 50; a lysine residue at position 54; a glutamic acid residue at position 55; an aspartic acid residue at position 56; a proline residue at position 64; a serine residue at position 65; and a glutamic acid residue at position 104.

Some such mutant CTLA-4-Ig dimers exhibit a binding avidity for CD86 (e.g., hCD86) or dimeric CD86-Ig (e.g., hCD86-Ig) that is about equal to or greater than the binding avidity of hCTLA-4, dimeric hCTLA-4-Ig, Orencia® protein, or dimeric LEA29Y-Ig for CD86 or dimeric CD86-Ig, respectively. Some such dimers have a binding avidity for CD80 (e.g., hCD80) or dimeric CD80-Ig (e.g., hCD80-Ig) that is greater than the binding avidity of hCTLA-4, a dimeric hCTLA-4-Ig, or Orencia® protein for CD80 or dimeric CD80-Ig, respectively.

Some such mutant CTLA-4-Ig monomers exhibit a binding affinity or avidity for CD86 (e.g., hCD86) or CD86-Ig (e.g., hCD86-Ig) that is about equal to or greater than the binding affinity or avidity of monomeric hCTLA-4, monomeric hCTLA-4-Ig, and/or monomeric LEA29Y-Ig for CD86 or CD86-Ig, respectively. Some such monomers have a binding affinity or avidity for CD80 (e.g., hCD80) or CD80-Ig (e.g., hCD80-Ig) that is greater than the binding affinity or avidity of monomeric hCTLA-4 or monomeric hCTLA-4-Ig for CD80 or dimeric CD80-Ig, respectively.

Some such mutant CTLA-4-Ig dimers and monomers have an ability to suppress or inhibit one or more immune responses (e.g., T cell activation or proliferation, cytokine production, induction of activation markers, inflammation, anti-collagen Ab production, T cell-dependent Ab responses), in in vitro and/or in vivo assays and/or methods (e.g., in vivo in a subject suffering from an immune system disease, disorder, or condition in which immunosuppressive therapy would be of benefit and to whom a therapeutically effective amount of at least one such mutant CTLA-4-Ig dimer is administered). Some such mutant CTLA-4-Ig dimers have an ability to suppress or inhibit one or more such immune responses to a greater degree than hCTLA-4, a dimeric hCTLA-4-Ig (e.g., dimeric CTLA-4-IgG1 or CTLA-4-IgG2), Orencia® protein, and/or dimeric LEAY29-Ig. Some such mutant CTLA-4-Ig monomers have an ability to suppress or inhibit one or more such immune responses to a greater degree than monomeric hCTLA-4, monomeric hCTLA-4-Ig, and/or monomeric LEAY29-Ig. Such mutant CTLA-4-Ig dimers and monomers are expected to be of beneficial use in a variety of therapeutic and/or prophylactic methods for treating diseases or disorders in which immunosuppressive treatment would be of benefit, including, e.g., methods for treating autoimmune diseases and methods for inhibiting rejection of organ, cell, or tissue graft transplant.

In yet another aspect, the invention provides an isolated or recombinant fusion protein dimer (e.g., mutant CTLA-4-Ig fusion protein dimer) comprising two monomeric fusion proteins (e.g., monomeric mutant CTLA-4-Ig fusion proteins), wherein each such monomeric fusion protein comprises: (1) a polypeptide (e.g., mutant CTLA-4 extracellular domain) comprising a polypeptide sequence which (a) differs from the polypeptide sequence of the human CTLA-4 extracellular domain polypeptide shown in SEQ ID NO:159 in no more than 6 amino acid residues, and (b) comprises at least one amino acid substitution, wherein said at least amino acid substitution comprises S70F, wherein amino acid residue positions are numbered according to SEQ ID NO:159; and (2) an IgG Fc polypeptide (e.g., IgG2 Fc, IgG1 Fc, IgG4 Fc, or a mutant IgG Fc that reduces effector function or Fc receptor binding), wherein said dimer binds hCD80 and/or hCD86 (and/or hCD86-Ig and/or hCD86-Ig), and/or inhibits an immune response (e.g., T cell activation or proliferation, cytokine production, induction of activation markers, inflammation, anti-collagen antibody production, T cell-dependent antibody response, etc.) in in vitro and/or in vivo assays and/or methods as discussed in detail below. The invention also includes an isolated or recombinant monomeric fusion protein as described above which binds CD80 (e.g., hCD80) and/or CD86 (e.g., hCD86) (and/or CD80-Ig, e.g., hDC80-Ig, and/or CD86-Ig, e.g., hCD86-Ig) and/or induces an immune response in vitro or in vivo. The Ig Fc polypeptide may comprise a sequence having at least 95%, 96%, 97%, 98%, 99%, or 100% identity to a polypeptide sequence selected from the group consisting of SEQ ID NOS:184-186 and 218. The N-terminus of the Ig Fc polypeptide may be covalently linked or fused directly or indirectly (via a linker comprising, e.g., from 1-10 amino acids) to the C-terminus of the mutant CTLA-4 ECD polypeptide. In some such mutant CTLA-4-Ig dimers or monomers, the mutant CTLA-4 ECD polypeptide further comprises at least one amino acid substitution selected from the group consisting of A24E, T30N, V32I, D41G, A50M, M54K, G55E, N56D, S64P, I65S, M85A, L104E, and I106F. In some such mutant CTLA-4-Ig dimers or monomers, the mutant CTLA-4 ECD polypeptide further comprises the substitution L104E and/or two, three, or four additional substitutions selected from the group of substitutions: T30N, V32I, A50M, M54K, G55E, N56D, S64P, and I65S.

Some such dimers have a binding avidity for CD86 (e.g., hCD86) or dimeric CD86-Ig (e.g., hCD86-Ig) that is about equal to or greater than the binding avidity of hCTLA-4, dimeric hCTLA-4-Ig, and/or Orencia® protein for CD86 or dimeric CD86-Ig, respectively. Some such dimers have a binding avidity for CD80 (e.g., hCD80) or dimeric CD80-Ig (e.g., hCD80-Ig) that is greater than the binding avidity of hCTLA-4, a dimeric hCTLA-4-Ig, and/or Orencia® for CD80 or dimeric CD80-Ig, respectively. Some such monomers exhibit a binding affinity or avidity for CD86 (e.g., hCD86) or CD86-Ig (e.g., hCD86-Ig) that is about equal to or greater than the binding affinity or avidity of monomeric hCTLA-4, monomeric hCTLA-4-Ig, or monomeric LEA29Y-Ig for CD86 or CD86-Ig, respectively. Some such monomers have a binding affinity or avidity for CD80 (e.g., hCD80) or CD80-Ig (e.g., hCD80-Ig) that is greater than the binding affinity or avidity of monomeric hCTLA-4 or monomeric hCTLA-4-Ig for CD80 or dimeric CD80-Ig, respectively.

Some such mutant CTLA-4-Ig dimers and monomers have an ability to suppress or inhibit one or more immune responses (e.g., T cell activation or proliferation, cytokine production, induction of activation markers, inflammation, anti-collagen antibody production, T cell-dependent antibody responses), in in vitro and/or in vivo assays and/or methods (e.g., in vivo in a subject suffering from a disease, disorder, or condition in which immunosuppressive therapy would be of benefit and to whom a therapeutically effective amount of at least one such mutant CTLA-4-Ig dimer is administered). Some such dimers have an ability to suppress or inhibit one or more such immune responses to a greater degree than hCTLA-4, a dimeric hCTLA-4-Ig (e.g., dimeric CTLA-4-IgG1 or CTLA-4-IgG2), Orencia® protein, and/or dimeric LEAY29-Ig. Some such monomers have an ability to suppress or inhibit one or more such immune responses to a greater degree than monomeric hCTLA-4, monomeric hCTLA-4-Ig, and/or monomeric LEAY29-Ig. Such mutant CTLA-4-Ig dimers and monomers are expected to be of beneficial use in a variety of therapeutic and/or prophylactic methods for treating diseases or disorders in which immunosuppressive treatment would be of benefit, including, e.g., methods for treating autoimmune diseases and disorders and methods for inhibiting organ or tissue graft transplantation.

In another aspect, the invention provides an isolated or recombinant fusion protein dimer (e.g., mutant CTLA-4-Ig fusion protein dimer) comprising two monomeric fusion proteins (e.g., mutant CTLA-4-Ig fusion protein), wherein each such monomeric fusion protein comprises: (1) a polypeptide (e.g., mutant CTLA-4 extracellular domain) comprising a polypeptide sequence which (a) differs from the polypeptide sequence of SEQ ID NO:31 in no more than 6 amino acid residues, and (b) comprises at least one of the following: a methionine residue at a position corresponding to position 50 of SEQ ID NO:31, a lysine residue at a position corresponding to position 54 of SEQ ID NO:31, a glutamic acid residue at a position corresponding to position 55 of SEQ ID NO:31, a proline residue at a position corresponding to position 64 of SEQ ID NO:31, a serine residue at a position corresponding to position 65 of SEQ ID NO:31, a phenylalanine residue at a position corresponding to position 70 of SEQ ID NO:31, wherein amino acid residue positions are numbered according to SEQ ID NO:31; and (2) an Ig Fc polypeptide, wherein said dimer binds hCD80 and/or hCD86 (and/or hCD86-Ig and/or hCD86-Ig), and/or inhibits an immune response. The invention also includes an isolated or recombinant monomeric fusion protein as described above which binds CD80 (e.g., hCD80) and/or CD86 (e.g., hCD86) (and/or CD80-Ig, e.g., hDC80-Ig, and/or CD86-Ig, e.g., hCD86-Ig) and/or induces an immune response in vitro or in vivo. The Ig Fc polypeptide may comprise a IgG2 Fc, IgG1 Fc, IgG4 Fc, or a mutant IgG Fc that reduces effector function or Fc receptor binding. The Ig Fc polypeptide may comprise a sequence having at least 95%, 96%, 97%, 98%, 99%, or 100% identity to a polypeptide sequence selected from the group consisting of SEQ ID NOS:184-186 and 218. The N-terminus of the Ig Fc polypeptide may be covalently linked or fused directly or indirectly (via a linker comprising, e.g., from 1-10 amino acids) to the C-terminus of the mutant CTLA-4 ECD polypeptide. In some such dimers or monomers, the mutant CTLA-4 ECD polypeptide comprises a glutamic acid residue at a position corresponding to position 104, an asparagine acid residue at a position corresponding to position 30, and/or an isoleucine residue at a position corresponding to position 32 of SEQ ID NO:31.

Some such dimers have a binding avidity for CD86 (e.g., hCD86) or dimeric CD86-Ig (e.g., hCD86-Ig) that is about equal to or greater than the binding avidity of hCTLA-4 protein, dimeric hCTLA-4-Ig, Orencia® protein, and/or dimeric LEAY29-Ig for CD86 or dimeric CD86-Ig, respectively. Some such dimers have a binding avidity for CD80 (e.g., hCD80) or dimeric CD80-Ig (e.g., hCD80-Ig) that is greater than the binding avidity of hCTLA-4, dimeric hCTLA-4-Ig, and/or Orencia® protein for CD80 or dimeric CD80-Ig, respectively. Some such monomers exhibit a binding affinity or avidity for CD86 (e.g., hCD86) or CD86-Ig (e.g., hCD86-Ig) that is about equal to or greater than the binding affinity or avidity of monomeric hCTLA-4, monomeric hCTLA-4-Ig, or monomeric LEA29Y-Ig for CD86 or CD86-Ig, respectively. Some such monomers have a binding affinity or avidity for CD80 (e.g., hCD80) or CD80-Ig (e.g., hCD80-Ig) that is greater than the binding affinity or avidity of monomeric hCTLA-4 or monomeric hCTLA-4-Ig for CD80 or dimeric CD80-Ig, respectively.

Some such mutant CTLA-4-Ig dimers and monomers have an ability to suppress or inhibit one or more immune responses (e.g., T cell activation or proliferation, cytokine production, induction of activation markers, inflammation, anti-collagen antibody production, T cell-dependent antibody responses) in vitro and/or in vivo as discussed in detail below. Some such dimers have an ability to suppress one or more such immune responses to a greater degree than hCTLA-4, a dimeric hCTLA-4-Ig, Orencia® protein, and/or dimeric LEAY29-Ig. Some such monomers have an ability to suppress or inhibit one or more such immune responses to a greater degree than monomeric hCTLA-4 or a monomeric hCTLA-4-Ig. Such mutant CTLA-4-Ig dimers and monomers are expected to be of beneficial use in a variety of therapeutic and/or prophylactic methods for treating immune system diseases or disorders in which immunosuppressive treatment would be of benefit (e.g., autoimmune diseases and disorders and methods for inhibiting organ or tissue graft transplantation).

Any such dimeric or monomeric mutant CTLA-4-Ig fusion protein dimer or monomer described above may further include a peptide that facilitates secretion of the fusion protein from a host cell. The peptide is optionally a signal peptide. The C-terminus of the signal peptide is typically covalently linked to the N-terminus of a fusion protein. The signal peptide may comprise an amino acid sequence having at least 90%, 91%, 92%, 93%, 94%, 95%, 96%, 97%, 98%, 99%, or 100% identity to the amino acid sequence of SEQ ID NO:182 or SEQ ID NO:216. The signal peptide may comprise an amino acid sequence having at least 90%, 91%, 92%, 93%, 94%, 95%, 96%, 97%, 98%, 99%, or 100% identity to an amino acid sequence comprising amino acid residues 1-35, 1-36, or 1-37 of SEQ ID NO:160. Furthermore, as discussed below, any such monomeric or dimeric mutant CTLA-4-Ig fusion protein described above may comprise one or more of the amino acid residues that are glycosylated or pegylated.

The invention also provides a mature/secreted mutant CTLA-4-IgG2 fusion protein that is 352 amino acids in length and comprises a mutant CTLA-4 ECD polypeptide comprising 124 amino acid residues and a human IgG2 Fc polypeptide comprising 228 amino acid residues. Exemplary mutant CTLA-4 ECD polypeptides include those polypeptides comprising sequences identified by any of SEQ ID NOS:1-73. Exemplary mutant CTLA-4-IgG2 fusion proteins include those comprising a polypeptide sequence identified by any of SEQ ID NOS:74-79, 197-200, 205-214, and 219-222. If desired, the amino acids of a mature mutant CTLA-4-IgG2 fusion protein can be numbered beginning with the first amino acid residue of the mutant CTLA-4-IgG2 (i.e., the first residue of the mutant CTLA-4 ECD polypeptide). In some aspects, the first residue of the mutant CTLA-4-IgG2 fusion protein (or mutant CTLA-4 ECD) is methionine and thus the numbering of amino acids of the mutant CTLA-4-IgG2 fusion protein (or mutant CTLA-4 ECD) would begin with methionine (designated as amino acid residue 1).

The invention also includes isolated or recombinant multimeric fusion proteins comprising two or more mutant CTLA-4-Ig fusion proteins described above. In some instances, the multimer is a fusion protein dimer comprising two mutant CTLA-4-Ig fusion proteins, which may be identical fusion proteins (i.e., homodimer) or different fusion proteins (i.e., heterodimer). In some instances, the multimer is a tetrameric fusion protein, which comprises four mutant CTLA-4-ECD polypeptides of the invention. The tetramer can comprise four identical mutant CTLA-4 ECD polypeptides (i.e., homotetramer) or any combination of four mutant CTLA-4 ECD polypeptides of the invention such that all four mutant CTLA-4 ECD polypeptides are not identical (i.e., heterotetramer). Some such multimers bind CD80 and/CD86 (and/or hCD80-Ig and/or hCD86-Ig) and/or suppress or inhibit an immune response.

The invention includes soluble forms of any of the polypeptides, fusion proteins, and multimers described above. Also included are soluble forms on the conjugate of the invention described below. Soluble molecules of the invention—e.g., soluble polypeptides, dimeric fusion proteins, monomeric fusion proteins, multimers, and conjugates of the invention—are not linked or joined or bound to a cell. Some such soluble molecules may be in solution or are capable of circulating, e.g., in a fluid (e.g., in a subject's body). A signal peptide may typically be used to facilitate secretion of such a molecule, but the signal peptide is cleaved during secretion of the molecule from a host cell. Thus, in most instances, a soluble molecule, such as a soluble polypeptide, dimeric fusion protein, monomeric fusion protein, or multimer, does not include a signal peptide. As discussed above, a mutant CTLA-4 extracellular domain polypeptide of the invention can be linked to an Ig molecule, including, e.g., a portion of an Ig polypeptide, such as, e.g., an Ig Fc polypeptide, which results in a soluble fusion protein. Thus, in one aspect, the invention includes soluble mutant CTLA-4-Ig fusion proteins which comprise any mutant CTLA-4 ECD polypeptide of the invention as described herein fused or linked to at least a portion of an Ig polypeptide, such as, e.g., a wild-type Ig Fc (e.g., human IgG2 Fc) or mutant Ig Fc polypeptide. Such soluble mutant CTLA-4-Ig fusion proteins may be monomeric or dimeric fusion proteins and include those mutant CTLA-4-Ig fusion protein monomers and dimers described in detail above and elsewhere, including in the Examples below. As described in detail above and elsewhere herein, some such soluble monomeric and dimeric fusion proteins may have an ability to bind CD80 and/or CD86 and/or an ability to suppress or inhibit an immune response (e.g., T cell activation or proliferation) in in vitro and/or in vivo applications.

Such soluble molecules of the invention are expected to be of particular benefit in a variety of applications, including, e.g., therapeutic and prophylactic methods for treating immune system diseases and disorders (e.g., autoimmune diseases) and prophylactic and therapeutic methods for inhibiting cell, organ or tissue graft transplantation. Soluble molecules of the invention—e.g., soluble recombinant mutant CTLA-4 ECD polypeptides, monomeric and dimeric mutant CTLA-4-Ig fusion proteins, mutant CTLA-4 ECD conjugates, mutant CTLA-4-Ig conjugates, multimers comprising mutant CTLA-4 ECD polypeptides or mutant CTLA-4-Ig, multimers comprising mutant CTLA-4 conjugates or mutant CTLA-4-Ig conjugates of the invention—which bind CD80 and/or CD86, when administered to a subject in a therapeutically or prophylactically effective amount, inhibit the interaction between endogenous CD80 and/or CD86 and endogenous CD28, thereby suppressing in the subject an immune system response or immune system attack on the subject's healthy body tissues, organs, and/or cells. In instances where a subject is the recipient of healthy body tissues, organs, and/or cells from a donor (e.g., such as where the subject recipient has received a donor tissue graft or cell or organ transplant), such soluble molecules inhibit the interaction between endogenous CD80 and/or CD86 and endogenous CD28, thereby inhibiting a harmful response or attack by the subject's immune system on the healthy body tissues, organs, or cells donated to the subject by the donor. By suppressing an immune system response or attack on healthy body tissues, the side effects (e.g., pain, joint inflammation, etc.) associated with such immune system response or attack on healthy tissues, organs, or cells in the subject can be decreased, and the damage resulting from such a response or attack can be retarded or prevented.

Methods for measuring binding affinities and avidities of polypeptides of the invention described above, including, e.g., mutant CTLA-4 ECD polypeptides, dimeric and monomeric mutant CTLA-4-Ig fusion proteins, and multimers of the invention would be known to those of ordinary skill in the art and include, e.g., but are not limited to, Biacore™ technology (GE Healthcare), isothermal titration microcalorimetry (MicroCal LLC, Northampton, Mass.), ELISA, binding affinity phage display methods, and FACS methods. Biacore methods are described in detail in Example 4 below. FACS or other sorting methods are described in greater detail above and elsewhere herein. Methods for measuring binding avidities of polypeptides of the invention to hCD80 and/or hCD86 by phage ELISA are described in Example 2 below.

Methods for detecting and measuring T cell responses induced by molecules of the invention (including, e.g., mutant CTLA-4 ECD polypeptides, dimeric and monomeric mutant CTLA-4-Ig fusion proteins, and multimers of the invention) are well known to those skilled in the art. T cell activation is commonly characterized by physiological events including, e.g., T cell-associated cytokine synthesis (e.g., IFN-γ production) and induction of activation markers (e.g., CD25, IL-2 receptor). CD4+ T cells recognize their immunogenic peptides in the context of MHC class II molecules, whereas CD8+ T cells recognize their immunogenic peptides in the context of MHC class I molecules. Exemplary methods for assessing and measuring the ability of molecules of the invention described above to inhibit or suppress T cell activation and/or T cell proliferation or to block signaling through CD86 and/or CD80 are described in Examples 5-8 and elsewhere herein.

Polypeptides, monomeric and dimeric fusion proteins, and multimers of the invention, including those discussed above, optionally further comprise an additional amino acid, such as a methionine, added to the N-terminus and/or a peptide tag for purification or identification. Polypeptides of the invention, including those discussed above, optionally further comprise a polypeptide purification subsequence, such as, e.g., a subsequence is selected from an epitope tag, a FLAG tag, a polyhistidine sequence, and a GST fusion.

In addition, as discussed in greater detail below, the invention includes isolated, recombinant, or synthetic nucleic acids encoding all polypeptides, fusion proteins, and multimers of the invention described above and in additional detail below.

Sequence Identity

As discussed above, in one aspect, the invention includes an isolated or recombinant polypeptide which comprises a polypeptide sequence having at least 85%, 86%, 87%, 88%, 89%, 90%, 91%, 92%, 93%, 94%, 95%, 96%, 97%, 98%, 99%, 99.5%, or 100% sequence identity to a polypeptide sequence selected from the group consisting of SEQ ID NOS: 1-73, wherein the polypeptide binds CD80 or CD86 or an extracellular domain of either and/or has an ability to suppress or inhibit an immune response. In another aspect, as described in detail below, the invention provides an isolated or recombinant nucleic acid comprising a polynucleotide sequence that encodes a polypeptide comprising a polypeptide sequence having at least 75%, 80%, 85%, 86%, 87%, 88%, 89%, 90%, 91%, 92%, 93%, 94%, 95%, 96%, 97%, 98%, 99%, 99.5%, or 100% sequence identity to at least one polypeptide sequence selected from the group consisting of SEQ ID NOS:1-73, wherein the polypeptide has an ability to bind CD80 and/or CD86 and/or an ECD thereof, and/or has an ability to suppress an immune response, or a complementary polynucleotide sequence thereof.

The degree to which a sequence (polypeptide or nucleic acid) is similar to another provides an indication of similar structural and functional properties for the two sequences. Accordingly, in the context of the present invention, sequences that have a similar sequence to any given exemplar sequence are a feature of the present invention. Sequences that have percent sequence identities as defined below are a feature of the invention. A variety of methods of determining sequence relationships can be used, including manual alignment and computer assisted sequence alignment and analysis. A variety of computer programs for performing sequence alignment are available, or can be produced by one of skill.

As noted above, the sequences of the nucleic acids and polypeptides employed in the subject invention need not be identical, but can be substantially identical to the corresponding sequence of a nucleic acid of the invention or polypeptide of the invention, respectively. For example, polypeptides of the invention can be subject to various changes, such as one or more amino acid insertions, deletions, and/or substitutions, either conservative or non-conservative, including where, e.g., such changes might provide for certain advantages in their use, such as, in their therapeutic or prophylactic use or administration or diagnostic application. The nucleic acids of the invention can also be subject to various changes, such as one or more substitutions of one or more nucleic acids in one or more codons such that a particular codon encodes the same or a different amino acid, resulting in either a silent variation (e.g., mutation in a nucleotide sequence results in a silent mutation in the amino acid sequence, e.g., when the encoded amino acid is not altered by the nucleic acid mutation) or non-silent variation, one or more deletions of one or more nucleic acids (or codons) in the sequence, one or more additions or insertions of one or more nucleic acids (or codons) in the sequence, cleavage of or one or more truncations of one or more nucleic acids (or codons) in the sequence. The nucleic acids can also be modified to include one or more codons that provide for optimum expression in an expression system (e.g., bacterial or mammalian), while, if desired, said one or more codons still encode the same amino acid(s). Such nucleic acid changes might provide for certain advantages in their therapeutic or prophylactic use or administration, or diagnostic application. The nucleic acids and polypeptides can be modified in a number of ways so long as they comprise a sequence substantially identical (as defined below) to a sequence in a respective nucleic acid or polypeptide of the invention.

The term "identical" or "identity," in the context of two or more nucleic acid or polypeptide sequences, refers to two or more sequences that are the same or have a specified percentage of amino acid residues or nucleotides that are the same, when compared and aligned for maximum similarity, as determined using the sequence comparison algorithm described below or by visual inspection. The "percent sequence identity" ("% identity") of a subject sequence to a reference (i.e. query) sequence means that the subject sequence is identical (i.e., on an amino acid-by-amino acid basis for a polypeptide sequence, or a nucleotide-by-nucleotide basis for a polynucleotide sequence) by a specified percentage to the query sequence over a comparison length.

The percent sequence identity ("% sequence identity" or "% identity") of a subject sequence to a query sequence can be calculated as follows. First, the optimal alignment of the two sequences is determined using a sequence comparison algorithm with specific alignment parameters. This determination of the optimal alignment may be performed using a computer, or may be manually calculated, as described below. Then, the two optimally aligned sequences are compared over the comparison length, and the number of positions in the optimal alignment at which identical residues occur in both sequences are determined, which provides the number of matched positions. The number of matched positions is then divided by the total number of positions of the comparison length (which, unless otherwise specified, is the length of the query sequence), and then multiplying the result by 100, to yield the percent sequence identity of the subject sequence to the query sequence.

With regard to polypeptide sequences, typically one sequence is regarded as a "query sequence" (for example, a polypeptide sequence of the invention) to which one or more other sequences, i.e., "subject sequence(s)" (for example, sequences present in a sequence database) are compared. The sequence comparison algorithm uses the designated alignment parameters to determine the optimal alignment between the query sequence and the subject sequence(s). When comparing a query sequence against a sequence database, such as, e.g., GENBANK® database (Genetic Sequence Data Bank; U.S. Department of Health and Human Services) or GENESEQ® database (Thomson Derwent; also available as DGENE® database on STN), usually only the query sequence and the alignment parameters are input into the computer; optimal alignments between the query sequence and each subject sequence are returned for up to a specified number of subject sequences.

1. Determining the Optimal Alignment

Two polypeptide sequences are "optimally aligned" when they are aligned using defined parameters, i.e., a defined amino acid substitution matrix, gap existence penalty (also termed gap open penalty), and gap extension penalty, so as to arrive at the highest similarity score possible for that pair of sequences. The BLOSUM62 matrix (Henikoff and Henikoff (1992) Proc. Natl. Acad. Sci. USA 89(22):10915-10919) is often used as a default scoring substitution matrix in polypeptide sequence alignment algorithms (such as BLASTP, described below). The gap existence penalty is imposed for the introduction of a single amino acid gap in one of the aligned sequences, and the gap extension penalty is imposed for each residue position in the gap. Unless otherwise stated, alignment parameters employed herein are: BLOSUM62 scoring matrix, gap existence penalty=11, and gap extension penalty=1. The alignment score is defined by the amino acid positions of each sequence at which the alignment begins and ends (e.g., the alignment window), and optionally by the insertion of a gap or multiple gaps into one or both sequences, so as to arrive at the highest possible similarity score.

While optimal alignment between two or more sequences can be determined manually (as described below), the process is facilitated by the use of a computer-implemented alignment algorithm such as BLAST® (National Library of Medicine), e.g., BLASTP for polypeptide sequences and BLASTN for nucleic acid sequences, described in Altschul et al. (1997) Nucleic Acids Res. 25:3389-3402, and made available to the public through various sources, such as the National Center for Biotechnology Information (NCBI) website. When using a computerized BLAST interface, if the option exists to use a "low complexity filter", this option should be turned off (i.e., no filter).

The optimal alignment between two polypeptide sequences can also be determined by a manual calculation of the BLASTP algorithm (i.e., without aid of a computer) using the same alignment parameters specified above (matrix=BLOSUM62, gap open penalty=11, and gap extension penalty=1). To begin, the two sequences are initially aligned by visual inspection. An initial alignment score is then calculated as follows: for each individual position of the alignment (i.e., for each pair of aligned residues), a numerical value is assigned according to the BLOSUM62 matrix (FIG. 13). The sum of the values assigned to each pair of residues in the alignment is the alignment score. If the two sequences being aligned are highly similar, often this initial alignment provides the highest possible alignment score. The alignment with the highest possible alignment score is the optimal alignment based on the alignment parameters employed.

Examples of the manual calculation of alignment scores for two sequences are provided in FIGS. 14A-14D. FIG. 14A shows is the calculation of an alignment score for an arbitrary alignment (alignment 14A) of a "query" sequence, identified herein as residues 39-53 of the human CTLA-4 ECD sequence (SEQ ID NO:159), and a "subject" sequence, identified herein as residues 40-54 of D3 (SEQ ID NO:61). The numerical value assigned by the BLOSUM62 matrix for each aligned pair of amino acids is shown beneath each position in the alignment.

FIG. 14B shows the alignment score for the optimal alignment of the same two sequences. To aid in visualization, each identical pair of amino acids in the alignment is shown in boldface. The alignment in FIG. 14B (alignment 14B) below results in the highest possible alignment score (the sum of the values shown beneath each aligned position) of these two sequences; any other alignment of these two sequences, with or without gaps, would result in a lower alignment score.

In some instances, a higher alignment score might be obtained by introducing one or more gaps into the alignment. Whenever a gap is introduced into an alignment, a gap open penalty is assigned, and in addition a gap extension penalty is assessed for each residue position within that gap. Therefore, using the alignment parameters described above (including gap open penalty=11 and gap extension penalty=1), a gap of one residue in the alignment would correspond to a value of $-(11+(1\times1))=-12$ assigned to the gap; a gap of two residues would correspond to a value of $-(11+(2\times1))=-13$ assigned to the gap, and so on. This calculation is repeated for each new gap introduced into the alignment.

The following is an example, which demonstrates how introduction of a gap into an alignment can result in a higher alignment score, despite the gap penalty. FIG. 14C shows an alignment (alignment 14C) of a "query" sequence, identified herein as residues 39-53 of the human CTLA-4 ECD sequence (SEQ ID NO:159), and a "subject" sequence, identified herein as residues 41-55 of D3 (SEQ ID NO:61), but in this instance with amino acids 49-50 deleted. Alignment 14C, which is the best possible alignment without introduction of any gaps, results in an alignment score of 34.

The alignment in FIG. 14D (alignment 14D) shows the effect of the introduction of a two-residue gap in the lower sequence on the alignment score. Despite the total gap penalty of 13 (the gap open penalty of 11, and 2 times the gap extension penalty of 1), the overall alignment score of the two sequences increases to 43. Alignment D below results in the highest possible alignment score, and is thus the optimal alignment of these two sequences; any other alignment of these two sequences (with or without gaps) would result in a lower alignment score.

It is to be understood that the examples of sequence alignment calculations described above, which use relatively short sequences, are provided for illustrative purposes only. In practice, the alignment parameters employed (BLOSUM62 matrix, gap open penalty=11, and gap extension penalty=1) are generally intended for polypeptide sequences 85 amino acids in length or longer. The NCBI website provides the following alignment parameters for sequences of other lengths, which are suitable for computer-aided as well as manual alignment calculation, using the same procedure as described above. For sequences of 50-85 amino acids in length, optimal parameters are the BLOSUM80 matrix (Henikoff and Henikoff, supra), gap open penalty=10, and gap extension penalty=1. For sequences of 35-50 amino acids in length, optimal parameters are the PAM70 matrix (Dayhoff, M. O., Schwartz, R. M. & Orcutt, B. C. (1978) "A model of evolutionary change in proteins" in *Atlas of Protein Sequence and Structure*, vol. 5, suppl. 3, M. O. Dayhoff (ed.), pp. 345-352, Natl. Biomed. Res. Found., Washington, D.C.), gap open penalty=10, and gap extension penalty=1. For sequences of less than 35 amino acids in length, optimal parameters are PAM30 matrix (Dayhoff, M. O., supra), gap open penalty=9, and gap extension penalty=1.

2. Calculating Percent Identity

Once the sequences are optimally aligned, the percent identity of the subject sequence relative to the query sequence is calculated by counting the number of positions in the optimal alignment which contain identical residue pairs, divide that by the number of residues in the comparison length (also termed the comparison window), which, unless otherwise specified, is the number of residues in the query sequence, and multiplying the resulting number by 100. Referring back to the alignments above, in each example the sequence designated as the query (upper) sequence is 15 amino acids in length. In alignment B, 12 pairs of aligned amino acid residues (shown in boldface) are identical in the optimal alignment of the query sequence (upper) with the subject sequence (lower). Thus, this particular subject sequence has ($^{12}/_{15}$)× 100=80% identity to the entire length of the 15-residue query sequence; in other words, the subject sequence in alignment B has at least 80% amino acid sequence identity to the query sequence. In alignment D, 11 pairs of amino acid residues (shown in boldface) in the optimal alignment are identical; thus this particular subject sequence has ($^{11}/_{15}$)×100=73.3% identity to the entire length of the 15-residue query sequence; in other words, the subject sequence in alignment D has at least 73% amino acid sequence identity to the query sequence.

As applied to polypeptides, the term "substantial identity" (or "substantially identical") typically means that when two amino acid sequences (i.e. a query sequence and a subject sequence) are optimally aligned using the BLASTP algorithm (manually or via computer) using appropriate parameters described above, the subject sequence has at least 70%, 75%, 80%, 85%, 86%, 87%, 88%, 89%, 90%, 91%, 92%, 93%, 94%, 95%, 96%, 97%, 98%, 99%, 99.5% or 100% amino acid sequence identity to the query sequence. In some instances, the substantial identity exists over a comparison length of at least 100 amino acid residues, such as, e.g., at least 110, 115, 118, 119, 120, 121, 122, 123, 124, 125, 130, 135, 140, 145, 150, 200, 250, 300, 345, 346, 347, 348, 349, 350, 351, 352, 353, 354, 355, 356, 357, 358, 359, 360, 375, 400, 450, or 500 amino acid residues.

Similarly, as applied in the context of two nucleic acid sequences, the term substantial identity (or substantially identical) means that when two nucleic acid sequences (i.e. a query and a subject sequence) are optimally aligned using the BLASTN algorithm (manually or via computer) using appropriate parameters described below, the subject sequence has at least about 70%, 75%, 80%, 85%, 90%, 91%, 92%, 93%, 94%, 95%, 96%, 97%, 98%, 99%, 99.5% or 100% nucleic acid sequence identity to the query sequence. Parameters used for nucleic acid sequence alignments are: match reward 1, mismatch penalty −3, gap existence penalty 5, gap extension penalty 2 (substitution matrices are not used in the BLASTN algorithm). In some instances, substantial identity exists over a comparison length of at least 300 nucleotide residues, e.g., at least 330, 345, 354, 357, 360, 363, 366, 369, 362, 365, 375, 390, 405, 420, 435, 450, 600, 750, 900, 1035, 1038, 1041, 1044, 1047, 1050, 1053, 1056, 1059, 1062, 1065, 1068, 1071, 1074, 1077, 1080, 1200, 1350, or 1500 nucleotide residues.

Other sequence alignment programs known in the art can be used. The ALIGN program produces an optimal global (overall) alignment of the two chosen protein or nucleic acid sequences using a modification of the dynamic programming algorithm described by Myers and Miller CABIOS 4:11-17 (1988). The ALIGN program typically, although not necessary, is used with weighted end-gaps. If gap opening and gap extension penalties are available, they are often set between about −5 to −15 and 0 to −3, respectively, more preferably about −12 and −0.5 to −2, respectively, for amino acid sequence alignments, and −10 to −20 and −3 to −5, respectively, more commonly about −16 and −4, respectively, for nucleic acid sequence alignments. The ALIGN program is further described in Pearson et al., Proc. Natl. Acad. Sci. USA 85:2444-48 (1988), and Pearson et al., Meth. Enzymol. 18:63-98 (1990).

Alternatively, and particularly for multiple sequence analysis (i.e., comparison of more than three sequences), the CLUSTALW program (described in, e.g., Thompson et al., Nucl. Acids Res. 22:4673-4680 (1994)) can be used. The CLUSTALW program is an algorithm suitable for multiple DNA and amino acid sequence alignments (Thompson et al., Nucl. Acids Res. 22:4673-4680 (1994)). CLUSTALW performs multiple pairwise comparisons between groups of sequences and assembles them into a multiple alignment based on homology. In one aspect, Gap open and Gap extension penalties are set at 10 and 0.05, respectively. Alternatively or additionally, the CLUSTALW program is run using "dynamic" (versus "fast") settings. Typically, nucleotide sequence analysis with CLUSTALW is performed using the BESTFIT matrix, whereas amino acid sequences are evaluated using a variable set of BLOSUM matrixes depending on the level of identity between the sequences (e.g., as used by the CLUSTALW version 1.6 program available through the San Diego Supercomputer Center (SDSC) or version W 1.8 available from European Bioinformatics Institute, Cambridge, UK). Preferably, the CLUSTALW settings are set to the SDSC CLUSTALW default settings (e.g., with respect to special hydrophilic gap penalties in amino acid sequence analysis). The CLUSTALW program is further described in, e.g., Higgins et al., CABIOS 8(2):189-91 (1992), Thompson et al., Nucleic Acids Res. 22:4673-80 (1994), and Jeanmougin et al., Trends Biochem. Sci. 2:403-07 (1998).

In an alternative format, the identity or percent identity between a particular pair of aligned amino acid sequences refers to the percent amino acid sequence identity that is obtained by CLUSTALW analysis (e.g., version W 1.8), counting the number of identical matches in the alignment and dividing such number of identical matches by the greater of (i) the length of the aligned sequences, and (ii) 96, and using the following default ClustalW parameters to achieve slow/accurate pairwise alignments—Gap Open Penalty:10; Gap Extension Penalty:0.10; Protein weight matrix:Gonnet series; DNA weight matrix: IUB; Toggle Slow/Fast pairwise alignments=SLOW or FULL Alignment.

Another useful algorithm for determining percent identity or percent similarity is the FASTA algorithm, which is described in Pearson et al., Proc Natl. Acad. Sci. USA 85:2444 (1988) and Pearson, Methods Enzymol. 266:227-258 (1996). Typical parameters used in a FASTA alignment of DNA sequences to calculate percent identity are optimized, BL50 Matrix 15: −5, k-tuple=2; joining penalty=40, optimization=28; gap penalty=−12, gap length penalty=−2; and width=16.

Other suitable algorithms include the BLAST and BLAST 2.0 algorithms, which facilitate analysis of at least two amino acid or nucleotide sequences, by aligning a selected sequence against multiple sequences in a database (e.g., GenSeq), or, when modified by an additional algorithm such as BL2SEQ, between two selected sequences. Software for performing BLAST analyses is publicly available through the National Center for Biotechnology Information (NCBI) (worldwide website address ncbi.nlm.nih.gov). The BLAST algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) can be used with a word length (W) of 11, an expectation (E) of 10, M=5, N=−4 and a comparison of both strands. For amino acid sequences, the BLASTP program (e.g., BLASTP 2.0.14; Jun. 29, 2000) can be used with a word length of 3 and an expectation (E) of 10. The BLOSUM62 scoring matrix (see Henikoff & Henikoff, (1989) Proc. Natl. Acad. Sci. USA 89:10915) uses alignments (B) of 50, expectation (E) of 10, M=5, N=−4, and a comparison of both strands. Again, as with other suitable algorithms, the stringency of comparison can be increased until the program identifies only sequences that are more closely related to those in the sequence listing herein (e.g., a polypeptide comprising a polypeptide sequence having at least 85, 90, 91, 92, 93, 49, 95, 96, 97, 98, 99%, or 100% identity to a polypeptide sequence selected from SEQ ID NOS:1-79, 197-200, 205-214, and 219-222; or nucleic acid comprising a nucleotide sequence having at least 85, 90, 91, 92, 93, 49, 95, 96, 97, 98, 99%, or 100% identity to a nucleotide sequence selected from any of SEQ ID NOS:80-158, 201-204, 223, and 224, or a complementary nucleotide sequence thereof.

The BLAST algorithm also performs a statistical analysis of the similarity or identity between two sequences (see, e.g., Karlin & Altschul, (1993) Proc. Natl. Acad. Sci. USA 90:5873-5787). One measure of similarity or identity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, such as less than about 0.01 or less than about 0.001.

BLAST program analysis also or alternatively can be modified by low complexity filtering programs such as the DUST or SEG programs, which are preferably integrated into the BLAST program operations (see, e.g., Wootton et al., Comput. Chem. 17:149-63 (1993), Altschul et al., Nat. Genet. 6:119-29 (1991), Hancock et al., Comput. Appl. Biosci. 10:67-70 (1991), and Wootton et al., Meth. Enzymol. 266: 554-71 (1996)). In such aspects, if a lambda ratio is used, useful settings for the ratio are between 0.75 and 0.95, including between 0.8 and 0.9. If gap existence costs (or gap scores) are used in such aspects, the gap existence cost typically is set between about −5 and −15, more typically about −10, and the per residue gap cost typically is set between about 0 to −5, such as between 0 and −3 (e.g., −0.5). Similar gap parameters can be used with other programs as appropriate. The BLAST programs and principles underlying them are further described in, e.g., Altschul et al., J. Mol. Biol. 215:403-10 (1990), Karlin and Altschul, Proc. Natl. Acad. Sci. USA 87:2264-68 (199) (as modified by Karlin and Altschul, Proc. Natl. Acad. Sci. USA 90:5873-77 (1993)), and Altschul et al., Nucl. Acids Res. 25:3389-3402 (1997).

Another example of a useful algorithm is incorporated in PILEUP software. The PILEUP program creates a multiple sequence alignment from a group of related sequences using progressive, pair-wise alignments to show relationship and percent sequence identity or percent sequence similarity. PILEUP uses a simplification of the progressive alignment method of Feng & Doolittle (1987) J. Mol. Evol. 35:351-360, which is similar to the method described by Higgins & Sharp (1989) CABIOS 5:151-153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity (or percent sequence similarity) relationship using specified parameters. Exemplary parameters for the PILEUP program are: default gap weight (3.00), default gap length weight (0.10), and weighted end gaps. PILEUP is a component of the GCG sequence analysis software package, e.g., version 7.0 (Devereaux et al. (1984) Nucl. Acids Res. 12:387-395).

Other useful algorithms for performing identity analysis include the local homology algorithm of Smith and Waterman (1981) Adv. Appl. Math. 2:482, the homology alignment algorithm of Needleman and Wunsch (1970) J. Mol. Biol. 48:443, and the search for similarity method of Pearson and Lipman (1988) Proc. Natl. Acad. Sci. USA 85:2444. Computerized implementations of these algorithms (e.g., GAP, BESTFIT, FASTA and TFASTA) are provided in the Wisconsin Genetics Software Package Release 7.0, Genetics Computer Group, 575 Science Dr., Madison, Wis.

Sequence Variation

As discussed above, in one aspect, the invention provides an isolated or recombinant mutant CTLA-4 extracellular domain polypeptide which comprises a polypeptide sequence which (a) differs from a polypeptide sequence selected from the group consisting of SEQ ID NOS:1-73 in no more than 6 amino acid residues (e.g., no more than 1, 2, 3, 4, 5, or 6 amino acid residues), wherein the mutant CTLA-4 ECD polypeptide binds CD80 and/or CD86 and/or an extracellular domain of either or both, and/or inhibits an immune response. Such amino acid substitution(s) include conservative amino acid substitution(s).

As a non-limiting example, a polypeptide of the invention may have a polypeptide sequence which differs from SEQ ID NO:1 in a total of up to 6 amino acids (which may be a combination of amino acid substitutions, deletions, and/or insertions, including those described above). In some instances, none, some, or all of the substitutions are substitutions according to a substitution group defined below.

Amino acid substitutions in accordance with the invention may include, but are not limited to, one or more conservative amino acid substitutions. A conservative amino acid residue substitution typically involves exchanging a member within one functional class of amino acid residues for a residue that belongs to the same functional class (identical amino acid residues are considered functionally homologous or conserved in calculating percent functional homology). Conservative substitution tables providing functionally similar amino acids are well known in the art. One example is provided in Table 1, which sets forth six exemplary groups containing amino acids that may be considered "conservative substitutions" for one another.

TABLE 1

| Conservative Amino Acid Residue Substitution Groups | | | | |
|---|---|---|---|---|
| 1 | Alanine (A) | Glycine (G) | Serine (S) | Threonine |
| 2 | Aspartic acid (D) | Glutamic acid (E) | | |
| 3 | Asparagine (N) | Glutamine (Q) | | |
| 4 | Arginine (R) | Lysine (K) | Histidine (H) | |
| 5 | Isoleucine (I) | Leucine (L) | Methionine (M) | Valine (V) |
| 6 | Phenylalanine (F) | Tyrosine (Y) | Tryptophan (W) | |

Other substitution groups of amino acids can be envisioned. For example, amino acids can be grouped by similar function or chemical structure or composition (e.g., acidic, basic, aliphatic, aromatic, sulfur-containing). For example, an Aliphatic grouping may comprise: Glycine (G), Alanine (A), Valine (V), Leucine (L), Isoleucine (I). Other groups containing amino acids that are considered conservative substitutions for one another include: Aromatic: Phenylalanine (F), Tyrosine (Y), Tryptophan (W); Sulfur-containing: Methionine (M), Cysteine (C); Basic: Arginine (R), Lysine (K), Histidine (H); Acidic: Aspartic acid (D), Glutamic acid (E); Non-polar uncharged residues, Cysteine (C), Methionine (M), and Proline (P); Hydrophilic Uncharged Residues: Serine (S), Threonine (T), Asparagine (N), and Glutamine (Q). See also Creighton (1984) *Proteins*, W.H. Freeman and Company, for additional groupings of amino acids. Listing of a polypeptide sequence herein, in conjunction with the above substitution groups, provides an express listing of all conservatively substituted polypeptide sequences.

More conservative substitutions exist within the amino acid residue classes described above, which also or alternatively can be suitable. Conservation groups for substitutions that are more conservative include: valine-leucine-isoleucine, phenylalanine-tyrosine, lysine-arginine, alanine-valine, and asparagine-glutamine. Thus, for example, in one particular aspect, the invention provides an isolated or recombinant polypeptide comprising a polypeptide sequence which has at least 90, 91, 92, 93, 94, 95, 96, 97, 98, or 99% identity to SEQ ID NO:1 (or any of SEQ ID NOS:1-79, 197-200, 205-214, and 219-222) and which differs from the sequence of SEQ ID NO:1 by mostly (e.g., at least 50%, 60%, 70%, 75%, 80%, 90%), if not entirely, by such more conservative amino acid substitutions.

Additional groups of amino acids substitutions that also can be suitable can be determined using the principles described in, e.g., Creighton (1984) Proteins: Structure and Molecular Properties (2d Ed. 1993), W.H. Freeman and Company. In some aspects, at least 33%, 50%, 60%, 70%, or more (e.g., at least 75%, 80%, 90%, 95%, 96%, 97% or more) of the substitutions in an amino acid sequence variant comprise substitutions of one or more amino acid residues in a polypeptide sequence of the invention with residues that are within the same functional homology class (as determined by any suitable classification system, such as those described above) as the amino acid residues of the polypeptide sequence that they replace.

Conservatively substituted variations of a polypeptide sequence of the present invention include substitutions of a small percentage, typically less than 10%, 9%, 8%, 7%, or 6% of the amino acids of the polypeptide sequence, or more typically less than 5%, 4%, 3%, 2%, or 1%, of the amino acids of the polypeptide sequence, with a conservatively selected amino acid of the same conservative substitution group.

The invention includes polypeptides that comprise amino acid variations of a polypeptide sequence of the invention described herein. As discussed above, in one aspect, the invention provides isolated or recombinant polypeptides (e.g., mutant CTLA-4 polypeptides, such as, e.g., mutant CTLA-4 ECD polypeptides) which each comprise a polypeptide sequence having at least 75%, 80%, 85%, 86%, 87%, 88%, 89%, 90%, 91%, 92%, 93%, 94%, 95%, 96%, 97%, 98%, 99%, 99.5%, or 100% sequence identity to at least one polypeptide sequence selected from the group consisting of SEQ ID NOS:1-73, wherein the polypeptide binds CD80 and/or CD86 or a polypeptide fragment of CD80 and/or CD86 (or an ECD of either or both), and/or suppresses an immune response. Such polypeptides may vary by one or more amino acid deletions, additions, or substitutions, including one or more conservative or non-conservative substitutions, provided, however, that the polypeptides possess the described functional properties. In a particular aspect, the invention provides polypeptide variants that comprise conservatively modified variations of any such polypeptide described herein, such as, e.g., one comprising a polypeptide sequence selected from the group of SEQ ID NOS:1-73.

As also discussed above, in another aspect, the invention provides isolated or recombinant fusion proteins (e.g., mutant CTLA-4-Ig fusion proteins) which each comprise a polypeptide sequence having at least 75%, 80%, 85%, 86%, 87%, 88%, 89%, 90%, 91%, 92%, 93%, 94%, 95%, 96%, 97%, 98%, 99%, 99.5%, or 100% sequence identity to at least one polypeptide sequence selected from the group consisting of SEQ ID NOS:74-79, 197-200, 205-214, and 219-222, wherein the fusion protein binds CD80 and/or CD86 (and/or CD80-Ig and/or CD86-Ig), and/or suppresses an immune response. Such fusion proteins may vary by one or more amino acid deletions, additions, or substitutions, including one or more conservative or non-conservative substitutions, provided, however, that the fusion proteins possess the described functional properties. In a particular aspect, the invention provides polypeptide variants that comprise conservatively modified variations of any such fusion protein described herein, such as, e.g., one comprising a polypeptide sequence selected from the group of SEQ ID NOS:74-79, 197-200, 205-214, and 219-222.

Also provided are polypeptide variants of any isolated or recombinant polypeptide of the invention described above or elsewhere herein, wherein the amino acid sequence of the polypeptide variant differs from the respective polypeptide sequence of the reference polypeptide by one or more conservative amino acid residue substitutions, although non-conservative substitutions are sometimes permissible or even preferred (examples of such non-conservative substitutions are discussed further herein). For example, the sequence of the polypeptide variant can vary from a mutant CTLA-4 polypeptide sequence by one or more substitutions of amino acid residues in the mutant CTLA-4 ECD polypeptide sequence with one or more amino acid residues having similar weight (i.e., a residue that has weight homology to the residue in the respective polypeptide sequence that it replaces). The weight (and correspondingly the size) of amino acid residues of a polypeptide can significantly impact the structure of the polypeptide. Weight-based conservation or homology is based on whether a non-identical corresponding amino acid is associated with a positive score on one of the weight-based matrices described herein (e.g., BLOSUM50 matrix; PAM250 matrix).

Similar to the above-described functional amino acid classes, naturally occurring amino acid residues can be divided into weight-based conservations groups (which are divided between "strong" and "weak" conservation groups). The eight commonly used weight-based strong conservation groups are Ser Thr Ala, Asn Glu Gln Lys, Asn His Gln Lys, Asn Asp Glu Gln, Gln His Arg Lys, Met Ile Leu Val, Met Ile Leu Phe, His Tyr, and Phe Tyr Trp. Weight-based weak conservation groups include Cys Ser Ala, Ala Thr Val, Ser Ala Gly, Ser Thr Asn Lys, Ser Thr Pro Ala, Ser Gly Asn Asp, Ser Asn Asp Glu Gln Lys, Asn Asp Glu Gln His Lys, Asn Glu Gln His Arg Lys, Phe Val Leu Ile Met, and His Phe Tyr. Some versions of the CLUSTAL W sequence analysis program provide an analysis of weight-based strong conservation and weak conservation groups in the output of an alignment, thereby offering a convenient technique for determining weight-based conservation (e.g., CLUSTAL W provided by the SDSC, which typically is used with the SDSC default settings). In some aspects, at least 33%, 50%, 60%, 70%, 80%, or 90% of the substitutions in such polypeptide variant comprise substitutions wherein a residue within a weight-based conservation replaces an amino acid residue of the polypeptide sequence that is in the same weight-based conservation group. In other words, such a percentage of substitutions are conserved in terms of amino acid residue weight characteristics.

The sequence of a polypeptide variant can differ from a mutant CTLA-4 polypeptide of the invention by one or more amino acid substitutions with one or more amino acid residues having a similar hydropathy profile (i.e., that exhibit similar hydrophilicity) to the substituted (original) residues of the mutant CTLA-4 polypeptide. A hydropathy profile can be determined using the Kyte & Doolittle index, the scores for each naturally occurring amino acid in the index being as follows: I (+4.5), V (+4.2), L (+3.8), F (+2.8), C (+2.5), M (+1.9); A (+1.8), G (−0.4), T (−0.7), S (−0.8), W (−0.9), Y (−1.3), P (−1.6), H (−3.2); E (−3.5), Q (−3.5), D (−3.5), N (−3.5), K (−3.9), and R (−4.5) (see, e.g., U.S. Pat. No. 4,554,101 and Kyte & Doolittle, J. Molec. Biol. 157:105-32 (1982) for further discussion). At least 75%, 85%, 90%, 91%, 92%, 93%, 94%, 95%, 96%, 97% 98%, 99%, or 100% of the amino acid residues in the variant polypeptide sequence that are not identical to the corresponding residues in the identical or functionally homologous mutant CTLA-4 polypeptide sequence disclosed herein ("most related homolog"), which homolog may be selected from any of SEQ ID NOS:1-73, exhibit less than a +/−2 change in hydrophilicity, including less than a +/−1 change in hydrophilicity and less than a +/−0.5 change in hydrophilicity with respect to the non-identical amino acid residue at the corresponding position in the most related homolog. The variant polypeptide may exhibit a total change in hydrophilicity with respect to its most related homolog selected from the group of SEQ ID NOS:1-73, of less than about 150, less than about 100, and/or less than about 50 (e.g., less than about 30, 20, or 10).

Examples of typical amino acid substitutions that retain similar or identical hydrophilicity include arginine-lysine substitutions, glutamate-aspartate substitutions, serine-threonine substitutions, glutamine-asparagine substitutions, and valine-leucine-isoleucine substitutions. Algorithms and software, such as the GREASE program available through the SDSC, provide a convenient way for quickly assessing the hydropathy profile of an amino acid sequence. Because a substantial proportion (e.g., at least about 33%), if not most (at least 50%) or nearly all (e.g., about 65, 80, 90, 95, 96, 97, 98, 99%) of the amino acid substitutions in the sequence of a polypeptide variant often will have a similar hydropathy score as the amino acid residue that they replace in the (reference) polypeptide sequence, the sequence of the polypeptide variant is expected to exhibit a similar GREASE program output as the polypeptide sequence. For example, in a particular aspect, a polypeptide variant of SEQ ID NO:61 may be expected to have a GREASE program (or similar program) output that is more like the GREASE output obtained by inputting the polypeptide sequence of SEQ ID NO:61 than that obtained by using a WT CTLA-4 polypeptide (e.g., hCTLA-4), which can be determined by visual inspection or computer-aided comparison of the graphical (e.g., graphical overlay/alignment) and/or numerical output provided by subjecting the test variant sequence and SEQ ID NO:1 to the program.

The conservation of amino acid residues in terms of functional homology, weight homology, and hydropathy characteristics, also apply to other polypeptide sequence variants provided by the invention, including, but not limited to, e.g., polypeptide sequence variants of a polypeptide sequence selected from the group consisting of SEQ ID NOS:1-79197-200, 205-214, and 219-222.

In a particular aspect, the invention includes at least one such polypeptide variant comprising an amino acid sequence that differs from a recombinant polypeptide sequence selected from the group of SEQ ID NOS:1-79, 197-200, 205-214, and 219-222, wherein the amino acid sequence of the variant has at least one such amino acid residue substitution selected according to weight-based conservation or homology or similar hydropathy profile as discussed above. Such polypeptide variants described above typically have an ability to bind CD80 and/or CD86 and/or an ability to suppress at least one type of immune response as described above and in greater detail below in the Examples.

Signal Peptide Sequences

Polypeptides of the invention can also further comprise any suitable number and type of additional amino acid sequences, such as one or more peptide fragments. In one embodiment, such a polypeptide of the invention further comprises a signal peptide. Generally, the signal peptide directs the recombinant polypeptide to the endoplasmic reticulum when the recombinant polypeptide is expressed in an animal cell. A signal sequence that directs organelle trafficking and/or secretion of at least a portion of the polypeptide upon expression in a cell may be included. Such sequences are typically present in the immature (i.e., not fully processed) form of the polypeptide, and are subsequently removed/degraded by cellular proteases to arrive at the mature form of the protein. For example, a mutant CTLA-4 polypeptide or fusion protein of the invention can include any suitable signal sequence or combinations of signal sequences that direct the polypeptide to intracellular compartments, such as a sequence that directs the polypeptide to be transported (e.g., translocated) into (e.g., such that the protein is processed by and released from) the endoplasmic reticulum or secretory pathway (e.g., the ER, golgi, and other secretory related organelles and cellular compartments), the nucleus, and/or which directs the polypeptide to be secreted from the cell, translocated in a cellular membrane, or target a second cell apart from the cell the protein is secreted from. In this respect, the polypeptide can include an intracellular targeting sequence (or "sorting signal") that directs the polypeptide to an endosomal and/or lysosomal compartment(s) or other compartment rich in MHC II to promote CD4+ and/or CD8+ T cell presentation and response, such as a lysosomal/endosomal-targeting sorting signal derived from lysosomal associated membrane protein 1 (e.g., LAMP-1—see, e.g., Wu et al. Proc. Natl. Acad. Sci. USA 92:1161-75 (1995) and Ravipraskash et al., Virology 290:74-82 (2001)), a portion or homolog thereof (see, e.g., U.S. Pat. No. 5,633,234), or other suitable lysosomal, endosomal, and/or ER targeting sequence (see, e.g., U.S. Pat. No. 6,248,565). In some aspects, it may be desirable for the intracellular targeting sequence to be located near or adjacent to a proven/identified epitope sequence(s) within the polypeptide, which can be identified by techniques known in the art, thereby increasing the likelihood of T cell presentation of polypeptide fragments that comprise such epitope(s). Such polypeptides may be expressed from an isolated, recombinant, or synthetic DNA or RNA delivered to a host cell by one or more of the nucleotide transfer vectors, including, e.g., one or more of the gene transfer vectors, described further herein.

The polypeptide may comprise a signal sequence that directs the polypeptide to the endoplasmic reticulum (ER) (e.g., facilitates ER translocation of the polypeptide) when the polypeptide is expressed in a mammalian cell. The polypeptide can comprise any suitable ER-targeting sequence. Many ER-targeting sequences are known in the art. Examples of such signal sequences are described in U.S. Pat. No. 5,846,540. Commonly employed ER/secretion signal sequences include the yeast alpha factor signal sequence, and mammalian viral signal sequences such as herpes virus gD signal sequence. Exemplary signal peptides for *E. coli* production include the STII or Ipp signal sequences of *E. coli*. Further examples of signal sequences are described in, e.g., U.S. Pat. Nos. 4,690,898, 5,284,768, 5,580,758, 5,652,139, and 5,932,445. Suitable signal sequences can be identified using skill known in the art. For example, the SignalP program (described in, e.g., Nielsen et al. (1997) Protein Engineering 10:1-6), which is publicly available through the Center for Biological Sequence Analysis at the worldwide website address designated cbs.dtu.dk/services/SignalP, or similar sequence analysis software capable of identifying signal-sequence-like domains can be used. Related techniques for identifying suitable signal peptides are provided in Nielsen et al., Protein Eng. 10(1): 1-6 (1997). Sequences can be manually analyzed for features commonly associated with signal sequences, as described in, e.g., European Patent Application (Appn) No. 0 621 337, Zheng and Nicchitta (1999) J. Biol. Chem. 274(51): 36623-30, and Ng et al. (1996) J. Cell Biol. 134(2):269-78.

Additional Aspects

Any polypeptide of the invention (including any fusion protein of the invention) may be present as part of a larger polypeptide sequence, such as occurs upon the addition of one or more domains or subsequences for stabilization or detection or purification of the polypeptide. Such domains or subsequences may be covalently fused to the polypeptide of the invention, as one of skill would readily understand and be able to construct. A polypeptide purification subsequence may include, e.g., an epitope tag, a FLAG tag, a polyhistidine sequence, a GST fusion, or any other detection/purification subsequence or "tag" known in the art. These additional domains or subsequences either have little or no effect on the activity of the polypeptide of the invention, or can be removed by post synthesis processing steps such as by treatment with a protease, inclusion of an intein, or the like.

Any polypeptide of the invention (including any fusion protein of the invention) may also comprise one or more modified amino acid. The modified amino acid may be, e.g., a glycosylated amino acid, a PEGylated amino acid, a farnesylated amino acid, an acetylated amino acid, a biotinylated amino acid, an amino acid conjugated to a lipid moiety, and/or an amino acid conjugated to an organic derivatizing agent. The presence of modified amino acids may be advantageous in, for example, (a) increasing polypeptide serum half-life and/or functional in vivo half-life, (b) reducing polypeptide antigenicity or immunogenicity, (c) increasing polypeptide storage stability, (d) increasing bioavailability, (e) decreasing effector function, and/or (f) decreasing or inhibiting undesired self-association (e.g., aggregate formation) between two or more molecules of the invention (such as between two or more fusion protein dimers of the invention). Amino acid(s) are modified, for example, co-translationally or post-translationally during recombinant production (e.g., N-linked glycosylation at N-X-S/T motifs during expression in mammalian cells) or modified by synthetic means.

Polypeptides of the invention (including fusion proteins of the invention) described herein can be further modified in a variety of ways by, e.g., post-translational modification and/or synthetic modification or variation. For example, polypeptides or fusion proteins of the invention may be suitably glycosylated, typically via expression in a mammalian cell. For example, in one aspect, the invention provides glycosylated polypeptides that are capable of binding CD86 and/or CD80, and/or have an ability to suppress an immune response (e.g., T cell proliferation or activation) as described elsewhere herein, wherein each said glycosylated polypeptide comprises a polypeptide sequence having at least 92%, 93%, 94%, 95%, 96%, 97%, 98%, 99% or 100% identity to a sequence selected from the group consisting of SEQ ID NOS: 1-79, 197-200, 205-214, and 219-222.

The polypeptides of the invention can be subject to any number of additional forms suitable of post translational and/or synthetic modification or variation. For example, the invention provides protein mimetics of the polypeptides of the invention. Peptide mimetics are described in, e.g., U.S. Pat. No. 5,668,110 and the references cited therein.

In another aspect, a polypeptide or fusion protein of the invention can be modified by the addition of protecting groups to the side chains of one or more the amino acids of the polypeptide or fusion protein. Such protecting groups can facilitate transport of the polypeptide or fusion protein through membrane(s), if desired, or through certain tissue(s), for example, by reducing the hydrophilicity and increasing the lipophilicity of the polypeptide or fusion protein. Examples of suitable protecting groups include ester protecting groups, amine protecting groups, acyl protecting groups, and carboxylic acid protecting groups, which are known in the art (see, e.g., U.S. Pat. No. 6,121,236). Synthetic fusion proteins of the invention can take any suitable form. For example, the fusion protein can be structurally modified from its naturally occurring configuration to form a cyclic peptide or other structurally modified peptide.

Polypeptides of the invention also can be linked to one or more nonproteinaceous polymers, typically a hydrophilic synthetic polymer, e.g., polyethylene glycol (PEG), polypropylene glycol, or polyoxyalkylene, using techniques well known in the art, such as described in, e.g., U.S. Pat. Nos. 4,179,337, 4,301,144, 4,496,689, 4,640,835, 4,670,417, and 4,791,192, or a similar polymer such as polyvinylalcohol or polyvinylpyrrolidone (PVP).

The invention includes conjugates comprising at least one polypeptide of the invention (e.g., mutant CTLA-4 ECD polypeptide, dimeric or monomeric mutant CTLA-4-Ig, multimeric mutant CTLA-4 ECD polypeptide, multimeric mutant CTLA-4-Ig) and a non-polypeptide moiety. The term "conjugate" (or interchangeably "conjugated polypeptide") is intended to indicate a heterogeneous (in the sense of composite or chimeric) molecule formed by the covalent attachment of one or more polypeptide(s) to one or more non-polypeptide moieties. The term "covalent attachment" means that the polypeptide and the non-polypeptide moiety are either directly covalently joined to one another, or else are indirectly covalently joined to one another through an intervening moiety or moieties, such as a bridge, spacer, or linkage moiety or moieties using an attachment group present in the polypeptide. Preferably, the conjugate is soluble at relevant concentrations and conditions, i.e., soluble in physiological fluids, such as blood. Examples of conjugated polypeptides of the invention include glycosylated and/or PEGylated polypeptides. The term "non-conjugated polypeptide" may be used about the polypeptide part of the conjugate. Such a conjugate typically binds CD80 (e.g., hCD80) and/or CD86 (e.g., hCD86) and/or an extracellular domain of either or both (including hCD80-Ig and/or hCD86-Ig), and/or has an ability to inhibit an immune response. Such an immune response can comprise, but is not limited to, e.g., T cell activation or proliferation, cytokine synthesis/production, induction of activation markers, production of inflammatory molecules, inflammation, anti-collagen Ab production, and/or T cell-dependent Ab response. Exemplary polypeptides include those having at least 95%, 96%, 97%, 98%, 99%, or 100% identity to a sequence selected from the group of SEQ ID NOS: 1-79, 197-200, 205-214, and 219-222.

The term "non-polypeptide moiety" is intended to indicate a molecule that is capable of conjugating to an attachment group of a polypeptide of the invention. Preferred examples of such molecule include polymer molecules, sugar moieties, lipophilic compounds, or organic derivatizing agents. When used in the context of a conjugate as described herein it will be understood that the non-polypeptide moiety is linked to the polypeptide part of the conjugate through an attachment group of the polypeptide.

The term "polymer molecule" is defined as a molecule formed by covalent linkage of two or more monomers, wherein none of the monomers is an amino acid residue, except where the polymer is human albumin or another abundant plasma protein. The term "polymer" may be used interchangeably with the term "polymer molecule".

An N-glycosylation site has the sequence N-X-S/T/C, wherein X is any amino acid residue except proline, N is asparagine and S/T/C is either serine, threonine or cysteine, preferably serine or threonine, and most preferably threonine.

An "O-glycosylation site" comprises the OH-group of a serine or threonine residue.

The term "attachment group" is intended to indicate an amino acid residue group of the polypeptide capable of coupling to the relevant non-polypeptide moiety, such as a polymer molecule or a sugar moiety. Non-limiting examples of useful attachment groups and some corresponding non-polypeptide moieties are provide in Table 2 below.

TABLE 2

Useful attachment groups and examples of corresponding non-polypeptide moieties

| Attachment group | Amino acid | Examples of non-polypeptide moieties | Examples of conjugation method/ activated PEG | Reference |
| --- | --- | --- | --- | --- |
| —$NH_2$ | N-terminus, Lys | Polymer, e.g., PEG | mPEG-SPA mPEG2-NHS mPEG2-butyrALD | Nektar Inc. 2003 Catalog; see also Nektar Therapeutics, 2005-06 Catalog |
| —COOH | C-terminus, Asp, Glu | Polymer, e.g., PEG Sugar moiety | mPEG-Hz In vitro coupling | Nektar, Inc. 2003 Catalog; see also Nektar Therapeutics 2005-06 Catalog |
| —SH | Cys | Polymer, e.g., PEG Sugar moiety | mPEG-VS mPEG2-MAL (mPEG-maleimide) In vitro coupling | Nektar Inc. 2003 Catalog; Nektar Therapeutics 2005-2006 Catalog; Delgado et al., Critical Reviews in Therapeutic Drug Carrier Systems 9(3, 4): 249-304 (1992) |
| —OH | Ser, Thr, OH— | Sugar moiety | In vivo O-linked glycosylation | |
| —$CONH_2$ | Asn as part of an N-glycosylation site | Sugar moiety | In vivo N-glycosylation | |
| Aromatic residue | Phe, Tyr, Trp | Sugar moiety | In vitro coupling | |
| —$CONH_2$ | Gln | Sugar moiety | In vitro coupling | Yan and Wold, Biochemistry, 1984, Jul. 31; 23(16): 3759-65 |
| Aldehyde Ketone | Oxidized carbohydrate | Polymer, e.g., PEG, PEG-hydrazide | PEGylation | Andresz et al., 1978, Makromol. Chem. 179: 301; WO 92/16555, WO 00/23114 |
| Guanidino | Arg | Sugar moiety | In vitro coupling | Lundblad and Noyes, Chemical Reagents for Protein Modification, CRC Press Inc. Boca Raton, FI |
| Imidazole ring | His | Sugar moiety | In vitro coupling | As for guanidine |

For in vivo N-glycosylation, the term "attachment group" is used in an unconventional way to indicate the amino acid residues constituting an N-glycosylation site (with the sequence N-X-S/T/C, wherein X is any amino acid residue except proline, N is asparagine and S/T/C is either serine, threonine or cysteine, preferably serine or threonine, and most preferably threonine). Although the asparagine residue of the N-glycosylation site is the one to which the sugar moiety is attached during glycosylation, such attachment cannot be achieved unless the other amino acid residues of the N-glycosylation site is present. Accordingly, when the non-polypeptide moiety is a sugar moiety and the conjugation is to be achieved by N-glycosylation, the term "amino acid residue comprising an attachment group for the non-polypeptide moiety" as used in connection with alterations of the amino acid sequence of the polypeptide of the invention is to be understood as one, two or all of the amino acid residues constituting an N-glycosylation site is/are to be altered in such a manner that either a functional N-glycosylation site is introduced into the amino acid sequence, removed from said sequence or a functional N-glycosylation site is retained in the amino acid sequence (e.g., by substituting a serine residue, which already constitutes part of an N-glycosylation site, with a threonine residue and vice versa).

The term "introduce" (i.e., an "introduced" amino acid residue, "introduction" of an amino acid residue) is primarily intended to mean substitution of an existing amino acid residue for another amino acid residue, but may also mean insertion of an additional amino acid residue.

The term "remove" (i.e., a "removed" amino acid residue, "removal" of an amino acid residue) is primarily intended to mean substitution of the amino acid residue to be removed for another amino acid residue, but may also mean deletion (without substitution) of the amino acid residue to be removed.

The term "amino acid residue comprising an attachment group for the non-polypeptide moiety" is intended to indicate that the amino acid residue is one to which the non-polypeptide moiety binds (in the case of an introduced amino acid residue) or would have bound (in the case of a removed amino acid residue).

By removing and/or introducing amino acid residues comprising an attachment group for the non-polypeptide moiety it is possible to specifically adapt the polypeptide of the invention so as to make the molecule more susceptible to conjugation to the non-polypeptide moiety of choice, to optimize the conjugation pattern (e.g., to ensure an optimal distribution of non-polypeptide moieties on the surface of the polypeptide and thereby, e.g., effectively shield epitopes and other surface parts of the polypeptide without significantly impairing the function thereof). For instance, by introduction of attachment groups, the polypeptide is altered in the content of the specific amino acid residues to which the relevant non-polypeptide moiety binds, whereby a more efficient, specific and/or extensive conjugation is achieved. By removal of one or more attachment groups it is possible to avoid conjugation to the non-polypeptide moiety in parts of the polypeptide in which such conjugation is disadvantageous, e.g., to an amino acid residue located at or near a functional site of the polypeptide (since conjugation at such a site may result in inactivation or reduced CD80- or CD86-binding or reduced immunosuppressive activity of the resulting conjugate). Further, it may be advantageous to remove an attachment group located close to another attachment group.

The amino acid residue comprising an attachment group for a non-polypeptide moiety, whether an existing residue or a removed or introduced residue, is selected on the basis of the nature of the non-polypeptide moiety and, in some instances, on the basis of the conjugation method to be used. For instance, when the non-polypeptide moiety is a polymer molecule, such as a polyethylene glycol (PEG) or polyalkylene oxide (POA) derived molecule, amino acid residues capable of functioning as an attachment group may be selected from the group consisting of cysteine, lysine (and/or the N-terminal amino group of the polypeptide), aspartic acid, glutamic acid, histidine and arginine. When the non-polypeptide moiety is a sugar moiety, the attachment group is an in vivo or in vitro N- or O-glycosylation site, preferably an N-glycosylation site.

In some instances, in the mutant CTLA-4 polypeptide part of a conjugate of the invention, attachment groups located at or near the receptor binding sites are removed, such as by substitution of the amino acid residue comprising such group. In some instances, amino acid residues comprising an attachment group for a non-polypeptide moiety, such as cysteine or lysine, are often not introduced at or near the receptor binding site of the mutant CTLA-4 polypeptide.

A mutant CTLA-4 polypeptide of the invention can be modified so as to shield and thereby modify or destroy or otherwise inactivate an epitope present in the mutant CTLA-4 polypeptide, by conjugation to a non-polypeptide moiety. Epitopes of mutant CTLA-4 polypeptides may be identified by use of methods known in the art, also known as epitope mapping, see e.g., Romagnoli et al., J. Biol. Chem. 380(5): 553-9 (1999), DeLisser H M, Methods Mol Biol, 1999, 96:11-20, Van de Water et al., Clin. Immunol. Immunopathol. 85(3):229-35 (1997), Saint-Remy J M, Toxicology 119(1): 77-81 (1997).

The exact number of attachment groups available for conjugation and present in the mutant CTLA-4 polypeptide is dependent on the effect desired to be achieved by conjugation. The effect to be obtained is, e.g., dependent on the nature and degree of conjugation (e.g., the identity of the non-polypeptide moiety, the number of non-polypeptide moieties desirable or possible to conjugate to the polypeptide, where they should be conjugated or where conjugation should be avoided, etc.). For instance, if reduced immunogenicity is desired, the number (and location of) attachment groups should be sufficient to shield most or all epitopes. This is normally obtained when a greater proportion of the mutant CTLA-4 polypeptide is shielded. Effective shielding of epitopes is normally achieved when the total number of attachment groups available for conjugation is in the range of 1-6 attachment groups, e.g., 1-5, such as in the range of 1-3, such as 1, 2, or 3 attachment groups.

Functional in vivo half-life can be dependent on the molecular weight of the conjugate, and the number of attachment groups needed for providing increased half-life thus depends on the molecular weight of the non-polypeptide moiety in question. Some such conjugates comprise 1-6, e.g., 1-5, such as 1-3, e.g., 1, 2, or 3 non-polypeptide moieties each having a molecular weight of about 100-2000 Daltons (Da), such as about 200 Da, about 300 Da, about 400 Da, about 600 Da, about 900 Da, about 1000 Da, or about 2-40 kDa, such as about 2 kDa, about 5 kDa, about 12 kDa, about 15 kDa, about 20 kDa, about 30 kDa, about 40 kDa, or about 60 kDa.

In the conjugate of the invention, some, most, or substantially all conjugatable attachment groups are occupied by the relevant non-polypeptide moiety.

The conjugate of the invention may exhibit one or more of the following improved properties: (a) increased serum half-life and/or functional in vivo half-life, (b) reduced antigenicity or immunogenicity, (c) increased storage stability, (d) increased bioavailability, (e) decreased effector function, or (f) decreased or inhibited self-association (e.g., decreased aggregate formation) between two or more molecules of the invention. For example, the conjugate may exhibit a reduced immunogenicity as compared to hCTLA-4 or as compared to the corresponding non-conjugated polypeptide, e.g., a reduction of at least 10%, such as a reduction of at least of 25%, such as a reduction of at least of 50%, e.g., a reduction of at least 75% compared to the non-conjugated polypeptide or compared to a hCTLA-4. The conjugate may exhibit an increased functional in vivo half-life and/or increased serum half-life as compared to a reference molecule, such as hCTLA-4 or as compared to the corresponding non-conjugated polypeptide. Particular preferred conjugates are such conjugates where the ratio between the functional in vivo half-life (or serum half-life) of said conjugate and the functional in vivo half-life (or serum half-life) of said reference molecule is at least 1.25, such as at least 1.50, such as at least 1.75, such as at least 2, such as at least 3, such as at least 4, such as at least 5, such as at least 6, such as at least 7, such as at least 8. The half-life is conveniently determined in an experimental animal, such as rat or monkey, and may be based on intravenously or subcutaneously administration. In a further aspect, the conjugate may exhibit an increased bioavailability as compared to a reference molecule such as an hCTLA-4 or a corresponding non-conjugated polypeptide.

The polymer molecule to be coupled to the polypeptide may be any suitable polymer molecule, such as a natural or synthetic homopolymer or heteropolymer, typically with a molecular weight in the range of 300-100,000 Da, such as 300-20,000 Da, more preferably in the range of 500-10,000 Da, even more preferably in the range of 500-5000 Da.

Examples of homopolymers include a polyol (i.e. poly-OH), a polyamine (i.e. poly-$NH_2$) and a polycarboxylic acid (i.e. poly-COOH). A heteropolymer is a polymer, which comprises one or more different coupling groups, such as, e.g., a hydroxyl group and an amine group. Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs, poly-vinyl alcohol (PVA), poly-carboxylate, poly-(vinylpyrrolidone), polyethylene-co-maleic acid anhydride, polystyrene-co-malic acid anhydride, dextran including carboxymethyl-dextran, or any other biopolymer suitable for reducing immunogenicity and/or increasing functional in vivo half-life and/or serum half-life. Another example of a polymer molecule is human albumin or another abundant plasma protein. Generally, polyalkylene glycol-derived polymers are biocompatible, non-toxic, non-antigenic, non-immunogenic, have various water solubility properties, and are easily excreted from living organisms.

PEG is the preferred polymer molecule to be used, since it has only few reactive groups capable of cross-linking compared, e.g., to polysaccharides such as dextran, and the like. In particular, monofunctional PEG, e.g., monomethoxypolyethylene glycol (mPEG), is of interest since its coupling chemistry is relatively simple (only one reactive group is available for conjugating with attachment groups on the polypeptide). Consequently, the risk of cross-linking is eliminated, the resulting polypeptide conjugates are more homogeneous and the reaction of the polymer molecules with the polypeptide is easier to control. When the molecule is PEGylated, it usually comprises 1, 2, 3, 4, or 5 polyethylene glycol (PEG) molecules. Each PEG molecule can have a molecular weight of about 5 kDa (kilo Dalton) to 100 kDa, including, e.g., about 10 kDa, about 12 kDa, about 20 kDa, about 40 kDa. Suitable PEG molecules are available from Shearwater Polymers, Inc. and Enzon, Inc. and may be selected from SS-PEG, NPC-PEG, aldehyde-PEG, mPEG-SPA, mPEG-SCM, mPEG-BTC, SC-PEG, tresylated mPEG (U.S. Pat. No. 5,880,255), or oxycarbonyl-oxy-N-dicarboxylmide-PEG (U.S. Pat. No. 5,122,614).

In one aspect, the invention provides an isolated or synthetic conjugate comprising: (a) a polypeptide of the invention (e.g., mutant CTLA-4 ECD polypeptide, dimeric or monomeric mutant CTLA-4-Ig, multimeric mutant CTLA-4 ECD polypeptide, multimeric mutant CTLA-4-Ig); and (b) at least one non-polypeptide moiety, such as, e.g., 1-10, 1-9, 1-8, 1-7, 1-7, 1-6, 1-5, 1-4, 1-3, 1, 2, or 3 non-polypeptide moieties attached to the polypeptide, wherein the conjugate binds CD80 (e.g., hCD80) and/or CD86 (e.g., hCD86) and/or an extracellular domain of either or both (including hCD80-Ig and/or hCD86-Ig), and/or has an ability to induce an immune response (e.g., T cell-dependent immune response). Exemplary polypeptides include those having at least 92%, 93%, 94%, 95%, 96%, 97%, 98%, 99%, or 100% identity to a polypeptide sequence selected from the group of SEQ ID NOS:1-79, 197-200, 205-214, and 219-222. In some instances, the conjugate comprises one non-polypeptide moiety. In some instances, the conjugate comprises two, three, four or more non-polypeptide moieties. In some instances, the amino acid sequence of the polypeptide of the conjugate further comprises one or more substitutions which each introduce an attachment group for the non-polypeptide moiety (e.g., by substitution of an amino acid residue of the polypeptide sequence with a different residue which comprises an attachment group for the non-polypeptide moiety, or by insertion into the polypeptide sequence of an additional amino acid residue which comprises an attachment group for the non-polypeptide moiety).

A conjugate can comprise two or more polypeptides of the invention. In some instances, a non-polypeptide moiety is covalently attached to either or both such polypeptides. If the conjugate comprises two or more identical polypeptides of the invention, the same type and number of non-polypeptide moieties are typically attached to each such polypeptide, usually in the same manner to the corresponding attachment group(s) on each polypeptide. As noted above, the non-polypeptide moiety can comprise, e.g., a sugar molecule, which optionally can be attached to an N-glycosylation site, or a polymer, such as, e.g., a polyethylene glycol moiety. The polyethylene glycol moiety can be covalently attached to a cysteine residue or lysine residue of the polypeptide of the invention. In some instances, the polyethylene glycol moiety is covalently attached to the N-terminal amino group of the polypeptide. A conjugate comprising a mutant CTLA-4-Ig of the invention may be described as a mutant CTLA-4-Ig conjugate of the invention. Multimers of conjugates are also included. Multimeric conjugates include two or more conjugates, wherein at least one conjugate is a conjugate of the invention comprising at least one polypeptide of the invention. The conjugates in a multimeric conjugate can be, but need not be, identical to one another.

As discussed above, polypeptides of the invention, including fusion proteins of the invention, can commonly be subject to glycosylation. Polypeptides and fusion proteins of the invention can further be subject to (or modified such that they are subjected to) other forms of post-translational modification including, e.g., hydroxylation, lipid or lipid derivative-attachment, methylation, myristylation, pegylation, phosphorylation, and sulfation. Other post-translational modifications that a polypeptide or fusion protein of the invention can be rendered subject to include acetylation, acylation, ADP-ribosylation, amidation, covalent attachment of flavin, covalent attachment of a heme moiety, covalent attachment of a nucleotide or nucleotide derivative, covalent attachment of phosphotidylinositol, cross-linking, cyclization, disulfide bond formation, demethylation, formylation, GPI anchor formation, iodination, oxidation, proteolytic processing, prenylation, racemization, selenoylation, arginylation, and ubiquitination. Other common protein modifications are described in, e.g., Creighton, supra, Seifter et al., Meth. Enzymol. 18:626-646 (1990), and Rattan et al., Ann. NY Acad. Sci. 663:48-62 (1992). Post-translational modifications for polypeptides or fusion proteins expressed from nucleic acids in host cells vary depending what kind of host or host cell type the peptide is expressed in. For instance, glycosylation often does not occur in bacterial hosts such as E. coli and varies considerably in baculovirus systems as compared to mammalian cell systems. Accordingly, when glycosylation is desired (which usually is the case for most polypeptides of the present invention), a polypeptide or fusion protein should be expressed (produced) in a glycosylating host, generally a eukaryotic cell (e.g., a mammalian cell or an insect cell). Modifications to the polypeptide or fusion protein in terms of post-translational modification can be verified by any suitable technique, including, e.g., x-ray diffraction, NMR imaging, mass spectrometry, and/or chromatography (e.g., reverse phase chromatography, affinity chromatography, or GLC).

The polypeptide or fusion protein also or alternatively can comprise any suitable number of non-naturally occurring amino acids (e.g., β amino acids) and/or alternative amino acids (e.g., selenocysteine), or amino acid analogs, such as those listed in the MANUAL OF PATENT EXAMINING PROCEDURE §2422 (7th Revision—2000), which can be incorporated by protein synthesis, such as through solid phase protein synthesis (as described in, e.g., Merrifield, Adv. Enzymol. 32:221-296 (1969) and other references cited herein). A polypeptide or fusion protein of the invention can further be modified by the inclusion of at least one modified amino acid. The inclusion of one or more modified amino acids may be advantageous in, for example, (a) increasing polypeptide or fusion protein serum half-life, (b) reducing polypeptide or fusion protein antigenicity, or (c) increasing polypeptide or fusion protein storage stability. Amino acid(s) are modified, for example, co-translationally or post-translationally during recombinant production (e.g., N-linked glycosylation site at N-X-S/T motifs during expression in mammalian cells) or modified by synthetic means. Non-limiting examples of a modified amino acid include a glycosylated amino acid, a sulfated amino acid, a prenylated (e.g., farnesylated, geranylgeranylated) amino acid, an acetylated amino acid, an acylated amino acid, a PEGylated amino acid, a biotinylated amino acid, a carboxylated amino acid, a phosphorylated amino acid, and the like. References adequate to guide one of skill in the modification of amino acids are replete throughout the literature. Example protocols are found in Walker (1998) Protein Protocols on CD-ROM Humana Press, Towata, N.J. The modified amino acid may be selected from a glycosylated amino acid, a PEGylated amino acid, a farnesylated amino acid, an acetylated amino acid, a biotinylated amino acid, an amino acid conjugated to a lipid moiety, and an amino acid conjugated to an organic derivatizing agent.

The invention further provides polypeptides (including fusion proteins) having the above-described characteristics that further comprise additional amino acid sequences that impact the biological function (e.g., immunogenicity, targeting, and/or half-life) of the polypeptide (or fusion protein).

A polypeptide or fusion protein of the invention may further include a targeting sequence other than, or in addition to, a signal sequence. For example, the polypeptide or fusion protein can comprise a sequence that targets a receptor on a particular cell type (e.g., a monocyte, dendritic cell, or associated cell) to provide targeted delivery of the polypeptide to such cells and/or related tissues. Signal sequences are described above, and include membrane localization/anchor sequences (e.g., stop transfer sequences, GPI anchor sequences), and the like.

A particularly useful fusion partner for a polypeptide of the invention (including a fusion protein of the invention) is a peptide sequence that facilitates purification of the polypeptide, e.g., a polypeptide purification subsequence. A polynucleotide of the invention may comprise a coding sequence fused in-frame to a marker amino acid sequence that, e.g., facilitates purification of the encoded polypeptide. Such purification facilitating peptide domains or polypeptide purification subsequences include, but are not limited to, metal chelating peptides, such as histidine-tryptophan modules that allow purification on immobilized metals, such as a hexa-histidine peptide or other a polyhistidine sequence, a sequence encoding such a tag is incorporated in the pQE vector available from QIAGEN, Inc. (Chatsworth, Calif.), a sequence which binds glutathione (e.g., glutathione-S-transferase (GST)), a hemagglutinin (HA) tag (corresponding to an epitope derived from the influenza hemagglutinin protein; Wilson et al., Cell 37:767 (1984)), maltose binding protein sequences, the FLAG epitope utilized in the FLAGS extension/affinity purification system (Immunex Corp, Seattle, Wash.) (commercially available FLAG epitopes also are available through Kodak (New Haven, Conn.)), an E-epitope tag (E-tag), thioredoxin (TRX), avidin, and the like. Purification-facilitating epitope tags have been described in the art (see, e.g., Whitehorn et al., Biotechnology 13:1215-19 (1995)). A polypeptide can include an e-his tag, which may comprise a polyhistidine sequence and an anti-e-epitope sequence (Pharmacia Biotech Catalog); e-his tags can be made by standard techniques. The inclusion of a protease-cleavable polypeptide linker sequence between the purification domain and the polypeptide is useful to facilitate purification. The histidine residues facilitate purification on IMIAC (immobilized metal ion affinity chromatography (IMAC), as described in Porath et al. Protein Expression and Purification 3:263-281 (1992)), while the enterokinase cleavage site provides a method for separating the polypeptide from the fusion protein. pGEX vectors (Promega; Madison, Wis.) can also be used to express foreign polypeptides as fusion proteins with glutathione S-transferase (GST). In general, such fusion proteins are soluble and can easily be purified from lysed cells by adsorption to ligand-agarose beads (e.g., glutathione-agarose in the case of GST-fusion) followed by elution in the presence of free ligand. Additional examples of polypeptide purification facilitating subsequences and the use thereof for protein purification are described in, e.g., Int'l Patent Appn Publ. No. WO 00/15823. After expression of the polypeptide of interest and isolation thereof by such fusion partners or otherwise as described above, protein refolding steps can be used, as desired, in completing configuration of the mature polypeptide.

A fusion protein of the invention also can include one or more additional peptide fragments or peptide portions which promote detection of the fusion protein. For example, a reporter peptide fragment or portion (e.g., green fluorescent protein (GFP), β-galactosidase, or a detectable domain thereof) can be incorporated in the fusion protein. Additional marker molecules that can be conjugated to the polypeptide of the invention include radionuclides, enzymes, fluorophores, small molecule ligands, and the like. Such detection-promoting fusion partners are particularly useful in fusion proteins used in diagnostic techniques discussed elsewhere herein.

In another aspect, a polypeptide of the invention can comprise a fusion partner that promotes stability of the polypeptide, secretion of the polypeptide (other than by signal targeting), or both. For example, the polypeptide can comprise an immunoglobulin (Ig) domain, such as an IgG polypeptide comprising an Fc hinge region, a CH2 domain, and a CH3 domain, that promotes stability and/or secretion of the polypeptide.

The fusion protein peptide fragments or peptide portions can be associated in any suitable manner. The various polypeptide fragments or portions of the fusion protein may be covalently associated (e.g., by means of a peptide or disulfide bond). The polypeptide fragments or portions can be directly fused (e.g., the C-terminus of an antigenic or immunogenic sequence of the invention can be fused to the N-terminus of a purification sequence or heterologous immunogenic sequence). The fusion protein can include any suitable number of modified bonds, e.g., isosteres, within or between the peptide portions. Alternatively or additionally, the fusion protein can include a peptide linker between one or more polypeptide fragments or portions that includes one or more amino acid sequences not forming part of the biologically active peptide portions. Any suitable peptide linker can be used. Such a linker can be any suitable size. Typically, the linker is less than about 30 amino acid residues, less than about 20 amino acid residues, and/or less than 10 amino acid residues. The linker predominantly may comprise or consist of neutral amino acid residues. Suitable linkers are generally described in, e.g., U.S. Pat. Nos. 5,990,275, 6,010,883, 6,197,946, and European Patent Application 0 035 384. If separation of peptide fragments or peptide portions is desirable a linker that facilitates separation can be used. An example of such a linker is described in U.S. Pat. No. 4,719,326. "Flexible" linkers, which are typically composed of combinations of glycine and/or serine residues, can be advantageous. Examples of such linkers are described in, e.g., McCafferty et al., Nature 348:552-554 (1990), Huston et al., Proc. Natl. Acad. Sci. USA 85:5879-5883 (1988), Glockshuber et al., Biochemistry 29:1362-1367 (1990), and Cheadle et al., Molecular Immunol. 29:21-30 (1992), Bird et al., Science 242:423-26 (1988), and U.S. Pat. Nos. 5,672,683, 6,165,476, and 6,132,992.

The use of a linker also can reduce undesired immune response to the fusion protein created by the fusion of the two peptide fragments or peptide portions, which can result in an unintended MHC I and/or MHC II epitope being present in the fusion protein. In addition to the use of a linker, identified undesirable epitope sequences or adjacent sequences can be PEGylated (e.g., by insertion of lysine residues to promote PEG attachment) to shield identified epitopes from exposure. Other techniques for reducing immunogenicity of the fusion protein of the invention can be used in association with the administration of the fusion protein include the techniques provided in U.S. Pat. No. 6,093,699.

Making Polypeptides

Recombinant methods for producing and isolating polypeptides of the invention (including fusion proteins of the invention) are described below. In addition to recombinant production, the polypeptides may be produced by direct peptide synthesis using solid-phase techniques (see, e.g., Stewart et al. (1969) Solid-Phase Peptide Synthesis, W.H. Freeman Co, San Francisco; Merrifield (1963) J. Am. Chem. Soc 85:2149-2154). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. For example, subsequences may be chemically synthesized separately and combined using chemical methods to provide mutant CTLA-4 polypeptides or functional fragments thereof. Alternatively, such sequences may be ordered from any number of companies that specialize in production of polypeptides. Most commonly, polypeptides of the invention are produced by expressing coding nucleic acids and recovering polypeptides, e.g., as described below.

The invention provides methods for producing polypeptides (including fusion proteins) of the invention. One such method comprises introducing into a population of cells any nucleic acid described herein, which is operatively linked to a regulatory sequence effective to produce the encoded polypeptide, culturing the cells in a culture medium to produce the polypeptide, and isolating the polypeptide from the cells or from the culture medium. An amount of nucleic acid sufficient to facilitate uptake by the cells (transfection) and/or expression of the polypeptide is utilized. The culture medium can be any described herein and in the Examples. Additional media are known to those of skill in the art. The nucleic acid is introduced into such cells by any delivery method described herein, including, e.g., injection, needleless injection device, gene gun, electroporation (e.g., DNA electroporation device, Inovio Biomedical Corp. (San Diego)), transdermal delivery, passive uptake, etc. The nucleic acid of the invention may be part of a vector, such as a recombinant expression vector, including a DNA plasmid vector, viral vector, or any vector described herein. The nucleic acid or vector comprising a nucleic acid of the invention may be prepared and formulated as described herein, above, and in the Examples below. Such a nucleic acid or expression vector may be introduced into a population of cells of a mammal in vivo, or selected cells of the mammal (e.g., tumor cells) may be removed from the mammal and the nucleic acid expression vector introduced ex vivo into the population of such cells in an amount sufficient such that uptake and expression of the encoded polypeptide results. Or, a nucleic acid or vector comprising a nucleic acid of the invention is produced using cultured cells in vitro. In one aspect, the method of producing a polypeptide of the invention comprises introducing into a population of cells a recombinant expression vector comprising any nucleic acid described herein in an amount and formula such that uptake of the vector and expression of the polypeptide will result; administering the expression vector into a mammal by any introduction/delivery format described herein; and isolating the polypeptide from the mammal or from a byproduct of the mammal. Suitable host cells, expression vectors, methods for transfecting host cells with an expression vector comprising a nucleic acid sequence encoding a polypeptide of the invention, cell cultures, and procedures for producing and recovering such polypeptide from a cell culture are described in detail below in the section entitled "Nucleic Acids of the Invention." Additional methods of production are discussed in the Examples, infra.

As noted above, polypeptides of the invention (which includes fusion proteins of the invention) can be subject to various changes, such as one or more amino acid or nucleic acid insertions, deletions, and substitutions, either conservative or non-conservative, including where, e.g., such changes might provide for certain advantages in their use, e.g., in their therapeutic or prophylactic use or administration or diagnostic application. Procedures for making variants of polypeptides by using amino acid substitutions, deletions, insertions, and additions are routine in the art. Polypeptides and variants thereof having the desired ability to bind CD80 and/or CD86, or a fragment thereof (e.g., ECD) or an ability to suppress an immune response in vitro or in vivo as described in detail elsewhere herein are readily identified by assays known to those of skill in the art and by the assays described herein. See, e.g., assays presented in the Examples below.

The nucleic acids of the invention, discussed in greater detail infra, can also be subject to various changes, such as one or more substitutions of one or more nucleic acids in one or more codons such that a particular codon encodes the same or a different amino acid, resulting in either a conservative or non-conservative substitution, or one or more deletions of one or more nucleic acids in the sequence. The nucleic acids can also be modified to include one or more codons that provide for optimum expression in an expression system (e.g., mammalian cell or mammalian expression system), while, if desired, said one or more codons still encode the same amino acid(s). Procedures for making variants of nucleic acids by using nucleic acid substitutions, deletions, insertions, and additions, and degenerate codons, are routine in the art, and nucleic acid variants encoding polypeptides having the desired properties described herein (e.g., an ability to bind CD80 and/or CD86, and/or suppress an immune response in vitro or in vivo) are readily identified using the assays described herein. Such nucleic acid changes might provide for certain advantages in their therapeutic or prophylactic use or administration, or diagnostic application. In one aspect, the nucleic acids and polypeptides can be modified in a number of ways so long as they comprise a nucleic acid or polypeptide sequence substantially identical to the nucleic acid sequence of a respective mutant CTLA-4 polypeptide-encoding nucleic acid or mutant CTLA-4 polypeptide of the invention, respectively.

Nucleic Acids of the Invention

The invention provides isolated or recombinant nucleic acids (also referred to herein as polynucleotides), collectively referred to as "nucleic acids of the invention" (or "polynucleotides of the invention"), which encode polypeptides of the invention. Nucleic acids of the invention, including all described below, are useful in recombinant production (e.g., expression) of polypeptides of the invention, typically through expression of a plasmid expression vector comprising a sequence encoding the polypeptide or fragment thereof; as therapeutics; as prophylactics; as diagnostic tools; as diagnostic probes for the presence of complementary or partially complementary nucleic acids (including for detection of a wild-type CTLA-4 nucleic acid). For example, nucleic acids of the invention, including all described below, are useful because they encode polypeptides that are useful in suppressing or inhibiting an immune response (e.g., T cell activation, T cell proliferation, cytokine synthesis or production (e.g., production of TNF-α, IFN-γ, IL-2), induction of activation markers (e.g., CD25, IL-2 receptor), inflammation, anti-collagen antibody production, and/or T cell-dependent antibody response) in vitro and/or in vivo applications, including, e.g., prophylactic and/or therapeutic methods for treating immune system diseases, disorders, and conditions in which suppression of an immune response is desirable (e.g., methods for treating autoimmune diseases and disorders and methods for inhibiting rejection of a tissue, cell, or organ transplant from a donor by a recipient). Nucleic acids of the invention can also be incorporated into expression vectors useful for gene therapy, DNA vaccination, and immunosuppressive therapy. Additional uses of the nucleic acids and vectors of the invention comprising such nucleic acids are described elsewhere herein.

In one aspect, the invention provides an isolated or recombinant nucleic acid comprising a nucleotide sequence encoding any polypeptide (including any fusion protein, etc.) of the invention described above in the section entitled "Polypeptides of the Invention" and elsewhere herein. The invention also provides an isolated or recombinant nucleic acid comprising a nucleotide sequence encoding a combination of two or more of any polypeptides (including any fusion proteins) of the invention described above and elsewhere herein. Also included is a nucleic acid that encodes any polypeptide of the invention, such as, e.g., a mutant CTLA-4 ECD polypeptide or mutant CTLA-4-Ig fusion protein, which comprises a sequence of codons substantially optimized for expression in a mammalian host, such as a human.

For example, in one aspect, the invention provides an isolated or recombinant nucleic acid comprising a polynucleotide sequence that encodes a polypeptide comprising a polypeptide sequence that has at least 75%, 80%, 85%, 86%, 87%, 88%, 89%, 90%, 91%, 92%, 93%, 94%, 95%, 96%, 97%, 98%, 99%, 99.5%, or 100% sequence identity to at least one polypeptide sequence selected from the group consisting of SEQ ID NOS:1-73, or a complementary polynucleotide sequence thereof, wherein the polypeptide binds CD80 and/or CD86 or a polypeptide fragment of CD80 and/or CD86 (e.g., an extracellular domain of CD80 and/or CD86), and/or suppress an immune response in vitro and/or in vivo, or a complementary polynucleotide sequence thereof. Additional details regarding the functional properties and characteristics of such polypeptides are discussed above in "Polypeptides of the Invention." Some such nucleic acids encode a polypeptide comprising a polypeptide sequence having an amino acid length about equal to the amino acid length of the hCTLA-4 ECD; as, e.g., 110-138, 112-132, 118-130, 119-129, 120-128, 121-127, 122-126, 123-125, or 124 amino acid residues. Exemplary nucleic acids which encode the mutant CTLA-4 ECD polypeptides comprising the sequences set forth in SEQ ID NOS:1-73, but are not limited to, e.g., nucleic acids having nucleotide sequences set forth in SEQ ID NOS:80-152, respectively. For example, an exemplary nucleic acid encoding the polypeptide shown in SEQ ID NO:1 (clone D3-1) is the nucleic acid shown in SEQ ID:80. Also included are fragments of any such nucleic acids, wherein such fragment encodes a polypeptide that binds CD80 and/or CD86 and/or an ECD of either or both, and/or has an ability to suppress an immune response.

In another aspect, the invention provides an isolated or recombinant nucleic acid comprising a polynucleotide sequence which encodes a polypeptide (e.g., mutant CTLA-4 ECD polypeptide) which comprises a polypeptide sequence (a) which differs from a polypeptide sequence selected from the group consisting of SEQ ID NOS:1-73 in no more than 6 amino acid residues (e.g., no more than 1, 2, 3, 4, 5, or 6 amino acid residues), and (b) wherein the amino acid residue in the polypeptide sequence at position 41, 50, 54, 55, 56, 64, 65, 70, or 85 is identical to the amino acid residue at the corresponding position of said polypeptide sequence selected from the group consisting of SEQ ID NOS:1-73, wherein the polypeptide binds CD80 and/or CD86 and/or an extracellular domain of either or both, and/or inhibits an immune response in vitro and/or in vivo, or a complementary polynucleotide sequence thereof. That is, the amino acid residue at such position 41, 50, 54, 55, 56, 64, 65, 70, or 85 in such selected polypeptide sequence is not deleted or substituted. Some such nucleic acids encode polypeptides comprising a sequence which differs from the selected polypeptide sequence by no more than 6 amino acid residues and which includes amino acid residues at 2, 3, 4, 5, 6, 7, 8, 9, 10, 11, 12, 13, and/or 14 positions selected from amino acid positions 24, 30, 32, 41, 50, 54, 55, 56, 64, 65, 70, 85, 104 and 106 that are identical to the amino acid residues at the corresponding positions in the selected polypeptide sequence. Such polypeptides can differ from the selected polypeptide sequence by amino acid deletion(s), addition(s), and/or amino acid substitution(s). An amino acid substitution may be a conservative or non-conservative substitution. Exemplary conservative substitutions are discussed in the section entitled "Sequence Variation." Some such polypeptides comprise a sequence having a length of about 118-130, 119-129, 120-128, 121-127, 122-126, 123-125, or 124 amino acid residues. Additional details of the functional properties and characteristics of such polypeptides are discussed above. Exemplary nucleic acids include, but are not limited to, e.g., those comprising nucleotide sequences set forth in SEQ ID NOS:80-152.

In another aspect, the invention provides an isolated or recombinant nucleic acid comprising a polynucleotide sequence which encodes a polypeptide (e.g., mutant CTLA-4 ECD) comprising a polypeptide sequence which (a) differs from the polypeptide sequence of the extracellular domain of human CTLA-4 shown in SEQ ID NO:159 in no more than 6 amino acid residues, and (b) comprises at least one amino acid substitution at an amino acid position corresponding to position 50, 54, 55, 56, 64, 65, 70, or 85 relative to the polypeptide sequence of SEQ ID NO:159, wherein the polypeptide binds hCD80 and/or hCD86 and/or an ECD of either or both, and/or inhibits an immune response in vitro and/or in vivo, or a complementary polynucleotide sequence thereof. Some such nucleic acids encode polypeptides comprising 2, 3, 4, 5, or 6 amino acid substitutions at positions relative to the sequence set forth in SEQ ID NO:159 selected from the group consisting of position 50, 54, 55, 56, 64, 65, 70, and 85. Some such nucleic acids encoding polypeptides further comprising an amino acid substitution at a position corresponding to position 104 and/or 30 relative to SEQ ID NO:159. Some such nucleic acids encode polypeptides comprising at least one amino acid substitution relative to SEQ ID NO:159 at position 70 (e.g., S70F), position 64 (e.g., S64P), position 50 (e.g., A50M), position 54 (e.g., M54K/V), position 65 (e.g., I65S), position 56 (e.g., N56D), position 55 (e.g., G55E), position 85 (e.g., M85A), and/or position 24 (e.g., A24E). Any such polypeptide may further comprise an amino acid substitution relative to SEQ ID NO:159 at position 104 (optionally L104E/D, e.g., L104E), position 30 (e.g., T30N/D/A), and/or position 32 (e.g., V32I). Some such nucleic acids encode polypeptides comprising one or more substitutions at amino acid positions relative to SEQ ID NO:159 selected from the group consisting of A50M, M54K, G55E, N56D, S64P, I65S, and S70F. Some such encoded polypeptides comprise a sequence having an amino acid length of about 118-130, 119-129, 120-128, 121-127, 122-126, 123-125, or 124 amino acid residues. Additional details of the functional properties and characteristics of such polypeptides are discussed above.

The invention also provides an isolated or recombinant nucleic acid comprising a polynucleotide sequence which encodes a polypeptide (e.g., mutant CTLA-4 ECD) comprising a polypeptide sequence comprising (i) at least 95%, 96%, 97%, 98%, 99%, or 100% identity to any polypeptide sequence selected from the group consisting of SEQ ID NOS: 1-73 and (ii) a phenylalanine residue at an amino acid position corresponding to position 70 of said polypeptide sequence selected from the group consisting of SEQ ID NO:1-73, wherein the polypeptide binds hCD80 and/or hCD86 or an ECD thereof and/or inhibits an immune response, or a complementary polynucleotide sequence thereof. Some such nucleic acids encode polypeptides comprising one or more of the following relative to the selected sequence: a glutamic acid residue at an amino acid position corresponding to position 24; an asparagine residue at an amino acid position corresponding to position 30; an isoleucine residue at an amino acid position corresponding to position 32; a methionine residue at an amino acid position corresponding to position 50; a lysine residue at an amino acid position corresponding to position 54; a glutamic acid residue at an amino acid position corresponding to position 55; an aspartic acid residue at an amino acid position corresponding to position 56; a proline residue at an amino acid position corresponding to position 64; a serine residue at an amino acid position corresponding to position 65; and a glutamic acid residue at an amino acid position corresponding to position 104. Some such nucleic acids encode polypeptides comprising a polypeptide sequence having a length of about 118-130, 119-129, 120-128, 121-127, 122-126, 123-125, or 124 amino acid residues. Additional details of the functional properties and characteristics of such polypeptides are discussed above.

In another aspect, the invention provides an isolated or recombinant nucleic acid comprising a polynucleotide sequence which encodes a polypeptide (e.g., mutant CTLA-4 ECD) comprising a polypeptide sequence which (a) differs from the polypeptide sequence of human CTLA-4 ECD polypeptide shown in SEQ ID NO:159 in no more than 6 amino acid residues, and (b) comprises at least one amino acid substitution, wherein said at least one amino acid substitution is S70F, wherein amino acid residue positions are numbered according to SEQ ID NO:159, wherein the polypeptide that binds hCD80 and/or hCD86 (and/or an ECD of either or both) and/or inhibits an immune response, or a complementary polynucleotide sequence thereof. Some such nucleic acids encode a polypeptide that further comprises at least one amino acid substitution selected from the group consisting of A24E, T30N, V32I, D41G, A50M, M54K, G55E, N56D, S64P, I65S, M85A, L104E, and I106F. Some such nucleic acids encode polypeptides comprising a polypeptide sequence having a length of about 118-130, 119-129, 120-128, 121-127, 122-126, 123-125, or 124 amino acid residues. Additional details of the functional properties and characteristics of such polypeptides are discussed above.

In another aspect, the invention provides an isolated or recombinant nucleic acid comprising a polynucleotide sequence which encodes a polypeptide (e.g., mutant CTLA-4 ECD) comprising a polypeptide sequence which (a) differs from the polypeptide sequence shown in SEQ ID NO:31 in no more than 6 amino acid residues, and (b) comprises at least one of the following: a methionine residue at a position corresponding to position 50 of SEQ ID NO:31, a lysine residue at a position corresponding to position 54 of SEQ ID NO:31, a glutamic acid residue at a position corresponding to position 55 of SEQ ID NO:31, a proline residue at a position corresponding to position 64 of SEQ ID NO:31, a serine residue at a position corresponding to position 65 of SEQ ID NO:31, a phenylalanine residue at a position corresponding to position 70 of SEQ ID NO:31, wherein amino acid residue positions are numbered according to SEQ ID NO:31, and wherein the polypeptide binds CD80 and/or CD86 and/or an ECD of either or both, and/or inhibits an immune response, or a complementary polynucleotide sequence thereof. Some such encoded polypeptides comprise a glutamic acid residue at a position corresponding to position 104, an asparagine acid residue at a position corresponding to position 30, and/or an isoleucine residue at a position corresponding to position 32 of SEQ ID NO:31. Some such nucleic acids encode polypeptides comprising a polypeptide sequence having a length of about 118-130, 119-129, 120-128, 121-127, 122-126, 123-

125, or 124 amino acid residues. Additional details of the functional properties and characteristics of such polypeptides are discussed above.

In another aspect, the invention provides an isolated or recombinant nucleic acid comprising a polynucleotide sequence having at least 80%, 85%, 86%, 87%, 88%, 89%, 90%, 91%, 92%, 93%, 94%, 95%, 96%, 97%, 98%, 99%, 99.5%, or 100% identity to at least one polynucleotide sequence selected from the group consisting of SEQ ID NOS: 80-158, 201-204, 223, and 224, or a complementary polynucleotide sequence thereof, wherein the nucleic acid encodes a polypeptide that binds hCD80 and/or hCD86 and/or an ECD of either or both, and/or suppresses an immune response, or a complementary polynucleotide sequence thereof. Exemplary nucleic acids comprising polynucleotide sequences identified by SEQ ID NOS:80-158 encode exemplary polypeptides comprising polypeptide sequences identified by SEQ ID NOS:1-79, respectively. Exemplary nucleic acids comprising polynucleotide sequences identified by SEQ ID NOS:201-204 encode exemplary polypeptides comprising polypeptide sequences identified by SEQ ID NOS: 197-200, respectively.

In another aspect, the invention includes an isolated or recombinant nucleic acid comprising: (a) a polynucleotide sequence having at least 95%, 96%, 97%, 98%, 99%, or 100% identity to an RNA polynucleotide sequence, wherein the RNA polynucleotide sequence comprises a DNA sequence selected from the group consisting of SEQ ID NOS:80-158, 201-204, 223, and 224 in which all of the thymine nucleotide residues in the DNA sequence are replaced with uracil nucleotide residues; (b) a complementary polynucleotide sequence of (a); or (c) a fragment of any polynucleotide sequence of (a) or (b), wherein the nucleic acid encodes a polypeptide that (i) binds CD80 and/or CD86 and/or an ECD of either or both, and/or (ii) has an ability to suppress an immune response in vitro or in vivo (e.g., T cell activation or proliferation, cytokine synthesis or production (e.g., production of TNF-$\alpha$, IFN-$\gamma$, IL-2), induction of activation markers (e.g., CD25, IL-2 receptor), inflammation, anti-collagen antibody production, and/or T cell-dependent antibody response), or a polynucleotide sequence thereof.

The invention includes an isolated or recombinant nucleic acid encoding any multimer of any polypeptide of the invention described above (e.g., dimer, tetramer, etc.). A discussed in greater detail elsewhere, a dimer comprising two polypeptides of the invention (including two fusion proteins) is typically formed during cellular processing by the generation of one or more covalent disulfide bonds between cysteine residue(s) in one polypeptide and cysteine residue(s) in the second polypeptide. Other multimers may be similarly formed. For example, in a non-limiting aspect, the invention provides an isolated or recombinant nucleic acid comprising a polynucleotide sequence which encodes a recombinant polypeptide dimer comprising two polypeptides, wherein each such polypeptide comprises a polypeptide sequence having at least 95%, 96%, 97%, 98%, 99%, or 100% identity to a sequence selected from the group consisting of SEQ ID NOS:1-73, wherein the dimer binds hCD80 and/or hCD86 and/or inhibits an immune response, or a complementary polynucleotide sequence thereof. Also included is an isolated or recombinant nucleic acid comprising a polynucleotide sequence which encodes a polypeptide dimer comprising two polypeptides, wherein each such polypeptide differs from the polypeptide sequence of the hCTLA-4 ECD (SEQ ID NO:159) in no more than 6 amino acid residues and comprises at least one substitution at an amino acid position relative to SEQ ID NO:159 selected from the group consisting of A50M, M54K, G55E, N56D, S64P, I65S, and S70F; and which polypeptide optionally further comprises the substitution L104E, wherein said dimer binds hCD80 and/or hCD86 and/or inhibits an immune response, or a complementary polynucleotide sequence thereof. Additional details of the functional properties of such dimers are discussed above.

The invention also provides an isolated or recombinant nucleic acid encoding any fusion protein of the invention, including any multimeric fusion protein of the invention (e.g., dimers, tetramers, etc.). In one aspect, the invention provides an isolated or recombinant nucleic acid comprising a polynucleotide sequence which encodes a fusion protein comprising (a) a polypeptide comprising a polypeptide sequence that has at least 80%, 85%, 90%, 91%, 92%, 93%, 94%, 95%, 96%, 97%, 98%, 99%, 99.5%, or 100% identity to at least one polypeptide sequence selected from the group consisting of SEQ ID NOS:1-73, and (b) an Ig polypeptide, wherein the fusion protein binds CD80 and/or CD86 (and/or CD80-Ig and/or CD86-Ig), and/or has an ability to suppress an immune response, or a complementary polynucleotide sequence thereof. The Ig polypeptide may comprise an Ig Fc polypeptide, including, e.g., an Ig Fc polypeptide comprising a polypeptide sequence having at least 95%, 96%, 97%, 98%, 99%, or 100% identity to a polypeptide sequence selected from the group consisting of SEQ ID NOS:184-186 and 218. A dimeric fusion protein comprising two such monomeric fusion proteins is typically formed during cellular processing by the generation of covalent disulfide bonds between cysteine residues in one monomeric fusion protein and cysteine residues in the second monomeric fusion protein. Other multimers may be similarly formed. Additional details of the functional properties and characteristics of such fusion proteins are discussed above.

In another aspect, the invention provides an isolated or recombinant nucleic acid comprising a polynucleotide sequence which encodes a protein dimer (e.g., mutant CTLA-4-Ig dimer) comprising two monomeric fusion proteins (e.g., monomeric mutant CTLA-4 Ig), each monomeric fusion protein comprising: (a) a polypeptide (e.g., mutant CTLA-4 ECD) comprising a polypeptide sequence having at least 90%, 91%, 92%, 93%, 94%, 95%, 96%, 97%, 98%, 99%, 99.5%, or 100% identity to at least one polypeptide sequence selected from the group consisting of SEQ ID NOS:1-73, and (b) an Ig polypeptide, wherein the fusion protein dimer binds CD80 and/or CD86 (and/or CD80-Ig and/or CD86-Ig), and/or has an ability to inhibit or suppress an immune response, or a complementary polynucleotide sequence thereof. The two monomeric fusion proteins, upon expression, are linked together via at least one disulfide bond formed between two cysteine residues present in each monomeric mutant CTLA-4-Ig fusion protein. The Ig polypeptide may comprise an Ig Fc polypeptide, including, e.g., an Ig Fc polypeptide comprising a sequence having at least 95%, 96%, 97%, 98%, 99%, or 100% identity to a sequence selected from the group consisting of SEQ ID NOS:184-186 and 218. In some instances, the C-terminus of the polypeptide of (a) is covalently linked or fused to the N-terminus of the Ig Fc polypeptide of (b). Additional details of the functional properties and characteristics of such dimers are discussed above.

A stop codon (e.g., tga) is typically included at the C-terminus of each nucleic acid sequence when the sequence is included in an expression vector for expression of a protein of interest. For example, each of the nucleotide sequences of the invention encoding a mutant CTLA-4 polypeptide or mutant CTLA-4 fusion protein may optionally further include a stop codon at the C terminus, such as TAA. A different stop codon may be substituted for the TAA, such as a TGA stop codon. A nucleic acid sequence encoding a wild-type fusion protein (e.g., hCTLA-4-Ig, hCD86-Ig, etc.) may also include a stop codon at its C-terminus. Each of the nucleotide sequences may optionally further includes at the N-terminus a nucleotide sequence encoding a signal peptide to facilitate secretion of a mutant CTLA-4 polypeptide or fusion protein.

Exemplary mutant CTLA-4-Ig fusion protein dimers include those comprising polypeptide sequences shown in SEQ ID NOS:74-79, 197-200, 205-214, and 219-222. Exemplary nucleic acids encoding the mutant CTLA-4 Ig fusion proteins of SEQ ID NOS:74-79, 197-200, 220 and 222 are set forth in SEQ ID NO:153-158, 201-204, and 223-224, respectively. The fusion protein sequences of SEQ ID NOS:205-210, 211-214, 219, and 221 are identical to the protein sequences of SEQ ID NOS:74-79, 197-200, 220, and 222, respectively, except that the protein sequences of SEQ ID NOS:205-210 do not include the C-terminal lysine (K) residue; as explained above, it is believed that the predicted C-terminal lysine residue, which is encoded by the AAA codon immediately preceding the TAA stop codon of each such polynucleotide sequence, is cleaved from the resulting fusion protein during processing or secretion. The nucleic acid sequences of SEQ ID NOS:153-158, 201-204, and 223-224 encode the fusion protein sequences of SEQ ID NOS:74-79, 197-200, 220, and 222, respectively, each of which after cleavage/loss of the C-terminal K residue results in the fusion protein sequences shown in SEQ ID NOS:205-210, 211-214, 219, and 221, respectively.

Each of the polynucleotide sequences SEQ ID NOS:153-158, 201-204, and 223-224 also includes at its N-terminus a nucleotide sequence encoding the signal peptide shown in SEQ ID NO:181 or 215, which signal peptide is ultimately cleaved to form the mature fusion protein. Nucleotide residues 1-111 of each of the polynucleotide sequences of SEQ ID NOS:153-158, 201-204, and 223-224, as counted from the N-terminus of each such polynucleotide sequence (nucleotide residues 1-111 are set forth in SEQ ID NO:215), encode the 37-amino acid residue WT hCTLA-4 signal peptide shown in SEQ ID NO:216, which signal peptide is ultimately cleaved upon expression of the mature mutant CTLA-4 fusion protein monomer or dimer; thus, for each of the nucleic acid sequences of SEQ ID NOS:153-158, 201-204, and 223-224, the first codon encoding the first amino acid residue (methionine) of the mature IgG2 fusion protein is composed of nucleotide residues 112-114 of said nucleotide sequence. As noted above, in some instances, the signal peptide sequence may comprise only amino acid residues 1-35 as shown in SEQ ID NO:182 and the nucleotide sequence encoding this 35-amino acid residue signal peptide is shown in SEQ ID NO:181. Nevertheless, the encoded lysine (K) and alanine (A) residues at positions 36 and 37, respectively (encoded by the two codons AAA-GCC), are not present in the resulting mature mutant CTLA-4-Ig fusion protein and are believed cleaved from the mature mutant CTLA-4-Ig fusion protein during processing. The mature mutant CTLA-4 protein sequence typically begins with the methionine residue present at amino acid residue position 38 of the encoded mutant CTLA-4-Ig fusion protein.

In another aspect, the invention provides an isolated or recombinant nucleic acid comprising a polynucleotide sequence which encodes a fusion protein dimer (e.g., mutant CTLA-4-Ig dimer) comprising two identical monomeric fusion proteins (e.g., monomeric mutant CTLA-4-Ig), wherein each such monomeric fusion protein comprises a polypeptide sequence having at least 95%, 96%, 97%, 98%, 99% or 100% identity to a polypeptide sequence selected from the group consisting of SEQ ID NOS:74-79, 197-200, 205-214, and 219-222, wherein the fusion protein dimer binds CD80 and/or CD86 (and/or a CD80-Ig and/or CD86-Ig), and/or has an ability to inhibit an immune response, or a complementary polynucleotide sequence thereof. Also provided is an isolated or recombinant nucleic acid encoding such monomeric fusion protein which binds CD80 and/or CD86 (and/or a CD80-Ig and/or CD86-Ig, and/or has an ability to inhibit an immune response. Exemplary mutant CTLA-4-Ig fusion protein dimers include those comprising polypeptide sequences shown in SEQ ID NOS:74-79, 197-200, 220, and 222; exemplary nucleic acids encoding such mutant CTLA-4 Ig fusion proteins, which are expressed as mutant CTLA-4-Ig fusion protein dimers, include those comprising polynucleotide sequences shown in SEQ ID NOS: 153-158, 201-204, and 223-224, respectively. Additional exemplary mutant CTLA-4-Ig fusion protein dimers comprise the polypeptide sequences of SEQ ID NOS:205-210, 211-214, 219, and 222, which are expressed as fusion protein dimers; these fusion proteins lack the C-terminal lysine residue because it is typically cleaved during processing or prior to secretion. Exemplary nucleic acids encoding these fusion protein sequences with the C-terminal lysine (the lysine is cleaved subsequently) include the polynucleotide sequences of SEQ ID NOS:153-158, 201-204, and 223-224, respectively.

In another aspect, the invention provides an isolated or recombinant nucleic acid comprising a polynucleotide sequence which encodes a fusion protein, wherein said fusion protein comprises a polypeptide sequence having at least 95%, 96%, 97%, 98%, 99% or 100% identity to a polypeptide sequence selected from the group consisting of SEQ ID NOS: 74-79, 197-200, 205-214, and 219-222, wherein the fusion protein binds CD80 and/or CD86 (and/or a CD80-Ig and/or CD86-Ig), and/or has an ability to inhibit an immune response, or a complementary polynucleotide sequence thereof.

In another aspect, the invention includes an isolated or recombinant nucleic acid comprising a nucleotide sequence having at least 95%, 96%, 97%, 98%, 99% or 100% sequence identity to a polynucleotide sequence selected from the group consisting of SEQ ID NOS:153-158, 201-204, and 223-224, wherein such nucleic acid encodes a mutant CTLA-4-Ig protein dimer binds CD80 and/or CD86 (and/or a CD80-Ig and/or CD86-Ig), and/or has an ability to inhibit an immune response, or a complementary polynucleotide sequence thereof.

In another aspect, the invention provides an isolated or recombinant nucleic acid comprising a polynucleotide sequence which encodes a fusion protein dimer (e.g., mutant CTLA-4-Ig dimer) comprising two monomeric fusion proteins (e.g., monomeric mutant CTLA-4-Ig), wherein each such monomeric fusion protein comprises: (1) a polypeptide (e.g., mutant CTLA-4 ECD) which comprises a polypeptide sequence which differs from a polypeptide sequence selected from the group consisting of SEQ ID NOS:1-73 in no more than 6 amino acid residues, and wherein the amino acid residue in the polypeptide sequence at position 41, 50, 54, 55, 56, 64, 65, 70, or 85 is identical to the amino acid residue at the corresponding position of said selected polypeptide sequence (e.g., a polypeptide selected from SEQ ID NOS:1-73), and (2) an Ig Fc polypeptide, wherein the dimer binds CD80 and/or CD86 (and/or CD80-Ig and/or CD86-Ig), and/or inhibits an immune response, or a complementary polynucleotide sequence thereof. Additional details of the functional properties and characteristics of such dimers are discussed above. Also provided is a recombinant or isolated nucleic acid comprising a nucleotide sequence which encodes such a monomeric fusion protein which binds CD80 and/or CD86 (and/or CD80-Ig and/or CD86-Ig) and/or has an ability to inhibit an immune response.

In another aspect, the invention provides an isolated or recombinant nucleic acid comprising a polynucleotide sequence which encodes a fusion protein dimer (e.g., mutant CTLA-4-Ig dimer) comprising two monomeric fusion proteins (e.g., two monomeric mutant CTLA-4-Ig), wherein each such monomeric fusion protein comprises: (1) a mutant CTLA-4 extracellular domain polypeptide comprising a polypeptide sequence which (a) differs from a polypeptide sequence selected from the group consisting of SEQ ID NOS: 1-73 in no more than 6 amino acid residues, and (b) comprises at least one amino acid substitution at an amino acid position corresponding to position 50, 54, 55, 56, 64, 65, 70, or 85 relative to the polypeptide sequence of SEQ ID NO:159; and (2) an Ig polypeptide, wherein the fusion protein dimer binds CD80 and/or CD86 (and/or CD80-Ig and/or CD86-Ig), and/or inhibits an immune response, or a complementary polynucleotide sequence thereof. Additional details of the functional properties and characteristics of such dimers are discussed above. The Ig polypeptide may comprise an Ig Fc polypeptide, including, e.g., an Ig Fc polypeptide comprising a sequence having at least 90%, 91%, 92%, 93%, 94%, 95%, 96%, 97%, 98%, 99%, or 100% identity to a sequence selected from the group consisting of SEQ ID NOS:184-186 and 218. Some such polypeptides of (a) comprise at least one substitution at an amino acid position relative to SEQ ID NO:159 selected from the group consisting of A50M, M54K, G55E, N56D, S64P, I65S, and S70F. Some such polypeptides of (a) further comprise an amino acid substitution relative to SEQ ID NO:159 at position 104 (e.g., L104E/D), position 30 (e.g., T30N/D/A), and/or position 32 (e.g., V32I). Also provided is a recombinant or isolated nucleic acid encoding such monomeric fusion protein which binds CD80 and/or CD86 (and/or CD80-Ig and/or CD86-Ig) and/or has an ability to inhibit an immune response.

In another aspect, the invention includes an isolated or recombinant nucleic acid encoding a fusion protein dimer (e.g., mutant CTLA-4-Ig dimer) comprising two monomeric fusion proteins (e.g., monomeric mutant CTLA-4-Ig), wherein each such monomeric fusion protein comprises: (1) a polypeptide (e.g., mutant CTLA-4 ECD) comprising a polypeptide sequence which (i) has at least 92%, 93%, 94%, 95%, 96%, 97%, 98%, 99%, or 100% identity to a polypeptide sequence selected from the group consisting of SEQ ID NOS:1-73 and (ii) includes a phenylalanine residue at an amino acid position corresponding to position 70 of said polypeptide sequence selected from the group consisting of SEQ ID NO:1-73; and (2) an Ig polypeptide, wherein the fusion protein dimer binds CD80 and/or CD86 (and/or CD80-Ig and/or CD86-Ig), and/or has an ability to inhibit an immune response, or a complementary polynucleotide sequence thereof. The encoded Ig polypeptide may comprise an Ig Fc polypeptide comprising a polypeptide sequence having at least 92%, 93%, 94%, 95%, 96%, 97%, 98%, 99%, or 100% identity to a polypeptide sequence selected from the group consisting of SEQ ID NOS:184-186 and 218. Some such encoded dimers comprise one or more of the following relative to said selected polypeptide sequence of (1) (i): a Glu residue at a position corresponding to position 24; an Asn at a position corresponding to position 30; an Ile residue at a position corresponding to position 32; a Met residue at a position corresponding to position 50; a Lys residue at a position corresponding to position 54; a Glu residue at a position corresponding to position 55; an Asp residue at a position corresponding to position 56; a Pro residue at a position corresponding to position 64; a Ser residue at an amino acid position corresponding to position 65; and a Glu residue at a position corresponding to position 104. Additional details of the functional properties and characteristics of such dimers are discussed above. Also provided is a recombinant or isolated nucleic acid comprising a nucleotide sequence which encodes such a monomeric fusion protein which binds CD80 and/or CD86 (and/or CD80-Ig and/or CD86-Ig) and/or has an ability to inhibit an immune response.

In another aspect, the invention includes an isolated or recombinant nucleic acid encoding fusion protein dimer (e.g., mutant CTLA-4-Ig dimer) comprising two monomeric fusion proteins (e.g., monomeric mutant CTLA-4-Ig), wherein each such monomeric fusion protein comprises: (1) a polypeptide (e.g., mutant CTLA-4 ECD) comprising a polypeptide sequence which (a) differs from the polypeptide sequence of the human CTLA-4 ECD polypeptide shown in SEQ ID NO:159 in no more than 6 amino acid residues, and (b) comprises at least one amino acid substitution, wherein said at least amino acid substitution comprises S70F, wherein amino acid residue positions are numbered according to SEQ ID NO:159; and (2) an IgG Fc polypeptide, wherein said dimer binds hCD80 and/or hCD86 (and/or hCD86-Ig and/or hCD86-Ig), and/or inhibits an immune response, or a complementary polynucleotide sequence thereof. The Ig Fc polypeptide may comprise a sequence having at least 95%, 96%, 97%, 98%, 99%, or 100% identity to a polypeptide sequence selected from the group consisting of SEQ ID NOS:184-186 and 218. The encoded polypeptide of (1) may further comprise at least one amino acid substitution selected from the group consisting of A24E, T30N, V32I, D41G, A50M, M54K, G55E, N56D, S64P, I65S, M85A, L104E, and I106F. Additional details of the functional properties and characteristics of such dimers are discussed above. Also provided is a recombinant or isolated nucleic acid comprising a nucleotide sequence which encodes such a monomeric fusion protein which binds CD80 and/or CD86 (and/or CD80-Ig and/or CD86-Ig) and/or has an ability to inhibit an immune response.

In another aspect, the invention provides an isolated or recombinant nucleic acid encoding fusion protein dimer (e.g., mutant CTLA-4-Ig dimer) comprising two monomeric fusion proteins (e.g., monomeric mutant CTLA-4-Ig), wherein each such monomeric fusion protein comprises: (1) a polypeptide (e.g., mutant CTLA-4 ECD) comprising a polypeptide sequence which (a) differs from the polypeptide sequence of SEQ ID NO:31 in no more than 6 amino acid residues, and (b) comprises at least one of the following: a methionine residue at a position corresponding to position 50 of SEQ ID NO:31, a lysine residue at a position corresponding to position 54 of SEQ ID NO:31, a glutamic acid residue at a position corresponding to position 55 of SEQ ID NO:31, a proline residue at a position corresponding to position 64 of SEQ ID NO:31, a serine residue at a position corresponding to position 65 of SEQ ID NO:31, a phenylalanine residue at a position corresponding to position 70 of SEQ ID NO:31, wherein amino acid residue positions are numbered according to SEQ ID NO:31; and (2) an Ig polypeptide, wherein said dimer binds hCD80 and/or hCD86 (and/or hCD86-Ig and/or hCD86-Ig), and/or inhibits an immune response, or a complementary polynucleotide sequence thereof. The Ig polypeptide may comprise an Ig Fc polypeptide, including, e.g., an Ig Fc polypeptide comprising a sequence having at least 95%, 96%, 97%, 98%, 99%, or 100% identity to a sequence selected from the group consisting of SEQ ID NOS:184-186 and 218. In some such dimers or monomers, the polypeptide of (1) comprises a glutamic acid residue at a position corresponding to position 104, an asparagine acid residue at a position corresponding to position 30, and/or an isoleucine residue at a position corresponding to position 32 of SEQ ID NO:31. Additional details of the functional properties and characteristics of such dimers are discussed above. Also provided is a recombinant or isolated nucleic acid comprising a nucleotide sequence which encodes such a monomeric fusion protein which binds CD80 and/or CD86 (and/or CD80-Ig and/or CD86-Ig) and/or has an ability to inhibit an immune response.

Also included in the invention are fragments of any such nucleic acids of the invention described above, wherein such fragments encode a polypeptide that binds hCD80 and/or hCD86 and/or an ECD of either or both, and/or has an ability to suppress or inhibit an immune response. Many fragments of these nucleic acids will express polypeptides that bind hCD80 and/hCD86 or an ECD thereof, or suppress an immune response, which properties can be readily identified with reasonable experimentation. Nucleotide fragments typically comprise at least 250, 300, 400, 500, 600, 700, 800, 900, 950, 1000 or more nucleotide bases.

The invention includes an isolated or recombinant nucleic acid that encodes a protein comprising a signal peptide and a polypeptide of the invention (which includes a dimeric or monomeric fusion protein of the invention), such as a mutant CTLA-4 ECD polypeptide or mutant CTLA-4-Ig fusion protein of the invention, that binds CD80 and/or CD86 and/or suppresses an immune response in in vitro or in vivo assays and/or methods as described in detail elsewhere herein. The encoded signal peptide sequence, which directs secretion of the mature polypeptide through a prokaryotic or eukaryotic cell membrane, is typically covalently linked to the amino terminus of said polypeptide. A variety of signal peptides can be used, including, e.g., the signal peptide sequence set forth in SEQ ID NO:182, which is encoded by, e.g., the nucleotide sequence shown in SEQ ID NO:181, or the signal peptide sequence set forth in SEQ ID NO:216, which is encoded by, e.g., the nucleotide sequence shown in SEQ ID NO:215. The invention also include an isolated or recombinant nucleic acid which encodes a protein comprising a signal peptide, mutant CTLA-4 ECD polypeptide, transmembrane domain, and/or cytoplasmic domain as discussed detail above.

The signal peptide sequence of the full-length human CTLA-4 protein can be used to direct expression or secretion of a recombinant mutant CTLA-4 ECD polypeptide or mutant CTLA-4-Ig fusion protein of the invention. In one aspect, the signal peptide (SP) of the hCTLA-4 protein comprises amino acid residues 1-37 of the hCTLA-4 protein; this signal peptide sequence is shown in SEQ ID NO:216. In this instance, the mature hCTLA-4 protein typically begins with the methionine residue at position 38, and the amino acid residues of the mature hCTLA-4 protein are numbered accordingly beginning with this methionine residue being designated as the first amino acid (i.e., occupying position 1). Thus, a signal peptide comprising the peptide sequence shown in SEQ ID NO:216 can be fused or linked to the amino (N) terminus of a mutant CTLA-4 ECD polypeptide or mutant CTLA-4-Ig fusion protein of the invention, such as by a covalent linkage, so as to facilitate expression or secretion of the mutant CTLA-4 ECD polypeptide or mutant CTLA-4-Ig fusion protein, respectively. An exemplary nucleic acid comprising a nucleotide sequence that encodes the hCTLA-4 signal peptide sequence of SEQ ID NO:216 is set forth in SEQ ID NO:215.

When the signal peptide sequence of SEQ ID NO:216 is fused to linked to the N-terminus of a mutant CTLA-4 ECD polypeptide or mutant CTLA-4-Ig fusion protein, upon expression or secretion of said polypeptide or fusion protein, the signal peptide is cleaved; the resulting mature mutant CTLA-4 ECD polypeptide or mature mutant CTLA-4-Ig fusion protein typically begins with the methionine residue at position 38, and the amino acid residues of the mature mutant CTLA-4 ECD polypeptide or mature mutant CTLA-4-Ig fusion protein are numbered accordingly beginning with this methionine residue being designated as the first amino acid (i.e., occupying position 1).

The invention includes an isolated or recombinant polypeptide comprising a signal peptide (e.g., SEQ ID NO:216) and a mutant CTLA-4 ECD polypeptide (e.g., a sequence selected from the group of SEQ ID NOS:1-73), wherein the signal peptide is covalently linked to the N-terminus of the mutant CTLA-4 ECD polypeptide. Also included is an isolated or recombinant polypeptide comprising a signal peptide (e.g., SEQ ID NO:216) and a mutant CTLA-4-Ig (e.g., a sequence selected from the group of SEQ ID NOS:74-79, 197-200, 205-214, and 219-222), wherein the signal peptide is covalently linked to the N-terminus of the mutant CTLA-4-Ig. Also provided is an isolated or recombinant nucleic acid comprising a nucleotide sequence (e.g., SEQ ID NO:215) encoding a signal peptide (e.g., SEQ NO:216) and a nucleotide sequence encoding a mutant CTLA-4 ECD polypeptide (e.g., a sequence selected from the group of SEQ ID NOS:1-73) or a mutant CTLA-4-Ig fusion protein (e.g., a sequence selected from the group of SEQ ID NOS:74-79, 197-200, 205-214, and 219-222).

In an alternative aspect, the signal peptide of the full-length hCTLA-4 protein comprises residues 1-35 of the full-length hCTLA-4 protein; this signal peptide comprises the peptide sequence shown in SEQ ID NO:182. In this instance, the two amino acid residues lysine (K) and alanine (A) at positions 36 and 37, respectively, of the hCTLA-4 protein are nevertheless typically absent from the mature secreted hCTLA-4 protein as determined by protein sequencing. Thus, the resulting mature hCTLA-4 protein similarly begins with the methionine residue at position 38, and the amino acid residues of the mature hCTLA-4 protein are numbered accordingly beginning with this methionine residue at position 38 of the hCTLA-4 protein being designated as the first amino acid of the mature hCTLA-4 protein. Because amino acid residues lysine (K) and alanine (A) at positions 36 and 37, respectively, of the full-length hCTLA-4 protein are not present in the resulting mature hCTLA-4 protein, it is believed they have been cleaved from the mature hCTLA-4 protein during processing. An exemplary nucleic acid comprising a nucleotide sequence that encodes the hCTLA-4 signal peptide sequence (SEQ ID NO:182) is shown in SEQ ID NO:181.

A signal peptide comprising the peptide sequence shown in SEQ ID NO:182 can be fused or linked to the N-terminus of a mutant CTLA-4 ECD polypeptide or mutant CTLA-4-Ig fusion protein of the invention, such as by a covalent linkage, so as to facilitate expression or secretion of the mutant CTLA-4 ECD polypeptide or mutant CTLA-4-Ig fusion protein, respectively. When the signal peptide sequence of SEQ ID NO:182 is fused or linked to the N-terminus of a mutant CTLA-4 ECD polypeptide or mutant CTLA-4-Ig fusion protein, upon expression or secretion of the polypeptide or fusion protein, the signal peptide is cleaved; the resulting mature mutant CTLA-4 ECD polypeptide or mature mutant CTLA-4-Ig fusion protein nevertheless typically begins with the methionine residue at position 38, and the amino acid residues of the mature mutant CTLA-4 ECD polypeptide or mature mutant CTLA-4-Ig fusion protein are numbered accordingly beginning with this methionine residue being designated as the first amino acid (i.e., occupying position 1). Because amino acid residues lysine (K) and alanine (A) at positions 36 and 37, respectively, of the full-length hCTLA-4 protein are not present in the resulting mature mutant CTLA-4 ECD polypeptide or mature mutant CTLA-4-Ig fusion protein, it is believed they have been cleaved from said mutant CTLA-4 ECD polypeptide or mutant CTLA-4-Ig fusion protein during processing.

The invention includes an isolated or recombinant polypeptide comprising a signal peptide (e.g., SEQ ID NO:182) and a mutant CTLA-4 ECD polypeptide (e.g., a sequence selected from the group of SEQ ID NOS:1-73), wherein the signal peptide is covalently linked to the N-terminus of the mutant CTLA-4 ECD polypeptide. Also included is an isolated or recombinant polypeptide comprising a signal peptide (e.g., SEQ ID NO:182) and a mutant CTLA-4-Ig (e.g., a sequence selected from the group of SEQ ID NOS:74-79, 197-200, 205-214, and 219-222), wherein the signal peptide is covalently linked to the N-terminus of the mutant CTLA-4-Ig. Also provided is an isolated or recombinant nucleic acid comprising a nucleotide sequence (e.g., SEQ ID NO:181) encoding a signal peptide (e.g., SEQ NO: 182) and a nucleotide sequence encoding a mutant CTLA-4 ECD polypeptide (e.g., a sequence selected from the group of SEQ ID NOS:1-73) or a mutant CTLA-4-Ig fusion protein (e.g., a sequence selected from the group of SEQ ID NOS: 74-79, 197-200, 205-214, and 219-222).

A nucleic acid of the invention can further comprise one or more suitable additional nucleotide sequences. For example, given that a polypeptide of the invention (which includes a fusion protein of the invention) can comprise one or more additional polypeptide sequences, such as, e.g., a polypeptide purification subsequence (such as, e.g., a subsequence is selected from an epitope tag, a FLAG tag, a polyhistidine sequence, and a GST fusion), signal peptide sequence, etc., the invention includes nucleic acids that encode all such polypeptides comprising such additional sequences. Exemplary signal peptides, which upon expression are typically covalently linked to the N-terminal of a polypeptide of the invention, are discussed above. For example, a nucleic acid encoding a polypeptide sequence of any of SEQ ID NOS:1-79, 197-200, 205-214, and 219-222 can further comprise a nucleic acid encoding a signal peptide, such as the signal peptide sequence of SEQ ID NO:182, such as, e.g., the nucleotide sequence set forth in SEQ ID NO:181, or the signal peptide sequence set forth in SEQ ID NO:216, which is encoded by, e.g., the nucleotide sequence shown in SEQ ID NO:215. Such nucleotide sequences can be directly fused together, in appropriate reading frame, such that the resulting nucleic acid comprises a nucleotide sequence encoding a signal peptide of the invention and a nucleotide sequence encoding a polypeptide of the invention.

A nucleic acid of the invention can be isolated by any suitable technique, of which several are known in the art. An isolated nucleic acid of the invention (e.g., a nucleic acid that is prepared in a host cell and subsequently substantially purified by any suitable nucleic acid purification technique) can be re-introduced into a host cell or re-introduced into a cellular or other biological environment or composition wherein it is no longer the dominant nucleic acid species and is no longer separated from other nucleic acids.

Nearly any isolated or recombinant nucleic acid of the invention can be inserted in or fused to a suitable larger nucleic acid molecule (including e.g., but not limited to, a chromosome, a plasmid, an expression vector or cassette, a viral genome, a gene sequence, a linear expression element, a bacterial genome, a plant genome, or an artificial chromosome, such as a mammalian artificial chromosome (MAC), or the yeast and bacterial counterparts thereof (i.e., a YAC or a BAC) to form a recombinant nucleic acid using standard techniques. As another example, an isolated nucleic acid of the invention can be fused to smaller nucleotide sequences, such as promoter sequences, immunostimulatory sequences, and/or sequences encoding other amino acids, such as other antigen epitopes and/or linker sequences to form a recombinant nucleic acid.

In some instances, a recombinant or synthetic nucleic acid may be generated by chemical synthesis techniques applied outside of the context of a host cell (e.g., a nucleic acid produced through polymerase chain reaction (PCR) or chemical synthesis techniques, examples of which are described further herein).

Nucleic acids encoding polypeptides (including fusion proteins) of the invention can have any suitable chemical composition that permits the expression of a polypeptide of the invention or other desired biological activity (e.g., hybridization with other nucleic acids). The polynucleotides of the invention can be in the form of RNA or in the form of DNA, and include mRNA, cRNA, recombinant or synthetic RNA and DNA, and cDNA. The nucleic acids of the invention are typically DNA molecules, and usually double-stranded DNA molecules. However, single-stranded DNA, single-stranded RNA, double-stranded RNA, and hybrid DNA/RNA nucleic acids or combinations thereof comprising any of the nucleotide sequences of the invention also are provided. A nucleic acid of the invention can include any suitable nucleotide base, base analog, and/or backbone (e.g., a backbone formed by, or including, a phosphothioate, rather than phosphodiester, linkage, e.g., DNA comprising a phosphothioate or phosphorothioate backbone). A nucleic acid of the invention, if single-stranded, can be the coding strand or the non-coding (i.e., antisense or complementary) strand. In addition to a nucleotide sequence encoding a polypeptide of the invention (e.g., nucleotide sequence that comprise the coding sequence of a mutant CTLA-4 ECD polypeptide or mutant CTLA-4-Ig), the polynucleotide of the invention can comprise one or more additional coding nucleotide sequences, so as to encode, e.g., a fusion protein, targeting sequence (other than a signal sequence), or the like (more particular examples of which are discussed further herein), and/or can comprise non-coding nucleotide sequences, such as introns, terminator sequence, or 5' and/or 3' untranslated regions, which regions can be effective for expression of the coding sequence in a suitable host, and/or control elements, such as a promoter (e.g., naturally occurring or recombinant or shuffled promoter).

Modifications to a nucleic acid are particularly tolerable in the 3rd position of an mRNA codon sequence encoding such a polypeptide. In particular aspects, at least a portion of the nucleic acid comprises a phosphorothioate backbone, incorporating at least one synthetic nucleotide analog in place of or in addition to the naturally occurring nucleotides in the nucleic acid sequence. Also or alternatively, the nucleic acid can comprise the addition of bases other than guanine, adenine, uracil, thymine, and cytosine. Such modifications can be associated with longer half-life, and thus can be desirable in nucleic acids vectors of the invention. Thus, in one aspect, the invention provides recombinant nucleic acids and nucleic acid vectors (discussed further below), which nucleic acids or vectors comprise at least one of the aforementioned modifications, or any suitable combination thereof, wherein the nucleic acid persists longer in a mammalian host than a substantially identical nucleic acid without such a modification or modifications. Examples of modified and/or non-cytosine, non-adenine, non-guanine, non-thymine nucleotides that can be incorporated in a nucleotide sequence of the invention are provided in, e.g., the MANUAL OF PATENT EXAMINING PROCEDURE §2422 (7th Revision—2000).

It is to be understood that a nucleic acid encoding at least one of the polypeptides of the invention (which includes a fusion protein of the invention), including those described above and elsewhere herein, is not limited to a sequence that directly codes for expression or production of a polypeptide of the invention. For example, the nucleic acid can comprise a nucleotide sequence which results in a polypeptide of the invention through intein-like expression (as described in, e.g., Colson and Davis (1994) Mol. Microbiol. 12(3):959-63, Duan et al. (1997) Cell 89(4):555-64, Perler (1998) Cell 92(1):1-4, Evans et al. (1999) Biopolymers 51(5):333-42, and de Grey, Trends Biotechnol. 18(9):394-99 (2000)), or a nucleotide sequence which comprises self-splicing introns (or other self-spliced RNA transcripts), which form an intermediate recombinant polypeptide-encoding sequence (as described in, e.g., U.S. Pat. No. 6,010,884). The nucleic acid also or alternatively can comprise sequences which result in other splice modifications at the RNA level to produce an mRNA transcript encoding the polypeptide and/or at the DNA level by way of trans-splicing mechanisms prior to transcription (principles related to such mechanisms are described in, e.g., Chabot, Trends Genet. (1996) 12(11):472-78, Cooper (1997) Am. J. Hum. Genet. 61(2):259-66, and Hertel et al. (1997) Curr. Opin. Cell. Biol. 9(3):350-57). Due to the inherent degeneracy of the genetic code, several nucleic acids can code for any particular polypeptide of the invention. Thus, for example, any of the particular nucleic acids described herein can be modified by replacement of one or more codons with an equivalent codon (with respect to the amino acid called for by the codon) based on genetic code degeneracy. Other nucleotide sequences that encode a polypeptide having the same or a functionally equivalent sequence as a polypeptide sequence of the invention can also be used to synthesize, clone and express such polypeptide.

In general, any of the nucleic acids of the invention can be modified to increase expression in a particular host, using the techniques exemplified herein with respect to the above-described nucleic acids encoding a polypeptide of the invention (e.g., nucleic acids encoding mutant CTLA-4 ECD or mutant CTLA-4-Ig). Any of the nucleic acids of the invention as described herein may be codon optimized for expression in a particular mammal (normally humans). A variety of techniques for codon optimization are known in the art. Codons that are utilized most often in a particular host are called optimal codons, and those not utilized very often are classified as rare or low-usage codons (see, e.g., Zhang, S. P. et al. (1991) Gene 105:61-72). Codons can be substituted to reflect the preferred codon usage of the host, a process called "codon optimization" or "controlling for species codon bias." Optimized coding sequence comprising codons preferred by a particular prokaryotic or eukaryotic host can be used to increase the rate of translation or to produce recombinant RNA transcripts having desirable properties, such as a longer half-life, as compared with transcripts produced from a non-optimized sequence. Techniques for producing codon-optimized sequences are known (see, e.g., E. et al. (1989) Nuc. Acids Res. 17:477-508). Translation stop codons can also be modified to reflect host preference. For example, preferred stop codons for *S. cerevisiae* and mammals are UAA and UGA respectively. The preferred stop codon for monocotyledonous plants is UGA, whereas insects and *E. coli* prefer to use UAA as the stop codon (see, e.g., Dalphin, M. E. et al. (1996) Nuc. Acids Res. 24:216-218). The arrangement of codons in context to other codons also can influence biological properties of a nucleic acid sequences, and modifications of nucleic acids to provide a codon context arrangement common for a particular host also is contemplated by the inventors. Thus, a nucleic acid sequence of the invention can comprise a codon optimized nucleotide sequence, i.e., codon frequency optimized and/or codon pair (i.e., codon context) optimized for a particular species (e.g., the polypeptide can be expressed from a polynucleotide sequence optimized for expression in humans by replacement of "rare" human codons based on codon frequency, or codon context, such as by using techniques such as those described in Buckingham et al. (1994) Biochimie 76(5):351-54 and U.S. Pat. Nos. 5,082,767, 5,786,464, and 6,114,148).

Nucleic acids of the invention can be modified by truncation or one or more residues of the C-terminus portion of the sequence. Additional, a variety of stop or termination codons may be included at the end of the nucleotide sequence as further discussed below.

One or more nucleic acids of the invention may be included in a vector, cell, or host environment in which a coding nucleotide sequence of the invention is a heterologous gene.

Polynucleotides of the invention include polynucleotide sequences that encode any polypeptide of the invention (or polypeptide fragment thereof) which binds CD80 and/or CD86 and/or suppresses an immune response, polynucleotides that hybridize under at least stringent conditions to one or more such polynucleotide sequences described herein, polynucleotide sequences complementary to any such polynucleotide sequences, and variants, analogs, and homologue derivatives of all of the above. A coding sequence refers to a nucleotide sequence encodes a particular polypeptide or a domain, subsequence, region, or fragment of said polypeptide. A coding sequence may code for a mutant CTLA-4 polypeptide or fragment thereof having a functional property, such as the ability to bind CD80 and/or CD86 and/or inhibit or suppress an immune response. A nucleic acid of the invention may comprise a respective coding sequence of a mutant CTLA-4 polypeptide of the invention, and variants, analogs, and homologue derivatives thereof.

Nucleic acids of the invention can also be found in combination with typical compositional formulations of nucleic acids, including in the presence of carriers, buffers, adjuvants, excipients, diluents, and the like, as are known to those of ordinary skill in the art.

Unless otherwise indicated, a particular nucleic acid sequence described herein also implicitly encompasses conservatively modified variants thereof (e.g., degenerate codon substitutions) and complementary sequences and as well as the sequence explicitly indicated. Specifically, degenerate codon substitutions may be achieved by generating sequences in which the third position of one or more selected (or all) codons is substituted with mixed-base and/or deoxyinosine residues (Batzer et al. (1991) Nucl. Acid Res. 19:5081; Ohtsuka et al. (1985) J. Biol. Chem. 260:2605-2608; Cassol et al. (1992); Rossolini et al. (1994) Mol. Cell. Probes 8:91-98).

Nucleic Acid Hybridization

As noted above, the invention includes nucleic acids that hybridize to a target nucleic acid of the invention, such as, e.g., a polynucleotide selected from the group consisting of SEQ ID NOS:80-158, 201-204, 223, and 224 or a complementary polynucleotide sequence thereof, wherein hybridization is over substantially the entire length of the target nucleic acid. The hybridizing nucleic acid may hybridize to a nucleotide sequence of the invention, such as, e.g., that of SEQ ID NO:80, under at least stringent conditions or under at least high stringency conditions. Moderately stringent, stringent, and highly stringent hybridization conditions for nucleic acid hybridization experiments are known. Examples of factors that can be combined to achieve such levels of stringency are briefly discussed herein.

Nucleic acids "hybridize" when they associate, typically in solution. Nucleic acids hybridize due to a variety of well-characterized physico-chemical forces, such as hydrogen bonding, solvent exclusion, base stacking and the like. An extensive guide to the hybridization of nucleic acids is found in P. Tijssen (1993) LABORATORY TECHNIQUES IN BIOCHEMISTRY AND MOLECULAR BIOLOGY—HYBRIDIZATION WITH NUCLEIC ACID PROBES, vol. 24, part I, chapter 2, "Overview of principles of hybridization and the strategy of nucleic acid probe assays," (Elsevier, N.Y.) (hereinafter "Tijssen"), as well as in Ausubel, supra, Hames and Higgins (1995) GENE PROBES 1, IRL Press at Oxford University Press, Oxford, England (Hames and Higgins 1) and Hames and Higgins (1995) GENE PROBES 2, IRL Press at Oxford University Press, Oxford, England (Hames and Higgins 2) provide details on the synthesis, labeling, detection and quantification of DNA and RNA, including oligonucleotides.

An indication that two nucleic acid sequences are substantially identical is that the two molecules hybridize to each other under at least stringent conditions. The phrase "hybridizing specifically to," refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target polynucleotide sequence.

"Stringent hybridization wash conditions" and "stringent hybridization conditions" in the context of nucleic acid hybridization experiments, such as Southern and northern hybridizations, are sequence dependent, and are different under different environmental parameters. An extensive guide to hybridization of nucleic acids is found in Tijssen (1993), supra, and in Hames and Higgins 1 and Hames and Higgins 2, supra.

Generally, high stringency conditions are selected such that hybridization occurs at about 5° C. or less than the thermal melting point ($T_m$) for the specific sequence at a defined ionic strength and pH. The $T_m$ is the temperature (under defined ionic strength and pH) at which 50% of the test sequence hybridizes to a perfectly matched probe. In other words, the $T_m$ indicates the temperature at which the nucleic acid duplex is 50% denatured under the given conditions and its represents a direct measure of the stability of the nucleic acid hybrid. Thus, the $T_m$ corresponds to the temperature corresponding to the midpoint in transition from helix to random coil; it depends on length, nucleotide composition, and ionic strength for long stretches of nucleotides. Typically, under "stringent conditions," a probe will hybridize to its target subsequence, but to no other sequences. "Very stringent conditions" are selected to be equal to the $T_m$ for a particular probe.

The $T_m$ of a DNA-DNA duplex can be estimated using equation (1): $T_m$ (° C.)=81.5° C.+16.6 ($\log_{10}$M)+0.41 (% G+C)−0.72 (% f)−500/n, where M is the molarity of the monovalent cations (usually Na+), (% G+C) is the percentage of guanosine (G) and cytosine (C) nucleotides, (% f) is the percentage of formalize and n is the number of nucleotide bases (i.e., length) of the hybrid. See Rapley, R. and Walker, J. M. eds., MOLECULAR BIOMETHODS HANDBOOK (1998), Humana Press, Inc. (hereinafter Rapley and Walker, Tijssen (1993), supra. The $T_m$ of an RNA-DNA duplex can be estimated using equation (2): $T_m$ (° C.)=79.8° C.+18.5 ($\log_{10}$M)+0.58 (% G+C)-11.8(% G+C)$^2$−0.56 (% f)−820/n, where M is the molarity of the monovalent cations (usually Na+), (% G+C) is the percentage of guanosine (G) and cytosine (C) nucleotides, (% f) is the percentage of formamide and n is the number of nucleotide bases (i.e., length) of the hybrid. Id. Equations 1 and 2 above are typically accurate only for hybrid duplexes longer than about 100-200 nucleotides. Id. The $T_m$ of nucleic acid sequences shorter than 50 nucleotides can be calculated as follows: $T_m$ (° C.)=4(G+C)+2(A+T), where A (adenine), C, T (thymine), and G are the numbers of the corresponding nucleotides.

In general, non-hybridized nucleic acid material is removed by a series of washes, the stringency of which can be adjusted depending upon the desired results, in conducting hybridization analysis. Low stringency washing conditions (e.g., using higher salt and lower temperature) increase sensitivity, but can product nonspecific hybridization signals and high background signals. Higher stringency conditions (e.g., using lower salt and higher temperature that is closer to the hybridization temperature) lower the background signal, typically with only the specific signal remaining. Addition useful guidance concerning such hybridization techniques is provided in, e.g., Rapley and Walker, supra (in particular, with respect to such hybridization experiments, part I, chapter 2, "Overview of principles of hybridization and the strategy of nucleic acid probe assays"), Elsevier, N.Y., as well as in Ausubel, supra, Sambrook, supra, Watson, supra, Hames and Higgins (1995) GENE PROBES 1, IRL Press at Oxford Univ. Press, Oxford, England, and Hames and Higgins (1995) GENE PROBES 2, IRL Press, Oxford Univ. Press, Oxford, England.

Exemplary stringent (or regular stringency) conditions for analysis of at least two nucleic acids comprising at least 100 nucleotides include incubation in a solution or on a filter in a Southern or northern blot comprises 50% formalin (or formamide) with 1 milligram (mg) of heparin at 42° C., with the hybridization being carried out overnight. A regular stringency wash can be carried out using, e.g., a solution comprising 0.2×SSC wash at about 65° C. for about 15 minutes (see Sambrook, supra, for a description of SSC buffer). Often, the regular stringency wash is preceded by a low stringency wash to remove background probe signal. A low stringency wash can be carried out in, for example, a solution comprising 2×SSC at about 40° C. for about 15 minutes. A highly stringent wash can be carried out using a solution comprising 0.15 M NaCl at about 72° C. for about 15 minutes. An example medium (regular) stringency wash, less stringent than the regular stringency wash described above, for a duplex of, e.g., more than 100 nucleotides, can be carried out in a solution comprising 1×SSC at 45° C. for 15 minutes. An example low stringency wash for a duplex of, e.g., more than 100 nucleotides, is carried out in a solution of 4-6×SSC at 40° C. for 15 minutes. For short probes (e.g., about 10-50 nucleotides), stringent conditions typically involve salt concentrations of less than about 1.0 M Na$^+$ ion, typically about 0.01 to 1.0 M Na$^+$ ion concentration (or other salts) at pH 7.0 to 8.3, and the temperature is typically at least about 30° C. Stringent conditions can also be achieved with the addition of destabilizing agents such as formamide.

Exemplary moderate stringency conditions include overnight incubation at 37° C. in a solution comprising 20% formalin (or formamide), 0.5×SSC, 50 mM sodium phosphate (pH 7.6), 5×Denhardt's solution, 10% dextran sulfate, and 20 mg/ml denatured sheared salmon sperm DNA, followed by washing the filters in 1×SSC at about 37-50° C., or substantially similar conditions, e.g., the moderately stringent conditions described in Sambrook, supra, and/or Ausubel, supra.

High stringency conditions are conditions that use, for example, (1) low ionic strength and high temperature for washing, such as 0.015 M sodium chloride/0.0015 M sodium citrate/0.1% sodium dodecyl sulfate (SDS) at 50° C., (2) employ a denaturing agent during hybridization, such as formamide, for example, 50% (v/v) formamide with 0.1% bovine serum albumin (BSA)/0.1% Ficoll/0.1% polyvinylpyrrolidone (PVP)/50 mM sodium phosphate buffer at pH 6.5 with 750 mM sodium chloride, 75 mM sodium citrate at 42° C., or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at (i) 42° C. in 0.2×SSC, (ii) at 55° C. in 50% formamide and (iii) at 55° C. in 0.1×SSC (preferably in combination with EDTA).

In general, a signal to noise ratio of 2× or 2.5×-5× (or higher) than that observed for an unrelated probe in the particular hybridization assay indicates detection of a specific hybridization. Detection of at least stringent hybridization between two sequences in the context of the present invention indicates relatively strong structural similarity or homology to, e.g., the nucleic acids of the present invention.

As noted, "highly stringent" conditions are selected to be about 5° C. or less lower than the thermal melting point ($T_m$) for the specific sequence at a defined ionic strength and pH. Target sequences that are closely related or identical to the nucleotide sequence of interest (e.g., "probe") can be identified under highly stringency conditions. Lower stringency conditions are appropriate for sequences that are less complementary. See, e.g., Rapley and Walker; Sambrook, all supra.

Comparative hybridization can be used to identify nucleic acids of the invention, and this comparative hybridization method is a preferred method of distinguishing nucleic acids of the invention. Detection of highly stringent hybridization between two nucleotide sequences in the context of the present invention indicates relatively strong structural similarity/homology to, e.g., the nucleic acids provided in the sequence listing herein. Highly stringent hybridization between two nucleotide sequences demonstrates a degree of similarity or homology of structure, nucleotide base composition, arrangement or order that is greater than that detected by stringent hybridization conditions. In particular, detection of highly stringent hybridization in the context of the present invention indicates strong structural similarity or structural homology (e.g., nucleotide structure, base composition, arrangement or order) to, e.g., the nucleic acids provided in the sequence listing herein. For example, it is desirable to identify test nucleic acids that hybridize to the exemplar nucleic acids herein under stringent conditions.

Thus, one measure of stringent hybridization is the ability to hybridize to a nucleic acid of the invention (e.g., a nucleic acid comprising a polynucleotide sequence selected from the group consisting of SEQ ID NOS:80-158, 201-204, 223, and 224, or a complementary polynucleotide sequence thereof) under highly stringent conditions (or very stringent conditions, or ultra-high stringency hybridization conditions, or ultra-ultra high stringency hybridization conditions). Stringent hybridization (including, e.g., highly stringent, ultra-high stringency, or ultra-ultra high stringency hybridization conditions) and wash conditions can easily be determined empirically for any test nucleic acid.

For example, in determining highly stringent hybridization and wash conditions, the hybridization and wash conditions are gradually increased (e.g., by increasing temperature, decreasing salt concentration, increasing detergent concentration and/or increasing the concentration of organic solvents, such as formalin, in the hybridization or wash), until a selected set of criteria is met. For example, the hybridization and wash conditions are gradually increased until a probe comprising one or more nucleic acid sequences selected from the group consisting of SEQ ID NOS:80-158, 201-204, 223, and 224 and complementary polynucleotide sequences thereof, binds to a perfectly matched complementary target (again, a nucleic acid comprising at least one nucleic acid sequences selected from the group consisting of SEQ ID NOS:80-158, 201-204, 223, and 224 or complementary polynucleotide sequences thereof), with a signal to noise ratio that is at least 2.5×, and optionally 5× or more as high as that observed for hybridization of the probe to an unmatched target. The unmatched target may comprise a nucleic acid corresponding to, e.g., a CTLA-4 polypeptide-encoding nucleic acid sequence.

Usually, the hybridization analysis is carried out under hybridization conditions selected such that a nucleic acid comprising a sequence that is perfectly complementary to the a disclosed reference (or known) nucleotide sequence (e.g., SEQ ID NO:80) hybridizes with the recombinant antigen-encoding sequence (e.g., a nucleotide sequence variant of the nucleic acid sequence of SEQ ID NO:80) with at least about 5, 7, or 10 times higher signal-to-noise ratio than is observed in the hybridization of the perfectly complementary nucleic acid to a nucleic acid that comprises a nucleotide sequence that is at least about 80 or 90% identical to the reference nucleic acid. Such conditions can be considered indicative for specific hybridization.

The above-described hybridization conditions can be adjusted, or alternative hybridization conditions selected, to achieve any desired level of stringency in selection of a hybridizing nucleic acid sequence. For example, the above-described highly stringent hybridization and wash conditions can be gradually increased (e.g., by increasing temperature, decreasing salt concentration, increasing detergent concentration and/or increasing the concentration of organic solvents, such as formalin, in the hybridization or wash), until a selected set of criteria are met. For example, the hybridization and wash conditions can be gradually increased until a desired probe, binds to a matched complementary target, with a signal-to-noise ratio that is at least about 2.5×, and optionally at least about 5× (e.g., about 10×, about 20×, about 50×, about 100×, or even about 500×), as high as the signal-to-noise ration observed from hybridization of the probe to a nucleic acid not of the invention, such as a nucleic acid encoding WT CTLA-4 ECD polypeptide.

Making and Modifying Nucleic Acids

Nucleic acids of the invention can be obtained and/or generated by application of any suitable synthesis, manipulation, and/or isolation techniques, or combinations thereof. Exemplary procedures are described infra. For example, polynucleotides of the invention are typically produced through standard nucleic acid synthesis techniques, such as solid-phase synthesis techniques known in the art. In such techniques, fragments of up to about 100 bases usually are individually synthesized, then joined (e.g., by enzymatic or chemical ligation methods, or polymerase mediated recombination methods) to form essentially any desired continuous nucleic acid sequence. The synthesis of the nucleic acids of the invention can be also facilitated (or alternatively accomplished), by chemical synthesis using, e.g., the classical phosphoramidite method, which is described in, e.g., Beaucage et al. (1981) Tetrahedron Letters 22:1859-69, or the method described by Matthes et al. (1984) EMBO J. 3:801-05, e.g., as is typically practiced in automated synthetic methods. The nucleic acid of the invention also can be produced by use of an automatic DNA synthesizer. Other techniques for synthesizing nucleic acids and related principles are described in, e.g., Itakura et al., Annu. Rev. Biochem. 53:323 (1984), Itakura et al., Science 198:1056 (1984), and Ike et al., Nucl. Acid Res. 11:477 (1983).

Conveniently, custom made nucleic acids can be ordered from a variety of commercial sources, such as The Midland Certified Reagent Company (mcrc@oligos.com), the Great American Gene Company (worldwide website address genco.com), ExpressGen Inc. (worldwide website address expressgen.com), Operon Technologies Inc. (Alameda, Calif.). Similarly, custom peptides and antibodies can be custom ordered from any of a variety of sources, e.g., PeptidoGenic (pkim@ccnet.com), HTI Bio-products, Inc. (worldwide website address htibio.com), and BMA Biomedicals Ltd. (U.K.), Bio.Synthesis, Inc.

Certain nucleotides of the invention may also be obtained by screening cDNA libraries using oligonucleotide probes that can hybridize to or PCR-amplify polynucleotides which encode the polypeptides of the invention. Procedures for screening and isolating cDNA clones and PCR amplification procedures are well known to those of skill in the art; exemplary procedures are described infra (see, e.g., procedures described in the Examples below). Such techniques are described in, e.g., Berger and Kimmel, "Guide to Molecular Cloning Techniques," in Methods in Enzymol. Vol. 152, Acad. Press, Inc., San Diego, Calif. ("Berger"); Sambrook, supra; and Ausubel, supra. Some nucleic acids of the invention can be obtained by altering a naturally occurring backbone, e.g., by mutagenesis, in vitro recombination (e.g., shuffling), or oligonucleotide recombination. In other cases, such polynucleotides can be made in silico or through oligonucleotide recombination methods as described in the references cited herein.

Recombinant DNA techniques useful in modification of nucleic acids are well known in the art (e.g., restriction endonuclease digestion, ligation, reverse transcription and cDNA production, and PCR). Useful recombinant DNA technology techniques and principles related thereto are provided in, e.g., Mulligan (1993) Science 260:926-932, Friedman (1991) THERAPY FOR GENETIC DISEASES, Oxford University Press, Ibanez et al. (1991) EMBO J. 10:2105-10, Ibanez et al. (1992) Cell 69:329-41 (1992), and U.S. Pat. Nos. 4,440,859, 4,530,901, 4,582,800, 4,677,063, 4,678,751, 4,704,362, 4,710,463, 4,757,006, 4,766,075, and 4,810,648, and are more particularly described in Sambrook et al. (1989) MOLECULAR CLONING: A LABORATORY MANUAL, Cold Spring Harbor Press, and the third edition thereof (2001), Ausubel et al. (1994-1999), Current Protocols in Molecular Biology, Wiley Interscience Publishers (with Greene Publishing Associates for some editions), Berger, supra, and Watson, supra.

Modified Coding Sequences

Where appropriate, nucleic acids of the invention can be modified to increase or enhance expression in a particular host by modification of the sequence with respect to codon usage and/or codon context, given the particular host(s) in which expression of the nucleic acid is desired. Codons that are utilized most often in a particular host are called optimal codons, and those not utilized very often are classified as rare or low-usage codons (see, e.g., Zhang, S. P. et al. (1991) Gene 105:61-72). Codons can be substituted to reflect the preferred codon usage of the host, a process called "codon optimization" or "controlling for species codon bias."

Optimized coding sequence comprising codons preferred by a particular prokaryotic or eukaryotic host can be used to increase the rate of translation or to produce recombinant RNA transcripts having desirable properties, such as a longer half-life, as compared with transcripts produced from a non-optimized sequence. Techniques for producing codon-optimized sequences are known (see, e.g., Murray, E. et al. (1989) Nucl. Acids Res. 17:477-508). Translation stop codons can also be modified to reflect host preference. For example, preferred stop codons for S. cerevisiae and mammals are UAA and UGA respectively. The preferred stop codon for monocotyledonous plants is UGA, whereas insects and E. coli prefer to use UAA as the stop codon (see, e.g., Dalphin, M. E. et al. (1996) Nucl. Acids Res. 24:216-218, for discussion). The arrangement of codons in context to other codons also can influence biological properties of a nucleic acid sequences, and modifications of nucleic acids to provide a codon context arrangement common for a particular host also is contemplated by the inventors. Thus, a nucleic acid sequence of the invention can comprise a codon optimized nucleotide sequence, i.e., codon frequency optimized and/or codon pair (i.e., codon context) optimized for a particular species (e.g., the polypeptide can be expressed from a polynucleotide sequence optimized for expression in humans by replacement of "rare" human codons based on codon frequency, or codon context, such as by using techniques such as those described in Buckingham et al. (1994) Biochimie 76(5): 351-54 and U.S. Pat. Nos. 5,082,767, 5,786,464, and 6,114,148). For example, the invention provides a nucleic acid comprising a nucleotide sequence variant of SEQ ID NO:80, wherein the nucleotide sequence variant differs from the nucleotide sequence of SEQ ID NO:80 by the substitution of "rare" codons for a particular host with codons commonly expressed in the host, which codons encode the same amino acid residue as the substituted "rare" codons in SEQ ID NO:80.

Vectors, Vector Components, and Expression Systems

The present invention also includes recombinant constructs comprising one or more of the nucleic acids of the invention as broadly described above. Such constructs may comprise a vector, such as a plasmid, a cosmid, a phage, a virus, a viral particle, a virus-like particle, a bacterial artificial chromosome (BAC), a yeast artificial chromosome (YAC), or the like, or a non-replicating vector, such as a liposome, naked or conjugated DNA, DNA-microparticle, into which at least one nucleic acid sequence of the invention has been inserted, in a forward or reverse orientation. In a particular aspect of this embodiment, the construct further comprises one or more regulatory sequences, including, for example, a promoter, operably linked to a nucleic acid sequence of the invention (e.g., nucleic acid encoding an isolated or recombinant mutant CTLA-4 ECD polypeptide or dimeric or monomeric mutant CTLA-4-Ig). Large numbers of suitable vectors and promoters are known to those of skill in the art and are commercially available. In some instances, a vector, such as, e.g., a virus or virus-like particle, may also or alternatively include one or more polypeptides of the invention such as, e.g., incorporated into the coat of the virus or virus-like particle. Vectors can be useful as delivery agents for the delivery or administration to a subject of exogenous genes or proteins. Vectors of the present invention, including those described herein, are useful as delivery agents for the delivery or administration of nucleic acids and/or polypeptides of the invention.

General texts that describe molecular biological techniques useful herein, including the use of vectors, promoters, and many other relevant topics, include Berger, supra, Sambrook (1989), supra, and Ausubel, supra. Examples of techniques sufficient to direct persons of skill through in vitro amplification methods, including the polymerase chain reaction (PCR) the ligase chain reaction (LCR), Qβ-replicase amplification and other RNA polymerase mediated techniques (e.g., NASBA), e.g., for the production of the homologous nucleic acids of the invention are found in Berger, Sambrook, and Ausubel, all supra, as well as Mullis et al. (1987) U.S. Pat. No. 4,683,202; PCR Protocols: A Guide to Methods and Applications (Innis et al., eds.) Academic Press Inc. San Diego, Calif. (1990) ("Innis"); Arnheim & Levinson (Oct. 1, 1990) C&EN 36-47; The Journal Of NIH Research (1991) 3:81-94; (Kwoh et al. (1989) Proc. Natl. Acad. Sci. USA 86:1173-1177; Guatelli et al. (1990) Proc. Natl. Acad. Sci. USA 87:1874-1878; Lomeli et al. (1989) J. Clin. Chem. 35:1826-1831; Landegren et al. (1988) Science 241:1077-1080; Van Brunt (1990) Biotechnology 8:291-294; Wu and Wallace (1989) Gene 4:560-569; Barringer et al. (1990) Gene 89:117-122, and Sooknanan and Malek (1995) Biotechnology 13:563-564.

PCR generally refers to a procedure wherein minute amounts of a specific piece of nucleic acid (e.g., RNA or DNA) are amplified by methods well known in the art (see, e.g., U.S. Pat. No. 4,683,195 and the other references cited above). Generally, sequence information from the ends of the region of interest or beyond is used for design of oligonucleotide primers. Such primers will be identical or similar in sequence to the opposite strands of the template to be amplified. The 5' terminal nucleotides of the opposite strands may coincide with the ends of the amplified material. PCR may be used to amplify specific RNA or specific DNA sequences, recombinant DNA or RNA sequences, DNA and RNA sequences from total genomic DNA, and cDNA transcribed from total cellular RNA, bacteriophage or plasmid sequences, etc. PCR is one example, but not the only example, of a nucleic acid polymerase reaction method for amplifying a nucleic acid test sample comprising the use of another (e.g., known) nucleic acid as a primer. Improved methods of cloning in vitro amplified nucleic acids are described in Wallace et al., U.S. Pat. No. 5,426,039. Improved methods of amplifying large nucleic acids by PCR are summarized in Cheng et al. (1994) Nature 369:684 685 and the references cited therein, in which PCR amplicons of up to 40 kilobases (kb) are generated. One of skill will appreciate that essentially any RNA can be converted into a double-stranded DNA suitable for restriction digestion, PCR expansion and sequencing using reverse transcriptase and a polymerase. See Ausubel, Sambrook, and Berger, all supra.

The nucleic acids of the present invention can be incorporated into any one of a variety of vectors, e.g., expression vectors, for expressing a polypeptide, including, e.g., a polypeptide of the invention. Expression vectors compatible with prokaryotic host cells may be used; such prokaryotic expression vectors are known in the art and commercially available. Such vectors include, but are not limited to, e.g., BLUESCRIPT vector (Stratagene), T7 expression vector (Invitrogen), pET vector (Novagen), and similar prokaryotic vectors.

Expression vectors compatible with eukaryotic host cells may alternatively be used; such eukaryotic expression vectors are known in the art and commercially available. Such vectors include, but are not limited to, e.g., pCMV vectors (e.g., Invitrogen), pIRES vector (Clontech), pSG5 vector (Stratagene), pcDNA3.1 (Invitrogen Life Technologies), pcDNA3 (Invitrogen Life Technologies), Ubiquitous Chromatin Opening Element (UCOE™) expression vector (Millipore), and similar eukaryotic expression vectors. The UCOE™ vector is typically used for protein production in mammalian cells (e.g., CHO cells). According to Millipore, the UCOE™ expression technology thwarts transgene silencing and provides stable high-level gene expression without respect to the site of chromosomal integration. See Millipore website at worldwide web address millipore.com. An exemplary UCOE expression vector into which, for example, a nucleic acid of the invention can be incorporated is the UCOE expression vector named CET1019AS-puro-SceI, which is available for licensing from Millipore. Information about the UCOE expression vector CET1019AS-puro-SceI can be found in, e.g., John Wynne, "UCOE™ Technology Maximizes Protein Expression," BioProcess International 4(7):104-105 (July/August 2006) (RP1725EN00) (available at worldwide web address millipore.com/bibliography/tech1/rp1725en00); additional information about this vector and licensing of this vector from Millipore can be found the Millipore website, including at, e.g., worldwide web addresses millipore.com/company/cp3/ucoe_licensing and millipore.com/techpublications/tech1/ps1013en00. Thus, for example, a DNA sequence encoding a mutant CTLA-4 ECD (e.g., SEQ ID NO:36 or SEQ ID NO:50) fused to a DNA sequence encoding an IgG2 Fc polypeptide (e.g., SEQ ID NO:184), resulting in the DNA sequence of SEQ ID NO:201 is inserted into a UCOE CET1019AS vector (Millipore) and the resulting DNA plasmid can be used for transfections of host cells.

Figure 1:
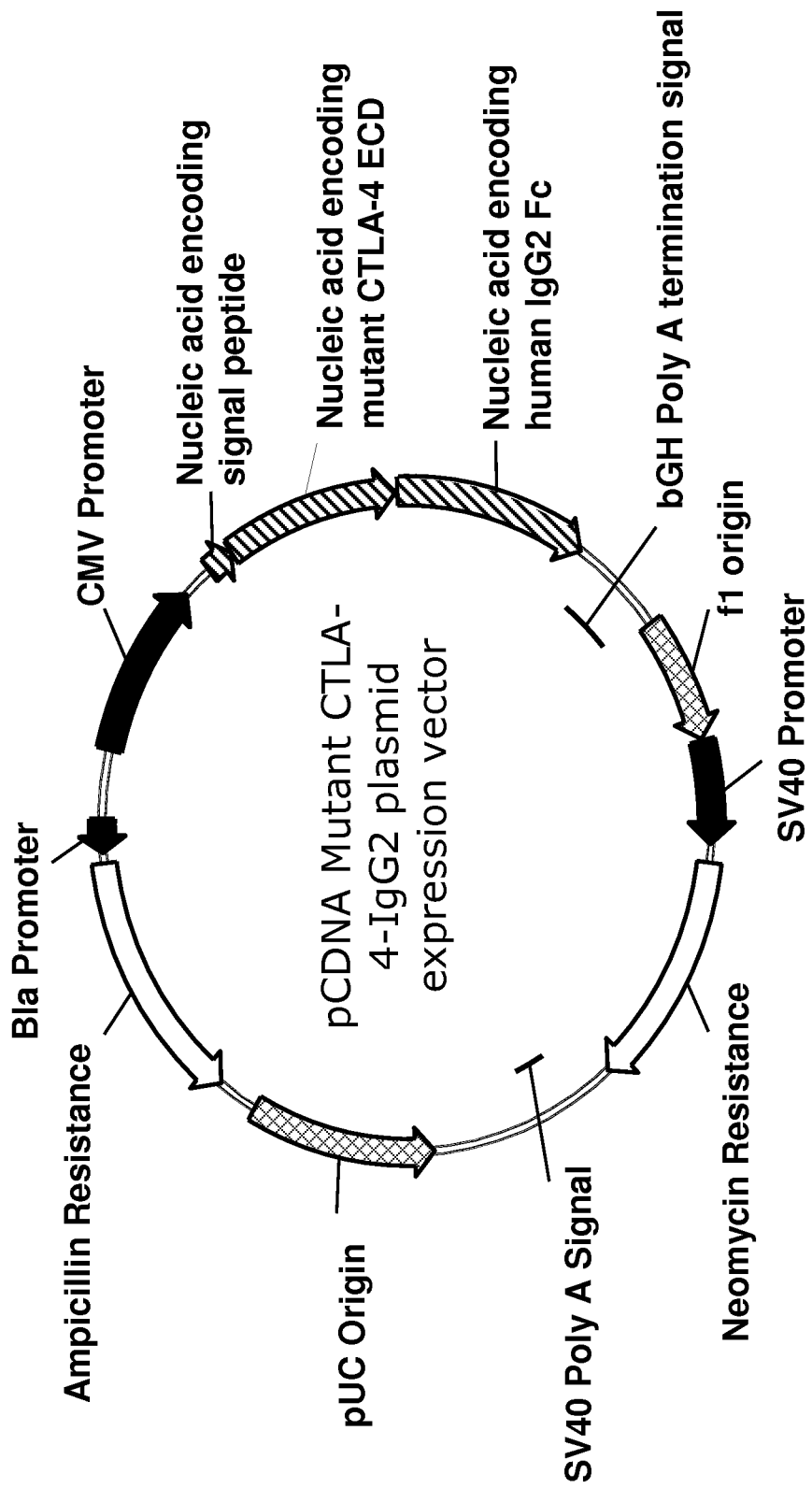
FIG. 1 is a schematic diagram of the plasmid expression vector pcDNA mutant CTLA-4-Ig, which comprises a nucleotide sequence encoding a mutant CTLA-4-Ig fusion protein.

Expression vectors include chromosomal, nonchromosomal and synthetic DNA sequences, e.g., derivatives of SV40, bacterial vectors (e.g., *S. typhimurium, S. typhi, S. flexneri, Listeria monocytogenes, B. anthracis*); plasmids; bacterial plasmids; phage DNA; baculovirus; yeast plasmids; vectors derived from combinations of plasmids and phage DNA; viral DNA or RNA vectors, including, e.g., vaccinia virus, adeno-associated virus (AAV), adenovirus, Semliki-Forest virus (e.g., Notka et al., Biol. Chem. 380:341-52 (1999), pox virus (e.g., MVA), alphavirus (e.g., Venezuelan equine encephalitis virus (VEE), Western equine encephalitis virus (WEE), Eastern equine encephalitis virus (EEE)), vesicular stomatitis virus (VSV), fowl pox virus, pseudorabies, herpes simplex viruses, retroviruses, and many others. Any vector that transduces genetic material into a cell, and, if replication is desired, which is replicable and viable in the relevant host can be used. Viral and bacterial vectors serving as delivery vehicles can be attenuated; attenuation should be sufficient to decrease if not eliminate induction of undesirable disease symptoms. FIG. 1 is a schematic diagram of an exemplary plasmid expression vector pcDNA mutant CTLA-4-Ig which encodes a mutant CTLA-4-Ig of the invention. Additional details regarding suitable expression vectors are provided below, including in the Examples.

A vector of the invention comprising a nucleic acid sequence of the invention as described herein, as well as an appropriate promoter or control sequence, can be employed to transform an appropriate host to permit the host to express the protein. Examples of appropriate expression hosts include: bacterial cells, such as *E. coli, Streptomyces,* and *Salmonella typhimurium*; fungal cells, such as *Saccharomyces cerevisiae, Pichia pastoris,* and *Neurospora crassa*; insect cells such as *Drosophila* and *Spodoptera frugiperda*; mammalian cells, such as Chinese Hamster Ovary (CHO) (e.g., CHO-K1), COS (e.g., COS-1, COS-7), baby hamster kidney (BHK), and Human Embryonic Kidney (HEK) (e.g., HEK 293), Bowes melanoma cells, and plant cells. It is understood that not all cells or cell lines need to be capable of producing fully functional polypeptides of the invention or fragments thereof. The invention is not limited by the host cells employed. Additional details regarding suitable host cells are provided below.

In bacterial systems, a number of expression vectors may be selected depending upon the use intended for the desired polypeptide or fragment thereof. For example, when large quantities of a particular polypeptide or fragments thereof are needed for the induction of antibodies, vectors which direct high level expression of fusion proteins that are readily purified may be desirable. Such vectors include, but are not limited to, multifunctional *E. coli* cloning and expression vectors such as BLUESCRIPT (Stratagene), in which nucleotide coding sequence of interest (e.g., nucleotide sequence encoding a recombinant mutant CTLA-4-Ig) may be ligated into the vector in-frame with sequences for the amino-terminal Met and the subsequent 7 residues of beta-galactosidase so that a hybrid protein is produced; pIN vectors (Van Heeke & Schuster (1989) J. Biol. Chem. 264:5503-5509); pET vectors (Novagen, Madison Wis.); and the like.

Similarly, in the yeast *Saccharomyces cerevisiae*, a number of vectors comprising constitutive or inducible promoters such as alpha factor, alcohol oxidase, and PGH may be used for production of the polypeptides of the invention. For reviews, see Ausubel, supra, Berger, supra, and Grant et al. (1987) Meth. Enzymol. 153:516-544.

In mammalian host cells, a number of expression systems, such as viral-based systems, may be utilized. In cases where an adenovirus is used as an expression vector, a coding sequence is optionally ligated into an adenovirus transcription/translation complex consisting of the late promoter and tripartite leader sequence. Insertion in a nonessential E1 or E3 region of the viral genome results in a viable virus capable of expressing a polypeptide of interest in infected host cells (Logan and Shenk (1984) Proc. Natl. Acad. Sci. USA 81:3655-3659). In addition, transcription enhancers, such as the Rous sarcoma virus (RSV) enhancer, are used to increase expression in mammalian host cells.

A vector, e.g., expression vector, or polynucleotide of the invention can comprise one or more expression control sequences. An expression control sequence is typically associated with and/or operably linked to a nucleic acid sequence of the invention, such as a nucleic acid encoding a recombinant mutant CTLA-4 ECD polypeptide or recombinant mutant CTLA-4-Ig fusion protein. An expression control sequence is typically a nucleotide sequence that promotes, enhances, or controls expression (typically transcription) of another nucleotide sequence. Suitable expression control sequences that may be employed include a promoter, including a constitutive promoter, inducible promoter, and/or repressible promoter, an enhancer for amplifying expression, an initiation sequence, a termination translation sequence, a splicing control sequence, and the like.

When a nucleic acid of the invention is included in a vector, the nucleic acid is typically operatively linked to an appropriate transcription control sequence (promoter) to direct mRNA synthesis. Promoters exert a particularly important impact on the level of recombinant polypeptide expression. Any suitable promoter can be utilized. Examples of suitable promoters include the cytomegalovirus (CMV) promoter with or without the first intron (intron A), the HIV long terminal repeat promoter, the phosphoglycerate kinase (PGK) promoter, Rous sarcoma virus (RSV) promoters, such as RSV long terminal repeat (LTR) promoters, SV40 promoters, mouse mammary tumor virus (MMTV) promoters, HSV promoters, such as the Lap2 promoter or the herpes thymidine kinase promoter (as described in, e.g., Wagner et al. (1981) Proc. Natl. Acad. Sci. 78:144-145), promoters derived from SV40 or Epstein Barr virus, adeno-associated viral (AAV) promoters, such as the p5 promoter, metallothionein promoters (e.g., the sheep metallothionein promoter or the mouse metallothionein promoter (see, e.g., Palmiter et al. (1983) Science 222:809-814), the human ubiquitin C promoter, *E. coli* promoters, such as the lac and trp promoters, phage lambda $P_L$ promoter, and other promoters known to control expression of genes in prokaryotic or eukaryotic cells (either directly in the cell or in viruses which infect the cell). Promoters that exhibit strong constitutive baseline expression in mammals, particularly humans, such as CMV promoters, such as the CMV immediate-early promoter (described in, e.g., U.S. Pat. Nos. 5,168,062, 5,385,839, 5,688,688, and 5,658,759), and promoters having substantial sequence identity with such CMV promoters, can be employed. Recombinant promoters having enhanced properties, such as in Int'l Pat. Publ. No. WO 02/00897, may also be used.

A promoter that is operably linked to a nucleic acid of the invention for expression of the nucleic acid can have any suitable mechanism of action. Thus, the promoter can be, for example, an "inducible" promoter, (e.g., a growth hormone promoter, metallothionein promoter, heat shock protein promoter, E1B promoter, hypoxia induced promoter, radiation inducible promoter, or adenoviral MLP promoter and tripartite leader), an inducible-repressible promoter, a developmental stage-related promoter (e.g., a globin gene promoter), or a tissue specific promoter (e.g., a smooth muscle cell α-actin promoter, myosin light-chain 1A promoter, or vascular endothelial cadherin promoter). Suitable inducible promoters include ecdysone and ecdysone-analog-inducible promoters. Ecdysone-analog-inducible promoters are commercially available, e.g., through Stratagene (La Jolla, Calif.). If desired, a nucleic acid of the invention can be induced by using an inducible on- and off-gene expression system. Examples of such on- and off-gene expression systems include the Tet-On™ Gene Expression System and Tet-Off™ Gene Expression System, respectively (Clontech, Palo Alto, Calif.; see, e.g., Clontech Catalog 2000, pg. 110-111 for a detailed description of each such system). The inducible promoter can be any promoter that is up- and/or downregulated in response to an appropriate signal. Additional inducible promoters include arabinose-inducible promoters, a steroid-inducible promoters (e.g., a glucocorticoid-inducible promoters), as well as pH, stress, and heat-inducible promoters.

The promoter can be, and often is, a host-native promoter, or a promoter derived from a virus that infects a particular host (e.g., a human beta actin promoter, human EF1α promoter, or a promoter derived from a human AAV operably linked to the nucleic acid of interest), particularly where strict avoidance of gene expression silencing due to host immunological reactions to sequences that are not regularly present in the host is of concern. A bi-directional promoter system (as described in, e.g., U.S. Pat. No. 5,017,478) linked to multiple nucleotide sequences of interest can also be utilized.

Other suitable promoters and principles related to the selection, use, and construction of suitable promoters are provided in, e.g., Werner (1999) Mamm Genome 10(2):168-75, Walther et al. (1996) J. Mol. Med. 74(7):379-92, Novina (1996) Trends Genet. 12(9):351-55, Hart (1996) Semin. Oncol. 23(1):154-58, Gralla (1996) Curr. Opin. Genet. Dev. 6(5):526-30, Fassler et al. (1996) Methods Enzymol 273:3-29, Ayoubi et al. (1996), 10(4) FASEB J 10(4):453-60, Goldsteine et al. (1995) Biotechnol. Annu. Rev. 1:105-28, Azizkhan et al. (1993) Crit. Rev. Eukaryot. Gene Expr. 3(4):229-54, Dynan (1989) Cell 58(1):1-4, Levine (1989) Cell 59(3):405-8, and Berk et al. (1986) Annu. Rev. Genet. 20:45-79, as well as U.S. Pat. No. 6,194,191. Other suitable promoters can be identified by use of the Eukaryotic Promoter Database (release 68) (available at the worldwide website address epd.isb-sib.ch/) and other similar databases, such as the Transcription Regulatory Regions Database (TRRD) (version 4.1) (available at the worldwide website address bionet.nsc.ru/trrd/) and the transcription factor database (TRANSFAC) (available at the worldwide website address transfac.gbf.de/TRANSFAC/index.html).

As an alternative to a promoter, particularly in RNA vectors and constructs, a vector or nucleic acid of the invention can comprise one or more internal ribosome entry sites (IRESs), IRES-encoding sequences, or RNA sequence enhancers (Kozak consensus sequence analogs), such as the tobacco mosaic virus omega prime sequence.

A vector or polynucleotide of the invention can include an upstream activator sequence (UAS), such as a Gal4 activator sequence (see, e.g., U.S. Pat. No. 6,133,028) or other suitable upstream regulatory sequence (see, e.g., U.S. Pat. No. 6,204,060).

A vector or polynucleotide of the invention can include a Kozak consensus sequence that is functional in a mammalian cell. The Kozak sequence can be a naturally occurring or modified sequence, such as the modified Kozak consensus sequences described in U.S. Pat. No. 6,107,477.

Specific initiation signals can aid in efficient translation of a coding sequence of the invention, such as a mutant CTLA-4 ECD polypeptide-encoding nucleotide sequence. Such signals can be included in a vector of the invention. These signals can include, e.g., the ATG initiation codon and adjacent sequences. In cases where a coding sequence, its initiation codon, and upstream sequences are inserted into an appropriate expression vector, no additional translational control signals may be needed. However, in cases where only a coding sequence (e.g., a mature protein coding sequence), or a portion thereof is inserted, exogenous nucleic acid transcriptional control signals including the ATG initiation codon must be provided. Furthermore, the initiation codon must be in the correct reading frame to ensure transcription of the entire insert. Exogenous transcriptional elements and initiation codons can be of various origins—both natural and synthetic. The efficiency of expression can be enhanced by the inclusion of enhancers appropriate to the cell system in use (see, e.g., Scharf et al., Results Probl. Cell. Differ. 20:125-62 (1994); and Bittner et al., Meth. Enzymol. 153:516-544 (1987)). Suitable enhancers include the Rous sarcoma virus (RSV) enhancer and the RTE enhancers described in U.S. Pat. No. 6,225,082.

The skilled artisan will recognize that the introduction of a start codon (ATG) to the 5' end of a particular nucleotide sequence of interest usually results in the addition of an N-terminal methionine to the encoded amino acid sequence when the sequence is expressed in a mammalian cell (other modifications may occur in bacterial and/or other eukaryotic cells, such as introduction of an formyl-methionine residue at a start codon). For expression of a nucleic acid of the invention in eukaryotic cells, a start codon and a nucleotide sequence encoding a signal peptide are typically be included at the 5' end of a nucleic acid sequence of the invention (e.g., SEQ ID NO:80), and a termination codon is typically included at the C terminus of the nucleic acid (e.g., SEQ ID NO:80). An exemplary signal peptide sequence is the hCTLA-4 signal peptide sequence (SEQ ID NO:182); the nucleic acid sequence encoding the tissue plasminogen activator signal peptide is shown in SEQ ID NO:181. Another exemplary signal peptide sequence is the hCTLA-4 signal peptide sequence (SEQ ID NO:216), which is encoded by the nucleic acid sequence shown in SEQ ID NO:215.

Termination sequences are discussed in detail below.

Such elements can be included in the vector construct of choice. Upon expression, the polypeptide variant encoded by the nucleic acid (e.g., SEQ ID NO:80) will initially include an N-terminal methionine residue and the signal peptide sequence. However, the N-terminal methionine and signal peptide sequence will be cleaved upon secretion, thereby generating the encoded polypeptide (e.g., SEQ ID NO:1).

The expression level of a nucleic acid of the invention (or a corresponding polypeptide of the invention can be assessed by any suitable technique. Examples include Northern Blot analysis (discussed in, e.g., McMaster et al., Proc. Natl. Acad. Sci. USA 74(11):4835-38 (1977) and Sambrook, infra), reverse transcriptase-polymerase chain reaction (RT-PCR) (as described in, e.g., U.S. Pat. No. 5,601,820 and Zaheer et al., Neurochem. Res. 20:1457-63 (1995)), and in situ hybridization techniques (as described in, e.g., U.S. Pat. Nos. 5,750,340 and 5,506,098). Quantification of proteins also can be accomplished by the Lowry assay and other protein quantification assays (see, e.g., Bradford, Anal. Biochem. 72:248-254 (1976); Lowry et al., J. Biol. Chem. 193:265 (1951)). Western blot analysis of recombinant polypeptides of the invention obtained from the lysate of cells transfected with polynucleotides encoding such recombinant polypeptides is another suitable technique for assessing levels of recombinant polypeptide expression.

A vector, e.g., expression vector, or polynucleotide of the invention can comprise a ribosome-binding site for translation initiation and a transcription-terminating region. A suitable transcription-terminating region is, for example, a polyadenylation sequence that facilitates cleavage and polyadenylation of an RNA transcript produced from a DNA sequence. Any suitable polyadenylation sequence can be used, including a synthetic optimized sequence, as well as the polyadenylation sequence of BGH (Bovine Growth Hormone), human growth hormone gene, polyoma virus, TK (Thymidine Kinase), EBV (Epstein Barr Virus), rabbit beta globin, and the papillomaviruses, including human papillomaviruses and BPV (Bovine Papilloma Virus). Suitable polyadenylation (polyA) sequences also include the SV40 (human Sarcoma Virus-40) polyadenylation sequence and the BGH polyA sequence. Such polyA sequences are described in, e.g., Goodwin et al. (1998) Nucleic Acids Res. 26(12): 2891-8, Schek et al. (1992) Mol. Cell. Biol. 12(12):5386-93, and van den Hoff et al. (1993) Nucleic Acids Res. 21(21): 4987-8. Additional principles related to selection of appropriate polyadenylation sequences are described in, e.g., Levitt et al. (1989) Genes Dev. 1989 3(7):1019-1025, Jacob et al. (1990) Crit. Rev. Eukaryot. Gene Expr. 1(1):49-59, Chen et al. (1995) Nucleic Acids Res. 23(14):2614-2620, Moreirai et al. (1995) EMBO J. 14(15):3809-3819, Carswell et al. (1989) Mol. Cell. Biol. 9(10):4248-4258.

A vector or polynucleotide of the invention can further comprise site-specific recombination sites, which can be used to modulate transcription of a nucleotide sequence of interest, as described in, e.g., U.S. Pat. Nos. 4,959,317, 5,801,030 and 6,063,627, European Patent Application No. 0 987 326 and Int'l Patent App. Publ. No. WO 97/09439.

A vector or polynucleotide of the invention can also comprise a nucleic acid encoding a secretion/localization sequence, to target polypeptide expression to a desired cellular compartment, membrane, or organelle, or to direct polypeptide secretion to the periplasmic space or into the cell culture media. Such sequences are known in the art, and include secretion leader peptides or signal peptides, organelle targeting sequences (e.g., nuclear localization sequences, ER retention signals, mitochondrial transit sequences, chloroplast transit sequences), membrane localization/anchor sequences (e.g., stop transfer sequences, GPI anchor sequences), and the like. Polynucleotides of the invention can be fused, for example, in-frame to such a nucleic acid encoding a secretion and/or localization sequence. Polypeptides expressed by such polynucleotides of the invention may include the amino acid sequence corresponding to the secretion and/or localization sequence(s).

In addition, a vector or polynucleotide of the invention can comprise one or more selectable marker nucleotide sequences or genes to provide a phenotypic trait for selection of transformed host cells, such as dihydrofolate reductase resistance, neomycin resistance, G418 resistance, puromycin resistance, and/or blasticidin resistance for eukaryotic cell culture, or such as tetracycline or ampicillin resistance in *E. coli*.

A vector or polynucleotide of the invention can also comprise an origin of replication useful for propagation in a microorganism. The bacterial origin of replication (Ori) utilized is preferably one that does not adversely affect gene expression in mammalian cells. Examples of useful origin of replication sequences include the f1 phage ori, RK2 oriV, pUC ori, and the pSC101 ori. Origin of replication sequences include the ColEI ori and the p15 (available from plasmid pACYC177, New England Biolab, Inc.), alternatively another low copy ori sequence (similar to p15) can be desirable in some contexts. The nucleic acid in this respect desirably acts as a shuttle vector, able to replicate and/or be expressed in both eukaryotic and prokaryotic hosts (e.g., a vector comprising an origin of replication sequences recognized in both eukaryotes and prokaryotes).

The invention includes a naked DNA or RNA vector, including, for example, a linear expression element (as described in, e.g., Sykes and Johnston (1997) Nat Biotech 17:355-59), a compacted nucleic acid vector (as described in, e.g., U.S. Pat. No. 6,077,835 and/or Int'l Pat. App. Publ. No. WO 00/70087), a plasmid vector such as pcDNA3.1, pBR322, pUC 19/18, or pUC 118/119, a "midge" minimal-sized nucleic acid vector (as described in, e.g., Schakowski et al. (2001) Mol. Ther. 3:793-800) or as a precipitated nucleic acid vector construct, such as a CaPO$_4$ precipitated construct (as described in, e.g., Int'l Patent Appn WO 00/46147, Benvenisty and Reshef (1986) Proc. Natl. Acad. Sci. USA 83:9551-55, Wigler et al. (1978), Cell 14:725, and Coraro and Pearson (1981) Somatic Cell Genetics 7:603), comprising a nucleic acid of the invention. For example, the invention provides a naked DNA plasmid comprising SEQ ID NO:80 operably linked to a CMV promoter or CMV promoter variant and a suitable polyadenylation sequence. Naked nucleotide vectors and the usage thereof are known in the art (see, e.g., U.S. Pat. Nos. 5,589,466 and 5,973,972).

A vector of the invention typically is an expression vector that is suitable for expression in a bacterial system, eukaryotic system, mammalian system, or other system (as opposed to a vector designed for replicating the nucleic acid sequence without expression, which can be referred to as a cloning vector). For example, in one aspect, the invention provides a bacterial expression vector comprising a nucleic acid sequence of the invention (e.g., nucleic acid sequence encoding a recombinant mutant CTLA-4-Ig). Suitable vectors include, for example, vectors which direct high level expression of fusion proteins that are readily purified (e.g., multifunctional *E. coli* cloning and expression vectors such as BLUESCRIPT (Stratagene), pIN vectors (Van Heeke & Schuster, J. Biol. Chem. 264:5503-5509 (1989); pET vectors (Novagen, Madison Wis.); and the like). While such bacterial expression vectors can be useful in expressing particular polypeptides of the invention, glycoproteins of the invention are preferably expressed in eukaryotic cells and as such the invention also provides eukaryotic expression vectors.

The expression vector can be a vector suitable for expression of the nucleic acid of the invention in a yeast cell. Any vector suitable for expression in a yeast system can be employed. Suitable vectors for use in, e.g., *Saccharomyces cerevisiae* include, e.g., vectors comprising constitutive or inducible promoters such as alpha factor, alcohol oxidase and PGH (reviewed in Ausubel, supra, Berger, supra, and Grant et al., Meth. Enzymol. 153:516-544 (1987)). Usually, the expression vector will be a vector suitable for expression of a nucleic acid of the invention in an animal cell, such as an insect cell (e.g., a SF-9 cell) or a mammalian cell (e.g., a CHO cell, 293 cell, HeLa cell, human fibroblast cell, or similar well-characterized cell). Suitable mammalian expression vectors are known in the art (see, e.g., Kaufman, Mol. Biotechnol. 16(2):151-160 (2000), Van Craenenbroeck, Eur. J. Biochem. 267(18):5665-5678 (2000), Makrides, Protein Expr. Purif. 17(2):183-202 (1999), and Yarranton, Curr. Opin. Biotechnol. 3(5):506-511 (1992)). Suitable insect cell plasmid expression vectors also are known (Braun, Biotechniques 26(6):1038-1040:1042 (1999)).

An expression vector typically can be propagated in a host cell, which may be a eukaryotic cell (such as a mammalian cell, yeast cell, or plant cell) or a prokaryotic cell, such as a bacterial cell. Introduction of a nucleic acid vector or expression vector into the host cell (e.g., transfection) can be effected by calcium phosphate transfection (see, e.g., calcium phosphate co-precipitation method of Graham et al., Virology 52:456-457 (1973)), DEAE-Dextran mediated transfection, electroporation, gene or vaccine gun, injection, lipofection and biolistics or other common techniques (see, e.g., Kriegler, GENE TRANSFER AND EXPRESSION: A LABORATORY MANUAL, Stockton Press (1990); see Davis, L., Dibner, M., and Battey, I., BASIC METHODS IN MOLECULAR BIOLOGY (1986) for a description of in vivo, ex vivo, and in vitro methods). Cells comprising these and other vectors of the invention form an important part of the invention.

In one aspect, the invention provides an expression vector comprising: (i) a first polynucleotide sequence that encodes a first polypeptide comprising a polypeptide sequence having at least 95%, 96% 97%, 98%, 99%, or 100% sequence identity to at least one polypeptide sequence selected from the group consisting of SEQ ID NOS:1-73, wherein said first polypeptide binds human CD86 and/or human CD80 and/or an extracellular domain of either or both, and/or suppresses an immune response, and (ii) a second polynucleotide sequence that encodes a second polypeptide comprising a hinge region, a CH2 domain, and a CH3 domain of an immunoglobulin (Ig) polypeptide. The Ig polypeptide is optionally a human Ig Fc polypeptide (e.g., IgG1, IgG2, IgG4, etc.) or a mutant Ig Fc polypeptide. (e.g., an Ig Fc polypeptide in which one or more cysteine residues have been substituted with another amino acid (e.g., a serine residue), thereby eliminating one or more disulfide bonds formed between two Ig chains, or in which one or more proline residues is substituted with another amino acid (e.g., proline) to reduce effector function (reduced Fc receptor binding). In another aspect, the invention provides an expression vector comprising a nucleotide sequence encoding a fusion protein having at least 95%, 96%, 97%, 98%, 99%, or 100% sequence identity to at least one polypeptide sequence selected from the group consisting of SEQ ID NOS: 74-79, 197-200, 205-214, and 219-222.

Additional nucleic acids provided by the invention include cosmids. Any suitable cosmid vector can be used to replicate, transfer, and express the nucleic acid sequence of the invention. Typically, a cosmid comprises a bacterial oriV, an antibiotic selection marker, a cloning site, and either one or two cos sites derived from bacteriophage lambda. The cosmid can be a shuttle cosmid or mammalian cosmid, comprising a SV40 oriV and, desirably, suitable mammalian selection marker(s). Cosmid vectors are further described in, e.g., Hohn et al. (1988) Biotechnology 10:113-27.

Nucleic acids of the invention can be included in and/or administered to a host or host cell in the form of a suitable delivery vehicle (i.e., a vector). The vector can be any suitable vector, including chromosomal, non-chromosomal, and synthetic nucleic acid vectors, or other vectors described above, and may include any combination of the above-described expression elements and/or other transfection-facilitating and/or expression-promoting sequence elements. Examples of such vectors include viruses, bacterial plasmids, phages, cosmids, phagemids, derivatives of SV40, baculovirus, yeast plasmids, vectors derived from combinations of plasmids and phage DNA, and viral nucleic acid (RNA or DNA) vectors, polylysine, and bacterial cells.

Delivery of a recombinant DNA sequence of the invention can be accomplished with a naked DNA plasmid or plasmid associated with one or more transfection-enhancing agents, as discussed further herein. The plasmid DNA vector can have any suitable combination of features. Plasmid DNA vectors may comprise a strong promoter/enhancer region (e.g., human CMV, RSV, SV40, SL3-3, MMTV, or HIV LTR promoter), an effective poly(A) termination sequence, an origin of replication for plasmid product in *E. coli*, an antibiotic resistance gene as selectable marker, and a convenient cloning site (e.g., a polylinker). A particular plasmid vector for delivery of the nucleic acid of the invention in this respect is shown in FIG. 1; the construction and features of this vector are described in the Examples below.

In another aspect, the invention provides a non-nucleic acid vector comprising at least one nucleic acid or polypeptide of the invention. Such a non-nucleic acid vector includes, e.g., but is not limited to, a recombinant virus, a viral nucleic acid-protein conjugate (which, with recombinant viral particles, may sometimes be referred to as a viral vector), or a cell, such as recombinant (and usually attenuated) *Salmonella, Shigella, Listeria*, and *Bacillus* Calmette-Guérin (BCG) bacterial cells. Thus, for example, the invention provides a viral vector, insect vector, bacterial vector, or plant vector comprising a nucleic acid of the sequence of the invention. Any suitable viral, insect, plant, or bacterial vector can be used in this respect and a number are known in the art. A viral vector can comprise any number of viral polynucleotides, alone (a viral nucleic acid vector) or more commonly in combination with one or more (typically two, three, or more) viral proteins, which facilitate delivery, replication, and/or expression of the nucleic acid of the invention in a desired host cell.

In one aspect, intracellular bacteria (e.g., *Listeria monocytogenes*) can be used to deliver a nucleic acid of the invention. An exemplary bacterial vector for plasmid DNA delivery of one or more nucleic acids of the invention is *Listeria monocytogenes* (Lieberman et al., Vaccine 20:2007-2010 (2002)).

The invention includes recombinant or isolated viral vectors that have been modified to comprise one or more nucleic acids or polypeptides of the invention. A viral vector may include a polynucleotide comprising all or part of a viral genome, a viral protein/nucleic acid conjugate, a virus-like particle (VLP), a vector similar to those described in U.S. Pat. No. 5,849,586 and Int'l Patent App. Publ. No. WO 97/04748, or an intact virus particle comprising one or more viral nucleic acids, and the viral vector is typically engineered to include at least one nucleic acid and/or polypeptide of the invention. A viral vector (i.e., a recombinant virus) can comprise a wild-type viral particle or a modified viral particle, particular examples of which are discussed below. Numerous viruses are typically used as vectors for the delivery of exogenous nucleic acids, including at least one nucleic acid of the invention, such as a nucleic acid encoding a mutant CTLA-4 ECD or mutant CTLA-4-Ig described herein. Such vectors include recombinantly modified enveloped or non-enveloped DNA and RNA viruses, typically selected from baculoviridiae, parvoviridiae, picomoviridiae, herpesveridiae, poxyiridae, adenoviridiae, or picornaviridiae. Viral vectors may be wild-type or may be modified by recombinant nucleic acid techniques to be replication deficient, replication competent, or conditionally replicating.

The viral vector can be a vector that requires the presence of another vector or wild-type virus for replication and/or expression (i.e., a helper-dependent virus), such as an adenoviral vector amplicon. Typically, such viral vectors comprise a wild-type viral particle, or a viral particle modified in its protein and/or nucleic acid content to increase transgene capacity or aid in transfection and/or expression of the nucleic acid (examples of such vectors include the herpes virus/AAV amplicons). The viral genome may be modified to include inducible promoters that achieve replication or expression only under certain conditions.

The viral vector can be derived from or comprise a virus that normally infects animals, preferably vertebrates, such as mammals, including, e.g., humans. Suitable viral vector particles in this respect, include, for example, adenoviral vector particles (including any virus of or derived from a virus of the adenoviridae), adeno-associated viral vector particles (AAV vector particles) or other parvoviruses and parvoviral vector particles, papillomaviral vector particles, Semliki-Forest viral vector, flaviviral vectors, picomaviral vectors, alphaviral vectors, herpes viral vectors, pox virus vectors, retroviral vectors, including lentiviral vectors. Examples of such viruses and viral vectors are provided in, e.g., Fields Virology, supra, Fields et al., eds., VIROLOGY, Raven Press, Ltd., New York (3rd ed., 1996 and 4th ed., 2001), ENCYCLOPEDIA OF VIROLOGY, R. G. Webster et al., eds., Academic Press (2nd ed., 1999), FUNDAMENTAL VIROLOGY, Fields et al., eds., Lippincott-Raven (3rd ed., 1995), Levine, "Viruses," Scientific American Library No. 37 (1992), MEDICAL VIROLOGY, D. O. White et al., eds., Academic Press (2nd ed. 1994), and INTRODUCTION TO MODERN VIROLOGY, Dimock, N. J. et al., eds., Blackwell Scientific Publications, Ltd. (1994).

Viral vectors that can be employed with nucleic acids of the invention and the methods described herein include adeno-associated virus vectors, which are reviewed in, e.g., Carter (1992) Curr. Opinion Biotech. 3:533-539 (1992) and Muzcyzka (1992) Curr. Top. Microbiol. Immunol. 158:97-129 (1992). Additional types and aspects of AAV vectors are described in, e.g., Buschacher et al., Blood 5(8):2499-504, Carter, Contrib. Microbiol. 4:85-86 (2000), Smith-Arica, Curr. Cardiol. Rep. 3(1):41-49 (2001), Taj, J. Biomed. Sci. 7(4):279-91 (2000), Vigna et al., J. Gene Med. 2(5):308-16 (2000), Klimatcheva et al., Front. Biosci. 4:D481-96 (1999), Lever et al., Biochem. Soc. Trans. 27(6):841-47 (1999), Snyder, J. Gene Med. 1(3):166-75 (1999), Gerich et al., Knee Surg. Sports Traumatol. Arthrosc. 5(2):118-23 (1998), and During, Adv. Drug Deliv. Review 27(1):83-94 (1997), and U.S. Pat. Nos. 4,797,368, 5,139,941, 5,173,414, 5,614,404, 5,658,785, 5,858,775, and 5,994,136, as well as other references discussed elsewhere herein). Adeno-associated viral vectors can be constructed and/or purified using the methods set forth, for example, in U.S. Pat. No. 4,797,368 and Laughlin et al., Gene 23:65-73 (1983).

Alphavirus vectors can be gene delivery vectors in other contexts. Alphavirus vectors are known in the art and described in, e.g., Carter (1992) Curr Opinion Biotech 3:533-539, Schlesinger Expert Opin. Biol. Ther. (2001) 1(2):177-91, Polo et al., Dev. Biol. (Basel). 2000; 104:181-5, Wahlfors et al., Gene Ther. (2000) 7(6):472-80, Int'l Pat. App. Publ. Nos. WO 01/81609, WO 00/39318, WO 01/81553, WO 95/07994, WO 92/10578.

Another advantageous group of viral vectors are the herpes viral vectors. Examples are described in, e.g., Lachmann et al., Curr. Opin. Mol. Ther. (1999) 1(5):622-32, Fraefel et al., Adv. Virus Res. (2000) 55:425-51, Huard et al., Neuromuscul. Disord. (1997) 7(5):299-313, Frenkel et al., Gene Ther. (1994) Suppl 1:S40-6, U.S. Pat. Nos. 6,261,552 and 5,599,691.

Retroviral vectors, including lentiviral vectors, also can be advantageous gene delivery vehicles in particular contexts. There are numerous retroviral vectors known in the art. Examples of retroviral vectors are described in, e.g., Miller, Curr Top Microbiol. Immunol. (1992) 158:1-24, Weber et al., Curr. Opin. Mol. Ther. (2001) 3(5):439-53, Hu et al., Pharmacol. Rev. (2000) 52(4):493-511, Kim et al., Adv. Virus Res. (2000) 55:545-63, Palu et al., Rev. Med. Virol. (2000) 10(3): 185-202, Takeuchi et al., Adv. Exp. Med. Biol. (2000) 465: 23-35, U.S. Pat. Nos. 6,326,195, 5,888,502, 5,580,766, and 5,672,510.

Baculovirus vectors are another advantageous group of viral vectors, particularly for the production of polypeptides of the invention. The production and use of baculovirus vectors is known (see, e.g., Kost, Curr. Opin. Biotechnol. 10(5): 428-433 (1999); Jones, Curr. Opin. Biotechnol. 7(5):512-516 (1996)). Where the vector is used for therapeutic uses, the vector will be selected such that it is able to adequately infect (or in the case of nucleic acid vectors transfect or transform) target cells in which the desired therapeutic effect is desired.

Adenoviral vectors also can be suitable viral vectors for gene transfer. Adenoviral vectors are well known in the art and described in, e.g., Graham et al. (1995) Mol. Biotechnol. 33(3):207-220, Stephenson (1998) Clin. Diagn. Virol. 10(2-3):187-94, Jacobs (1993) Clin Sci (Lond). 85(2):117-22, U.S. Pat. Nos. 5,922,576, 5,965,358 and 6,168,941 and International Patent Applications WO 98/22588, WO 98/56937, WO 99/15686, WO 99/54441, and WO 00/32754. Adenoviral vectors, herpes viral vectors, and Sindbis viral vectors, useful in the practice of the invention and suitable for organismal in vivo transduction and expression of nucleic acids of the invention, are generally described in, e.g., Jolly (1994) Cancer Gene Therapy 1:51-64, Latchman (1994) Molec. Biotechnol. 2:179-195, and Johanning et al. (1995) Nucl. Acids Res. 23:1495-1501.

The virus vector may be replication-deficient in a host cell. Adeno-associated virus (AAV) vectors, which are naturally replication-deficient in the absence of complementing adenoviruses or at least adenovirus gene products (provided by, e.g., a helper virus, plasmid, or complementation cell), are included. By "replication-deficient" is meant that the viral vector comprises a genome that lacks at least one replication-essential gene function. A deficiency in a gene, gene function, or gene or genomic region, as used herein, is defined as a deletion of sufficient genetic material of the viral genome to impair or obliterate the function of the gene whose nucleic acid sequence was deleted in whole or in part. Replication-essential gene functions are those gene functions that are required for replication (i.e., propagation) of a replication-deficient viral vector. The essential gene functions of the viral vector particle vary with the type of viral vector particle at issue. Examples of replication-deficient viral vector particles are described in, e.g., Marconi et al., Proc. Natl. Acad. Sci. USA 93(21):11319-20 (1996), Johnson and Friedmann, Methods Cell Biol. 43 (pt. A):211-30 (1994), Timiryasova et al., J. Gene Med. 3(5):468-77 (2001), Burton et al., Stem Cells 19(5):358-77 (2001), Kim et al., Virology 282(1):154-67 (2001), Jones et al., Virology 278(1):137-50 (2000), Gill et al., J. Med. Virol. 62(2):127-39 (2000). Other replication-deficient vectors are based on simple MLV vectors (Miller et al. (1990) Mol. Cell. Biol. 10:4239; Kolberg (1992) J. NIH Res. 4:43, and Cornetta et al. (1991) Hum. Gene. Ther. 2:215). Canary pox vectors are advantageous in infecting human cells but being naturally incapable of replication therein (i.e., without genetic modification).

The basic construction of recombinant viral vectors is well understood in the art and involves using standard molecular biological techniques such as those described in, e.g., Sambrook et al., MOLECULAR CLONING: A LABORATORY MANUAL (Cold Spring Harbor Press 1989) and the third edition thereof (2001), Ausubel et al., CURRENT PROTOCOLS IN MOLECULAR BIOLOGY (Wiley Interscience Publishers 1995), and Watson, supra, and several of the other references mentioned herein. For example, adenoviral vectors can be constructed and/or purified using the methods set forth, for example, in Graham et al., Mol. Biotechnol. 33(3):207-220 (1995), U.S. Pat. No. 5,965, 358, Donthine et al., Gene Ther. 7(20):1707-14 (2000), and other references described herein. Adeno-associated viral vectors can be constructed and/or purified using the methods set forth, for example, in U.S. Pat. No. 4,797,368 and Laughlin et al., Gene 23:65-73 (1983). Similar techniques are known in the art with respect to other viral vectors, particularly with respect to herpes viral vectors (see e.g., Lachman et al., Curr. Opin. Mol. Ther. 1(5):622-32 (1999)), lentiviral vectors, and other retroviral vectors. In general, the viral vector comprises an insertion of the nucleic acid (for example, a wild-type adenoviral vector can comprise an insertion of up to 3 KB without deletion), or, more typically, comprises one or more deletions of the virus genome to accommodate insertion of the nucleic acid and additional nucleic acids, as desired, and to prevent replication in host cells.

Non-viral vectors, such as, e.g., DNA plasmids, naked nucleic acids, and nucleic acid complexed with a delivery vehicle such as a liposome, also can be associated with molecules that target the vector to a particular region in the host (e.g., a particular organ, tissue, and/or cell type). For example, a nucleotide can be conjugated to a targeting protein, such as a viral protein that binds a receptor or a protein that binds a receptor of a particular target (e.g., by modification of the techniques in Wu et al., J. Biol. Chem. 263(29):14621-24 (1988)). Targeted cationic lipid compositions are known (see, e.g., U.S. Pat. No. 6,120,799). Other techniques for targeting genetic constructs are provided in Int'l Pat. App. Publ. No. WO 99/41402.

Expression Hosts

The present invention also provides engineered host cells transduced, transfected or transformed with a vector of the invention (e.g., a cloning vector or expression vector) or a nucleic acid of the invention. The engineered host cells can be cultured in conventional nutrient media modified as appropriate for activating promoters, selecting transformants, or amplifying the nucleic acid of interest. The culture conditions, such as temperature, pH, and the like, are those previously used with the host cell selected for expression, and will be apparent to those skilled in the art and in the references cited herein, including, e.g., Freshney (1994) Culture of Animal Cells, a Manual of Basic Technique, 3rd ed., Wiley-Liss, New York and the references cited therein. Polypeptides of the invention encoded by such vectors or nucleic acids of the invention are expressed in such host cells and can be isolated by standard techniques. For example, polypeptides released into the cell culture can be isolated from the culture by ultracentrifugation or similar techniques.

The polypeptides of the invention can be produced in a variety of expression hosts, including, but not limited to, animal cells, such as mammalian cells (e.g., CHO cells), including human and non-human primate cells, and in non-animal cells, such as plants, yeast, fungi, bacteria, and the like. Examples of suitable expression hosts include bacterial cells, such as E. coli, Streptomyces, and Salmonella typhimurium; fungal cells, such as Saccharomyces cerevisiae, Pichia pastoris, and Neurospora crassa; insect cells such as Drosophila and Spodoptera frugiperda; mammalian cells, such as CHO (e.g., CHO-K1), COS (e.g., COS-1, COS-7), BHK, and HEK (e.g., HEK 293) cells, Bowes melanoma cells, and plant cells. As noted above, the invention is not limited by the host cells employed. In addition to Sambrook, Berger and Ausubel, all supra, details regarding cell culture are found in, e.g., Payne et al. (1992) Plant Cell and Tissue Culture in Liquid Systems John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg NY); Atlas & Parks (eds.) The Handbook of Microbiological Media (1993) CRC Press, Boca Raton, Fla. Such host cells can be adapted to growth in serum-free, protein-free medium, animal component-free medium, such as, e.g., a chemically defined (CD) medium (such as, e.g., CD OptiCHO™ (Invitrogen, #12681) using procedures known in the art.

The invention provides a cell(s) comprising any one or more of the nucleic acids, vectors, or other constructs of the invention (e.g., a construct expressing a mutant CTLA-4 ECD or mutant CTLA-4-Ig) described herein or any combination thereof. Also included is a cell comprising one or more of any of the polypeptides, antibodies, or fusion proteins, or other constructs of the invention described herein, or any combination of one or more of these. A cell of the invention is typically an isolated or recombinant cell and may comprise a host cell. Such a cell, e.g., recombinant cell, may be modified by transformation, transfection, and/or infection with at least one nucleic acid, vector, or other construct of the invention. Such a cell can be a eukaryotic cell (e.g., mammalian, yeast, or plant cell) or a prokaryotic cell (e.g., bacterial cell) and can be transformed with any such construct of the invention using a variety of known methods, including, e.g., calcium phosphate transfection (see, e.g., calcium phosphate co-precipitation method), DEAE-Dextran mediated transfection, electroporation (Irving et al., Cell 64:891-901 (1991)), gene or vaccine gun, injection, lipofection and biolistics or other common techniques as noted above. See also Inovio Biomedical Corp. electroporation methods and technology at the worldwide website address inovio.com.

A host cell strain is optionally chosen for its ability to modulate the expression of the inserted sequences or to process the expressed protein in the desired fashion. Such modifications of the protein include, but are not limited to, acetylation, carboxylation, glycosylation, phosphorylation, lipidation and acylation. Different host cells such as E. coli, Bacillus sp., yeast, or mammalian cells, such as CHO, HeLa, BHK, MDCK, HEK 293, WI38, etc. have specific cellular machinery and characteristic mechanisms for such post-translational activities and may be chosen to ensure the correct modification and processing of the introduced foreign protein.

A nucleic acid of the invention can be inserted into an appropriate host cell (in culture or in a host organism) to permit the host to express a protein of interest (e.g., mutant CTLA-4 ECD or mutant CTLA-4-Ig). Any suitable host cell can be transformed/transduced by the nucleic acids of the invention. Examples of appropriate expression hosts include: bacterial cells, such as E. coli, Streptomyces, Bacillus sp., and Salmonella typhimurium; fungal cells, such as Saccharomyces cerevisiae, Pichia pastoris, and Neurospora crassa; insect cells such as Drosophila and Spodoptera frugiperda; mammalian cells such as Vero cells, HeLa cells, CHO cells (e.g., CHO-K1), COS cells, WI38 cells, NIH-3T3 cells (and other fibroblast cells, such as MRC-5 cells), MDCK cells, KB cells, SW-13 cells, MCF7 cells, BHK cells, HEK-293 cells, Bowes melanoma cells, and plant cells, etc.

The present invention also provides host cells that are transduced, transformed or transfected with at least one nucleic acid or vector of the invention. As discussed above, a vector of the invention typically comprises a nucleic acid of the invention. Host cells are genetically engineered (e.g., transduced, transformed, infected, or transfected) with the vectors of the invention, which may be, e.g., a cloning vector or an expression vector. The vector may be in the form of a plasmid, a viral particle, a phage, attenuated bacteria, or any other suitable type of vector. Host cells suitable for transduction and/or infection with viral vectors of the invention for production of the recombinant polypeptides of the invention and/or for replication of the viral vector of the invention include the above-described cells. Examples of cells that have been demonstrated as suitable for packaging of viral vector particles are described in, e.g., Polo et al., Proc. Natl. Acad. Sci. 96(8):4598-603 (1999), Farson et al., J. Gene Med. 1(3): 195-209 (1999), Sheridan et al., Mol. Ther. 2(3):262-75 (2000), Chen et al., Gene Ther. 8(9):697-703 (2001), and Pizzaro et al., Gene Ther. 8(10):737-745 (2001). For replication-deficient viral vectors, such as AAV vectors, complementing cell lines, cell lines transformed with helper viruses, or cell lines transformed with plasmids encoding essential genes, are needed for replication of the viral vector.

The engineered host cells can be cultured in conventional nutrient media modified as appropriate for activating promoters, selecting transformants, or amplifying the gene of interest. Host cells can be cultured in serum-containing medium or serum-free medium. Host cells can be cultured in a serum-free, protein-free, animal component-free medium, including, e.g., a chemically defined medium (e.g., CD OptiCHO™ (Invitrogen, #12681)). The cell culture medium can be supplemented, if desired, with supplements known to those of skill, such as, e.g., one or more amino acid(s), such L-glutamine (e.g., 2% v/v 200 mM L-glutamine (Invitrogen, #25031)). The culture conditions, such as temperature, pH, and the like, are those previously used with the host cell selected for expression, and will be apparent to those skilled in the art and in the references cited herein, including, e.g., ANIMAL CELL TECHNOLOGY, Rhiel et al., eds., (Kluwer Academic Publishers 1999), Chaubard et al., Genetic Eng. News 20(18) (2000), Hu et al., ASM News 59:65-68 (1993), Hu et al., Biotechnol. Prog. 1:209-215 (1985), Martin et al., Biotechnol. (1987), Freshney, CULTURE OF ANIMAL CELLS: A MANUAL OF BASIC TECHNIQUE, 4th ed., (Wiley, 2000), Mather, INTRODUCTION TO CELL AND TISSUE CULTURE: THEORY AND TENCHNIQUE, (Plenum Press, 1998), Freshney, CULTURE OF IMMORTALIZED CELLS, 3rd ed., (John Wiley & Sons, 1996), CELL CULTURE: ESSENTIAL TECHNIQUES, Doyle et al., eds. (John Wiley & Sons 1998), and GENERAL TECHNIQUES OF CELL CULTURE, Harrison et al., eds., (Cambridge Univ. Press 1997).

The nucleic acid also can be contained, replicated, and/or expressed in plant cells. Techniques related to the culture of plant cells are described in, e.g., Payne et al. (1992) PLANT CELL AND TISSUE CULTURE IN LIQUID SYSTEMS John Wiley & Sons, Inc. New York, N.Y.; Gamborg and Phillips (eds.) (1995) PLANT CELL, TISSUE AND ORGAN CULTURE: FUNDAMENTAL METHODS SPRINGER LAB MANUAL, Springer-Verlag (Berlin Heidelberg N.Y.) and Plant Molecular Biology (1993) R. R. D. Croy (ed.) Bios Scientific Publishers, Oxford, U.K. ISBN 0 12 198370 6. Cell culture media in general are set forth in Atlas and Parks (eds.) THE HANDBOOK OF MICROBIOLOGICAL MEDIA (1993) CRC Press, Boca Raton, Fla.

For long-term, high-yield production of recombinant proteins, stable expression systems can be used. For example, cell lines that stably express a polypeptide of the invention can be transduced with expression vectors comprising viral origins of replication and/or endogenous expression elements and a selectable marker gene. Following the introduction of the vector, cells in the cell line may be allowed to grow for 1-2 days in an enriched media before they are switched to selective media. The purpose of the selectable marker is to confer resistance to selection, and its presence allows growth and recovery of cells that successfully express the introduced sequences. For example, resistant clumps of stably transformed cells can be proliferated using tissue culture techniques appropriate to the cell type. Serum-free media are readily available (e.g., JRH Biosciences, SAFC Biosciences, Sigma-Aldrich Corporation, worldwide web at sigmaaldrich.com). Serum-free media or conditioned medium (e.g., growth medium previously harvested from untransfected or naïve cell cultures) may be preferred for protein production or cell-banking in some instances.

The invention includes immortalized cells or cell lines comprising one or more polypeptides (including, e.g., dimeric or monomeric fusion proteins and multimeric polypeptides), conjugates, nucleic acids, or vectors or the invention.

Host cells transformed with an expression vector and/or polynucleotide are optionally cultured under conditions suitable for the expression and recovery of the encoded protein from cell culture. The polypeptide or fragment thereof produced by such a recombinant cell may be secreted, membrane-bound, or contained intracellularly, depending on the sequence and/or the vector used. Expression vectors comprising polynucleotides encoding mature polypeptides of the invention can be designed with signal sequences that direct secretion of the mature polypeptides through a prokaryotic or eukaryotic cell membrane. Such signal sequences are typically incorporated into the vector such that the signal sequence is expressed at the N-terminus of the polypeptide of the invention. Principles related to such signal sequences are discussed elsewhere herein.

Polypeptide Production and Recovery

Following transduction of a suitable host strain and growth of the host strain to an appropriate cell density, the selected promoter is induced by appropriate means (e.g., temperature shift or chemical induction) and cells are cultured for an additional period. Cells are typically harvested by centrifugation, disrupted by physical or chemical means, and the resulting crude extract retained for further purification. Microbial cells employed in expression of proteins can be disrupted by any convenient method, including freeze-thaw cycling, sonication, mechanical disruption, or use of cell lysing agents, or other methods, which are well know to those skilled in the art.

As noted, many references are available for the culture and production of many cells, including cells of bacterial, plant, animal (especially mammalian) and archebacterial origin. See e.g., Sambrook, Ausubel, and Berger (all supra), as well as Freshney (1994) Culture of Animal Cells, a Manual of Basic Technique, Third edition, Wiley-Liss, New York and the references cited therein; Doyle and Griffiths (1997) Mammalian Cell Culture: Essential Techniques, John Wiley and Sons, NY; Humason (1979) Animal Tissue Techniques, fourth edition W.H. Freeman and Company; and Ricciardelli, et al., (1989) In vitro Cell Dev. Biol. 25:1016 1024. For plant cell culture and regeneration, Payne et al. (1992) Plant Cell and Tissue Culture in Liquid Systems, John Wiley & Sons, Inc. New York, N.Y.; Gamborg and Phillips (eds.) (1995) Plant Cell, Tissue and Organ Culture; Fundamental Methods Springer Lab Manual, Springer-Verlag (Berlin Heidelberg New York) and Plant Molecular Biology (1993) R. R. D. Croy, Ed. Bios Scientific Publishers, Oxford, U.K. ISBN 0 12 198370 6. Cell culture media in general are set forth in Atlas and Parks (eds.) The Handbook of Microbiological Media (1993) CRC Press, Boca Raton, Fla. Additional information for cell culture is found in available commercial literature such as the Life Science Research Cell Culture Catalogue (1998) from Sigma-Aldrich, Inc. (St. Louis, Mo.) ("Sigma-LSRCCC") and, e.g., the Plant Culture Catalogue and supplement (1997) also from Sigma-Aldrich, Inc (St. Louis, Mo.) ("Sigma-PCCS").

Polypeptides of the invention can be recovered and purified from recombinant cell cultures by any of a number of methods well known in the art, including ammonium sulfate or ethanol precipitation, acid extraction, anion or cation exchange chromatography, phosphocellulose chromatography, hydrophobic interaction chromatography, affinity chromatography (e.g., using any of the tagging systems noted herein), hydroxylapatite chromatography, and lectin chromatography. Protein refolding steps can be used, as desired, in completing configuration of the mature protein. Finally, high performance liquid chromatography (HPLC) can be employed in the final purification steps. In addition to the references noted supra, a variety of purification methods are well known in the art, including, e.g., those set forth in Sandana (1997) Bioseparation of Proteins, Academic Press, Inc.; and Bollag et al. (1996) Protein Methods, 2.sup.nd Edition Wiley-Liss, NY; Walker (1996) The Protein Protocols Handbook Humana Press, NJ, Harris and Angal (1990) Protein Purification Applications: A Practical Approach IRL Press at Oxford, Oxford, England; Harris and Angal Protein Purification Methods: A Practical Approach IRL Press at Oxford, Oxford, England; Scopes (1993) Protein Purification: Principles and Practice 3.sup.rd Edition Springer Verlag, NY; Janson and Ryden (1998) Protein Purification Principles, High Resolution Methods and Applications, Second Edition Wiley-VCH, NY; and Walker (1998) Protein Protocols on CD-ROM Humana Press, NJ.

One of skill would understand that fusion proteins of the invention (e.g., mutant CTLA-4-Ig fusion protein) can be made by a variety of methods described herein, including, e.g., those set forth in Example 1 for making LEA29Y-Ig. For example, in place of the LEA29Y-encoding nucleic acid, a nucleic acid sequence encoding a mutant CTLA-4 ECD polypeptide of the invention (e.g., D3-54 polypeptide) can be cloned into the IgG2 Fc fusion vector to produce a vector encoding the mutant CTLA-4-Ig fusion protein (e.g., D3-54-IgG2), stable CHO-K1 cells expressing such mutant CTLA-4-Ig fusion protein can be made by transfecting such cells with the mutant CTLA-4-Ig fusion protein-encoding vector, and the resultant mutant CTLA-4-Ig fusion protein (e.g., D3-54-IgG2) can be expressed (typically in dimeric form) and purified as described in Example 1.

In Vitro Expression Systems

Cell-free transcription/translation systems can also be employed to produce recombinant polypeptides of the invention or fragments thereof using DNAs and/or RNAs of the present invention or fragments thereof. Several such systems are commercially available. A general guide to in vitro transcription and translation protocols is found in Tymms (1995) IN VITRO TRANSCRIPTION AND TRANSLATION PROTOCOLS: METHODS IN MOLECULAR BIOLOGY, Volume 37, Garland Publishing, New York.

Methods of the Invention

Polypeptides (including, e.g., dimeric and monomeric fusion proteins and multimeric polypeptides), conjugates, compositions, nucleic acids, vectors, and cells of the invention exhibit a variety of properties and characteristics and are believed useful in a variety of applications, including, but not limited to, e.g., in prophylactic or therapeutic methods for treating a variety of immune system diseases, disorders and conditions in which modulation or regulation of the immune system and immune system responses may be of benefit. For example, polypeptides, conjugates, compositions, nucleic acids, vectors, and cells of the invention that have an ability to bind CD80 and/or CD86 or an ECD of either or both and/or an ability to inhibit an immune response are believed to be useful in prophylactic and/or therapeutic methods for inhibiting or suppressing an immune response in a subject, methods for inhibiting rejection of a tissue, cell, or organ transplant from a donor by a recipient, and other methods described elsewhere herein. Some such polypeptides, conjugates, compositions, nucleic acids, vectors, and cells of the invention are expected to be useful in methods for method of modulating or inhibiting the interaction of T cells expressing CD28 and/or CTLA-4 with B7-positive cells.

In one aspect, therapeutic or prophylactic methods of the invention involve administering to a subject an effective amount of at least one such polypeptide (including, e.g., fusion protein, multimer, etc.), conjugate, composition, nucleic acid, vector, and/or cell to suppress or inhibit an immune response. In a therapeutic context, the subject is typically one inflicted with an immune system disease, disorder, or condition, and administration is conducted to prevent further progression of the disease, disorder or condition. For example, administration of a molecule of the invention to a subject suffering from an immune system disease (e.g., autoimmune disease) can result in suppression or inhibition of such immune system attack or biological responses associated therewith. By suppressing this immune system attack on healthy body tissues, the resulting physical symptoms (e.g., pain, joint inflammation, joint swelling or tenderness) resulting from or associated with such attack on healthy tissues can be decreased or alleviated, and the biological and physical damage resulting from or associated with the immune system attack can be decreased, retarded, or stopped.

In a prophylactic context, the subject may be one inflicted with, susceptible to, or believed to present an immune system disease, disorder or condition, and administration is typically conducted to prevent progression of the disease, disorder or condition, inhibit or alleviate symptoms, signs, or biological responses associated therewith, prevent bodily damage potentially resulting therefrom, and/or maintain or improve the subject's physical functioning.

In one aspect, the invention provides a method of modulating the interaction of T cells expressing CD28 and/or CTLA-4 with B7-positive cells, the method comprising contacting B7-positive cells with at least one of the following in an effective amount to modulate the interaction of B7-positive cells with CD28-positive T cells and/or CTLA-4-positive T cells: (1) a polypeptide of the invention (e.g., mutant CTLA-4-ECD polypeptide or dimeric or monomeric mutant CTLA-4-Ig fusion protein); (2) a multimer comprising one of more polypeptides of the invention (e.g., a dimer comprising any two such polypeptides or a tetramer comprising any four such polypeptides); (3) a conjugate comprising at least one polypeptide of the invention; (4) a nucleic acid of the invention (e.g., a nucleic acid encoding a polypeptide of the invention); (5) a vector comprising a nucleic acid of the invention or encoding a polypeptide of the invention; (6) a cell or population of cells comprising a polypeptide, nucleic acid, conjugate, and/or vector of the invention; and/or (7) composition of the invention, wherein the interaction of B7-positive cells with CD28-positive T cells and/or CTLA-4-positive T cells is modulated. Typically, the modulatory effect is an inhibitory effect such that the interaction of B7-positive cells with CD28-positive T cells and/or CTLA-4-positive T cells is inhibited. In some instances, the B7-positive cells are antigen-presenting cells (APCs). In some such methods, the interaction of B7-2-positive cells (e.g., APCs expressing B7-2 (CD86)) with CD28-positive T cells is inhibited. In some such methods, the interaction of B7-1-positive cells (e.g., APCs expressing B7-1 (CD80)) with CD28-positive T cells is inhibited.

In another aspect, the invention provides a method of inhibiting the interaction of CD28-positive T cells and/or CTLA-4-positive T cells with B7-positive cells, the method comprising contacting B7-positive cells (e.g., B7-1-positive cells and/or B7-2-positive cells) with at least one of the following molecules or components of the invention in an effective amount to inhibit the interaction of CD28-positive T cells and/or CTLA-4-positive T cells with B7-positive cells: (1) a polypeptide of the invention (e.g., mutant CTLA-4-ECD polypeptide or dimeric or monomeric mutant CTLA-4-Ig fusion protein); (2) a multimer comprising one of more polypeptides of the invention (e.g., a dimer comprising any two such polypeptides or a tetramer comprising any four such polypeptides); (3) a conjugate comprising at least one polypeptide of the invention; (4) a nucleic acid of the invention (e.g., a nucleic acid encoding a polypeptide of the invention); (5) a vector comprising a nucleic acid of the invention or encoding a polypeptide of the invention; (6) a cell or population of cells comprising a polypeptide, nucleic acid, conjugate, and/or vector of the invention; and/or (7) composition of the invention, wherein the interaction of CD28-positive T cells and/or CTLA-4-positive T cells with B7-positive cells is inhibited. In some instances, the B7-positive cells are APCs. In some instances, the interaction of CD28-positive T cells with hB7-1-positive cells and/or hB7-2-positive cells is inhibited. In some such methods, inhibition of the interaction of CD28-positive T cells with hB7-1-positive cells and/or hB7-2-positive cells results in suppression or inhibition of one or more of the following: T cell activation or proliferation, cytokine synthesis or production (e.g., production of TNF-α, IFN-γ, IL-2), induction of various activation markers (e.g., CD25, IL-2 receptor), inflammation, joint swelling or tenderness, serum level of C-reactive protein, anti-collagen antibody production, and/or T cell-dependent antibody response(s).

In some such methods, at least one such molecule or component of the invention is administered to a subject in an effective amount to inhibit the interaction of endogenous CD28-positive T cells with endogenous B7-1-positive cells and/or B7-2-positive cells in the subject. In some such methods, the interaction of endogenous CD28-positive T cells with endogenous B7-positive cells expressing B7-2 (CD86) or B7-1 (CD80) is inhibited. In some instances, the B7-positive cells are APCs which express B7-2 or B7-1, and the interaction of B7-2 or B7-1 with CD28-positive T cells is inhibited. In some instances, the interaction of both B7-2 and B7-1 expressed on APCs with CD28-positive T cells is inhibited.

In another aspect, the invention provides a method of suppressing an immune response in vitro or in vivo. The method comprises contacting a B7-positive cells with at least one of the following molecules or components of the invention in effective amount to suppress an immune response: (1) a polypeptide of the invention (e.g., mutant CTLA-4-ECD polypeptide or dimeric or monomeric mutant CTLA-4-Ig fusion protein); (2) a multimer comprising one of more polypeptides of the invention (e.g., a dimer comprising any two such polypeptides or a tetramer comprising any four such polypeptides); (3) a conjugate comprising at least one polypeptide of the invention; (4) a nucleic acid of the invention (e.g., a nucleic acid encoding a polypeptide of the invention); (5) a vector comprising a nucleic acid of the invention or encoding a polypeptide of the invention; (6) a cell or population of cells comprising a polypeptide, nucleic acid, conjugate, and/or vector of the invention; and/or (7) composition of the invention, wherein an immune response is thereby suppressed. One or more immune responses may be suppressed, including, e.g., T cell response, T cell proliferation or activation, cytokine synthesis or production, inflammation, joint swelling or tenderness, serum level of C-reactive protein, anti-collagen antibody production, and/or T cell-dependent antibody response(s). In such methods comprising contacting a B7-positive cell with a polypeptide of the invention, the polypeptide binds B7-1 (e.g., human B7-1) expressed on B7-positive cells, and/or binds B7-2 (e.g., human B7-2) expressed on B7-positive cells. In some instances, the B7-positive cells are APCs. In some instances, an immune response is suppressed in vitro, such as in, e.g., an in vitro assay, including those described in detail elsewhere herein (see, e.g., the Examples below). In some instances, an immune response is suppressed in vivo in a subject to whom an effective amount to suppress an immune response is administered, such as, e.g., in the therapeutic or prophylactic treatment methods (e.g., method of treating rheumatic disease, such as rheumatoid arthritis, or other autoimmune disease) discussed in detail elsewhere herein.

In another aspect, the invention provides a method of suppressing an immune response in a subject (e.g., mammal, such as a human). The method comprises administering to a subject in need thereof with at least one of the following molecules or components of the invention in a therapeutically or prophylactically effective amount (e.g., therapeutically or prophylactically effective dose) which suppresses an immune response in the subject: (1) a polypeptide of the invention (e.g., mutant CTLA-4-ECD polypeptide or dimeric or monomeric mutant CTLA-4-Ig fusion protein); (2) a multimer comprising one of more polypeptides of the invention (e.g., a dimer comprising any two such polypeptides or a tetramer comprising any four such polypeptides); (3) a conjugate comprising at least one polypeptide of the invention; (4) a nucleic acid of the invention (e.g., a nucleic acid encoding a polypeptide of the invention); (5) a vector comprising a nucleic acid of the invention or encoding a polypeptide of the invention; (6) a cell or population of cells comprising a polypeptide, nucleic acid, conjugate, and/or vector of the invention; and/or (7) composition of the invention, wherein an immune response is thereby suppressed in the subject.

In another aspect, the invention provides a method of treating a subject having an immune system disease or disorder modulated by interaction of endogenous T cells with endogenous cells expressing CD80 and/or CD86. The method comprises administering to a subject in need of such treatment a therapeutically effective amount of: (1) a polypeptide of the invention (e.g., mutant CTLA-4-ECD polypeptide or dimeric or monomeric mutant CTLA-4-Ig fusion protein); (2) a multimer comprising one of more polypeptides of the invention (e.g., a dimer comprising any two such polypeptides or a tetramer comprising any four such polypeptides); (3) a conjugate comprising at least one polypeptide of the invention; (4) a nucleic acid of the invention (e.g., a nucleic acid encoding a polypeptide of the invention); (5) a vector comprising a nucleic acid of the invention or encoding a polypeptide of the invention; (6) a cell or population of cells comprising a polypeptide, nucleic acid, conjugate, and/or vector of the invention; and/or (7) composition of the invention, thereby treating the immune system disease or disorder in the subject. If the subject is a human, CD80 is human CD80, CD86 is human CD86, and CD28 is human CD28. In some such methods, interaction between endogenous T cells expressing CD28 and endogenous cells expressing CD86 and/or endogenous cells expressing CD80 is inhibited.

It is believed that a variety of immune system diseases or disorders, including rheumatic or autoimmune system disease or disorder, may be effectively treated using one or more of the molecules of the invention disclosed herein, such as, e.g., a mutant CTLA-4 ECD polypeptide (e.g., any of SEQ ID NOS:1-73, such as, e.g., D3-54 (SEQ ID NO:36), D3-69 (SEQ ID NO:50), or D3-27 (SEQ ID NO:24) mutant CTLA-4 ECD), or a fusion protein thereof (e.g., D3-54-IgG2 (SEQ ID NO:197 or 211), D3-69-IgG2 (SEQ ID NO:199 or 213), D3-29-IgG2 (SEQ ID NO:79 or 210)). The immune system disease or disorder may be or involve, e.g., but is not limited to, Addison's Disease, Allergy, Alopecia Areata, Alzheimer's, Antineutrophil cytoplasmic antibodies (ANCA)-associated vasculitis, Ankylosing Spondylitis, Antiphospholipid Syndrome (Hughes Syndrome), arthritis, Asthma, Atherosclerosis, Atherosclerotic plaque, autoimmune disease (e.g., lupus, RA, MS, Graves' disease, etc.), Autoimmune Hemolytic Anemia, Autoimmune Hepatitis, Autoimmune inner ear disease, Autoimmune Lymphoproliferative syndrome, Autoimmune Myocarditis, Autoimmune Oophoritis, Autoimmune Orchitis, Azoospermia, Behcet's Disease, Berger's Disease, Bullous Pemphigoid, Cardiomyopathy, Cardiovascular disease, Celiac Sprue/Coeliac disease, Chronic Fatigue Immune Dysfunction Syndrome (CFIDS), Chronic idiopathic polyneuritis, Chronic Inflammatory Demyelinating, Polyradicalneuropathy (CIPD), Chronic relapsing polyneuropathy (Guillain-Barré syndrome), Churg-Strauss Syndrome (CSS), Cicatricial Pemphigoid, Cold Agglutinin Disease (CAD), COPD, CREST syndrome, Crohn's disease, Dermatitis, Herpetiformus, Dermatomyositis, diabetes, Discoid Lupus, Eczema, Epidermolysis bullosa acquisita, Essential Mixed Cryoglobulinemia, Evan's Syndrome, Exopthalmos, Fibromyalgia, Goodpasture's Syndrome, graft-related disease or disorder, Graves'Disease, GVHD, Hashimoto's Thyroiditis, Idiopathic Pulmonary Fibrosis, Idiopathic Thrombocytopenia Purpura (ITP), IgA Nephropathy, immunoproliferative disease or disorder (e.g., psoriasis), Inflammatory bowel disease (IBD), Insulin Dependent Diabetes Mellitus (IDDM), Interstitial lung disease, juvenile diabetes, Juvenile Arthritis, juvenile idiopathic arthritis (JIA), Kawasaki's Disease, Lambert-Eaton Myasthenic Syndrome, Lichen Planus, lupus, Lupus Nephritis, Lymphoscytic Lypophisitis, Ménière's Disease, Miller Fish Syndrome/acute disseminated encephalomyeloradiculopathy, Mixed Connective Tissue Disease, Multiple Sclerosis (MS), muscular rheumatism, Myalgic encephalomyelitis (ME), Myasthenia Gravis, Ocular Inflammation, Pemphigus Foliaceus, Pemphigus Vulgaris, Pernicious Anaemia, Polyarteritis Nodosa, Polychondritis, Polyglandular Syndromes (Whitaker's syndrome), Polymyalgia Rheumatica, Polymyositis, Primary Agammaglobulinemia, Primary Biliary Cirrhosis/Autoimmune cholangiopathy, Psoriasis, Psoriatic arthritis, Raynaud's Phenomenon, Reiter's Syndrome/Reactive arthritis, Restenosis, Rheumatic Fever, rheumatic disease, Rheumatoid Arthritis, Sarcoidosis, Schmidt's syndrome, Scleroderma, Sjörgen's Syndrome, Solid-organ transplant rejection (kidney, heart, liver, lung, etc.), Stiff-Man Syndrome, Systemic Lupus Erythematosus (SLE), systemic scleroderma, Takayasu Arteritis, Temporal Arteritis/Giant Cell Arteritis, Thyroiditis, Type 1 diabetes, Type 2 diabetes, Ulcerative colitis, Uveitis, Vasculitis, Vitiligo, Wegener's Granulomatosis, and preventing or suppressing an immune response associated with rejection of a donor tissue, cell, graft, or organ transplant by a recipient subject. Graft-related diseases or disorders include graft versus host disease (GVDH), such as associated with bone marrow transplantation, and immune disorders resulting from or associated with rejection of organ, tissue, or cell graft transplantation (e.g., tissue or cell allografts or xenografts), including, e.g., grafts of skin, muscle, neurons, islets, organs, parenchymal cells of the liver, etc. With regard to a donor tissue, cell, graft or solid organ transplant in a recipient subject, it is believed such molecules of the invention disclosed herein (e.g., mutant CTLA-4 ECD polypeptide or mutant CTLA-4-Ig fusion protein) may be effective in preventing acute rejection of such transplant in the recipient and/or for long-term maintenance therapy to prevent rejection of such transplant in the recipient (e.g., inhibiting rejection of insulin-producing islet cell transplant from a donor in the subject recipient suffering from diabetes).

The invention includes any such mutant CTLA-4 ECD polypeptide or mutant CTLA-4-Ig fusion protein of the invention for use in suppressing an immune response associated with at least one of the above immune system diseases or disorders. Also provided is the use of any such mutant CTLA-4 ECD polypeptide or mutant CTLA-4-Ig fusion protein of the invention in the manufacture of a medicament for suppressing an immune response with at least one of the above immune system diseases or disorders.

An effective amount of a molecule of the invention, such as, e.g., a mutant CTLA-4 ECD polypeptide (e.g., D3-54, D3-69, D3-29, D3-56, D3-75) or an Ig fusion protein comprising a mutant CTLA-4 ECD polypeptide of the invention (e.g., D3-54-IgG2, D3-69-IgG2, D3-29-IgG2, D3-56-IgG2, D3-75-IgG2, respectively), for suppressing an immune response in a subject or treating an immune system disease or disorder modulated by interaction of endogenous T cells with endogenous cells expressing CD80 and/or CD86 in a subject in the methods described herein may comprise from about 0.0001 milligrams per kilogram (mg/kg) weight of the subject to about 200 milligrams per kilogram (mg/kg) body weight of the subject, such as, e.g., from about 0.001 milligrams per kilogram (mg/kg) body weight of the subject to about 100 milligrams per kilogram (mg/kg) weight of the subject, or, e.g., from about 0.001 mg/kg weight of the subject to at least about 0.005, 0.01, 0.025, 0.05, 0.1, 0.2, 0.3, 0.4, 0.5, 0.6, 0.7, 0.8, 0.9, 1, 2, 3, 4, 5, 6, 7, 8, 9, 10, 25, 50, or 75 mg/kg body weight of the subject. One or more immune responses may be suppressed in the subject, including, e.g., T cell response, T cell activation or proliferation, cytokine synthesis or production (e.g., production of TNF-α, IFN-γ, IL-2, etc.), induction of various activation markers (e.g., CD25, IL-2 receptor, etc.), synthesis or production of inflammatory molecules, inflammation, joint swelling, joint tenderness, pain, stiffness, serum levels of C-reactive protein, anti-collagen antibody production, and/or T cell-dependent antibody response(s)). An effective amount of a molecule or component of the invention for suppressing an immune response may be an amount that suppresses an immune response or a symptom or sign thereof by a detectable or measurable amount. The immune response may be partially or completely suppressed. An effective amount for treating an immune system disease or disorder may be an amount that relieves, lessens, or alleviates at least one symptom or biological response or effect associated with the disease or disorder, prevents progression of the disease or disorder, or improves physical functioning of the subject.

An effective amount of a molecule or component of the invention for modulating or inhibiting the interaction of T cells expressing CD28 and/or CTLA-4 with B7-positive cells may be an amount that modulates or inhibits the binding between B7-positive cells and CD28-positive and/or CTLA-4-positive T cells, respectively. Such binding interaction(s) may be may be partially or completely modulated or inhibited.

In some such methods, a mutant CTLA-4-Ig fusion protein dimer of the invention is administered to the subject in a therapeutically or prophylactically effective amount (or dose) sufficient to suppress an immune response, treat an immune system disease or disorder modulated by interaction of T cells with B7-expressing cells, or modulate or inhibit the interaction of T cells expressing CD28 and/or CTLA-4 with B7-positive cells. The fusion protein dimer administered is typically a soluble Ig fusion protein dimer. In some such methods, the effective amount or dose of the fusion protein dimer of the invention comprises from about 0.001 milligrams per kilogram (mg/kg) body weight of the subject to about 200 milligrams per kilogram (mg/kg) body weight of the subject (such as, e.g., a human) or from about 0.001 mg/kg to about 300 mg/kg body weight of the subject. For example, the effective amount or dose of the fusion protein dimer may comprise from about 0.001 mg/kg body weight of the subject to at least about 0.005, 0.01, 0.05, 0.1, 0.2, 0.3, 0.4, 0.5, 0.6, 0.7, 0.8, 0.9, 1, 2, 3, 4, 5, 10, 25, 30, 40, 50, 60, 75, 80, 90, 100, 125, 150, 175, 200, 225, 250, or 300 mg/kg body weight of the subject (such as, e.g., human, including an adult human). In some instances, the effective amount or dose is from about 0.001 milligrams (mg) to about 50 milligrams per kilogram (kg) body weight of the subject, including, but not limited to, e.g., from about 0.01 mg/kg to about 100 mg/kg body weight of the subject (e.g., human), from about 0.01 mg/kg to about 50 mg/kg body weight of the subject, or from about 0.01 mg/kg to about 25 mg/kg weight of the subject; for example, about 0.05 mg/kg, 0.075 mg/kg, 0.1 mg/kg, 0.15 mg/kg, 0.2 mg/kg, 0.25 mg/kg, 0.3 mg/kg, 0.5 mg/kg, 0.75 mg/kg, 1 mg/kg, 1.5 mg/kg, 2 mg/kg, 2.5 mg/kg, 3 mg/kg, 5 mg/kg, about 10 mg/kg, 20 mg/kg, 25 mg/kg, 50 mg/kg, 75 mg/kg or 100 mg/kg body weight of the subject (e.g., adult human patient) is administered to the subject. In some instances, the effective amount or dose of the fusion protein dimer is from about 2 to 10 mg/kg, about 3 to 10 mg/kg, about 3 to 5 mg/kg, about 5 to 10 mg/kg, 0.1 to 5 mg/kg, about 0.05 to 1.0 mg/kg, about 0.05 to 3 mg/kg, about 0.05 to 2.0 mg/kg, about 0.05 to 1.0 mg/kg, about 0.1 to 2.0 mg/kg, about 0.1 to 3.0 mg/kg, about 0.1 to 0.5 mg/kg, about 0.1 to 0.8 mg/kg, about 0.1 to 0.6 mg/kg, about 0.01 mg/kg to about 0.05 mg/kg, about 0.01 mg/kg to about 0.1 mg/kg, about 0.01 mg/kg to about 0.05 mg/kg, about 0.01 mg/kg to about 1 mg/kg, about 0.01 to about 5 mg/kg, about 0.01 mg/kg to about 3 mg/kg, about 0.05 mg/kg to about 2.5 mg/kg, about 0.1 mg/kg to about 1 mg/kg, about 0.1 mg/kg to about 5 mg/kg, about 0.2 to 1 mg/kg, about 0.2 to 0.6 mg/kg, about 0.2 to 0.5 mg/kg about 0.3 to 1 mg/kg, about 0.3 to 0.6 mg/kg, about 0.3 to 0.5 mg/kg weight of a subject. In some instances, the effective amount or dose is less than about 500 mg for a subject weighing less than 60 kg (e.g., less than about 100 mg, 75 mg, 50 mg, 25 mg, 12.5 mg. or 10 mg), less than about 750 mg for a subject weighing between 60-100 kg (e.g., less than about 150 mg, 100 mg, 75 mg, 37.5 mg, or 20 mg), or less than about 1000 mg for a subject weighing more than 100 kg (e.g., less than about 500 mg, 100 mg, 50 mg, 25 mg, or 10 mg).

In another aspect, in some such methods of the invention, a mutant CTLA-4-Ig fusion protein of the invention is administered to the subject in a therapeutically or prophylactically effective amount or dose that is, e.g., sufficient to suppress an immune response, treat an immune system disease or disorder modulated by interaction of T cells with B7-expressing cells, or modulate or inhibit the interaction of T cells expressing CD28 and/or CTLA-4 with B7-positive cells. The effective amount or dose of the fusion protein, which is usually a soluble fusion protein, can comprise from about 0.001 mg/kg to about 300 mg/kg, about 0.001 mg/kg to about 200 mg/kg, or about 0.001 mg/kg to about 300 mg/kg body weight of the subject (e.g., human). In one aspect, the effective amount or dose of the fusion protein comprises from about 0.001 mg/kg to at least about 0.005, 0.01, 0.05, 0.1, 0.2, 0.3, 0.4, 0.5, 0.6, 0.7, 0.8, 0.9, 1, 2, 3, 4, 5, 10, 25, 30, 40, 50, 60, 75, 80, 90, 100, 125, 150, 175, 200, 225, 250, or 300 mg/kg body weight of the subject. In another aspect, the effective amount or dose is from about 0.01 mg/kg to about 100 mg/kg, from about 0.01 mg/kg to about 50 mg/kg, or from about 0.01 mg/kg to about 25 mg/kg weight of the subject. Exemplary doses or amounts include about 0.05 mg/kg, 0.075 mg/kg, 0.1 mg/kg, 0.15 mg/kg, 0.2 mg/kg, 0.25 mg/kg, 0.3 mg/kg, 0.5 mg/kg, 0.75 mg/kg, 1 mg/kg, 1.5 mg/kg, 2 mg/kg, 2.5 mg/kg, 3 mg/kg, 5 mg/kg, about 10 mg/kg, 20 mg/kg, 25 mg/kg, 50 mg/kg, 75 mg/kg, and 100 mg/kg body weight of the subject (e.g., adult human). In another aspect, the effective amount or dose of the fusion protein is from about 2 to 10 mg/kg, about 3 to 10 mg/kg, about 3 to 5 mg/kg, about 5 to 10 mg/kg, 0.1 to 5 mg/kg, about 0.05 to 1.0 mg/kg, about 0.05 to 3 mg/kg, about 0.05 to 2.0 mg/kg, about 0.05 to 1.0 mg/kg, about 0.1 to 2.0 mg/kg, about 0.1 to 3.0 mg/kg, about 0.1 to 0.5 mg/kg, about 0.1 to 0.8 mg/kg, about 0.1 to 0.6 mg/kg, about 0.01 mg/kg to about 0.05 mg/kg, about 0.01 mg/kg to about 0.1 mg/kg, about 0.01 mg/kg to about 0.05 mg/kg, about 0.01 mg/kg to about 1 mg/kg, about 0.01 to about 5 mg/kg, about 0.01 mg/kg to about 3 mg/kg, about 0.05 mg/kg to about 2.5 mg/kg, about 0.1 mg/kg to about 1 mg/kg, about 0.1 mg/kg to about 5 mg/kg, about 0.2 to 1 mg/kg, about 0.2 to 0.6 mg/kg, about 0.2 to 0.5 mg/kg about 0.3 to 1 mg/kg, about 0.3 to 0.6 mg/kg, about 0.3 to 0.5 mg/kg weight of a subject. In some aspects, the effective amount or dose is less than about 500 mg for a subject weighing less than 60 kg (e.g., less than about 100 mg, 75 mg, 50 mg, 25 mg, 12.5 mg. or 10 mg), less than about 750 mg for a subject weighing between 60-100 kg (e.g., less than about 150 mg, 100 mg, 75 mg, 37.5 mg, or 20 mg), or less than about 1000 mg for a subject weighing more than 100 kg (e.g., less than about 500 mg, 100 mg, 50 mg, 25 mg, or 10 mg).

The effective amount or dose of a nucleic acid, vector, composition, and/or cell of the invention sufficient to similarly suppress an immune response or modulate, treat an immune system disease or disorder modulated by interaction of T cells with B7-expressing cells, or modulate or inhibit the interaction of T cells expressing CD28 and/or CTLA-4 with B7-positive cells can be determined. For example, if a vector encoding such a fusion protein dimer of the invention is to be administered to the subject, one skilled in the art can readily determine the amount of the vector to be administered such that a desired therapeutically or prophylactically effective amount of the fusion protein dimer is likely produced in the subject.

Exemplary fusion protein dimers of the invention include any of those described in detail above and herein, including, e.g., a fusion protein dimer comprising two identical fusion protein monomers, wherein each fusion protein monomer comprises a mutant CTLA-4 ECD polypeptide of the invention fused at its C-terminus to the N-terminus of an Ig Fc polypeptide (e.g., IgG2 Fc, IgG1, IgG4 or mutant Ig Fc polypeptide which reduces effector function). An exemplary mutant CTLA-4 ECD polypeptide is one comprising a polypeptide sequence selected from the group consisting of SEQ ID NOS:1-73. An exemplary fusion protein dimer is one comprising two fusion protein monomers, wherein each fusion protein monomer comprises a polypeptide sequence selected from the group consisting of SEQ ID NOS:74-79, 197-200, 205-214, and 219-222. Typically, the two monomeric fusion proteins in a dimeric fusion protein are covalently linked together via at least one disulfide bond formed between cysteine residue(s) present in each monomer.

In any of the methods described above, the molecule or component of the invention (e.g., polypeptide (including, e.g., dimeric or monomeric fusion protein or polypeptide multimer), conjugate, nucleic acid, vector, composition, and/or cell of the invention) may be administered to the subject as a composition. The composition typically comprises at least one such molecule or component and an excipient, carrier, or diluent. The composition may comprise a pharmaceutical composition comprising at least one such molecule or component and a pharmaceutically acceptable excipient, carrier, or diluent (e.g., PBS). The pH of compositions of the invention typically ranges from about pH 6.0 to about pH 9.0, including, e.g., from about pH 6.5 to about pH 8.5, usually from about pH 7.0 to about pH 8.0. In one aspect, the pH of compositions of the invention typically ranges from about pH 3 to about pH 10, from about pH 4 to about pH 10, from about pH 5 to about pH 9, from about pH 6 to about pH 9, from about pH 5.5 to about pH 8.5, from about pH 6.0 to about pH 6.7, from about pH 6.0 to about pH 6.5, from about pH 6.2 to about pH 8.7, from about pH 6.5 to about pH 7.5, from about pH 6.2 to about pH 7.0, from about pH 6.3 to about pH 6.8, from about pH 6.4 to about pH 6.8, and about pH 7.0 to about pH 7.4. In one aspect, a composition comprising at least one such molecule or component of the invention, such as, e.g., a mutant CTLA-4-Ig fusion protein, has a pH of pH 5.5, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, pH 9.0, pH 9.1, pH 9.2, pH 9.3, pH 9.4, pH 9.5, pH 9.6, pH 9.7, pH 9.8, pH, 9.9, or pH 10.0. Some compositions of the invention include one or more salts (e.g., sodium chloride, sodium phosphate, calcium chloride, and the like), one or more buffers (e.g., HEPES, sodium citrate, sodium phosphate (e.g., $Na_2HPO_4/Na_3PO_4$), succinate, tartrate, fumarate, gluconate, oxalate, lactate, acetate, tris(hydroxymethyl)aminomethane (Tris), and the like), one, two three, four, five, or more saccharides or sugars (e.g., sucrose, mannose, maltose, trehalose, dextrose, and the like), and/or one, two, three, four or more polyalcohols or sugar alcohols (e.g., mannitol, sorbitol, glycol, glycerol, arabitol, erythritol, xylitol, ribitol, lactitol, and the like). One, two three, four, five, or more monosaccharides, disaccharides and/or polysaccharides can be included in the composition. The composition of the invention may comprise any concentration of such molecule or component effective to suppress an immune response when administered to the subject. For example, in some such methods (including, e.g., methods in which immunosuppression is desirable, such as, but not limited, to, e.g., treatment of rheumatoid arthritis or similar immune disorders, or for inhibiting rejection of a tissue, cell, graft, or organ transplant from a donor by a recipient subject), a pharmaceutical composition comprising a pharmaceutically acceptable carrier, excipient, or diluent and a fusion protein dimer of the invention is administered to the subject (e.g., parentally, subcutaneously, intravenously, intramuscularly, etc.), wherein the pharmaceutical composition comprises a fusion protein dimer of the invention at a concentration of from about 0.001 mg/ml to about 200 mg/ml, about 0.001 mg/ml to about 300 mg/ml, about 0.01 mg/ml to about 200 mg/ml, about 0.01 mg/ml to about 250 mg/ml, about 0.1 mg/ml to about 200 mg/ml, about 0.001 mg/ml to about 100 mg/ml, about 0.001 mg/ml to about 90 mg/ml, about 0.01 mg/ml to about 90 mg/ml, about 0.01 mg/ml to about 75 mg/ml, about 0.1 to about 80 mg/ml, about 0.1 to about 75 mg/ml, about 0.1 to about 60 mg/ml, about 0.1 to about 50 mg/ml, about 0.1 to about 40 mg/ml, about 0.1 to about 30 mg/ml, about 1 to about 90 mg/ml, about 1 to about 80 mg/ml, about 1 to about 75 mg/ml, about 1 to about 60 mg/ml, about 1 to about 50 mg/ml, about 1 to about 40 mg/ml, about 1 to about 30 mg/ml, about 1 to about 20 mg/ml, about 1 to about 10 mg/ml, about 1 to about 5 mg/ml, about 5 to about 90 mg/ml, about 5 to about 80 mg/ml, about 5 to about 75 mg/ml, about 5 to about 60 mg/ml, about 5 to about 50 mg/ml, about 5 to about 40 mg/ml, about 5 to about 30 mg/ml, about 5 to about 20 mg/ml, about 5 to about 10 mg/ml, about 1 to about 5 mg/ml, about 10 to about 75 mg/ml, about 25 mg/ml to about 75 mg/ml, about 30 mg/ml to about 60 mg/ml, about 25 to about 50 mg/ml, about 50 mg/ml to about 100 mg/ml, including, e.g., about 1 mg/ml, 5 mg/ml, 10 mg/ml, about 15 mg/ml, about 25 mg/ml, about 30 mg/ml, about 40 mg/ml, about 50 mg/ml, about 60 mg/ml, about 70 mg/ml, about 80 mg/ml, about 90 mg/ml, or 100 mg/ml. Other concentrations are contemplated. In some methods of the invention described herein, including some therapeutic or prophylactic methods, a volume of any such composition (e.g., pharmaceutical composition) comprising a fusion protein of the invention in a range of about 0.01 milliliter (ml) to about 10 ml, about 0.01 ml to about 5 ml, about 0.1 ml to about 5 ml, about 0.5 ml to about 2 ml, about 1 ml to about 2 ml, including, e.g., a volume of 0.01 ml, 0.025 ml, 0.05 ml, 0.1 ml, 0.2 ml, 0.3 ml, 0.4 ml, 0.5 ml, 0.75 ml, 1 ml, 2 ml, 3 ml, 4 ml, 5 ml, 10 ml, 20 ml, 25 ml, 50 ml, 75 ml, 100 ml, 200 ml, 250 ml, 300 ml, 500 ml, 1000 ml, etc. is administered to a subject via a single i.v., s.c., i.m., or i.p. injection. Further details of exemplary compositions of the invention are discussed elsewhere herein.

The effective amount or dose of a molecule of the invention that is administered to a particular subject may vary depending upon, e.g., the disease, disorder, or condition being treated, the potency of the particular mutant CTLA-4 molecule of the invention (i.e., its efficacy) (e.g., a mutant CTLA-4-Ig fusion protein dimer of the invention) to be administered, the mode of administration of the molecule, and the subject's individual ability to tolerate a specific amount of the particular molecule. For example, in a method for suppressing an immune response in a subject having rheumatoid arthritis (RA) or a method for treating RA, the effective amount or dose of a mutant CTLA-4-Ig dimer of the invention (e.g., D3-29-IGg2, D3-54-IgG2, D3-56-IgG2, D3-69-IgG2, D3-75-IgG2, etc.) to be administered to the subject can be determined based on a variety of factors, including the potency of the mutant CTLA-4-Ig dimer, the mode of administration of the dimer, and/or the severity of the subject's symptoms or signs of rheumatoid arthritis. In one aspect, an effective amount or dose of a particular mutant CTLA-4-Ig dimer of the invention can be determined by comparing the potency of such mutant CTLA-4-Ig dimer with that of the Orencia® dimer. Doses of the Orencia® dimer effective for treating rheumatoid arthritis and related disorders are known in the art. For example, the Orencia® dimer is typically administered intravenously to a human suffering from rheumatoid arthritis in a dose of about 10 mg Orencia® per kilogram (kg) body weight of the human. A mutant CTLA-4-Ig dimer of the invention that is about "X" times more potent than Orencia® can be administered (e.g., intravenously, subcutaneously, or in another manner described herein) to a human suffering from rheumatoid arthritis in a dose that is about "X" times less than the Orencia® dimer dose to achieve a therapeutic effect (e.g., suppressing an immune response) that is approximately equivalent to that of the Orencia® dimer. If a greater therapeutic effect is desired, a proportionally increased amount or dose of the mutant CTLA-4-Ig dimer can be readily determined and administered to the human.

In any of the methods described herein, the molecule or component of the invention (e.g., a polypeptide (including, e.g., dimeric or monomeric fusion protein or polypeptide multimer), conjugate, nucleic acid, vector, composition, and/or cell of the invention) can be administered parentally, subcutaneously, or intravenously, or as described elsewhere herein. The molecule or component of the invention may be administered in a therapeutically effective amount one, two, three or four times per month, two times per week, biweekly (every two weeks), or bimonthly (every two months). Administration may last for a period of 1, 2, 3, 4, 5, 6, 7, 8, 9, 10, 11, or 12 months or longer (e.g., one, two, three, four or more years, including for the life of the subject).

Any of the methods described herein may further comprise administering to the subject an effective amount of at least one additional therapeutic or immunosuppressive agent or compound. Thus, for example, the invention provides a method of suppressing an immune response comprising administering to a subject in need thereof (1) an effective amount of at least one first immunosuppressive agent, wherein each such first immunosuppressive agent is a polypeptide, nucleic acid, vector, composition, and/or cell of the invention, and (2) an effective amount of at least one second immunosuppressive agent, wherein an immune response in the subject is suppressed.

A variety of additional therapeutic or immunosuppressive agents (that are not molecules of the invention) may be used or administered in conjunction with a molecule of the invention (e.g., polypeptide, nucleic acid, vector, composition, and/or cell of the invention). Such agents include, e.g., a disease-modifying anti-rheumatic drug (DMARD) (such as, e.g., methotrexate (MTX), cytokine antagonist (e.g., IL-2 or IL-6 antagonist), steroidal compound (e.g., corticosteroid, glucocosteroid, e.g., prednisone or methylprednisone), non-steroidal compound, sodium or magnesium salicylate, ibuprofen, acetylsalicylic acid, acetaminophen, antibody, biological agent that blocks synthesis of an production anti-inflammatory cytokine, Raptiva® efalizumab, anti-inflammatory agent or compound, and non-steroidal anti-inflammatory drug (NSAID). Such additional therapeutic or immunosuppressive agent can be administered to the subject in a pharmaceutical composition comprising the additional agent and a pharmaceutically acceptable excipient or carrier. The effective amount or dose of the agent to be administered will depend upon the specific agent. Some such agents are currently used in immunosuppressive therapies and appropriate dosages can be determined by based upon the disease, disorder or condition being treated and the subject's ability to tolerate specific amounts or doses, and the agent's immunosuppressive effectiveness. Exemplary doses for immunosuppressive agents described above which are not molecules of the invention are known. The additional immunosuppressive agent that is not a molecule of the invention can be administered simultaneously with or before or after administration of the molecule of the invention (e.g., mutant CTLA-4-Ig fusion protein).

A treatment regimen, including, e.g., dose, schedule of administration, method of administration (e.g., intravenous injection, subcutaneous injection, etc.) and pharmaceutical composition comprising at least one such molecule or component of the invention may vary depending upon the disease, disorder or condition to be treated. One or more such molecules or components of the invention may be administered to a subject; each such molecule or component need not be administered in the same pharmaceutical formulation, by the same administration methods, in the same amount, or by the same dosing frequency schedule.

In some such methods, for example, about 1 ml of a pharmaceutical composition comprising a pharmaceutically acceptable excipient, carrier, or diluent and a concentration of a fusion protein dimer of the invention of about 50 mg/ml is administered subcutaneously to a subject (e.g., adult human) in need of immunosuppression (e.g., a subject suffering from rheumatoid arthritis). Such initial dose is 50 mg of fusion protein dimer. For a subject having a body weight of 100 kg, this initial dose corresponds to 0.5 mg fusion protein dimer per kg body weight of the subject. A second of the same amount is administered subcutaneously at one or two weeks after the first dose. Further doses are administered subcutaneously every week, biweekly, or once per month, or more or less frequently as necessary. Such compositions and administration formats are believed useful, for example, for treating a human suffering from rheumatoid arthritis or another immune disorder in which immunosuppression is desirable or for inhibiting rejection of a tissue, cell, graft, or organ transplant from a human donor by a human recipient.

Methods of Treating Rheumatoid Arthritis

Rheumatoid arthritis is one of the most common systemic inflammatory autoimmune diseases and is estimated to affect 1-2% of the adult population. See, e.g., Dipiro, J. T., *Rheumatoid arthritis*, in PHARMACOTHERAPY: A PATHOPHYSIOLOGIC APPROACH, 1671-1682 (Talbert, R. T. et al. eds., McGraw-Hill, New York, 6$^{th}$ ed. 2005). The disease is characterized by synovial membrane hyperplasia and infiltration of inflammatory cells, including activated T cells. Activated T cells play a pivotal role in the progression of rheumatoid arthritis by stimulating a variety of cell types to produce proinflammatory cytokines, such as IL-1, IL-6, and TNF-alpha, autoantibodies, and matrix metalloproteinases (Hoffman, R. W., Front. Biosci. 6:1369-1378 (2001); Choy, E. K. et al., N. Engl. J. Med 344:907-916 (2001)). The strong contribution of T cells to the progression of rheumatoid arthritis makes T cell activation a rational target for therapeutic intervention. Such inflammatory molecules are believed to cause the inflammatory response, tissue damage (e.g., joint damage), and pain associated with rheumatoid arthritis.

Co-stimulation of T cells mediated by interactions between CD28 receptor and CD80 and/or CD86 ligand(s) is essential for the activation of most T cells (Riley, J. L. et al., Blood 105:13-21 (2005)). Therapeutic or prophylactic agents that antagonize the CD80/CD86-CD28 co-stimulation pathway, such as the Orencia® (Abatacept) fusion protein, which is a soluble dimeric hCTLA-4-Ig fusion protein, have been shown to be clinically effective in the treatment of rheumatoid arthritis (Kremer, J. M. et al., Ann. Intern. Med. 144:865-876 (2006); Genovese, M. C. et al., N. Engl. J. Med. 353:1114-1123 (2005)). Abatacept is believed to exert immunosuppressive function by binding to CD80 and/or CD86 ligands on antigen-presenting cells when administered to a subject (e.g., adult human) in vivo in a therapeutically or prophylactically effective amount, thus preventing the interaction of either or both of these ligands with the CD28 receptor on T cells.

Abatacept is presently approved to treat adult human patients with moderately to severely active RA who have had an inadequate response to one or more DMARDs, such as methotrexate or TNF antagonists. Abatacept is administered to an adult RA patient at a dose of 10 mg/kg body weight of the subject by intravenous infusion. Following the first dose, second and third doses of 10 mg/kg of the fusion protein are administered to the subject at two and four weeks, respectively, after the first dose. Subsequent doses are administered every four weeks (i.e., once per month). Intravenous infusion of Abatacept is believed necessary to deliver the high dose level required to obtain desirable efficacy in rheumatoid arthritis therapy.

Other current therapies for rheumatoid arthritis include the administration of non-specific immunosuppressive agents, such as methotrexate, and steroidal and non-steroidal anti-inflammatory drugs. Additionally, biologic agents are approved that target specific pro-inflammatory cytokines, such as TNF-α (e.g., Remicade® infliximab, Enbrel® entaercept, Humira® adalimumab) and IL-1 (e.g., Kineret® anakinra). However, many of these therapies have significant side effects—some of which are toxic—particularly when administered over a long time period.

Despite the availability of various therapies, significant unmet need exists for the treatment of RA. For example, 60% of human RA patients who have failed previous DMARD treatment and 80% of human RA patients who have failed previous anti-TNF therapy did not achieve an ACR50 scores after treatment with Orencia for 6 months (Kremer J. M. et al., Ann. Intern. Med. 144:865-876 (2006); Genovese, M. C. et al., N. Engl. J. Med. 353:1114-11 (2005)). Dose response studies using Abatacept and Belatacept (LEA29Y-Ig) fusion protein in the treatment of RA in adults indicated that efficacy was dose-dependent and was not saturated at the highest dose levels tested (Kremer, J. M. et al., N. Engl. J. Med. 349:1907-1915 (2003); Moreland, L. W. et al., Arthrit. Rheum. 46:1470-1479 (2002)).

A soluble dimeric mutant CTLA-4-Ig of the invention having a higher binding avidity to hCD80 and/or hCD86 than Abatacept is expected to be able to exert more potent immunosuppressive effects than Abatacept when administered to a subject with RA. Such a mutant CTLA-4-Ig binds a similar number of CD80 and/or CD86 ligands at a lower concentration than Abatacept.

A mutant CTLA-4-Ig with a higher binding avidity to CD80 or CD86 and slower dissociation rate from CD80 or CD86, respectively, has a longer residence time on such ligand. This longer residence time is expected to be associated with higher efficacy in vivo. It is believed that such a mutant CTLA-4-Ig may be effective in therapeutically or prophylactically treating a subject with RA at a dose that is lower than the Abatacept. That is, it is believed that such a mutant CTLA-4-Ig may achieve a degree of efficacy equivalent to that of Abatacept when administered to the RA subject at a dose that is less than that of the Abatacept dose of 10 mg/kg body weight of the subject. The invention provides soluble dimeric mutant CTLA-4-Ig fusion proteins of varied binding avidities to hCD80 and/or hCD86. Soluble dimeric mutant CTLA-4-Ig fusion proteins that have substantially higher binding avidities to hCD86 than Abatacept may a degree of efficacy equivalent to that of Abatacept when administered to the RA subject at a dose that is substantially less than that of Abatacept. Administration of a lower dose of such a mutant CTLA-4-Ig may allow a more convenient method of administration (e.g., subcutaneous injection) to be used than is currently used for administration of Abatacept (intravenous injection).

It is also believed that a soluble mutant CTLA-4-Ig fusion protein of the invention with a higher immunosuppressive potency than Abatacept or Belatacept fusion protein would enable a higher level of efficacy to be obtained in the treatment of RA patients. A more immunosuppressive mutant CTLA-4-Ig is expected to be able to alleviate symptoms associated with RA and inhibit progressive of the deleterious physical effects of RA more effectively than Abatacept. Such a mutant CTLA-4-Ig can be formulated in a pharmaceutically acceptable diluent, excipient, or carrier (e.g., PBS) at a concentration ranging from of 0.1-200 mg/ml. Treatment of a subject with RA can be accomplished by administering to the subject a therapeutically or prophylactically effective amount (dose) of the mutant CTLA-4-Ig by subcutaneous injection or intravenous infusion at an appropriately determined dosing frequency (e.g., initial dose following by one dose 2 to 4 times per month, one dose per month, or one dose every two months). The dose would depend upon the severity of the subject's disease or symptoms. For example, an amount or dose of a mutant CTLA-4-Ig of no more than about 10 mg/kg (including e.g., about 1 mg/kg, 0.5 mg/kg, 0.25 mg/kg, 1 mg/kg, 2 mg/kg, 3 mg/kg, 4 mg/kg, 5 mg/kg, 6 mg/kg, 7 mg/kg, 8 mg/kg, or 9 mg/kg) body weight of the subject may be administered. A more immunosuppressive mutant CTLA-4-Ig may allow for a less frequent dosing schedule (e.g., once very two months) than the dosing schedule typically used with Abatacept. Alternatively, an amount or dose of a mutant CTLA-4-Ig greater than about 10 mg/kg weight of the subject (e.g., from about 10 mg/kg to about 100 mg/kg, from about 10 mg/kg to about 25 mg/kg, about 10 mg/kg to about 50 mg/kg, about 10 mg/kg to about 75 mg/kg, etc., including, e.g., about 15 mg/kg, 20 mg/kg, 30 mg/kg, 40 mg/kg, 50 mg/kg, 60 g/kg, 70 mg/kg, 75 mg/kg, 80 mg/kg, 90 mg/kg, 100 mg/kg) may be administered to a subject with RA if the subject's disease condition and/or symptoms warrants such amount or dose.

The effective amount or dose of a mutant CTLA-4-Ig dimer of the invention for treating RA in a human suffering therefrom can be determined based on various factors, such as the potency of the mutant CTLA-4-Ig dimer, the mode of administration of the dimer, and/or the severity of the subject's symptoms or signs of rheumatoid arthritis. For example, an effective amount or dose of a mutant CTLA-4-Ig dimer of the invention can be ascertained by comparing the potency of such dimer to that of the Orencia® dimer and determining the amount or dose of the mutant CTLA-4-Ig dimer that would yield the desired immunosuppressive effect compared to Orencia® (e.g., an improved or approximately equivalent effect) based on amount or dose of Orencia® that would typically be administered to a human subject exhibiting similar symptoms or signs of RA.

In one embodiment, for example, the invention provides a method of treating rheumatoid arthritis in a subject in need of such treatment, the method comprising administering to the subject an effective amount of a soluble dimeric mutant CTLA-4-Ig fusion protein of the invention by, e.g., intravenous or subcutaneous injection. The effective amount or dose may comprise from about 0.001 milligrams (mg) to about 10 milligrams per kilogram (kg) body weight of the subject, including, but not limited to, e.g., from about 0.01 mg/kg to about 10 mg/kg weight of the subject, from about 0.05 mg/kg, 0.1 mg/kg, 0.2 mg/kg, 0.25 mg/kg, 0.3 mg/kg, 0.5 mg/kg, 1 mg/kg, 2 mg/kg, 5 mg/kg, 6 mg/kg, 7 mg/kg, 8 mg/kg, 9 mg/kg, or 10 mg/kg body weight of the adult human patient is administered to the subject. In some instances, the effective amount or dose is from about 2 to 10 mg/kg, about 3 to 10 mg/kg, about 3 to 5 mg/kg, about 5 to 10 mg/kg, 0.1 to 5 mg/kg weight, about 0.05 to 1.0 mg/kg, about 0.05 to 3 mg/kg weight, about 0.05 to 2.0 mg/kg, about 0.05 to 1.0 mg/kg, about 0.05 to 2.0 mg/kg, about 0.1 to 2.0 mg/kg, about 0.1 to 3.0 mg/kg, about 0.1 to 0.5 mg/kg, about 0.1 to 0.8 mg/kg, about 0.1 to 0.6 mg/kg, about 0.2 to 1 mg/kg, about 0.2 to 0.6 mg/kg, about 0.2 to 0.5 mg/kg about 0.3 to 1 mg/kg, about 0.3 to 0.6 mg/kg, about 0.3 to 0.5 mg/kg weight of a subject. In some instances, the effective amount or dose is less than about 500 mg for a subject weighing less than 60 kg (e.g., less than about 100 mg, 75 mg, 50 mg, 25 mg, or 12.5 mg), less than about 750 mg for a subject weighing between 60-100 kg (e.g., less than about 150 mg, 100 mg, 75 mg, 37.5 mg, or 20 mg), or less than about 1000 mg for a subject weighing more than 100 kg (e.g., less than about 500 mg, 100 mg, 50 mg, 25 mg, or 10 mg). Following the first dose, subsequent equivalent doses are administered at intervals of 1, 2, 4, 8, 10, 12, 14, or 16 weeks. Subsequent dosing frequency can be determined as needed.

Such a mutant CTLA-4-Ig fusion may be formulated with a pharmaceutically acceptable excipient, carrier, or diluent to produce a pharmaceutical composition suitable for administration to a subject (e.g., mammal, including a human). The concentration of the fusion protein in the composition may range from about 0.01 mg/ml to about 300 mg/ml or from about 0.01 mg/ml to about 200 mg/ml, including, but not limited to, e.g., from about 0.1 mg/ml to about 300 mg/ml, from about 0.1 mg/ml to about 200 mg/ml, about 0.1 mg/ml to about 100 mg/ml, about 0.5 mg/ml to about 100 mg/ml, about 0.5 mg/ml to about 50 mg/ml, about 1 to about 100 mg/ml, about 1 to about 75 mg/ml, about 5 to about 75 mg/ml, about 10 to about 75 mg/ml, about 10 to about 60 mg/ml, about 25 to about 60 mg/ml, about 30 to about 60 mg/ml, about 25 to about 50 mg/ml, about 40 to about 50 mg/ml, about 25 mg/ml, or about 50 mg/ml. Other compositions, including those discussed above and below, are also contemplated.

Such treatment is expected to reduce one or more signs and/or symptoms associated with rheumatoid arthritis, such as, e.g., inflammation, joint tenderness, joint swelling, pain, and stiffness, in the subject. Such treatment may reduce the further progression of the disease in the patient. For example, such treatment may reduce the progression of structural damage in the patient. Such treatment may improve physical functioning of the subject.

Methods of Inhibiting Tissue, Cell, Graft, or Organ Transplantation Rejection

In another aspect, the invention provides a method of inhibiting rejection of, or suppressing an immune response associated with, a tissue, cell, skin graft, or organ transplant from a donor by a recipient subject, the method comprising administering to the recipient subject a therapeutically effective amount of one or more of the following: (1) a polypeptide of the invention (e.g., mutant CTLA-4-ECD polypeptide or dimeric or monomeric mutant CTLA-4-Ig fusion protein); (2) a multimer comprising one or more polypeptides of the invention (e.g., a dimer comprising any two such polypeptides or a tetramer comprising any four such polypeptides); (3) a conjugate comprising at least one polypeptide of the invention; (4) a nucleic acid of the invention (e.g., a nucleic acid encoding a polypeptide of the invention); (5) a vector comprising a nucleic acid of the invention or encoding a polypeptide of the invention; (6) a cell or population of cells comprising a polypeptide, nucleic acid, conjugate, and/or vector of the invention; and/or (7) a composition of the invention, thereby inhibiting rejection of the tissue, cell, skin graft, or organ transplant by the recipient subject. The donor and recipient may be the same species or different species. The donor or recipient may be a mammal, such as a human, non-human primate (e.g., monkey, gorilla), sheep, cat, dog, pig, cow, horse, etc. In some such methods, the polypeptide, conjugate, vector, and/or cell of the invention is administered to the recipient subject prior to, simultaneously with, or after tissue, cell, skin graft, or organ transplantation. The effective amount typically comprises from about 0.001 mg/kg weight of the subject to about 200 mg/kg body weight of the subject. In some such methods, for example, the effective amount comprises from about 0.001 milligrams per kilogram (mg/kg) weight of the subject to at least about 0.005, 0.01, 0.05, 0.1, 0.2, 0.3, 0.4, 0.5, 0.6, 0.7, 0.8, 0.9, 1, 2, 3, 4, 5, 10, 25, 50, 75, 100, 125, 150, 175, 200, 225, 250, or 300 milligrams per kilogram (mg/kg) body weight of the subject. In some such methods, the effective amount comprises from about 0.001 milligrams per kilogram (mg/kg) weight of the subject to at least about 0.005, 0.01, 0.05, 0.1, 0.2, 0.5, 1, 2, 3, 4, 5, 6, 7, 8, 9, 10, 20, 25, 50, or 75 milligrams per kilogram (mg/kg) body weight of the subject. The polypeptide, conjugate, nucleic acid, vector, and/or cell of the invention may be administered to the recipient subject during, prior to, or immediately after the transplantation. Alternatively or additionally, such molecule of the invention may be administered one or more hours after transplantation, on the day following transplantation, and/or daily thereafter, or at least once per week, at least once every two weeks, or at least one per month after transplantation, as necessary, for up to 12, 24, or 36 or more months or longer as needed. The organ transplant may involve any organ, such as, e.g., a kidney, liver, heart, or lung.

The effective amount or dose of a mutant CTLA-4 molecule of the invention (e.g., mutant CTLA-4-Ig fusion protein dimer) to be administered to an organ, tissue, or cell transplant recipient subject so as to inhibit transplant rejection (or suppress an immune response associated with such transplant) is typically determined based on the potency of such molecule, mode of administration, the type of transplantation (e.g., cell, tissue, organ), the subject's history, and/or the severity of the transplant recipient subject's symptoms or signs of an immune response(s) suggestive of transplant rejection. For example, an effective amount or dose of a mutant CTLA-4-Ig dimer of the invention (e.g., D3-29-IGg2, D3-54-IgG2, D3-56-IgG2, D3-69-IgG2, D3-75-IgG2 dimer, etc.) can be determined by comparing the potency of such dimer with that of the Belatacept dimer. Effective doses of Belatacept useful for preventing or suppressing an immune response associated with kidney/renal transplantation are known. For example, Belatacept is administered by intravenous infusion to a human following kidney transplantation in the human from a kidney donor in an amount or dose of about 5 mg or 10 mg per kilogram body weight of the human per month. A mutant CTLA-4-Ig dimer of the invention that is about "X" times more potent than Belatacept can be administered (e.g., intravenously, subcutaneously, or in another manner described herein) to a human who has had kidney transplant in an amount or dose that is about "X" times less than the Belatacept dose to achieve a therapeutic effect (e.g., suppressing an immune response) approximately equivalent to that of Belatacept. If a greater therapeutic effect is desired, a proportionally increased amount or dose of the CTLA-4-Ig fusion protein dimer of the invention can be determined and administered.

In another aspect, the invention provides a method of treating tissue, cell, or organ transplant rejection (e.g., solid organ transplant rejection (e.g., kidney, liver, lung, heart, etc.)) in a subject who receives such tissue, cell, or organ from a donor, the method comprising administering to the recipient a therapeutically effective amount of at least one polypeptide, conjugate, nucleic acid, vector, and/or cell of the invention, thereby inhibiting rejection of the donor tissue, cell, or organ transplant by the recipient subject. The polypeptide, conjugate, nucleic acid, vector, and/or cell of the invention can be administered to the subject prior to, simultaneously with, or after cell, tissue or organ transplantation.

In one aspect, the invention provides a method of inhibiting rejection of islet cell transplantation from a donor in a recipient subject in need thereof, the method comprising administering to the subject an effective amount or dose of a mutant CTLA-4 molecule of the invention (e.g., mutant CTLA-4-Ig fusion protein) prior to, simultaneously with, or after transplantation of islet cell(s) from the pancreas of a donor into the subject. The subject (e.g., human) typically suffers from diabetes (e.g., IDDM) and such method is useful in treating a subject diagnosed with or suffering from diabetes. Islet transplantation procedures are known in the art. Typically, islets are removed from the pancreas of a deceased organ donor, purified and processed, and implanted into a recipient subject suffering from diabetes. After transplantation, the beta cells in the islets begin to make and release insulin, thereby reducing the recipient subject's need for insulin.

In such methods of inhibiting transplant rejection, the mutant CTLA-4 molecule of the invention (e.g., mutant CTLA-4-Ig) can be formulated with a pharmaceutically acceptable excipient, carrier, or diluent to produce a pharmaceutical composition suitable for administration to a subject (e.g., mammal, including a human). Some such methods comprise administration of a pharmaceutical composition comprising a pharmaceutically acceptable excipient, carrier, or diluent and a mutant CTLA-4-Ig dimer of the invention having a concentration of from about 0.01 mg/ml to about 300 mg/ml or about 0.01 mg/ml to about 200 mg/ml, including, but not limited to, e.g., from about 0.1 mg/ml to about 300 mg/ml, from about 0.1 mg/ml to about 200 mg/ml, about 0.1 mg/ml to about 100 mg/ml, about 0.5 mg/ml to about 100 mg/ml, about 0.5 mg/ml to about 50 mg/ml, about 1 to about 100 mg/ml, about 1 to about 75 mg/ml, about 5 to about 75 mg/ml, about 10 to about 75 mg/ml, about 10 to about 60 mg/ml, about 25 to about 60 mg/ml, about 30 to about 60 mg/ml, about 25 to about 50 mg/ml, about 40 to about 50 mg/ml, about 25 mg/ml, or about 50 mg/ml. Other compositions, including those discussed above and below, are also contemplated.

Methods of Inhibiting an Immune Response

In another aspect, the invention includes the use of a polypeptide (including, e.g., a dimeric or monomeric fusion protein or multimeric polypeptide), conjugate, nucleic acid, vector, or cell of the invention for the manufacture of a medicament for inhibiting or suppressing an immune response in a mammal (e.g., human or non-human primate). Immune responses that may be suppressed include, e.g., T cell activation or proliferation, cytokine synthesis or production, induction of activation markers, synthesis or production of inflammatory molecules, inflammation, anti-collagen Ab production, T cell-dependent Ab response.

The invention also includes the use of a polypeptide (including, e.g., a dimeric or monomeric fusion protein or multimeric polypeptide), conjugate, nucleic acid, vector, or cell of the invention for the manufacture of a medicament for the treatment of an immune system disease or disorder. The immune system disease or disorder may be one that is mediated by interaction of T cells with CD80-positive cells and/or CD86-positive cells in a mammal. The immune system disease or disorder may be an immune system disease or disease, such as a rheumatic disease or disorder or an autoimmune disease or autoimmune disorder. Such immune system disease or disorder may be or involve, e.g., but is not limited to, Addison's Disease, Allergy, Alopecia Areata, Alzheimer's, Antineutrophil cytoplasmic antibodies (ANCA)-associated vasculitis, Ankylosing Spondylitis, Antiphospholipid Syndrome (Hughes Syndrome), arthritis, Asthma, Atherosclerosis, Atherosclerotic plaque, autoimmune disease (e.g., lupus, RA, MS, Graves' disease, etc.), Autoimmune Hemolytic Anemia, Autoimmune Hepatitis, Autoimmune inner ear disease, Autoimmune Lymphoproliferative syndrome, Autoimmune Myocarditis, Autoimmune Oophoritis, Autoimmune Orchitis, Azoospermia, Behcet's Disease, Behcet's syndrome, Berger's Disease, Bullous Pemphigoid, Cardiomyopathy, Cardiovascular disease, Celiac Sprue/Coeliac disease, Chronic Fatigue Immune Dysfunction Syndrome (CFIDS), Chronic idiopathic polyneuritis, Chronic Inflammatory Demyelinating, Polyradicalneuropathy (CIPD), Chronic relapsing polyneuropathy (Guillain-Barré syndrome), Churg-Strauss Syndrome (CSS), Cicatricial Pemphigoid, Cold Agglutinin Disease (CAD), COPD, CREST syndrome, Crohn's Disease, Dermatitis, Herpetiformis, Dermatomyositis, diabetes, Discoid Lupus, Eczema, Epidermolysis bullosa acquisita, Essential Mixed Cryoglobulinemia, Evan's Syndrome, Exopthalmos, Fibromyalgia, Goodpasture's Syndrome, graft-related disease or disorder, Graves' Disease, GVHD, Hashimoto's Thyroiditis, Idiopathic Pulmonary Fibrosis, Idiopathic Thrombocytopenia Purpura (ITP), IgA Nephropathy, immunoproliferative disease or disorder (e.g., psoriasis), Inflammatory bowel disease (IBD), Insulin Dependent Diabetes Mellitus (IDDM), Interstitial lung disease, juvenile diabetes, Juvenile Arthritis, juvenile idiopathic arthritis (JIA), Kawasaki's Disease, Lambert-Eaton Myasthenic Syndrome, Lichen Planus, lupus, Lupus Nephritis, Lymphoscytic Lypophisitis, Ménière's Disease, Miller Fish Syndrome/acute disseminated encephalomyeloradiculopathy, Mixed Connective Tissue Disease, Multiple Sclerosis (MS), muscular rheumatism, Myalgic encephalomyelitis (ME), Myasthenia Gravis, Ocular Inflammation, Pemphigus Foliaceus, Pemphigus Vulgaris, Pernicious Anaemia, Polyarteritis Nodosa, Polychondritis, Polyglandular Syndromes (Whitaker's syndrome), Polymyalgia Rheumatica, Polymyositis, Primary Agammaglobulinemia, Primary Biliary Cirrhosis/Autoimmune cholangiopathy, Psoriasis, Psoriatic arthritis, Raynaud's Phenomenon, Reiter's Syndrome/Reactive arthritis, Restenosis, Rheumatic Fever, rheumatic disease, Rheumatoid Arthritis, Sarcoidosis, Schmidt's syndrome, Scleroderma, Sjörgen's Syndrome, Solid-organ transplant rejection (kidney, heart, liver, lung, etc.), Stiff-Man Syndrome, Systemic Lupus Erythematosus (SLE), systemic scleroderma, Takayasu Arteritis, Temporal Arteritis/Giant Cell Arteritis, Thyroiditis, Type 1 diabetes, Type 2 diabetes, Ulcerative colitis, Uveitis, Vasculitis, Vitiligo, Wegener's Granulomatosis, and preventing or suppressing an immune response associated with rejection of a donor tissue, cell, graft, or organ transplant by a recipient subject.

The invention also provides for the use of a polypeptide, conjugate, nucleic acid, vector, or cell of the invention for the manufacture of a medicament for inhibiting interaction of CD80-positive cells and/or CD86-positive cells with CD28-positive and/or CTLA-4-positive T cells. In another aspect, the invention includes the use of a polypeptide, conjugate, nucleic acid, vector, or cell of the invention for the manufacture of a medicament for the treatment of a tissue or organ transplant rejection (e.g., solid organ transplant rejection (e.g., kidney, lung, liver, heart, etc.)) in a mammal.

Assessing Immune Responses

Immune responses suppressed by a polypeptide, nucleic acid, vector, virus, pseudovirus, VLP, or composition of the invention can be measured by any suitable technique. Examples of useful techniques in assessing humoral immune responses include flow cytometry, immunoblotting assays, immunohistochemistry assays, immunoprecipitation assays, radioimmunoassays (RIA), and enzyme immunoassays. Enzyme immunoassays include enzyme-linked immunoflow assays (ELIFA) and enzyme-linked immunosorbent assays (ELISA), including sandwich ELISA and competitive ELISA assays. HPLC and capillary electrophoresis (CE) also can be utilized in immunoassays to detect complexes of antibodies and target substances. General guidance performing such techniques and related principles are described in, e.g., Harlow and Lane (1988) ANTIBODIES, A LABORATORY MANUAL, Cold Spring Harbor Publications, New York, Hampton R et al. (1990) SEROLOGICAL METHODS A LABORATORY MANUAL, APS Press, St. Paul Minn., Stevens (1995) CLINICAL IMMUNOLOGY AND SEROLOGY: A LABORATORY PERSPECTIVE, CRC press, Bjerrum (1988) HANDBOOK OF IMMUNOBLOTTING OF PROTEINS, Vol. 2, Zoa (1995) DIAGNOSTIC IMMUNOPATHOLOGY: LABORATORY PRACTICE AND CLINICAL APPLICATION, Cambridge University Press, Folds (1998) CLINICAL DIAGNOSTIC IMMUNOLOGY: PROTOCOLS IN QUALITY ASSURANCE AND STANDARDIZATION Blackwell Science Inc., Bryant (1992) LABORATORY IMMUNOLOGY & SEROLOGY 3rd edition, W B Saunders Co., and Maddox D E et al. (1983) J. Exp. Med. 158:1211. Guidance with respect to ELISA techniques and related principles are described in, e.g., Reen (1994) Methods Mol. Biol. 32:461-6, Goldberg et al. (1993) Curr. Opin. Immunol. 5(2):278-81, Voller et al. (1982) Lab. Res. Methods Biol. Med. 5:59-81, Yolken et al. (1983) Ann. NY Acad. Sci. 420:381-90, Vaughn et al. (1999) Am. J. Trop. Med. Hyg. 60(4):693-8, and Kuno et al. (1991) J. Virol. Methods 33(1-2):101-13. Guidance with respect to flow cytometry techniques is provided in, e.g., Diamond (2000) IN LIVING COLOR: PROTOCOLS IN FLOW CYTOMETRY AND CELL SORTING, Springer Verlag, Jaroszeki (1998) FLOW CYTOMETRY PROTOCOLS, 1st Ed., Shapiro (1995) PRACTICAL FLOW CYTOMETRY, 3rd edition, Rieseberg et al. (2001) Appl. Microbiol. Biotechnol. 56(3-4):350-60, Scheffold and Kern (2000) J. Clin. Immunol. 20(6):400-7, and McSharry (1994) Clin. Microbiol. Rev. (4): 576-604.

Cytotoxic and other T cell immune responses also can be measured by any suitable technique. Examples of such techniques include ELISpot assay (particularly, IFN-gamma ELISpot), intracellular cytokine staining (ICC) (particularly in combination with FACS analysis), CD8+ T cell tetramer staining/FACS, standard and modified T cell proliferation assays, chromium release CTL assay, limiting dilution analysis (LDA), and CTL killing assays. Guidance and principles related to T cell proliferation assays are described in, e.g., Plebanski and Burtles (1994) J. Immunol. Meth. 170:15, Sprent et al. (2000) Philos. Trans. R. Soc. Lond. B Biol. Sci. 355(1395):317-22 and Messele et al. (2000) Clin. Diagn. Lab. Immunol. 7(4):687-92. LDA is described in, e.g., Sharrock et al. (1990) Immunol. Today 11:281-286. ELISpot assays and related principles are described in, e.g., Czerinsky et al. (1988) J. Immunol. Meth. 110:29-36, Olsson et al. (1990) J. Clin. Invest. 86:981-985, Schmittel et al. (2001) J. Immunol. Meth. 247(1-2):17-24, Ogg and McMichael (1999) Immunol. Lett. 66(1-3):77-80, Schmittel et al. (2001) J. Immunol. Meth. 247(1-2):17-24, Kurane et al. (1989) J. Exp. Med. 170(3):763-75, Chain et al. (1987) J. Immunol. Meth. 99(2):

221-8, Czerkinsky et al. (1988) J. Immunol. Meth. 110:29-36, and U.S. Pat. Nos. 5,750,356 and 6,218,132. Tetramer assays are discussed in, e.g., Skinner et al. (2000) J. Immunol. 165 (2):613-7. Other T cell analytical techniques are described in Hartel et al. (1999) Scand. J. Immunol. 49(6):649-54 and Parish et al. (1983) J. Immunol. Meth. 58(1-2):225-37.

T cell activation also can be analyzed by measuring CTL activity or expression of activation antigens such as IL-2 receptor, CD69 or HLA-DR molecules. Proliferation of purified T cells can be measured in a mixed lymphocyte reaction (MLR) assay; such assays are well-known in the art.

ELISpot assays measure the number of T-cells secreting a specific cytokine, such as IFN-γ or TNF-α, which serves as a marker of T-cell effectors. Cytokine-specific ELISA kits are commercially available (e.g., an IFN-γ-specific ELISPot is available through R&D Systems, Minneapolis, Minn.).

Additional methods for assessing and measuring the ability of molecules of the invention (e.g., polypeptides of the invention, including, e.g., soluble mutant CTLA-4-Ig fusion proteins of the invention) to suppress or inhibit T cell activation and/or T cell proliferation are described in Examples 5-8 in the Examples section below.

Methods of Administration

In any of the methods described herein, an injectable pharmaceutical composition comprising a suitable pharmaceutically acceptable excipient or carrier (e.g., PBS) and an effective amount of a molecule of the invention, such as a polypeptide (e.g., mutant CTLA-4 ECD or monomeric, dimeric, or multimeric mutant CTLA-4-Ig) or conjugate of the invention, can be administered parenterally, intramuscularly, intraperitoneally, intravenously, subdermally, transdermally, subcutaneously, or intradermally to a host. Alternatively, biolistic protein delivery techniques (vaccine gun delivery) can be used (examples of which are discussed elsewhere herein). Any other suitable technique also can be used. Polypeptide administration can be facilitated via liposomes. Any such delivery technique can be used to deliver a polypeptide or conjugate of the invention in conjunction with any therapeutic or prophylactic method described herein.

While the following discussion is primarily directed to nucleic acids, it will be understood that it applies equally to nucleic acid vectors of the invention. A nucleic acid of the invention or composition thereof can be administered to a host by any suitable administration route. In some aspects of the invention, administration of the nucleic acid is parenteral (e.g., subcutaneous (s.c.), intramuscular (i.m.), or intradermal (i.d.)), topical, or transdermal. The nucleic acid can be introduced directly into a tissue, such as muscle, by injection using a needle or other similar device. See, e.g., Nabel et al. (1990), supra; Wolff et al. (1990) Science 247:1465-1468), Robbins (1996) Gene Therapy Protocols, Humana Press, NJ, and Joyner (1993) Gene Targeting: A Practical Approach, IRL Press, Oxford, England, and U.S. Pat. Nos. 5,580,859 and 5,589,466. Other methods such as "biolistic" or particle-mediated transformation (see, e.g., U.S. Pat. Nos. 4,945,050 and 5,036,006, Sanford et al., J. Particulate Sci. Tech. 5:27-37 (1987), Yang et al., Proc. Natl. Acad. Sci. USA 87:9568-72 (1990), and Williams et al., Proc. Natl. Acad. Sci. USA 88:2726-30 (1991)). These methods are useful not only for in vivo introduction of DNA into a subject, such as a mammal, but also for ex vivo modification of cells for reintroduction into a mammal (which is discussed further elsewhere herein).

For standard gene gun administration, the vector or nucleic acid of interest is precipitated onto the surface of microscopic metal beads. The microprojectiles are accelerated with a shock wave or expanding helium gas, and penetrate tissues to a depth of several cell layers. For example, the Accel™ Gene Delivery Device manufactured by Agacetus, Inc. Middleton Wis. is suitable for use in this embodiment. The nucleic acid or vector can be administered by such techniques, e.g., intramuscularly, intradermally, subdermally, subcutaneously, and/or intraperitoneally. Additional devices and techniques related to biolistic delivery Int'l Patent Appn. Publ. Nos. WO 99/2796, WO 99/08689, WO 99/04009, and WO 98/10750, and U.S. Pat. Nos. 5,525,510, 5,630,796, 5,865,796, and 6,010,478.

The nucleic acid can be administered in association with a transfection-facilitating agent, examples of which were discussed above. The nucleic acid can be administered topically and/or by liquid particle delivery (in contrast to solid particle biolistic delivery). Examples of such nucleic acid delivery techniques, compositions, and additional constructs that can be suitable as delivery vehicles for the nucleic acids of the invention are provided in, e.g., U.S. Pat. Nos. 5,591,601, 5,593,972, 5,679,647, 5,697,901, 5,698,436, 5,739,118, 5,770,580, 5,792,751, 5,804,566, 5,811,406, 5,817,637, 5,830,876, 5,830,877, 5,846,949, 5,849,719, 5,880,103, 5,922,687, 5,981,505, 6,087,341, 6,107,095, 6,110,898, and Int'l Pat. Appn. Publ. Nos. WO 98/06863, WO 98/55495, and WO 99/57275.

Alternatively, the nucleic acid can be administered to the host by way of liposome-based gene delivery. Exemplary techniques and principles related to liposome-based gene delivery is provided in, e.g., Debs and Zhu (1993) WO 93/24640; Mannino and Gould-Fogerite (1988) BioTechniques 6(7):682-691; Rose U.S. Pat. No. 5,279,833; Brigham (1991) WO 91/06309; Brigham et al. (1989) Am. J. Med. Sci. 298:278-281; Nabel et al. (1990) Science 249:1285-1288; Hazinski et al. (1991) Am. J. Resp. Cell Molec. Biol. 4:206-209; and Wang and Huang (1987) Proc. Natl. Acad. Sci. USA 84:7851-7855), and Felgner et al. (1987) Proc. Natl. Acad. Sci. USA 84:7413-7414). Suitable liposome pharmaceutically acceptable compositions that can be used to deliver the nucleic acid are further described elsewhere herein.

Any amount of nucleic acid of the invention can be used in the methods of the invention. For example, sufficient nucleic acid may be formulated in a pharmaceutically acceptable excipient or carrier and administered to a subject such that the encoded polypeptide or conjugate is produced in the subject in an amount believed effective to, for example, suppress immune response in the subject, inhibit interaction between endogenous B7-positive cells and CD28-positive cells in the subject, or inhibit rejection of a tissue, cell, organ, or graft transplant. In one format, where the nucleic acid is administered by injection, about 50 micrograms (μg) to 100 mg nucleic acid is administered. In one exemplary application, to suppress an immune response, a pharmaceutical composition comprising PBS and an amount of a DNA vector that encodes an effective amount of a mutant CTLA-4 polypeptide is administered by injection or electroporation or other suitable delivery method (e.g., gene gun, impressing through the skin, and lipofection) to a subject in need of treatment (e.g., a subject suffering from an immune system disease or disorder in which immunosuppressive treatment is desirable). An exemplary vector is shown in FIG. 1.

The amount of DNA plasmid for use in the methods of the invention where administration is via a gene gun, e.g., is often from about 100 to about 1000 times less than the amount used for direct injection (e.g., via standard needle injection). Despite such sensitivity, at least about 1 μg of the nucleic acid may be used in such biolistic delivery techniques.

RNA or DNA viral vector systems can be useful for delivery nucleic acids encoding polypeptides of the invention. Viral vectors can be administered directly to a subject in vivo or they can be used to treat cells in vitro and the modified cells are administered to the subject in an ex vivo format. Useful viral vectors include those discussed above, such as adeno-associated, adenoviral, retroviral, lentivirus, and herpes simplex virus vectors. With such viral vectors, a nucleic acid of the invention can be readily transferred into target cells and tissues of the subject. Additionally, with the retrovirus, lentivirus, and adeno-associated virus gene transfer methods, a nucleic acid of the invention can be integrated into the host genome may be possible, thereby resulting in continuing expression of the inserted nucleic acid.

Delivery of a viral vector of the invention comprising at least one nucleic acid of the invention to a subject is believed capable of suppressing an immune response in the subject to whom the vector is administered. Optionally, some prophylactic and/or therapeutic methods of the invention are practiced with a dosage of a suitable viral vector sufficient to inhibit a detectable immune response. Any suitable viral vector comprising a nucleic acid of the invention, in any suitable concentration, can be used to suppress the immune response. For example, to the subject host can be administered a population of retroviral vectors (examples of which are described in, e.g., Buchscher et al. (1992) J. Virol. 66(5) 2731-2739, Johann et al. (1992) J. Virol. 66 (5):1635-1640 (1992), Sommerfelt et al., (1990) Virol. 176:58-59, Wilson et al. (1989) J. Virol. 63:2374-2378, Miller et al., J. Virol. 65:2220-2224 (1991), Wong-Staal et al., PCT/US94/05700, Rosenburg and Fauci (1993) in FUNDAMENTAL IMMUNOLOGY, THIRD EDITION Paul (ed.) Raven Press, Ltd., New York and the references therein), an AAV vector (as described in, e.g., West et al. (1987) Virology 160:38-47, Kotin (1994) Human Gene Therapy 5:793-801, Muzyczka (1994) J. Clin. Invest. 94:1351, Tratschin et al. (1985) Mol. Cell. Biol. 5(11):3251-3260, U.S. Pat. Nos. 4,797,368 and 5,173,414, and Int'l Patent Appn Publ. No. WO 93/24641), or an adenoviral vector (as described in, e.g., Berns et al. (1995) Ann. NY Acad. Sci. 772:95-104; Ali et al. (1994) Gene Ther. 1:367-384; and Haddada et al. (1995) Curr. Top. Microbiol. Immunol. 199 (Pt 3):297-306), such that immunosuppressive levels of expression of the nucleic acid included in the vector result, thereby resulting in the desired immunosuppressive response. Other suitable types of viral vectors are described elsewhere herein (including alternative examples of suitable retroviral, AAV, and adenoviral vectors).

Suitable infection conditions for these and other types of viral vector particles are described in, e.g., Bachrach et al., J. Virol., 74(18), 8480-6 (2000), Mackay et al., J. Virol., 19(2), 620-36 (1976), and FIELDS VIROLOGY, supra. Additional techniques useful in the production and application of viral vectors are provided in, e.g., "Practical Molecular Virology: Viral Vectors for Gene Expression" in METHODS IN MOLECULAR BIOLOGY, vol. 8, Collins, M. Ed., (Humana Press 1991), VIRAL VECTORS: BASIC SCIENCE AND GENE THERAPY, 1st Ed. (Cid-Arregui et al., Eds.) (Eaton Publishing 2000), "Viral Expression Vectors," in CURRENT TOPICS IN MICROBIOLOGY AND IMMUNOLOGY, Oldstone et al., Eds. (Springer-Verlag, NY, 1992), and "Viral Vectors" in CURRENT COMMUNICATIONS IN BIOTECHNOLOGY, Gluzman and Hughes, eds. (Cold Spring Harbor Laboratory Press, 1988).

The toxicity and therapeutic efficacy of vectors or viruses that include one or more molecules of the invention are determined using standard pharmaceutical procedures in cell cultures or experimental animals. One can determine the $MLD_{50}$ (the minimum dose lethal to 50% of the population) and/or the $ED_{50}$ (the dose therapeutically effective in 50% of the population) using procedures presented herein and those otherwise known in the art. See also S. Plotkin and W. Orenstein, VACCINES (W. B. Saunders Co. 1999 3d ed.) for suggested doses for known viral vaccines. Nucleic acids, polypeptides, proteins, fusion proteins, transduced cells and other formulations of the present invention can be administered in an amount determined, e.g., by the $MLD_{50}$ of the formulation, and the side-effects thereof at various concentrations, as applied to the mass and overall health of the patient. Thus, for example, the invention provides a method of inducing an immune response by administering a dose equal or greater to the $ED_{50}$ of a pharmaceutically acceptable composition comprising a population of virus-like particles or viruses (e.g., attenuated or replication-deficient virus) that comprises a polypeptide or nucleic acid of the invention. Administration can be accomplished via single dose or divided doses (either by co-administration, serial administration, or combinations thereof). Administration techniques and protocols are described in, e.g., Plotkin (VACCINES) supra and other references cited herein. In a related sense, techniques for assessing dosage of the nucleic acid, polypeptide, vector, and cell compositions effective for inducing immunity are described in, e.g., European Patent Appn No. 1 156 333 and references cited therein.

The viral vector can be targeted to particular tissues, cells, and/or organs of a subject, e.g., mammal. Examples of such vectors are described above. For example, the viral vector or nucleic acid vector can be used to selectively deliver the nucleic acid sequence of the invention to monocytes, dendritic cells, cells associated with dendritic cells (e.g., keratinocytes associated with Langerhans cells), T-cells, and/or B-cells. The viral vector can be a replication-deficient viral vector. The viral vector particle also can be modified to reduce host immune response to the viral vector, thereby achieving persistent gene expression. Such "stealth" vectors are described in, e.g., Martin, Exp. Mol. Pathol. 66(1):3-7 (1999), Croyle et al., J. Virol. 75(10):4792-801 (2001), Rollins et al., Hum. Gene Ther. 7(5):619-26 (1996), Ikeda et al., J. Virol. 74(10):4765-75 (2000), Halbert et al., J. Virol. 74(3):1524-32 (2000), and Int'l Patent Appn Publ. No. WO 98/40509. Alternatively or additionally, the viral vector particles can be administered by a strategy selected to reduce host immune response to the vector particles. Strategies for reducing immune response to the viral vector particle upon administration to a host are provided in, e.g., Maione et al., Proc. Natl. Acad. Sci. USA 98(11):5986-91 (2001), Morral et al., Proc. Natl. Acad. Sci. USA 96(22):2816-21 (1999), Pastore et al., Hum. Gene Ther. 10(11):1773-81 (1999), Morsy et al., Proc. Natl. Acad. Sci. USA 95(14):7866-71 (1998), Joos et al., Hum. Gene Ther. 7(13):1555-66 (1996), Kass-Eisler et al., Gene Ther. 3(2):154-62 (1996), U.S. Pat. Nos. 6,093,699, 6,211,160, 6,225,113, U.S. Patent Application Publ. No. 2001-0066947A1.

The skin and muscle are generally preferred targets for administration of the polypeptides, conjugates, nucleic acids, and vectors of the invention, by any suitable technique. Thus, the delivery of a polypeptide, conjugate, nucleic acid, or vector of the invention into or through the skin of a subject (e.g., mammal), is a feature of the invention. Such molecules of the invention can be administered in a pharmaceutically acceptable injectable solution into or through the skin, e.g., intramuscularly, or intraperitoneally. Administration can also be accomplished by transdermal devices, or, more typically, biolistic delivery of the polypeptide, conjugate, nucleic acid, and/or vector to, into, or through the skin of the subject or into exposed muscle of the subject. Transdermal devices provided by the invention, described elsewhere herein, for example, can be applied to the skin of a host for a suitable period such that sufficient transfer of a polynucleotide and/or vector to the subject occurs, thereby suppressing an immune response in the subject or inhibiting rejection of a graft, cell, or tissue transplant. Muscular administration is more typically facilitated by injection of a liquid solution comprising a polypeptide, polynucleotide, or vector of the invention. Particular cells that can be targeted include dendritic cells, other APCs, B cells, monocytes, T cells (including T helper cells), and cells associated with such immune system cells (e.g., keratinocytes or other skin cells associated with Langerhans cells). Targeting of vectors and nucleic acids of the invention is described elsewhere herein. Such targeted administration can be performed with nucleic acids or vectors comprising nucleic acids operably linked to cell and/or tissue-specific promoters, examples of which are known in the art.

The polynucleotide of the invention can be administered by any suitable delivery system, such that expression of a recombinant polypeptide occurs in the host resulting in an suppression of an immune response, inhibition of interaction between B7-positive cells and CD28-positive, or inhibition of tissue, cell, organ, or graft transplant rejection. For example, an effective amount of a population of bacterial cells comprising a nucleic acid of the invention can be administered to a subject, resulting in expression of a recombinant mutant CTLA-4 polypeptide of the invention, and suppression of an immune response in the subject. Bacterial cells developed for mammalian gene delivery are known in the art.

Administration of a polynucleotide or vector of the invention to a subject is facilitated by application of electroporation to an effective number of cells or an effective tissue target, such that the nucleic acid and/or vector is taken up by the cells, and expressed therein, resulting in production of a recombinant polypeptide of the invention therein and subsequent suppression of an immune response in the subject.

Production and Purification Methods

The invention further provides methods of making and purifying the polypeptides, nucleic acids, vectors, and cells of the invention. In one aspect, the invention provides a method of making a recombinant polypeptide of the invention by introducing a nucleic acid of the invention into a population of cells in a culture medium, culturing the cells in the medium (for a time and under conditions suitable for desired level of gene expression) to produce the polypeptide, and isolating the polypeptide from the cells, culture medium, or both. The nucleic acid is typically operatively linked to a regulatory sequence effective to express the polypeptide encoded by the nucleic acid.

The polypeptide can be isolated from cell lysates, cell supernatants, and/or cell culture medium a variety of suitable techniques known in the art, including, e.g., various chromatography of cell lysates and/or cell supernatants. For example, the polypeptide can be isolated from cell lysates and/or cell culture medium by first concentrating the culture medium using centrifugal filters (Amicon), alternatively, by precipitating the polypeptides with ammonium sulfate or polyethylene glycol and then resuspending the polypeptides in PBS or other suitable buffers. The polypeptide can then be purified using either size-exclusion chromatography on Sephacryl S-400 column (Amersham Biosciences) as described in, e.g., Hjorth, R. and J. Moreno-Lopez, J. Virol. Methods 5:151-158 (1982), or another affinity chromatography, or by centrifugation through 20-60% sucrose gradients as described in, e.g., Konish et al., Virology 188:714-720 (1992). Fractions containing the desired polypeptides can be identified by ELISA or SDS-PAGE followed by protein silver stain and immunoblotting. The desired fractions are pooled and further concentrated. Sucrose in gradient centrifugation fractions can be removed using PD-10 column (Amersham Biosciences) gel filtration. Additional purification techniques include those described in the Examples below and hydrophobic interaction chromatography (Diogo, M. M, et al., J. Gene Med. 3:577-584 (2001)), and any other suitable technique known in the art.

Any suitable purification technique that is known in the art can also be used. Polypeptide purification methods known in the art include those set forth in, e.g., Sandana (1997) BIO-SEPARATION OF PROTEINS, Academic Press, Inc., Bollag et al. (1996) PROTEIN METHODS, 2$^{nd}$ Edition Wiley-Liss, NY, Walker (1996) THE PROTEIN PROTOCOLS HANDBOOK Humana Press, NJ, Harris and Angal (1990) PROTEIN PURIFICATION APPLICATIONS: A PRACTICAL APPROACH IRL Press at Oxford, Oxford, England, Scopes (1993) PROTEIN PURIFICATION: PRINCIPLES AND PRACTICE 3$^{rd}$ Edition Springer Verlag, NY, Janson and Ryden (1998) PROTEIN PURIFICATION: PRINCIPLES, HIGH RESOLUTION METHODS AND APPLICATIONS, Second Edition Wiley-VCH, NY; and Walker (1998) PROTEIN PROTOCOLS ON CD-ROM Humana Press, NJ. Cells suitable for polypeptide production are known in the art and are discussed elsewhere herein (e.g., Vero cells, 293 cells, BHK, CHO (e.g., CHO-K1), and COS cells can be suitable). Cells can be lysed by any suitable technique including, e.g., sonication, microfluidization, physical shear, French press lysis, or detergent-based lysis.

In one aspect, the invention provides a method of purifying a polypeptide of the invention, which comprises transforming a suitable host cell with a nucleic acid of the invention (e.g., a recombinant nucleic acid that encodes a recombinant polypeptide comprising the polypeptide sequence of SEQ ID NO:1) in the host cell (e.g., a CHO cell or 293 cell), lysing the cell by a suitable lysis technique (e.g., sonication, detergent lysis, or other appropriate technique), and subjecting the lysate to affinity purification with a chromatography column comprising a resin that includes at least one novel antibody of the invention (usually a monoclonal antibody of the invention) or antigen-binding fragment thereof, such that the lysate is enriched for the desired polypeptide (e.g., a polypeptide comprising the polypeptide sequence of SEQ ID NO:1).

In another aspect, the invention provides a method of purifying such target polypeptides, which method differs from the above-described method in that a nucleic acid comprising a nucleotide sequence encoding a fusion protein that comprises a polypeptide of the invention (e.g., SEQ ID NO:1) and a suitable tag (e.g., an e-epitope/his tag), and purifying the polypeptide by immunoaffinity, lentil-lectin affinity column chromatography, immobilized metal affinity chromatography (IMAC), or metal-chelating affinity chromatography (MCAC) enrichment techniques. Additional purification methods are disclosed elsewhere herein.

In another aspect, the invention provides a method of producing a polypeptide of the invention, which method comprises introducing into a population of cells a recombinant expression vector comprising a nucleic acid of the invention, culturing the cells in a culture medium under appropriately sufficient conditions for expression of the nucleic acid from the vector and production of the polypeptide encoded by the nucleic acid, and isolating the polypeptide from the cells, culture medium, or both. The cells chosen are based on the desired processing of the polypeptide and based on the appropriate vector (e.g., E. coli cells are preferred for bacterial plasmids, whereas 293 cells are preferred for mammalian shuttle plasmids and/or adenoviruses, particularly E1-deficient adenoviruses).

In yet another aspect, the invention includes a method of producing a polypeptide, the method comprising: (a) introducing into a population of cells a recombinant expression vector comprising at least one nucleic acid of the invention the encodes a polypeptide of the invention; (b) administering the expression vector into a mammal; and (c) isolating the polypeptide from the mammal or from a byproduct of the mammal.

A polypeptide of the invention can also be produced by culturing a cell or population of cells of the invention (which, e.g., have been transformed with a nucleic acid of the invention that encodes such polypeptide) under conditions sufficient for expression of the polypeptide and recovering the polypeptide expressed in or by the cell using standard techniques known in the art.

In another aspect, the invention provides a method of producing a polypeptide of the invention, which comprises (a) introducing into a population of cells a nucleic acid of the invention, wherein the nucleic acid is operatively linked to a regulatory sequence effective to produce the polypeptide encoded by the nucleic acid; (b) culturing the cells in a culture medium to produce the polypeptide; and (c) isolating the polypeptide from the cells or culture medium. Also included is a cultured cell into which has been introduced a vector of the invention (e.g., an expression vector of the invention).

Also included is a method of producing a polypeptide of the invention which comprises introducing a nucleic acid encoding said polypeptide into a population of cells in a medium, which cells are permissive for expression of the nucleic acid, maintaining the cells under conditions in which the nucleic acid is expressed, and thereafter isolating the polypeptide from the medium.

In another aspect, the invention provides a method of making a fusion protein. The method comprises: (1) culturing a host cell transformed with a nucleic acid in a culture medium, wherein the nucleic acid comprises: (i) a first nucleotide sequence that encodes a polypeptide having at least 95% identity to a polypeptide sequence selected from the group consisting of SEQ ID NOS:1-73, which polypeptide binds CD86 and/or CD80, and/or an extracellular domain of either CD86 or CD80, and (ii) a second nucleotide sequence encoding an Ig Fc polypeptide comprising a hinge region, CH2 domain, and CH3 domain, whereby the nucleic acid is expressed and a fusion protein is produced; and (2) recovering the fusion protein. Any Ig Fc polypeptide may be any employed, including e.g., an IgG1 Fc, IgG2 Fc, IgG4 Fc, or mutant Ig Fc polypeptide. In some such methods, the nucleic acid further comprises a third nucleotide sequence that encodes a secretory or signal peptide operably linked to the fusion protein, and the fusion protein is secreted from the host cell as a disulfide-bonded fusion protein dimer comprising identical first and second fusion proteins, and the disulfide-bonded fusion protein dimer is recovered from the culture medium. In some such methods, the disulfide-bonded fusion protein dimer is formed via a covalent disulfide bond between a cysteine residue of the first fusion protein and a cysteine residue of the second fusion protein. In some such methods, the fusion protein is recovered from the culture medium, host cell, or host cell periplasm.

In another aspect, the invention provides an isolated or recombinant nucleic acid molecule comprising a nucleotide sequence which encodes (i) a first polypeptide comprising a polypeptide sequence having at least 95% sequence identity to at least one polypeptide sequence selected from the group consisting of SEQ ID NOS:1-73, wherein the first polypeptide binds CD80 and/or CD86 and/or an extracellular domain of either or both, and (ii) a second polypeptide comprising a comprising a hinge region, CH2 domain, and CH3 domain of an IgG polypeptide. The second polypeptide may comprise any suitable Ig polypeptide discussed elsewhere herein, including, e.g., that comprising the polypeptide sequence of SEQ ID NO:184 or SEQ ID NO:218.

In another aspect, the invention provides a method of making a soluble fusion protein dimer. The method comprises culturing a host cell transformed with an expression vector comprising a nucleotide sequence that encodes a soluble fusion protein dimer of the invention. Exemplary fusion proteins include those comprising the polypeptide sequence of any of SEQ ID NOS:74-79, 197-200, 205-214, and 219-222. The vector includes a nucleotide sequence that facilitates expression of the fusion protein (e.g., a nucleotide sequence encoding a signal peptide). The fusion protein is secreted from the host cell as a disulfide-bonded fusion protein dimer comprising two identical fusion proteins, and the disulfide-bonded fusion protein dimer is recovered from the culture medium. In some such methods, the disulfide-bonded fusion protein dimer is formed via a covalent disulfide bond between a cysteine residue on each fusion protein. The fusion protein dimer is typically recovered from the culture medium, host cell, or host cell periplasm. Example 12 provides an exemplary procedure for creating a stably transfected cell line expressing a mutant CTLA4-Ig fusion protein of the invention, producing the mutant CTLA4-Ig fusion protein, and the purifying the mutant fusion protein from culture.

In addition to recombinant production, the polypeptides of the invention may be produced by direct peptide synthesis using solid-phase techniques (see, e.g., Stewart et al. (1969) SOLID-PHASE PEPTIDE SYNTHESIS, W.H. Freeman Co, San Francisco and Merrifield J. (1963) J. Am. Chem. Soc. 85:2149-2154). Peptide synthesis may be performed using manual techniques or by automation. Automated synthesis may be achieved, for example, using Applied Biosystems 431A Peptide Synthesizer (Perkin Elmer, Foster City, Calif.) in accordance with the instructions provided by the manufacturer. For example, subsequences may be chemically synthesized separately and combined using chemical methods to produce a polypeptide of the invention or fragments thereof. Alternatively, synthesized polypeptides may be ordered from any number of companies that specialize in production of polypeptides. Most commonly, polypeptides of the invention are produced by expressing coding nucleic acids and recovering polypeptides, e.g., as described above.

The invention includes a method of producing a polypeptide of the invention comprising introducing a nucleic acid of the invention, a vector of the invention, or a combination thereof, into an animal, such as a mammal (including, e.g., rat, nonhuman primate, bat, marmoset, pig, or chicken), such that a polypeptide of the invention is expressed in the animal, and the polypeptide is isolated from the animal or from a byproduct of the animal. Isolation of the polypeptide from the animal or animal byproduct can be by any suitable technique, depending on the animal and desired recovery strategy. For example, the polypeptide can be recovered from sera of mice, monkeys, or pigs expressing the polypeptide of the invention. Transgenic animals (including the aforementioned mammals) comprising at least one nucleic acid of the invention are provided by the invention. The transgenic animal can have the nucleic acid integrated into its host genome (e.g., by an AAV vector, lentiviral vector, biolistic techniques performed with integration-promoting sequences, etc.) or can have the nucleic acid in maintained epichromosomally (e.g., in a non-integrating plasmid vector or by insertion in a non-integrating viral vector). Epichromosomal vectors can be engineered for more transient gene expression than integrating vectors. RNA-based vectors offer particular advantages in this respect.

Compositions

The invention further provides novel and useful compositions comprising at least one component of the invention, such as, e.g., at least one polypeptide (including, e.g., fusion proteins and multimeric polypeptides), conjugate, nucleic acid, vector, virus, virus-like particle (VLP), and/or cell of the invention, or any combination thereof and a carrier, excipient, or diluent. The carrier, excipient or diluent may be a pharmaceutically acceptable carrier, excipient, or diluent. Such a composition can comprise any suitable amount of any suitable number of polypeptides, conjugates, nucleic acids, vectors, viruses, VLPs, and/or cells of the invention. Also provided are pharmaceutical compositions comprising at least one polypeptide, conjugate, nucleic acid, vector, virus, VLP, and/or cell, or any combination thereof, and a pharmaceutically acceptable carrier, excipient, or diluent. Such compositions are useful in the methods of the invention described herein, including, e.g., methods of suppressing immune responses.

For example, in one non-limiting embodiment, the invention provides a composition comprising an excipient, diluent, or carrier and at least one such polypeptide of the invention (e.g., 1, 2, 3, 4, 5, 6, 7, 8, 9, 10 or more polypeptides), such as a mutant CTLA-4 ECD polypeptide (e.g., any of SEQ ID NOS:1-73) or mutant CTLA-4-Ig fusion protein (e.g., any of SEQ ID NOS:74-79, 197-200, 205-214, and 219-222), wherein the at least one polypeptide is present in the composition in an amount effective to suppress an immune response, including, e.g., an immune response(s) involved in transplant rejection and/or autoimmunity, inhibit rejection of a donated tissue, cell, or organ transplant, or inhibit interaction of endogenous B7-positive cells with CD28-positive T cells in a subject to whom the composition is administered.

Also included is a pharmaceutical composition comprising a pharmaceutically acceptable excipient, diluent, or carrier and an effective amount of one or more such components of the invention. The effective amount may be a therapeutically or prophylactically effective amount or dose for use in a therapeutic or prophylactic method described elsewhere herein, such as a method of treating an autoimmune disease or a method of inhibiting rejection of a tissue, cell, graft, or organ transplant from a donor by a recipient subject.

The composition (or pharmaceutical composition) can be any non-toxic composition that does not interfere with the immunosuppressive properties of the polypeptide, conjugate, nucleic acid, vector, virus, VLP, or cell of the invention included therein. The composition can comprise one or more excipients, diluents, or carriers, and the pharmaceutical composition comprises one or more pharmaceutically acceptable excipients, diluents, or carriers. A wide variety of acceptable carriers, diluents, and excipients are known in the art and can be included in the compositions and pharmaceutical compositions of the invention. For example, a variety of aqueous carriers can be used, e.g., distilled or purified water, sterile saline, buffered saline, such as phosphate-buffered saline (PBS), and the like are advantageous in injectable formulations of the polypeptide, fusion proteins, conjugate, nucleic acid, vector, virus, VLP, and/or cell of the invention. Numerous suitable excipients, carriers, and diluents for administration of therapeutic proteins are known in the art. Such solutions are preferably sterile and generally free of undesirable matter. Compositions may be sterilized by conventional, well-known sterilization techniques. Compositions of the invention may comprise pharmaceutically acceptable auxiliary substances, as required, to approximate physiological conditions. Such substances include, e.g., pH adjusting agents, buffering agents, and tonicity adjusting agents, including, e.g., sodium acetate, sodium ascorbate, sodium chloride, potassium chloride, calcium chloride, sodium lactate, and the like. Compositions of the invention, including pharmaceutical compositions, can also include one or more components, such as diluents, fillers, salts, buffers, surfactants, emulsifiers, detergents (e.g., a nonionic detergent or emulsifier, such as Tween®-20, Tween®-40, Tween®-60, Tween®-80, pluronic F-68, and the like), stabilizers (e.g., sugars or protein-free amino acids), preservatives, tissue fixatives, solubilizers, and/or other materials, suitable for inclusion in a pharmaceutically composition.

Examples of suitable components that may be used in the pharmaceutical composition are described in, e.g., Berge et al., J. Pharm. Sci. 66(1):1-19 (1977), Wang and Hanson, J. Parenteral. Sci. Tech. 42:S4-S6 (1988), U.S. Pat. Nos. 6,165,779 and 6,225,289, and elsewhere herein. Pharmaceutical compositions also can include preservatives (such as benzyl alcohol, sodium azide, m-cresol, etc.), antioxidants, metal chelators (such as methionine, EDTA, etc.), and/or other additives known to those of skill in the art. Examples of suitable pharmaceutically acceptable carriers for use in the pharmaceutical compositions are described in, e.g., Urquhart et al., Lancet 16:367 (1980), Lieberman et al., PHARMACEUTICAL DOSAGE FORMS—DISPERSE SYSTEMS (2nd ed., Vol. 3, 1998), Ansel et al., PHARMACEUTICAL DOSAGE FORMS & DRUG DELIVERY SYSTEMS (7th ed. 2000), Martindale, THE EXTRA PHARMACOPEIA (31st edition), Remington's PHARMACEUTICAL SCIENCES (16th-20th editions), THE PHARMACOLOGICAL BASIS OF THERAPEUTICS, Goodman and Gilman, Eds. (9th ed.—1996), WILSON AND GISVOLDS TEXTBOOK OF ORGANIC MEDICINAL AND PHARMACEUTICAL CHEMISTRY, Delgado and Remers, Eds. (10th ed.—1998), and U.S. Pat. Nos. 5,708,025 and 5,994,106. Principles of formulating pharmaceutically acceptable compositions are described in, e.g., Platt, Clin. Lab Med. 7:289-99 (1987), Aulton, PHARMACEUTICS: THE SCIENCE OF DOSAGE FORM DESIGN, Churchill Livingstone (New York) (1988), EXTEMPORANEOUS ORAL LIQUID DOSAGE PREPARATIONS, CSHP (1998), and "Drug Dosage," J. Kans. Med. Soc. 70(1):30-32 (1969). Additional pharmaceutically acceptable carriers particularly suitable for administration of vectors are described in, e.g., Int'l Patent Appn Publ. No. WO 98/32859.

Compositions of the invention, including pharmaceutical compositions, can include one or more aqueous carriers or excipients (including, e.g., pharmaceutically acceptable carriers or excipients) and one or more components, such as one or more buffers, one or more salts, one or more detergents or emulsifiers, and/or one or more sugars. The buffer system is typically one suitable to maintain the pH of the composition within a range which is conducive to the stability of the molecule of the invention present in the composition (e.g., mutant CTLA-4-Ig). Exemplary buffers for use in the composition include, but are not limited to, e.g., N-2-hydroxyethylpiperazine-N'-2-aminoethane sulfonic acid (HEPES) buffer, citrate buffer (e.g., disodium citrate-trisodium citrate mixture, sodium citrate-citric acid mixture, citric acid-trisodium citrate mixture, monosodium citrate-disodium citrate mixture, citric acid-monosodium citrate mixture), sodium phosphate buffer (e.g., disodium phosphate-trisodium phosphate mixture ($Na_2HPO_4/Na_3PO_4$), sodium dibasic phosphate-sodium monobasic phosphate mixture), acetate buffer (e.g., acetic acid-sodium acetate mixture, acetic acid-sodium hydroxide mixture), histidine buffer, Tris buffer, Tris-maleate buffer, succinate buffer (e.g., succinic acid-sodium hydroxide mixture, succinic acid-monosodium succinate mixture, succinic acid-disodium succinate mixture, monosodium succinate-disodium succinate mixture), maleate buffer, imidazole buffer, tartrate buffer, fumarate buffer, gluconate buffer, oxalate buffer, lactate buffer, acetate buffer, and the like, or a combination of any thereof (e.g., cocktail of citrate and acetate buffers, etc.). The concentration of buffer in the composition can be any that is appropriate for the molecule(s) of the invention (e.g., a mutant CTLA-4-Ig) included in the composition solution, such as, but not limited to, e.g., in the range of from about 1 mM to about 100 mM, about 1 mM to about 50 mM, about 5 mM to about 50 mM, or about 5 mM to about 25 mM, including, e.g., 1 mM, 5 mM, 10 mM, 15 mM, 20 mM, 25 mM, 30 mM, 40 mM, 50 mM (such as, e.g., 20 mM HEPES buffer, 20 mM disodium citrate-trisodium citrate buffer, 20 mM succinate buffer, etc.).

Exemplary salts for use in the composition include, but are not limited to, e.g., water-soluble salts, including an organic salt or inorganic salt (e.g., water-soluble inorganic salt), such as sodium chloride, magnesium chloride, sodium bicarbonate, potassium chloride, calcium chloride, and ammonium chloride, and the like, or any pharmaceutically acceptable or physiologically compatible salt. Exemplary concentrations of salt in the composition solution include, but are not limited to, e.g., in the range of from about 1 mM to about 150 mM, about 10 mM to about 125 mM, or about 75 mM to about 125 mM, including, e.g., 10 mM, 50 mM, 75 mM, 100 mM, 125 mM, 150 mM (such as, e.g., 100 mM NaCl).

Exemplary sugars or carbohydrates for use in the composition include, but are not limited to, e.g., sucrose, maltose, trehalose, dextrose, mannose, raffinose, lactose, malto dextrin, dextran, saccharose, etc., in a concentration range including, but not limited to, e.g., from about 0.1% to about 10% by weight sugar, about 1% to about 5% by weight sugar, or about 1% to about 3% by weight sugar, including e.g., 0.1%, 0.5%, 1%, 1.5%, 2%, 2.5%, 3%, 4%, 5%, 6%, 7%, 8%, 9%, or 10% by weight sugar (e.g., 2% by weight sucrose, 2% by weight trehalose, or 2% by weight mannose) based on the composition. Exemplary sugar alcohols for use in the composition include, but are not limited to, e.g., mannitol, sorbitol, glycol, glycerol, arabitol, erythritol, xylitol, ribitol, lactitol, and the like in a concentration range including, but not limited to, e.g., from about 0.1% to about 10% by weight sugar alcohol, about 1-5%, about 1-3%, including e.g., 0.1%, 0.5%, 1%, 1.5%, 2%, 2.5%, 3%, 4%, 5%, 6%, 7%, 8%, 9%, or 10% by weight sugar alcohol based on the composition.

The osmolality of the compositions of the invention, including pharmaceutical compositions, is typically similar to the serum osmolality of blood, which ranges from about 250 to about 350 milliosmoles per kilogram (mOSm/kg) of water. The concentration of salt in the composition is typically less than 125 mM. The salt and sugar concentrations may be adjusted or varied such that the osmolality of the composition is from about 250-350 mOSm/kg of water.

Exemplary detergents or emulsifiers for use in the composition include, but are not limited to, e.g., polysorbates, such as Tween®-20, Tween®-40, Tween®-60, Tween®-80, or pluronic F-68 in a range including, but not limited to, e.g., from about 0.001% to about 0.2% by weight of a detergent or emulsifier based on the composition, including, e.g., 0.001%, 0.002%, 0.003%, 0.004%, 0.005%, 0.006%, 0.007%, 0.008%, 0.009%, 0.01%, 0.02%, 0.03%, 0.04%, 0.05%, 0.075%, and 0.1% by weight of detergent or emulsifier (e.g., Tween®-20, Tween®-40, Tween®-60, Tween®-80, or pluronic F-68) based on the composition.

Compositions of the invention, including pharmaceutical compositions, can comprise a polymer, such as a PEG molecule, in a concentration sufficient to reduce or inhibit undesired association between two or more molecules of the invention, such as, e.g., two or more mutant CTLA-4-Ig fusion protein dimers of the invention. The composition can comprise two or more different polymers (e.g., PEGs). The polymer (e.g., PEG molecule) typically has a molecular weight of from about 200 Da to about 8000 Da (e.g., about 200, 300, 400, 600, 900, 1000, 1450, 3350, 4500, or 8000 Da, available from Dow Chemical). The addition of a polymer (e.g., PEG molecule) to the composition is believed to reduce the formation of undesired aggregates, particularly undesired aggregates of two or more fusion protein dimers of the invention.

Compositions of the invention, including pharmaceutical compositions, can include a cyclic oligosaccharide, such as a cyclodextrin (e.g., Captisol® (Cydex)). In one aspect, the composition comprises two or more different cyclic oligosaccharides. The addition of cyclic oligosaccharide(s) to the composition improves the solubility, stability, bioavailability, and/or dosing of active pharmaceutical ingredient(s) (e.g., mutant CTLA-4 molecule).

The pH of a composition of the invention, including a pharmaceutical composition, can range from about pH 3 to about pH 10, from about pH 4 to about pH 10, from about pH 5 to about pH 9, from about pH 6 to about pH 9, from about pH 5.5 to about pH 8.5, from about pH 6.0 to about pH 6.7, from about pH 6.0 to about pH 6.5, from about pH 6.2 to about pH 8.7, from about pH 6.5 to about pH 8.5, from about pH 6.5 to about pH 7.5, from about pH 6.2 to about pH 7.0, from about pH 6.3 to about pH 6.8, from about pH 6.4 to about pH 6.8, from about pH 7.0 to about pH 8.0, and about pH 7.0 to about pH 7.4. In one aspect, compositions comprising a molecule of the invention, such as, e.g., a mutant CTLA-4-IgG2, have a pH of pH 5.0, pH 5.1, pH 5.2, pH 5.3, pH 5.4, 5.5, pH 5.6, pH 5.7, pH 5.8, pH 5.9, pH 6.0, pH 6.1, pH 6.2, pH 6.3, pH 6.4, pH 6.5, pH 6.6, pH 6.7, pH 6.8, pH 6.9, pH 7.0, pH 7.1, pH 7.2, pH 7.3, pH 7.4, pH 7.5, pH 7.6, pH 7.7, pH 7.8, pH 7.9, pH 8.0, pH 8.1, pH 8.2, pH 8.3, pH 8.4, pH 8.5, pH 8.6, pH 8.7, pH 8.8, pH 8.9, pH 9.0, pH 9.1, pH 9.2, pH 9.3, pH 9.4, pH 9.5, pH 9.6, pH 9.7, pH 9.8, pH, 9.9, or pH 10.0.

In one aspect, the invention provides a composition of the invention comprising an excipient or carrier (including, e.g., a pharmaceutical composition comprising a pharmaceutically acceptable excipient or carrier) and an effective amount of any CTLA-4 polypeptide, multimer, dimer, conjugate, fusion protein, or fusion protein dimer of the invention described throughout and herein, and further comprising a buffer capable of maintaining the pH of the composition within the range of about pH 3 to about pH 10, water, optionally a non-ionic detergent, optionally a salt, and optionally a sugar alcohol, monosaccharide, disaccharide, or polysaccharide. Some such compositions are at a physiological pH. Some such compositions have a pH of from about 4 to about 7.5, about 5.0 to about 7.5, or from about 6.4 to about 6.6, including, e.g., about pH 6.5, about pH 7.4, or pH 7.5. Some such compositions comprise a buffer in a concentration of from about 1 mM to about 100 mM, about 1 mM to about 50 mM, about 5 mM to about 35 mM, about 10 mM to about 25 mM, including, e.g., about 20 mM, 25 mM, or 30 mM. Some such compositions comprise a buffer selected from the group consisting of a HEPES buffer, citrate buffer, succinate buffer, acetate buffer, citrate buffer, maleate buffer, phosphate buffer, and Tris buffer. Some such compositions comprise a buffer is selected from the group consisting of a HEPES buffer, sodium citrate buffer, and sodium succinate buffer. For some such compositions, the pH is from about 6.0 to about 6.7 and the buffer is sodium succinate or sodium citrate. For some such compositions, the pH is about 7.0 to about 7.7 and the buffer is HEPES. Some such compositions further comprise a sugar alcohol or saccharide, wherein the saccharide is a monosaccharide, disaccharide (e.g., sucrose or trehalose), or polysaccharide. Some such compositions comprise a salt present in a concentration of about 1 mM to about 50 mM, including, e.g., about 20 mM, 25 mM, or 30 mM. Some such compositions comprise a non-ionic detergent, such as, e.g., a non-ionic detergent selected from the group consisting of from the group consisting of Tween®-80, Tween®-60, Tween®-40, Tween®-20, or pluronic F-68.

In some such compositions (including pharmaceutical compositions) described in the paragraph above, the polypeptide, multimer, dimer, conjugate, fusion protein, or fusion protein dimer is present at a concentration in the range of about 1 mg/ml (weight/volume or w/v) to about 200 mg/ml (w/v), about 25 mg/ml (w/v) to about 100 mg/ml (w/v), about 50 mg/ml to about 300 mg/ml, optionally about in a range of about 50 mg/ml (w/v) to about 100 mg/ml (w/v). Some such compositions comprise an effective amount of the polypeptide, multimer, dimer, conjugate, fusion protein, or fusion protein dimer of from about 0.1 mg/kg to about 15 mg/kg, and the composition is administered to a mammal (e.g., human). Some such compositions comprise an effective amount of the polypeptide, multimer, dimer, conjugate, fusion protein, or fusion protein dimer of from about 0.5 mg/kg to about 10 mg/kg, and the composition is administered parenterally. Some such compositions comprise an effective amount of the polypeptide, multimer, dimer, conjugate, fusion protein, or fusion protein dimer of from about 0.1 mg/kg to about 5 mg/kg, and optionally about 0.5 mg/kg, and the composition is administered subcutaneously. Some such compositions comprise an effective amount of the polypeptide, multimer, dimer, conjugate, fusion protein, or fusion protein dimer of from about 5 mg/kg to about 15 mg/kg (optionally about 10 mg/kg), and the composition is administered intravenously. For some such compositions, the polypeptide, multimer, dimer, conjugate, fusion protein, or fusion protein dimer comprises an amino acid sequence having at least 95%, at least 96%, at least 97%, at least 98%, or at least 99% sequence identity to the amino acid sequence of SEQ ID NO:36. For some such compositions, the polypeptide, multimer, dimer, conjugate, fusion protein, or fusion protein dimer comprises an amino acid sequence having at least 95%, at least 96%, at least 97%, at least 98%, or at least 99% sequence identity to the amino acid sequence of SEQ ID NO:50. Some such compositions are sterile and/or are isotonic to blood. Some such compositions are liquid compositions. Some such compositions are in a liquid or a dried form, wherein the dried form is selected from the group consisting of a lyophilized form, an air-dried form, and a spray-dried form.

In an exemplary aspect, the invention provides a pharmaceutical composition comprising: (i) a CTLA-4-Ig fusion protein of the invention having a concentration of from about 1 mg/ml to about 300 mg/ml (e.g., about 1 mg/ml to about 100 mg/ml, about 50 mg/ml or about 100 mg/ml, etc.) (optionally a dimeric fusion protein); (ii) a buffer having a buffering capacity of between about pH 5.0 and about pH 9.0 at a concentration of about 5 mM to about 50 mM; (iii) a pharmaceutically acceptable diluent to bring the composition to a designated volume; (iv) a sugar at a concentration of about 0.5% to about 10% by weight sugar based on the composition; (v) a salt at a concentration of about 1 mM to about 200 mM; (vi) optionally a non-ionic detergent (e.g., Tween®-20, Tween®-40, Tween®-60, Tween®-80, or pluronic F-68) at a concentration of about 0.01 mg/ml to about 0.5 mg/ml, e.g., about 0.01 mg/ml to about 0.1 mg/ml; and (vii) optionally a cyclic oligosaccharide (e.g., cyclodextrin (Captisol®), wherein the pH of the composition is in a range of about pH 5.0 to about pH 8.0. Exemplary CTLA-4-Ig fusion protein of the invention include those comprising a polypeptide sequence having at least 91%, 92%, 93%, 94%, 95%, 96%, 97%, 98%, 99%, or 100% sequence identity to at least one polypeptide sequence selected from the group consisting of SEQ ID NOS:74-79, 197-200, 205-214, and 219-222 (optionally, e.g., selected from the group consisting of SEQ ID NOS:197, 199, 211, and 213), wherein the fusion protein binds CD80 and/or CD86 and/or an extracellular domain thereof and/or suppresses an immune response. Such fusion proteins may be in monomeric or dimeric form.

In another aspect, the invention provides a pharmaceutical composition comprising: (i) a conjugate comprising a CTLA-4-Ig fusion protein of the invention (optionally a dimeric fusion protein) and a non-polypeptide moiety covalently attached to the fusion protein, said conjugate having a concentration of from about 1 mg/ml to about 300 mg/ml (e.g., about 1 mg/ml to about 100 mg/ml, about 50 mg/ml or about 100 mg/ml, etc.); (ii) a buffer having a buffering capacity of between about pH 5.0 and about pH 8.0 at a concentration of about 5 mM to about 50 mM; (iii) a pharmaceutically acceptable diluent to bring the composition to a designated volume; (iv) a sugar at a concentration of about 0.5% to about 10% by weight sugar based on the composition; (v) a salt at a concentration of about 1 mM to about 200 mM; and (vi) optionally a non-ionic detergent (e.g., Tween®-20, Tween®-40, Tween®-60, Tween®-80, or pluronic F-68) at a concentration of about 0.01 mg/ml to about 0.5 mg/ml, e.g., about 0.01 mg/ml to about 0.1 mg/ml, wherein the pH of the composition is in a range of about pH 5.0 to about pH 8.0. The conjugate may comprise one, two, three, four or more non-polypeptide moieties. Each non-polypeptide moiety may comprise a polymer (e.g., PEG or PAO) or a sugar moiety. In some instances, non-polypeptide moiety is a polymer molecule, such as a PEG molecule. The polymer molecule can have any desired molecular weight dependent on the desired functional effect (e.g., increased half life, decreased association between fusion protein molecules, etc.). In some instances, e.g., the polymer is a PEG having a molecular weight of from about 1 kDa to about 100 kDa Da (e.g., 1, 2, 2.5, 3, 5, 8, 10, 12, 20, 25, 30, 40, 60 kDa, etc.). The non-polypeptide moiety (e.g., sugar moiety or polymer molecule) is covalently attached to an attachment group of an amino acid residue of the fusion protein using standard procedures as described above. Exemplary CTLA-4-Ig fusion proteins include those comprising a polypeptide sequence having at least 91%, at least 92%, at least 93%, at least 94%, least 95%, at least 96%, at least 97%, at least 98%, at least 99%, or 100% sequence identity to at least one polypeptide sequence selected from the group consisting of SEQ ID NOS:74-79, 197-200, 205-214, and 219-222 (optionally, e.g., selected from the group consisting of SEQ ID NOS:197, 199, 211, and 213), wherein the fusion protein binds CD80 and/or CD86 and/or an extracellular domain thereof and/or suppresses an immune response. Such fusion proteins may be in monomeric or dimeric form.

In another aspect, the invention provides a pharmaceutical composition comprising: (a) a polypeptide comprising a polypeptide sequence having at least about 94%, 95%, 96%, 97%, 98%, 99%, or 100% identity to a polypeptide sequence selected from the group of SEQ ID NOS:1-73, such as, e.g., SEQ ID NOS:36 and 50, wherein said polypeptide is present in a concentration range of about 1 to about 200 mg/ml (w/v); (b) a buffer having a buffering capacity of between about pH 5.0 and about pH 8.0 at a concentration range of about 5 mM to about 50 mM; (c) a pharmaceutically acceptable diluent to bring the composition to a designated volume; (d) a sugar at a concentration of 0.5% to 10% by weight; (e) a salt at a concentration of about 1 mM to about 200 mM; and (f) optionally a detergent, wherein the pH is in a range of about pH 5.0 to about pH 8.0. In some such pharmaceutical compositions, (a) the polypeptide comprises the polypeptide sequence of SEQ ID NO:36 present in a concentration range of from about 50 mg/ml to about 100 mg/ml; (b) the buffer is HEPES buffer present at a concentration of about 20 mM; (c) the pharmaceutically acceptable diluent is water; (d) the sugar is sucrose or trehalose at a concentration of 2% by weight; (e) the salt is sodium chloride at a concentration of about 100 mM; and (f) optionally a detergent selected from the group consisting of Tween®-80, Tween®-60, Tween®-40, Tween®-20, or pluronic F-68 at a concentration less than or equal to about 0.1 mg/ml, wherein the pH of the composition is about pH 7.4. In another such compositions, (a) the polypeptide comprises the polypeptide sequence of SEQ ID NO:50 present in a concentration range of from about 50 mg/ml to about 100 mg/ml; (b) the buffer is sodium citrate buffer present at a concentration of about 20 mM; (c) the pharmaceutically acceptable diluent is water; (d) the sugar is sucrose or trehalose at a concentration of 2% by weight; (e) the salt is sodium chloride at a concentration of about 100 mM; and (f) optionally a detergent selected from the group consisting of Tween®-80, Tween®-60, Tween®-40, Tween®-20, or pluronic F-68 at a concentration less than or equal to about 0.1 mg/ml, wherein the pH is about pH 6.5.

In another aspect, the invention provides a pharmaceutical composition comprising: (a) a polypeptide comprising an amino acid sequence having at least 96%, at least 97%, at least 98%, or at least 99% sequence identity to the amino acid sequence of SEQ ID NO:36; and (b) HEPES or sodium citrate buffer (e.g., disodium citrate-trisodium citrate mixture, sodium citrate-citric acid mixture, citric acid-trisodium citrate mixture, monosodium citrate-disodium citrate mixture, or citric acid-monosodium citrate mixture).

Also provided is a pharmaceutical composition comprising: (a) a polypeptide comprising an amino acid sequence having at least 97%, at least 98%, or at least 99% sequence identity to the amino acid sequence of SEQ ID NO:36; and (b) a pharmaceutically acceptable excipient or a pharmaceutically acceptable carrier, wherein the composition has a pH from about 7 to about 8. Some such pharmaceutical compositions have a pH of about 7.4 or 7.5. Some such pharmaceutical compositions comprise HEPES or sodium citrate buffer.

Also provided is a pharmaceutical composition comprising: (a) a polypeptide comprising an amino acid sequence having at least 96%, at least 97%, at least 98%, or at least 99% sequence identity to the amino acid sequence of SEQ ID NO:50; and (b) sodium citrate buffer (e.g., disodium citrate-trisodium citrate mixture, sodium citrate-citric acid mixture, citric acid-trisodium citrate mixture, monosodium citrate-disodium citrate mixture, or citric acid-monosodium citrate mixture).

Also provided is a pharmaceutical composition comprising: (a) a polypeptide comprising an amino acid sequence having at least 97%, at least 98%, or at least 99% sequence identity to the amino acid sequence of SEQ ID NO:50; and (b) a pharmaceutically acceptable excipient or a pharmaceutically acceptable carrier, wherein the composition has a pH from about 6 to about 7. Some such pharmaceutical compositions have a pH of about 6.5. Some such pharmaceutical compositions comprise sodium citrate buffer.

In one exemplary aspect, the invention provides a pharmaceutical composition comprising from about 1 mg/ml to about 300 mg/ml of a CTLA-4-Ig fusion protein of the invention (e.g., D3-54-IgG2) (e.g., about 1 mg/ml to about 100 mg/ml, e.g., about 50 mg/ml or about 100 mg/ml) which is typically expressed as a dimeric fusion protein, in 20 mM HEPES buffer in water, 100 mM NaCl, 2% by weight sucrose based on the composition, pH 7.4, optionally including a non-ionic detergent (e.g., Tween®-20, Tween®-40, Tween®-60, Tween®-80, or pluronic F-68) at a concentration of about 0.01 mg/ml to about 0.5 mg/ml, e.g., about 0.01 mg/ml to about 0.1 mg/ml, and optionally including a polyethylene glycol (PEG), such as a PEG molecule having a molecular weight of from about 200 Daltons (Da) to about 8000 Da (e.g., about 200, 300, 400, 600, 900, 1000, 1450, 3350, 4500, or 8000 Da, available from Dow Chemical). In another exemplary aspect, the invention provides a pharmaceutical composition comprising from about 1 mg/ml to about 300 mg/ml of a CTLA-4-Ig fusion protein of the invention (e.g., D3-69-IgG2), which is typically expressed as a dimeric fusion protein, in 20 mM sodium citrate buffer in water, 100 mM NaCl, 2% by weight sucrose based on the composition, pH 6.5, optionally including a non-ionic detergent (e.g., Tween®-20, Tween®-40, Tween®-60, Tween®-80, or pluronic F-68) at a concentration of about 0.01 mg/ml to about 0.5 mg/ml, e.g., about 0.01 mg/ml to about 0.1 mg/ml, and optionally including a PEG molecule, such as a PEG molecule having a molecular weight of from about 200 Da to about 8000 Da (e.g., about 200, 300, 400, 600, 900, 1000, 1450, 3350, 4500, or 8000 Da, available from Dow Chemical).

The invention includes receptacles for containing a composition of the invention comprising a molecule of the invention (e.g., mutant CTLA-4 molecule, such as a mutant CTLA-4-Ig) and an excipient, diluent, or carrier. The composition may be a pharmaceutical composition comprising a molecule of the invention and a pharmaceutically acceptable excipient, diluent or carrier. Receptacles include, but are not limited to, e.g., vials (e.g., glass vial, such as a Type I glass vial), autoinjectors, pen injectors (fixed dose or variable dose), and pre-filled syringes, or other suitable containers. If desired, a receptacle can contain one or more pre-determined doses of the molecule of the invention effective to suppress an immune response or treat an immune system disease or disorder as described elsewhere herein. Some such receptacles are useful for administration of the composition contained therein to a subject suffering from an immune disease or disorder (e.g., autoinjectors, pen injectors, pre-filled syringes, etc.). Some such receptacles allow for self-administration of the composition by the subject (e.g., pen injectors, autoinjectors, pre-filled syringes, etc.).

Also provided are stable compositions or formulations of a molecule (e.g., mutant CTLA-4 ECD or mutant CTLA-4-Ig) of the invention, including pharmaceutically acceptable compositions of a molecule of the invention with a pharmaceutically acceptable carrier. In another aspect, the invention includes freeze-dried or lyophilized compositions or formulations. The term "freeze-dried" or "lyophilized" generally refers to the state of a substance which has been subjected to a drying procedure such as freeze-drying or lyophilization, where at least 50% of moisture has been removed. Pre-lyophilization and lyophilization procedures are well known in the art (see, e.g., LYOPHILIZATION OF BIOPHARMACEUTICALS, Vol. 2 of BIOTECHNOLOGY: PHARMACEUTICAL ASPECTS (Henry R. Costantino et al. eds., 2004), U.S. Pat. No. 6,436,897, WO 06/104852), and would be readily understood by a skilled artisan. Any suitable lyophilization procedure can be employed or modified as appropriate by one skilled on the art in preparing the lyophilized composition of the invention. A freeze-dried, air-dried, spray-dried, or lyophilized composition is usually prepared from a liquid, such as a solution, suspension, emulsion, etc. The liquid to be freeze-dried, air-dried, spray-dried, or lyophilized typically includes all of the components (except the liquid, e.g., water) that are to be in the final reconstituted liquid composition. In this way, the freeze-dried, air-dried, spray-dried, or lyophilized composition will have the desired liquid composition (e.g., pharmaceutical composition) when reconstituted. Exemplary compositions of the invention, including pharmaceutical compositions, comprising a molecule of the invention (e.g., mutant CTLA-4-Ig fusion protein of the invention, such as, e.g., SEQ ID NO:197, 199, 211, or 213), which are described throughout this application, can be freeze-dried, air-dried, spray-dried, or lyophilized to produce a stable freeze-dried, air-dried, spray-dried, or lyophilized composition, respectively, by using standard procedures known in the art. See e.g., exemplary procedures described in LYOPHILIZATION OF BIOPHARMACEUTICALS, supra.

For example, a container (e.g., vial, such as a glass vial) containing a liquid composition a molecule of the invention (e.g., mutant CTLA-4-Ig, fusion protein of the invention, such as, e.g., SEQ ID NO:197, 199, 211, or 213) to be lyophilized can be lyophilized by using standard procedures known by those of ordinary skill in the art. See, e.g., LYOPHILIZATION OF BIOPHARMACEUTICALS, supra. The lyophilized molecule of the invention (e.g., mutant CTLA-4-Ig of the invention) can subsequently be reconstituted with a liquid to generate a reconstituted liquid composition. Lyophilized formulations are typically reconstituted by the addition of an aqueous solution to dissolve the lyophilized formulation. Any suitable aqueous liquid or solution can be used to reconstitute a lyophilized formulation. A lyophilized formulation is often reconstituted using sterile or distilled water, but solutions comprising carriers, excipients, diluents buffers, and/or other components, including those described throughout, can be used for reconstitution.

In one aspect, the invention provides a pharmaceutical composition in lyophilized form, wherein the composition comprises from about 1 mg/ml to about 300 mg/ml of a CTLA-4-Ig fusion protein of the invention, which is typically expressed as a dimeric fusion protein, in appropriate buffer (e.g., HEPES, disodium citrate-trisodium citrate, etc.) in water at a concentration to maintain the desired pH (e.g., about pH 6.0 to about pH 7.5), salt (e.g., 50 mM NaCl), sugar (e.g., 4-6% by weight sucrose based on the composition), and optionally including a non-ionic detergent (Tween®-20, Tween®-40, Tween®-60, Tween®-80, or pluronic F-68) at a concentration of about 0.01 mg/ml to about 0.5 mg/ml, e.g., about 0.01 mg/ml to about 0.1 mg/ml (e.g., Tween®-20, Tween®-60, Tween®-80, or pluronic F-68). A lyphophilized form of a pharmaceutical typically includes a lower salt concentration and a higher sugar concentration compared to a non-lyophilized liquid composition.

In one particular aspect, the invention provides a stable lyophilized composition for therapeutic administration upon reconstitution with sterile water which comprises a therapeutically effective amount of a molecule of the invention and optionally one or more of the following pharmaceutically acceptable components: (a) a sugar or saccharide, such a sucrose, mannose, dextrose, or trehalose in an amount of from about 1% by weight to about 10% by weight; (b) a detergent or emulsifier, such as Tween®-20, Tween®-40, Tween®-60, Tween®-80, or pluronic F-68; (c) an isotonic agent or salt, such as an inorganic salt (e.g., sodium chloride) in a concentration of from 0 mM to about 50 mM (including, e.g., the concentrations set forth above; (d) a suitable buffer to maintain the pH of the composition within a range which is conducive to the stability of the molecule; (e) dispersing agent (e.g., in an amount sufficient for long-term dispersion of the molecule of the invention, such as, e.g., from 0.001 w/v % to about 1.0 w/v %) (e.g., polysorbate, such as Tween®-20, Tween®-40, Tween®-60, or Tween®-80, or pluronic F-68); and (f) a stabilizer (e.g., saccharide, dextrans, low molecular weight (MW) PEG group, such as PEG having MW of from about 200 Da to about 8000 Da (e.g., 200, 300, 400, 600, 900, 1000, 1450, 3350, 4500, or 8000 Da) or preservative. In some such stable lyophilized compositions, the molecule of the invention is a recombinant or isolated fusion protein of the invention, such as a fusion protein comprising a polypeptide sequence having at least 95%, at least 96%, at least 97%, at least 98%, at least 99%, or 100% sequence identity to at least one polypeptide sequence selected from the group consisting of SEQ ID NOS:74-79, 197-200, 205-214, and 219-222 (optionally, e.g., selected from the group consisting of SEQ ID NOS:197, 199, 211, and 213), wherein the fusion protein binds CD80 and/or CD86 and/or an extracellular domain thereof and/or suppresses an immune response. Such fusion proteins may be in monomeric or dimeric form.

Exemplary amounts of each such component in the lyophilized composition include those described above and herein. In one aspect, the buffer is selected so as to maintain the pH of the composition within a range of from about pH 3 to about pH 8, from about pH 4 to about pH 7.5. A lyophilized composition of the invention comprising a recombinant mutant CTLA-4-Ig fusion protein of the invention is typically stable at −80° to +40° C. and/or substantially maintains its biological activity for at least one week, one or more months (e.g., six months), one year, two years, three years, four years, or more when stored at ambient temperatures (e.g., about 22° C. to about 30° C.). Upon reconstitution with a liquid (e.g., sterile water for injection (WFI)), the lyophilized composition is suitable for administration (e.g., i.v., s.c., parenteral, i.m., i.d., i.p., etc.) to a subject (e.g., human).

The invention also provides a kit comprising a lyophilized or freeze-dried composition comprising a lyophilized or freeze-dried molecule of the invention (e.g., mutant CTLA-4-Ig fusion protein, such as, e.g., SEQ ID NO:197, 199, 211, or 213) in a first container (e.g., vial, such as a glass vial) and instructions for reconstituting the freeze-dried or lyophilized composition using a liquid (e.g., sterile water, WFI, or buffer). Optionally, the kit further comprises a second container (e.g., vial, such as a glass vial) containing a sufficient amount of liquid (e.g., sterile water, WFI or buffer) for reconstitution of the lyophilized or freeze-dried composition into a liquid composition. In this instance, reconstitution is achieved by using a syringe to remove a desired volume of water from the second container and to introduce the water into the first container. The first container is then rocked gently to put the molecule of the invention (e.g., fusion protein) into solution. The kit may include a device(s) for reconstituting the lyophilized or freeze-dried composition and/or administering the reconstituted liquid composition. Exemplary devices include, but are not limited to, e.g., a two-component mixing syringe, dual-chambered syringe, and dual-chambered autoinjector. One component or chamber contains the lyophilized composition and the second component or chamber contains the liquid for reconstitution. With such devices, reconstitution is typically carried out just prior to administration, and the reconstituted composition is usually administered parenterally (e.g., s.c., i.v., i.m., i.d. injection).

The composition or pharmaceutical composition of the invention can comprise or be in the form of a liposome. Suitable lipids for liposomal formulation include, without limitation, monoglycerides, diglycerides, sulfatides, lysolecithin, phospholipids, saponin, bile acids, and the like. Preparation of such liposomal formulations is described in, e.g., U.S. Pat. Nos. 4,837,028 and 4,737,323.

The form of the compositions or pharmaceutical composition can be dictated, at least in part, by the route of administration of the polypeptide, conjugate, nucleic acid, vector, virus, VLP, or cell of interest. Because numerous routes of administration are possible, the form of the pharmaceutical composition and its components can vary. For example, in transmucosal or transdermal administration, penetrants appropriate to the barrier to be permeated can be included in the composition. Such penetrants are generally known in the art, and include, for example, for transmucosal administration, detergents, bile salts, and fusidic acid derivatives. In contrast, in transmucosal administration can be facilitated through the use of nasal sprays or suppositories.

A common administration form for compositions of the invention, including pharmaceutical compositions, is by injection. Injectable pharmaceutically acceptable compositions typically comprise one or more suitable liquid carriers such as water, petroleum, physiological saline, bacteriostatic water, Cremophor EL™ (BASF, Parsippany, N.J.), PBS, or oils. Liquid pharmaceutical compositions can further include physiological saline solution, dextrose (or other saccharide solution), alcohols (e.g., ethanol), polyols (polyalcohols, such as mannitol, sorbitol, etc.), or glycols, such as ethylene glycol, propylene glycol, PEG molecules, coating agents which promote proper fluidity, such as lecithin, isotonic agents, such as mannitol or sorbitol, organic esters such as ethyoleate, and absorption-delaying agents, such as aluminum monostearate and gelatins. The injectable composition can be in the form of a pyrogen-free, stable, aqueous solution. An injectable aqueous solution may comprise an isotonic vehicle such as sodium chloride, Ringer's injection solution, dextrose, lactated Ringer's injection solution, or an equivalent delivery vehicle (e.g., sodium chloride/dextrose injection solution). Formulations suitable for injection by intraarticular, intravenous, intramuscular, intradermal, subdermal, intraperitoneal, and subcutaneous routes, include aqueous and non-aqueous, isotonic sterile injection solutions, which can include solvents, co-solvents, antioxidants, reducing agents, chelating agents, buffers, bacteriostats, antimicrobial preservatives, and solutes that render the formulation isotonic with the blood of the intended recipient (e.g., PBS and/or saline solutions, such as 0.1 M NaCl), and aqueous and non-aqueous sterile suspensions that can include suspending agents, solubilizers, thickening agents, emulsifying agents, stabilizers, and preservatives.

The administration of a polypeptide, conjugate, nucleic acid, vector, virus, pseudovirus, VLP or cell of the invention (or a composition comprising any such component) can be facilitated by a delivery device formed of any suitable material. Examples of suitable matrix materials for producing non-biodegradable administration devices include hydroxyapatite, bioglass, aluminates, or other ceramics. In some applications, a sequestering agent, such as carboxymethylcellulose (CMC), methylcellulose, or hydroxypropylmethylcellulose (HPMC), can be used to bind the particular component to the device for localized delivery.

A nucleic acid or vector of the invention can be formulated with one or more poloxamers, polyoxyethylene/polyoxypropylene block copolymers, or other surfactants or soap-like lipophilic substances for delivery of the nucleic acid or vector to a population of cells or tissue or skin of a subject. See e.g., U.S. Pat. Nos. 6,149,922, 6,086,899, and 5,990,241.

Nucleic acids and vectors of the invention can be associated with one or more transfection-enhancing agents. In some embodiments, a nucleic acid and/or nucleic acid vector of the invention typically is associated with one or more stability-promoting salts, carriers (e.g., PEG), and/or formulations that aid in transfection (e.g., sodium phosphate salts, dextran carriers, iron oxide carriers, or biolistic delivery ("gene gun") carriers, such as gold bead or powder carriers). See, e.g., U.S. Pat. No. 4,945,050. Additional transfection-enhancing agents include viral particles to which the nucleic acid or nucleic acid vector can be conjugated, a calcium phosphate precipitating agent, a protease, a lipase, a bipuvicaine solution, a saponin, a lipid (e.g., a charged lipid), a liposome (e.g., a cationic liposome), a transfection facilitating peptide or protein-complex (e.g., a poly(ethylenimine), polylysine, or viral protein-nucleic acid complex), a virosome, or a modified cell or cell-like structure (e.g., a fusion cell).

Nucleic acids and vectors of the invention can also be delivered by in vivo or ex vivo electroporation methods, including, e.g., those described in U.S. Pat. Nos. 6,110,161 and 6,261,281, and Widera et al., J. of Immunol. 164:4635-4640 (2000).

Transdermal administration of a component of the invention (e.g., polypeptide, conjugate, nucleic acid, vector, virus, VLP, and/or cell of the invention) can be facilitated by a transdermal patch comprising such component in any suitable composition in any suitable form. Such transdermal patch devices are provided by the invention. For example, such component can be contained in a liquid reservoir in a drug reservoir patch device, or, alternatively, the component can be dispersed throughout a material suitable for incorporation in a simple monolithic transdermal patch device. Typically, the patch comprises an immunosuppressive amount of at least one such component—such as an amount effective to suppress an immune response in a subject contacted with the patch. Examples of such patch devices are known in the art. The patch device can be either a passive device or a device capable of iontophoretic delivery of at least one such component to the skin or tissue of the subject.

A composition, particularly a pharmaceutical composition, may comprise any suitable dose of at least one such component of the invention (e.g., polypeptide, conjugate, nucleic acid, vector, virus, VLP, and/or cell) sufficient to achieve the desired immunosuppressive response in a subject following administration. Proper dosage can be determined by any suitable technique and considerations for determining the proper are known in the art. In a simple dosage testing regimen, low doses of the composition are administered to a test subject or system (e.g., an animal model, cell-free system, or whole-cell assay system). Dosage is commonly determined by the efficacy of the particular component to be administered, the condition of the subject, the body weight of the subject, and/or target area of the subject to be treated. The size of the dose is also determined by the existence, nature, and extent of any adverse side-effects that accompany the administration of any such particular component in a particular subject. Principles related to dosage of therapeutic and prophylactic agents are provided in, e.g., Platt, Clin. Lab Med. 7:289-99 (1987), "Drug Dosage," J. Kans. Med. Soc. 70(1):30-32 (1969), and other references described herein (e.g., Remington's, supra).

By way of example, a therapeutically effective amount of a polypeptide of the invention for an initial dosage for treating an autoimmune disease may comprise from about 0.001 mg/kg body weight of the subject to about 100 mg/kg body weight of the subject, such as, e.g., from about 0.001 milligrams per kilogram (mg/kg) body weight of the subject to about 100 milligrams per kilogram (mg/kg) weight of the subject, or, e.g., from about 0.001 mg/kg weight of the subject to at least about 0.005, 0.01, 0.025, 0.05, 0.1, 0.2, 0.25, 0.3, 0.4, 0.5, 0.6, 0.7, 0.8, 0.9, 1, 2, 3, 4, 5, 6, 7, 8, 9, 10, 20, 25, 30, 40, 50, 60, 70, 75, 80, 90, or 100 mg/kg body weight of the subject. Such dosage can be by any suitable protocol, e.g., such as administered daily, weekly, or biweekly, or any combination thereof (e.g., at about 0, 1, 2, 4, 5, 6, and 7 days, weekly thereafter, or at about 0, 1, 2, 4, and 6 weeks), followed by 1-, 2-, 3-month intervals, and by any suitable delivery method, such as, e.g., by electroporation or a subcutaneous (s.c.), intramuscular (i.m.), intravenous (i.v.), or intraperitoneal (i.p.), subdermal, transdermal, parenteral, or intradermal (i.d.) injection. In some instances, a polypeptide of the invention is typically administered as a soluble polypeptide, such as, e.g., a fusion protein comprising a mutant CTLA-4 ECD polypeptide of the invention covalently linked to an Ig Fc polypeptide. For example, a pharmaceutical composition comprising a mutant CTLA-4-Ig fusion protein of the invention in a pharmaceutically acceptable carrier, diluent, or excipient may be administered by any appropriate route (e.g., intradermally, intravenously, or subcutaneously) in an effective amount depending upon the autoimmune disease (e.g., rheumatoid arthritis) or condition to be treated (e.g., to inhibit rejection of a tissue, cell, graft, or solid organ transplant from a donor by the recipient subject).

In one exemplary aspect, the invention provides a method of suppressing an immune response in a subject in need thereof, comprising administering to the subject a pharmaceutical composition comprising, e.g., from about 1 mg/ml to about 300 mg/ml, including from about 25 mg/ml to about 150 mg/ml (e.g., 50 or 100 mg/ml) of D3-54-IgG2 fusion protein in 20 mM HEPES buffer in water, 100 mM NaCl, 2% by weight sucrose, pH 7.4, wherein the subject suffers from an autoimmune disorder (e.g., rheumatoid arthritis). In another exemplary aspect, the invention provides method of inhibiting rejection of a tissue, cell, graft or solid organ transplant from a donor in a recipient subject, comprising administering to the recipient subject a pharmaceutical composition comprising from about 25 mg/ml to about 100 mg/ml (e.g., 50 or 100 mg/ml) of D3-69-IgG2 fusion protein in 20 mM sodium citrate buffer in water, 100 mM NaCl, 2% by weight sucrose, pH 6.5.

Also provided is a viral vector composition, which comprises a carrier or excipient and a viral vector of the invention. Pharmaceutical compositions comprising a pharmaceutically acceptable carrier or excipient and a viral vector are also provided. The amount or dosage of viral vector particles or viral vector particle-encoding nucleic acid depends on: (1) the type of viral vector particle with respect to origin of vector, including, but not limited to, e.g., whether the vector is an alphaviral vector, Semliki-Forest viral vector, adenoviral vector, adeno-associated (AAV) viral vector, flaviviral vector, papillomaviral vector, and/or herpes simplex viral (HSV) vector, (2) whether the vector is a transgene expressing or recombinant peptide displaying vector, (3) the host, and (4) other considerations discussed above. Generally, with respect to gene transfer vectors, the pharmaceutically acceptable composition comprises at least about $1 \times 10^2$ viral vector particles in a volume of about 1 ml (e.g., at least about $1 \times 10^2$ to $1 \times 10^8$ particles in about 1 ml). Higher dosages also can be suitable (e.g., at least about $1 \times 10^6$, about $1 \times 10^8$, about $1 \times 10^9$, about $1 \times 10^{10}$ particles/ml).

The invention also provides a composition (including a pharmaceutical composition) comprising an aggregate of two or more polypeptides or conjugates of the invention. Moreover, the invention provides a composition (including a pharmaceutical composition) comprising a population of one or more multimeric polypeptides or multimeric conjugates of the invention. As noted above, pharmaceutical compositions include a pharmaceutically acceptable excipient, diluent, or carrier.

Kits

The present invention also provides kits including one, two, three, or more of the polypeptides (e.g., mutant CTLA-4 ECD polypeptides, mutant CTLA-4-Ig fusion proteins, including dimeric fusion proteins), conjugates, nucleic acids, vectors, cells, and/or compositions of the invention. Kits of the invention optionally comprise: (1) at least one polypeptide (e.g., mutant CTLA-4-Ig fusion protein), conjugate, nucleic acid, vector, VLP, cell, and/or composition of the invention; (2) optionally at least one second immunosuppressive agent (e.g., nonsteroidal anti-inflammatory agent, methotrexate, steroid, TNFα antagonist, etc.); (3) instructions for practicing any method described herein, including a therapeutic or prophylactic method and instructions for using any component identified in (1) or (2); (4) a container for holding the at least one such component identified in (1) or (2); and/or (5) packaging materials. One or more of the polypeptides (e.g., mutant CTLA-4-Ig fusion protein), conjugates, nucleic acids, vectors, VLPs, cells, and/or compositions of the invention, optionally with one or more second immunosuppressive agents, can be packaged in packs, dispenser devices, and kits for administration to a subject, such as a mammal, including a human. An effective amount of each such polypeptide (e.g., mutant CTLA-4-Ig fusion protein), conjugate, nucleic acid, vector, VLP, cell, and/or composition of the invention or optional second immunosuppressive agent (e.g., dose) for the indicated therapeutic or prophylactic method is indicated and one or more such doses is provided. The one or more polypeptides (e.g., mutant CTLA-4-Ig fusion protein), conjugates, nucleic acids, vectors, and/or cells compositions, and, if desired, the optional second immunosuppressive agent, may be provided in powder (e.g., lyophilized) or liquid form, and may be formulated with an excipient or carrier (including, e.g., a pharmaceutically acceptable excipient or carrier), thereby forming a composition (including, e.g., pharmaceutical composition). Packs or dispenser devices that comprise one or more unit dosage forms are provided. Typically, instructions for administration of such components are provided with the packaging, along with a suitable indication on the label that the compound is suitable for treatment of an indicated condition.

EXAMPLES

The following examples further illustrate the invention, but should not be construed as limiting its scope in any way.

Example 1

This example provides a description of the methods for creating a LEA29Y-Ig fusion protein, which was used as a control and for comparative purposes in Biacore™ binding and cell-based activity assays.

Creation of DNA Plasmid Vector Encoding LEA29Y-Ig Fusion Protein.

This example describes the making of a DNA plasmid vector that encodes the LEA29Y-Ig fusion protein. LEA29Y-Ig comprises a specific known mutant CTLA-4 ECD polypeptide, termed "LEA29Y" (or "LEA" or "L104EA29Y" or "A29YL104E"), which is covalently linked at its C-terminus to the N-terminus of a specific mutant human IgG1 Fc polypeptide. The LEA29Y polypeptide is a mutant CTLA-4 ECD polypeptide comprising a polypeptide sequence that differs from the polypeptide sequence of the human CTLA-4 extracellular domain by two mutations—an A29Y substitution and a L104E substitution—where positions 29 and 104 are numbered by reference to the polypeptide sequence of the human CTLA-4 ECD polypeptide, with the first amino acid residue of human CTLA-4 designated as amino acid residue position 1. See U.S. Pat. No. 7,094,874. The plasmid vector pcDNA3.1-LEA, which includes a nucleotide sequence that encodes LEA29Y-Ig, was created to produce this fusion protein.

DNA encoding LEA29Y-Ig is created by PCR assembly using overlapping oligonucleotides designed based on sequence homology to the nucleotide sequence encoding LEA29Y-Ig shown in SEQ ID NO:167. The oligonucleotides are designed, made, and assembled using standard procedures well known by those of ordinary skill in the art and can include stop and start codons and restriction sites as necessary. The PCR amplification procedures employed are also well known in the art. See, e.g., Berger, Ausubel, and Sambrook, all supra.

The oligonucleotides are assembled in a 100 µl PCR reaction with 1 µM oligonucleotides, 1×Taq buffer (Qiagen; #201225) and 200 µM dNTPs for 30 amplification cycles (94° C., 30 s; 60° C., 30 s; 72° C., 60 s). Amplified DNA is purified by QiaQuick PCR Spin Columns (Qiagen, Cat. #28104) and digested with restriction enzymes NheI and SacII. The fragments were separated by agarose-gel electrophoresis, purified using Qiaquick Gel Extraction Kit (Qiagen, #28704) as per manufacturer's recommendation, and ligated into similarly digested plasmid pcDNA 3.1 (+) (Invitrogen, Cat. #V790-20). Ligations are transformed into TOP10 E. coli cells (Qiagen, Cat. #C4040-10) as per manufacturer's recommendations. The resulting cells are incubated overnight at 37° C. in LB medium containing 50 µg/ml carbenicillin with shaking at 250 rpm and then used to make a maxiprep (Qiagen; #12362) stock of plasmid DNA (referred to hereinafter as plasmid vector pcDNA3.1-LEA).

The plasmid vector pcDNA3.1-LEA is identical to the plasmid vector pcDNA mutant CTLA-4-IgG2 vector shown in FIG. 1 except that the nucleic acid sequence encoding the mutant CTLA-4-IgG2 polypeptide has been replaced by a nucleic acid sequence encoding the LEA29Y-Ig fusion protein. A nucleic acid encoding the human CTLA-4 signal peptide was included as the signal peptide-encoding nucleotide sequence.

A nucleic acid sequence encoding the predicted LEA29Y-Ig fusion protein is shown in SEQ ID NO:167. SEQ ID NO:167 includes the nucleotide sequence encoding the signal peptide (e.g., amino acid residues 1-37 of SEQ ID NO:165). The polypeptide sequences of the predicted LEA29Y-Ig and mature LEA29Y-Ig fusion protein (without the signal peptide) are shown in SEQ ID NOS:165 and 166, respectively. As indicated in FIG. 2C, the predicted amino acid sequence of LEA29Y-Ig includes the following segments: the predicted signal peptide (amino acid residues 1-37), the LEA29Y ECD polypeptide (amino acid residues 38-161), linker (amino acid residue 162), and a mutant (modified) Fc domain of a human IgG1 polypeptide (amino acid residues 163-394). The amino acid residues at the junctions between these various segments are also shown in FIG. 2C. Specifically, the last four amino acid residues of the signal peptide, the first five and last five amino acid residues of the LEA29Y ECD, the single linker amino acid residue (Q), and the first five and last five amino acid residues of the mutant IgG1 Fc polypeptide are shown.

The signal peptide is typically cleaved during processing and thus the secreted fusion protein (i.e., mature fusion protein) of LEA29Y-Ig does not usually contain the signal peptide sequence. The mature/secreted form of LEA29Y-Ig, which has a total of 357 amino acids, comprises amino acid residues 38-394 (the full-length sequence without the signal peptide) of the predicted sequence shown in SEQ ID NO:165, and begins with the amino acid sequence: methionine-histidine-valine-alanine. SEQ ID NO:165 includes the signal peptide (e.g., residues 1-37) at its N-terminus; the signal peptide is typically cleaved to form the mature protein shown in SEQ ID NO:166. If desired, the amino acids of the mature form can be numbered beginning with the Met of the Met-His-Val-Ala sequence, designating Met as the first residue (e.g., the ECD comprises amino acid residues numbered 1-124), as in the mature LEA29Y-Ig fusion protein having the sequence shown in SEQ ID NO:166. In one aspect, the sequence of SEQ ID NO:165 or 166 does not include the C-terminal lysine residue; this residue may cleaved during processing or prior to secretion.

The protein sequence of the LEA29Y-Ig fusion protein is described in U.S. Pat. No. 7,094,874. Specifically, SEQ ID NO:4 of U.S. Pat. No. 7,094,874 shows a protein sequence encoding the non-mature form of monomeric LEA29Y-Ig. In U.S. Pat. No. 7,094,874, the LEA29Y-Ig fusion protein is termed "L104EA29YIg." The mature LEA29Y-Ig fusion protein comprising the sequence shown in SEQ ID NO:166 set forth herein differs from the fusion protein sequence shown in SEQ ID NO:4 in U.S. Pat. No. 7,094,874 because SEQ ID NO:4 of U.S. Pat. No. 7,094,874 includes a signal peptide (i.e., residues 1-26 of SEQ ID NO:4). This signal peptide is typically cleaved during processing and thus the mature (secreted) form of the LEA29Y-Ig fusion protein does not usually include the signal peptide sequence. SEQ ID NO:3 of U.S. Pat. No. 7,094,874 presents a nucleic acid sequence that encodes the L104EA29YIg fusion protein (i.e., LEA29Y-Ig).

LEA29Y-Ig typically exists in solution as a dimeric fusion protein comprising two identical monomeric fusion proteins. In this instance, each monomeric mature LEA29Y-Ig fusion protein comprises a LEA29Y ECD (SEQ ID NO:168) polypeptide fused at its C-terminus to the N-terminus of a mutant IgG1 Fc (SEQ ID NO:186). The two LEA29Y-Ig monomers are covalently linked together by disulfide bonds formed between cysteine residues in each monomer, thereby forming the LEA29Y-Ig fusion protein dimer. The LEA29Y-Ig dimer is the form of the fusion protein molecule used in the assays described in these Examples, unless explicitly stated otherwise.

Creation of Stable CHO-K1 Cell Line Expressing LEA29Y-Ig Fusion Protein.

A stable cell line was created to generate multi-milligram quantities of the LEA29Y-Ig fusion protein discussed above.

Transfection of CHO-K1 Cells.

CHO-K1 cells were seeded at a density of $1 \times 10^6$ in T-175 flasks (BD Falcon, #353112) containing 40 ml Growth Medium (DMEM/F12 medium (Invitrogen, #10565-018) supplemented with 10% fetal bovine serum (FBS) (Hyclone, #SV30014.03) and 1×PS (Penicillin+Streptomycin) (Invitrogen, #15140-122)). Cells were incubated for 24 hours (hrs) at 37° C. and then transfected with 10 µg Maxiprep plasmid DNA (e.g., plasmid vector encoding LEA29Y-Ig as described above) mixed with 60 µl Fugene 6 (Roche, #11814443001) as per the manufacturer's recommended conditions. Cells were incubated for 2 days (d) at 37° C. in Growth Medium and then for 10 d in Selection Medium (Growth Medium containing 300 µg/ml Geneticin (Invitrogen, #10131-027), changing the media every 2 d. The medium was removed and cells were dispersed by addition of 3 ml 0.05% trypsin (Invitrogen, Cat. #25300-054) and incubation at 37° C. for 3 min. Dispersed cells were diluted into 10 ml Growth Medium and harvested by centrifugation at 1000 rpm for 5 min at room temperature (RT) in a GH-3.8 rotor (Beckman Coulter, #360581). After discarding the supernatant, cells were suspended in 1 ml growth medium, filtered through 40 µm membranes (BD Falcon, #352340), and adjusted to a density of $1 \times 10^6$ cells/ml.

Separation of Unique Clones.

Using a cell-sorter (Dako, MoFlo), live cells were individually dispersed into 96-well culture plates (Sigma-Aldrich, #CLS-3596) containing 200 µl/well Growth Medium containing 25% Conditioned Medium (Growth Medium previously harvested from untransfected (or naïve) cell cultures). After incubation at 37° C. for 10-14 d, cells were dispersed by trypsin hydrolysis and transferred to new culture plates containing 200 μl/well Growth Medium. Cells were cultured at 37° C. in Growth Medium until cell density reached 70% confluence (approximately 14 d, with medium changed every 7 d).

Identification of Desired Clones.

Clones expressing high levels of recombinant LEA29Y-Ig fusion protein were identified by dot-blot and western analysis. For dot-blot analysis, 100 μl of medium was harvested from each well of the 96-well culture plates and transferred to nitrocellulose membranes (Whatman, #10439388) as per the manufacturer's recommendations. Membranes were washed twice with 200 ml PBST (PBST is phosphate-buffered saline (PBS)+0.05% Tween®-20) for 10 min at room temperature (RT) and then incubated with PBST containing 5% nonfat dry milk (EMD, #1.15363.0500) for 1 hour (hr) at RT. Membranes were washed as described above and incubated for 1 hr at RT in 20 ml PBST containing horseradish peroxidase (HRP)-conjugated goat anti-human Ig antibody (VectorLabs, #BA-3000) diluted to 1:4000. Membranes were washed as described above and incubated for 1 hr at RT with PBST containing streptavidin-HRP reagent (BD Biosciences, #554066) diluted 1:2000. Membranes were washed as described above and signals were detected using ECL Western Blot Detection Reagent (Amersham, Cat. #RPN2132) as per the manufacturer's recommended conditions. Positive clones identified by high signal intensity (i.e., expressing high levels of fusion protein) were dispersed by trypsin hydrolysis and transferred to 6-well culture plates (BD Falcon, Cat. #353046) containing 2 ml/well Growth Medium. After incubation at 37° C. for 3-4 d, cells were dispersed by trypsin hydrolysis and transferred to T-75 flasks (BD Falcon, Cat. #353136) containing 20 ml Growth Medium. After incubation at 37° C. for 2 d, 100 μl of medium was harvested and analyzed for protein expression levels by western analysis. For western analysis, equal amounts (15 μl) of medium from each cell culture was run through 4-12% Bis-Tris NuPAGE gels (Invitrogen, #NP0322BOX) in MES (MES is 2-(N-morpholino)ethanesulfonic acid, pH 7.3) running buffer (Invitrogen, #NP0002) as per the manufacturer's recommended conditions. Proteins were transferred from gels to nitrocellulose membranes (Invitrogen, Cat. #LC2001) by electro-transfer as per the manufacturer's recommended conditions. Membranes were processed as described above for dot-blotting and positive clones (expressing the fusion protein of interest) were identified by signal intensity and apparent molecular weight. Positive clones were dispersed by trypsin hydrolysis as described above and propagated in T-175 flasks containing 40 ml Growth Medium.

Production and Purification of LEA29Y-Ig Fusion Protein.

Propagation of Roller Bottle Cultures.

A Stable CHO-K1 cell line that had been transfected as described above with nucleic acid encoding the fusion protein of interest was grown to confluence in T-175 flasks containing 40 ml Growth Medium (DMEM/F-12 medium (Invitrogen, #10565-018) supplemented with 10% FBS (Hyclone #SV30014.03) and 1×PS (Invitrogen, #15140-122)). Cells were harvested by incubation in 3 ml 0.05% trypsin (Invitrogen, Cat. #25300-054) for 3 min at 37° C., diluted into 12 ml Growth Medium and then transferred to roller bottles (Corning, Cat. #431191) containing 250 ml Growth Medium. After incubation of roller bottle cultures at 37° C. in a humidified rolling incubator for 2 d, the media was removed and replaced with 250 ml fresh Growth Medium. Cultures were incubated for 2 d at 37° C. and the medium was replaced with 250 ml UltraCHO Medium (UltraCHO medium (BioWhittaker, Cat. #12-724) supplemented with 1/1000 EX-CYTE (Serologicals Proteins, Cat. #81129N) and 1×PS). After incubation for 2 d at 37° C., the media was replaced with 250 ml fresh Ultra-CHO Medium. Cultures were incubated for 2 d at 37° C. and the medium was replaced with 250 ml Production Medium (DMEM/F-12 medium supplemented with 1/100×ITSA (Life Technologies #51300-044), 1/1000× EX-CYTE and 1×PS). During production, media was harvested and replaced with fresh Production Media every other day.

Protein Purification.

Production media from roller bottle cultures was clarified by centrifugation at 2500×g for 30 min at RT followed by filtration through 0.2 μM membranes (VWR, Cat. #73520-986). Media were concentrated 10-fold by tangential flow filtration using 10 kDa MWCO membranes (Millipore, Cat. #P3C010C00) and then used for Protein-A affinity chromatography using a BioCad vision HPLC system. Ig-fusion protein was bound to Poros 20 Protein-A resin (Applied Biosystems, Cat. #1-5029-01) in PBS buffer, washed with the same buffer, eluted with 80 mM citric acid buffer (pH 4.0) containing 160 mM sodium chloride and then neutralized by addition of 2M Tris base. The protein solution was finally dialyzed against 6 liters (l) PBS using 10 kDa MWCO membranes (Pierce, Cat. #PI66810).

Example 2

This example describes exemplary methods used to create and screen libraries of CTLA-4 mutants for altered human CD80 and/or human CD86 binding activities by phage display.

Human CD80-Ig Fusion Protein.

Human CD80-Ig ("hCD80-Ig") and human CD86-Ig ("hCD86-Ig") fusion proteins were used as ligands in phage panning and phage ELISA experiments to identify mutant CTLA-4 molecules that bind human CD80 ("hCD80") and/or human CD86 ("hCD86") and/or an extracellular domain of either or both. Human CD80-Ig (also termed "hB7.1-Ig" or "hB7-1-Ig") and human CD86-Ig (also termed "hB2.1-Ig" or "hB2-1-Ig") fusion proteins are available from R&D Systems (Minneapolis, Minn.).

A representative nucleic acid sequence encoding the predicted WT human CD80-IgG1 fusion protein, which comprises the human CD80 signal peptide, human CD80 ECD, and human IgG1 Fc, is shown in SEQ ID NO:172. The predicted and mature polypeptide sequences of the hCD80-IgG1 fusion protein are shown in SEQ ID NO:170 and SEQ ID NO:171, respectively. The predicted fusion protein shown in SEQ ID NO:170 comprises WT human CD80 ECD covalently fused at its C-terminus to the N-terminus of a human IgG1 Fc polypeptide and includes a signal peptide at its N-terminus. The signal peptide is typically cleaved to form the mature CD80-Ig fusion protein shown in SEQ ID NO:171.

Human CD80-IgG1 is typically abbreviated herein as hCD80-Ig. As shown in FIG. 2A, the predicted amino acid sequence of the hCD80-Ig fusion protein (also designated "CD80-IgG1") includes the following segments: the predicted signal peptide (amino acid residues 1-34), human CD80 ECD (amino acid residues 35-242), linker (amino acid residues 243-245), and human IgG1 Fc polypeptide (amino acid residues 246-476). The amino acid residues at the junctions between these various segments are shown in FIG. 2A. Specifically, the last four amino acid residues of the signal peptide, the first five and last five amino acid residues of the human CD80 ECD, the amino acid residues of the linker (GVT), and the first five and last five amino acid residues of the human IgG1 Fc polypeptide are shown. In the CD80-Ig fusion protein, three residues GVT are present as a cloning artifact (or linker) between the C-terminus of the CD80 ECD (which ends with the amino acid residues FPDN) and the N-terminus of the IgG1 Fc polypeptide (which begins with the amino acid residues PKSC). This GVT cloning artifact or linker is shown in the predicted and mature CD80-Ig polypeptide sequences shown in SEQ ID NO:170 and 171, respectively.

The signal peptide is typically cleaved during processing and thus the secreted fusion protein (i.e., mature fusion protein) of hCD80-Ig does not usually contain the signal peptide. The mature/secreted form of hCD80-Ig, which has a total of 442 amino acids, comprises amino acid residues 35-476 (the full-length sequence without the signal peptide) of SEQ ID NO:170, and begins with the amino acid residue sequence: valine-isoleucine-histidine-valine. If desired, the amino acids of the mature form can be numbered beginning with the valine (Val) of the Val-Ile-His-Val sequence, designating Val as the first residue (e.g., the ECD comprises amino acid residues numbered 1-208), as in the mature form of hCD80-Ig comprising the polypeptide sequence shown in SEQ ID NO:171.

The hCD80-Ig fusion protein typically exists in solution as a dimeric fusion protein comprising two identical monomeric mature hCD80-Ig fusion proteins. In this instance, each monomeric mature hCD80-Ig fusion protein (SEQ ID NO:171) comprises a human CD80 ECD (SEQ ID NO:174) fused at its C-terminus to the N-terminus of a human IgG1 Fc (SEQ ID NO:185). The two hCD80-Ig monomers are covalently linked together by disulfide bonds formed between cysteine residues in each monomer, thereby forming the hCD80-Ig fusion protein dimer. The hCD80-Ig fusion protein dimer is the form of the fusion protein molecule used in the assays described in these Examples, unless explicitly stated otherwise.

A representative nucleic acid encoding the predicted full-length human CD80 polypeptide is shown in SEQ ID NO:196. The nucleic acid sequence shown in SEQ ID NO:196 encodes the human CD80 signal peptide, ECD, transmembrane domain, and cytoplasmic domain, and includes the TAA stop codon at the C-terminus.

Human CD86-Ig Fusion Protein.

A representative nucleic acid sequence encoding the predicted amino acid sequence of human CD86-human IgG1 (typically abbreviated herein as "hCD86-Ig") fusion protein is shown in SEQ ID NO:179. This nucleic acid sequence includes a nucleotide sequence encoding a signal peptide the mature human CD86-human IgG1 fusion protein. The predicted amino acid sequence of hCD86-Ig fusion protein is shown in SEQ ID NO:177, and an exemplary nucleic acid encoding the predicted hCD86-Ig fusion protein is shown in SEQ ID NO:179.

As shown in FIG. 2B, the predicted amino acid sequence of the hCD86-Ig fusion protein includes the following segments: the predicted signal peptide (amino acid residues 1-23), human CD86 extracellular domain (amino acid residues 24-243), linker sequence (amino acid residues 244-246), and human IgG1 Fc polypeptide (amino acid residues 247-477). The amino acid residues at the junctions between these various segments are also shown in FIG. 2B. Specifically, the last four amino acid residues of the signal peptide, the first five and last seven amino acid residues of the human CD86 ECD, the amino acid residues of the linker (GVT), and the first five and last five amino acid residues of the human IgG1 Fc polypeptide are shown.

The CD86 signal peptide is typically cleaved from the predicted hCD86-Ig polypeptide during processing and thus the secreted human CD86-Ig fusion protein (i.e., mature fusion protein) does not usually include the signal peptide. The mature/secreted form of hCD86-Ig, which has a total of 454 amino acids, comprises amino acid residues 24-477 (the full-length sequence without the signal peptide) of SEQ ID NO:177, and begins with the following amino acid residue sequence: alanine-proline-leucine. If desired, the amino acids of the mature fusion protein can be numbered beginning with the alanine residue (Ala) of the Ala-Pro-Leu sequence, designating Ala as the first residue (e.g., the ECD comprises amino acid residues numbered 1-218), as in the mature form of hCD86-Ig comprising the polypeptide sequence shown in SEQ ID NO:178. The mature fusion protein (SEQ ID NO:178) comprises a WT hCD86 ECD protein covalently fused at its C-terminus to the N-terminus of a hIgG1 Fc polypeptide.

The hCD86-Ig fusion protein typically exists in solution as a dimeric fusion protein comprising two identical monomeric mature hCD86-Ig fusion proteins. In this instance, each monomeric mature CD86-Ig fusion protein (SEQ ID NO:178) comprises a human CD86 ECD (SEQ ID NO:180) fused at its C-terminus to the N-terminus of a human IgG1 Fc (SEQ ID NO:185). The two hCD86-Ig monomers are covalently linked together by disulfide bonds formed between cysteine residues in each monomer, thereby forming the hCD86-Ig fusion protein dimer. The hCD86-Ig fusion protein dimer is the form of the fusion protein molecule used in the assays described in these Examples, unless explicitly stated otherwise.

In the CD86-Ig fusion protein (e.g., predicted and mature forms), three residues GVT are present as a cloning artifact (or linker) between the C-terminus of the CD86 ECD and the N-terminus of the IgG1 Fc polypeptide. In another aspect, the WT human CD86 ECD protein comprises a polypeptide sequence comprising amino acid residues 1-218 of SEQ ID NO:180 (i.e., excluding the last two C-terminal amino acid residues at the (PP)).

Orencia® Fusion Protein.

As an additional control and for comparative purposes, a commercially available fusion protein known as the Orencia® fusion protein (Bristol-Myers Squibb Co., Princeton, N.J.) was purchased. The Orencia® fusion protein is composed of the WT human CTLA-4 extracellular domain covalently fused at its C-terminus to the N-terminus of a specific mutant IgG1 Fc polypeptide. The Orencia® protein is a dimeric fusion protein comprising two identical monomeric fusion proteins covalently linked together by disulfide bonds formed between cysteine residues present in each monomeric fusion protein. The polypeptide sequence of each mature Orencia® fusion protein monomer is shown in SEQ ID NO:164 and is composed of the following segments: a WT human CTLA-4 extracellular domain (amino acid residues 1-124), linker sequence (amino acid residue 125), and a mutant IgG1 Fc polypeptide (amino acid residues 126-357). Each Orencia® fusion protein monomer has a structure similar to that of the LEA29Y-Ig fusion protein monomer shown schematically in FIG. 2C, except that the LEA29Y ECD is replaced with WT human CTLA-4 ECD, and no signal peptide is present in either Orencia® fusion protein monomer, because each monomer is a secreted or mature fusion protein. The polypeptide sequence of the non-mature form of an Orencia® monomer (which includes a signal peptide) and a nucleic acid sequence encoding the non-mature form of an Orencia® fusion protein monomer are shown in SEQ ID NO:8 and SEQ ID NO:7, respectively, of U.S. Pat. No. 7,094, 874. Methods of making and using the Orencia® fusion protein are also disclosed in U.S. Pat. No. 7,094,874.

Creation of DNA Sequences Encoding Mutant CTLA-4 Polypeptides.

Directed evolution methods were used to generate libraries of recombinant non-naturally-occurring polynucleotides encoding recombinant mutant CTLA-4 extracellular domain polypeptides. The protein and nucleotide sequences of a number of naturally-occurring mammalian CTLA-4 homologues are known. See, e.g., National Center for Biotechnology Information (NCBI). Sequence diversity identified in a variety of naturally-occurring mammalian CTLA-4 extracellular domain homologues was used in directed evolution methods to generate libraries of recombinant polynucleotides encoding mutant CTLA-4 ECD domain polypeptides. Directed evolution procedures include, e.g., in vitro recombination and mutagenesis procedures as substantially described in Stemmer, Proc. Natl. Acad. Sci. USA 91:10747-10751 (1994); Chang et al., Nature Biotech 17:793-797 (1999); Int'l Pat. Appn. Publ. No. WO 98/27230; and U.S. Pat. Nos. 6,117,679 and 6,537,776.

Creation of Libraries of DNA Sequences Encoding Mutant CTLA-4 Polypeptides.

Mutant DNA sequences encoding recombinant mutant CTLA-4 ECD polypeptides were amplified from assembly reactions by PCR using forward and reverse primers designed based on sequence homology. The primers were designed, made, and assembled using standard procedures well known by those of ordinary skill in the art and included stop and start codons and restriction sites as necessary. The PCR amplification procedures employed are also well known in the art. See, e.g., Berger, Ausubel, and Sambrook, all supra. Exemplary forward and reverse primers include, but are not limited, to the following: forward primer (5'-CTATTGCTACGGCCGCTATGGCCMTKCACGTCGCTCAACCAGCCGTCGTACTC GCGTCC-3') (SEQ ID NO:191) and reverse primer (5'-GTGATGGTGATGGTGTGCGGCCGCATCAGA-3') (SEQ ID NO:192). 5 μl of assembly reaction was used as template in a 100 μl PCR reaction with 1 μM forward and reverse primers, Taq buffer (Qiagen; #201225) and 200 μM dNTPs for 15 amplification cycles (94° C. 30 s; 50° C. 30 s; 72° C. 40 s). Amplified DNA encoding mutant CTLA-4 ECD polypeptides was digested with restriction enzymes (SfiI and NotI) and the fragments were separated by agarose-gel electrophoresis, purified using the Qiaquick Gel Extraction Kit (Qiagen, #28704) as per manufacturer's recommendation, and ligated into similarly digested phage-display vector pSB0124 (procedure similar to that described in Chang et al., Nature Biotech 17:793-797 (1999)). The resulting library ligation was transformed by electroporation into TOP10 *E. coli* cells (Invitrogen, Inc; #C4040-50) following the manufacturer's recommend conditions. Transformed cells were incubated in LB (Luria broth media) containing 50 μg/ml carbenicillin at 250 rpm overnight at 37° C. and then used to make a maxiprep (Qiagen; #12362) stock of library DNA as per the manufacturer's recommended conditions.

Screening of Phage Libraries Displaying Mutant CTLA-4 Polypeptides Having Improved Human CD80 and/or Human CD86 Binding Avidities Generation of Phage Displaying Libraries of Mutant CTLA-4 Polypeptides.

Library DNA (e.g., a library of DNA sequences encoding CTLA-4 ECD mutants) was transformed by electroporation into TG-1 *E. coli* cells (Stratagene; #200123) as per the manufacturer's recommended conditions. The culture was grown under phagemid-selection conditions (LB medium containing carbenicillin at 50 μg/ml) for 1-2 generations, infected with helper phage M13KO7 (at a multiplicity of infection level of 5-10), and incubated with shaking at 250 rpm overnight at 37° C. under dual selection for phagemid (carbenicillin at 50 μg/ml) and helper phage (kanamycin at 70 μg/ml). The cultures were clarified by centrifugation (6000 rpm, 15 min, 4° C. in a Sorvall 600TC rotor) and phage particles were precipitated by incubating 32 ml culture supernatant with 8 ml PEG/NaCl solution (20% PEG-8000; 2.5 M NaCl) on ice for 30 min followed by centrifugation (9500 rpm, 40 min, 4° C. in a Sorvall 600TC rotor). The phage pellet was suspended in 1 ml PBS containing 1% BSA (bovine serum albumin, Sigma; #A7906), transferred to a microfuge tube, and clarified by centrifugation (max speed, 5 min, RT in an Eppendorf table-top centrifuge).

Panning of CTLA-4 Mutant Phage Libraries.

Phage libraries were panned in up to five rounds against hCD80-Ig or hCD86-Ig fusion proteins using standard conditions. See, e.g., Lowman, et al., Biochemistry 12; 30(45): 10832-10838 (1991); Smith, G. P. et al., Chem. Rev. 97:391-410 (1997). Each round of panning included: (a) binding of phage displaying mutant CTLA-4 ECD polypeptides to hCD80-Ig or hCD86-Ig ligands; (b) removal of unbound phage; (c) elution of bound phage; and (d) amplification of eluted phage for the next round of panning. An aliquot of phage from each round was transduced into *E. coli* cells to obtain individual transductant colonies.

Identification of CTLA-4 Mutants Having Improved Binding Avidities to Human CD80 and/or Human CD86 by Phage ELISA.

Individual colonies obtained from each round of panning were inoculated into 96-well culture plates (NUNC; #243656) containing 150 μl/well of 2×YT (yeast-tryptone) media containing 50 μg/ml carbenicillin and incubated at 250 rpm overnight at 37° C. The overnight cultures were used to inoculate deepwell blocks (Scienceware; #378600001) containing 600 μl/well of the same media. Cultures were incubated at 250 rpm for 2 hrs at 37° C., infected with M13K07 helper phage (multiplicity of infection (moi) 5-10) and then incubated at 250 rpm at overnight at 37° C. under dual selection for phagemid and helper phage markers (carbenicillin at 50 μg/ml and kanamycin at 70 μg/ml, respectively). Cultures were clarified by centrifugation at 4000 rpm for 20 min at 4° C. in a Beckman GH 3.8 rotor. ELISA plates (NUNC; #449824) were coated by addition of 50 μl/well PBS containing 10 μg/ml hCD80-Ig or hCD86-Ig and incubated overnight at 4° C. Plates were washed three times with 200 μl/well PBST and blocked by addition of 200 μl/well PBS containing 3% non-fat dry milk and incubation at RT for 1 hour (hr). 25 μl/well of phage supernatants from the deepwell block was transferred to ELISA plates containing 25 μl/well 6% non-fat dry milk and plates were incubated for 1 hr at room temperature (RT). Plates were washed three times with 200 μl/well PBST and incubated with 50 μl/well HRP-conjugated anti-M13 monoclonal antibody (GE Healthcare, #27-9421-01) diluted 1:5000 in PBST containing 3% non-fat dry milk for 1 hr at RT. Plates were washed three times with 200 μl/well PBST and signal was detected using a TMB substrate kit (Pierce; #34021) according to manufacturer's recommended conditions. Mutant CTLA-4 ECD polypeptides exhibiting increased binding avidity to human CD80 and/or human CD86 (as measured by an increased avidity to hCD80-Ig and/or hCD86-Ig), compared to the binding avidity of human CTLA-4 to human CD80 and/or human CD86 (as measured by the binding avidity of human CTLA-4 ECD to hCD80-Ig and/or hCD86-Ig), were selected for further analysis.

Example 3

Creation of an IgG2 Fc Fusion Protein Vector

A plasmid IgG2-Fc fusion protein expression vector was created to produce a fusion protein comprising a mutant CTLA-4 ECD polypeptide of the invention and human IgG2 Fc polypeptide. DNA encoding the human IgG2 Fc polypeptide was generated by PCR amplification of human leukocyte cDNA (BD Biosciences, Cat. #HL4050AH) using forward primer (5'-AAGCTGTCACCGGTGGATCGATC-CCGAACCCTGCCCTGAT TCTGATGAGCGCAAATGT-TGTGTCGAGTGCCCACCGT-3') (SEQ ID NO:189) and reverse primer (5'-CAGAATTCATTATTTACCCGGAGA-CAGGGAGAGGCT CTTCTG-3') (SEQ ID NO:190). The primers were designed, made, and assembled using standard techniques well known by those of ordinary skill in the art and included stop and start codons and restriction sites as necessary. The PCR amplification procedures employed are also well known in the art. See, e.g., Berger, Ausubel, and Sambrook, all supra. 50-100 ng of cDNA was used as template in a 100 µl PCR reaction with 1 µM forward and reverse primers, Taq buffer (Stratagene; #200435) and 200 µM dNTPs for 25 amplification cycles (94° C., 30 s; 55° C., 30 s; 72° C., 60 s). The PCR product was purified by QiaQuick PCR Spin Columns (Qiagen #28106) as per the manufacturer's recommended conditions and digested with restriction enzymes AgeI and EcoRI. The PCR digestion fragment was separated by agarose-gel electrophoresis and purified using Qiaquick Gel Extraction Kit (Qiagen, #28704) as per the manufacturer's recommended conditions. A modified version of the pcDNA3.1-LEA vector (described above), which contains an AgeI restriction site in the CTLA-4 signal sequence (introduced as a silent mutation), may be digested with AgeI and EcoRI and ligated to the fragment mentioned above. The ligation is transformed into One-shot TOP10 E. coli cells (Invitrogen Cat. #C4040-03) as per the manufacturer's recommended conditions. Transformed cells are incubated in LB (Luria broth media) containing 50 µg/ml carbenicillin at 250 rpm overnight at 37° C. and then used to make a maxiprep (Qiagen; #12362) stock of plasmid DNA as per the manufacturer's recommended conditions.

The resulting plasmid expression vector is designated as the pcDNA IgG2 Fc fusion protein expression vector. This vector is identical to the pcDNA mutant CTLA-4-IgG2 plasmid vector shown in FIG. 1 except that the nucleic acid sequence encoding the mutant CTLA-4 ECD polypeptide is removed. The nucleic acid sequence encoding the signal peptide in pcDNA IgG2 Fc fusion vector (which in FIG. 1 can be any suitable signal peptide-encoding nucleotide sequence) is a nucleic acid encoding the human CTLA-4 signal peptide (SEQ ID NO:181 or SEQ ID NO:215). This IgG2 Fc fusion vector does not include any nucleic acid encoding a mutant CTLA-4 ECD polypeptide of the invention or any other CTLA-4 ECD polypeptide.

Cloning of Nucleotide Sequences Encoding Mutant CTLA-4 Polypeptides into the IgG2 Fc Fusion Vector.

To produce mutant CTLA-4 polypeptides as soluble Fc fusion proteins, DNA sequences encoding mutant CTLA-4 ECD polypeptides identified as having improved binding avidities to human CD80 and/or human CD86 (as compared to the binding avidity of human CTLA-4-ECD to human CD80 and/or human CD86) from the phage library screening were each cloned into the IgG2 Fc fusion protein vector described above using, e.g., the following procedure.

DNA sequences encoding mutant CTLA-4 ECD polypeptides exhibiting higher binding avidities to hCD80-Ig and/or hCD86-Ig were first recovered from the phage display vector by PCR amplification using forward and reverse primers designed based on sequence homology to a number of nucleotide residues (e.g., 30-60 nucleotides) at the N- and C-termini of the mutant CTLA-4 ECD polypeptides and standard procedures known in the art. See, e.g., procedures described in, e.g., Berger, Ausubel, and Sambrook, all supra. For example, in one exemplary aspect, DNA sequences encoding mutant CTLA-4 ECD polypeptides were recovered from the phage display vector by PCR amplification using forward primer (5'-GGAATACCGGTTTTTTGTAAAGCCATG-CACGTCG CTCAACCAGCCGTCGTACTC-3') (SEQ ID NO:191) and reverse primer (5'-GGCACTCAGATCTACGT-CATCGATCCCGAA-3') (SEQ ID NO:192). 10 nanograms (ng) of plasmid DNA (phage display vector containing a mutant CTLA-4 ECD-encoding nucleotide sequence) was used as template in a 100 µl PCR reaction with 1 µM forward and reverse primers described above, Taq buffer (Stratagene; #200435) and 200 µM dNTPs for 25 amplification cycles (94° C., 30 s; 55° C., 30 s; 72° C., 60 s). The PCR product was purified by QiaQuick PCR Spin Columns (Qiagen #28106) as per the manufacturer's recommended conditions and digested with restriction enzymes AgeI and ClaI. The fragments were separated by agarose-gel electrophoresis, purified using Qiaquick Gel Extraction Kit (Qiagen, #28704) as per the manufacturer's recommended conditions, and ligated into similarly digested plasmid IgG2 Fc Fusion vector. The ligation was transformed into One-shot TOP10 E. coli cells (Invitrogen Cat. #C4040-03) as per the manufacturer's recommended conditions. Transformed cells were incubated in LB (Luria broth media) containing 50 µg/ml carbenicillin at 250 rpm overnight at 37° C. and then used to make a maxiprep (Qiagen; #12362) stock of plasmid DNA as per the manufacturer's recommended conditions.

The resulting plasmid expression vector, which comprises a nucleic acid encoding a mutant CTLA-4-IgG2 fusion protein of the invention, is designated as the pcDNA mutant CTLA-4 ECD IgG2 Fc plasmid expression vector. A schematic diagram of this vector is shown in FIG. 1. This vector includes a Bla promoter; ampicillin resistant gene; pUC origin; SV40 polyadenylation (poly A) signal sequence; f1 origin; SV40 promoter; neomycin resistance gene; CMV promoter to facilitate expression of a mutant CTLA-4-Ig fusion protein of the invention (comprising, e.g., human CTLA-4 signal peptide, mutant CTLA-4 ECD polypeptide, and human IgG2 Fc polypeptide); a nucleic acid sequence encoding a human CTLA-4 signal peptide (SEQ ID NO:181 or SEQ ID NO:215); a nucleic acid sequence encoding a mutant CTLA-4 ECD polypeptide of the invention (including, but not limited to, e.g., a nucleotide sequence encoding any one of SEQ ID NOS:80-152); an exemplary nucleic acid sequence encoding a human IgG2 Fc polypeptide is shown in SEQ ID NO:183 or SEQ ID NO:217; and a bovine growth hormone (bGH) poly A termination signal sequence. The nucleic acid sequence of SEQ ID NO:183 encodes the hIgG2 Fc polypeptide with the C-terminal lysine (K) residue (SEQ ID NO:184); the nucleic acid sequence of SEQ ID NO:217 encodes the hIgG2 Fc polypeptide without the C-terminal lysine residue (SEQ ID NO:218).

The plasmid IgG2 Fc fusion protein vector can also be used to produce a human CTLA-4-IgG2 ("hCTLA-4-Ig") fusion protein. In this instance, a nucleic acid sequence encoding human CTLA-4 ECD (e.g., SEQ ID NO:193) is cloned into the plasmid IgG2 Fc fusion protein vector using standard cloning procedures similar to those described above in place of the nucleotide sequence encoding the mutant CTLA-4 ECD. The hCTLA-4-Ig fusion protein typically exists in solution as a dimeric fusion protein comprising two identical monomeric mature hCTLA-4-Ig fusion proteins. In this instance, each monomeric mature hCTLA-4-Ig fusion protein comprises a human CTLA-4 ECD (SEQ ID NO:159) fused at its C-terminus to the N-terminus of a human IgG2 Fc (SEQ ID NO:218 or SEQ ID NO:184). The two hCTLA-4-Ig monomers are covalently linked together by disulfide bonds formed between cysteine residues in each monomer, thereby forming the hCTLA-4-Ig fusion protein dimer. The mature hCTLA-4-Ig fusion protein dimer is the form of the fusion protein used in the assays described in these Examples, unless explicitly stated otherwise.

We have found experimentally that a human CTLA-4-Ig fusion protein or mutant CTLA-4-Ig fusion protein made in CHO cells by transfecting an expression vector comprising a nucleotide sequence encoding the hCTLA-4-Ig or mutant CTLA-4-Ig fusion protein and the hIgG2 Fc polypeptide shown in SEQ ID NO:184 does not typically include the predicted C-terminal lysine (K) residue, as determined by LCMS analysis; thus, the hIgG2 Fc polypeptide sequence of a hCTLA-4-IgG2 or a mutant CTLA-4-IgG2 is that shown in SEQ ID NO:218, which hIgG2 Fc polypeptide sequence does not typically include the C-terminal lysine residue as compared to the polypeptide sequence shown in SEQ ID NO:184.

Transient Transfection of COS Cells.

COS-7 cells were grown to 80-90% confluence in T-175 flasks containing 40 ml Growth Medium (DMEM/F12 medium (Invitrogen, Cat. #10565-018) supplemented with 10% FBS (Hyclone Cat. #SV30014.03) and 1×PSG (penicillin, streptomycin and glutamine) (Invitrogen, Cat. #10378-016)). Immediately prior to transfection of the cells with a plasmid expression vector, the medium was removed and replaced with 35 ml Expression Medium (OptiMem media (Gibco #51985) containing 1×PSG). Plasmid DNA (10 µg) (e.g., a pcDNA mutant CTLA-4 ECD IgG2 Fc expression vector encoding a mutant CTLA-4-IgG2 fusion protein of the invention) was mixed with FuGENE6 transfection reagent (Roche #11 815 075 001) in a 1:3 volume ratio and added to 1 ml of Growth Medium. This mixture was then added slowly to the T-175 flask and swirled gently to mix. After incubation at 37° C. for 3 days, the media was harvested, fresh Expression Medium was added, and the cultures were incubated for an additional 3 d.

A similar procedure can be used to make COS-7 cells transfected with a similar plasmid vector encoding human CTLA-4-IgG2 or a pcDNA3.1-LEA plasmid vector encoding LEA29Y-Ig.

Purification of Proteins.

Supernatants from transfection cultures (e.g., comprising cells transfected with a pcDNA mutant CTLA-4 ECD IgG2 Fc vector encoding mutant CTLA-4-Ig fusion protein) were clarified by centrifugation at 1000×g for 10 min at RT and filtration through 0.2 µm membranes (Nalgene, VWR #73520-982). Proteins were purified by Protein-A affinity chromatography using an AKTA Explorer HPLC system (GE Healthcare). A mutant CTLA-4-Ig fusion protein was bound to Hitrap Protein A FF columns (GE Healthcare, #17-5079-01) in PBS buffer, washed with the same buffer, eluted with 100 mM citric acid buffer (pH 4.0), and then neutralized by addition of 1/10 volume of 2M Tris base. The buffer in the protein solution was finally exchanged to PBS by dialysis using 10 kDa MWCO membranes (Pierce, Cat. #PI66810).

A similar procedure can be used to purify human CTLA-4-IgG2 or LEA29Y-Ig fusion proteins.

Evaluation of Protein Quality.

SDS/PAGE Analysis.

The apparent molecular weight (MW) of a purified mutant CTLA-4-Ig fusion protein of the invention was measured by SDS/PAGE analysis under non-reducing conditions. Under non-reducing conditions, a mutant CTLA-4-Ig fusion protein of the invention typically exists as a dimeric fusion protein comprising two monomeric mutant CTLA-4-Ig fusion proteins. In one aspect, the dimer is a homodimer comprising two identical mutant CTLA-4-Ig fusion protein monomers. In one aspect, each CTLA-4-Ig fusion protein monomer comprises a mature/secreted mutant CTLA-4 ECD fused at its C-terminus to the N-terminus of a human IgG2 Fc polypeptide. The two mutant CTLA-4-Ig monomers are covalently linked together by disulfide bonds formed between cysteine residues in each monomer. The homodimer is the form of the mutant fusion protein molecule of the invention typically described in these Examples, unless explicitly stated otherwise. The data shown in these Examples pertain to mutant CTLA-4-Ig fusion protein homodimers, unless explicitly stated otherwise.

SDS/PAGE analyses were performed as follows. 2 µg of purified protein was added to 20 µl LDS Sample Buffer (Invitrogen #NP0007) and run through NuPAGE 4-12% Bis-Tris gels (Invitrogen #NP0321BOX) in 1×MES sodium docecyl sulfate (SDS)/PAGE running buffer (Invitrogen #NP0002) following the manufacturer's recommended conditions. Gels were stained by incubation in 50 ml SimplyBlue SafeStain (Invitrogen #LC6060) for 1 hr with gentle agitation at RT. Gels were de-stained by two incubations with 200 ml water for 1 hr with gentle agitation at RT and processed in drying buffer (Bio RAD 161-0752) according to the manufacturer's recommended conditions.

A representative SDS/PAGE gel of two exemplary mutant CTLA-4-Ig fusion protein homodimers of the invention (designated as clones D3 and D4) and the Orencia® fusion protein, which serves as a comparative control, is presented in FIG. 3. The D3-Ig fusion protein dimer comprises two identical D3-Ig fusion protein monomers that are covalently linked by disulfide bonds formed between cysteine residues in each D3-Ig monomer. Each D3-Ig monomer comprises a mutant CTLA-4 ECD polypeptide (named "D3") comprising the polypeptide sequence shown in SEQ ID NO:61 fused directly (i.e., with no "linker" amino acid residue(s)) at its C-terminus to the N-terminus of the hIgG2 Fc polypeptide shown in SEQ ID NO:218. The D4-Ig fusion protein dimer similarly comprises two identical D4-Ig monomers that are covalently linked by disulfide bonds formed between cysteine residues in each D3-Ig monomer. Each monomeric D4-IgG2 fusion protein comprises a mutant CTLA-4 ECD polypeptide (named "D4") comprising the polypeptide sequence shown in SEQ ID NO:62 fused directly (i.e., with no "linker" amino acid residue(s)) at its C-terminus to the N-terminus of the hIgG2 Fc polypeptide sequence shown in SEQ ID NO:218.

As explained above, we have found experimentally that a mutant CTLA-4-Ig fusion protein made in CHO cells using a vector comprising a nucleotide sequence encoding the predicted hIgG2 Fc polypeptide shown in SEQ ID NO:184 does not typically include the predicted C-terminal lysine (K) residue, as determined by LCMS analysis; thus, the hIgG2 Fc polypeptide sequence of a mutant CTLA-4-IgG2 described herein is that shown in SEQ ID NO:218, which hIgG2 Fc polypeptide sequence does not typically include the C-terminal lysine residue, as compared to the polypeptide sequence shown in SEQ ID NO:184.

SDS/PAGE analyses were performed on all protein preparations to verify protein quality in terms of apparent molecular weight, protein concentration, and purity. The results of the SDS/PAGE analyses were similar for all protein preparations. From the exemplary gel results shown in FIG. 3, purified D3-IgG2 and D4-IgG2 fusion protein dimers have an apparent MW of approximately 80 kDa, which is consistent with the predicted MW of the exemplary homodimeric mutant CTLA-4-IgG2 fusion protein structure depicted in FIG. 10 (predicted MW=78-79 kDa). (Purified mutant CTLA-4-IgG2 protein monomers typically have apparent MWs of 39-40 kDa.) The protein bands in the gel shown in FIG. 3 have been stained with equivalent intensities; this confirms the accuracy of measuring protein concentration for different samples. As for protein purity, a lower MW band can be observed in FIG. 3 at an apparent MW of approximately 44 kDa, which is consistent with the predicted MW of a monomeric IgG2 fusion protein. The relative intensity of this lower MW band is consistently low and is estimated to be less than 5% of the total protein.

Analogous SDS/PAGE analyses can be used to evaluate the purity of human CTLA-4-IgG2 or LEA29Y-Ig fusion proteins produced using methods similar to those describe above.

Endotoxin Analysis.

Endotoxin levels of mutant CTLA-4 fusion proteins were measured using a QCL-1000 limulus amoebocyte lysate assay kit (Cambrex #50-648U) following the manufacturers recommended conditions. The maximum endotoxin level for proteins used in cell-based assays was set at 10 endotoxin units (EU)/mg protein.

Analogous analyses can be used to measure the endotoxin levels of human CTLA-4-IgG2 or LEA29Y-Ig protein preparations.

Size Exclusion Chromatography (SEC) Analysis.

Protein aggregation levels (including aggregation levels of mutant CTLA-4 polypeptides and control polypeptides) were measured by size exclusion chromatography using a Dionex BioLC system (Dionex). Protein (5 µg) was run through a Tosoh G3000W×1 column (Tosoh Bioscience) in PBS running buffer using a 20 min isocratic run and detection by absorbance (A) at 214 nanometers (nm). The maximum level of aggregation for protein used in further assays was set at 10%.

SEC analysis was performed on all protein preparations to verify protein quality in terms of protein aggregation levels. The results were similar for all protein preparations and a representative elution profile from an SEC analysis of a mutant CTLA-4-Ig fusion protein dimer (D3-Ig) is shown in FIG. 4. The y-axis shows milliAbsorbance units (mAU); the x-axis shows elution time in minutes. The structure of the D3-Ig dimer is explained above in the "SDS/PAGE Analyses" section. This purified mutant CTLA-4-Ig dimer is largely homogeneous in size and does not contain high levels of aggregated species. Other mutant CTLA-4-Ig fusion proteins of the invention were similarly analyzed and showed similar results (data not shown). Purified mutant CTLA-4-Ig fusion proteins of the invention were found to be homogenous in size and did not contain high levels (>10%) of aggregated proteins. It is important to verify the aggregation states of the purified mutant CTLA-4-Ig fusion proteins of the invention because highly aggregated mutant CTLA-4-Ig fusion proteins may bind with higher avidity to human CD80 and/or human CD86 molecules and thus may exhibit higher biological activity.

Example 4

Measuring Binding Avidities of Mutant CTLA-4-Ig Fusion Proteins to Human CD80-Murine Ig (hCD80-mIg) and Human CD86-Murine Ig (hCD86-mIg) Fusion Proteins Using Surface Plasmon Resonance (SPR)

Biacore™ Analysis

This example describes a procedure for screening mutant CTLA-4-Ig fusion proteins for improved binding avidity to hCD80-mIg and/or hCD86-mIg ligands using a Biacore interaction analysis. In the nomenclature used to describe this type of analysis, the immobilized binding partner is referred to as the "ligand", and the binding partner in the mobile phase is referred to as the "analyte". Fusion proteins containing an Ig domain typically form dimeric structures in solution by virtue of strong association between two Ig domains. Unless indicated otherwise, such dimeric conformations are expected to exist for the fusion proteins described in this Example (i.e., mutant CTLA-4-Ig, Orencia® fusion protein, LEA29Y-Ig, hCD80-mIg, and hCD86-mIg). The term "avidity" typically relates to the strength of binding between dimeric analytes (e.g., mutant CTLA-4-Ig fusion proteins) and dimeric ligands (e.g., hCD80-mIg or hCD86-mIg fusion proteins). The increases in binding avidity described for mutant CTLA-4-Ig fusion proteins result from increases in binding affinity between each CTLA-4 ECD domain and its corresponding ligand. The strength of binding avidity is typically described in terms of the equilibrium dissociation constant ($K_D$), which describes the molar concentration of analyte at which 50% of available ligand is bound at equilibrium.

In this screening method, Biacore sensor chips were derivatized with hCD80-mIg or hCD86-mIg ligands and mutant CTLA-4-Ig fusion proteins in buffer were allowed to flow over the ligand-coated sensor chips. The ability of a mutant CTLA-4-Ig fusion protein molecule to bind to a specific binding partner (i.e., hCD80-mIg or hCD86-mIg) was evaluated. Control fusion proteins (i.e., human CTLA-4-IgG2 fusion protein, Orencia® fusion protein, and mutant LEA29Y-Ig fusion protein) were also allowed to flow over the ligand-coated sensor chips and the abilities of these molecules to bind to hCD80-mIg or hCD86-mIg were similarly evaluated for comparison. Using the Biacore system, the association ($k_{on}$) and dissociation ($k_{off}$) rate constant of a protein of interest binding to hCD80-mIg or hCD86-mIg ligands can be evaluated and used to calculate the equilibrium dissociation constant, $K_D$. The human CTLA-4-IgG2 fusion protein, which comprises the WT human CTLA-4 ECD polypeptide fused to the human IgG2 polypeptide, can serve as a wild-type human CTLA-4-Ig "control". In addition or alternatively, because the Orencia® fusion protein is composed of the WT human CTLA-4 ECD polypeptide fused to a modified IgG1 Fc polypeptide, it also effectively serves as a wild-type human CTLA-4-Ig control for comparative purposes. Mutant CTLA-4-Ig fusion proteins having increased binding avidities for hCD80-mIg and/or hCD86-mIg, compared to human CTLA-4-IgG2, Orencia® fusion protein, and/or LEA29Y-Ig, were identified. As discussed in greater detail below, the increased binding avidity of a mutant CTLA-4-Ig fusion protein of the invention for hCD80-mIg and/or hCD86-mIg, as compared to the binding avidity of Orencia® fusion protein (i.e., hCTLA-4-IgG1) and/or LEA29Y-Ig for hCD80-mIg and/or hCD86-mIg, was not due to differences between IgG2 present in the mutant CTLA-4-Ig molecules and the mutant IgG1 present in the Orencia® or LEA29Y-Ig molecules.

All Biacore™ analyses were performed on a Biacore™ 2000 system (GE Healthcare) at room temperature (RT, 25° C.). HBS-EP buffer (10 mM HEPES (pH 7.4), 150 mM NaCl, 3 mM EDTA, 0.005% surfactant P20) was used as the flow buffer for all experiments.

Standard Kinetic Assay.

The standard kinetic assay measures binding kinetics of dimeric ligand (e.g., hCD80-mIg fusion protein or hCD86-mIg fusion protein) coated to sensor chips and dimeric analytes (e.g., mutant CTLA-4-Ig fusion proteins of the invention) in the mobile phase. Rabbit anti-mouse IgG antibody (GE Healthcare, #BR-1005-14) was immobilized on CM5 sensor chips (GE Healthcare, #BR-1000-14) according to the manufacturer's protocol. Antibody was diluted to 30 µg/ml in immobilization buffer (10 mM sodium acetate, pH 5.0 (BR-1003-51)). At a flow rate of 5 µl/minute, sensor chip CM5 was activated with a 35 µl injection of a mixture of 1-Ethyl-3-[3-dimethylaminopropyl]carbodiimide hydrochloride (EDC) and N-hydroxysuccinimide (NHS) (made by mixing equal volumes of 11.5 mg/ml EDC and 75 mg/ml NHS) (GE Healthcare, #BR-1000-50), followed by a 35 µl injection of undiluted antibody. Un-reacted sites were quenched with 35 µl of 1M ethanolamine-HCL, pH 8.5 (GE Healthcare, #BR-1000-50). This procedure typically yielded 15,000 response units (RU) of coupled antibody. CTLA-4 ligands human CD80-murine Ig (hCD80-mIg) (Ancell, #510-820) or human CD86-murine Ig (hCD86-mIg) (Ancell, #509-820) were bound to antibody-coated sensor chips by injection of 10 µl or 16 µl, respectively, ligand solution (2 µg/ml protein in HBS-EP buffer [10 mM HEPES pH 7.4, 150 mM NaCl, 3 mM EDTA, 0.005% (v/v) surfactant P-20, GE Healthcare, #BR-1001-88]) at a flow rate of 10 µl/min. Ligand capture levels were typically 135-170 RU. Mutant CTLA-4-Ig proteins (or were diluted in HBS-EP buffer and flowed over ligand-coated sensor chips for 2 min at 30 µl/min, followed by 5 min incubation with HBS-EP buffer containing no protein at the same flow rate. For mutant CTLA-4-Ig fusion proteins having very slow dissociation rates from hCD86-mIg, kinetic assays were also conducted using longer dissociation times (e.g., 20 min). Rmax signal levels for mutant CTLA-4-Ig proteins ranged from approximately 70-100 RU. Regeneration between cycles was performed by 3 min incubation with 10 mM glycine buffer (pH 1.7) at 50 µl/min. New chips were subjected to 4-5 cycles of capture/binding/regeneration prior to use in actual experiments. Data from a reference cell containing rabbit anti-mouse IgG capture antibody alone was subtracted from data obtained from flow cells containing captured hCD80-mIg or hCD86-mIg. Typically, 8 dilutions of mutant CTLA-4-Ig proteins ranging from 500 nM to 0.2 nM were analyzed against a blank reference (HBS-EP buffer alone).

Sensorgram traces from a typical Biacore analysis are shown in FIG. 5. This figure shows the response (RU) over time (in seconds (s)) generated by the binding of the following three fusion proteins to the hCD86-mIg fusion protein: (1) Orencia® fusion protein (serving as a control and for comparison) (Bristol-Myers Squibb Co.; see, e.g., Larson C. P. et al., Am. J. Trans. 5:443-453 (2005)); (2) LEA29Y-Ig fusion protein (for comparison); and (3) an exemplary mutant CTLA-4-Ig fusion protein of the invention designated "clone D3" (also termed D3-IgG2). The D3-IgG2 fusion protein comprises two identical monomeric fusion proteins that are covalently linked together by one or more disulfide bonds formed between cysteine residues in each monomer. See the discussion in the "SDS/PAGE Analyses" section above. Each monomeric fusion protein comprises a mature mutant CTLA-4 ECD polypeptide shown in SEQ ID NO:159 covalently fused at its C-terminus to the N-terminus of the human IgG2 polypeptide shown in SEQ ID NO:184 or 218. Other dimeric fusion proteins of the invention may comprise structures similar to that of the dimeric D3-IgG2 fusion protein—except that the D3 mutant CTLA-4 ECD polypeptide of each monomeric fusion protein is replaced by a different mutant CTLA-4 ECD polypeptide.

The association phase reflects the binding between the analyte of interest and the ligand of interest. In FIG. 5, the association phase for each analyte is represented by the curve at times prior to the time marked by the arrow and is characterized by the binding of analyte (D3-IgG2, Orencia® fusion protein, or LEA29Y-Ig) to the hCD86-mIg ligand. The rate at which an analyte associates with the hCD86-mIg ligand is reflected in the curve—see, e.g., the sharp rate of increase in the response units beginning at about 510 seconds.

The dissociation phase of the analysis begins at the time marked by the arrow in FIG. 5. During the dissociation phase, the analyte and ligand dissociate from their bound conformation. In FIG. 5, the rate at which an analyte dissociates from the hCD86-mIg ligand is represented by the decrease in response units (rate of decrease of the response units over time). Based on these data, the relative dissociation rate constant ("off" rates, $k_{off}$ or $k_d$) and association rate constants ("on" rates, $k_{on}$ or $k_a$) can be determined. The total avidity of the interaction can be described by the $K_D$, $(k_{off})/(k_{on})$. Increased binding avidities are often manifested in slower dissociation rates. If the slower dissociation rate is accompanied by an equal, higher, or marginally slower association rate, such that the calculated equilibrium dissociation constant $K_D$ is lower, the avidity will be greater. In this case, a mutant CTLA-4-Ig fusion protein that has a binding avidity for the hCD86-mIg ligand that is greater than the binding avidity of the Orencia® fusion protein for the same ligand will also have a slower dissociation rate from the ligand than the Orencia® protein. A mutant CTLA-4-Ig fusion protein that has a binding avidity for the hCD86-mIg ligand that is greater than the binding avidity of LEA29Y-Ig for the same ligand will also have a slower dissociation rate from the ligand than LEA29Y-Ig.

FIG. 5 shows that the dissociation rate of LEA29Y-Ig from the hCD86-mIg ligand is significantly slower than the dissociation rate of the Orencia® protein from the same ligand. LEA29Y-Ig also has an association rate for binding to hCD86-mIg similar to that observed for the Orencia® fusion protein. Thus, LEA29Y-Ig has a higher avidity for hCD86-mIg than does the Orencia® protein. This finding is consistent with previous studies describing LEA29Y-Ig as having a higher binding avidity for the hCD86-mIg ligand than the Orencia® fusion protein (Larson C. P. et al., Am. J. Trans. 5:443-453 (2005)). FIG. 5 also shows that the mutant D3-IgG2 fusion protein of the invention has a slower dissociation rate from the hCD86-mIg ligand than either the Orencia® or LEA29Y-Ig fusion protein. The D3-IgG2 fusion protein also has a similar (but somewhat faster) association rate for binding to hCD86-mIg ligand compared to the association rates of either the Orencia® or LEA29Y-Ig fusion proteins for hCD86-mIg ligand. Thus, the D3-IgG2 fusion protein exhibits a higher binding avidity for the hCD86-mIg ligand than either the Orencia® or LEA29Y-Ig fusion protein. Therefore, the D3-IgG2 fusion protein is expected to bind to native CD86, including, e.g., CD86 as expressed in vivo on APCs in mammals, such as humans, with higher binding avidity. This view is further supported by the functional cell-based assays discussed in the Examples below.

Biacore analyses were performed using other mutant CTLA-4-Ig fusion proteins of the invention. In addition, Biacore analyses were performed using hCD80-mIg-coated sensor chips and mutant CTLA-4-Ig fusion proteins of the invention. The dissociation rates and binding avidities of these mutant molecules were determined and compared to the dissociation rates and binding avidities of the Orencia® and LEA29Y-Ig fusion proteins. Representative results are shown in Tables 3 and 4 and discussed in greater detail below.

Standard Biacore Data Analyses.

After deletion of the regeneration and capture portions of the sensorgrams, curves were zeroed to a 5 s average of all curves approximately 10 s prior to sample injection. A blank curve was subtracted from each test curve. Data were analyzed by BIAevaluation software (v4.1, available from GE Healthcare) using the "Fit kinetics, Simultaneous $k_a/k_d$" function. The injection start time was defined as a time prior to the association phase where all curves were close to zero. Data selection for the association phase began approximately 10 s after the injection start time and ended approximately 10 s prior to the injection stop time. The injection stop time was defined as a time prior to the appearance of any signal spikes associated with the dissociation phase. The dissociation phase was selected to start 10 s after the injection stop time and included 280-295 s of the 5 min dissociation phase. The 1:1 Langmuir model describes the reaction A+B<=>AB. This model represents a single ligand binding to a single protein of interest (e.g., receptor). The 1:1 Langmuir model from the BIAevaluation software was used to determine the association rate constant ($k_a$) and the dissociation rate constant ($k_d$) and to calculate the equilibrium dissociation constant, $K_D$. $K_D=k_d/k_a$. $K_D=([A]\cdot[B])/[AB]$. The equilibrium dissociation constant, $K_D$, is equal to the inverse of the equilibrium association constant, $K_A$. $K_D=1/K_A$. The rate equations for the reaction (analyte A plus ligand B yielding complex AB), where A=analyte injected, B=free ligand, and t=time, are: $d[B]/dt=-(k_a[A][B]-k_d[AB])$ and $d[AB]/dt=k_a[A][B]-k_d[AB]$. Substituting R, Biacore response units (RU) at a given time, for [AB], Rmax-R for [B], and C (analyte concentration) for [A], the net rate expression in Biacore units is $dR/dt=k_aC(Rmax-R)-k_dR$, where R at t0=0, B[0]=Rmax, and AB[0]=0 RU, with the total response=[AB]+RI. The bulk shift (RI) was set to zero, and Rmax, $k_a$ and $k_d$ were fit globally for all curves.

The standard kinetic assays and data analyses described above were performed on protein preparations of mutant CTLA-4-Ig fusion protein of the invention, as well as LEA29Y-Ig and Orencia® fusion proteins. Tables 3 and 4 summarize the binding data for representative mutant CTLA-4-Ig fusion proteins of the invention.

Table 3 presents binding avidities of representative mutant CTLA-4-Ig fusion proteins to hCD86-mIg, as measured by the standard Biacore assay described above. Specifically, Table 3 shows the name of each mutant CTLA-4Ig fusion protein; the sequence identification number (SEQ ID NO) corresponding to the polypeptide sequence of the monomeric mutant CTLA-4 ECD fusion protein; the equilibrium dissociation constant ($K_D$ (Molar (M)) determined based on the binding avidity of the mutant protein to the hCD86-mIg; and the binding avidity of each mutant CTLA-4-Ig to the hCD86-mIg relative to the binding avidity of the Orencia® fusion protein to the hCD86-mIg. This relative binding avidity (shown in the far-right column) is shown as a fold improvement in binding avidity of the mutant fusion protein to the hCD86-mIg compared to the binding avidity of the Orencia® fusion protein to the hCD86-mIg. Each mutant CTLA-4-Ig fusion protein of the invention in Table 3 typically exists in solution as a dimeric fusion protein comprising two identical monomeric fusion proteins, wherein each monomeric protein comprises a mutant CTLA-4 ECD polypeptide (e.g., named D1, D1T, D2, D3, D4, etc.) fused directly at its C-terminus to the N-terminus of an IgG2 Fc polypeptide comprising the sequence of SEQ ID NO:184 or 218. Each such dimeric mutant CTLA-4-Ig can be made by using standard techniques known in the art. Alternatively, each such dimeric mutant CTLA-4-Ig fusion protein dimer can be made by using methods set forth in Example 3 above. Briefly, a nucleic acid sequence encoding a particular mutant CTLA-4 ECD identified in Table 3 (e.g., a nucleic acid sequence encoding a mutant CTLA-4 ECD polypeptide sequence identified in Table 3) can be cloned into the IgG2 Fc fusion vector, mammalian cells can be transfected with the vector, and the resultant fusion protein can be expressed, purified, and evaluated as described in Example 3. An exemplary nucleic acid sequence for each mutant CTLA-4 ECD is presented in the Sequence Listing included herewith. The Orencia® fusion protein, which comprises two monomeric fusion proteins, each monomeric fusion protein comprising a wild-type human CTLA-4 ECD fused to a modified IgG1 Fc, serves as the reference, i.e., with the binding avidity to hCD86-mIg set to 1. The $K_D$ values for LEA29Y-Ig fusion protein and the human CTLA-4-Ig fusion protein are also shown. In addition, the fold improvement in hCD86-mIg binding avidity of the LEA29Y-Ig compared to the hCD86-mIg binding avidity of the Orencia® protein is also shown. The binding avidities of the CTLA-4-IgG2 and Orencia® fusion proteins for hCD86-mIg are approximately equal, confirming that the differences between the human IgG2 polypeptide present in human CTLA-4-IgG2 and the modified IgG1 present in the Orencia® protein contribute little, if at all, to the respective hCD86-mIg binding affinities of these molecules. As is discussed in greater detail in Example 5 below, we have confirmed that the differences in immunosuppressive functional activities between mutant CTLA-4-Ig polypeptides of the invention and the Orencia® protein (or LEA29Y-Ig) cannot be attributed to their respective Ig Fc regions comprising different IgG isotypes.

As shown in Table 3, representative mutant CTLA-4-Ig fusion proteins of the invention have hCD86-mIg binding avidities that are: (1) at least about equal to or greater than the binding avidity of human CTLA-4-IgG2 ("hCTLA-4-IgG2") (which comprises two covalently linked monomeric fusion proteins, each such monomeric protein comprising the human CTLA-4 ECD polypeptide fused to an IgG2 Fc polypeptide); (2) at least about equal to or greater than the binding avidity of the Orencia® protein to the hCD86-mIg ligand; and/or (3) at least about equal to or greater than the binding avidity of the LEA29Y-Ig to the hCD86-mIg ligand. The fold improvement in binding avidity to the hCD86-mIg ligand relative to the binding avidity of the Orencia® protein to hCD86-mIg is indicated for each CTLA-4-Ig mutant (4th column in Table 3).

A majority of mutant CTLA-4-Ig fusion proteins were found to have a rate of dissociation from hCD86-mIg fusion protein that is slower than the rate of dissociation of the Orencia® fusion protein from hCD86-mIg (data not shown). A number of the mutant CTLA-4-Ig fusion proteins were found to have a rate of association to hCD86-mIg greater than the rate of association of Orencia® fusion protein to the same ligand (data not shown).

All of the mutant CTLA-4-Ig fusion proteins shown in Table 3 had hCD86-mIg equilibrium dissociation constants ($K_D$) that were lower than the hCD86-mIg equilibrium dissociation constant of human CTLA-4-IgG2 or Orencia® fusion protein. Furthermore, most of the mutant CTLA-4-Ig fusion proteins shown in Table 3 had hCD86-mIg equilibrium dissociation constants that were lower than hCD86-mIg equilibrium constant of LEA29Y-Ig.

All of the mutant CTLA-4-Ig fusion proteins shown in Table 3 had binding avidities for hCD86-mIg that are greater than the binding avidities of the human CTLA-4-IgG2 or Orencia® fusion protein for hCD86-mIg (the calculated fold improvement in hCD86-mIg binding avidity relative to the Orencia® fusion protein is shown the 4th column of Table 3). Moreover, many of the mutant CTLA-4-Ig fusion proteins shown in Table 3 had binding avidities for hCD86-mIg that are greater than the binding avidity of LEA29Y-Ig for hCD86-mIg (4th column of Table 3).

A mutant CTLA-4-Ig of the invention that has a higher binding avidity to the hCD86-mIg ligand than does the Orencia® or LEA29Y-Ig fusion protein will likely have an increased in vivo immunosuppressive potency compared to the hCTLA-4-IgG2, Orencia®, or LEA29Y-Ig fusion protein, respectively, such as in, e.g., therapeutic and/or prophylactic methods for suppressing an immune response in a subject (e.g., in the in vivo treatment of immune system diseases or disorders of mammals, such as e.g., humans, in which immunoinhibition or immunosuppression is desirable), methods for inhibiting rejection of a tissue or organ transplant from a donor by a recipient (e.g., by a mammal, such as, e.g., a human), and other methods described elsewhere herein.

TABLE 3

| Fusion Protein (dimer) | SEQ ID NO* (e.g., of mutant CTLA-4 ECD) | hCD86-mIg $K_D$ (M) | Binding Avidity for hCD86-mIg (Relative to Orencia ® fusion protein dimer) |
|---|---|---|---|
| Human CTLA-4-IgG2 | 162 | $3.95 \times 10^{-9}$ | 1.32x |
| Orencia ® fusion protein dimer | 164 | $5.23 \times 10^{-9}$ | 1 |
| LEA29Y-Ig | 166 | $1.05 \times 10^{-9}$-$5.23 \times 10^{-10}$ | 5x-10x |
| D1-IgG2 | 58 | $2.65 \times 10^{-9}$-$5.23 \times 10^{-10}$ | 2x-10x |
| D1T-IgG2 | 59 | $5.23 \times 10^{-10}$-$2.62 \times 10^{-10}$ | 10x-20x |
| D2-IgG2 | 60 | $2.62 \times 10^{-10}$-$1.31 \times 10^{-10}$ | 20x-40x |
| D3-IgG2 | 61 | $<1.31 \times 10^{-10}$ | >40x |
| D4-IgG2 | 62 | $2.65 \times 10^{-9}$-$5.23 \times 10^{-10}$ | 2x-10x |
| D5-IgG2 | 63 | $2.65 \times 10^{-9}$-$5.23 \times 10^{-10}$ | 2x-10x |
| D6-IgG2 | 64 | $2.65 \times 10^{-9}$-$5.23 \times 10^{-10}$ | 2x-10x |
| D20-IgG2 | 65 | $2.62 \times 10^{-10}$-$1.31 \times 10^{-10}$ | 20x-40x |
| D21-IgG2 | 66 | $2.62 \times 10^{-10}$-$1.31 \times 10^{-10}$ | 20x-40x |
| D23-IgG2 | 67 | $<1.31 \times 10^{-10}$ | >40x |
| D24-IgG2 | 68 | $<1.31 \times 10^{-10}$ | >40x |
| D26-IgG2 | 69 | $<1.31 \times 10^{-10}$ | >40x |
| D27-IgG2 | 70 | $<1.31 \times 10^{-10}$ | >40x |
| D28-IgG2 | 71 | $<1.31 \times 10^{-10}$ | >40x |
| D29-IgG2 | 72 | $<1.31 \times 10^{-10}$ | >40x |
| D31-IgG2 | 73 | $2.62 \times 10^{-10}$-$1.31 \times 10^{-10}$ | 20x-40x |
| D3-1-IgG2 | 1 | $<1.31 \times 10^{-10}$ | >40x |
| D3-2-IgG2 | 2 | $2.62 \times 10^{-10}$-$1.31 \times 10^{-10}$ | 20x-40x |
| D3-3-IgG2 | 3 | $2.62 \times 10^{-10}$-$1.31 \times 10^{-10}$ | 20x-40x |
| D3-4-IgG2 | 4 | $<1.31 \times 10^{-10}$ | >40x |
| D3-5-IgG2 | 5 | $2.62 \times 10^{-10}$-$1.31 \times 10^{-10}$ | 20x-40x |
| D3-6-IgG2 | 6 | $2.62 \times 10^{-10}$-$1.31 \times 10^{-10}$ | 20x-40x |
| D3-7-IgG2 | 7 | $<1.31 \times 10^{-10}$ | >40x |
| D3-8-IgG2 | 8 | $2.62 \times 10^{-10}$-$1.31 \times 10^{-10}$ | 20x-40x |
| D3-9-IgG2 | 9 | $<1.31 \times 10^{-10}$ | >40x |
| D3-11-IgG2 | 10 | $<1.31 \times 10^{-10}$ | >40x |
| D3-12-IgG2 | 11 | $<1.31 \times 10^{-10}$ | >40x |

TABLE 3-continued

| Fusion Protein (dimer) | SEQ ID NO* (e.g., of mutant CTLA-4 ECD) | hCD86-mIg $K_D$ (M) | Binding Avidity for hCD86-mIg (Relative to Orencia ® fusion protein dimer) |
|---|---|---|---|
| D3-14-IgG2 | 12 | $<1.31 \times 10^{-10}$ | >40x |
| D3-15-IgG2 | 13 | $<1.31 \times 10^{-10}$ | >40x |
| D3-16-IgG2 | 14 | $<1.31 \times 10^{-10}$ | >40x |
| D3-17-IgG2 | 15 | $<1.31 \times 10^{-10}$ | >40x |
| D3-19-IgG2 | 16 | $2.62 \times 10^{-10}$-$1.31 \times 10^{-10}$ | 20x-40x |
| D3-20-IgG2 | 17 | $2.62 \times 10^{-10}$-$1.31 \times 10^{-10}$ | 20x-40x |
| D3-21-IgG2 | 18 | $2.62 \times 10^{-10}$-$1.31 \times 10^{-10}$ | 20x-40x |
| D3-22-IgG2 | 19 | $2.62 \times 10^{-10}$-$1.31 \times 10^{-10}$ | 20x-40x |
| D3-23-IgG2 | 20 | $2.62 \times 10^{-10}$-$1.31 \times 10^{-10}$ | 20x-40x |
| D3-24-IgG2 | 21 | $2.62 \times 10^{-10}$-$1.31 \times 10^{-10}$ | 20x-40x |
| D3-25-IgG2 | 22 | $2.62 \times 10^{-10}$-$1.31 \times 10^{-10}$ | 20x-40x |
| D3-26-IgG2 | 23 | $2.62 \times 10^{-10}$-$1.31 \times 10^{-10}$ | 20x-40x |
| D3-27-IgG2 | 24 | $2.62 \times 10^{-10}$-$1.31 \times 10^{-10}$ | 20x-40x |
| D3-28-IgG2 | 25 | $5.23 \times 10^{-10}$-$2.62 \times 10^{-10}$ | 10x-20x |
| D3-29-IgG2 | 26 | $<1.31 \times 10^{-10}$ | >40x |
| D3-30-IgG2 | 27 | $2.62 \times 10^{-10}$-$1.31 \times 10^{-10}$ | 20x-40x |
| D3-31-IgG2 | 28 | $<1.31 \times 10^{-10}$ | >40x |
| D3-32-IgG2 | 29 | $<1.31 \times 10^{-10}$ | >40x |
| D3-33-IgG2 | 30 | $<1.31 \times 10^{-10}$ | >40x |
| D3-34-IgG2 | 31 | $2.62 \times 10^{-10}$-$1.31 \times 10^{-10}$ | 20x-40x |
| D3-39-IgG2 | 32 | $5.23 \times 10^{-10}$-$2.62 \times 10^{-10}$ | 10x-20x |
| D3-50-IgG2 | 33 | $2.62 \times 10^{-10}$-$1.31 \times 10^{-10}$ | 20x-40x |
| D3-52-IgG2 | 34 | $5.23 \times 10^{-10}$-$2.62 \times 10^{-10}$ | 10x-20x |
| D3-53-IgG2 | 35 | $<1.31 \times 10^{-10}$ | >40x |
| D3-54-IgG2 | 36 | $<1.31 \times 10^{-10}$ | >40x |
| D3-56-IgG2 | 38 | $<1.31 \times 10^{-10}$ | >40x |
| D3-62-IgG2 | 44 | $<1.31 \times 10^{-10}$ | >40x |
| D3-65-IgG2 | 47 | $<1.31 \times 10^{-10}$ | >40x |
| D3-66-IgG2 | 48 | $<1.31 \times 10^{-10}$ | >40x |
| D3-69-IgG2 | 50 | $<1.31 \times 10^{-10}$ | >40x |
| D3-70-IgG2 | 51 | $<1.31 \times 10^{-10}$ | >40x |
| D3-71-IgG2 | 52 | $<1.31 \times 10^{-10}$ | >40x |
| D3-72-IgG2 | 53 | $<1.31 \times 10^{-10}$ | >40x |
| D3-73-IgG2 | 54 | $<1.31 \times 10^{-10}$ | >40x |
| D3-74-IgG2 | 55 | $<1.31 \times 10^{-10}$ | >40x |
| D3-75-IgG2 | 56 | $<1.31 \times 10^{-10}$ | >40x |
| D3-76-IgG2 | 57 | $<1.31 \times 10^{-10}$ | >40x |

*Note:
The sequence identification numbers (SEQ ID NOS) shown in Table 3 for human CTLA-4-IgG2, Orencia ®, and LEA29Y-Ig fusion proteins are those of the polypeptide sequences of these Ig fusion proteins, respectively. The SEQ ID NO shown in Table 3 for each mutant CTLA-4-Ig fusion protein identifies the polypeptide sequence of the mutant CTLA-4 ECD of the identified mutant CTLA-4-Ig fusion protein. The data pertain to a mutant CTLA-4-Ig comprising a mutant CTLA-4 ECD (e.g., any of SEQ ID NOS: 1-48 and 58-73) fused at its N-terminus to the C-terminus of the IgG2 Fc polypeptide shown in SEQ ID NO: 184 or 218. Methods for making such fusion proteins are known in the art and are described herein. However, as noted above, we have found experimentally that a mutant CTLA-4-Ig made in CHO cells using a vector comprising a nucleotide sequence encoding the predicted hIgG2 Fc polypeptide shown in SEQ ID NO: 184 does not typically include the predicted C-terminal lysine (K) residue; thus, the hgG2 Fc polypeptide sequence of a mutant CTLA-4-IgG2 is that shown in SEQ ID NO: 218, which hIgG2 Fc polypeptide sequence does not include the C-terminal lysine residue as compared to the sequence shown in SEQ ID NO: 184. Exemplary fusion protein sequences which do not include the C-terminal lysine residue are shown in SEQ ID NOS: 205-214, 219, and 221.

Table 4 presents binding avidities of mutant CTLA-4-Ig fusion proteins to hCD80-mIg, as measured by the standard Biacore assay. Specifically, Table 4 shows the clone name of a mutant CTLA-4-Ig fusion protein; the sequence identification number (SEQ ID NO) corresponding to the polypeptide sequence of the monomeric mutant CTLA-4 ECD fusion protein; the equilibrium dissociation constant ($K_D$ (Molar (M)) for the hCD80-mIg ligand binding avidity assay; and the binding avidity of the mutant CTLA-4-Ig fusion protein to the hCD80-mIg ligand relative to the binding avidity of the Orencia® fusion protein to the same ligand. For each mutant protein, the fold improvement in binding avidity to the hCD80-mIg ligand compared to the binding avidity of the Orencia® fusion protein to the hCD80-mIg ligand is shown (4th column in Table 4). The Orencia® fusion protein serves as the reference, i.e., with the binding avidity to hCD80-mIg set to 1. The mutant CTLA-4-Ig fusion proteins typically exist as dimeric fusion proteins in solution. As shown in Table 4, dimeric mutant CTLA-4-Ig fusion proteins of the invention have binding avidities to the hCD80-mIg ligand that are: (1) at least about equal to or greater than the binding avidity of human CTLA-4-IgG2; (2) at least about equal to or greater than the binding avidity of the Orencia® fusion protein to the hCD80-mIg ligand; and/or (3) at least about equal to or greater than the binding avidity of the LEA29Y-Ig to the hCD80-mIg ligand. As discussed above, each dimeric mutant CTLA-4-Ig dimer can be made by using methods set forth in Example 3 above.

A number of mutant CTLA-4-Ig fusion proteins were found to have a rate of dissociation from hCD80-mIg fusion protein that is about equal to or greater than the rate of dissociation of the Orencia® fusion protein from the same ligand (data not shown). Some mutant CTLA-4-Ig fusion proteins were found to have a rate of association to hCD80-mIg about equal to or greater than the rate of association of Orencia® fusion protein to the same ligand (data not shown).

Many mutant CTLA-4-Ig fusion proteins shown in Table 4 had hCD80-mIg equilibrium dissociation constants ($K_D$) that were lower than the hCD80-mIg equilibrium dissociation constant of human CTLA-4-IgG2 or Orencia® fusion protein. Furthermore, several mutant CTLA-4-Ig fusion proteins shown in Table 4 had hCD80-mIg equilibrium dissociation constants that were at least about equal to the hCD80-mIg equilibrium constant of LEA29Y-Ig.

Many mutant CTLA-4-Ig fusion proteins shown in Table 4 had binding avidities for hCD80-mIg that are greater than the binding avidities of human CTLA-4-IgG2 or Orencia® fusion protein for the same ligand (fold improvement in hCD80-mIg binding avidity relative to the Orencia® fusion protein is shown the $4^{th}$ column). Additionally, several mutant CTLA-4-Ig fusion proteins shown in Table 4 had binding avidities for hCD80-mIg that are at least about equal to the binding avidity of LEA29Y-Ig for the same ligand.

A mutant CTLA-4-Ig of the invention that has a higher binding avidity to the hCD80-mIg than does the hCTLA-4-IgG1, Orencia®, or LEA29Y-Ig fusion protein will likely have an increased in vivo immunosuppressive potency compared to the hCTLA-4-IgG2, Orencia®, or LEA29Y-Ig fusion protein, respectively, such as in, e.g., therapeutic and/or prophylactic methods for suppressing an immune response in a subject (e.g., in the in vivo treatment of immune system diseases or disorders of mammals, such as e.g., humans, in which immunoinhibition or immunosuppression is desirable), methods for inhibiting rejection of a tissue or organ transplant from a donor by a recipient (e.g., by a mammal, such as, e.g., a human), and other methods described elsewhere herein.

TABLE 4

| Fusion Protein (dimer) | SEQ ID NO* (e.g., of mutant CTLA-4 ECD) | hCD80-mIg $K_D$ (M) | Binding Avidity for hCD80-mIg (Relative to Orencia ® fusion protein dimer) |
|---|---|---|---|
| hCTLA-4-IgG2 | 162 | $6.55 \times 10^{-10}$ | 1.34x |
| Orencia ® fusion protein dimer | 164 | $8.77 \times 10^{-10}$ | 1 |
| LEA29Y-Ig | 166 | $4.39 \times 10^{-10}$-$2.19 \times 10^{-10}$ | 2x-4x |
| D1-IgG2 | 58 | $<4.39 \times 10^{-10}$ | >2x |
| D1T-IgG2 | 59 | $<4.39 \times 10^{-10}$ | >2x |
| D2-IgG2 | 60 | $<4.39 \times 10^{-10}$ | >2x |

TABLE 4-continued

| Fusion Protein (dimer) | SEQ ID NO* (e.g., of mutant CTLA-4 ECD) | hCD80-mIg $K_D$ (M) | Binding Avidity for hCD80-mIg (Relative to Orencia ® fusion protein dimer) |
|---|---|---|---|
| D3-IgG2 | 61 | $1.75 \times 10^{-9}$-$4.39 \times 10^{-10}$ | 0.5x-2x |
| D4-IgG2 | 62 | $1.75 \times 10^{-9}$-$4.39 \times 10^{-10}$ | 0.5x-2x |
| D5-IgG2 | 63 | $1.75 \times 10^{-9}$-$4.39 \times 10^{-10}$ | 0.5x-2x |
| D6-IgG2 | 64 | $1.75 \times 10^{-9}$-$4.39 \times 10^{-10}$ | 0.5x-2x |
| D20-IgG2 | 65 | $1.75 \times 10^{-9}$-$4.39 \times 10^{-10}$ | 0.5x-2x |
| D21-IgG2 | 66 | $1.75 \times 10^{-9}$-$4.39 \times 10^{-10}$ | 0.5x-2x |
| D23-IgG2 | 67 | $<4.39 \times 10^{-10}$ | >2x |
| D24-IgG2 | 68 | $1.75 \times 10^{-9}$-$4.39 \times 10^{-10}$ | 0.5x-2x |
| D26-IgG2 | 69 | $1.75 \times 10^{-9}$-$4.39 \times 10^{-10}$ | 0.5x-2x |
| D27-IgG2 | 70 | $1.75 \times 10^{-9}$-$4.39 \times 10^{-10}$ | 0.5x-2x |
| D28-IgG2 | 71 | $1.75 \times 10^{-9}$-$4.39 \times 10^{-10}$ | 0.5x-2x |
| D29-IgG2 | 72 | $1.75 \times 10^{-9}$-$4.39 \times 10^{-10}$ | 0.5x-2x |
| D31-IgG2 | 73 | $1.75 \times 10^{-9}$-$4.39 \times 10^{-10}$ | 0.5x-2x |
| D3-1-IgG2 | 1 | $1.75 \times 10^{-9}$-$4.39 \times 10^{-10}$ | 0.5x-2x |
| D3-2-IgG2 | 2 | $1.75 \times 10^{-9}$-$4.39 \times 10^{-10}$ | 0.5x-2x |
| D3-3-IgG2 | 3 | $1.75 \times 10^{-9}$-$4.39 \times 10^{-10}$ | 0.5x-2x |
| D3-4-IgG2 | 4 | $1.75 \times 10^{-9}$-$4.39 \times 10^{-10}$ | 0.5x-2x |
| D3-5-IgG2 | 5 | $1.75 \times 10^{-9}$-$4.39 \times 10^{-10}$ | 0.5x-2x |
| D3-6-IgG2 | 6 | $1.75 \times 10^{-9}$-$4.39 \times 10^{-10}$ | 0.5x-2x |
| D3-7-IgG2 | 7 | $1.75 \times 10^{-9}$-$4.39 \times 10^{-10}$ | 0.5x-2x |
| D3-8-IgG2 | 8 | $1.75 \times 10^{-9}$-$4.39 \times 10^{-10}$ | 0.5x-2x |
| D3-9-IgG2 | 9 | $1.75 \times 10^{-9}$-$4.39 \times 10^{-10}$ | 0.5x-2x |
| D3-11-IgG2 | 10 | $1.75 \times 10^{-9}$-$4.39 \times 10^{-10}$ | 0.5x-2x |
| D3-12-IgG2 | 11 | $<4.39 \times 10^{-10}$ | >2x |
| D3-14-IgG2 | 12 | $1.75 \times 10^{-9}$-$4.39 \times 10^{-10}$ | 0.5x-2x |
| D3-15-IgG2 | 13 | $1.75 \times 10^{-9}$-$4.39 \times 10^{-10}$ | 0.5x-2x |
| D3-16-IgG2 | 14 | $1.75 \times 10^{-9}$-$4.39 \times 10^{-10}$ | 0.5x-2x |
| D3-17-IgG2 | 15 | $1.75 \times 10^{-9}$-$4.39 \times 10^{-10}$ | 0.5x-2x |
| D3-19-IgG2 | 16 | $1.75 \times 10^{-9}$-$4.39 \times 10^{-10}$ | 0.5x-2x |
| D3-20-IgG2 | 17 | $1.75 \times 10^{-9}$-$4.39 \times 10^{-10}$ | 0.5x-2x |
| D3-21-IgG2 | 18 | $1.75 \times 10^{-9}$-$4.39 \times 10^{-10}$ | 0.5x-2x |
| D3-22-IgG2 | 19 | $1.75 \times 10^{-9}$-$4.39 \times 10^{-10}$ | 0.5x-2x |
| D3-23-IgG2 | 20 | $1.75 \times 10^{-9}$-$4.39 \times 10^{-10}$ | 0.5x-2x |
| D3-24-IgG2 | 21 | $1.75 \times 10^{-9}$-$4.39 \times 10^{-10}$ | 0.5x-2x |
| D3-25-IgG2 | 22 | $1.75 \times 10^{-9}$-$4.39 \times 10^{-10}$ | 0.5x-2x |
| D3-26-IgG2 | 23 | $1.75 \times 10^{-9}$-$4.39 \times 10^{-10}$ | 0.5x-2x |
| D3-27-IgG2 | 24 | $1.75 \times 10^{-9}$-$4.39 \times 10^{-10}$ | 0.5x-2x |
| D3-28-IgG2 | 25 | $1.75 \times 10^{-9}$-$4.39 \times 10^{-10}$ | 0.5x-2x |
| D3-29-IgG2 | 26 | $1.75 \times 10^{-9}$-$4.39 \times 10^{-10}$ | 0.5x-2x |
| D3-30-IgG2 | 27 | $1.75 \times 10^{-9}$-$4.39 \times 10^{-10}$ | 0.5x-2x |
| D3-31-IgG2 | 28 | $<4.39 \times 10^{-10}$ | >2x |
| D3-32-IgG2 | 29 | $1.75 \times 10^{-9}$-$4.39 \times 10^{-10}$ | 0.5x-2x |
| D3-33-IgG2 | 30 | $1.75 \times 10^{-9}$-$4.39 \times 10^{-10}$ | 0.5x-2x |
| D3-34-IgG2 | 31 | $1.75 \times 10^{-9}$-$4.39 \times 10^{-10}$ | 0.5x-2x |
| D3-39-IgG2 | 32 | $1.75 \times 10^{-9}$-$4.39 \times 10^{-10}$ | 0.5x-2x |
| D3-50-IgG2 | 33 | $1.75 \times 10^{-9}$-$4.39 \times 10^{-10}$ | 0.5x-2x |
| D3-52-IgG2 | 34 | $1.75 \times 10^{-9}$-$4.39 \times 10^{-10}$ | 0.5x-2x |
| D3-53-IgG2 | 35 | $<4.39 \times 10^{-10}$ | >2x |
| D3-54-IgG2 | 36 | $1.75 \times 10^{-9}$-$4.39 \times 10^{-10}$ | 0.5x-2x |
| D3-56-IgG2 | 38 | $1.75 \times 10^{-9}$-$4.39 \times 10^{-10}$ | 0.5x-2x |
| D3-62-IgG2 | 44 | $<4.39 \times 10^{-10}$ | >2x |
| D3-65-IgG2 | 47 | $<4.39 \times 10^{-10}$ | >2x |
| D3-66-IgG2 | 48 | $<4.39 \times 10^{-10}$ | >2x |
| D3-69-IgG2 | 50 | $<4.39 \times 10^{-10}$ | >2x |
| D3-70-IgG2 | 51 | $<4.39 \times 10^{-10}$ | >2x |
| D3-71-IgG2 | 52 | $<4.39 \times 10^{-10}$ | >2x |
| D3-72-IgG2 | 53 | $<4.39 \times 10^{-10}$ | >2x |
| D3-73-IgG2 | 54 | $<4.39 \times 10^{-10}$ | >2x |
| D3-74-IgG2 | 55 | $<4.39 \times 10^{-10}$ | >2x |

TABLE 4-continued

| Fusion Protein (dimer) | SEQ ID NO* (e.g., of mutant CTLA-4 ECD) | hCD80-mIg $K_D$ (M) | Binding Avidity for hCD80-mIg (Relative to Orencia ® fusion protein dimer) |
|---|---|---|---|
| D3-75-IgG2 | 56 | $<4.39 \times 10^{-10}$ | >2x |
| D3-76-IgG2 | 57 | $1.75 \times 10^{-9}$-$4.39 \times 10^{-10}$ | 0.5x-2x |

*Note:
The SEQ ID NOS shown in Table 4 for human CTLA-4-IgG2, Orencia ®, and LEA29Y-Ig fusion proteins are those of the polypeptide sequences of these fusion proteins, respectively. The SEQ ID NO shown in Table 4 for each mutant CTLA-4-Ig fusion protein identifies the polypeptide sequence of the mutant CTLA-4 ECD of the identified mutant CTLA-4-Ig fusion protein. The data pertain to a mutant CTLA-4-Ig comprising a mutant CTLA-4 ECD (e.g., any of SEQ ID NOS: 1-48 and 58-73) fused at its N-terminus to the C-terminus of the IgG2 Fc polypeptide shown in SEQ ID NO: 184 or 218. However, we have found experimentally by LCMS analysis that a mutant CTLA-4-Ig made in CHO cells using a vector comprising a nucleotide sequence encoding the predicted hIgG2 Fc polypeptide shown in SEQ ID NO: 184 does not typically include the predicted C-terminal lysine (K) residue; thus, the hIgG2 Fc polypeptide sequence of a mutant CTLA-4-IgG2 is that shown in SEQ ID NO: 218, which hIgG2 Fc polypeptide sequence does not typically include the C-terminal lysine residue as compared to the sequence shown in SEQ ID NO: 184. Exemplary fusion protein sequences that do not include the C-terminal lysine residue are shown in SEQ ID NOS: 205-214, 219, and 221.

Monomeric Kinetic Assays.

Further confirmation of binding properties of mutant CTLA-4-Ig fusion proteins was obtained by monovalent kinetic binding assays. These assays measure the binding kinetics of a bivalent test protein (e.g., a dimeric mutant CTLA-4-Ig fusion protein) coated to sensor chips and monovalent ligand (papain-digested hCD86-mIg) in the mobile phase. Goat anti-human IgG antibody (Jackson ImmunoResearch, #109-005-098) was coupled to CM5 sensor chips according to the manufacturer's protocols, typically yielding 15,000 response units (RU). Ligand was captured by incubation of antibody-coated sensor chips with 10 µl of a 2 µg/ml solution of dimeric mutant CTLA-4-Ig fusion proteins in HBS-EP buffer at a flow rate of 10 µl/min. Ligand capture levels were typically 25-80 RU. Monomeric hCD86-mIg ligands (created by papain digestion and protein-A sepharose adsorption of hCD86-mIg, as described in Hermanson, G. T. BIOCONJUGATE TECHNIQUES, Academic Press, 1996) were diluted in HBS-EP buffer and flowed through test protein-coated sensor chips for 2 min at 30 µl/min, followed by 2 min incubation with HBS-EP buffer containing no protein at the same flow rate. Regeneration between cycles was performed by 3 min incubation with 10 mM glycine buffer (pH 1.7) at 30 µl/min. Typically, 8 dilutions of monomeric analyte proteins ranging from 3000 nM to 0.2 nM were analyzed against a blank reference (HBS-EP buffer alone) in duplicate. Rmax signal levels for binding to mutant CTLA-4-Ig proteins ranged from 10-60 RU.

For kinetic analysis, data from monomeric binding assays were selected as described above except that association data selection began and ended 5 s from the injection start and stop times, and dissociation data selection started 5 s after the injection stop time, and typically included 1-60 s of the dissociation period. Such data were also analyzed for steady state equilibrium affinities using the BIAevaluation software. Steady state binding levels for each concentration (Response$_{eq}$ ("Req") values) were averaged over 5-20 s range near the end of the sample injection using the BIAevaluation "General fit: average" function. Steady state affinity was determined from the Req vs. concentration plot using the BIAevaluation software according to the formula Req=$K_A \times C \times $Rmax$/(K_A \times C \times n+1)$, where C is the analyte concentration and n, the steric interference factor, is 1, and $K_D$=1/$K_A$. In some cases, substantial non-specific binding, represented by a residual flat R-value trace after dissociation, was observed. Such data were corrected by subtracting the residual R-values from the Req values. The $K_D$ was then calculated in GraphPad Prism software (GraphPad Software, Inc.) using the "one site-specific binding" model.

This monomeric binding assay was performed on a subset of representative mutant CTLA-4-Ig proteins and the results are summarized in Table 5. Overall, the degree of improvement in hCD86 ECD binding to mutant CTLA-4-Ig fusion proteins relative to LEA29Y-Ig observed in the monomeric binding assays was similar to that observed for hCD86-mIg binding to mutant CTLA-4-Ig fusion proteins relative to LEA29Y-Ig in the standard kinetic assays. Such results support the conclusion that the observed improvements in binding kinetics for the mutant proteins are due to real improvements in binding affinities of the mutant proteins (e.g., compared to Orencia® and/or LEA29Y-Ig fusion proteins) and are not due to potential artifacts caused by higher valency of aggregated protein preparations.

TABLE 5

| Fusion Protein (dimer) | SEQ ID NO* (e.g., of mutant CTLA-4 ECD) | Monomeric hCD86 ECD $K_D$ (M) | Binding Affinity for Monomeric hCD86 ECD (Relative to LEA29Y-Ig) |
|---|---|---|---|
| LEA29Y-Ig | 166 | $1.68 \times 10^{-6}$ | 1 |
| D3-IgG2 | 61 | $<3.36 \times 10^{-7}$ | >5x |
| D3-4-IgG2 | 4 | $<3.36 \times 10^{-7}$ | >5x |
| D3-11-IgG2 | 10 | $<3.36 \times 10^{-7}$ | >5x |
| D3-12-IgG2 | 11 | $<3.36 \times 10^{-7}$ | >5x |
| D3-14-IgG2 | 12 | $<3.36 \times 10^{-7}$ | >5x |
| D3-17-IgG2 | 15 | $<3.36 \times 10^{-7}$ | >5x |
| D3-20-IgG2 | 17 | $8.4 \times 10^{-7}$-$3.36 \times 10^{-7}$ | 2x-5x |
| D3-27-IgG2 | 24 | $8.4 \times 10^{-7}$-$3.36 \times 10^{-7}$ | 2x-5x |
| D3-29-IgG2 | 26 | $<3.36 \times 10^{-7}$ | >5x |
| D3-31-IgG2 | 28 | $<3.36 \times 10^{-7}$ | >5x |
| D3-53-IgG2 | 35 | $<3.36 \times 10^{-7}$ | >5x |

*Note:
The SEQ ID NO shown in Table 5 for LEA29Y-Ig is that of the polypeptide sequence of the LEA29Y-Ig fusion protein. The SEQ ID NO shown in Table 5 for each mutant CTLA-4-Ig fusion protein identifies the polypeptide sequence of the mutant CTLA-4 ECD present in the identified mutant CTLA-4-Ig fusion protein. The data pertain to a mutant CTLA-4-Ig comprising a mutant CTLA-4 ECD (e.g., any of SEQ ID NOS: 4, 10-12, 15, 17, 24, 26, 28, 35, and 61) fused at its N-terminus to the C-terminus of the IgG2 Fc polypeptide shown in SEQ ID NO: 184 or 218. However, we have found experimentally by LCMS analysis that a mutant CTLA-4-Ig made in CHO cells using a vector comprising a nucleotide sequence encoding the predicted hIgG2 Fc polypeptide shown in SEQ ID NO: 184 does not typically include the predicted C-terminal lysine (K) residue; thus, the hIgG2 Fc polypeptide sequence of a mutant CTLA-4-IgG2 is that shown in SEQ ID NO: 208, which hIgG2 Fc polypeptide sequence does not typically include the C-terminal lysine residue as compared to the sequence shown in SEQ ID NO: 184. Exemplary fusion protein sequences that do not include the C-terminal lysine residue are shown in SEQ ID NOS: 205-214, 219, and 221. Exemplary fusion protein sequences that include the C-terminal lysine residue are shown in SEQ ID NOS: 74-79, 197-200, 220, and 222.

Example 5

Measuring Biological Activity of CTLA-4 Mutants Using Human PBMC Proliferation Assays Anti-CD3 Antibody Stimulation CTLA-4-Ig and particular variants thereof have been shown to be potent inhibitors of T cell proliferation in vitro (see, e.g., Larson et al., Am. J. Transplant. 5, 443). To measure improved activity of mutant CTLA-4-Ig proteins in such assays, a peripheral blood mononuclear cell (PBMC) proliferation assay was developed.

Human blood (freshly collected from a donor program) was diluted with an equal volume of PBS and fractionated to isolate PBMCs using a Histopaque (Sigma, #10771) Ficoll gradient as per the manufacturer's recommended conditions. PBMCs were diluted in Growth Medium (DMEM/F12 medium (Invitrogen, #10565-018) supplemented with 10% FBS (Hyclone #SV30014.03) and 1×PSG (Invitrogen,

10378-016) and added to 96-well culture plates (BD Biosciences, #353077) at a density of 1×10⁵ cells/well. Test compounds were serially diluted in Growth Medium and added to wells in triplicate. Cell proliferation was initiated by addition of mouse anti-human CD3 antibody (BD Pharmingen: 555329) to a final concentration of 5 μg/ml. After incubation at 37° C. for 2 days (d), $^3$H thymidine (GE Healthcare, #TRK758-5MCI) was added at 1 μCi/well and plates were incubated at 37° C. for an additional 16 hr. Cells were harvested with a cell harvester (FilterMate Omnifilter-96 Harvester) using the manufacturer's recommended conditions and measured for $^3$H thymidine incorporation using a scintillation counter (Wallac Trilux, #1450-421). The degree of $^3$H thymidine incorporation ($^3$H thymidine uptake) is indicative of the degree of T cell proliferation. $^3$H-thymidine incorporation is measured by standard techniques. Proliferation of T cells is expressed as the mean counts per minute (cpm) of triplicate wells.

Cell proliferation data was analyzed with GraphPad Prism 5 software using a non-linear regression curve fit model (sigmoidal dose-response, variable slope) and the least squares fit method. The IC50 (also shown as $IC_{50}$) parameters and their associated 95% confidence intervals from the results are reported (Table 6). FIG. 6 shows cell proliferation curves from a representative PBMC proliferation assay (using anti-CD3 antibody stimulation) involving a set of exemplary mutant CTLA-4-Ig fusion proteins of the invention—i.e., D3-04-IgG2, D3-11-IgG2, D3-12-IgG2, and D3-14-IgG2 fusion proteins. The graph is a plot of $^3$H thymidine incorporation (counts per minute (cpm)) versus protein concentration (nanoMolar (nM)). $^3$H thymidine incorporation (3H thymidine uptake), which is indicative of the degree of cell proliferation, is measured by standard techniques.

The Orencia® and LEA29Y-Ig fusion proteins were included as controls for comparison. These results demonstrate that mutant CTLA-4-Ig Ig fusion proteins of the invention have significantly higher potency or greater ability than the Orencia® and/or LEA29Y-Ig fusion protein(s) in inhibiting or suppressing polyclonal T cell activation or T cell proliferation in vitro.

The PBMC proliferation assay was performed using other mutant CTLA-4-Ig fusion proteins of the invention. Table 6 provides a summary of the data for a representative set of mutant CTLA-4-Ig fusion proteins of the invention. Table 6 presents comparisons of mean IC50 values (nanomolar (nM)) for exemplary mutant CTLA-4-Ig fusion proteins versus controls (Orencia®, hCTLA-4-IgG2, and LEA29Y-Ig fusion proteins) in the PBMC proliferation assay (with anti-CD3 antibody stimulation). An IC50 value represents the concentration of a compound (e.g., mutant CTLA-4-Ig, hCTLA-4-IgG2, Orencia®, or LEA29Y-Ig fusion protein) that is required for 50% inhibition of T cell proliferation in vitro. IC50 values from individual experiments were averaged to provide mean IC50 values, which were used for statistical analyses. A one-way ANOVA with post hoc Dunnett or Bonferroni test was used to compare mutant CLTA-4-Ig fusion proteins and hCTLA-4-IgG2 to the Orencia® or LEA29Y-Ig fusion protein, respectively (C. W. Dunnett, New Tables for Multiple Comparisons with a Control, Biometrics 20(3):482-491 (September 1964); Abdi, Herve, "The Bonferroni and Sidak corrections for multiple comparisons", in ENCYCLOPEDIA OF MEASUREMENT AND STATISTICS (N.J. Salkind ed., Thousand Oaks, Calif. 2007); also available on the worldwide web at the web address utdallas.edu/~herve/Abdi-Bonferroni2007-pretty.pdf.). Statistical analysis of Ig fusion protein composed of one of the following mutant CTLA-4 ECD polypeptides—clones D24, D3-07, D3-15 and D3-16—was not performed as n=1. The term "SD (mean log IC50)" represents the standard deviation in mean log IC50 values.

TABLE 6

Summary of Data From Exemplary PBMC Proliferation Assays Using Anti-CD3 Antibody Stimulation

| Fusion Protein (dimer) | Mean IC50 (nM) | Mean Log IC50 (nM) | SD (Mean Log IC50) (nM) |
|---|---|---|---|
| Orencia ® fusion protein dimer | 5.16 | 0.71 | 0.51 |
| hCTLA-4-IgG2 | 8.46 | 0.93 | 0.43 |
| LEA29Y-Ig | 0.48[1] | −0.32 | 0.54 |
| D3-4-IgG2 | 0.05[1,2] | −1.27 | 0.45 |
| D3-7-IgG2 | 0.12 | −0.93 | NA |
| D3-11-IgG2 | 0.08[1,2] | −1.07 | 0.40 |
| D3-12-IgG2 | 0.06[1,2] | −1.27 | 0.17 |
| D3-14-IgG2 | 0.07[1,2] | −1.17 | 0.15 |
| D3-15-IgG2 | 0.21 | −0.69 | NA |
| D3-17-IgG2 | 0.04[1,2] | −1.36 | 0.37 |
| D3-20-IgG2 | 0.07[1,2] | −1.19 | 0.37 |
| D3-26-IgG2 | 0.15[1] | −0.83 | 0.49 |
| D3-27-IgG2 | 0.10[1,2] | −1.00 | 0.41 |
| D3-29-IgG2 | 0.07[1,2] | −1.13 | 0.53 |
| D3-30-IgG2 | 0.18[1] | −0.74 | 0.35 |
| D3-31-IgG2 | 0.04[1,2] | −1.42 | 0.25 |
| D3-32-IgG2 | 0.10[1] | −1.00 | 0.47 |
| D3-33-IgG2 | 0.12[1] | −0.94 | 0.69 |
| D3-34-IgG2 | 0.41[1] | −0.39 | 0.18 |
| D3-39-IgG2 | 0.47[1] | −0.33 | 0.21 |
| D3-50-IgG2 | 0.35[1] | −0.46 | 0.23 |
| D3-52-IgG2 | 0.49[1] | −0.31 | 0.20 |
| D3-53-IgG2 | 0.02[1,2] | −1.69 | 0.24 |
| D3-54-IgG2 | 0.17[1] | −0.77 | 0.22 |
| D3-56-IgG2 | 0.08[1] | −1.08 | 0.20 |
| D3-62-IgG2 | 0.05[1,2] | −1.29 | 0.23 |
| D3-69-IgG2 | 0.05[1,2] | −1.34 | 0.19 |
| D3-70-IgG2 | 0.08[1] | −1.10 | 0.10 |
| D3-71-IgG2 | 0.05 | −1.32 | NA |
| D3-72-IgG2 | 0.03[1,2] | −1.54 | 0.19 |
| D3-73-IgG2 | 0.23[1] | −0.64 | 0.25 |
| D3-75-IgG2 | 0.08[1] | −1.11 | 0.33 |
| D3-76-IgG2 | 0.13[1] | −0.88 | 0.36 |
| D3-IgG2 | 0.14[1] | −0.85 | 0.13 |
| D24-IgG2 | 0.12 | −0.93 | NA |

The superscripts shown in Table 6 are as follows:
[1]Statistically different to Orencia with p < 0.05, as determined by 1 way ANOVA with post hoc Dunnett test.
[2]Statistically different to LEA with p < 0.05, as determined by 1 way ANOVA post hoc Bonferroni test. The fusion proteins comprising D3-7, D3-15, D3-71 and D24 mutant CTLA-4 ECDs were tested once and therefore no statistical comparison could be performed.
Note:
The term "NA" in Table 6 means "not available".

Statistical analysis revealed that all of the mutant CTLA-4-Ig fusion proteins that were tested in at least two separate assays and are designated with the superscript (1) (see Table 6) were statistically superior in potency to the Orencia® and hCTLA-4-IgG2 fusion proteins (p<0.05) (i.e., have a greater ability to suppress or inhibit T cell proliferation in in vitro PBMC assays than the Orencia® and hCTLA-4-IgG2 fusion proteins). Those designated with the superscript (2) (see Table 6) were also statistically superior in potency to the LEA29Y-Ig fusion protein (p<0.05) (i.e., have a greater ability to suppress or inhibit T cell proliferation in in vitro PBMC assays than the LEA29Y-Ig fusion protein), as determined by one-way ANOVA with post hoc Dunnett and Bonferroni tests discussed supra. There was no statistical difference between human CTLA-4 fusion proteins comprising either the modified IgG1 Fc (as in Orencia®) or the wild-type IgG2 Fc (as in hCTLA4-IgG2). This finding implies that the differences in functional activities shown in Table 6 between the mutant CTLA-4-Ig fusion proteins of the invention (which each comprise a human IgG2 Fc) and either Orencia® or hCTLA4-IgG2 were as a direct consequence of amino acid changes (i.e., amino acid substitutions) made in the CTLA-4 ECD region. The differences in functional activities between these mutant CTLA-4-Ig fusion proteins of the invention and, for example, Orencia® (which comprises a modified IgG1 Fc) were not due to differences in their respective Ig Fc polypeptide sequences.

It is believed that given the increased abilities of mutant CTLA-4-Ig fusion proteins of the invention to suppress or inhibit T cell proliferation in in vitro assays as compared to Orencia®, LEA29Y-Ig, and/or hCTLA-4-IgG2 fusion proteins, such mutant proteins should also exhibit increased immunosuppressive potencies in in vivo therapeutic and/or prophylactic methods as compared to Orencia®, LEA29Y-Ig, and/or hCTLA-4-IgG2 fusion proteins. Each such mutant CTLA-4-Ig fusion protein of the invention is believed to have a greater ability to suppress or inhibit T cell proliferation in in vivo methods or applications relative to Orencia®, LEA29Y-Ig, and/or hCTLA-4-IgG2 fusion proteins, such as in, e.g., therapeutic and/or prophylactic methods for suppressing or inhibiting an immune response in a subject (e.g., in the in vivo treatment of immune system diseases or disorders in a mammal, such as e.g., a human), methods for suppressing or inhibiting rejection of a tissue or organ transplant from a donor by a recipient (e.g., by a mammal, such as e.g., a human), and/or other treatment or diagnostic methods described elsewhere herein.

Applying the same statistical analyses, we found no statistical difference between the Orencia® fusion protein (comprising human CTLA-4 ECD-mutant IgG1) and human CTLA-4-IgG2. Thus, it is believed that the differences in the Ig domains of these molecules (i.e., the mutant IgG1 of the Orencia® fusion protein and the human IgG2 of hCTLA-4-IgG2) did not affect the functionality of these molecules. See FIG. 11. The inhibition of proliferation observed with increasing doses of the Orencia® fusion protein was not significantly different from that observed with CTLA-4-IgG2, indicating that their respective immunosuppressive activities are not biased according to their different IgG isotypes, but rather result from their hCTLA-4 ECD polypeptides. Thus, the different immunosuppressive activities between mutant CTLA-4-Ig polypeptides of the invention and Orencia® fusion protein (or LEA29Y-Ig, since it contains the same Ig as in the Orencia® protein) cannot be attributed to their respective Fc regions comprising different IgG isotypes.

The invention includes monomeric mutant CTLA-4 ECD proteins that have an ability and, in some instances, a greater ability to suppress or inhibit T cell activation or proliferation than a monomeric human CTLA-4 protein or an extracellular domain thereof. Also provided are monomeric mutant CTLA-4 ECD fusion proteins that have an ability and, in some instances, a greater ability to suppress or inhibit T cell activation or proliferation than a monomeric hCTLA-4 Ig fusion protein or an extracellular domain thereof. Also included are mutant CTLA-4 ECD protein dimers that have an ability and, in some instances, a greater ability to suppress or inhibit T cell activation or proliferation than a dimer comprising two human CTLA-4 extracellular domains. Some mutant CTLA-4 ECD fusion protein dimers of the invention (e.g., mutant CTLA-4-ECD-Ig fusion protein dimers) have an ability and, in some instances, a greater ability to suppress or inhibit T cell activation or proliferation than a hCTLA-4-IgG2 fusion protein dimer, Orencia® fusion protein dimer, and/or LEA29YIg fusion protein dimer.

Example 6

Measuring Biological Activity of Mutant CTLA-4-Ig Molecules Using Human $CD4^+$ T Cell Proliferation Assays Human CTLA-4-Ig and particular variants thereof have been shown to inhibit T cell proliferation by blocking signaling of CD80 and CD86 though CD28 (Linsley P. S., Immunity 1:793-801 (1994); Larson C. P. et al., Am. J. Transplant. 5:443-453 (2005)). Because the mutant CTLA-4-Ig proteins of the invention are improved in binding avidity for the CD86-Ig ligand, a $CD4^+$ T cell proliferation assay was developed to measure activity of the mutant CTLA-4-Ig proteins in blocking signaling through CD86.

Creation of DNA Sequence Encoding a Full-Length Human CD86 Protein.

Plasmid pcDNA3.1 hB7.2 FL was created to encode the full-length human CD86 protein for expression on the surface of transfected cells. DNA encoding human CD86 was generated by PCR amplification of cDNA derived from human leukocytes (BD Biosciences, Cat#HL4050AH) using forward and reverse oligonucleotide primers designed based on sequence homology to the CD86-encoding nucleotide sequence set forth in SEQ ID NO:176. The primers were designed, made, and assembled using standard techniques well known by those of ordinary skill in the art and included stop and start codons and restriction sites as necessary. The PCR amplification procedures employed are also well known in the art. Such techniques are described in, e.g., Berger, Ausubel, and Sambrook, all supra. 50 nanogram (ng) cDNA was used as template in a 100 μl PCR reaction with 1 μM forward and reverse primers, Herculase Polymerase buffer (Stratagene; #600260) and 200 μM dNTPs for 30 amplification cycles (94° C., 30 s; 50° C., 30 s; 72° C., 60 s). The PCR product was purified by QiaQuick PCR Spin Columns (Qiagen #28106) and digested with restriction enzymes KpnI and NotI. Fragments were separated by agarose-gel electrophoresis, purified using Qiaquick Gel Extraction Kit (Qiagen, #28704) as per manufacturer's recommendation, and ligated into similarly digested plasmid pcDNA 3.1(+) (Invitrogen, Cat. #V790-20). Ligations were transformed into TOP10 *E. coli* cells (Qiagen, Cat. #C4040-10) as per manufacturer's recommendations. Transformed cells were incubated in LB (Luria broth media) containing 50 μg/ml carbenicillin at 250 rpm overnight at 37° C. and then used to make a maxiprep (Qiagen; #12362) stock of plasmid DNA as per the manufacturer's recommended conditions.

The predicted amino acid sequence of the full-length human CD86 protein is shown in SEQ ID NO:175. In this sequence, amino acid residues 1-23 comprise the predicted signal sequence, amino acid residues 24-241 comprise the human CD86 extracellular domain, amino acid residues 242-270 comprise the transmembrane domain, and amino acid residues 271-329 comprise the cytoplasmic domain.

Creation of Stable Cell Lines Expressing Human CD86 on the Cell Surface.

HEK293 cells were grown to 80-90% confluence in T-75 flasks containing 20 ml Growth Medium (DMEM/F12 medium (Invitrogen, Cat. #10565-018) supplemented with 10% FBS (Hyclone Cat. #SV30014.03) and 1×PSG (Invitrogen, Cat. #10378-016)). Cells were transfected with 10 μg plasmid DNA (pcDNA3.1 hB7.2 FL) mixed with 60 μl Fugene 6 (ROCHE, #11814443001) as per the manufacturer's recommended conditions. Cells were incubated for 2 days (d) at 37° C. in Growth Medium and further incubated for 10 d at 37° C. in Selection Medium (Growth Medium containing 300 µg/ml Geneticin (Invitrogen, #10131-027), changing the media every 2 d. To enable FACS sorting, transfected cells were stained with FITC-labeled anti-CD86 antibody (BD Biosciences, #555) as per the manufacturer's recommend conditions. Using a cell-sorter (Dako, MoFlo) gated for FITC signal, CD86-positive cells were individually sorted into 96-well culture plates (Sigma-Aldrich, #CLS-3596) containing 200 µl/well Growth Medium containing 25% Conditioned Medium (Growth Medium previously harvested from untransfected (or naïve) cell cultures). After incubation at 37° C. for 13-19 d, cells were dispersed by trypsin hydrolysis and transferred to 24-well culture plates containing 0.5 ml/well of Growth Medium. After incubation at 37° C. for 7 d, cells were dispersed by trypsin hydrolysis and transferred to T-75 flasks containing 20 ml Growth Medium. Final cell lines were selected based upon high levels of cell-surface CD86 expression as measured by FACS analysis of FITC-labeled anti-CD86 antibody stained cells using FACS Caliber (BD Biosciences), as per the manufacturer's recommended conditions.

$CD4^+$ T Cell Proliferation Assays.

$CD4^+$ T cells were enriched to >96% from human Buffy coat preps (Stanford University Blood Center, Stanford, Calif.) using the EasySep Human CD4 Positive Selection Kit (StemCell Technologies, #18052R) with a magnetic cell separator (RoboSep, StemCell Technologies, #20000) following manufacturer's recommendations. Enriched $CD4^+$ T cells were adjusted to a density of $1 \times 10^6$ cells/ml in Yssel's media (Gemini Bio-Products, #400-102) supplemented with 10% FBS (Hyclone SV30014.03) and added to 96 well tissue culture plates at 50 µl/well. HEK293 cells expressing membrane-bound human CD86 were irradiated at 6000 rads (Stanford Research Institute, Menlo Park, Calif.), adjusted to $1 \times 10^6$ cells/ml in the same medium and added to the culture plates at 50 µl/well. Test compounds were serially diluted in the same medium and added to wells in triplicate. Cell proliferation was initiated by addition of mouse anti-human CD3 antibody (BD Pharmingen: 555329) to a final concentration of 5 µg/ml. After incubation at 37° C. for 3 d, $^3H$ thymidine (GE Healthcare, #TRK758-5MCI) was added at 1 µCi/well and plates were incubated at 37° C. for an additional 18 hr. Cells were harvested using a cell harvester (Perkin Elmer Filter Harvester D961962) and $^3H$ thymidine was measured using a liquid scintillation counter (Wallac Trilux 1450) as per the manufacturer's recommended conditions. Cell proliferation data were analyzed with GraphPad Prism 5 software using a variable slope equation (Y=Bottom+(Top−Bottom)/$(1+10^{((LogIC50-X)(HillSlope))})$) to generate an IC50 for each test compound. The term "(LogIC50−X)(HillSlope)" is an exponent in the equation.

FIG. 7 shows cell proliferation curves from representative $CD4^+$ T cell proliferation assays involving an exemplary set of mutant CTLA-4-Ig fusion proteins of the invention—i.e., D3-04-IgG2, D3-11-IgG2, D3-12-IgG2, and D3-14-IgG2. Orencia® and LEA29Y-Ig fusion proteins were included as controls for comparison. The graph is a plot of $^3H$ thymidine incorporation (cpm) versus concentration (nM) of protein. $^3H$ thymidine incorporation is indicative of the degree of cell proliferation and is measured by standard techniques. These results demonstrate that mutant CTLA-4-Ig fusion proteins of the invention have significantly higher potency or greater ability than the Orencia® and/or LEA29Y-Ig fusion proteins in inhibiting or suppressing CD86 co-stimulation in vitro.

This $CD4^+$ T cell proliferation assay was performed on a number of other mutant CTLA-4-Ig fusion proteins of the invention. Table 7 provides a summary of the data for a set of exemplary mutant CTLA-4-Ig fusion proteins of the invention. Table 7 presents comparisons of mean IC50 values (nanomolar (nM)) for exemplary mutant CTLA-4-Ig fusion proteins versus reference controls (Orencia®, LEA29Y-Ig, and human CTLA-4-IgG2 fusion proteins) using the $CD4^+$ T cell proliferation assay. IC50s from individual experiments were averaged to provide mean IC50 values, which were used for statistical analyses. The term "SD (mean log IC50)" represents the standard deviation in mean log IC50 values.

TABLE 7

Summary of Data From Exemplary $CD4^+$ T Cell Proliferation Assays

| Fusion Protein (dimer) | Mean IC50 (nM) | Mean Log IC50 (nM) | SD (Mean Log IC50) (nM) |
|---|---|---|---|
| Orencia ® fusion protein dimer | 1.56 | 0.19 | 0.22 |
| hCTLA-4-IgG2 | 2.24 | 0.35 | 0.28 |
| LEA29Y-Ig | 0.21[1] | −0.67 | 0.25 |
| D3-02-IgG2 | 0.03 | −1.56 | NA |
| D3-03-IgG2 | 0.04[1,2] | −1.40 | 0.11 |
| D3-04-IgG2 | 0.03[1,2] | −1.47 | 0.02 |
| D3-06-IgG2 | 0.05[1] | −1.32 | 0.03 |
| D3-11-IgG2 | 0.03[1,2] | −1.52 | 0.07 |
| D3-12-IgG2 | 0.04[1,2] | −1.45 | 0.09 |
| D3-14-IgG2 | 0.04[1,2] | −1.37 | 0.11 |
| D3-15-IgG2 | 0.02[1,2] | −1.62 | 0.08 |
| D3-17-IgG2 | 0.03[1,2] | −1.47 | 0.11 |
| D3-20-IgG2 | 0.04[1,2] | −1.40 | 0.11 |
| D3-27-IgG2 | 0.04[1,2] | −1.37 | 0.10 |
| D3-29-IgG2 | 0.04[1,2] | −1.36 | 0.13 |
| D3-31-IgG2 | 0.03[1,2] | −1.58 | 0.21 |
| D3-34-IgG2 | 0.05[1,2] | −1.28 | 0.13 |
| D3-39-IgG2 | 0.05[1,2] | −1.35 | 0.10 |
| D3-50-IgG2 | 0.06[1,2] | −1.23 | 0.24 |
| D3-52-IgG2 | 0.07[1,2] | −1.14 | 0.24 |
| D3-53-IgG2 | 0.02[1,2] | −1.70 | 0.25 |
| D3-54-IgG2 | 0.04[1,2] | −1.40 | 0.12 |
| D3-56-IgG2 | 0.04[1,2] | −1.41 | 0.07 |
| D3-62-IgG2 | 0.04[1,2] | −1.44 | 0.09 |
| D3-65-IgG2 | 0.06[1,2] | −1.26 | 0.14 |
| D3-69-IgG2 | 0.03[1,2] | −1.59 | 0.14 |
| D3-70-IgG2 | 0.05[1,2] | −1.30 | 0.06 |
| D3-71-IgG2 | 0.04[1,2] | −1.43 | 0.09 |
| D3-72-IgG2 | 0.03[1,2] | −1.48 | 0.05 |
| D3-73-IgG2 | 0.06[1,2] | −1.26 | 0.18 |
| D3-75-IgG2 | 0.03[1,2] | −1.51 | 0.12 |
| D2-IgG2 | 0.03[1,2] | −1.52 | 0.18 |
| D3-IgG2 | 0.04[1,2] | −1.45 | 0.17 |

The superscripts shown in Table 7 are as follows:
[1] Statistically different to Orencia with p < 0.05, as determined by 1 way ANOVA with post hoc Dunnett test.
[2] Statistically different to LEA with p < 0.05, as determined by 1 way ANOVA post hoc Bonferroni test. The fusion protein comprising the D3-02 mutant CTLA-4 ECD was tested once and therefore no statistical comparison could be performed.

Statistical analysis revealed that all of the mutant CTLA-4-Ig fusion proteins that were tested in at least two separate assays and are designated with the superscript (1) (see Table 7) were statistically superior in potency to the Orencia® and hCTLA-4-IgG2 fusion proteins (p<0.05) (i.e., have a greater ability to suppress or inhibit T cell proliferation in in vitro $CD4^+$ T cell assays than the Orencia® and hCTLA-4-IgG2 fusion proteins). Those designated with the superscript (2) (see Table 7) were also statistically superior in potency to the LEA29Y-Ig fusion protein (p<0.05) (i.e., have a greater ability to suppress or inhibit T cell proliferation in in vitro $CD4^+$ T cell assays than the LEA29Y-Ig fusion protein), as determined by one-way ANOVA with post hoc Dunnett and Bonferroni tests discussed supra. There was no statistical difference between human CTLA-4 fusion proteins comprising either the modified IgG1 Fc (as in Orencia®) or the wild-type IgG2 Fc (as in hCTLA4-IgG2). This finding implies that the differences in functional activities shown in Table 7 between the mutant CTLA-4-Ig fusion proteins of the invention (which each comprise a human IgG2 Fc) and either Orencia® or hCTLA4-IgG2 were as a direct consequence of amino acid changes (i.e., amino acid substitutions) made in the CTLA-4 ECD region. The differences in functional activities between these mutant CTLA-4-Ig fusion proteins of the invention and, for example, Orencia® (which comprises a modified IgG1 Fc) were not due to differences in their respective Ig Fc polypeptide sequences.

It is believed that given the increased abilities of mutant CTLA-4-Ig proteins of the invention to suppress or inhibit CD86-mediated co-stimulation of T cells (e.g., human T cells) in in vitro assays as compared to Orencia®, LEA29Y-Ig, and/or hCTLA-4-IgG2 fusion proteins, such mutant proteins should also exhibit increased immunosuppressive potencies in in vivo therapeutic and/prophylactic methods or applications as compared to Orencia®, LEA29Y-Ig, and/or human CTLA-4-Ig fusion proteins (e.g., human CTLA-4-IgG2 ("hCTLA-4-IgG2")), respectively. In one aspect, mutant CTLA-4-Ig fusion proteins of the invention are believed to have a greater ability to suppress or inhibit CD86-mediated co-stimulation of T cells (e.g., human T cells) in in vivo methods or applications compared to Orencia®, LEA29Y-Ig, and/or human CTLA-4-Ig (e.g., hCTLA-4-IgG2) fusion proteins, respectively, such as in, e.g., therapeutic and/or prophylactic methods for suppressing or inhibiting an immune response in a subject (e.g., in the in vivo treatment of immune system diseases or disorders in e.g., a mammal, such as, e.g., a human), methods for suppressing or inhibiting rejection of a tissue or organ transplant from a donor by a recipient (e.g., by a mammal, such as, e.g., a human), and/or other treatment or diagnostic methods described elsewhere herein.

Example 7

Measuring Biological Activity of Mutant CTLA-4-Ig Molecules Using Human PBMC Proliferation Assays Recall Antigen Stimulation The activation of memory T cells is an important aspect of autoimmunity (Rogers N. J., et al. Eur. J. Immunol. 35:2909-2919 (2005)). To measure immunosuppressive activity of mutant CTLA-4-Ig proteins in this respect, a peripheral blood mononuclear cell (PBMC) proliferation assay was developed using PPD antigen stimulation.

Human blood (freshly collected from a donor program) was diluted with an equal volume of PBS and fractionated to isolate PBMCs using a Histopaque (Sigma, #10771) Ficoll gradient as per the manufacturer's recommended conditions. PBMCs were diluted in RPMI medium (Sigma, #R8758) supplemented with 10% FBS (Hyclone #SV30014.03) and 1×PSG (penicillin, streptomycin and glutamine) (Invitrogen, #10378-016) and added to 96-well culture plates (BD Biosciences, #353077) at a density of $1 \times 10^5$ cells/well. Test compounds were serially diluted in the same medium and added to wells in quadruplicate. Cell proliferation was initiated by addition of PPD antigen (purified protein derivative from *Mycobacterium tuberculosis*, Mycos, #P-1000-001) to a final concentration of 5 µg/ml. After incubation at 37° C. for 5 d, $^3$H thymidine (GE Healthcare, #TRK758-5MCI) was added at 1 µCi/well and plates were incubated at 37° C. for an additional 18 hr. Cells were harvested with a cell harvester (FilterMate Omnifilter-96 Harvester, Perkin Elmer) using the manufacturer's recommended conditions and measured for $^3$H thymidine incorporation using a scintillation counter (Wallac Trilux, #1450-421). Cell proliferation data was analyzed with GraphPad Prism 5 software using a non-linear regression curve fit model (sigmoidal dose-response, variable slope) and the least squares fit method. The $IC_{50}$ (or "IC50") parameters and their associated 95% confidence intervals are reported.

FIG. 8 shows cell proliferation curves from representative PBMC proliferation assays involving a set of exemplary mutant CTLA-4-Ig fusion proteins of the invention—i.e., D3-IgG2, D3-12-IgG2, D3-17-IgG2, and D3-29-IgG2 fusion proteins. Orencia® and LEA29Y-Ig fusion proteins were included as controls for comparison. The graph is a plot of $^3$H thymidine incorporation (cpm) versus protein concentration (nM). $^3$H thymidine incorporation, which is indicative of the degree of cell proliferation, is measured by standard techniques. These results demonstrate that, in one aspect, mutant CTLA-4-Ig fusion proteins of the invention have significantly higher potency than Orencia® and/or LEA29Y-Ig proteins in inhibiting or suppressing memory T cell proliferation in vitro (e.g., mutant CTLA-4-Ig proteins have a greater ability than Orencia® and/or LEA29Y-Ig proteins in inhibiting or suppressing memory T cell proliferation in vitro in human PBMC proliferation assays (recall antigen stimulation)).

This PBMC proliferation assay with PPD antigen stimulation was performed on a number of other mutant CTLA-4-Ig fusion proteins of the invention. Table 8 provides a summary of the data for a set of exemplary mutant CTLA-4-Ig fusion proteins of the invention. Table 8 presents comparisons of mean IC50 values (nanomolar (nM)) for exemplary mutant CTLA-4-Ig fusion proteins versus reference controls (Orencia® and LEA29Y-Ig fusion proteins) using the PBMC proliferation assay with recall antigen stimulation. IC50 values from individual experiments were averaged to provide mean IC50 values, which were used for statistical analyses. The term "SD (mean log IC50)" represents the standard deviation in mean log IC50 values.

TABLE 8

Summary of Data From Exemplary PBMC Proliferation Assays Using PPD Antigen Stimulation

| Fusion Protein (dimer) | Mean IC50 (nM) | Mean Log IC50 (nM) | SD (Mean Log IC50) (nM) |
| --- | --- | --- | --- |
| Orencia ® fusion protein dimer | 5.92 | 0.67 | 0.37 |
| LEA29Y-Ig | 0.31 | −0.71 | 0.53 |
| D3-IgG2 | 0.03 | −1.49 | NA |
| D3-12-IgG2 | 0.06 | −1.27 | 0.17 |
| D3-14-IgG2 | 0.07 | −1.17 | 0.15 |
| D3-17-IgG2 | 0.07 | −1.24 | 0.25 |
| D3-20-IgG2 | 0.13 | −0.91 | 0.18 |
| D3-27-IgG2 | 0.17 | −0.84 | 0.30 |
| D3-29-IgG2 | 0.07 | −1.16 | 0.18 |
| D3-34-IgG2 | 0.51 | −0.29 | NA |
| D3-50-IgG2 | 0.28 | −0.55 | NA |
| D3-53-IgG2 | 0.05 | −1.29 | NA |
| D3-54-IgG2 | 0.01 | −2.00 | NA |
| D3-56-IgG2 | 0.01 | −1.92 | NA |
| D3-69-IgG2 | 0.01 | −2.00 | NA |
| D3-71-IgG2 | 0.01 | −1.87 | NA |
| D3-75-IgG2 | 0.01 | −2.02 | NA |
| D3-76-IgG2 | 0.01 | −1.89 | NA |

Note:
The term "NA" in Table 8 means "not available".

Statistical analyses revealed that all mutant CTLA-4-Ig fusion proteins tested were statistically superior in potency to both Orencia® and LEA29Y-Ig fusion proteins with p<0.05, as determined by 1 way ANOVA with post hoc Dunnett and Bonferroni tests, respectively, discussed supra (e.g., the mutant CTLA-4-Ig fusion proteins have a greater ability than Orencia® and/or LEA29Y-Ig fusion proteins in inhibiting or suppressing memory T cell proliferation in vitro in human PBMC proliferation assays (recall antigen stimulation)).

It is believed that given the increased abilities of mutant CTLA-4-Ig fusion proteins of the invention to suppress or inhibit proliferation of memory T cells (e.g., human memory T cells) in in vitro assays as compared to Orencia® and/or LEA29Y-Ig fusion proteins, such mutant proteins should also exhibit increased immunosuppressive potencies in in vivo therapeutic and/or prophylactic methods or applications as compared to Orencia®, LEA29Y-Ig, and/or human CTLA-4-Ig (e.g., human CTLA-4-IgG2) fusion proteins. In one aspect, mutant CTLA-4-Ig proteins of the invention are believed to have a greater ability to suppress or inhibit proliferation of memory T cells (e.g., human memory T cells) in an in vivo method or application compared to Orencia®, LEA29Y-Ig, and/or human CTLA-4-Ig (e.g., human CTLA-4-IgG2) fusion proteins, such as in, e.g., therapeutic and/or prophylactic methods for suppressing or inhibiting an immune response in a subject (e.g., in the in vivo treatment of immune system diseases or disorders in, e.g., a mammal, such as, e.g., a human), methods for suppressing or inhibiting rejection of a tissue or organ transplant from a donor by a recipient (e.g., by a mammal, such as, e.g., a human), and/or other treatment or diagnostic methods described elsewhere herein.

Example 8

Measuring Biological Activity of Mutant CTLA-4-Ig Molecules Using Human MLR (Mixed Lymphocyte Reaction) Assays CTLA-4-Ig and variants thereof are potent inhibitors of primary alloresponses in vitro (Vaughan, A. N. et al., J. Immunol. 165:3175-3181 (2000); Wallace P. M., et al., Transplantation 58:602-610 (1994)). To measure improved activity of mutant CTLA-4-Ig proteins in such assays, a human mixed lymphocyte reaction (MLR) cell proliferation assay was developed.

Human blood (freshly collected from a human donor program) was diluted with an equal volume of PBS and fractionated to isolate PBMCs using a Histopaque (Sigma, #10771) Ficoll gradient as per the manufacturer's recommended conditions. PBMC from one donor were diluted in RPMI medium (Sigma, #R8758) supplemented with 10% FBS (Hyclone #SV30014.03) and 1×PSG (Invitrogen, #10378-016) and added to 96-well culture plates (BD Biosciences, #353077) at a density of $1\times10^5$ cells/well. PBMC from a different donor were irradiated at 2500 rads, diluted in the same media and added to the same plates at a density of $1\times10^5$ cells/well. Test compounds were serially diluted in the same medium and added to wells in quadruplicate. After incubation at 37° C. for 5 d, $^3$H thymidine (GE Healthcare, #TRK758-5MCI) was added at 1 μCi/well and plates were incubated at 37° C. for an additional 18 hr. Cells were harvested with a cell harvester (FilterMate Omnifilter-96 Harvester, Perkin Elmer) using the manufacturer's recommended conditions and measured for $^3$H thymidine incorporation using a scintillation counter (Wallac Trilux, #1450-421). Cell proliferation data was analyzed with GraphPad Prism 5 software using a non-linear regression curve fit model (sigmoidal dose-response, variable slope) and the least squares fit method. The IC50 parameters and their associated 95% confidence intervals are reported.

FIG. 9 shows cell proliferation curves from representative MLR proliferation assays involving an exemplary mutant CTLA-4-Ig fusion protein of the invention: D3-IgG2. Orencia® and LEA29Y-Ig fusion proteins were included as controls for comparison. The graph is a plot of $^3$H thymidine incorporation (cpm) versus protein concentration (nM). $^3$H thymidine incorporation, which is indicative of the degree of cell proliferation, is measured by standard techniques. These results demonstrate that D3-IgG2 has significantly higher potency than Orencia® and/or LEA29Y-Ig fusion proteins in inhibiting or suppressing primary allostimulation of T cells in vitro (e.g., D3-IgG2 has a greater ability to suppress or inhibit primary allostimulation of T cell proliferation in an in vitro MLR assay than Orencia® or LEA29Y-Ig fusion proteins).

This MLR assay was performed on a number of other mutant CTLA-4-Ig fusion proteins of the invention. Table 9 provides a summary of the data for a set of exemplary mutant CTLA-4-Ig fusion proteins of the invention. Table 9 presents comparisons of mean IC50 values (nanomolar (nM)) for exemplary mutant CTLA-4-Ig fusion proteins versus reference controls (Orencia® and LEA29Y-Ig fusion proteins) in the MLR assay. IC50 values from two separate experiments were averaged to provide mean IC50 values. The term "SD (mean log IC50)" represents the standard deviation in mean log IC50 values. The mean IC50 values for the mutant CTLA-4-Ig fusion proteins shown in Table 9 were lower than the respective mean IC50 values of Orencia® and LEA29Y-Ig fusion proteins.

In one aspect, the invention provides mutant CTLA-4-Ig fusion proteins that are believed to be superior in potency to Orencia® and/or LEA29Y-Ig fusion proteins (e.g., the mutant CTLA-4-Ig fusion proteins are believed to have a greater ability to suppress or inhibit primary allostimulation of T cell proliferation in an in vitro MLR assay than Orencia® and/or LEA29Y-Ig fusion proteins).

It is believed that based on the expected enhanced abilities of mutant CTLA-4-Ig fusion proteins of the invention to suppress or inhibit primary allostimulation of T cells (e.g., human T cells) in in vitro assays as compared to Orencia® and/or LEA29Y-Ig fusion proteins, such mutant proteins should also exhibit increased immunosuppressive potencies in in vivo therapeutic and/prophylactic methods or applications as compared to Orencia® and/or LEA29Y-Ig fusion proteins.

In one aspect, mutant CTLA-4-Ig fusion proteins of the invention have significantly higher potency than Orencia®, LEA29Y-Ig, and/or human CTLA-4-Ig (e.g., human CTLA-4-IgG2) fusion proteins in inhibiting or suppressing primary allostimulation of T cells in vitro (e.g., mutant CTLA-4-Ig fusion proteins have a greater ability to suppress or inhibit primary allostimulation of T cell proliferation in an in vitro MLR assay than Orencia®, LEA29Y-Ig, and/or human CTLA-4-Ig) fusion proteins. In one aspect, a mutant CTLA-4-Ig of the invention is believed to have a greater ability to suppress or inhibit primary allostimulation of T cells (e.g., human T cells) in an in vivo method or application compared to Orencia®, LEA29Y-Ig, and/or human CTLA-4-Ig fusion proteins, such as in, e.g., a therapeutic and/or prophylactic method of suppressing or inhibiting an immune response in a subject (e.g., in the in vivo treatment of immune system diseases or disorders in a mammal, such as e.g., a human), a method of suppressing or inhibiting rejection of a tissue or organ transplant from a donor by a recipient (e.g., by a mammal, such as e.g., a human), and/or other treatment or diagnostic methods described elsewhere herein.

TABLE 9

Summary of Data From Exemplary MLR Assays

| Fusion Protein (dimer) | Mean IC50 (nM) | Mean Log IC50 (nM) | SD (Mean Log IC50) (nM) |
|---|---|---|---|
| Orencia ® fusion protein dimer | 12.53 | 1.05 | 0.23 |
| LEA29Y-Ig | 0.92 | −0.19 | 0.48 |
| D3-IgG2 | 0.06 | −1.26 | NA |
| D3-12-IgG2 | 0.09 | −1.11 | 0.34 |
| D3-14-IgG2 | 0.08 | −1.20 | 0.43 |
| D3-17-IgG2 | 0.09 | −1.15 | 0.43 |
| D3-20-IgG2 | 0.14 | −1.11 | 0.64 |
| D3-27-IgG2 | 0.13 | −1.29 | 0.86 |
| D3-29-IgG2 | 0.11 | −1.14 | 0.54 |
| D3-34-IgG2 | 0.10 | −1.09 | 0.39 |
| D3-53-IgG2 | 0.02 | −1.64 | 0.11 |
| D3-54-IgG2 | 0.07 | −1.13 | NA |
| D3-56-IgG2 | 0.06 | −1.23 | NA |
| D3-69-IgG2 | 0.04 | −1.41 | NA |
| D3-71-IgG2 | 0.05 | −1.32 | NA |
| D3-75-IgG2 | 0.08 | −1.11 | NA |
| D3-76-IgG2 | 0.08 | −1.11 | NA |

Note:
The term "NA" in Table 9 means "not available".

Example 9

An adult human patient suffering from rheumatoid arthritis may be treated with a soluble mutant CTLA-4-Ig fusion protein as follows. A pharmaceutical composition comprising a soluble mutant CTLA-4-Ig fusion protein of the invention and a pharmaceutically acceptable excipient or carrier (e.g., PBS) is prepared. An exemplary soluble mutant CTLA-4-Ig fusion protein comprises two identical monomeric mutant CTLA-4-Ig fusion proteins linked together by one or more disulfide bonds, wherein each such monomeric fusion protein comprises a mutant CTLA-4 ECD polypeptide of the invention comprising a polypeptide sequence selected from any of SEQ ID NOS:1-73 fused at its C-terminus to the N-terminus of a human IgG2 Fc polypeptide. Exemplary fusion proteins include those comprising polypeptide sequences set forth in any of SEQ ID NOS:74-79, 197-200, 205-214, and 219-222. Such fusion proteins are typically expressed in dimeric form. The concentration of the fusion protein in the pharmaceutical composition may be in a range of from about 0.05 mg/ml to about 200 mg/ml, from about 1 mg/ml to about 150 mg/ml, from about 25 mg/ml to about 120 mg/ml, from about 1 mg/ml to about 100 mg/ml, from about 25 mg/ml to about 100 mg/ml, from about 50 mg/ml to about 100 mg/ml, from about 50 mg/ml to about 75 mg/ml, from about 100 mg/ml to about 150 mg/ml, and the like. For example, the fusion protein concentration in the pharmaceutical composition may be about 1 mg/ml, 5 mg/ml, 10 mg/ml, 15 mg/ml, 25 mg/ml, 30 mg/ml, 40 mg/ml, 50 mg/ml, 60 mg/ml, 70 mg/ml, 80 mg/ml, 90 mg/ml, 100 mg/ml, 150 mg/ml, or 200 mg/ml. The pH of such pharmaceutical composition is about pH 4 to about pH 10, including about pH 5 to about pH 9, about pH 6.5 to about pH 8.5, preferably about pH 6.0 to pH 8.0, about 6.5 to pH 7.5, or about pH 7.0 to about pH 8.0.

Treatment of the patient's rheumatoid arthritis is carried out by administering a therapeutically effective amount of the mutant CTLA-4-Ig to the patient (e.g., effective dose) by intravenous or subcutaneous injection. The site of injection may be, e.g., the patient's arm, torso, or leg. The effective dose of the mutant CTLA-4-Ig fusion protein administered is typically, but not limited to, e.g., from about 0.01 mg/kg to about 100 mg/kg body weight of the adult human patient, such as, e.g., from about 0.01-5.0 mg/kg, about 0.01-3.0 mg/kg, about 0.05-2.5 mg/kg, about 0.1-2.0 mg/kg, about 0.1-1.0 mg/kg, about 0.01-0.05 mg/kg, about 0.5-1.5 mg/kg, about 1.0-4.0 mg/kg, about 1.0-3.0 mg/kg, about 1.0-2.0 mg/kg, including, but not limited to, about 0.01 mg/kg, 0.05 mg/kg, 0.075 mg/kg, 0.1 mg/kg, 0.15 mg/kg, 0.2 mg/kg, 0.25 mg/kg, 0.3 mg/kg, 0.5 mg/kg, 0.75 mg/kg, 1 mg/kg, 1.25 mg/ml, 1.5 mg/kg, 2 mg/kg, 2.5 mg/kg, 3 mg/kg, 4 mg/kg, 5 mg/kg, 10 mg/kg, 20 mg/kg, 25 mg/kg, 50 mg/kg, 75 mg/kg, or 100 mg/kg body weight of the patient is administered to the patient. Alternatively, an effective amount or dose or dose range described in the "Methods of the Invention" section above may be used. The dose of the fusion protein to be administered is determined based on the potency of the fusion protein and/or the severity of the patient's symptoms or signs of rheumatoid arthritis. The total amount of mutant CTLA-4-Ig fusion protein administered to the patient may be, e.g., from about 0.01 mg to about 100 mg, typically from about 1 mg to 100 mg, from about 10 mg to 100 mg, from about 10 mg to about 75 mg, or from about 10 to about 50 mg. The volume of pharmaceutical composition administered to the patient is determined based upon the concentration of fusion protein in the composition and the dose of fusion protein to be administered. For subcutaneous injection, one to two milliliters of the pharmaceutical composition comprising the fusion protein is typically administered per injection. For intravenous injection, an appropriate volume of the pharmaceutical composition comprising the fusion protein can be administered.

Following injection of the initial dose, a second identical dose of the fusion protein may be administered to the patient subcutaneously (e.g., s.c. injection) or intravenously (e.g., i.v. injection) at, e.g., 1, 2, 3, or 4 weeks after the initial dose. The dosing schedule may be one dose every two weeks, one dose/month, one dose every two months, etc. depending, e.g., upon the patient's condition. Subsequent doses may be administered every four weeks or more or less frequently, as necessary. The frequency of dosing may vary depending upon the patient's condition and may depend upon the severity of the patient's symptoms or signs of rheumatoid arthritis.

In an exemplary aspect, an amount of a pharmaceutical composition comprising a mutant CTLA-4-Ig fusion protein dimer of the invention (such as D3-29-IgG2, D3-54-IgG2, D3-56-IgG2, D3-69-IgG2, etc.) and a pharmaceutically acceptable excipient sufficient to provide a dose of the fusion protein dimer of about 0.5 mg/kg body weight is administered by subcutaneous injection to a human suffering from rheumatoid arthritis once per week or once per month, as needed, depending upon the patient's condition and response to the drug.

In another exemplary aspect, an amount of a pharmaceutical composition comprising a CTLA-4-Ig fusion protein dimer of the invention (such as D3-29-IgG2, D3-54-IgG2, D3-56-IgG2, D3-69-IgG2, etc.) and a pharmaceutically acceptable excipient sufficient to provide a dose of the fusion protein dimer of about 10 mg/kg is administered intravenously to a human suffering from rheumatoid arthritis once per week or once per month, as needed, depending upon the patient's condition and response to the drug. Standard i.v. procedures can be used for such administration. For example, the pharmaceutical composition can be infused into the human with another fluid, such as a sterile saline solution, dextrose solution, or other isotonic solution, using a standard continuous intravenous drip through a standard intravenous access device.

Each above-described treatment method by s.c. or i.v. injection is expected to reduce or alleviate one or more signs, symptoms, or biological responses associated with rheumatoid arthritis, such as, e.g., inflammation, joint tenderness, joint swelling, pain, tissue atrophy, and stiffness, in the patient. Such treatment may reduce further progression of the disease in the patient, particularly in the connective, muscular, and skeletal tissues. For example, such treatment may reduce the progression of damage to or deterioration of connective tissue, atrophy muscular tissue, bone, joints, cartilage, and/or spinal column, and the like in the patient. Additional clinical symptoms of the disease, including damage caused to the skin, central nervous system or organs, may also be lessened or alleviated. Such treatment may also improve physical functioning of the patient.

Example 10

An adult human patient undergoing maintenance therapy for prevention of organ transplant rejection may be treated with a soluble mutant CTLA-4-Ig fusion protein as follows. A pharmaceutical composition comprising a soluble mutant CTLA-4-Ig fusion protein of the invention and a pharmaceutically acceptable excipient or carrier (e.g., PBS or the like) is prepared. An exemplary soluble mutant CTLA-4-Ig fusion protein comprises two identical monomeric mutant CTLA-4-Ig fusion proteins linked together by one or more disulfide bonds, wherein each such monomeric fusion protein comprises a mutant CTLA-4 ECD polypeptide of the invention comprising a polypeptide sequence selected from any of SEQ ID NOS:1-73 fused at its C-terminus to the N-terminus of a human IgG2 Fc polypeptide. Exemplary fusion proteins include those comprising polypeptide sequences set forth in any of SEQ ID NOS:74-79, 197-200, 205-214, and 219-222. The concentration of the fusion protein in the pharmaceutical composition may be in a range of from about 0.05 mg/ml to about 200 mg/ml, from about 1 mg/ml to about 150 mg/ml, from about 25 mg/ml to about 120 mg/ml, from about 1 mg/ml to about 100 mg/ml, from about 25 mg/ml to about 100 mg/ml, from about 50 mg/ml to about 100 mg/ml, from about 50 mg/ml to about 75 mg/ml, from about 100 mg/ml to about 150 mg/ml, and the like. For example, the fusion protein concentration in the pharmaceutical composition may be about 1 mg/ml, 5 mg/ml, 10 mg/ml, 15 mg/ml, 25 mg/ml, 30 mg/ml, 40 mg/ml, 50 mg/ml, 60 mg/ml, 70 mg/ml, 80 mg/ml, 90 mg/ml, 100 mg/ml, 150 mg/ml, or 200 mg/ml. The pH of such pharmaceutical composition is about pH 4 to about pH 10, including about pH 5 to about pH 9, about pH 6.5 to about pH 8.5, about pH 6.0 to about pH 8.0, about 6.5 to pH 7.5, or about pH 7.0 to about pH 8.0.

Maintenance therapy for prevention or suppression of organ transplant rejection is carried out by administering a therapeutically effective amount of the mutant CTLA-4-Ig to the patient (e.g., effective dose) who has received an organ transplant (e.g., kidney transplant) by intravenous or subcutaneous injection. The site of injection may be, e.g., the patient's arm, torso, or leg. The effective dose of the mutant CTLA-4-Ig fusion protein administered is typically, but not limited to, e.g., from about 0.01 mg/kg to about 100 mg/kg body weight of the adult human patient, such as, e.g., from about 0.01-5.0 mg/kg, about 0.01-3.0 mg/kg, about 0.05-2.5 mg/kg, about 0.1-2.0 mg/kg, about 0.1-1.0 mg/kg, about 0.01-0.05 mg/kg, about 0.5-1.5 mg/kg, about 1.0-4.0 mg/kg, about 1.0-3.0 mg/kg, about 1.0-2.0 mg/kg, including, but not limited to, about 0.01 mg/kg, 0.05 mg/kg, 0.075 mg/kg, 0.1 mg/kg, 0.15 mg/kg, 0.2 mg/kg, 0.25 mg/kg, 0.3 mg/kg, 0.5 mg/kg, 0.75 mg/kg, 1 mg/kg, 1.25 mg/ml, 1.5 mg/kg, 2 mg/kg, 2.5 mg/kg, 3 mg/kg, 4 mg/kg, 5 mg/kg, 10 mg/kg, 20 mg/kg, 25 mg/kg, 50 mg/kg, 75 mg/kg, or 100 mg/kg body weight of the patient is administered to the patient. Alternatively, an effective amount or dose or dose range described in the "Methods of the Invention" section above may be used. The dose of the fusion protein to be administered is determined based on the potency of the fusion protein and/or the severity of the patient's symptoms or signs of organ transplant rejection. The total amount of mutant CTLA-4-Ig fusion protein administered to the patient may be, e.g., from about 0.01 mg to about 100 mg, typically from about 1 mg to 100 mg, from about 10 mg to 100 mg, from about 10 mg to about 75 mg, or from about 10 to about 50 mg. The volume of pharmaceutical composition administered to the patient is determined based upon the concentration of fusion protein in the composition and the dose of fusion protein to be administered. The fusion protein can be administered on any day post-transplant, e.g., day 1, 4, 7, 14, 28, 56, 84, etc. post-transplant. For subcutaneous injection, one to two milliliters of the pharmaceutical composition is typically administered. For intravenous injection, an appropriate volume of the pharmaceutical composition comprising the fusion protein can be administered.

Following injection of the initial dose, a second identical dose of the fusion protein may be administered to the patient subcutaneously or intravenously at 1, 2, 3, or 4 weeks after the initial dose. The dosing schedule may be one dose every two weeks, one dose/month, one dose every two months, etc. depending, e.g., upon the patient's condition. Subsequent doses may be administered every four weeks or more or less frequently, as necessary, and continued, if desired, on a monthly basis. The frequency of dosing may vary depending upon the patient's condition and may depend upon the severity of the patient's symptoms or signs of organ transplant rejection.

Such treatment is expected to reduce or alleviate one or more signs, symptoms, or biological responses associated with organ transplant rejection, such as, e.g., acute rejection of the transplanted organ, chronic rejection of the transplanted organ, decrease in function of the transplanted organ, increase in serum creatinine levels in the patient, and/or increased infiltration of T cells into the transplanted organ. Such treatment may reduce the likelihood of rejection of the transplanted organ by the patient's immune system.

Example 11

Pharmacokinetic Assessment of Mutant CTLA-4-IgG2 Fusion Proteins in Rats

The serum concentration of a therapeutic after external administration to a living organism greatly influences therapeutic efficacy, and is determined by pharmacokinetic (PK) evaluation. In the following procedure, PK profiles were assessed in rats for representative mutant CTLA-4-IgG2 test articles D3-29-IgG2, D3-54-IgG2, D3-56-IgG2, D3-69-IgG2, and D3-75-IgG2 in comparison to both hCTLA-4-IgG2 and Orencia® fusion protein test articles. The study design, and data generation and interpretation are described forthwith.

In Life Study Design.

Weight-matched, male Hans Wistar rats were used after an acclimatization period of at least 5 days. Test article dosing volumes were calculated for individual animals based on their weight such that all received 1 mg/kg of test article. A typical 150 gram (g) rat therefore received 150 μl dosing volume since every test article was prepared at 1 mg/ml in PBS. A single administration of a mutant CTLA-4-IgG2 test article described above, hCTLA-4IgG2, or Orencia® fusion protein was delivered, either as an intravenous (i.v. or IV) bolus, or by the subcutaneous (abbreviated as "s.c." or "SC") route. The study size was sufficient for a minimum of four blood samplings of 300 µl per timepoint, while restricting the blood volume removed from any given rat to no more than 10% total blood volume. The blood sampling time course was either pre-dose, 5 minutes (min), 30 min, 2 hours (h), 4 h, 8 h, 1 day (d), 2 d, 3 d, 4 d, 6 d, 8 d, 10 d, 12 d, and 14 d post-dose, or 5 min, 30 min, 2 h, 4 h, 8 h, 1 d, 2 d, 3d, 4 d, 6 d, 8d, 10 d, 11 d, 12 d, 13 d, 14 d and 15 d post-dose for i.v and s.c. administrations, respectively. Serum was prepared from individual blood samples, and tested by ELISA to quantify the presence of the administered test article.

PK ELISA Method.

The mutant CTLA-4-IgG2, hCTLA-4IgG2, or Orencia® fusion protein present in the serum samples were bound to human CD80-murine IgG (described above) pre-coated onto microtiter plates. Detection was achieved by addition of a Horse Radish Peroxidase (HRP) conjugated goat anti-human IgG (Jackson ImmunoResearch #109-035-098). Quantification was through the use of a chromogenic HRP substrate, 3,3',5,5'-tetramethylbenzidine (TMB), plus hydrogen peroxide (Kem-En-Tec #4390A), whereby the reaction was stopped by addition of 0.2N sulphuric acid ($H_2SO_4$), and optical absorbance was measured at 450 nm by a spectrophotometer. Serum samples were pre-diluted 1/20 before addition to the ELISA plate such that matrix was normalized to 5% rat sera, and further diluted in 5% rat sera for a total of eight dilutions. The concentration of each diluted serum sample was quantified against a standard curve prepared using titrations of the same test article spiked into 5% rat sera. The standard curve ranged from 10 to 0.078 ng/ml, and the accuracy range was determined to be from twice background to 5 ng/ml in 5% rat sera. The quality of the standard curve was assessed by quality controls (QC) of the same test article prepared in 5% rat sera at high, middle and low concentrations of the standard curve accuracy range. The QC acceptance criterion was for the observed QC concentration to be within 20% of the expected QC concentration. The concentration of an individual unknown serum sample was generated by averaging the concentrations assigned to dilutions with optical densities (ODs) within the accuracy range of the standard curve. At least 4 individual serum samples were used to calculate the mean serum concentration at each nominal timepoint.

PK Parameters.

FIGS. 15A and 15B show PK profiles for Orencia® fusion protein, hCTLA-4-IgG2, and the mutant CTLA-4-IgG2 fusion proteins administered at 1 mg/kg as a single (A) intravenous (IV) bolus or (B) subcutaneous (SC) injection in rats. The error bars represent standard deviation of the mean (SD). The dashed line represents the lower limit of quantification for the ELISA (~3 ng/ml for test article in 100% sera). The mean serum concentration at each nominal timepoint after test article administration at time 0 h comprises the datapoints of the semi-log concentration-time profile in FIG. 15.

The mean serum concentrations were used to generate PK parameters using WinNonLin model 201 (i.v.—bolus input), or model 200 (extravascular input) for the i.v. (IV) or s.c. (SC) dosing routes, respectively. Table 10 summarizes the key PK parameters for s.c. and i.v. administration routes, respectively.

TABLE 10

Summary of PK Parameters for Orencia ® fusion protein, hCTLA-4-IgG2, and Mutant CTLA-4-IgG2 Fusion Proteins Administered at 1 mg/kg as a Single I.V. or S.C. Bolus to Rats

| Compound | Route | Cmax (ug/L) | T½ (h) | AUC (h*ng/L) | Cl (ml/h/kg) | Vz (ml/kg) |
|---|---|---|---|---|---|---|
| Orencia | SC | 3.3 | 70.0 | 391 | 2.6 | 258.13 |
| CTLA-4IgG2 | SC | 5.9 | 45.0 | 838 | 1.2 | 77.49 |
| D3-29 | SC | 4.6 | 11.2 | 650 | 1.5 | 24.90 |
| D3-54 | SC | 4.5 | 23.6 | 528 | 1.9 | 64.52 |
| D3-56 | SC | 7.4 | 23.7 | 1049 | 1.0 | 32.67 |
| D3-69 | SC | 6.0 | 28.1 | 967 | 1.0 | 41.97 |
| D3-75 | SC | 9.0 | 56.4 | 1204 | 0.8 | 67.59 |
| Orencia | IV | 22.3 | 42.3 | 728 | 1.37 | 83.9 |
| CTLA-4IgG2 | IV | 66.2 | 49.8 | 2483 | 0.40 | 29.0 |
| D3-29 | IV | 43.0 | 33.0 | 912 | 1.10 | 52.2 |
| D3-54 | IV | 20.6 | 39.4 | 1034 | 0.97 | 55.0 |
| D3-56 | IV | 34.2 | 15.3 | 1822 | 0.55 | 12.1 |
| D3-69 | IV | 81.9 | 83.0 | 2133 | 0.47 | 56.1 |
| D3-75 | IV | 30.1 | 65.4 | 2326 | 0.43 | 40.5 |

Cmax refers to the maximum serum concentration of test article. The terminal half-life value (T½) is the time taken in hours for the concentration of test article in the serum to decline by half during the termination phase of the concentration-time profile. The area under the serum concentration-time curve (AUC) is quantified from time zero to infinity using the trapezoidal rule. The clearance (Cl) was calculated using the equation dose/AUC, whilst the volume of distribution (Vz) of the terminal phase was calculated using the equation Cl/k.

The bioavailability factor (F) for each compound is presented in Table 11, and was determined by calculating the AUC by the subcutaneous route/AUC by the intravenous route.

TABLE 11

Bioavailability Comparison of Orencia ® Fusion Protein, hCTLA-4-Ig2, D3-29-IgG2, D3-54-IgG2, D3-56-IgG2, D3-69-IgG2, and D3-75-IgG2 Fusion Proteins

| Compound | Bioavailability |
|---|---|
| Orencia | 0.54 |
| CTLA-4IgG2 | 0.34 |
| D3-29 | 0.71 |
| D3-54 | 0.51 |
| D3-56 | 0.58 |
| D3-69 | 0.45 |
| D3-75 | 0.52 |

Human CTLA-4IgG2 and Orencia® fusion protein displayed similar PK profiles despite their difference in IgG frameworks, implying that the human IgG2 and mutated human IgG1 Fc portions of these respective test articles have comparable PK activity when the functional domain is constant. By inference, any changes seen in PK profile for mutant CTLA-4-IgG2 fusion proteins as compared to Orencia® fusion protein should therefore be attributable to differences in the functional domain, and not the Fc portion.

For each mutant CTLA-4-IgG2 fusion protein, elimination was slow as suggested by the long half-life values and large area under the curves. Half-lives ranged from 11.2 to 56.4 hr for SC dosing, and from 15.3 to 83.0 hours (h) for IV dosing in comparison to Orencia® fusion protein, which had a half-life of 70.0 or 42.3 hours when administered by SC or IV routes, respectively. AUC values for the mutant CTLA-4-IgG2 fusion proteins were on average superior to the Orencia® fusion protein. After SC dosing the mean was 879.5+/−

281.6 h*kg*ng/L/mg as compared to 391 h*kg*ng/L/mg for SC Orencia® fusion protein, while an IV administration gave an average AUC of 1645.5+/−641.1 h*kg*ng/L/mg as compared to 728 h*kg*ng/L/mg for IV Orencia® fusion protein.

The volume of distribution was similar for both routes of administration in that mutant CTLA-4-IgG2 fusion proteins were distributed outside the serum but inside the extravascular fluid as suggested by the average value of 44.8 ml/kg, which is above the plasma reference volume of 30 ml/kg, and within the extracellular fluid reference limit of 300 ml/kg for a standard rat (Davies, B. et al., Pharm. Res. 10(7):1093-95 (1993)).

Bioavailability was also similar for the majority of the mutant CTLA-4-IgG2 fusion proteins, with an average of 0.6+/−0.1, which compared favorably to the 0.53 bioavailability of Orencia® fusion protein.

Finally, Cmax was generally higher for the mutant CTLA-4-IgG2 fusion proteins as compared to the Orencia® fusion protein. Cmax values ranged from 4.5 to 9.3 ug/L for dosing, and from 20.6 to 81.9 ug/L for IV dosing in comparison to the Orencia® fusion protein, which had a Cmax of 3.3 or 22.3 ug/L when administered by SC or IV routes, respectively.

Overall, the PK data showed that all assessed mutant CTLA-4-IgG2 fusion proteins typically had a non-inferior PK profile to the Orencia® fusion protein when administered to rats at 1 mg/kg via SC or IV routes, and that IgG1 or IgG2 Fc portions were comparable when the functional domain was constant.

Example 12

This example describes a method for creating a stably transfected cell line for expressing mutant CTLA4-Ig fusion proteins of the invention, using the cell line for routine laboratory scale production of the mutant CTLA4-Ig fusion protein, and purifying the mutant CTLA-4-Ig fusion proteins from cell expression media. Although this example specifically describes a method for creating a stably transfected CHO-K1 cell line for expressing the D3-54-IgG2 fusion protein, using such cell for laboratory scale production and purifying the protein from media, the methods described herein can be used with any mutant CTLA-4-Ig fusion protein of the invention and/or any appropriate cell line disclosed above.

Creation of Stably Transfected Cell Line.

Materials.

CHO-K1 Naïve (Untransfected) Cells:

CHO-K1 cells adapted to serum-free suspension growth in chemically-defined medium (Cell ID: M4-PeM-0436-112-01) were stored in liquid nitrogen vapor phase (Dewar MVE1536P). One vial of M4-PeM-0436-112-01 was thawed and cultured with CD OptiCHO™ medium (Invitrogen, #12681) in shake flasks. The cultures provided cells for transfection and conditioned medium for growth and cloning. All cultures were grown at 37° C., 5% $CO_2$.

Plasmid:

DNA encoding the D3-54 mutant CTLA-4 ECD fused to a human IgG2a Fc region was inserted into the CET1019AS UCOE vector (Millipore) and the resulting plasmid CET1019AS-D3-54-IgG2 was used for all transfections.

Cell Culture Medium:

CD Opti-CHO (Invitrogen #12681) chemically-defined animal component-free medium, supplemented with 2% v/v 200 mM L-glutamine (Invitrogen #25031), was used for all cultures.

Conditioned Medium:

Conditioned medium was obtained by cultivating the parental CHO-K1 cell line in CD Opti-CHO medium. At cell counts $\geq 5 \times 10^5$ cells/ml, the cell culture was centrifuged and the conditioned medium supernatant was sterile-filtered. Conditioned medium was made fresh each day for use or stored at 2-8° C. for up to 7 days.

50% Conditioned Medium:

Conditioned medium (above) combined with an equal volume of fresh cell culture medium; made fresh each day it is used.

Analytical Methods.

Cell count and viability determination were performed with a Cedex or Cedex HiRes cell counter (Innovatis).

Initial screening of clones expressing the mutant CTLA-4-Ig fusion protein (D3-54-IgG2) for production was performed by ELISA. ELISA plates were coated with hCD80-murine Ig fusion protein overnight. The following day, samples to be analyzed were transferred to the ELISA plates at 50- and 200-fold dilutions in duplicate. After two hours incubation, anti-human IgG-HRP antibody was added and incubated for 30 minutes. The plates were developed with TMB and read at 450 nm. Raw optical densities (OD) were reported.

Quantitative determination of the D3-54-IgG2 fusion protein concentration was performed by a Protein A HPLC method using a Poros A/20 column (ABI #1-5024-12). Two buffers were used: Buffer A: 50 mM phosphoric acid, 150 mM potassium chloride, pH 7.6±0.1 and Buffer B: 50 mM phosphoric acid, 150 mM potassium chloride, pH 2.5±0.1. Both buffers additionally had 5% isopropanol added. Equilibration and wash after sample injection was with 42% Buffer A and 58% Buffer B (pH 6.5). Elution was a linear gradient to 12% Buffer A and 88% Buffer B over 1 minute.

Procedure.

The naïve adherent CHO-K1 cells used for the creation of stable cell lines used in GMP production of D3-54-IgG2 fusion protein were adapted to suspension growth in chemically defined CD OptiCHO™ medium. A vial of these naïve CHO-K1 cells was thawed and grown in 125 ml shake flasks containing CD OptiCHO™ medium to a density of $5 \times 10^5$ viable cells/ml. $2 \times 10^6$ viable cells were resuspended in 400 µl of 50% conditioned medium and combined with 20 µg plasmid DNA (D3-54-IgG2 in a CET1019AS UCEO vector) in a cuvette. Electroporation was performed with a Gene Xcell Pulser (BioRad) at 320 volts (V) with a square wave pulse length of 15 milliseconds (ms). Duplicate transfections were performed and then the cells were pooled. The pooled cells were transferred to a T-25 flask containing 5 ml of 50% conditioned medium and incubated for two days.

Transfected cells were either directly dispensed into 96-well plates for cloning or cultured with antibiotic selection until a stable pool was obtained, and then dispensed into 96-well plates. Two days after electroporation, the culture was diluted to 1250 cells/ml in conditioned medium containing 8 µg/ml of puromycin for selection pressure. The cells were dispensed into 96-well plates at 200 µl per well (250 cells/well). The plates were incubated for approximately 10 days to kill untransfected and transiently-transfected cells. After 10-12 days, every well in every plate was visually inspected to identify wells with single colonies. These wells were later re-inspected to verify they contained single, healthy colonies suitable for expansion into 24-well plates.

Two days after electroporation, the culture was centrifuged and resuspended in 50% conditioned medium containing 7 µg/ml of puromycin for selection pressure. A control flask was also inoculated with untransfected cells in the same medium. Based on on-going optimization studies, the puromycin concentration was increased to 8 µg/ml after 3 days. The stable pool was generated 10-12 days after selection, when all cells in the control flask died. Product expression in the stable pool was verified by protein A HPLC and culture viability was verified to be >95%. The cells were serially diluted in conditioned medium without puromycin to a final density of 3.8 cells/ml. The cells were seeded onto 96-well plates at 200 µl per well (75 cells/plate or 0.8 cells/well).

After one day every well in every plate was visually inspected to identify wells with single cells or colonies. The next day, wells with single colonies of 2-4 cells were selected. Any wells with more than two colonies were eliminated. A second operator verified the selections. The wells were later re-inspected to verify they contained single, healthy colonies suitable for expansion into 24-well plates Clones from 96-well plates were expanded into 24-well plates containing 1 ml of conditioned medium per well with 8 µg/ml of puromycin. The entire contents of the selected wells from the 96-well plates with single colonies were transferred to individual wells in the 24-well plates. 200 µl was taken from each new well in the 24-well plate to wash the corresponding well in the 96-well plate and transferred back. For backup, 200 µl of conditioned medium containing 8 µg/ml of puromycin was added back to each well in the 96-well plates.

After 1-3 days, each well in the 24-well plates was sampled and tested for D3-54-IgG2 expression by ELISA. Clones for further expansion were selected based on the raw ELISA OD values as well as demonstration of adequate growth.

The top 35-40 clones, based on ELISA and observable growth results were expanded into T-25 flasks containing 5 ml of conditioned medium with 8 µg/ml of puromycin. The entire contents of each of the selected wells from the 24-well plates were transferred to individual T-25 flasks. Residual cells in the wells were washed with the same medium and added to the corresponding T-25 flask. For backup, 1 ml of conditioned medium containing 8 µg/ml of puromycin was added back to each well in the 24-well plates.

The number of clones was further reduced by selecting for clones with the highest productivity. Cells were resuspended in fresh medium at $1-2 \times 10^5$ viable cells/ml and seeded into T25 flasks (5 ml culture) or 125 ml shake flasks (12 ml culture). The cultures were incubated for 22-24 hours and then a final cell density and viability determination was made and a sample was taken for product concentration determination by Protein A HPLC. Productivity was calculated by dividing the total amount of protein produced by the total number of viable cells in the flask and dividing by the culture duration. The units were converted to picograms per cell per day or "pcd". Clones were ranked according to their pcd values, but clones that did not exhibit significant growth were omitted. The top clones were expanded to 125 ml shake flasks for cryopreservation and further evaluation of growth and productivity.

Clones to be further evaluated were seeded into 250 ml shake flasks at $1 \times 10^5$ viable cells/ml in 50 ml fresh medium. When the cell density reached $1 \times 10^6$ viable cells/ml, the culture was passaged into a new shake flask, again at $1 \times 10^5$ viable cells/ml in 50 ml fresh medium. The passaging was repeated once more. During this third passage, the culture was sampled daily for cell count, viability, and product concentration determination by Protein A HPLC.

The top clones expressing D3-54-IgG2 fusion protein based on the growth and specific production rates were selected for subcloning. Subcloning was performed by limiting dilution as described in the section above for stable pools, with the exception that puromycin was not used at any time. Expansion, screening, and evaluation of subclones were also performed as described above.

Selected subclones were repeatedly passaged in shake flasks for approximately 90 days to evaluate production stability. At each passage, cells were seeded in 125 ml shake flasks at $1 \times 10^5$ viable cells/ml in 25 ml fresh medium. The cultures were passaged every 3-4 days. Before each passage, the cell density and viability were measured and a sample was taken for product concentration determination by Protein A HPLC.

Selected clones and subclones were cryopreserved from the time of ranking by pcd values to various points in the stability evaluation. Freezing medium was freshly made with 90% growth medium and 10% DMSO (Sigma). Cells from shake flask cultures were centrifuged and resuspended in freezing medium at densities ranging from $2-10 \times 10^6$ cells/ml. The cell suspension was dispensed in 1 ml aliquots into cryogenic vials. The cryogenic vials were placed in an isopropanol freezing containers and stored at −80° C. overnight. The frozen vials were transferred to liquid nitrogen vapor phase storage the following day.

Production of Mutant CTLA4-IgG2 Fusion Proteins.

A cryovial containing 1 ml volume of CHO-K1 cells expressing D3-54-IgG2 fusion protein is thawed and grown in 125 ml shake flasks containing CD OptiCHO™ medium at 37° C. and 5% $CO_2$ to a density of $5 \times 10^5$ viable cells/ml. Several flasks are combined to inoculate a wave bag at $1-2 \times 10^5$ cells/ml in a 5 or 10 L volume of CD OptiCHO™ medium with 4 mM glutamine. The wave bag culture is maintained in a 37° C. incubator supplemented with 5% $CO_2$ at a rocking platform setting of 18-22 rpm and angle of 8 degrees for equipment purchased from Sartorius Stedim Biotech. The culture is sampled daily for cell count, viability, nutrient level, metabolite profile and expression level of the mutant CTLA-4-IgG2 (i.e., D3-54-IgG2) using a Protein A HPLC assay. The culture is harvested when the viability declines to ~50% typically 9-11 days post inoculation. The cell culture material is clarified by filtration using a combination of depth filtration and sterile filtration and either used immediately for further processing or stored at 2-8° C.

Purification of Mutant CTLA-4-IgG2 Fusion Proteins.

Mutant CTLA4-IgG2 fusion proteins (D3-54-IgG2) were purified by Protein-A affinity chromatography using an AKTA Explorer HPLC system (GE Healthcare). A mutant CTLA-4-Ig fusion protein (D3-54-IgG2) was bound to MabSelect Protein A FF columns (GE Healthcare, #17-5079-01) in PBS buffer (Invitrogen), loaded at ~10 mg/ml of chromatography media, washed with the same buffer, eluted with 100 mM citric acid buffer (pH 4.0), and then neutralized by addition of 1/10 volume of 2M Tris base. The Protein A purified sample is further processed by diafiltration using a tangential flow filtration (TFF) system with a buffer exchange into 20 mM Tris-Cl, pH 7.5.

The buffer exchanged protein sample is further purified by anion exchange chromatography on a Q-Sepharose column loaded at 10 mg/ml loading density. The bound protein is eluted using a 20 column volume (CV) linear NaCl gradient from 0-500 mM NaCl in 20 mM Tris-Cl, pH 7.5. Major peak fractions are pooled and the concentration is determined by measuring absorbance at 280 nm.

The protein purity is confirmed by SDS-PAGE analysis and the monomer content is determined using a size exclusion-HPLC method. Samples are stored in aliquots at 2-8° C. or at −20° C. for extended periods prior to use.

While the foregoing invention has been described in some detail for purposes of clarity and understanding, it will be clear to one skilled in the art from a reading of this disclosure that various changes in form and detail can be made without departing from the true scope of the invention. It is understood that the materials, examples, and embodiments described herein are for illustrative purposes only and not intended to be limiting and that various modifications or changes in light thereof will be suggested to persons skilled in the art and are to be included within the spirit and purview of this application and scope of the appended claims. All publications, patent applications, patents, or other documents mentioned herein are incorporated by reference in their entirety for all purposes to the same extent as if each such individual publication, patent, patent application or other document were individually specifically indicated to be incorporated by reference herein in its entirety for all purposes and were set forth in its entirety herein. In case of conflict, the present specification, including definitions, will control.

What is claimed is:

1. A method of inhibiting or suppressing rejection of a tissue, cell, graft, or organ transplant from a donor by a recipient human subject in need thereof, the method comprising administering to the recipient human subject a therapeutically effective amount of an isolated or recombinant fusion protein,
   wherein the isolated or recombinant fusion protein comprises (a) a first polypeptide comprising a polypeptide sequence that has at least 96% identity to the polypeptide sequence of SEQ ID NO:50, and (b) a second polypeptide, wherein the second polypeptide comprises an IgFc polypeptide, wherein the fusion protein has an ability to bind human CD80 or human CD86 or an extracellular domain of either human CD80 or human CD86, and/or an ability to inhibit or suppress a T cell-dependent immune response,
   thereby inhibiting or suppressing rejection of the tissue, cell, graft, or organ transplant by the recipient human subject.

2. The method of claim 1, wherein the fusion protein is administered to the recipient human subject prior to, simultaneously with, or after tissue, cell, graft, or organ transplantation.

3. The method of claim 1, wherein the donor is human.

4. The method of claim 1, wherein the effective amount comprises from about 0.001 mg/kg weight of the subject to about 200 mg/kg weight of the subject.

5. The method of claim 1, wherein the organ transplant is a kidney transplant, a liver transplant, a lung transplant, or a heart transplant.

6. A method of inhibiting or suppressing rejection of a tissue, cell, graft, or organ transplant from a donor by a recipient human subject in need thereof, the method comprising administering to the recipient human subject a therapeutically effective amount of an isolated or recombinant fusion protein dimer,
   wherein the isolated or recombinant fusion protein dimer comprises two monomeric fusion proteins linked via at least one disulfide bond formed between two cysteine residues present in each monomeric fusion protein,
   wherein each monomeric fusion protein comprises (a) a first polypeptide comprising a polypeptide sequence having at least 96% identity to SEQ ID NO:50; and (b) a second polypeptide comprising an IgFc polypeptide,
   wherein the fusion protein dimer has an ability to bind human CD80 and/or human CD86, and/or human CD80-Ig and/or human CD86-Ig, and/or has an ability to inhibit or suppress a T cell-dependent immune response,
   thereby inhibiting or suppressing rejection of the tissue, cell, graft, or organ transplant by the recipient subject.

7. The method of claim 6, wherein, the fusion protein dimer is administered to the recipient subject prior to, simultaneously with, or after tissue, cell graft, or organ transplantation.

8. The method of claim 6, wherein the donor is human.

9. The method of claim 6, wherein the effective amount comprises from about 0.001 mg/kg weight of the subject to about 200 mg/kg weight of the subject.

10. The method of claim 6, wherein the organ transplant is a kidney transplant, a liver transplant, a lung transplant, or a heart transplant.

11. The method of claim 1 or 6, wherein the first polypeptide comprises SEQ ID NO:50.

12. The method of claim 11, wherein the fusion protein comprises the sequence SEQ ID NO:213.

13. The method of claim 12, wherein the fusion protein consists of a sequence selected from the group consisting of SEQ ID NO:213 and SEQ ID NO:199.

14. The method of claim 1, wherein the first polypeptide comprises a polypeptide sequence that has at least 97% identity to the polypeptide sequence of SEQ ID NO:50.

15. The method of claim 1, wherein the first polypeptide comprises a polypeptide sequence that has at least 98% identity to the polypeptide sequence of SEQ ID NO:50.

16. The method of claim 1, wherein the first polypeptide comprises a polypeptide sequence that has at least 99% identity to the polypeptide sequence of SEQ ID NO:50.

17. The method of claim 1, wherein the Ig Fc polypeptide is an IgG2 Fc polypeptide.

18. The method of claim 6, wherein the first polypeptide comprises a polypeptide sequence that has at least 97% identity to the polypeptide sequence of SEQ ID NO:50.

19. The method of claim 6, wherein the first polypeptide comprises a polypeptide sequence that has at least 98% identity to the polypeptide sequence of SEQ ID NO:50.

20. The method of claim 6, wherein the first polypeptide comprises a polypeptide sequence that has at least 99% identity to the polypeptide sequence of SEQ ID NO:50.

21. The method of claim 6, wherein the Ig Fc polypeptide is an IgG2 Fc polypeptide.

* * * * *

SEQUENCE LISTING

```
<160> NUMBER OF SEQ ID NOS: 228

<210> SEQ ID NO 1
<211> LENGTH: 124
<212> TYPE: PRT
<213> ORGANISM: Artificial Sequence
<220> FEATURE:
<223> OTHER INFORMATION: CTLA-4 ECD mutant D3-1

<400> SEQUENCE: 1

Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Ala Asn Glu Ile
            20                  25                  30

Arg Val Thr Val Leu Arg Gln Ala Gly Ser Gln Val Thr Glu Val Cys
        35                  40                  45

Ala Met Thr Tyr Met Lys Gly Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
            100                 105                 110

Tyr Val Ile Asp Pro Glu Pro Cys Pro Asp Ser Asp
        115                 120

<210> SEQ ID NO 2
<211> LENGTH: 124
<212> TYPE: PRT
<213> ORGANISM: Artificial Sequence
<220> FEATURE:
<223> OTHER INFORMATION: CTLA-4 ECD mutant D3-2

<400> SEQUENCE: 2

Met His Val Ala Gln Pro Ala Val Val Leu Ala Ser Ser Arg Gly Ile
 1               5                  10                  15

Ala Ser Phe Val Cys Glu Tyr Glu Ser Pro Gly Lys Ala Thr Glu Ile
            20                  25                  30

Arg Val Thr Val Leu Arg Gln Ala Gly Ser Gln Val Thr Glu Val Cys
        35                  40                  45

Ala Met Thr Tyr Met Lys Gly Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
            100                 105                 110
```

Tyr Val Ile Asp Pro Glu Pro Cys Pro Asp Ser Asp
        115                 120

<210> SEQ ID NO 3
<211> LENGTH: 124
<212> TYPE: PRT
<213> ORGANISM: Artificial Sequence
<220> FEATURE:
<223> OTHER INFORMATION: CTLA-4 ECD mutant D3-3

<400> SEQUENCE: 3

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Val
            20                  25                  30

Arg Val Thr Val Leu Arg Gln Ala Gly Ser Gln Val Thr Glu Val Cys
        35                  40                  45

Ala Met Thr Tyr Met Lys Gly Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
            100                 105                 110

Tyr Val Ile Asp Pro Glu Pro Cys Pro Asp Ser Asp
        115                 120

<210> SEQ ID NO 4
<211> LENGTH: 124
<212> TYPE: PRT
<213> ORGANISM: Artificial Sequence
<220> FEATURE:
<223> OTHER INFORMATION: CTLA-4 ECD mutant D3-4

<400> SEQUENCE: 4

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
            20                  25                  30

Arg Val Thr Val Leu Arg Gln Ala Asp Ser Gln Val Thr Glu Val Cys
        35                  40                  45

Ala Met Thr Tyr Met Lys Gly Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
            100                 105                 110

Tyr Val Ile Asp Pro Glu Pro Cys Pro Asp Ser Asp
        115                 120

<210> SEQ ID NO 5
<211> LENGTH: 124
<212> TYPE: PRT
<213> ORGANISM: Artificial Sequence
<220> FEATURE:
<223> OTHER INFORMATION: CTLA-4 ECD mutant D3-5

<400> SEQUENCE: 5

```
Met His Val Ala Gln Pro Ala Val Val Leu Ala Ser Ser Arg Gly Ile
 1               5                   10                  15

Ala Ser Phe Val Cys Glu Tyr Glu Ser Pro Gly Lys Ala Asn Glu Ile
            20                  25                  30

Arg Val Thr Val Leu Arg Gln Ala Gly Ser Gln Val Thr Glu Val Cys
        35                  40                  45

Ala Ala Thr Tyr Met Lys Gly Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
            100                 105                 110

Tyr Val Ile Asp Pro Glu Pro Cys Pro Asp Ser Asp
        115                 120
```

<210> SEQ ID NO 6
<211> LENGTH: 124
<212> TYPE: PRT
<213> ORGANISM: Artificial Sequence
<220> FEATURE:
<223> OTHER INFORMATION: CTLA-4 ECD mutant D3-6

<400> SEQUENCE: 6

```
Met His Val Ala Gln Pro Ala Val Val Leu Ala Ser Ser Arg Gly Ile
 1               5                   10                  15

Ala Ser Phe Val Cys Glu Tyr Glu Ser Pro Gly Lys Ala Asn Glu Ile
            20                  25                  30

Arg Val Thr Val Leu Arg Gln Ala Gly Ser Gln Val Thr Glu Val Cys
        35                  40                  45

Ala Met Thr Tyr Met Met Gly Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
            100                 105                 110

Tyr Val Ile Asp Pro Glu Pro Cys Pro Asp Ser Asp
        115                 120
```

<210> SEQ ID NO 7
<211> LENGTH: 124
<212> TYPE: PRT
<213> ORGANISM: Artificial Sequence
<220> FEATURE:
<223> OTHER INFORMATION: CTLA-4 ECD mutant D3-7

<400> SEQUENCE: 7

```
Met His Val Ala Gln Pro Ala Val Val Leu Ala Ser Ser Arg Gly Ile
 1               5                   10                  15

Ala Ser Phe Val Cys Glu Tyr Glu Ser Pro Gly Lys Ala Asn Glu Ile
            20                  25                  30

Arg Val Thr Val Leu Arg Gln Ala Gly Ser Gln Val Thr Glu Val Cys
        35                  40                  45

Ala Met Thr Tyr Met Lys Gly Asn Glu Leu Thr Phe Leu Asp Asp Pro
    50                  55                  60
```

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
            100                 105                 110

Tyr Val Ile Asp Pro Glu Pro Cys Pro Asp Ser Asp
        115                 120

<210> SEQ ID NO 8
<211> LENGTH: 124
<212> TYPE: PRT
<213> ORGANISM: Artificial Sequence
<220> FEATURE:
<223> OTHER INFORMATION: CTLA-4 ECD mutant D3-8

<400> SEQUENCE: 8

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
                20                  25                  30

Arg Val Thr Val Leu Arg Gln Ala Gly Ser Gln Val Thr Glu Val Cys
            35                  40                  45

Ala Met Thr Tyr Met Lys Gly Asp Glu Leu Thr Phe Leu Asp Asp Ser
        50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
            100                 105                 110

Tyr Val Ile Asp Pro Glu Pro Cys Pro Asp Ser Asp
        115                 120

<210> SEQ ID NO 9
<211> LENGTH: 124
<212> TYPE: PRT
<213> ORGANISM: Artificial Sequence
<220> FEATURE:
<223> OTHER INFORMATION: CTLA-4 ECD mutant D3-9

<400> SEQUENCE: 9

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
                20                  25                  30

Arg Val Thr Val Leu Arg Gln Ala Gly Ser Gln Val Thr Glu Val Cys
            35                  40                  45

Ala Met Thr Tyr Met Lys Gly Asp Glu Leu Thr Phe Leu Asp Asp Pro
        50                  55                  60

Ile Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
            100                 105                 110

Tyr Val Ile Asp Pro Glu Pro Cys Pro Asp Ser Asp
        115                 120

<210> SEQ ID NO 10
<211> LENGTH: 124
<212> TYPE: PRT
<213> ORGANISM: Artificial Sequence
<220> FEATURE:
<223> OTHER INFORMATION: CTLA-4 ECD mutant D3-11

<400> SEQUENCE: 10

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
            20                  25                  30

Arg Val Thr Val Leu Arg Gln Ala Gly Ser Gln Val Thr Glu Val Cys
        35                  40                  45

Ala Met Thr Tyr Met Lys Gly Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
            100                 105                 110

Tyr Val Ile Asp Pro Glu Pro Cys Pro Asp Ser Asp
        115                 120

<210> SEQ ID NO 11
<211> LENGTH: 124
<212> TYPE: PRT
<213> ORGANISM: Artificial Sequence
<220> FEATURE:
<223> OTHER INFORMATION: CTLA-4 ECD mutant D3-12

<400> SEQUENCE: 11

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
            20                  25                  30

Arg Val Thr Val Leu Arg Gln Ala Gly Ser Gln Val Thr Glu Val Cys
        35                  40                  45

Ala Met Thr Tyr Met Lys Gly Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 12
<211> LENGTH: 124
<212> TYPE: PRT
<213> ORGANISM: Artificial Sequence
<220> FEATURE:
<223> OTHER INFORMATION: CTLA-4 ECD mutant D3-14

<400> SEQUENCE: 12

Met His Val Ala Gln Pro Ala Val Val Leu Ala Ser Ser Arg Gly Ile

```
                1               5                  10                 15
Ala Ser Phe Val Cys Glu Tyr Glu Ser Pro Gly Lys Ala Asn Glu Ile
                20                 25                 30

Arg Val Thr Val Leu Arg Gln Ala Asp Ser Gln Val Thr Glu Val Cys
                35                 40                 45

Ala Met Thr Tyr Met Lys Gly Asp Glu Leu Thr Phe Leu Asp Asp Pro
                50                 55                 60

Ser Cys Thr Gly Thr Phe Ser Gly Asn Gln Val Asn Leu Thr Ile Gln
65                 70                 75                 80

Gly Leu Arg Ala Ala Asp Thr Gly Leu Tyr Ile Cys Lys Val Glu Leu
                85                 90                 95

Met Tyr Pro Pro Pro Tyr Tyr Leu Gly Ile Gly Asn Gly Thr Gln Ile
                100                105                110

Tyr Val Ile Asp Pro Glu Pro Cys Pro Asp Ser Asp
                115                120

<210> SEQ ID NO 13
<211> LENGTH: 124
<212> TYPE: PRT
<213> ORGANISM: Artificial Sequence
<220> FEATURE:
<223> OTHER INFORMATION: CTLA-4 ECD mutant D3-15

<400> SEQUENCE: 13

Met His Val Ala Gln Pro Ala Val Val Leu Ala Ser Ser Arg Gly Ile
1               5                  10                 15

Ala Ser Phe Val Cys Glu Tyr Glu Ser Pro Gly Lys Ala Asn Glu Ile
                20                 25                 30

Arg Val Thr Val Leu Arg Gln Ala Asp Ser Gln Val Thr Glu Val Cys
                35                 40                 45

Ala Met Thr Tyr Met Lys Gly Asp Glu Leu Thr Phe Leu Asp Asp Pro
                50                 55                 60

Ser Cys Thr Gly Thr Phe Ser Gly Asn Gln Val Asn Leu Thr Ile Gln
65                 70                 75                 80

Gly Leu Arg Ala Met Asp Thr Gly Leu Tyr Ile Cys Lys Val Glu Leu
                85                 90                 95

Met Tyr Pro Pro Pro Tyr Tyr Leu Gly Phe Gly Asn Gly Thr Gln Ile
                100                105                110

Tyr Val Ile Asp Pro Glu Pro Cys Pro Asp Ser Asp
                115                120

<210> SEQ ID NO 14
<211> LENGTH: 124
<212> TYPE: PRT
<213> ORGANISM: Artificial Sequence
<220> FEATURE:
<223> OTHER INFORMATION: CTLA-4 ECD mutant D3-16

<400> SEQUENCE: 14

Met His Val Ala Gln Pro Ala Val Val Leu Ala Ser Ser Arg Gly Ile
1               5                  10                 15

Ala Ser Phe Val Cys Glu Tyr Glu Ser Pro Gly Lys Ala Asn Glu Ile
                20                 25                 30

Arg Val Thr Val Leu Arg Gln Ala Gly Ser Gln Val Thr Glu Val Cys
                35                 40                 45

Ala Met Thr Tyr Met Lys Gly Asp Glu Leu Thr Phe Leu Asp Asp Pro
                50                 55                 60

Ser Cys Thr Gly Thr Phe Ser Gly Asn Gln Val Asn Leu Thr Ile Gln
```

```
                    65                  70                  75                  80
Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp
            115                 120

<210> SEQ ID NO 15
<211> LENGTH: 124
<212> TYPE: PRT
<213> ORGANISM: Artificial Sequence
<220> FEATURE:
<223> OTHER INFORMATION: CTLA-4 ECD mutant D3-17

<400> SEQUENCE: 15

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
                20                  25                  30

Arg Val Thr Val Leu Arg Gln Ala Asp Ser Gln Val Thr Glu Val Cys
            35                  40                  45

Ala Met Thr Tyr Met Lys Gly Asp Glu Leu Thr Phe Leu Asp Asp Pro
        50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp
            115                 120

<210> SEQ ID NO 16
<211> LENGTH: 124
<212> TYPE: PRT
<213> ORGANISM: Artificial Sequence
<220> FEATURE:
<223> OTHER INFORMATION: CTLA-4 ECD mutant D3-19

<400> SEQUENCE: 16

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
                20                  25                  30

Arg Val Thr Val Leu Arg Gln Ala Asp Ser Gln Val Thr Glu Val Cys
            35                  40                  45

Ala Met Thr Tyr Met Lys Gly Asn Glu Leu Thr Phe Leu Asp Asp Pro
        50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp
            115                 120
```

```
<210> SEQ ID NO 17
<211> LENGTH: 124
<212> TYPE: PRT
<213> ORGANISM: Artificial Sequence
<220> FEATURE:
<223> OTHER INFORMATION: CTLA-4 ECD mutant D3-20

<400> SEQUENCE: 17

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
            20                  25                  30

Arg Val Thr Val Leu Arg Gln Ala Asp Ser Gln Val Thr Glu Val Cys
        35                  40                  45

Ala Met Thr Tyr Met Lys Gly Asn Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 18
<211> LENGTH: 124
<212> TYPE: PRT
<213> ORGANISM: Artificial Sequence
<220> FEATURE:
<223> OTHER INFORMATION: CTLA-4 ECD mutant D3-21

<400> SEQUENCE: 18

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
            20                  25                  30

Arg Val Thr Val Leu Arg Gln Ala Asp Ser Gln Val Thr Glu Val Cys
        35                  40                  45

Ala Met Thr Tyr Met Lys Gly Asn Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
            100                 105                 110

Tyr Val Ile Asp Pro Glu Pro Cys Pro Asp Ser Asp
        115                 120

<210> SEQ ID NO 19
<211> LENGTH: 124
<212> TYPE: PRT
<213> ORGANISM: Artificial Sequence
<220> FEATURE:
<223> OTHER INFORMATION: CTLA-4 ECD mutant D3-22

<400> SEQUENCE: 19

Met His Val Ala Gln Pro Ala Val Val Leu Ala Ser Ser Arg Gly Ile
1               5                   10                  15
```

```
Ala Ser Phe Val Cys Glu Tyr Glu Ser Pro Gly Lys Ala Asn Glu Ile
        20                  25                  30

Arg Val Thr Val Leu Arg Gln Ala Gly Ser Gln Val Thr Glu Val Cys
        35                  40                  45

Ala Met Thr Tyr Met Lys Gly Asn Glu Leu Thr Phe Leu Asp Asp Pro
50                      55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp
            115                 120
```

<210> SEQ ID NO 20
<211> LENGTH: 124
<212> TYPE: PRT
<213> ORGANISM: Artificial Sequence
<220> FEATURE:
<223> OTHER INFORMATION: CTLA-4 ECD mutant D3-23

<400> SEQUENCE: 20

```
Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
        20                  25                  30

Arg Val Thr Val Leu Arg Gln Ala Asp Ser Gln Val Thr Glu Val Cys
        35                  40                  45

Ala Met Thr Tyr Met Lys Gly Asn Glu Leu Thr Phe Leu Asp Asp Pro
50                      55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
                100                 105                 110

Tyr Val Ile Asp Pro Glu Pro Cys Pro Asp Ser Asp
            115                 120
```

<210> SEQ ID NO 21
<211> LENGTH: 124
<212> TYPE: PRT
<213> ORGANISM: Artificial Sequence
<220> FEATURE:
<223> OTHER INFORMATION: CTLA-4 ECD mutant D3-24

<400> SEQUENCE: 21

```
Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
        20                  25                  30

Arg Val Thr Val Leu Arg Gln Ala Gly Ser Gln Val Thr Glu Val Cys
        35                  40                  45

Ala Met Thr Tyr Met Lys Gly Asn Glu Leu Thr Phe Leu Asp Asp Pro
50                      55                  60

Ser Cys Thr Gly Thr Phe Ser Gly Asn Gln Val Asn Leu Thr Ile Gln
65                  70                  75                  80
```

Gly Leu Arg Ala Met Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
            100                 105                 110

Tyr Val Ile Asp Pro Glu Pro Cys Pro Asp Ser Asp
        115                 120

<210> SEQ ID NO 22
<211> LENGTH: 124
<212> TYPE: PRT
<213> ORGANISM: Artificial Sequence
<220> FEATURE:
<223> OTHER INFORMATION: CTLA-4 ECD mutant D3-25

<400> SEQUENCE: 22

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
            20                  25                  30

Arg Val Thr Val Leu Arg Gln Ala Gly Ser Gln Val Thr Glu Val Cys
        35                  40                  45

Ala Met Thr Tyr Met Lys Gly Asn Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 23
<211> LENGTH: 124
<212> TYPE: PRT
<213> ORGANISM: Artificial Sequence
<220> FEATURE:
<223> OTHER INFORMATION: CTLA-4 ECD mutant D3-26

<400> SEQUENCE: 23

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asn Glu Ile
            20                  25                  30

Arg Val Thr Val Leu Arg Gln Ala Asp Ser Gln Val Thr Glu Val Cys
        35                  40                  45

Ala Met Thr Tyr Met Lys Gly Asn Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 24
<211> LENGTH: 124

<212> TYPE: PRT
<213> ORGANISM: Artificial Sequence
<220> FEATURE:
<223> OTHER INFORMATION: CTLA-4 ECD mutant D3-27

<400> SEQUENCE: 24

```
Met His Val Ala Gln Pro Ala Val Val Leu Ala Ser Ser Arg Gly Ile
 1               5                  10                  15

Ala Ser Phe Val Cys Glu Tyr Glu Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Gly Asn Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 25
<211> LENGTH: 124
<212> TYPE: PRT
<213> ORGANISM: Artificial Sequence
<220> FEATURE:
<223> OTHER INFORMATION: CTLA-4 ECD mutant D3-28

<400> SEQUENCE: 25

```
Met His Val Ala Gln Pro Ala Val Val Leu Ala Ser Ser Arg Gly Ile
 1               5                  10                  15

Ala Ser Phe Val Cys Glu Tyr Glu Ser Pro Gly Lys Ala Asn Glu Ile
            20                  25                  30

Arg Val Thr Val Leu Arg Gln Ala Asp Ser Gln Val Thr Glu Val Cys
        35                  40                  45

Ala Met Thr Tyr Met Lys Gly Asn Glu Leu Thr Phe Leu Asp Asp Pro
    50                  55                  60

Ile Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 26
<211> LENGTH: 124
<212> TYPE: PRT
<213> ORGANISM: Artificial Sequence
<220> FEATURE:
<223> OTHER INFORMATION: CTLA-4 ECD mutant D3-29

<400> SEQUENCE: 26

```
Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Ala Asn Glu Ile
            20                  25                  30
```

```
Arg Val Thr Val Leu Arg Gln Ala Asp Ser Gln Val Thr Glu Val Cys
            35                  40                  45

Ala Met Thr Tyr Met Lys Gly Asp Glu Leu Thr Phe Leu Asp Asp Pro
 50                  55                  60

Ser Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp
            115                 120
```

<210> SEQ ID NO 27
<211> LENGTH: 124
<212> TYPE: PRT
<213> ORGANISM: Artificial Sequence
<220> FEATURE:
<223> OTHER INFORMATION: CTLA-4 ECD mutant D3-30

<400> SEQUENCE: 27

```
Met His Val Ala Gln Pro Ala Val Val Leu Ala Ser Ser Arg Gly Ile
 1               5                  10                  15

Ala Ser Phe Val Cys Glu Tyr Glu Ser Pro Gly Lys Ala Asn Glu Ile
                 20                  25                  30

Arg Val Thr Val Leu Arg Gln Ala Asp Ser Gln Val Thr Glu Val Cys
            35                  40                  45

Ala Met Thr Tyr Met Lys Gly Asp Glu Leu Thr Phe Leu Asp Asp Pro
 50                  55                  60

Ile Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp
            115                 120
```

<210> SEQ ID NO 28
<211> LENGTH: 124
<212> TYPE: PRT
<213> ORGANISM: Artificial Sequence
<220> FEATURE:
<223> OTHER INFORMATION: CTLA-4 ECD mutant D3-31

<400> SEQUENCE: 28

```
Met His Val Ala Gln Pro Ala Val Val Leu Ala Ser Ser Arg Gly Ile
 1               5                  10                  15

Ala Ser Phe Val Cys Glu Tyr Glu Ser Pro Gly Lys Ala Asn Glu Ile
                 20                  25                  30

Arg Val Thr Val Leu Arg Gln Ala Asp Ser Gln Val Thr Glu Val Cys
            35                  40                  45

Ala Met Thr Tyr Met Lys Glu Asp Glu Leu Thr Phe Leu Asp Asp Pro
 50                  55                  60

Ser Cys Thr Gly Thr Phe Ser Gly Asn Gln Val Asn Leu Thr Ile Gln
 65                  70                  75                  80

Gly Leu Arg Ala Ala Asp Thr Gly Leu Tyr Ile Cys Lys Val Glu Leu
                 85                  90                  95
```

```
Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
            115                 120

<210> SEQ ID NO 29
<211> LENGTH: 124
<212> TYPE: PRT
<213> ORGANISM: Artificial Sequence
<220> FEATURE:
<223> OTHER INFORMATION: CTLA-4 ECD mutant D3-32

<400> SEQUENCE: 29

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
            20                  25                  30

Arg Val Thr Val Leu Arg Lys Ala Asp Ser Gln Val Thr Glu Val Cys
        35                  40                  45

Ala Met Thr Tyr Met Lys Gly Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
            115                 120

<210> SEQ ID NO 30
<211> LENGTH: 124
<212> TYPE: PRT
<213> ORGANISM: Artificial Sequence
<220> FEATURE:
<223> OTHER INFORMATION: CTLA-4 ECD mutant D3-33

<400> SEQUENCE: 30

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
            20                  25                  30

Arg Val Thr Val Leu Arg Lys Ala Asp Ser Gln Val Thr Glu Val Cys
        35                  40                  45

Ala Met Thr Tyr Met Lys Glu Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
            115                 120

<210> SEQ ID NO 31
<211> LENGTH: 124
<212> TYPE: PRT
<213> ORGANISM: Artificial Sequence
```

```
<220> FEATURE:
<223> OTHER INFORMATION: CTLA-4 ECD mutant D3-34

<400> SEQUENCE: 31

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Gly Asn Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 32
<211> LENGTH: 124
<212> TYPE: PRT
<213> ORGANISM: Artificial Sequence
<220> FEATURE:
<223> OTHER INFORMATION: CTLA-4 ECD mutant D3-39

<400> SEQUENCE: 32

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Gly Asn Glu Leu Thr Phe Leu Asp Asp Pro
    50                  55                  60

Ile Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 33
<211> LENGTH: 124
<212> TYPE: PRT
<213> ORGANISM: Artificial Sequence
<220> FEATURE:
<223> OTHER INFORMATION: CTLA-4 ECD mutant D3-50

<400> SEQUENCE: 33

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
```

```
                   35                  40                  45

Ala Met Thr Tyr Met Lys Gly Asp Glu Leu Thr Phe Leu Asp Pro
         50                  55                  60

Ile Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Leu Gly Ile Gly Asn Gly Thr Gln Ile
                100                 105                 110

Tyr Val Ile Asp Pro Glu Pro Cys Pro Asp Ser Asp
                115                 120

<210> SEQ ID NO 34
<211> LENGTH: 124
<212> TYPE: PRT
<213> ORGANISM: Artificial Sequence
<220> FEATURE:
<223> OTHER INFORMATION: CTLA-4 ECD mutant D3-52

<400> SEQUENCE: 34

Met His Val Ala Gln Pro Ala Val Val Leu Ala Ser Ser Arg Gly Ile
  1               5                  10                  15

Ala Ser Phe Val Cys Glu Tyr Ala Ser Pro Gly Lys Ala Asn Glu Ile
                 20                  25                  30

Arg Val Thr Val Leu Arg Gln Ala Asp Ser Gln Val Thr Glu Val Cys
                 35                  40                  45

Ala Met Thr Tyr Met Lys Gly Asn Glu Leu Thr Phe Leu Asp Asp Pro
         50                  55                  60

Ile Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp
                115                 120

<210> SEQ ID NO 35
<211> LENGTH: 124
<212> TYPE: PRT
<213> ORGANISM: Artificial Sequence
<220> FEATURE:
<223> OTHER INFORMATION: CTLA-4 ECD mutant D3-53

<400> SEQUENCE: 35

Met His Val Ala Gln Pro Ala Val Val Leu Ala Ser Ser Arg Gly Ile
  1               5                  10                  15

Ala Ser Phe Val Cys Glu Tyr Glu Ser Pro Gly Lys Ala Asn Glu Ile
                 20                  25                  30

Arg Val Thr Val Leu Arg Gln Ala Gly Ser Gln Val Thr Glu Val Cys
                 35                  40                  45

Ala Met Thr Tyr Met Lys Gly Asp Glu Leu Thr Phe Leu Asp Asp Pro
         50                  55                  60

Ser Cys Thr Gly Thr Phe Ser Gly Asn Gln Val Asn Leu Thr Ile Gln
 65                  70                  75                  80

Gly Leu Arg Ala Ala Asp Thr Gly Leu Tyr Ile Cys Lys Val Glu Leu
                 85                  90                  95

Met Tyr Pro Pro Pro Tyr Tyr Glu Gly Ile Gly Asn Gly Thr Gln Ile
```

```
                       100                 105                 110

Tyr Val Ile Asp Pro Glu Pro Cys Pro Asp Ser Asp
        115                 120

<210> SEQ ID NO 36
<211> LENGTH: 124
<212> TYPE: PRT
<213> ORGANISM: Artificial Sequence
<220> FEATURE:
<223> OTHER INFORMATION: CTLA-4 ECD mutant D3-54

<400> SEQUENCE: 36

Met His Val Ala Gln Pro Ala Val Val Leu Ala Ser Ser Arg Gly Ile
  1               5                  10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Glu Asn Glu Leu Thr Phe Leu Asp Asp Pro
    50                  55                  60

Ile Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 37
<211> LENGTH: 124
<212> TYPE: PRT
<213> ORGANISM: Artificial Sequence
<220> FEATURE:
<223> OTHER INFORMATION: CTLA-4 ECD mutant D3-55

<400> SEQUENCE: 37

Met His Val Ala Gln Pro Ala Val Val Leu Ala Ser Ser Arg Gly Ile
  1               5                  10                  15

Ala Ser Phe Val Cys Glu Tyr Glu Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Glu Asn Glu Leu Thr Phe Leu Asp Asp Pro
    50                  55                  60

Ile Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 38
<211> LENGTH: 124
<212> TYPE: PRT
<213> ORGANISM: Artificial Sequence
<220> FEATURE:
<223> OTHER INFORMATION: CTLA-4 ECD mutant D3-56
```

-continued

```
<400> SEQUENCE: 38

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Glu Asn Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
            115                 120

<210> SEQ ID NO 39
<211> LENGTH: 124
<212> TYPE: PRT
<213> ORGANISM: Artificial Sequence
<220> FEATURE:
<223> OTHER INFORMATION: CTLA-4 ECD mutant D3-57

<400> SEQUENCE: 39

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asn Glu Ile
            20                  25                  30

Arg Val Thr Val Leu Arg Gln Ala Asp Ser Gln Val Thr Glu Val Cys
        35                  40                  45

Ala Met Thr Tyr Met Lys Glu Asp Glu Leu Thr Phe Leu Asp Asp Pro
    50                  55                  60

Ile Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
            115                 120

<210> SEQ ID NO 40
<211> LENGTH: 124
<212> TYPE: PRT
<213> ORGANISM: Artificial Sequence
<220> FEATURE:
<223> OTHER INFORMATION: CTLA-4 ECD mutant D3-58

<400> SEQUENCE: 40

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
        35                  40                  45
```

-continued

```
Ala Met Thr Tyr Met Lys Glu Asp Glu Leu Thr Phe Leu Asp Asp Pro
        50                  55                  60

Ser Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
            115                 120
```

<210> SEQ ID NO 41
<211> LENGTH: 124
<212> TYPE: PRT
<213> ORGANISM: Artificial Sequence
<220> FEATURE:
<223> OTHER INFORMATION: CTLA-4 ECD mutant D3-59

<400> SEQUENCE: 41

```
Met His Val Ala Gln Pro Ala Val Val Leu Ala Ser Ser Arg Gly Ile
  1               5                  10                  15

Ala Ser Phe Val Cys Glu Tyr Glu Ser Pro Gly Lys Ala Asn Glu Ile
                20                  25                  30

Arg Val Thr Val Leu Arg Gln Ala Asp Ser Gln Val Thr Glu Val Cys
            35                  40                  45

Ala Met Thr Tyr Met Lys Glu Asn Glu Leu Thr Phe Leu Asp Asp Pro
        50                  55                  60

Ile Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
            115                 120
```

<210> SEQ ID NO 42
<211> LENGTH: 124
<212> TYPE: PRT
<213> ORGANISM: Artificial Sequence
<220> FEATURE:
<223> OTHER INFORMATION: CTLA-4 ECD mutant D3-60

<400> SEQUENCE: 42

```
Met His Val Ala Gln Pro Ala Val Val Leu Ala Ser Ser Arg Gly Ile
  1               5                  10                  15

Ala Ser Phe Val Cys Glu Tyr Ala Ser Pro Gly Lys Ala Asn Glu Ile
                20                  25                  30

Arg Val Thr Val Leu Arg Gln Ala Asp Ser Gln Val Thr Glu Val Cys
            35                  40                  45

Ala Met Thr Tyr Met Lys Glu Asn Glu Leu Thr Phe Leu Asp Asp Pro
        50                  55                  60

Ser Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110
```

Tyr Val Ile Asp Pro Glu Pro Cys Pro Asp Ser Asp
          115                 120

<210> SEQ ID NO 43
<211> LENGTH: 124
<212> TYPE: PRT
<213> ORGANISM: Artificial Sequence
<220> FEATURE:
<223> OTHER INFORMATION: CTLA-4 ECD mutant D3-61

<400> SEQUENCE: 43

Met His Val Ala Gln Pro Ala Val Val Leu Ala Ser Ser Arg Gly Ile
 1               5                  10                  15

Ala Ser Phe Val Cys Glu Tyr Glu Ser Pro Gly Lys Ala Asn Glu Ile
            20                  25                  30

Arg Val Thr Val Leu Arg Gln Ala Asp Ser Gln Val Thr Glu Val Cys
        35                  40                  45

Ala Met Thr Tyr Met Lys Glu Asn Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
          115                 120

<210> SEQ ID NO 44
<211> LENGTH: 124
<212> TYPE: PRT
<213> ORGANISM: Artificial Sequence
<220> FEATURE:
<223> OTHER INFORMATION: CTLA-4 ECD mutant D3-62

<400> SEQUENCE: 44

Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Ala Asn Glu Ile
            20                  25                  30

Arg Val Thr Val Leu Arg Gln Ala Asp Ser Gln Val Thr Glu Val Cys
        35                  40                  45

Ala Met Thr Tyr Met Lys Glu Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
          115                 120

<210> SEQ ID NO 45
<211> LENGTH: 124
<212> TYPE: PRT
<213> ORGANISM: Artificial Sequence
<220> FEATURE:
<223> OTHER INFORMATION: CTLA-4 ECD mutant D3-63

<400> SEQUENCE: 45

```
Met His Val Ala Gln Pro Ala Val Val Leu Ala Ser Ser Arg Gly Ile
 1               5                   10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Ala Thr Tyr Met Lys Glu Asn Glu Leu Thr Phe Leu Asp Asp Pro
    50                  55                  60

Ile Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
            115                 120
```

<210> SEQ ID NO 46
<211> LENGTH: 124
<212> TYPE: PRT
<213> ORGANISM: Artificial Sequence
<220> FEATURE:
<223> OTHER INFORMATION: CTLA-4 ECD mutant D3-64

<400> SEQUENCE: 46

```
Met His Val Ala Gln Pro Ala Val Val Leu Ala Ser Ser Arg Gly Ile
 1               5                   10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Met Glu Asn Glu Leu Thr Phe Leu Asp Asp Pro
    50                  55                  60

Ile Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
            115                 120
```

<210> SEQ ID NO 47
<211> LENGTH: 124
<212> TYPE: PRT
<213> ORGANISM: Artificial Sequence
<220> FEATURE:
<223> OTHER INFORMATION: CTLA-4 ECD mutant D3-65

<400> SEQUENCE: 47

```
Met His Val Ala Gln Pro Ala Val Val Leu Ala Ser Ser Arg Gly Ile
 1               5                   10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Gly Asn Glu Leu Thr Phe Leu Asp Asp Pro
    50                  55                  60
```

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 48
<211> LENGTH: 124
<212> TYPE: PRT
<213> ORGANISM: Artificial Sequence
<220> FEATURE:
<223> OTHER INFORMATION: CTLA-4 ECD mutant D3-66

<400> SEQUENCE: 48

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Gly Asp Glu Leu Thr Phe Leu Asp Asp Pro
    50                  55                  60

Ile Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 49
<211> LENGTH: 124
<212> TYPE: PRT
<213> ORGANISM: Artificial Sequence
<220> FEATURE:
<223> OTHER INFORMATION: CTLA-4 ECD mutant D3-68

<400> SEQUENCE: 49

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
            20                  25                  30

Arg Val Thr Val Leu Arg Gln Ala Asp Ser Gln Val Thr Glu Val Cys
        35                  40                  45

Ala Met Thr Tyr Met Lys Gly Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp
        115                 120

```
<210> SEQ ID NO 50
<211> LENGTH: 124
<212> TYPE: PRT
<213> ORGANISM: Artificial Sequence
<220> FEATURE:
<223> OTHER INFORMATION: CTLA-4 ECD mutant D3-69

<400> SEQUENCE: 50

Met His Val Ala Gln Pro Ala Val Val Leu Ala Ser Ser Arg Gly Ile
 1               5                  10                  15

Ala Ser Phe Val Cys Glu Tyr Glu Ser Pro Gly Lys Ala Asn Glu Ile
            20                  25                  30

Arg Val Thr Val Leu Arg Gln Ala Asp Ser Gln Val Thr Glu Val Cys
        35                  40                  45

Ala Met Thr Tyr Met Lys Gly Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 51
<211> LENGTH: 124
<212> TYPE: PRT
<213> ORGANISM: Artificial Sequence
<220> FEATURE:
<223> OTHER INFORMATION: CTLA-4 ECD mutant D3-70

<400> SEQUENCE: 51

Met His Val Ala Gln Pro Ala Val Val Leu Ala Ser Ser Arg Gly Ile
 1               5                  10                  15

Ala Ser Phe Val Cys Glu Tyr Glu Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Gly Asn Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 52
<211> LENGTH: 124
<212> TYPE: PRT
<213> ORGANISM: Artificial Sequence
<220> FEATURE:
<223> OTHER INFORMATION: CTLA-4 ECD mutant D3-71

<400> SEQUENCE: 52

Met His Val Ala Gln Pro Ala Val Val Leu Ala Ser Ser Arg Gly Ile
```

```
                1               5                  10                 15
Ala Ser Phe Val Cys Glu Tyr Ala Ser Pro Gly Lys Ala Asn Glu Ile
                20                 25                 30

Arg Val Thr Val Leu Arg Gln Ala Asp Ser Gln Val Thr Glu Val Cys
                35                 40                 45

Ala Met Thr Tyr Met Lys Gly Asp Glu Leu Thr Phe Leu Asp Asp Pro
                50                 55                 60

Ser Cys Thr Gly Thr Phe Ser Gly Asn Gln Val Asn Leu Thr Ile Gln
 65                 70                 75                 80

Gly Leu Arg Ala Met Asp Thr Gly Leu Tyr Ile Cys Lys Val Glu Leu
                85                 90                 95

Met Tyr Pro Pro Pro Tyr Tyr Glu Gly Ile Gly Asn Gly Thr Gln Ile
                100                105                110

Tyr Val Ile Asp Pro Glu Pro Cys Pro Asp Ser Asp
                115                120
```

<210> SEQ ID NO 53
<211> LENGTH: 124
<212> TYPE: PRT
<213> ORGANISM: Artificial Sequence
<220> FEATURE:
<223> OTHER INFORMATION: CTLA-4 ECD mutant D3-72

<400> SEQUENCE: 53

```
Met His Val Ala Gln Pro Ala Val Val Leu Ala Ser Ser Arg Gly Ile
 1               5                  10                 15

Ala Ser Phe Val Cys Glu Tyr Glu Ser Pro Gly Lys Ala Asn Glu Ile
                20                 25                 30

Arg Val Thr Val Leu Arg Gln Ala Asp Ser Gln Val Thr Glu Val Cys
                35                 40                 45

Ala Met Thr Tyr Met Lys Gly Asn Glu Leu Thr Phe Leu Asp Asp Pro
                50                 55                 60

Ser Cys Thr Gly Thr Phe Ser Gly Asn Gln Val Asn Leu Thr Ile Gln
 65                 70                 75                 80

Gly Leu Arg Ala Met Asp Thr Gly Leu Tyr Ile Cys Lys Val Glu Leu
                85                 90                 95

Met Tyr Pro Pro Pro Tyr Tyr Glu Gly Ile Gly Asn Gly Thr Gln Ile
                100                105                110

Tyr Val Ile Asp Pro Glu Pro Cys Pro Asp Ser Asp
                115                120
```

<210> SEQ ID NO 54
<211> LENGTH: 124
<212> TYPE: PRT
<213> ORGANISM: Artificial Sequence
<220> FEATURE:
<223> OTHER INFORMATION: CTLA-4 ECD mutant D3-73

<400> SEQUENCE: 54

```
Met His Val Ala Gln Pro Ala Val Val Leu Ala Ser Ser Arg Gly Ile
 1               5                  10                 15

Ala Ser Phe Val Cys Glu Tyr Glu Ser Pro Gly Lys Ala Asn Glu Val
                20                 25                 30

Arg Val Thr Val Leu Arg Gln Ala Asp Ser Gln Val Thr Glu Val Cys
                35                 40                 45

Ala Met Thr Tyr Met Lys Gly Asn Glu Leu Thr Phe Leu Asp Asp Pro
                50                 55                 60

Ile Cys Thr Gly Thr Phe Ser Gly Asn Gln Val Asn Leu Thr Ile Gln
```

```
              65                  70                  75                  80
Gly Leu Arg Ala Met Asp Thr Gly Leu Tyr Ile Cys Lys Val Glu Leu
                    85                  90                  95

Met Tyr Pro Pro Pro Tyr Tyr Glu Gly Ile Gly Asn Gly Thr Gln Ile
                100                 105                 110

Tyr Val Ile Asp Pro Glu Pro Cys Pro Asp Ser Asp
            115                 120

<210> SEQ ID NO 55
<211> LENGTH: 124
<212> TYPE: PRT
<213> ORGANISM: Artificial Sequence
<220> FEATURE:
<223> OTHER INFORMATION: CTLA-4 ECD mutant D3-74

<400> SEQUENCE: 55

Met His Val Ala Gln Pro Ala Val Val Leu Ala Ser Ser Arg Gly Ile
  1               5                  10                  15

Ala Ser Phe Val Cys Glu Tyr Ala Ser Pro Gly Lys Ala Asn Glu Ile
                 20                  25                  30

Arg Val Thr Val Leu Arg Gln Ala Asp Ser Gln Val Thr Glu Val Cys
             35                  40                  45

Ala Met Thr Tyr Met Lys Gly Asn Glu Leu Thr Phe Leu Asp Asp Pro
         50                  55                  60

Ile Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                    85                  90                  95

Met Tyr Pro Pro Pro Tyr Tyr Glu Gly Ile Gly Asn Gly Thr Gln Ile
                100                 105                 110

Tyr Val Ile Asp Pro Glu Pro Cys Pro Asp Ser Asp
            115                 120

<210> SEQ ID NO 56
<211> LENGTH: 124
<212> TYPE: PRT
<213> ORGANISM: Artificial Sequence
<220> FEATURE:
<223> OTHER INFORMATION: CTLA-4 ECD mutant D3-75

<400> SEQUENCE: 56

Met His Val Ala Gln Pro Ala Val Val Leu Ala Ser Ser Arg Gly Ile
  1               5                  10                  15

Ala Ser Phe Val Cys Glu Tyr Glu Ser Pro Gly Lys Ala Asn Glu Val
                 20                  25                  30

Arg Val Thr Val Leu Arg Gln Ala Asp Ser Gln Val Thr Glu Val Cys
             35                  40                  45

Ala Met Thr Tyr Met Lys Glu Asn Glu Leu Thr Phe Leu Asp Asp Pro
         50                  55                  60

Ser Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                    85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp
            115                 120
```

```
<210> SEQ ID NO 57
<211> LENGTH: 124
<212> TYPE: PRT
<213> ORGANISM: Artificial Sequence
<220> FEATURE:
<223> OTHER INFORMATION: CTLA-4 ECD mutant D3-76

<400> SEQUENCE: 57

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Glu Asp Glu Leu Thr Phe Leu Asp Asp Pro
    50                  55                  60

Ile Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 58
<211> LENGTH: 124
<212> TYPE: PRT
<213> ORGANISM: Artificial Sequence
<220> FEATURE:
<223> OTHER INFORMATION: CTLA-4 ECD mutant D1

<400> SEQUENCE: 58

Met His Val Ala Gln Pro Ala Val Val Leu Ala Ser Ser Arg Gly Ile
1               5                   10                  15

Ala Ser Phe Val Cys Glu Tyr Glu Ser Pro His Lys Ala Thr Glu Ile
            20                  25                  30

Arg Val Thr Val Leu Arg Gln Ala Asn Ser Gln Val Thr Glu Val Cys
        35                  40                  45

Ala Met Thr Tyr Met Lys Gly Asp Glu Leu Thr Phe Leu Asp Asp Pro
    50                  55                  60

Phe Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 59
<211> LENGTH: 124
<212> TYPE: PRT
<213> ORGANISM: Artificial Sequence
<220> FEATURE:
<223> OTHER INFORMATION: CTLA-4 ECD mutant D1T

<400> SEQUENCE: 59

Met His Val Ala Gln Pro Ala Val Val Leu Ala Ser Ser Arg Gly Ile
1               5                   10                  15
```

```
Ala Ser Phe Val Cys Glu Tyr Glu Ser Pro His Lys Ala Asn Glu Ile
         20                  25                  30

Arg Val Thr Val Leu Arg Gln Ala Asn Ser Gln Val Thr Glu Val Cys
         35                  40                  45

Ala Met Thr Tyr Met Lys Gly Asp Glu Leu Thr Phe Leu Asp Asp Pro
 50                  55                  60

Phe Cys Thr Gly Thr Phe Ser Gly Asn Gln Val Asn Leu Thr Ile Gln
 65                  70                  75                  80

Gly Leu Arg Ala Ala Asp Thr Gly Leu Tyr Ile Cys Lys Val Glu Leu
                 85                  90                  95

Met Tyr Pro Pro Pro Tyr Tyr Leu Gly Ile Gly Asn Gly Thr Gln Ile
             100                 105                 110

Tyr Val Ile Asp Pro Glu Pro Cys Pro Asp Ser Asp
             115                 120

<210> SEQ ID NO 60
<211> LENGTH: 124
<212> TYPE: PRT
<213> ORGANISM: Artificial Sequence
<220> FEATURE:
<223> OTHER INFORMATION: CTLA-4 ECD mutant D2

<400> SEQUENCE: 60

Met His Val Ala Gln Pro Ala Val Val Leu Ala Ser Ser Arg Gly Ile
 1               5                  10                  15

Ala Ser Phe Val Cys Glu Tyr Glu Ser Pro His Lys Ala Asn Glu Ile
         20                  25                  30

Arg Val Thr Val Leu Arg Gln Ala Asn Ser Gln Val Thr Glu Val Cys
         35                  40                  45

Ala Met Thr Tyr Met Lys Gly Asp Glu Leu Thr Phe Leu Asp Asp Pro
 50                  55                  60

Phe Cys Thr Gly Thr Phe Ser Gly Asn Gln Val Asn Leu Thr Ile Gln
 65                  70                  75                  80

Gly Leu Arg Ala Ala Asp Thr Gly Leu Tyr Ile Cys Lys Val Glu Leu
                 85                  90                  95

Met Tyr Pro Pro Pro Tyr Tyr Leu Gly Met Gly Asn Gly Thr Gln Ile
             100                 105                 110

Tyr Val Ile Asp Pro Glu Pro Cys Pro Asp Ser Asp
             115                 120

<210> SEQ ID NO 61
<211> LENGTH: 124
<212> TYPE: PRT
<213> ORGANISM: Artificial Sequence
<220> FEATURE:
<223> OTHER INFORMATION: CTLA-4 ECD mutant D3

<400> SEQUENCE: 61

Met His Val Ala Gln Pro Ala Val Val Leu Ala Ser Ser Arg Gly Ile
 1               5                  10                  15

Ala Ser Phe Val Cys Glu Tyr Glu Ser Pro Gly Lys Ala Asn Glu Ile
         20                  25                  30

Arg Val Thr Val Leu Arg Gln Ala Gly Ser Gln Val Thr Glu Val Cys
         35                  40                  45

Ala Met Thr Tyr Met Lys Gly Asp Glu Leu Thr Phe Leu Asp Asp Pro
 50                  55                  60

Ser Cys Thr Gly Thr Phe Ser Gly Asn Gln Val Asn Leu Thr Ile Gln
 65                  70                  75                  80
```

```
Gly Leu Arg Ala Ala Asp Thr Gly Leu Tyr Ile Cys Lys Val Glu Leu
            85                  90                  95

Met Tyr Pro Pro Pro Tyr Tyr Leu Gly Phe Gly Asn Gly Thr Gln Ile
                100                 105                 110

Tyr Val Ile Asp Pro Glu Pro Cys Pro Asp Ser Asp
        115                 120

<210> SEQ ID NO 62
<211> LENGTH: 124
<212> TYPE: PRT
<213> ORGANISM: Artificial Sequence
<220> FEATURE:
<223> OTHER INFORMATION: CTLA-4 ECD mutant D4

<400> SEQUENCE: 62

Met His Val Ala Gln Pro Ala Val Val Leu Ala Ser Ser Arg Gly Ile
1               5                   10                  15

Ala Ser Phe Val Cys Glu Tyr Ser Ser Pro Gly Lys Ala Asp Glu Ile
                20                  25                  30

Arg Val Thr Val Leu Arg Gln Ala Ser Ser Gln Val Thr Glu Val Cys
            35                  40                  45

Ala Met Thr Tyr Met Glu Gly Asp Glu Leu Thr Phe Leu Asp Asp Pro
    50                  55                  60

Thr Cys Thr Gly Thr Phe Ser Gly Asn Gln Val Asn Leu Thr Ile Gln
65                  70                  75                  80

Gly Leu Arg Ala Val Asp Thr Gly Leu Tyr Ile Cys Lys Val Glu Leu
            85                  90                  95

Met Tyr Pro Pro Pro Tyr Tyr Leu Gly Phe Gly Asn Gly Thr Gln Ile
                100                 105                 110

Tyr Val Ile Asp Pro Glu Pro Cys Pro Asp Ser Asp
        115                 120

<210> SEQ ID NO 63
<211> LENGTH: 124
<212> TYPE: PRT
<213> ORGANISM: Artificial Sequence
<220> FEATURE:
<223> OTHER INFORMATION: CTLA-4 ECD mutant D5

<400> SEQUENCE: 63

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asp Glu Leu Thr Phe Leu Asp Asp Pro
    50                  55                  60

Ile Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
            85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp
        115                 120

<210> SEQ ID NO 64
<211> LENGTH: 124
```

```
<212> TYPE: PRT
<213> ORGANISM: Artificial Sequence
<220> FEATURE:
<223> OTHER INFORMATION: CTLA-4 ECD mutant D6

<400> SEQUENCE: 64

Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Ala Thr Glu Ile
            20                  25                  30

Arg Val Thr Val Leu Arg Gln Ala Asp Ser Gln Val Thr Glu Val Cys
        35                  40                  45

Ala Met Thr Tyr Met Met Gly Asp Glu Leu Thr Phe Leu Asp Asp Pro
    50                  55                  60

Ile Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 65
<211> LENGTH: 124
<212> TYPE: PRT
<213> ORGANISM: Artificial Sequence
<220> FEATURE:
<223> OTHER INFORMATION: CTLA-4 ECD mutant D20

<400> SEQUENCE: 65

Met His Val Ala Gln Pro Ala Val Val Leu Ala Ser Ser Arg Gly Ile
 1               5                  10                  15

Ala Ser Phe Val Cys Glu Tyr Glu Ser Pro His Lys Ala Thr Glu Ile
            20                  25                  30

Arg Val Thr Val Leu Arg Gln Ala Asp Ser Gln Val Thr Glu Val Cys
        35                  40                  45

Ala Met Thr Tyr Met Met Glu Asp Glu Leu Thr Phe Leu Asp Asp Pro
    50                  55                  60

Ile Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp
        115                 120

<210> SEQ ID NO 66
<211> LENGTH: 124
<212> TYPE: PRT
<213> ORGANISM: Artificial Sequence
<220> FEATURE:
<223> OTHER INFORMATION: CTLA-4 ECD mutant D21

<400> SEQUENCE: 66

Met His Val Ala Gln Pro Ala Val Val Leu Ala Ser Ser Arg Gly Ile
 1               5                  10                  15

Ala Ser Phe Val Cys Glu Tyr Ser Ala Pro His Asn Ala Asp Glu Ile
            20                  25                  30
```

```
Arg Val Thr Val Leu Arg Lys Ala Ser Ser Gln Val Thr Glu Val Cys
            35                  40                  45

Ala Met Thr Tyr Met Glu Asp Glu Leu Thr Phe Leu Asp Asp Pro
 50                  55                  60

Thr Cys Thr Gly Thr Phe Ser Gly Asn Gln Val Asn Leu Thr Ile Gln
 65                  70                  75                  80

Gly Leu Arg Ala Val Asp Thr Gly Leu Tyr Ile Cys Lys Val Glu Leu
                85                  90                  95

Met Tyr Pro Pro Pro Tyr Tyr Leu Gly Phe Gly Asn Gly Thr Gln Ile
                    100                 105                 110

Tyr Val Ile Asp Pro Glu Pro Cys Pro Asp Ser Asp
                115                 120

<210> SEQ ID NO 67
<211> LENGTH: 124
<212> TYPE: PRT
<213> ORGANISM: Artificial Sequence
<220> FEATURE:
<223> OTHER INFORMATION: CTLA-4 ECD mutant D23

<400> SEQUENCE: 67

Met His Val Ala Gln Pro Ala Val Val Leu Ala Ser Ser Arg Gly Ile
 1               5                  10                  15

Ala Ser Phe Val Cys Glu Tyr Ser Ala Pro His Asn Ala Ala Glu Ile
                20                  25                  30

Arg Val Thr Val Leu Arg Lys Ala Gly Ser Gln Val Thr Glu Val Cys
            35                  40                  45

Ala Met Thr Tyr Met Lys Glu Asp Glu Leu Thr Phe Leu Asp Asp Pro
 50                  55                  60

Ser Cys Thr Gly Thr Phe Ser Gly Asn Gln Val Asn Leu Thr Ile Gln
 65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Leu Gly Asn Gly Thr Gln Ile
                    100                 105                 110

Tyr Val Ile Asp Pro Glu Pro Cys Pro Asp Ser Asp
                115                 120

<210> SEQ ID NO 68
<211> LENGTH: 124
<212> TYPE: PRT
<213> ORGANISM: Artificial Sequence
<220> FEATURE:
<223> OTHER INFORMATION: CTLA-4 ECD mutant D24

<400> SEQUENCE: 68

Met His Val Ala Gln Pro Ala Val Val Leu Ala Ser Ser Arg Gly Ile
 1               5                  10                  15

Ala Ser Phe Val Cys Glu Tyr Glu Ser Pro Gly Lys Ala Asn Glu Ile
                20                  25                  30

Arg Val Thr Val Leu Arg Lys Ala Gly Ser Gln Val Thr Glu Val Cys
            35                  40                  45

Ala Met Thr Tyr Met Lys Glu Asp Glu Leu Thr Phe Leu Asp Asp Pro
 50                  55                  60

Ser Cys Thr Gly Thr Phe Ser Gly Asn Gln Val Asn Leu Thr Ile Gln
 65                  70                  75                  80

Gly Leu Arg Ala Ala Asp Thr Gly Leu Tyr Ile Cys Lys Val Glu Leu
                85                  90                  95
```

Met Tyr Pro Pro Pro Tyr Tyr Leu Gly Leu Gly Asn Gly Thr Gln Ile
            100                 105                 110

Tyr Val Ile Asp Pro Glu Pro Cys Pro Asp Ser Asp
            115                 120

<210> SEQ ID NO 69
<211> LENGTH: 124
<212> TYPE: PRT
<213> ORGANISM: Artificial Sequence
<220> FEATURE:
<223> OTHER INFORMATION: CTLA-4 ECD mutant D26

<400> SEQUENCE: 69

Met His Val Ala Gln Pro Ala Val Val Leu Ala Ser Ser Arg Gly Ile
1               5                   10                  15

Ala Ser Phe Val Cys Glu Tyr Glu Ala Pro His Lys Ala Asn Glu Val
            20                  25                  30

Arg Val Thr Val Leu Arg Glu Ala Gly Ser Gln Val Thr Glu Val Cys
        35                  40                  45

Ala Met Thr Tyr Met Val Glu Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Leu Gly Asn Gly Thr Gln Ile
            100                 105                 110

Tyr Val Ile Asp Pro Glu Pro Cys Pro Asp Ser Asp
            115                 120

<210> SEQ ID NO 70
<211> LENGTH: 124
<212> TYPE: PRT
<213> ORGANISM: Artificial Sequence
<220> FEATURE:
<223> OTHER INFORMATION: CTLA-4 ECD mutant D27

<400> SEQUENCE: 70

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Val
            20                  25                  30

Arg Val Thr Val Leu Arg Glu Ala Gly Ser Gln Val Thr Glu Val Cys
        35                  40                  45

Ala Met Thr Tyr Met Val Glu Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Leu Gly Asn Gly Thr Gln Ile
            100                 105                 110

Tyr Val Ile Asp Pro Glu Pro Cys Pro Asp Ser Asp
            115                 120

<210> SEQ ID NO 71
<211> LENGTH: 124
<212> TYPE: PRT
<213> ORGANISM: Artificial Sequence
<220> FEATURE:
<223> OTHER INFORMATION: CTLA-4 ECD mutant D28

<400> SEQUENCE: 71

Met His Val Ala Gln Pro Ala Val Val Leu Ala Ser Ser Arg Gly Ile
1               5                   10                  15

Ala Ser Phe Val Cys Glu Tyr Glu Ala Pro His Lys Ala Asn Glu Val
            20                  25                  30

Arg Val Thr Val Leu Arg Gln Ala Gly Ser Gln Val Thr Glu Val Cys
        35                  40                  45

Ala Met Thr Tyr Met Met Glu Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Leu Gly Asn Gly Thr Gln Ile
            100                 105                 110

Tyr Val Ile Asp Pro Glu Pro Cys Pro Asp Ser Asp
        115                 120

<210> SEQ ID NO 72
<211> LENGTH: 124
<212> TYPE: PRT
<213> ORGANISM: Artificial Sequence
<220> FEATURE:
<223> OTHER INFORMATION: CTLA-4 ECD mutant D29

<400> SEQUENCE: 72

Met His Val Ala Gln Pro Ala Val Val Leu Ala Ser Ser Arg Gly Ile
1               5                   10                  15

Ala Ser Phe Val Cys Glu Tyr Glu Ala Pro His Lys Ala Asp Glu Ile
            20                  25                  30

Arg Val Thr Val Leu Arg Lys Ala Asp Ser Gln Val Thr Glu Val Cys
        35                  40                  45

Ala Met Thr Tyr Met Met Glu Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Leu Gly Asn Gly Thr Gln Ile
            100                 105                 110

Tyr Val Ile Asp Pro Glu Pro Cys Pro Asp Ser Asp
        115                 120

<210> SEQ ID NO 73
<211> LENGTH: 124
<212> TYPE: PRT
<213> ORGANISM: Artificial Sequence
<220> FEATURE:
<223> OTHER INFORMATION: CTLA-4 ECD mutant D31

<400> SEQUENCE: 73

Met His Val Ala Gln Pro Ala Val Val Leu Ala Ser Ser Arg Gly Ile
1               5                   10                  15

Ala Ser Phe Val Cys Glu Tyr Glu Ala Pro His Asn Ala Asp Glu Ile
            20                  25                  30

Arg Val Thr Val Leu Arg Gln Ala Gly Ser Gln Val Thr Glu Val Cys

```
                    35                  40                  45
Ala Met Thr Tyr Met Val Glu Asp Glu Leu Thr Phe Leu Asp Lys Ser
 50                  55                  60

Ile Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Tyr Tyr Leu Gly Ile Gly Asn Gly Thr Gln Ile
                100                 105                 110

Tyr Val Ile Asp Pro Glu Pro Cys Pro Asp Ser Asp
            115                 120

<210> SEQ ID NO 74
<211> LENGTH: 352
<212> TYPE: PRT
<213> ORGANISM: Artificial Sequence
<220> FEATURE:
<223> OTHER INFORMATION: D3-12-IgG2 fusion protein (with C-terminal
      lysine)

<400> SEQUENCE: 74

Met His Val Ala Gln Pro Ala Val Val Leu Ala Ser Ser Arg Gly Ile
 1               5                  10                  15

Ala Ser Phe Val Cys Glu Tyr Glu Ser Pro Gly Lys Ala Asn Glu Ile
                 20                  25                  30

Arg Val Thr Val Leu Arg Gln Ala Gly Ser Gln Val Thr Glu Val Cys
             35                  40                  45

Ala Met Thr Tyr Met Lys Gly Asp Glu Leu Thr Phe Leu Asp Asp Pro
 50                  55                  60

Ser Cys Thr Gly Thr Phe Ser Gly Asn Gln Val Asn Leu Thr Ile Gln
 65                  70                  75                  80

Gly Leu Arg Ala Ala Asp Thr Gly Leu Tyr Ile Cys Lys Val Glu Leu
                 85                  90                  95

Met Tyr Pro Pro Pro Tyr Leu Gly Ile Gly Asn Gly Thr Gln Ile
                100                 105                 110

Tyr Val Ile Asp Pro Glu Pro Cys Pro Asp Ser Asp Glu Arg Lys Cys
            115                 120                 125

Cys Val Glu Cys Pro Pro Cys Pro Ala Pro Pro Val Ala Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
    210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
```

-continued

```
                275                 280                 285

Asn Gly Gln Pro Glu Asn Asn Tyr Lys Thr Thr Pro Pro Met Leu Asp
            290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 75
<211> LENGTH: 352
<212> TYPE: PRT
<213> ORGANISM: Artificial Sequence
<220> FEATURE:
<223> OTHER INFORMATION: D3-14-IgG2 fusion protein (with C-terminal
      lysine)

<400> SEQUENCE: 75

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
            20                  25                  30

Arg Val Thr Val Leu Arg Gln Ala Asp Ser Gln Val Thr Glu Val Cys
        35                  40                  45

Ala Met Thr Tyr Met Lys Gly Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Glu Arg Lys Cys
        115                 120                 125

Cys Val Glu Cys Pro Pro Cys Pro Ala Pro Pro Val Ala Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
    210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Met Leu Asp
```

```
              290                 295                 300
Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
                340                 345                 350

<210> SEQ ID NO 76
<211> LENGTH: 352
<212> TYPE: PRT
<213> ORGANISM: Artificial Sequence
<220> FEATURE:
<223> OTHER INFORMATION: D3-17-IgG2 fusion protein (with C-terminal
      lysine)

<400> SEQUENCE: 76

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
                20                  25                  30

Arg Val Thr Val Leu Arg Gln Ala Asp Ser Gln Val Thr Glu Val Cys
            35                  40                  45

Ala Met Thr Tyr Met Lys Gly Asp Glu Leu Thr Phe Leu Asp Asp Pro
        50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Glu Arg Lys Cys
            115                 120                 125

Cys Val Glu Cys Pro Pro Cys Pro Ala Pro Pro Val Ala Gly Pro Ser
        130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
    210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Met Leu Asp
    290                 295                 300

Ser Asp Gly Ser Phe Phe Leu Tyr Ser Lys Leu Thr Val Asp Lys Ser
```

```
305                 310                 315                 320
Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 77
<211> LENGTH: 352
<212> TYPE: PRT
<213> ORGANISM: Artificial Sequence
<220> FEATURE:
<223> OTHER INFORMATION: D3-20-IgG2 fusion protein (with C-terminal
      lysine)

<400> SEQUENCE: 77

Met His Val Ala Gln Pro Ala Val Val Leu Ala Ser Ser Arg Gly Ile
 1               5                  10                  15

Ala Ser Phe Val Cys Glu Tyr Glu Ser Pro Gly Lys Ala Asn Glu Ile
                20                  25                  30

Arg Val Thr Val Leu Arg Gln Ala Asp Ser Gln Val Thr Glu Val Cys
            35                  40                  45

Ala Met Thr Tyr Met Lys Gly Asn Glu Leu Thr Phe Leu Asp Asp Pro
        50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Glu Arg Lys Cys
            115                 120                 125

Cys Val Glu Cys Pro Pro Cys Pro Ala Pro Pro Val Ala Gly Pro Ser
        130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Tyr Lys Thr Thr Pro Pro Met Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
```

325                 330                 335

Leu His Asn His Tyr Thr Gln Lys Ser Leu Ser Leu Ser Pro Gly Lys
        340                 345                 350

<210> SEQ ID NO 78
<211> LENGTH: 352
<212> TYPE: PRT
<213> ORGANISM: Artificial Sequence
<220> FEATURE:
<223> OTHER INFORMATION: D3-27-IgG2 fusion protein (with C-terminal
      lysine)

<400> SEQUENCE: 78

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Gly Asn Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Glu Arg Lys Cys
        115                 120                 125

Cys Val Glu Cys Pro Pro Cys Pro Ala Pro Pro Val Ala Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
    210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Met Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys

<210> SEQ ID NO 79
<211> LENGTH: 352
<212> TYPE: PRT
<213> ORGANISM: Artificial Sequence
<220> FEATURE:
<223> OTHER INFORMATION: D3-29-IgG2 fusion protein (with C-terminal lysine)

<400> SEQUENCE: 79

```
Met His Val Ala Gln Pro Ala Val Val Leu Ala Ser Ser Arg Gly Ile
  1               5                  10                  15

Ala Ser Phe Val Cys Glu Tyr Ala Ser Pro Gly Lys Ala Asn Glu Ile
             20                  25                  30

Arg Val Thr Val Leu Arg Gln Ala Asp Ser Gln Val Thr Glu Val Cys
         35                  40                  45

Ala Met Thr Tyr Met Lys Gly Asp Glu Leu Thr Phe Leu Asp Asp Pro
     50                  55                  60

Ser Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Glu Arg Lys Cys
        115                 120                 125

Cys Val Glu Cys Pro Pro Cys Pro Ala Pro Pro Val Ala Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
    210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Met Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350
```

```
<210> SEQ ID NO 80
<211> LENGTH: 372
<212> TYPE: DNA
<213> ORGANISM: Artificial Sequence
<220> FEATURE:
<223> OTHER INFORMATION: CTLA-4 ECD mutant D3-1 coding sequence

<400> SEQUENCE: 80
atgcacgtcg ctcaaccagc cgtcgtactc gcgtcctcta gaggtatcgc ttccttcgtg      60
tgtgaatatg cgtcacccgg caaagccaac gaaattagag tcacagtgct ccgccaagcc     120
ggaagtcaag ttacagaagt ctgcgctatg acatacatga agggagatga actaaccttc     180
cttgacgatc ccagctgcac aggtaccttt tccggaaatc aagttaatct tactattcaa     240
ggacttcgag ccgcggatac cggactctat atttgtaaag tcgaactcat gtacccccc     300
ccttactact tgggttttgg taatggcact cagatctacg tcatcgatcc cgaaccctgc     360
cctgattctg at                                                         372

<210> SEQ ID NO 81
<211> LENGTH: 372
<212> TYPE: DNA
<213> ORGANISM: Artificial Sequence
<220> FEATURE:
<223> OTHER INFORMATION: CTLA-4 ECD mutant D3-2 coding sequence

<400> SEQUENCE: 81
atgcacgtcg ctcaaccagc cgtcgtactc gcgtcctcta gaggtatcgc ttccttcgtg      60
tgtgaatatg agtcacccgg caaagccacc gaaattagag tcacagtgct ccgccaagcc     120
ggaagtcaag ttacagaagt ctgcgctatg acatacatga agggagatga actaaccttc     180
cttgacgatc ccagctgcac aggtaccttt tccggaaatc aagttaatct tactattcaa     240
ggacttcgag ccgcggatac cggactctat atttgtaaag tcgaactcat gtacccccc     300
ccttactact tgggttttgg taatggcact cagatctacg tcatcgatcc cgaaccctgc     360
cctgattctg at                                                         372

<210> SEQ ID NO 82
<211> LENGTH: 372
<212> TYPE: DNA
<213> ORGANISM: Artificial Sequence
<220> FEATURE:
<223> OTHER INFORMATION: CTLA-4 ECD mutant D3-3 coding sequence

<400> SEQUENCE: 82
atgcacgtcg ctcaaccagc cgtcgtactc gcgtcctcta gaggtatcgc ttccttcgtg      60
tgtgaatatg agtcacccgg caaagccaac gaagttagag tcacagtgct ccgccaagcc     120
ggaagtcaag ttacagaagt ctgcgctatg acatacatga agggagatga actaaccttc     180
cttgacgatc ccagctgcac aggtaccttt tccggaaatc aagttaatct tactattcaa     240
ggacttcgag ccgcggatac cggactctat atttgtaaag tcgaactcat gtacccccc     300
ccttactact tgggttttgg taatggcact cagatctacg tcatcgatcc cgaaccctgc     360
cctgattctg at                                                         372

<210> SEQ ID NO 83
<211> LENGTH: 372
<212> TYPE: DNA
<213> ORGANISM: Artificial Sequence
<220> FEATURE:
<223> OTHER INFORMATION: CTLA-4 ECD mutant D3-4 coding sequence

<400> SEQUENCE: 83
```

| | |
|---|---|
| atgcacgtcg ctcaaccagc cgtcgtactc gcgtcctcta gaggtatcgc ttccttcgtg | 60 |
| tgtgaatatg agtcacccgg caaagccaac gaaattagag tcacagtgct ccgccaagcc | 120 |
| gatagtcaag ttacagaagt ctgcgctatg acatacatga agggagatga actaaccttc | 180 |
| cttgacgatc ccagctgcac aggtaccttt tccggaaatc aagttaatct tactattcaa | 240 |
| ggacttcgag ccgcggatac cggactctat atttgtaaag tcgaactcat gtaccccccc | 300 |
| ccttactact tgggttttgg taatggcact cagatctacg tcatcgatcc cgaaccctgc | 360 |
| cctgattctg at | 372 |

<210> SEQ ID NO 84
<211> LENGTH: 372
<212> TYPE: DNA
<213> ORGANISM: Artificial Sequence
<220> FEATURE:
<223> OTHER INFORMATION: CTLA-4 ECD mutant D3-5 coding sequence

<400> SEQUENCE: 84

| | |
|---|---|
| atgcacgtcg ctcaaccagc cgtcgtactc gcgtcctcta gaggtatcgc ttccttcgtg | 60 |
| tgtgaatatg agtcacccgg caaagccaac gaaattagag tcacagtgct ccgccaagcc | 120 |
| ggaagtcaag ttacagaagt ctgcgctgcg acatacatga agggagatga actaaccttc | 180 |
| cttgacgatc ccagctgcac aggtaccttt tccggaaatc aagttaatct tactattcaa | 240 |
| ggacttcgag ccgcggatac cggactctat atttgtaaag tcgaactcat gtaccccccc | 300 |
| ccttactact tgggttttgg taatggcact cagatctacg tcatcgatcc cgaaccctgc | 360 |
| cctgattctg at | 372 |

<210> SEQ ID NO 85
<211> LENGTH: 372
<212> TYPE: DNA
<213> ORGANISM: Artificial Sequence
<220> FEATURE:
<223> OTHER INFORMATION: CTLA-4 ECD mutant D3-6 coding sequence

<400> SEQUENCE: 85

| | |
|---|---|
| atgcacgtcg ctcaaccagc cgtcgtactc gcgtcctcta gaggtatcgc ttccttcgtg | 60 |
| tgtgaatatg agtcacccgg caaagccaac gaaattagag tcacagtgct ccgccaagcc | 120 |
| ggaagtcaag ttacagaagt ctgcgctatg acatacatga tgggagatga actaaccttc | 180 |
| cttgacgatc ccagctgcac aggtaccttt tccggaaatc aagttaatct tactattcaa | 240 |
| ggacttcgag ccgcggatac cggactctat atttgtaaag tcgaactcat gtaccccccc | 300 |
| ccttactact tgggttttgg taatggcact cagatctacg tcatcgatcc cgaaccctgc | 360 |
| cctgattctg at | 372 |

<210> SEQ ID NO 86
<211> LENGTH: 372
<212> TYPE: DNA
<213> ORGANISM: Artificial Sequence
<220> FEATURE:
<223> OTHER INFORMATION: CTLA-4 ECD mutant D3-7 coding sequence

<400> SEQUENCE: 86

| | |
|---|---|
| atgcacgtcg ctcaaccagc cgtcgtactc gcgtcctcta gaggtatcgc ttccttcgtg | 60 |
| tgtgaatatg agtcacccgg caaagccaac gaaattagag tcacagtgct ccgccaagcc | 120 |
| ggaagtcaag ttacagaagt ctgcgctatg acatacatga agggaaatga actaaccttc | 180 |
| cttgacgatc ccagctgcac aggtaccttt tccggaaatc aagttaatct tactattcaa | 240 |

```
ggacttcgag ccgcggatac cggactctat atttgtaaag tcgaactcat gtaccccccc    300
ccttactact tgggttttgg taatggcact cagatctacg tcatcgatcc cgaaccctgc    360
cctgattctg at                                                        372
```

<210> SEQ ID NO 87
<211> LENGTH: 372
<212> TYPE: DNA
<213> ORGANISM: Artificial Sequence
<220> FEATURE:
<223> OTHER INFORMATION: CTLA-4 ECD mutant D3-8 coding sequence

<400> SEQUENCE: 87

```
atgcacgtcg ctcaaccagc cgtcgtactc gcgtcctcta gaggtatcgc ttccttcgtg     60
tgtgaatatg agtcacccgg caaagccaac gaaattagag tcacagtgct ccgccaagcc    120
ggaagtcaag ttacagaagt ctgcgctatg acatacatga agggagatga actaaccttc    180
cttgacgatt ccagctgcac aggtaccttt tccggaaatc aagttaatct tactattcaa    240
ggacttcgag ccgcggatac cggactctat atttgtaaag tcgaactcat gtaccccccc    300
ccttactact tgggttttgg taatggcact cagatctacg tcatcgatcc cgaaccctgc    360
cctgattctg at                                                        372
```

<210> SEQ ID NO 88
<211> LENGTH: 372
<212> TYPE: DNA
<213> ORGANISM: Artificial Sequence
<220> FEATURE:
<223> OTHER INFORMATION: CTLA-4 ECD mutant D3-9 coding sequence

<400> SEQUENCE: 88

```
atgcacgtcg ctcaaccagc cgtcgtactc gcgtcctcta gaggtatcgc ttccttcgtg     60
tgtgaatatg agtcacccgg caaagccaac gaaattagag tcacagtgct ccgccaagcc    120
ggaagtcaag ttacagaagt ctgcgctatg acatacatga agggagatga actaaccttc    180
cttgacgatc ccatctgcac aggtaccttt tccggaaatc aagttaatct tactattcaa    240
ggacttcgag ccgcggatac cggactctat atttgtaaag tcgaactcat gtaccccccc    300
ccttactact tgggttttgg taatggcact cagatctacg tcatcgatcc cgaaccctgc    360
cctgattctg at                                                        372
```

<210> SEQ ID NO 89
<211> LENGTH: 372
<212> TYPE: DNA
<213> ORGANISM: Artificial Sequence
<220> FEATURE:
<223> OTHER INFORMATION: CTLA-4 ECD mutant D3-11 coding sequence

<400> SEQUENCE: 89

```
atgcacgtcg ctcaaccagc cgtcgtactc gcgtcctcta gaggtatcgc ttccttcgtg     60
tgtgaatatg agtcacccgg caaagccaac gaaattagag tcacagtgct ccgccaagcc    120
ggaagtcaag ttacagaagt ctgcgctatg acatacatga agggagatga actaaccttc    180
cttgacgatc ccagctgcac aggtaccttt tccggaaatc aagttaatct tactattcaa    240
ggacttcgag ccatggatac cggactctat atttgtaaag tcgaactcat gtaccccccc    300
ccttactact tgggttttgg taatggcact cagatctacg tcatcgatcc cgaaccctgc    360
cctgattctg at                                                        372
```

```
<210> SEQ ID NO 90
<211> LENGTH: 372
<212> TYPE: DNA
<213> ORGANISM: Artificial Sequence
<220> FEATURE:
<223> OTHER INFORMATION: CTLA-4 ECD mutant D3-12 coding sequence

<400> SEQUENCE: 90
atgcacgtcg ctcaaccagc cgtcgtactc gcgtcctcta gaggtatcgc ttccttcgtg      60
tgtgaatatg agtcacccgg caaagccaac gaaattagag tcacagtgct ccgccaagcc     120
ggaagtcaag ttacagaagt ctgcgctatg acatacatga agggagatga actaaccttc     180
cttgacgatc ccagctgcac aggtaccttt tccggaaatc aagttaatct tactattcaa     240
ggacttcgag ccgcggatac cggactctat atttgtaaag tcgaactcat gtacccccc      300
ccttactact tgggtattgg taatggcact cagatctacg tcatcgatcc cgaaccctgc     360
cctgattctg at                                                         372

<210> SEQ ID NO 91
<211> LENGTH: 372
<212> TYPE: DNA
<213> ORGANISM: Artificial Sequence
<220> FEATURE:
<223> OTHER INFORMATION: CTLA-4 ECD mutant D3-14 coding sequence

<400> SEQUENCE: 91
atgcacgtcg ctcaaccagc cgtcgtactc gcgtcctcta gaggtatcgc ttccttcgtg      60
tgtgaatatg agtcacccgg caaagccaac gaaattagag tcacagtgct ccgccaagcc     120
gatagtcaag ttacagaagt ctgcgctatg acatacatga agggagatga actaaccttc     180
cttgacgatc ccagctgcac aggtaccttt tccggaaatc aagttaatct tactattcaa     240
ggacttcgag ccgcggatac cggactctat atttgtaaag tcgaactcat gtacccccc      300
ccttactact tgggtattgg taatggcact cagatctacg tcatcgatcc cgaaccctgc     360
cctgattctg at                                                         372

<210> SEQ ID NO 92
<211> LENGTH: 372
<212> TYPE: DNA
<213> ORGANISM: Artificial Sequence
<220> FEATURE:
<223> OTHER INFORMATION: CTLA-4 ECD mutant

<400> SEQUENCE: 92
atgcacgtcg ctcaaccagc cgtcgtactc gcgtcctcta gaggtatcgc ttccttcgtg      60
tgtgaatatg agtcacccgg caaagccaac gaaattagag tcacagtgct ccgccaagcc     120
gatagtcaag ttacagaagt ctgcgctatg acatacatga agggagatga actaaccttc     180
cttgacgatc ccagctgcac aggtaccttt tccggaaatc aagttaatct tactattcaa     240
ggacttcgag ccatggatac cggactctat atttgtaaag tcgaactcat gtacccccc      300
ccttactact tgggttttgg taatggcact cagatctacg tcatcgatcc cgaaccctgc     360
cctgattctg at                                                         372

<210> SEQ ID NO 93
<211> LENGTH: 372
<212> TYPE: DNA
<213> ORGANISM: Artificial Sequence
<220> FEATURE:
<223> OTHER INFORMATION: CTLA-4 ECD mutant D3-16 coding sequence

<400> SEQUENCE: 93
```

```
atgcacgtcg ctcaaccagc cgtcgtactc gcgtcctcta gaggtatcgc ttccttcgtg      60
tgtgaatatg agtcacccgg caaagccaac gaaattagag tcacagtgct ccgccaagcc     120
ggaagtcaag ttacagaagt ctgcgctatg acatacatga agggagatga actaaccttc     180
cttgacgatc ccagctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                          372

<210> SEQ ID NO 94
<211> LENGTH: 372
<212> TYPE: DNA
<213> ORGANISM: Artificial Sequence
<220> FEATURE:
<223> OTHER INFORMATION: CTLA-4 ECD mutant D3-17 coding sequence

<400> SEQUENCE: 94
atgcacgtcg ctcaaccagc cgtcgtactc gcgtcctcta gaggtatcgc ttccttcgtg      60
tgtgaatatg agtcacccgg caaagccaac gaaattagag tcacagtgct ccgccaagcc     120
gatagtcaag ttacagaagt ctgcgctatg acatacatga agggagatga actaaccttc     180
cttgacgatc ccagctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                          372

<210> SEQ ID NO 95
<211> LENGTH: 372
<212> TYPE: DNA
<213> ORGANISM: Artificial Sequence
<220> FEATURE:
<223> OTHER INFORMATION: CTLA-4 ECD mutant D3-19 coding sequence

<400> SEQUENCE: 95
atgcacgtcg ctcaaccagc cgtcgtactc gcgtcctcta gaggtatcgc ttccttcgtg      60
tgtgaatatg agtcacccgg caaagccaac gaaattagag tcacagtgct ccgccaagcc     120
gatagtcaag ttacagaagt ctgcgctatg acatacatga agggaaatga actaaccttc     180
cttgacgatc ccagctgcac aggtaccttt tccggaaatc aagttaatct tactattcaa     240
ggacttcgag ccgcggatac cggactctat atttgtaaag tcgaactcat gtaccccccc     300
ccttactact tgggtattgg taatggcact cagatctacg tcatcgatcc cgaaccctgc     360
cctgattctg at                                                          372

<210> SEQ ID NO 96
<211> LENGTH: 372
<212> TYPE: DNA
<213> ORGANISM: Artificial Sequence
<220> FEATURE:
<223> OTHER INFORMATION: CTLA-4 ECD mutant D3-20 coding sequence

<400> SEQUENCE: 96
atgcacgtcg ctcaaccagc cgtcgtactc gcgtcctcta gaggtatcgc ttccttcgtg      60
tgtgaatatg agtcacccgg caaagccaac gaaattagag tcacagtgct ccgccaagcc     120
gatagtcaag ttacagaagt ctgcgctatg acatacatga agggaaatga actaaccttc     180
cttgacgatc ccagctgcac aggtaccttt tccggaaatc aagttaatct tactattcaa     240
```

```
ggacttcgag ccatggatac cggactctat atttgtaaag tcgaactcat gtacccccc    300 ccttactact tgggtattgg taatggcact cagatctacg tcatcgatcc cgaaccctgc   360
cctgattctg at                                                       372
```

<210> SEQ ID NO 97
<211> LENGTH: 372
<212> TYPE: DNA
<213> ORGANISM: Artificial Sequence
<220> FEATURE:
<223> OTHER INFORMATION: CTLA-4 ECD mutant D3-21 coding sequence

<400> SEQUENCE: 97

```
atgcacgtcg ctcaaccagc cgtcgtactc gcgtcctcta gaggtatcgc ttccttcgtg    60
tgtgaatatg agtcacccgg caaagccaac gaaattagag tcacagtgct ccgccaagcc   120
gatagtcaag ttacagaagt ctgcgctatg acatacatga agggaaatga actaaccttc   180
cttgacgatc ccagctgcac aggtaccttt tccggaaatc aagttaatct tactattcaa   240
ggacttcgag ccatggatac cggactctat atttgtaaag tcgaactcat gtacccccc    300 ccttactact tgggttttgg taatggcact cagatctacg tcatcgatcc cgaaccctgc   360
cctgattctg at                                                       372
```

<210> SEQ ID NO 98
<211> LENGTH: 372
<212> TYPE: DNA
<213> ORGANISM: Artificial Sequence
<220> FEATURE:
<223> OTHER INFORMATION: CTLA-4 ECD mutant D3-22 coding sequence

<400> SEQUENCE: 98

```
atgcacgtcg ctcaaccagc cgtcgtactc gcgtcctcta gaggtatcgc ttccttcgtg    60
tgtgaatatg agtcacccgg caaagccaac gaaattagag tcacagtgct ccgccaagcc   120
ggaagtcaag ttacagaagt ctgcgctatg acatacatga agggaaatga actaaccttc   180
cttgacgatc ccagctgcac aggtaccttt tccggaaatc aagttaatct tactattcaa   240
ggacttcgag ccatggatac cggactctat atttgtaaag tcgaactcat gtacccccc    300 ccttactact tgggtattgg taatggcact cagatctacg tcatcgatcc cgaaccctgc   360
cctgattctg at                                                       372
```

<210> SEQ ID NO 99
<211> LENGTH: 372
<212> TYPE: DNA
<213> ORGANISM: Artificial Sequence
<220> FEATURE:
<223> OTHER INFORMATION: CTLA-4 ECD mutant D3-23 coding sequence

<400> SEQUENCE: 99

```
atgcacgtcg ctcaaccagc cgtcgtactc gcgtcctcta gaggtatcgc ttccttcgtg    60
tgtgaatatg agtcacccgg caaagccaac gaaattagag tcacagtgct ccgccaagcc   120
gatagtcaag ttacagaagt ctgcgctatg acatacatga agggaaatga actaaccttc   180
cttgacgatc ccagctgcac aggtaccttt tccggaaatc aagttaatct tactattcaa   240
ggacttcgag ccgcggatac cggactctat atttgtaaag tcgaactcat gtacccccc    300 ccttactact tgggttttgg taatggcact cagatctacg tcatcgatcc cgaaccctgc   360
cctgattctg at                                                       372
```

<210> SEQ ID NO 100
<211> LENGTH: 372
<212> TYPE: DNA
<213> ORGANISM: Artificial Sequence
<220> FEATURE:
<223> OTHER INFORMATION: CTLA-4 ECD mutant D3-24 coding sequence

<400> SEQUENCE: 100

```
atgcacgtcg ctcaaccagc cgtcgtactc gcgtcctcta gaggtatcgc ttccttcgtg    60
tgtgaatatg agtcacccgg caaagccaac gaaattagag tcacagtgct ccgccaagcc   120
ggaagtcaag ttacagaagt ctgcgctatg acatacatga agggaaatga actaaccttc   180
cttgacgatc ccagctgcac aggtaccttt tccggaaatc aagttaatct tactattcaa   240
ggacttcgag ccatggatac cggactctat atttgtaaag tcgaactcat gtaccccccc   300
ccttactact tgggttttgg taatggcact cagatctacg tcatcgatcc cgaaccctgc   360
cctgattctg at                                                       372
```

<210> SEQ ID NO 101
<211> LENGTH: 372
<212> TYPE: DNA
<213> ORGANISM: Artificial Sequence
<220> FEATURE:
<223> OTHER INFORMATION: CTLA-4 ECD mutant D3-25 coding sequence

<400> SEQUENCE: 101

```
atgcacgtcg ctcaaccagc cgtcgtactc gcgtcctcta gaggtatcgc ttccttcgtg    60
tgtgaatatg agtcacccgg caaagccaac gaaattagag tcacagtgct ccgccaagcc   120
ggaagtcaag ttacagaagt ctgcgctatg acatacatga agggaaatga actaaccttc   180
cttgacgatc ccagctgcac aggtaccttt tccggaaatc aagttaatct tactattcaa   240
ggacttcgag ccgcggatac cggactctat atttgtaaag tcgaactcat gtaccccccc   300
ccttactact tgggtattgg taatggcact cagatctacg tcatcgatcc cgaaccctgc   360
cctgattctg at                                                       372
```

<210> SEQ ID NO 102
<211> LENGTH: 372
<212> TYPE: DNA
<213> ORGANISM: Artificial Sequence
<220> FEATURE:
<223> OTHER INFORMATION: CTLA-4 ECD mutant D3-26 coding sequence

<400> SEQUENCE: 102

```
atgcacgtcg ctcaaccagc cgtcgtactc gcgtcctcta gaggtatcgc ttccttcgtg    60
tgtgaatatg cgtcacccgg caaagccaac gaaattagag tcacagtgct ccgccaagcc   120
gatagtcaag ttacagaagt ctgcgctatg acatacatga agggaaatga actaaccttc   180
cttgacgatc ccagctgcac aggtaccttt tccggaaatc aagttaatct tactattcaa   240
ggacttcgag ccatggatac cggactctat atttgtaaag tcgaactcat gtaccccccc   300
ccttactact tgggtattgg taatggcact cagatctacg tcatcgatcc cgaaccctgc   360
cctgattctg at                                                       372
```

<210> SEQ ID NO 103
<211> LENGTH: 372
<212> TYPE: DNA
<213> ORGANISM: Artificial Sequence
<220> FEATURE:
<223> OTHER INFORMATION: CTLA-4 ECD mutant D3-27 coding sequence

<400> SEQUENCE: 103

```
atgcacgtcg ctcaaccagc cgtcgtactc gcgtcctcta gaggtatcgc ttccttcgtg      60
tgtgaatatg agtcacccgg caaagccaac gaagttagag tcacagtgct ccgccaagcc     120
gatagtcaag ttacagaagt ctgcgctatg acatacatga agggaaatga actaaccttc     180
cttgacgatc ccagctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                          372
```

<210> SEQ ID NO 104
<211> LENGTH: 372
<212> TYPE: DNA
<213> ORGANISM: Artificial Sequence
<220> FEATURE:
<223> OTHER INFORMATION: CTLA-4 ECD mutant D3-28 coding sequence

<400> SEQUENCE: 104

```
atgcacgtcg ctcaaccagc cgtcgtactc gcgtcctcta gaggtatcgc ttccttcgtg      60
tgtgaatatg agtcacccgg caaagccaac gaaattagag tcacagtgct ccgccaagcc     120
gatagtcaag ttacagaagt ctgcgctatg acatacatga agggaaatga actaaccttc     180
ctcgacgatc ccatctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                          372
```

<210> SEQ ID NO 105
<211> LENGTH: 372
<212> TYPE: DNA
<213> ORGANISM: Artificial Sequence
<220> FEATURE:
<223> OTHER INFORMATION: CTLA-4 ECD mutant D3-29 coding sequence

<400> SEQUENCE: 105

```
atgcacgtcg ctcaaccagc cgtcgtactc gcgtcctcta gaggtatcgc ttccttcgtg      60
tgtgaatatg cgtcacccgg caaagccaac gaaattagag tcacagtgct ccgccaagcc     120
gatagtcaag ttacagaagt ctgcgctatg acatacatga agggagatga actaaccttc     180
cttgacgatc ccagctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                          372
```

<210> SEQ ID NO 106
<211> LENGTH: 372
<212> TYPE: DNA
<213> ORGANISM: Artificial Sequence
<220> FEATURE:
<223> OTHER INFORMATION: CTLA-4 ECD mutant D3-30 coding sequence

<400> SEQUENCE: 106

```
atgcacgtcg ctcaaccagc cgtcgtactc gcgtcctcta gaggtatcgc ttccttcgtg      60
tgtgaatatg agtcacccgg caaagccaac gaaattagag tcacagtgct ccgccaagcc     120
gatagtcaag ttacagaagt ctgcgctatg acatacatga agggagatga actaaccttc     180
cttgacgatc ccatctgcac aggtaccttt tccggaaatc aagttaatct tactattcaa     240
```

```
ggacttcgag ccatggatac cggactctat atttgtaaag tcgaactcat gtaccccccc    300
ccttactact tgggtattgg taatggcact cagatctacg tcatcgatcc cgaaccctgc    360
cctgattctg at                                                        372
```

<210> SEQ ID NO 107
<211> LENGTH: 372
<212> TYPE: DNA
<213> ORGANISM: Artificial Sequence
<220> FEATURE:
<223> OTHER INFORMATION: CTLA-4 ECD mutant D3-31 coding sequence

<400> SEQUENCE: 107

```
atgcacgtcg ctcaaccagc cgtcgtactc gcgtcctcta gaggtatcgc ttccttcgtg     60
tgtgaatatg agtcacccgg caaagccaac gaaattagag tcacagtgct ccgccaagcc    120
gatagtcaag ttacagaagt ctgcgctatg acatacatga aggaagatga actaaccttc    180
cttgacgatc ccagctgcac aggtaccttt tccggaaatc aagttaatct tactattcaa    240
ggacttcgag ccgcggatac cggactctat atttgtaaag tcgaactcat gtaccccccc    300
ccttactact tgggtattgg taatggcact cagatctacg tcatcgatcc cgaaccctgc    360
cctgattctg at                                                        372
```

<210> SEQ ID NO 108
<211> LENGTH: 372
<212> TYPE: DNA
<213> ORGANISM: Artificial Sequence
<220> FEATURE:
<223> OTHER INFORMATION: CTLA-4 ECD mutant D3-32 coding sequence

<400> SEQUENCE: 108

```
atgcacgtcg ctcaaccagc cgtcgtactc gcgtcctcta gaggtatcgc ttccttcgtg     60
tgtgaatatg agtcacccgg caaagccaac gaaattagag tcacagtgct ccgcaaagcc    120
gatagtcaag ttacagaagt ctgcgctatg acatacatga agggagatga actaaccttc    180
cttgacgatc ccagctgcac aggtaccttt tccggaaatc aagttaatct tactattcaa    240
ggacttcgag ccgcggatac cggactctat atttgtaaag tcgaactcat gtaccccccc    300
ccttactact tgggtattgg taatggcact cagatctacg tcatcgatcc cgaaccctgc    360
cctgattctg at                                                        372
```

<210> SEQ ID NO 109
<211> LENGTH: 372
<212> TYPE: DNA
<213> ORGANISM: Artificial Sequence
<220> FEATURE:
<223> OTHER INFORMATION: CTLA-4 ECD mutant D3-33 coding sequence

<400> SEQUENCE: 109

```
atgcacgtcg ctcaaccagc cgtcgtactc gcgtcctcta gaggtatcgc ttccttcgtg     60
tgtgaatatg agtcacccgg caaagccaac gaaattagag tcacagtgct ccgcaaagcc    120
gatagtcaag ttacagaagt ctgcgctatg acatacatga aggaagatga actaaccttc    180
cttgacgatc ccagctgcac aggtaccttt tccggaaatc aagttaatct tactattcaa    240
ggacttcgag ccgcggatac cggactctat atttgtaaag tcgaactcat gtaccccccc    300
ccttactact tgggtattgg taatggcact cagatctacg tcatcgatcc cgaaccctgc    360
cctgattctg at                                                        372
```

<210> SEQ ID NO 110
<211> LENGTH: 372
<212> TYPE: DNA
<213> ORGANISM: Artificial Sequence
<220> FEATURE:
<223> OTHER INFORMATION: CTLA-4 ECD mutant D3-34 coding sequence

<400> SEQUENCE: 110

```
atgcacgtcg ctcaaccagc cgtcgtactc gcgtcctcta gaggtatcgc ttccttcgtg      60
tgtgaatatg cgtcacccgg caaagccaac gaagttagag tcacagtgct ccgccaagcc     120
gatagtcaag ttacagaagt ctgcgctatg acatacatga agggaaatga actaaccttc     180
cttgacgatc ccagctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                         372
```

<210> SEQ ID NO 111
<211> LENGTH: 372
<212> TYPE: DNA
<213> ORGANISM: Artificial Sequence
<220> FEATURE:
<223> OTHER INFORMATION: CTLA-4 ECD mutant D3-39 coding sequence

<400> SEQUENCE: 111

```
atgcacgtcg ctcaaccagc cgtcgtactc gcgtcctcta gaggtatcgc ttccttcgtg      60
tgtgaatatg agtcacccgg caaagccaac gaagttagag tcacagtgct ccgccaagcc     120
gatagtcaag ttacagaagt ctgcgctatg acatacatga agggaaatga actaaccttc     180
cttgacgatc ccatctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                         372
```

<210> SEQ ID NO 112
<211> LENGTH: 372
<212> TYPE: DNA
<213> ORGANISM: Artificial Sequence
<220> FEATURE:
<223> OTHER INFORMATION: CTLA-4 ECD mutant D3-50 coding sequence

<400> SEQUENCE: 112

```
atgcacgtcg ctcaaccagc cgtcgtactc gcgtcctcta gaggtatcgc ttccttcgtg      60
tgtgaatatg cgtcacccgg caaagccaac gaagttagag tcacagtgct ccgccaagcc     120
gatagtcaag ttacagaagt ctgcgctatg acatacatga agggagatga actaaccttc     180
cttgacgatc ccatctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                         372
```

<210> SEQ ID NO 113
<211> LENGTH: 372
<212> TYPE: DNA
<213> ORGANISM: Artificial Sequence
<220> FEATURE:
<223> OTHER INFORMATION: CTLA-4 ECD mutant D3-52 coding sequence

<400> SEQUENCE: 113

```
atgcacgtcg ctcaaccagc cgtcgtactc gcgtcctcta gaggtatcgc ttccttcgtg    60
tgtgaatatg cgtcacccgg caaagccaac gaaattagag tcacagtgct ccgccaagcc   120
gatagtcaag ttacagaagt ctgcgctatg acatacatga agggaaatga actaaccttc   180
cttgacgatc ccatctgcac aggtaccttt tccggaaatc aagttaatct tactattcaa   240
ggacttcgag ccatggatac cggactctat atttgtaaag tcgaactcat gtaccccccc   300
ccttactact tgggtattgg taatggcact cagatctacg tcatcgatcc cgaaccctgc   360
cctgattctg at                                                        372
```

<210> SEQ ID NO 114
<211> LENGTH: 372
<212> TYPE: DNA
<213> ORGANISM: Artificial Sequence
<220> FEATURE:
<223> OTHER INFORMATION: CTLA-4 ECD mutant D3-53 coding sequence

<400> SEQUENCE: 114

```
atgcacgtcg ctcaaccagc cgtcgtactc gcgtcctcta gaggtatcgc ttccttcgtg    60
tgtgaatatg agtcacccgg caaagccaac gaaattagag tcacagtgct ccgccaagcc   120
ggaagtcaag ttacagaagt ctgcgctatg acatacatga agggagatga actaaccttc   180
cttgacgatc ccagctgcac aggtaccttt tccggaaatc aagttaatct tactattcaa   240
ggacttcgag ccgcggatac cggactctat atttgtaaag tcgaactcat gtaccccccc   300
ccttactacg agggtatagg taatggcact cagatctacg tcatcgatcc cgaaccctgc   360
cctgattctg at                                                        372
```

<210> SEQ ID NO 115
<211> LENGTH: 372
<212> TYPE: DNA
<213> ORGANISM: Artificial Sequence
<220> FEATURE:
<223> OTHER INFORMATION: CTLA-4 ECD mutant D3-54 coding sequence

<400> SEQUENCE: 115

```
atgcacgtcg ctcaaccagc cgtcgtactc gcgtcctcta gaggtatcgc ttccttcgtg    60
tgtgaatatg cgtcacccgg caaagccaac gaagttagag tcacagtgct ccgccaagcc   120
gatagtcaag ttacagaagt ctgcgctatg acatacatga aggaaaatga actaaccttc   180
cttgacgatc ccatctgcac aggtaccttt tccggaaatc aagttaatct tactattcaa   240
ggacttcgag ccatggatac cggactctat atttgtaaag tcgaactcat gtaccccccc   300
ccttactact tgggtattgg taatggcact cagatctacg tcatcgatcc cgaaccctgc   360
cctgattctg at                                                        372
```

<210> SEQ ID NO 116
<211> LENGTH: 372
<212> TYPE: DNA
<213> ORGANISM: Artificial Sequence
<220> FEATURE:
<223> OTHER INFORMATION: CTLA-4 ECD mutant D3-55 coding sequence

<400> SEQUENCE: 116

```
atgcacgtcg ctcaaccagc cgtcgtactc gcgtcctcta gaggtatcgc ttccttcgtg    60
tgtgaatatg agtcacccgg caaagccaac gaagttagag tcacagtgct ccgccaagcc   120
gatagtcaag ttacagaagt ctgcgctatg acatacatga aggaaaatga actaaccttc   180
cttgacgatc ccatctgcac aggtaccttt tccggaaatc aagttaatct tactattcaa   240
```

```
ggacttcgag ccatggatac cggactctat atttgtaaag tcgaactcat gtaccccccc    300
ccttactact tgggtattgg taatggcact cagatctacg tcatcgatcc cgaaccctgc    360
cctgattctg at                                                       372
```

<210> SEQ ID NO 117
<211> LENGTH: 372
<212> TYPE: DNA
<213> ORGANISM: Artificial Sequence
<220> FEATURE:
<223> OTHER INFORMATION: CTLA-4 ECD mutant D3-56 coding sequence

<400> SEQUENCE: 117

```
atgcacgtcg ctcaaccagc cgtcgtactc gcgtcctcta gaggtatcgc ttccttcgtg    60
tgtgaatatg cgtcacccgg caaagccaac gaagttagag tcacagtgct ccgccaagcc   120
gatagtcaag ttacagaagt ctgcgctatg acatacatga aggaaaatga actaaccttc   180
cttgacgatc ccagctgcac aggtaccttt tccggaaatc aagttaatct tactattcaa   240
ggacttcgag ccatggatac cggactctat atttgtaaag tcgaactcat gtaccccccc   300
ccttactact tgggtattgg taatggcact cagatctacg tcatcgatcc cgaaccctgc   360
cctgattctg at                                                       372
```

<210> SEQ ID NO 118
<211> LENGTH: 372
<212> TYPE: DNA
<213> ORGANISM: Artificial Sequence
<220> FEATURE:
<223> OTHER INFORMATION: CTLA-4 ECD mutant D3-57 coding sequence

<400> SEQUENCE: 118

```
atgcacgtcg ctcaaccagc cgtcgtactc gcgtcctcta gaggtatcgc ttccttcgtg    60
tgtgaatatg cgtcacccgg caaagccaac gaaattagag tcacagtgct ccgccaagcc   120
gatagtcaag ttacagaagt ctgcgctatg acatacatga aggaagatga actaaccttc   180
cttgacgatc ccatctgcac aggtaccttt tccggaaatc aagttaatct tactattcaa   240
ggacttcgag ccatggatac cggactctat atttgtaaag tcgaactcat gtaccccccc   300
ccttactact tgggtattgg taatggcact cagatctacg tcatcgatcc cgaaccctgc   360
cctgattctg at                                                       372
```

<210> SEQ ID NO 119
<211> LENGTH: 372
<212> TYPE: DNA
<213> ORGANISM: Artificial Sequence
<220> FEATURE:
<223> OTHER INFORMATION: CTLA-4 ECD mutant D3-58 coding sequence

<400> SEQUENCE: 119

```
atgcacgtcg ctcaaccagc cgtcgtactc gcgtcctcta gaggtatcgc ttccttcgtg    60
tgtgaatatg cgtcacccgg caaagccaac gaagttagag tcacagtgct ccgccaagcc   120
gatagtcaag ttacagaagt ctgcgctatg acatacatga aggaagatga actaaccttc   180
cttgacgatc ccagctgcac aggtaccttt tccggaaatc aagttaatct tactattcaa   240
ggacttcgag ccatggatac cggactctat atttgtaaag tcgaactcat gtaccccccc   300
ccttactact tgggtattgg taatggcact cagatctacg tcatcgatcc cgaaccctgc   360
cctgattctg at                                                       372
```

```
<210> SEQ ID NO 120
<211> LENGTH: 372
<212> TYPE: DNA
<213> ORGANISM: Artificial Sequence
<220> FEATURE:
<223> OTHER INFORMATION: CTLA-4 ECD mutant D3-59 coding sequence

<400> SEQUENCE: 120
atgcacgtcg ctcaaccagc cgtcgtactc gcgtcctcta gaggtatcgc ttccttcgtg      60
tgtgaatatg agtcacccgg caaagccaac gaaattagag tcacagtgct ccgccaagcc     120
gatagtcaag ttacagaagt ctgcgctatg acatacatga aggaaaatga actaaccttc     180
cttgacgatc ccatctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                        372

<210> SEQ ID NO 121
<211> LENGTH: 372
<212> TYPE: DNA
<213> ORGANISM: Artificial Sequence
<220> FEATURE:
<223> OTHER INFORMATION: CTLA-4 ECD mutant D3-60 coding sequence

<400> SEQUENCE: 121
atgcacgtcg ctcaaccagc cgtcgtactc gcgtcctcta gaggtatcgc ttccttcgtg      60
tgtgaatatg cgtcacccgg caaagccaac gaaattagag tcacagtgct ccgccaagcc     120
gatagtcaag ttacagaagt ctgcgctatg acatacatga aggaaaatga actaaccttc     180
cttgacgatc ccagctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                        372

<210> SEQ ID NO 122
<211> LENGTH: 372
<212> TYPE: DNA
<213> ORGANISM: Artificial Sequence
<220> FEATURE:
<223> OTHER INFORMATION: CTLA-4 ECD mutant D3-61 coding sequence

<400> SEQUENCE: 122
atgcacgtcg ctcaaccagc cgtcgtactc gcgtcctcta gaggtatcgc ttccttcgtg      60
tgtgaatatg agtcacccgg caaagccaac gaaattagag tcacagtgct ccgccaagcc     120
gatagtcaag ttacagaagt ctgcgctatg acatacatga aggaaaatga actaaccttc     180
cttgacgatc ccagctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                        372

<210> SEQ ID NO 123
<211> LENGTH: 372
<212> TYPE: DNA
<213> ORGANISM: Artificial Sequence
<220> FEATURE:
<223> OTHER INFORMATION: CTLA-4 ECD mutant D3-62 coding sequence

<400> SEQUENCE: 123
```

```
atgcacgtcg ctcaaccagc cgtcgtactc gcgtcctcta gaggtatcgc ttccttcgtg      60
tgtgaatatg cgtcacccgg caaagccaac gaaattagag tcacagtgct ccgccaagcc     120
gatagtcaag ttacagaagt ctgcgctatg acatacatga aggaagatga actaaccttc     180
cttgacgatc ccagctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                         372

<210> SEQ ID NO 124
<211> LENGTH: 372
<212> TYPE: DNA
<213> ORGANISM: Artificial Sequence
<220> FEATURE:
<223> OTHER INFORMATION: CTLA-4 ECD mutant D3-63 coding sequence

<400> SEQUENCE: 124
atgcacgtcg ctcaaccagc cgtcgtactc gcgtcctcta gaggtatcgc ttccttcgtg      60
tgtgaatatg cgtcacccgg caaagccaac gaagttagag tcacagtgct ccgccaagcc     120
gatagtcaag ttacagaagt ctgcgctgcg acatacatga aggaaaatga actaaccttc     180
cttgacgatc ccatctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                         372

<210> SEQ ID NO 125
<211> LENGTH: 372
<212> TYPE: DNA
<213> ORGANISM: Artificial Sequence
<220> FEATURE:
<223> OTHER INFORMATION: CTLA-4 ECD mutant D3-64 coding sequence

<400> SEQUENCE: 125
atgcacgtcg ctcaaccagc cgtcgtactc gcgtcctcta gaggtatcgc ttccttcgtg      60
tgtgaatatg cgtcacccgg caaagccaac gaagttagag tcacagtgct ccgccaagcc     120
gatagtcaag ttacagaagt ctgcgctatg acatacatga tggaaaatga actaaccttc     180
cttgacgatc ccatctgcac aggtaccttt tccggaaatc aagttaatct tactattcaa     240
ggacttcgag ccatggatac cggactctat atttgtaaag tcgaactcat gtaccccccc     300
ccttactact tgggtattgg taatggcact cagatctacg tcatcgatcc cgaaccctgc     360
cctgattctg at                                                         372

<210> SEQ ID NO 126
<211> LENGTH: 372
<212> TYPE: DNA
<213> ORGANISM: Artificial Sequence
<220> FEATURE:
<223> OTHER INFORMATION: CTLA-4 ECD mutant D3-65 coding sequence

<400> SEQUENCE: 126
atgcacgtcg ctcaaccagc cgtcgtactc gcgtcctcta gaggtatcgc ttccttcgtg      60
tgtgaatatg cgtcacccgg caaagccaac gaagttagag tcacagtgct ccgccaagcc     120
gatagtcaag ttacagaagt ctgcgctatg acatacatga agggaaatga actaaccttc     180
cttgacgatc ccagctgcac aggtaccttt tccggaaatc aagttaatct tactattcaa     240
```

| | |
|---|---|
| ggacttcgag ccatggatac cggactctat atttgtaaag tcgaactcat gtaccccccc | 300 |
| ccttactacg agggtatagg taatggcact cagatctacg tcatcgatcc cgaaccctgc | 360 |
| cctgattctg at | 372 |

<210> SEQ ID NO 127
<211> LENGTH: 372
<212> TYPE: DNA
<213> ORGANISM: Artificial Sequence
<220> FEATURE:
<223> OTHER INFORMATION: CTLA-4 ECD mutant D3-66 coding sequence

<400> SEQUENCE: 127

| | |
|---|---|
| atgcacgtcg ctcaaccagc cgtcgtactc gcgtcctcta gaggtatcgc ttccttcgtg | 60 |
| tgtgaatatg cgtcacccgg caaagccaac gaagttagag tcacagtgct ccgccaagcc | 120 |
| gatagtcaag ttacagaagt ctgcgctatg acatacatga agggagatga actaaccttc | 180 |
| cttgacgatc ccatctgcac aggtaccttt tccggaaatc aagttaatct tactattcaa | 240 |
| ggacttcgag ccatggatac cggactctat atttgtaaag tcgaactcat gtaccccccc | 300 |
| ccttactacg agggtatagg taatggcact cagatctacg tcatcgatcc cgaaccctgc | 360 |
| cctgattctg at | 372 |

<210> SEQ ID NO 128
<211> LENGTH: 372
<212> TYPE: DNA
<213> ORGANISM: Artificial Sequence
<220> FEATURE:
<223> OTHER INFORMATION: CTLA-4 ECD mutant D3-68 coding sequence

<400> SEQUENCE: 128

| | |
|---|---|
| atgcacgtcg ctcaaccagc cgtcgtactc gcgtcctcta gaggtatcgc ttccttcgtg | 60 |
| tgtgaatatg agtcacccgg caaagccaac gaaattagag tcacagtgct ccgccaagcc | 120 |
| gatagtcaag ttacagaagt ctgcgctatg acatacatga agggagatga actaaccttc | 180 |
| cttgacgatc ccagctgcac aggtaccttt tccggaaatc aagttaatct tactattcaa | 240 |
| ggacttcgag ccgcggatac cggactctat atttgtaaag tcgaactcat gtaccccccc | 300 |
| ccttactacg agggtattgg taatggcact cagatctacg tcatcgatcc cgaaccctgc | 360 |
| cctgattctg at | 372 |

<210> SEQ ID NO 129
<211> LENGTH: 372
<212> TYPE: DNA
<213> ORGANISM: Artificial Sequence
<220> FEATURE:
<223> OTHER INFORMATION: CTLA-4 ECD mutant D3-69 coding sequence

<400> SEQUENCE: 129

| | |
|---|---|
| atgcacgtcg ctcaaccagc cgtcgtactc gcgtcctcta gaggtatcgc ttccttcgtg | 60 |
| tgtgaatatg agtcacccgg caaagccaac gaaattagag tcacagtgct ccgccaagcc | 120 |
| gatagtcaag ttacagaagt ctgcgctatg acatacatga agggagatga actaaccttc | 180 |
| cttgacgatc ccagctgcac aggtaccttt tccggaaatc aagttaatct tactattcaa | 240 |
| ggacttcgag ccatggatac cggactctat atttgtaaag tcgaactcat gtaccccccc | 300 |
| ccttactacg agggtattgg taatggcact cagatctacg tcatcgatcc cgaaccctgc | 360 |
| cctgattctg at | 372 |

<210> SEQ ID NO 130
<211> LENGTH: 372
<212> TYPE: DNA
<213> ORGANISM: Artificial Sequence
<220> FEATURE:
<223> OTHER INFORMATION: CTLA-4 ECD mutant D3-70 coding sequence

<400> SEQUENCE: 130

```
atgcacgtcg ctcaaccagc cgtcgtactc gcgtcctcta gaggtatcgc ttccttcgtg    60
tgtgaatatg agtcacccgg caaagccaac gaagttagag tcacagtgct ccgccaagcc   120
gatagtcaag ttacagaagt ctgcgctatg acatacatga agggaaatga actaaccttc   180
cttgacgatc ccagctgcac aggtaccttt tccggaaatc aagttaatct tactattcaa   240
ggacttcgag ccatggatac cggactctat atttgtaaag tcgaactcat gtaccccccc   300
ccttactacg agggtattgg taatggcact cagatctacg tcatcgatcc cgaaccctgc   360
cctgattctg at                                                       372
```

<210> SEQ ID NO 131
<211> LENGTH: 372
<212> TYPE: DNA
<213> ORGANISM: Artificial Sequence
<220> FEATURE:
<223> OTHER INFORMATION: CTLA-4 ECD mutant D3-71 coding sequence

<400> SEQUENCE: 131

```
atgcacgtcg ctcaaccagc cgtcgtactc gcgtcctcta gaggtatcgc ttccttcgtg    60
tgtgaatatg cgtcacccgg caaagccaac gaaattagag tcacagtgct ccgccaagcc   120
gatagtcaag ttacagaagt ctgcgctatg acatacatga agggagatga actaaccttc   180
cttgacgatc ccagctgcac aggtaccttt tccggaaatc aagttaatct tactattcaa   240
ggacttcgag ccatggatac cggactctat atttgtaaag tcgaactcat gtaccccccc   300
ccttactacg agggtattgg taatggcact cagatctacg tcatcgatcc cgaaccctgc   360
cctgattctg at                                                       372
```

<210> SEQ ID NO 132
<211> LENGTH: 372
<212> TYPE: DNA
<213> ORGANISM: Artificial Sequence
<220> FEATURE:
<223> OTHER INFORMATION: CTLA-4 ECD mutant D3-72 coding sequence

<400> SEQUENCE: 132

```
atgcacgtcg ctcaaccagc cgtcgtactc gcgtcctcta gaggtatcgc ttccttcgtg    60
tgtgaatatg agtcacccgg caaagccaac gaaattagag tcacagtgct ccgccaagcc   120
gatagtcaag ttacagaagt ctgcgctatg acatacatga agggaaatga actaaccttc   180
cttgacgatc ccagctgcac aggtaccttt tccggaaatc aagttaatct tactattcaa   240
ggacttcgag ccatggatac cggactctat atttgtaaag tcgaactcat gtaccccccc   300
ccttactacg agggtattgg taatggcact cagatctacg tcatcgatcc cgaaccctgc   360
cctgattctg at                                                       372
```

<210> SEQ ID NO 133
<211> LENGTH: 372
<212> TYPE: DNA
<213> ORGANISM: Artificial Sequence
<220> FEATURE:
<223> OTHER INFORMATION: CTLA-4 ECD mutant D3-73 coding sequence

<400> SEQUENCE: 133

```
atgcacgtcg ctcaaccagc cgtcgtactc gcgtcctcta gaggtatcgc ttccttcgtg    60
tgtgaatatg agtcacccgg caaagccaac gaagttagag tcacagtgct ccgccaagcc   120
gatagtcaag ttacagaagt ctgcgctatg acatacatga agggaaatga actaaccttc   180
cttgacgatc ccatctgcac aggtaccttt tccggaaatc aagttaatct tactattcaa   240
ggacttcgag ccatggatac cggactctat atttgtaaag tcgaactcat gtaccccccc   300
ccttactacg agggtattgg taatggcact cagatctacg tcatcgatcc cgaaccctgc   360
cctgattctg at                                                       372

<210> SEQ ID NO 134
<211> LENGTH: 372
<212> TYPE: DNA
<213> ORGANISM: Artificial Sequence
<220> FEATURE:
<223> OTHER INFORMATION: CTLA-4 ECD mutant D3-74 coding sequence

<400> SEQUENCE: 134
atgcacgtcg ctcaaccagc cgtcgtactc gcgtcctcta gaggtatcgc ttccttcgtg    60
tgtgaatatg cgtcacccgg caaagccaac gaaattagag tcacagtgct ccgccaagcc   120
gatagtcaag ttacagaagt ctgcgctatg acatacatga agggaaatga actaaccttc   180
cttgacgatc ccatctgcac aggtaccttt tccggaaatc aagttaatct tactattcaa   240
ggacttcgag ccatggatac cggactctat atttgtaaag tcgaactcat gtaccccccc   300
ccttactacg agggtattgg taatggcact cagatctacg tcatcgatcc cgaaccctgc   360
cctgattctg at                                                       372

<210> SEQ ID NO 135
<211> LENGTH: 372
<212> TYPE: DNA
<213> ORGANISM: Artificial Sequence
<220> FEATURE:
<223> OTHER INFORMATION: CTLA-4 ECD mutant D3-75 coding sequence

<400> SEQUENCE: 135
atgcacgtcg ctcaaccagc cgtcgtactc gcgtcctcta gaggtatcgc ttccttcgtg    60
tgtgaatatg agtcacccgg caaagccaac gaagttagag tcacagtgct ccgccaagcc   120
gatagtcaag ttacagaagt ctgcgctatg acatacatga aggaaaatga actaaccttc   180
cttgacgatc ccagctgcac aggtaccttt tccggaaatc aagttaatct tactattcaa   240
ggacttcgag ccatggatac cggactctat atttgtaaag tcgaactcat gtaccccccc   300
ccttactact gggtattggt aatggcact cagatctacg tcatcgatcc cgaaccctgc   360
cctgattctg at                                                       372

<210> SEQ ID NO 136
<211> LENGTH: 372
<212> TYPE: DNA
<213> ORGANISM: Artificial Sequence
<220> FEATURE:
<223> OTHER INFORMATION: CTLA-4 ECD mutant D3-76 coding sequence

<400> SEQUENCE: 136
atgcacgtcg ctcaaccagc cgtcgtactc gcgtcctcta gaggtatcgc ttccttcgtg    60
tgtgaatatg cgtcacccgg caaagccaac gaagttagag tcacagtgct ccgccaagcc   120
gatagtcaag ttacagaagt ctgcgctatg acatacatga aggaagatga actaaccttc   180
cttgacgatc ccatctgcac aggtaccttt tccggaaatc aagttaatct tactattcaa   240
```

```
ggacttcgag ccatggatac cggactctat atttgtaaag tcgaactcat gtaccccccc    300
ccttactact tgggtattgg taatggcact cagatctacg tcatcgatcc cgaaccctgc    360
cctgattctg at                                                        372
```

<210> SEQ ID NO 137
<211> LENGTH: 372
<212> TYPE: DNA
<213> ORGANISM: Artificial Sequence
<220> FEATURE:
<223> OTHER INFORMATION: CTLA-4 ECD mutant D1 coding sequence

<400> SEQUENCE: 137

```
atgcacgtcg ctcaaccagc cgtcgtactc gcgtcctcta gaggtatcgc ttccttcgtt    60
tgtgaatatg agtcacccca taaagccacc gaaattagag tcacagtgct ccgccaagcc   120
aacagtcaag tgacagaagt ctgcgctatg acatacatga agggagatga actaaccttc   180
ctggacgatc ccttctgcac aggtaccttt tccggaaatc aggttaatct tactattcaa   240
ggacttcgag ccgcggatac cggactctat atctgtaaag tcgaactcat gtaccccccc   300
ccttactacc tgggtatagg taatggcact cagatctacg tcatcgatcc cgaaccctgc   360
cctgattctg at                                                       372
```

<210> SEQ ID NO 138
<211> LENGTH: 372
<212> TYPE: DNA
<213> ORGANISM: Artificial Sequence
<220> FEATURE:
<223> OTHER INFORMATION: CTLA-4 ECD mutant D1T coding sequence

<400> SEQUENCE: 138

```
atgcacgtcg ctcaaccagc cgtcgtactc gcgtcctcta gaggtatcgc ttccttcgtt    60
tgtgaatatg agtcacccca taaagccaac gaaattagag tcacagtgct ccgccaagcc   120
aacagtcaag tgacagaagt ctgcgctatg acatacatga agggagatga actaaccttc   180
ctggacgatc ccttctgcac aggtaccttt tccggaaatc aggttaatct tactattcaa   240
ggacttcgag ccgcggatac cggactctat atctgtaaag tcgaactcat gtaccccccc   300
ccttactacc tgggtatagg taatggcact cagatctacg tcatcgatcc cgaaccctgc   360
cctgattctg at                                                       372
```

<210> SEQ ID NO 139
<211> LENGTH: 372
<212> TYPE: DNA
<213> ORGANISM: Artificial Sequence
<220> FEATURE:
<223> OTHER INFORMATION: CTLA-4 ECD mutant D2 coding sequence

<400> SEQUENCE: 139

```
atgcacgtcg ctcaaccagc cgtcgtactc gcgtcctcta gaggtatcgc ttccttcgtt    60
tgtgaatatg agtcacccca taaagccaac gaaattagag tcacagtgct ccgccaagcc   120
aacagtcaag tgacagaagt ctgcgctatg acatacatga agggagatga actaaccttc   180
ctggacgatc ccttctgcac aggtaccttt tccggaaatc aggttaatct tactattcaa   240
ggacttcgag ccgcggatac cggactctat atctgtaaag tcgaactcat gtatcccccc   300
ccttactacc tgggtatggg taatggcact cagatctacg tcatcgatcc cgaaccctgc   360
cctgattctg at                                                       372
```

<210> SEQ ID NO 140
<211> LENGTH: 372
<212> TYPE: DNA
<213> ORGANISM: Artificial Sequence
<220> FEATURE:
<223> OTHER INFORMATION: CTLA-4 ECD mutant D3 coding sequence

<400> SEQUENCE: 140

```
atgcacgtcg ctcaaccagc cgtcgtactc gcgtcctcta gaggtatcgc ttccttcgtg      60
tgtgaatatg agtcacccgg caaagccaac gaaattagag tcacagtgct ccgccaagcc     120
ggaagtcaag ttacagaagt ctgcgctatg acatacatga agggagatga actaaccttc     180
cttgacgatc ccagctgcac aggtaccttt tccggaaatc aagttaatct tactattcaa     240
ggacttcgag ccgcggatac cggactctat atttgtaaag tcgaactcat gtacccccccc    300
ccttactact tgggttttgg taatggcact cagatctacg tcatcgatcc cgaaccctgc     360
cctgattctg at                                                         372
```

<210> SEQ ID NO 141
<211> LENGTH: 372
<212> TYPE: DNA
<213> ORGANISM: Artificial Sequence
<220> FEATURE:
<223> OTHER INFORMATION: CTLA-4 ECD mutant D4 coding sequence

<400> SEQUENCE: 141

```
atgcacgtcg ctcaaccagc cgtcgtactc gcgtcctcta gaggtatcgc ttccttcgtt      60
tgtgaatata gctcacccgg aaagccgac gaaattagag tcacagtgct ccgccaagcc     120
tctagtcaag tcacagaagt ctgcgctatg acatacatgg agggagatga actaaccttc     180
cttgacgacc ccacctgcac aggtaccttt tccggaaatc aagttaatct tactattcaa     240
ggacttcgag ccgtcgatac cggactctat atttgtaaag tcgaactcat gtacccccccc    300
ccttactacc tgggttttcgg taatggcact cagatctacg tcatcgatcc cgaaccctgc    360
cctgattctg at                                                         372
```

<210> SEQ ID NO 142
<211> LENGTH: 372
<212> TYPE: DNA
<213> ORGANISM: Artificial Sequence
<220> FEATURE:
<223> OTHER INFORMATION: CTLA-4 ECD mutant D5 coding sequence

<400> SEQUENCE: 142

```
atgcacgtcg ctcaaccagc cgtcgtactc gcgtcctcta gaggtatcgc ttccttcgtt      60
tgtgaatatg catccccgg aaaagccact gaagttagag tcacagtcct ccgccaggct      120
gattcacaag taacagaagt ctgcgctgca acatatatga tgggcgacga actcaccttc     180
ctcgacgacc caatttgcac aggtaccttt tccggaaatc aagttaatct tactattcaa     240
ggacttcgag caatggatac cggactctat atttgtaaag tcgaactcat gtacccccccc    300
ccttactacc ttggtatagg taatggcact cagatctacg tcattgaccc cgaaccctgc     360
cctgattctg at                                                         372
```

<210> SEQ ID NO 143
<211> LENGTH: 372
<212> TYPE: DNA
<213> ORGANISM: Artificial Sequence
<220> FEATURE:
<223> OTHER INFORMATION: CTLA-4 ECD mutant D6 coding sequence

<400> SEQUENCE: 143

```
atgcacgtcg ctcaaccagc cgtcgtactc gcgtcctcta gaggtatcgc ttccttcgtt    60
tgtgaatatg catcccccgg aaaagccact gaaattagag tcacagtcct ccgccaggct   120
gattcacaag taacagaagt ctgcgctatg acatatatga tgggcgacga actcaccttc   180
ctcgacgacc caatttgcac aggtaccttt tccggaaatc aagttaatct tactattcaa   240
ggacttcgag caatggatac cggactctat atttgtaaag tcgaactcat gtaccccccc   300
ccttactacc ttggtatagg taatggcact cagatctacg tcattgaccc cgaaccctgc   360
cctgattctg at                                                      372
```

<210> SEQ ID NO 144
<211> LENGTH: 372
<212> TYPE: DNA
<213> ORGANISM: Artificial Sequence
<220> FEATURE:
<223> OTHER INFORMATION: CTLA-4 ECD mutant D20 coding sequence

<400> SEQUENCE: 144

```
atgcacgtcg ctcaaccagc cgtcgtactc gcgtcctcta gaggtatcgc ttccttcgtt    60
tgtgaatatg agtccccca caaagccact gaaattagag tcacagtgct ccgccaggct   120
gattcacaag taacagaagt ctgcgctatg acatatatga tggaggacga actcaccttc   180
ctcgacgacc caatttgcac aggtaccttt tccggaaatc aagttaatct tactattcaa   240
ggacttcgag caatggatac cggactctat atttgtaaag tcgaactcat gtaccccccc   300
ccttactacc ttggtatagg taatggcact cagatctacg tcatcgatcc cgaaccctgc   360
cctgattctg at                                                      372
```

<210> SEQ ID NO 145
<211> LENGTH: 372
<212> TYPE: DNA
<213> ORGANISM: Artificial Sequence
<220> FEATURE:
<223> OTHER INFORMATION: CTLA-4 ECD mutant D21 coding sequence

<400> SEQUENCE: 145

```
atgcacgtcg ctcaaccagc cgtcgtactc gcgtcctcta gaggtatcgc ttccttcgtt    60
tgtgaatatt ccgcccccca caacgccgac gaaatcagag tcacagtcct ccgcaaagct   120
tcttcacaag taacagaagt ctgcgctatg acatatatgg aagaagatga actcaccttc   180
ctcgacgacc ccacctgcac aggtaccttt tccggaaatc aagttaatct tactattcaa   240
ggacttcgag ccgtcgatac cggactctat atttgtaaag tcgaactcat gtaccccccc   300
ccttactacc tgggtttcgg taatggcact cagatctacg tcattgaccc cgaaccctgc   360
cctgattctg at                                                      372
```

<210> SEQ ID NO 146
<211> LENGTH: 372
<212> TYPE: DNA
<213> ORGANISM: Artificial Sequence
<220> FEATURE:
<223> OTHER INFORMATION: CTLA-4 ECD mutant D23 coding sequence

<400> SEQUENCE: 146

```
atgcacgtcg ctcaaccagc cgtcgtactc gcgtcctcta gaggtatcgc ttccttcgtt    60
tgtgaatatt ccgcccccca caacgccgcc gaaatcagag tcacagtcct ccgcaaagct   120
ggttcacaag taacagaagt ctgcgctatg acatatatga agaagacga actcaccttc   180 ctcgacgacc cgtcctgcac aggtaccttc tccggaaatc aagttaatct tactattcaa   240
```

```
ggacttcgag cagccgatac cggactctat atttgtaaag tcgaactcat gtacccccc    300 ccttactacc ttggtctagg taatggcact cagatctacg tcattgaccc cgaaccctgc   360
cctgattctg at                                                        372
```

<210> SEQ ID NO 147
<211> LENGTH: 372
<212> TYPE: DNA
<213> ORGANISM: Artificial Sequence
<220> FEATURE:
<223> OTHER INFORMATION: CTLA-4 ECD mutant D24 coding sequence

<400> SEQUENCE: 147

```
atgcacgtcg ctcaaccagc cgtcgtactc gcgtcctcta gaggtatcgc ttccttcgtg    60
tgtgaatatg agtcacccgg caaagccaac gaaattagag tcacagtgct ccgcaaagct   120
ggttcacaag taacagaagt ctgcgctatg acatatatga agaagacga actcaccttc    180 ctcgacgacc cgtcctgcac aggtaccttc tccggaaatc aagttaatct tactattcaa   240
ggacttcgag cagccgatac cggactctat atttgtaaag tcgaactcat gtacccccc    300 ccttactacc ttggtctagg taatggcact cagatctacg tcatcgatcc cgaaccctgc   360
cctgattctg at                                                        372
```

<210> SEQ ID NO 148
<211> LENGTH: 372
<212> TYPE: DNA
<213> ORGANISM: Artificial Sequence
<220> FEATURE:
<223> OTHER INFORMATION: CTLA-4 ECD mutant D26 coding sequence

<400> SEQUENCE: 148

```
atgcacgtcg ctcaaccagc cgtcgtactc gcgtcctcta gaggtatcgc ttccttcgtt    60
tgtgaatatg aggccccca caaagccaac gaagttagag tcacagtcct ccgcgaagct   120
ggttcacaag taacagaagt ctgcgctatg acatatatgg tcgaggacga actcaccttc   180
ctcgacgacc cgtcctgcac aggtaccttc tccggaaatc aagttaatct tactattcaa   240
ggacttcgag cagccgatac cggactctat atttgtaaag tcgaactcat gtacccccc    300 ccttactacc ttggtctagg taatggcact cagatctacg tcattgaccc cgaaccctgc   360
cctgattctg at                                                        372
```

<210> SEQ ID NO 149
<211> LENGTH: 372
<212> TYPE: DNA
<213> ORGANISM: Artificial Sequence
<220> FEATURE:
<223> OTHER INFORMATION: CTLA-4 ECD mutant D27 coding sequence

<400> SEQUENCE: 149

```
atgcacgtcg ctcaaccagc cgtcgtactc gcgtcctcta gaggtatcgc ttccttcgtt    60
tgtgaatatg agtcacccgg caaagccaac gaagttagag tcacagtcct ccgcgaagct   120
ggttcacaag taacagaagt ctgcgctatg acatatatgg tcgaggacga actcaccttc   180
ctcgacgacc cgtcctgcac aggtaccttc tccggaaatc aagttaatct tactattcaa   240
ggacttcgag cagccgatac cggactctat atttgtaaag tcgaactcat gtacccccc    300 ccttactacc ttggtctagg taatggcact cagatctacg tcattgaccc cgaaccctgc   360
cctgattctg at                                                        372
```

```
<210> SEQ ID NO 150
<211> LENGTH: 372
<212> TYPE: DNA
<213> ORGANISM: Artificial Sequence
<220> FEATURE:
<223> OTHER INFORMATION: CTLA-4 ECD mutant D28 coding sequence

<400> SEQUENCE: 150
atgcacgtcg ctcaaccagc cgtcgtactc gcgtcctcta gaggtatcgc ttccttcgtt      60
tgtgaatatg aggcccccca caaagccaac gaagttagag tcacagtcct ccgccaagct     120
ggatcacaag taacagaagt ctgcgctatg acatatatga tggaggacga actcaccttc     180
ctcgacgacc cgtcctgcac aggtaccttc tccggaaatc aagttaatct tactattcaa     240
ggacttcgag cagccgatac cggactctat atttgtaaag tcgaactcat gtaccccccc     300
ccttactacc ttggtctagg taatggcact cagatctacg tcattgaccc cgaaccctgc     360
cctgattctg at                                                         372

<210> SEQ ID NO 151
<211> LENGTH: 372
<212> TYPE: DNA
<213> ORGANISM: Artificial Sequence
<220> FEATURE:
<223> OTHER INFORMATION: CTLA-4 ECD mutant D29 coding sequence

<400> SEQUENCE: 151
atgcacgtcg ctcaaccagc cgtcgtactc gcgtcctcta gaggtatcgc ttccttcgtt      60
tgtgaatatg aggcccccca caaagccgat gaaattagag tcacagtcct ccgcaaggct     120
gattcacaag taacagaagt ctgcgctatg acatatatga tggaggacga actcaccttc     180
ctcgacgacc cgtcctgcac aggtaccttc tccggaaatc aagttaatct tactattcaa     240
ggacttcgag caatggatac cggactctat atttgtaaag tcgaactcat gtaccccccc     300
ccttactacc ttggtctagg taatggcact cagatctacg tcattgaccc cgaaccctgc     360
cctgattctg at                                                         372

<210> SEQ ID NO 152
<211> LENGTH: 372
<212> TYPE: DNA
<213> ORGANISM: Artificial Sequence
<220> FEATURE:
<223> OTHER INFORMATION: CTLA-4 ECD mutant D31 coding sequence

<400> SEQUENCE: 152
atgcacgtcg ctcaaccagc cgtcgtactc gcgtcctcta gaggtatcgc ttccttcgtt      60
tgtgaatatg aggcccccca caacgccgat gaaatcagag tcacagtcct ccgccaagct     120
ggttcacaag taacagaagt ctgcgctatg acatatatgg tcgaggacga actcaccttc     180
ctcgacaagt caatttgcac aggtaccttt tccggaaatc aagttaatct tactattcaa     240
ggacttcgag caatggatac cggactctat atttgtaaag tcgaactcat gtaccccccc     300
ccttactacc ttggtatagg taatggcact cagatctacg tcattgaccc cgaaccctgc     360
cctgattctg at                                                         372

<210> SEQ ID NO 153
<211> LENGTH: 1170
<212> TYPE: DNA
<213> ORGANISM: Artificial Sequence
<220> FEATURE:
<223> OTHER INFORMATION: D3-12-IgG2 fusion protein coding sequence

<400> SEQUENCE: 153
```

```
atggcttgtc ttggatttca acgccacaaa gctcaactca atctcgctac ccgaacatgg      60
ccttgtactc ttctcttttt tctcctcttc ataccggttt tttgtaaagc catgcacgtc     120
gctcaaccag ccgtcgtact cgcgtcctct agaggtatcg cttccttcgt gtgtgaatat     180
gagtcacccg gcaaagccaa cgaaattaga gtcacagtgc tccgccaagc cggaagtcaa     240
gttacagaag tctgcgctat gacatacatg aagggagatg aactaacctt ccttgacgat     300
cccagctgca caggtacctt ttccggaaat caagttaatc ttactattca aggacttcga     360
gccgcggata ccggactcta tatttgtaaa gtcgaactca tgtacccccc cccttactac     420
ttgggtattg gtaatggcac tcagatctac gtcatcgatc ccgaaccctg ccctgattct     480
gatgagcgca atgttgtgt cgagtgccca ccgtgccag caccacctgt ggcaggaccg      540
tcagtcttcc tcttcccccc aaaacccaag acaccctca tgatctcccg gacccctgag      600
gtcacgtgcg tggtggtgga cgtgagccac gaagaccccg aggtccagtt caactggtac     660
gtggacggcg tggaggtgca taatgccaag acaaagccac gggaggagca gttcaacagc     720
acgttccgtg tggtcagcgt cctcaccgtt gtgcaccagg actggctgaa cggcaaggag     780
tacaagtgca aggtctccaa caaaggcctc ccagccccca tcgagaaaac catctccaaa     840 accaagggc agccccgaga ccacaggtg tacaccctgc ccccatcccg ggaggagatg       900
accaagaacc aggtcagcct gacctgcctg gtcaaaggct tctacccag cgacatcgcc      960 gtggagtggg agagcaatgg gcagccggag aacaactaca agaccacacc tcccatgctg    1020
gactccgacg gctccttctt cctctacagc aagctcaccg tggacaagag caggtggcag    1080
caggggaacg tcttctcatg ctccgtgatg catgaggctc tgcacaacca ctacacgcag    1140
aagagcctct ccctgtctcc gggtaaataa                                      1170

<210> SEQ ID NO 154
<211> LENGTH: 1170
<212> TYPE: DNA
<213> ORGANISM: Artificial Sequence
<220> FEATURE:
<223> OTHER INFORMATION: D3-14-IgG2 fusion protein coding sequence

<400> SEQUENCE: 154
atggcttgtc ttggatttca acgccacaaa gctcaactca atctcgctac ccgaacatgg      60
ccttgtactc ttctcttttt tctcctcttc ataccggttt tttgtaaagc catgcacgtc     120
gctcaaccag ccgtcgtact cgcgtcctct agaggtatcg cttccttcgt gtgtgaatat     180
gagtcacccg gcaaagccaa cgaaattaga gtcacagtgc tccgccaagc cgatagtcaa     240
gttacagaag tctgcgctat gacatacatg aagggagatg aactaacctt ccttgacgat     300
cccagctgca caggtacctt ttccggaaat caagttaatc ttactattca aggacttcga     360
gccgcggata ccggactcta tatttgtaaa gtcgaactca tgtacccccc cccttactac     420
ttgggtattg gtaatggcac tcagatctac gtcatcgatc ccgaaccctg ccctgattct     480
gatgagcgca atgttgtgt cgagtgccca ccgtgccag caccacctgt ggcaggaccg      540
tcagtcttcc tcttcccccc aaaacccaag acaccctca tgatctcccg gacccctgag      600
gtcacgtgcg tggtggtgga cgtgagccac gaagaccccg aggtccagtt caactggtac     660
gtggacggcg tggaggtgca taatgccaag acaaagccac gggaggagca gttcaacagc     720
acgttccgtg tggtcagcgt cctcaccgtt gtgcaccagg actggctgaa cggcaaggag     780
tacaagtgca aggtctccaa caaaggcctc ccagccccca tcgagaaaac catctccaaa     840 accaagggc agccccgaga ccacaggtg tacaccctgc ccccatcccg ggaggagatg       900
```

| | |
|---|---|
| accaagaacc aggtcagcct gacctgcctg gtcaaaggct tctacccag cgacatcgcc | 960 |
| gtggagtggg agagcaatgg gcagccggag aacaactaca agaccacacc tcccatgctg | 1020 |
| gactccgacg gctccttctt cctctacagc aagctcaccg tggacaagag caggtggcag | 1080 |
| caggggaacg tcttctcatg ctccgtgatg catgaggctc tgcacaacca ctacacgcag | 1140 |
| aagagcctct ccctgtctcc gggtaaataa | 1170 |

```
<210> SEQ ID NO 155
<211> LENGTH: 1170
<212> TYPE: DNA
<213> ORGANISM: Artificial Sequence
<220> FEATURE:
<223> OTHER INFORMATION: D3-17-IgG2 fusion protein coding sequence

<400> SEQUENCE: 155
```

| | |
|---|---|
| atggcttgtc ttggatttca acgccacaaa gctcaactca atctcgctac ccgaacatgg | 60 |
| ccttgtactc ttctcttttt tctcctcttc ataccggttt tttgtaaagc catgcacgtc | 120 |
| gctcaaccag ccgtcgtact cgcgtcctct agaggtatcg cttccttcgt gtgtgaatat | 180 |
| gagtcacccg gcaaagccaa cgaaattaga gtcacagtgc tccgccaagc cgatagtcaa | 240 |
| gttacagaag tctgcgctat gacatacatg aagggagatg aactaaccct ccttgacgat | 300 |
| cccagctgca caggtacctt ttccggaaat caagttaatc ttactattca aggcttcga | 360 |
| gccatggata ccggactcta tatttgtaaa gtcgaactca tgtaccccc cccttactac | 420 |
| ttgggtattg gtaatggcac tcagatctac gtcatcgatc ccgaaccctg ccctgattct | 480 |
| gatgagcgca atgttgtgt cgagtgccca ccgtgcccag caccacctgt ggcaggaccg | 540 |
| tcagtcttcc tcttcccccc aaaacccaag gacaccctca tgatctcccg gacccctgag | 600 |
| gtcacgtgcg tggtggtgga cgtgagccac gaagaccccg aggtccagtt caactggtac | 660 |
| gtggacggcg tggaggtgca taatgccaag acaaagccac gggaggagca gttcaacagc | 720 |
| acgttccgtg tggtcagcgt cctcaccgtt gtgcaccagg actggctgaa cggcaaggag | 780 |
| tacaagtgca aggtctccaa caaaggcctc ccagccccca tcgagaaaac catctccaaa | 840 |
| accaaaggc agccccgaga accacaggtg tacaccctgc cccatcccg ggaggagatg | 900 |
| accaagaacc aggtcagcct gacctgcctg gtcaaaggct tctacccag cgacatcgcc | 960 |
| gtggagtggg agagcaatgg gcagccggag aacaactaca agaccacacc tcccatgctg | 1020 |
| gactccgacg gctccttctt cctctacagc aagctcaccg tggacaagag caggtggcag | 1080 |
| caggggaacg tcttctcatg ctccgtgatg catgaggctc tgcacaacca ctacacgcag | 1140 |
| aagagcctct ccctgtctcc gggtaaataa | 1170 |

```
<210> SEQ ID NO 156
<211> LENGTH: 1170
<212> TYPE: DNA
<213> ORGANISM: Artificial Sequence
<220> FEATURE:
<223> OTHER INFORMATION: D3-20-IgG2 fusion protein coding sequence

<400> SEQUENCE: 156
```

| | |
|---|---|
| atggcttgtc ttggatttca acgccacaaa gctcaactca atctcgctac ccgaacatgg | 60 |
| ccttgtactc ttctcttttt tctcctcttc ataccggttt tttgtaaagc catgcacgtc | 120 |
| gctcaaccag ccgtcgtact cgcgtcctct agaggtatcg cttccttcgt gtgtgaatat | 180 |
| gagtcacccg gcaaagccaa cgaaattaga gtcacagtgc tccgccaagc cgatagtcaa | 240 |
| gttacagaag tctgcgctat gacatacatg aagggaaatg aactaaccct ccttgacgat | 300 |

```
cccagctgca caggtacctt ttccggaaat caagttaatc ttactattca aggacttcga    360
gccatggata ccggactcta tatttgtaaa gtcgaactca tgtaccccccc cccttactac   420
ttgggtattg gtaatggcac tcagatctac gtcatcgatc ccgaaccctg ccctgattct    480
gatgagcgca aatgttgtgt cgagtgccca ccgtgcccag caccacctgt ggcaggaccg    540
tcagtcttcc tcttcccccc aaaacccaag gacaccctca tgatctcccg gacccctgag   600
gtcacgtgcg tggtggtgga cgtgagccac gaagacccccg aggtccagtt caactggtac   660
gtggacggcg tggaggtgca taatgccaag acaaagccac gggaggagca gttcaacagc    720
acgttccgtg tggtcagcgt cctcaccgtt gtgcaccagg actggctgaa cggcaaggag    780
tacaagtgca aggtctccaa caaaggcctc ccagccccca tcgagaaaac catctccaaa   840
accaaagggc agccccgaga accacaggtg tacaccctgc ccccatcccg ggaggagatg    900
accaagaacc aggtcagcct gacctgcctg gtcaaaggct tctaccccag cgacatcgcc    960
gtggagtggg agagcaatgg gcagccggag aacaactaca agaccacacc tcccatgctg   1020
gactccgacg gctccttctt cctctacagc aagctcaccg tggacaagag caggtggcag   1080
caggggaacg tcttctcatg ctccgtgatg catgaggctc tgcacaacca ctacacgcag   1140
aagagcctct ccctgtctcc gggtaaataa                                    1170
```

<210> SEQ ID NO 157
<211> LENGTH: 1170
<212> TYPE: DNA
<213> ORGANISM: Artificial Sequence
<220> FEATURE:
<223> OTHER INFORMATION: D3-27-IgG2 fusion protein coding sequence

<400> SEQUENCE: 157

```
atggcttgtc ttggatttca acgccacaaa gctcaactca atctcgctac ccgaacatgg    60
ccttgtactc ttctcttttt tctcctcttc ataccggttt tttgtaaagc catgcacgtc    120
gctcaaccag ccgtcgtact cgcgtcctct agaggtatcg cttccttcgt gtgtgaatat   180
gagtcacccg gcaaagccaa cgaagttaga gtcacagtgc tccgccaagc cgatagtcaa   240
gttacagaag tctgcgctat gacatacatg aagggaaatg aactaacctt ccttgacgat   300
cccagctgca caggtacctt ttccggaaat caagttaatc ttactattca aggacttcga    360
gccatggata ccggactcta tatttgtaaa gtcgaactca tgtaccccccc cccttactac   420
ttgggtattg gtaatggcac tcagatctac gtcatcgatc ccgaaccctg ccctgattct    480
gatgagcgca aatgttgtgt cgagtgccca ccgtgcccag caccacctgt ggcaggaccg    540
tcagtcttcc tcttcccccc aaaacccaag gacaccctca tgatctcccg gacccctgag   600
gtcacgtgcg tggtggtgga cgtgagccac gaagacccccg aggtccagtt caactggtac   660
gtggacggcg tggaggtgca taatgccaag acaaagccac gggaggagca gttcaacagc    720
acgttccgtg tggtcagcgt cctcaccgtt gtgcaccagg actggctgaa cggcaaggag    780
tacaagtgca aggtctccaa caaaggcctc ccagccccca tcgagaaaac catctccaaa   840
accaaagggc agccccgaga accacaggtg tacaccctgc ccccatcccg ggaggagatg    900
accaagaacc aggtcagcct gacctgcctg gtcaaaggct tctaccccag cgacatcgcc    960
gtggagtggg agagcaatgg gcagccggag aacaactaca agaccacacc tcccatgctg   1020
gactccgacg gctccttctt cctctacagc aagctcaccg tggacaagag caggtggcag   1080
caggggaacg tcttctcatg ctccgtgatg catgaggctc tgcacaacca ctacacgcag   1140
aagagcctct ccctgtctcc gggtaaataa                                    1170
```

<210> SEQ ID NO 158
<211> LENGTH: 1170
<212> TYPE: DNA
<213> ORGANISM: Artificial Sequence
<220> FEATURE:
<223> OTHER INFORMATION: D3-29-IgG2 fusion protein coding sequence

<400> SEQUENCE: 158

```
atggcttgtc ttggatttca acgccacaaa gctcaactca atctcgctac ccgaacatgg      60
ccttgtactc ttctcttttt tctcctcttc ataccggttt tttgtaaagc catgcacgtc     120
gctcaaccag ccgtcgtact cgcgtcctct agaggtatcg cttccttcgt gtgtgaatat     180
gcgtcacccg gcaaagccaa cgaaattaga gtcacagtgc tccgccaagc cgatagtcaa     240
gttacagaag tctgcgctat gacatacatg aagggagatg aactaacctt ccttgacgat     300
cccagctgca caggtacctt ttccggaaat caagttaatc ttactattca aggacttcga     360
gccatggata ccggactcta tatttgtaaa gtcgaactca tgtacccccc cccttactac     420
ttgggtattg gtaatggcac tcagatctac gtcatcgatc ccgaaccctg ccctgattct     480
gatgagcgca atgttgtgt cgagtgccca ccgtgcccag caccacctgt ggcaggaccg     540
tcagtcttcc tcttcccccc aaaacccaag gacaccctca tgatctcccg gacccctgag     600
gtcacgtgcg tggtggtgga cgtgagccac gaagaccccg aggtccagtt caactggtac     660
gtggacggcg tggaggtgca taatgccaag acaaagccac gggaggagca gttcaacagc     720
acgttccgtg tggtcagcgt cctcaccgtt gtgcaccagg actggctgaa cggcaaggag     780
tacaagtgca aggtctccaa caaaggcctc ccagccccca tcgagaaaac catctccaaa     840
accaaagggc agccccgaga accacaggtg tacaccctgc ccccatcccg ggaggagatg     900
accaagaacc aggtcagcct gacctgcctg gtcaaaggct tctaccccag cgacatcgcc     960
gtggagtggg agagcaatgg gcagccggag aacaactaca agaccacacc tcccatgctg    1020
gactccgacg gctccttctt cctctacagc aagctcaccg tggacaagag caggtggcag    1080
caggggaacg tcttctcatg ctccgtgatg catgaggctc tgcacaacca ctacacgcag    1140
aagagcctct ccctgtctcc gggtaaataa                                      1170
```

<210> SEQ ID NO 159
<211> LENGTH: 124
<212> TYPE: PRT
<213> ORGANISM: Homo sapiens
<220> FEATURE:
<223> OTHER INFORMATION: wild-type human CTLA-4 ECD

<400> SEQUENCE: 159

```
Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
```

```
                        100                 105                 110
Tyr Val Ile Asp Pro Glu Pro Cys Pro Asp Ser Asp
            115                 120

<210> SEQ ID NO 160
<211> LENGTH: 223
<212> TYPE: PRT
<213> ORGANISM: Homo Sapiens
<220> FEATURE:
<223> OTHER INFORMATION: wild-type human full-length CTLA-4

<400> SEQUENCE: 160

Met Ala Cys Leu Gly Phe Gln Arg His Lys Ala Gln Leu Asn Leu Ala
 1               5                  10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
        115                 120                 125

Cys Lys Val Glu Leu Met Tyr Pro Pro Pro Tyr Tyr Leu Gly Ile Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Ala Ala Val Ser Ser Gly Leu Phe Phe
                165                 170                 175

Tyr Ser Phe Leu Leu Thr Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220

<210> SEQ ID NO 161
<211> LENGTH: 389
<212> TYPE: PRT
<213> ORGANISM: Artificial Sequence
<220> FEATURE:
<223> OTHER INFORMATION: predicted WT human CTLA4-IgG2 fusion protein

<400> SEQUENCE: 161

Met Ala Cys Leu Gly Phe Gln Arg His Lys Ala Gln Leu Asn Leu Ala
 1               5                  10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
        35                  40                  45

Ser Ser Arg Gly Ile Ala Ser Phe Val Cys Glu Tyr Ala Ser Pro Gly
    50                  55                  60

Lys Ala Thr Glu Val Arg Val Thr Val Leu Arg Gln Ala Asp Ser Gln
```

```
                    65                  70                  75                  80
Val Thr Glu Val Cys Ala Ala Thr Tyr Met Met Gly Asn Glu Leu Thr
                        85                  90                  95

Phe Leu Asp Asp Ser Ile Cys Thr Gly Thr Ser Ser Gly Asn Gln Val
                        100                 105                 110

Asn Leu Thr Ile Gln Gly Leu Arg Ala Met Asp Thr Gly Leu Tyr Ile
                115                 120                 125

Cys Lys Val Glu Leu Met Tyr Pro Pro Pro Tyr Leu Gly Ile Gly
        130                 135                 140

Asn Gly Thr Gln Ile Tyr Val Ile Asp Pro Glu Pro Cys Pro Asp Ser
145                 150                 155                 160

Asp Glu Arg Lys Cys Cys Val Glu Cys Pro Pro Cys Pro Ala Pro Pro
                165                 170                 175

Val Ala Gly Pro Ser Val Phe Leu Phe Pro Pro Lys Pro Lys Asp Thr
                180                 185                 190

Leu Met Ile Ser Arg Thr Pro Glu Val Thr Cys Val Val Val Asp Val
                195                 200                 205

Ser His Glu Asp Pro Glu Val Gln Phe Asn Trp Tyr Val Asp Gly Val
        210                 215                 220

Glu Val His Asn Ala Lys Thr Lys Pro Arg Glu Glu Gln Phe Asn Ser
225                 230                 235                 240

Thr Phe Arg Val Val Ser Val Leu Thr Val Val His Gln Asp Trp Leu
                245                 250                 255

Asn Gly Lys Glu Tyr Lys Cys Lys Val Ser Asn Lys Gly Leu Pro Ala
                260                 265                 270

Pro Ile Glu Lys Thr Ile Ser Lys Thr Lys Gly Gln Pro Arg Glu Pro
                275                 280                 285

Gln Val Tyr Thr Leu Pro Pro Ser Arg Glu Glu Met Thr Lys Asn Gln
        290                 295                 300

Val Ser Leu Thr Cys Leu Val Lys Gly Phe Tyr Pro Ser Asp Ile Ala
305                 310                 315                 320

Val Glu Trp Glu Ser Asn Gly Gln Pro Glu Asn Asn Tyr Lys Thr Thr
                325                 330                 335

Pro Pro Met Leu Asp Ser Asp Gly Ser Phe Phe Leu Tyr Ser Lys Leu
                340                 345                 350

Thr Val Asp Lys Ser Arg Trp Gln Gln Gly Asn Val Phe Ser Cys Ser
                355                 360                 365

Val Met His Glu Ala Leu His Asn His Tyr Thr Gln Lys Ser Leu Ser
        370                 375                 380

Leu Ser Pro Gly Lys
385

<210> SEQ ID NO 162
<211> LENGTH: 352
<212> TYPE: PRT
<213> ORGANISM: Artificial Sequence
<220> FEATURE:
<223> OTHER INFORMATION: WT human mature CTLA4-IgG2 fusion protein

<400> SEQUENCE: 162

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
                20                  25                  30

Arg Val Thr Val Leu Arg Gln Ala Asp Ser Gln Val Thr Glu Val Cys
            35                  40                  45
```

Ala Ala Thr Tyr Met Met Gly Asn Glu Leu Thr Phe Leu Asp Asp Ser
 50                  55                  60

Ile Cys Thr Gly Thr Ser Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
             85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Glu Arg Lys Cys
        115                 120                 125

Cys Val Glu Cys Pro Pro Cys Pro Ala Pro Pro Val Ala Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Met Leu Asp
290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 163
<211> LENGTH: 1167
<212> TYPE: DNA
<213> ORGANISM: Artificial Sequence
<220> FEATURE:
<223> OTHER INFORMATION: WT human CTLA4-IgG2 fusion protein coding
      sequence

<400> SEQUENCE: 163
atggcttgtc ttggatttca acgccacaaa gctcaactca atctcgctac ccgaacatgg      60
ccttgtactc ttctcttttt tctcctcttc ataccggttt tttgtaaagc catgcacgtc     120
gctcaaccag ccgtcgtact cgcgtcctct agaggtatcg cttccttcgt ttgtgaatat     180 gcatccccg gaaaagccac tgaagttaga gtcacagtcc tccgccaggc tgattcacaa     240
gtaacagaag tctgcgctgc aacatatatg atgggcaacg aactcacctt cctcgacgac     300
tcaatttgca caggtaccct ctccggaaat caagttaatc ttactattca aggacttcga     360

```
gcaatggata ccggactcta tatttgtaaa gtcgaactca tgtaccccccc cccttactac      420 cttggtatag gtaatggcac tcagatctac gtcatcgatc ccgaaccctg ccctgattct      480
gatgagcgca aatgttgtgt cgagtgccca ccgtgcccag caccacctgt ggcaggaccg      540
tcagtcttcc tcttcccccc aaaacccaag gacaccctca tgatctcccg gacccctgag      600
gtcacgtgcg tggtggtgga cgtgagccac gaagacccccg aggtccagtt caactggtac      660
gtggacggcg tggaggtgca taatgccaag acaaagccac gggaggagca gttcaacagc      720
acgttccgtg tggtcagcgt cctcaccgtt gtgcaccagg actggctgaa cggcaaggag      780
tacaagtgca aggtctccaa caaaggcctc ccagccccca tcgagaaaac catctccaaa      840
accaaagggc agccccgaga accacaggtg tacaccctgc ccccatcccg ggaggagatg      900
accaagaacc aggtcagcct gacctgcctg gtcaaaggct tctacccccag cgacatcgcc      960 gtggagtggg agagcaatgg gcagccggag aacaactaca agaccacacc tcccatgctg     1020
gactccgacg gctccttctt cctctacagc aagctcaccg tggacaagag caggtggcag     1080
caggggaacg tcttctcatg ctccgtgatg catgaggctc tgcacaacca ctacacgcag     1140
aagagcctct ccctgtctcc gggtaaa                                         1167
```

<210> SEQ ID NO 164
<211> LENGTH: 357
<212> TYPE: PRT
<213> ORGANISM: Artificial Sequence
<220> FEATURE:
<223> OTHER INFORMATION: Orencia(R) (Bristol-Myers Squibb Co.)

<400> SEQUENCE: 164

```
Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Gln Glu Pro Lys
        115                 120                 125

Ser Ser Asp Lys Thr His Thr Ser Pro Pro Ser Pro Ala Pro Glu Leu
    130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
        195                 200                 205

Thr Tyr Arg Val Val Ser Val Leu Thr Val Leu His Gln Asp Trp Leu
    210                 215                 220
```

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
            245                 250                 255

Gln Val Tyr Thr Leu Pro Pro Ser Arg Asp Glu Leu Thr Lys Asn Gln
            260                 265                 270

Val Ser Leu Thr Cys Leu Val Lys Gly Phe Tyr Pro Ser Asp Ile Ala
            275                 280                 285

Val Glu Trp Glu Ser Asn Gly Gln Pro Glu Asn Asn Tyr Lys Thr Thr
            290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
            340                 345                 350

Leu Ser Pro Gly Lys
            355

<210> SEQ ID NO 165
<211> LENGTH: 394
<212> TYPE: PRT
<213> ORGANISM: Artificial Sequence
<220> FEATURE:
<223> OTHER INFORMATION: predicted LEA29Y-Ig fusion protein

<400> SEQUENCE: 165

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala Met His Val Ala Gln Pro Ala Val Val Leu Ala
            35                  40                  45

Ser Ser Arg Gly Ile Ala Ser Phe Val Cys Glu Tyr Ala Ser Pro Gly
        50                  55                  60

Lys Tyr Thr Glu Val Arg Val Thr Val Leu Arg Gln Ala Asp Ser Gln
65                  70                  75                  80

Val Thr Glu Val Cys Ala Ala Thr Tyr Met Met Gly Asn Glu Leu Thr
                85                  90                  95

Phe Leu Asp Asp Ser Ile Cys Thr Gly Thr Ser Ser Gly Asn Gln Val
            100                 105                 110

Asn Leu Thr Ile Gln Gly Leu Arg Ala Met Asp Thr Gly Leu Tyr Ile
            115                 120                 125

Cys Lys Val Glu Leu Met Tyr Pro Pro Pro Tyr Tyr Glu Gly Ile Gly
130                 135                 140

Asn Gly Thr Gln Ile Tyr Val Ile Asp Pro Glu Pro Cys Pro Asp Ser
145                 150                 155                 160

Asp Gln Glu Pro Lys Ser Ser Asp Lys Thr His Thr Ser Pro Pro Ser
                165                 170                 175

Pro Ala Pro Glu Leu Leu Gly Gly Ser Ser Val Phe Leu Phe Pro Pro
            180                 185                 190

Lys Pro Lys Asp Thr Leu Met Ile Ser Arg Thr Pro Glu Val Thr Cys
            195                 200                 205

Val Val Val Asp Val Ser His Glu Asp Pro Glu Val Lys Phe Asn Trp
        210                 215                 220

```
Tyr Val Asp Gly Val Glu Val His Asn Ala Lys Thr Lys Pro Arg Glu
225                 230                 235                 240

Glu Gln Tyr Asn Ser Thr Tyr Arg Val Val Ser Val Leu Thr Val Leu
                245                 250                 255

His Gln Asp Trp Leu Asn Gly Lys Glu Tyr Lys Cys Lys Val Ser Asn
            260                 265                 270

Lys Ala Leu Pro Ala Pro Ile Glu Lys Thr Ile Ser Lys Ala Lys Gly
        275                 280                 285

Gln Pro Arg Glu Pro Gln Val Tyr Thr Leu Pro Pro Ser Arg Asp Glu
    290                 295                 300

Leu Thr Lys Asn Gln Val Ser Leu Thr Cys Leu Val Lys Gly Phe Tyr
305                 310                 315                 320

Pro Ser Asp Ile Ala Val Glu Trp Glu Ser Asn Gly Gln Pro Glu Asn
                325                 330                 335

Asn Tyr Lys Thr Thr Pro Pro Val Leu Asp Ser Asp Gly Ser Phe Phe
                340                 345                 350

Leu Tyr Ser Lys Leu Thr Val Asp Lys Ser Arg Trp Gln Gln Gly Asn
            355                 360                 365

Val Phe Ser Cys Ser Val Met His Glu Ala Leu His Asn His Tyr Thr
        370                 375                 380

Gln Lys Ser Leu Ser Leu Ser Pro Gly Lys
385                 390

<210> SEQ ID NO 166
<211> LENGTH: 357
<212> TYPE: PRT
<213> ORGANISM: Artificial Sequence
<220> FEATURE:
<223> OTHER INFORMATION: mature LEA29Y-Ig fusion protein

<400> SEQUENCE: 166

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
                20                  25                  30

Arg Val Thr Val Leu Arg Gln Ala Asp Ser Gln Val Thr Glu Val Cys
            35                  40                  45

Ala Ala Thr Tyr Met Met Gly Asn Glu Leu Thr Phe Leu Asp Asp Ser
        50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
                100                 105                 110

Tyr Val Ile Asp Pro Glu Pro Cys Pro Asp Ser Asp Gln Glu Pro Lys
            115                 120                 125

Ser Ser Asp Lys Thr His Thr Ser Pro Pro Ser Pro Ala Pro Glu Leu
        130                 135                 140

Leu Gly Gly Ser Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
            180                 185                 190

Glu Val His Asn Ala Lys Thr Lys Pro Arg Glu Glu Gln Tyr Asn Ser
```

|  |  |  |  |  |  |  |  |  |  |  |  |
|---|---|---|---|---|---|---|---|---|---|---|---|
|  |  | 195 |  |  |  | 200 |  |  |  | 205 |  |
| Thr | Tyr | Arg | Val | Val | Ser | Val | Leu | Thr | Val | Leu | His | Gln | Asp | Trp | Leu |
| 210 |  |  |  | 215 |  |  |  | 220 |  |  |  |
| Asn | Gly | Lys | Glu | Tyr | Lys | Cys | Lys | Val | Ser | Asn | Lys | Ala | Leu | Pro | Ala |
| 225 |  |  |  | 230 |  |  |  | 235 |  |  |  | 240 |
| Pro | Ile | Glu | Lys | Thr | Ile | Ser | Lys | Ala | Lys | Gly | Gln | Pro | Arg | Glu | Pro |
|  |  |  | 245 |  |  |  | 250 |  |  |  | 255 |  |
| Gln | Val | Tyr | Thr | Leu | Pro | Pro | Ser | Arg | Asp | Glu | Leu | Thr | Lys | Asn | Gln |
|  |  | 260 |  |  |  | 265 |  |  |  | 270 |  |
| Val | Ser | Leu | Thr | Cys | Leu | Val | Lys | Gly | Phe | Tyr | Pro | Ser | Asp | Ile | Ala |
|  | 275 |  |  |  | 280 |  |  |  | 285 |  |  |
| Val | Glu | Trp | Glu | Ser | Asn | Gly | Gln | Pro | Glu | Asn | Asn | Tyr | Lys | Thr | Thr |
| 290 |  |  |  | 295 |  |  |  | 300 |  |  |  |
| Pro | Pro | Val | Leu | Asp | Ser | Asp | Gly | Ser | Phe | Phe | Leu | Tyr | Ser | Lys | Leu |
| 305 |  |  |  | 310 |  |  |  | 315 |  |  |  | 320 |
| Thr | Val | Asp | Lys | Ser | Arg | Trp | Gln | Gln | Gly | Asn | Val | Phe | Ser | Cys | Ser |
|  |  |  | 325 |  |  |  | 330 |  |  |  | 335 |  |
| Val | Met | His | Glu | Ala | Leu | His | Asn | His | Tyr | Thr | Gln | Lys | Ser | Leu | Ser |
|  |  | 340 |  |  |  | 345 |  |  |  | 350 |  |
| Leu | Ser | Pro | Gly | Lys |
|  |  | 355 |  |  |

<210> SEQ ID NO 167
<211> LENGTH: 1182
<212> TYPE: DNA
<213> ORGANISM: Artificial Sequence
<220> FEATURE:
<223> OTHER INFORMATION: LEA29Y-Ig fusion protein coding sequence

<400> SEQUENCE: 167

| atggcttgtc ttggatttca acgccacaaa gctcaactca atctcgctac ccgaacatgg | 60 |
| ccttgtactc ttctcttttt tctcctcttc atcccagttt tttgtaaagc catgcacgtc | 120 |
| gctcaaccag ccgtcgtact cgcgtcctct agaggtatcg cttccttcgt tgtgaatat | 180 |
| gcatccccg gaaaatatac tgaagttaga gtcacagtcc tccgccaggc tgattccaca | 240 |
| gtaacagaag tctgcgctgc aacatatatg atgggcaacg aactcacctt cctcgacgac | 300 |
| tcaatttgca caggtaccct ctccggaaat caagttaatc ttactattca aggacttcga | 360 |
| gcaatggata ccggactcta tatttgtaaa gtcgaactca tgtaccccc cccttactac | 420 |
| gagggtatag gtaatggcac tcagatctac gtcattgacc ccgaaccctg ccctgattct | 480 |
| gatcaggagc ccaaatcttc tgacaaaact cacacatccc caccgtcccc agcacctgaa | 540 |
| ctcctgggtg gatcgtcagt cttcctcttc cccccaaaac ccaaggacac cctcatgatc | 600 |
| tcccggaccc ctgaggtcac atgcgtggtg gtggacgtga gccacgaaga ccctgaggtc | 660 |
| aagttcaact ggtacgtgga cggcgtggag gtgcataatg ccaagacaaa gccgcgggag | 720 |
| gagcagtaca acagcacgta ccgtgtggtc agcgtcctca ccgtcctgca ccaggactgg | 780 |
| ctgaatggca aggagtacaa gtgcaaggtc tccaacaaag ccctcccagc ccccatcgag | 840 |
| aaaaccatct ccaaagccaa agggcagccc cgagaaccac aggtgtacac cctgccccca | 900 |
| tcccgggatg agctgaccaa gaaccaggtc agcctgacct gcctggtcaa aggcttctat | 960 |
| cccagcgaca tcgccgtgga gtgggagagc aatgggcagc cggagaacaa ctacaagacc | 1020 |
| acgcctcccg tgctggactc cgacggctcc ttcttcctct acagcaagct caccgtggac | 1080 |
| aagagcaggt ggcagcaggg gaacgtcttc tcatgctccg tgatgcatga ggctctgcac | 1140 |

```
aaccactaca cgcagaagag cctctccctg tctccgggta aa                          1182
```

<210> SEQ ID NO 168
<211> LENGTH: 124
<212> TYPE: PRT
<213> ORGANISM: Artificial Sequence
<220> FEATURE:
<223> OTHER INFORMATION: LEA29Y ECD

<400> SEQUENCE: 168

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Tyr Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp
        115                 120
```

<210> SEQ ID NO 169
<211> LENGTH: 372
<212> TYPE: DNA
<213> ORGANISM: Artificial Sequence
<220> FEATURE:
<223> OTHER INFORMATION: LEA29Y ECD coding sequence

<400> SEQUENCE: 169

```
atgcacgtcg ctcaaccagc cgtcgtactc gcgtcctcta gaggtatcgc ttccttcgtt    60
tgtgaatatg catcccccgg aaaatatact gaagttagag tcacagtcct ccgccaggct   120
gattcacaag taacagaagt ctgcgctgca acatatatga tgggcaacga actcaccttc   180
ctcgacgact caatttgcac aggtacctcc tccggaaatc aagttaatct tactattcaa   240
ggacttcgag caatggatac cggactctat atttgtaaag tcgaactcat gtaccccccc   300
ccttactacg agggtatagg taatggcact cagatctacg tcatcgatcc cgaaccctgc   360
cctgattctg at                                                       372
```

<210> SEQ ID NO 170
<211> LENGTH: 476
<212> TYPE: PRT
<213> ORGANISM: Artificial Sequence
<220> FEATURE:
<223> OTHER INFORMATION: Predicted WT human CD80-human IgG1 fusion
     protein

<400> SEQUENCE: 170

```
Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
            20                  25                  30

Ser Gly Val Ile His Val Thr Lys Glu Val Lys Glu Val Ala Thr Leu
        35                  40                  45
```

```
Ser Cys Gly His Asn Val Ser Val Glu Glu Leu Ala Gln Thr Arg Ile
 50                  55                  60

Tyr Trp Gln Lys Glu Lys Met Val Leu Thr Met Met Ser Gly Asp
 65                  70                  75                  80

Met Asn Ile Trp Pro Glu Tyr Lys Asn Arg Thr Ile Phe Asp Ile Thr
                 85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
        130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
        210                 215                 220

Val Asn Gln Thr Phe Asn Trp Asn Thr Thr Lys Gln Glu His Phe Pro
225                 230                 235                 240

Asp Asn Gly Val Thr Pro Lys Ser Cys Asp Lys Thr His Thr Cys Pro
                245                 250                 255

Pro Cys Pro Ala Pro Glu Leu Leu Gly Gly Pro Ser Val Phe Leu Phe
            260                 265                 270

Pro Pro Lys Pro Lys Asp Thr Leu Met Ile Ser Arg Thr Pro Glu Val
        275                 280                 285

Thr Cys Val Val Val Asp Val Ser His Glu Asp Pro Glu Val Lys Phe
        290                 295                 300

Asn Trp Tyr Val Asp Gly Val Glu Val His Asn Ala Lys Thr Lys Pro
305                 310                 315                 320

Arg Glu Glu Gln Tyr Asn Ser Thr Tyr Arg Val Val Ser Val Leu Thr
                325                 330                 335

Val Leu His Gln Asp Trp Leu Asn Gly Lys Glu Tyr Lys Cys Lys Val
            340                 345                 350

Ser Asn Lys Ala Leu Pro Ala Pro Ile Glu Lys Thr Ile Ser Lys Ala
        355                 360                 365

Lys Gly Gln Pro Arg Glu Pro Gln Val Tyr Thr Leu Pro Pro Ser Arg
    370                 375                 380

Asp Glu Leu Thr Lys Asn Gln Val Ser Leu Thr Cys Leu Val Lys Gly
385                 390                 395                 400

Phe Tyr Pro Ser Asp Ile Ala Val Glu Trp Glu Ser Asn Gly Gln Pro
                405                 410                 415

Glu Asn Asn Tyr Lys Thr Thr Pro Pro Val Leu Asp Ser Asp Gly Ser
            420                 425                 430

Phe Phe Leu Tyr Ser Lys Leu Thr Val Asp Lys Ser Arg Trp Gln Gln
        435                 440                 445

Gly Asn Val Phe Ser Cys Ser Val Met His Glu Ala Leu His Asn His
    450                 455                 460

Tyr Thr Gln Lys Ser Leu Ser Leu Ser Pro Gly Lys
465                 470                 475
```

<210> SEQ ID NO 171
<211> LENGTH: 442
<212> TYPE: PRT
<213> ORGANISM: Artificial Sequence
<220> FEATURE:
<223> OTHER INFORMATION: Mature WT human CD80-human IgG1 fusion protein

<400> SEQUENCE: 171

```
Val Ile His Val Thr Lys Glu Val Lys Glu Val Ala Thr Leu Ser Cys
 1               5                  10                  15
Gly His Asn Val Ser Val Glu Glu Leu Ala Gln Thr Arg Ile Tyr Trp
            20                  25                  30
Gln Lys Glu Lys Lys Met Val Leu Thr Met Met Ser Gly Asp Met Asn
        35                  40                  45
Ile Trp Pro Glu Tyr Lys Asn Arg Thr Ile Phe Asp Ile Thr Asn Asn
    50                  55                  60
Leu Ser Ile Val Ile Leu Ala Leu Arg Pro Ser Asp Glu Gly Thr Tyr
65                  70                  75                  80
Glu Cys Val Val Leu Lys Tyr Glu Lys Asp Ala Phe Lys Arg Glu His
                85                  90                  95
Leu Ala Glu Val Thr Leu Ser Val Lys Ala Asp Phe Pro Thr Pro Ser
            100                 105                 110
Ile Ser Asp Phe Glu Ile Pro Thr Ser Asn Ile Arg Arg Ile Ile Cys
        115                 120                 125
Ser Thr Ser Gly Gly Phe Pro Glu Pro His Leu Ser Trp Leu Glu Asn
    130                 135                 140
Gly Glu Glu Leu Asn Ala Ile Asn Thr Thr Val Ser Gln Asp Pro Glu
145                 150                 155                 160
Thr Glu Leu Tyr Ala Val Ser Ser Lys Leu Asp Phe Asn Met Thr Thr
                165                 170                 175
Asn His Ser Phe Met Cys Leu Ile Lys Tyr Gly His Leu Arg Val Asn
            180                 185                 190
Gln Thr Phe Asn Trp Asn Thr Thr Lys Gln Glu His Phe Pro Asp Asn
        195                 200                 205
Gly Val Thr Pro Lys Ser Cys Asp Lys Thr His Thr Cys Pro Pro Cys
    210                 215                 220
Pro Ala Pro Glu Leu Leu Gly Gly Pro Ser Val Phe Leu Phe Pro Pro
225                 230                 235                 240
Lys Pro Lys Asp Thr Leu Met Ile Ser Arg Thr Pro Glu Val Thr Cys
                245                 250                 255
Val Val Val Asp Val Ser His Glu Asp Pro Glu Val Lys Phe Asn Trp
            260                 265                 270
Tyr Val Asp Gly Val Glu Val His Asn Ala Lys Thr Lys Pro Arg Glu
        275                 280                 285
Glu Gln Tyr Asn Ser Thr Tyr Arg Val Val Ser Val Leu Thr Val Leu
    290                 295                 300
His Gln Asp Trp Leu Asn Gly Lys Glu Tyr Lys Cys Lys Val Ser Asn
305                 310                 315                 320
Lys Ala Leu Pro Ala Pro Ile Glu Lys Thr Ile Ser Lys Ala Lys Gly
                325                 330                 335
Gln Pro Arg Glu Pro Gln Val Tyr Thr Leu Pro Pro Ser Arg Asp Glu
            340                 345                 350
Leu Thr Lys Asn Gln Val Ser Leu Thr Cys Leu Val Lys Gly Phe Tyr
        355                 360                 365
```

```
Pro Ser Asp Ile Ala Val Glu Trp Glu Ser Asn Gly Gln Pro Glu Asn
        370                 375                 380

Asn Tyr Lys Thr Thr Pro Pro Val Leu Asp Ser Asp Gly Ser Phe Phe
385                 390                 395                 400

Leu Tyr Ser Lys Leu Thr Val Asp Lys Ser Arg Trp Gln Gln Gly Asn
            405                 410                 415

Val Phe Ser Cys Ser Val Met His Glu Ala Leu His Asn His Tyr Thr
            420                 425                 430

Gln Lys Ser Leu Ser Leu Ser Pro Gly Lys
            435                 440

<210> SEQ ID NO 172
<211> LENGTH: 1428
<212> TYPE: DNA
<213> ORGANISM: Artificial Sequence
<220> FEATURE:
<223> OTHER INFORMATION: WT human CD80-human IgG1 fusion protein coding
      sequence

<400> SEQUENCE: 172
atgggccaca cacggaggca gggaacatca ccatccaagt gtccatacct caatttcttt     60
cagctcttgg tgctggctgg tctttctcac ttctgttcag gtgttatcca cgtgaccaag    120
gaagtgaaag aagtggcaac gctgtcctgt ggtcacaatg tttctgttga agagctggca    180
caaactcgca tctactggca aaaggagaag aaaatggtgc tgactatgat gtctggggac    240
atgaatatat ggcccgagta caagaaccgg accatctttg atatcactaa taacctctcc    300
atcgtgatcc tggctctgcg cccatctgac gagggcacat acgagtgtgt tgttctgaag    360
tatgaaaaag acgctttcaa gcgggaacac ctggctgaag tgacgttatc agtcaaagct    420
gacttcccta cacctagtat atctgacttt gaaattccaa cttctaatat tagaaggata    480
atttgctcaa cctctggagg ttttcctgag cctcacctct cctggctgga aaatggagaa    540
gaattaaatg ccatcaacac aacagtttcc caagatcctg aaactgagct ctatgctgtt    600
agcagcaaac tggatttcaa tatgacaacc aaccacagct tcatgtgtct catcaagtat    660
ggacatttaa gagtgaatca gaccttcaac tggaatacac gaagcaaga gcattttcct    720 gataacgggg tgaccccaaa gagctgcgac aaaactcaca catgcccacc gtgcccagca    780
cctgaactcc tggggggacc gtcagtcttc ctcttccccc caaaacccaa ggacaccctc    840
atgatctccc ggacccctga ggtcacatgc gtggtggtgg acgtgagcca cgaagaccct    900
gaggtcaagt tcaactggta cgtggacggc gtggaggtgc ataatgccaa gacaaagccg    960
cgggaggagc agtacaacag cacgtaccgt gtggtcagcg tcctcaccgt cctgcaccag   1020
gactggctga atggcaagga gtacaagtgc aaggtctcca acaaagccct cccagccccc   1080
atcgagaaaa ccatctccaa agccaaaggg cagccccgag aaccacaggt gtacaccctg   1140
cccccatccc gggatgagct gaccaagaac caggtcagcc tgacctgcct ggtcaaaggc   1200
ttctatccca gcgacatcgc cgtggagtgg gagagcaatg ggcagccgga gaacaactac   1260
aagaccacgc ctcccgtgct ggactccgac ggctccttct tcctctacag caagctcacc   1320
gtggacaaga gcaggtggca gcaggggaac gtcttctcat gctccgtgat gcatgaggct   1380
ctgcacaacc actacacgca gaagagcctc tccctgtctc cgggtaaa              1428

<210> SEQ ID NO 173
<211> LENGTH: 726
<212> TYPE: DNA
<213> ORGANISM: Artificial Sequence
<220> FEATURE:
```

<223> OTHER INFORMATION: Coding sequence of WT human CD80 signal peptide and WT human CD80 ECD

<400> SEQUENCE: 173

```
atgggccaca cacggaggca gggaacatca ccatccaagt gtccatacct caatttcttt      60
cagctcttgg tgctggctgg tctttctcac ttctgttcag gtgttatcca cgtgaccaag     120
gaagtgaaag aagtggcaac gctgtcctgt ggtcacaatg tttctgttga agagctggca     180
caaactcgca tctactggca aaaggagaag aaaatggtgc tgactatgat gtctggggac     240
atgaatatat ggcccgagta caagaaccgg accatctttg atatcactaa taacctctcc     300
atcgtgatcc tggctctgcg cccatctgac gagggcacat acgagtgtgt tgttctgaag     360
tatgaaaaag acgctttcaa gcgggaacac ctggctgaag tgacgttatc agtcaaagct     420
gacttcccta cacctagtat atctgacttt gaaattccaa cttctaatat tagaaggata     480
atttgctcaa cctctggagg ttttcctgag cctcacctct cctggctgga aaatggagaa     540
gaattaaatg ccatcaacac aacagtttcc caagatcctg aaactgagct ctatgctgtt     600
agcagcaaac tggatttcaa tatgacaacc aaccacagct tcatgtgtct catcaagtat     660
ggacatttaa gagtgaatca gaccttcaac tggaatacaa cgaagcaaga gcattttcct     720
gataac                                                                726
```

<210> SEQ ID NO 174
<211> LENGTH: 208
<212> TYPE: PRT
<213> ORGANISM: Homo Sapiens
<220> FEATURE:
<223> OTHER INFORMATION: WT human CD80 ECD

<400> SEQUENCE: 174

```
Val Ile His Val Thr Lys Glu Val Lys Glu Val Ala Thr Leu Ser Cys
  1               5                  10                  15

Gly His Asn Val Ser Val Glu Glu Leu Ala Gln Thr Arg Ile Tyr Trp
             20                  25                  30

Gln Lys Glu Lys Lys Met Val Leu Thr Met Met Ser Gly Asp Met Asn
         35                  40                  45

Ile Trp Pro Glu Tyr Lys Asn Arg Thr Ile Phe Asp Ile Thr Asn Asn
     50                  55                  60

Leu Ser Ile Val Ile Leu Ala Leu Arg Pro Ser Asp Glu Gly Thr Tyr
 65                  70                  75                  80

Glu Cys Val Val Leu Lys Tyr Glu Lys Asp Ala Phe Lys Arg Glu His
                 85                  90                  95

Leu Ala Glu Val Thr Leu Ser Val Lys Ala Asp Phe Pro Thr Pro Ser
            100                 105                 110

Ile Ser Asp Phe Glu Ile Pro Thr Ser Asn Ile Arg Arg Ile Ile Cys
        115                 120                 125

Ser Thr Ser Gly Gly Phe Pro Glu Pro His Leu Ser Trp Leu Glu Asn
    130                 135                 140

Gly Glu Glu Leu Asn Ala Ile Asn Thr Thr Val Ser Gln Asp Pro Glu
145                 150                 155                 160

Thr Glu Leu Tyr Ala Val Ser Ser Lys Leu Asp Phe Asn Met Thr Thr
                165                 170                 175

Asn His Ser Phe Met Cys Leu Ile Lys Tyr Gly His Leu Arg Val Asn
            180                 185                 190

Gln Thr Phe Asn Trp Asn Thr Thr Lys Gln Glu His Phe Pro Asp Asn
        195                 200                 205
```

<210> SEQ ID NO 175
<211> LENGTH: 329
<212> TYPE: PRT
<213> ORGANISM: Homo Sapiens
<220> FEATURE:
<223> OTHER INFORMATION: Predicted full-length WT human CD86

<400> SEQUENCE: 175

```
Met Asp Pro Gln Cys Thr Met Gly Leu Ser Asn Ile Leu Phe Val Met
  1               5                  10                  15

Ala Phe Leu Leu Ser Gly Ala Ala Pro Leu Lys Ile Gln Ala Tyr Phe
             20                  25                  30

Asn Glu Thr Ala Asp Leu Pro Cys Gln Phe Ala Asn Ser Gln Asn Gln
         35                  40                  45

Ser Leu Ser Glu Leu Val Val Phe Trp Gln Asp Gln Glu Asn Leu Val
     50                  55                  60

Leu Asn Glu Val Tyr Leu Gly Lys Glu Lys Phe Asp Ser Val His Ser
 65                  70                  75                  80

Lys Tyr Met Gly Arg Thr Ser Phe Asp Ser Asp Ser Trp Thr Leu Arg
                 85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Asp His Ile Pro Trp Ile Thr Ala Val Leu Pro Thr Val
                245                 250                 255

Ile Ile Cys Val Met Val Phe Cys Leu Ile Leu Trp Lys Trp Lys Lys
            260                 265                 270

Lys Lys Arg Pro Arg Asn Ser Tyr Lys Cys Gly Thr Asn Thr Met Glu
        275                 280                 285

Arg Glu Glu Ser Glu Gln Thr Lys Lys Arg Glu Lys Ile His Ile Pro
    290                 295                 300

Glu Arg Ser Asp Glu Ala Gln Arg Val Phe Lys Ser Ser Lys Thr Ser
305                 310                 315                 320

Ser Cys Asp Lys Ser Asp Thr Cys Phe
                325
```

<210> SEQ ID NO 176
<211> LENGTH: 987
<212> TYPE: DNA
<213> ORGANISM: Artificial Sequence
<220> FEATURE:
<223> OTHER INFORMATION: full-length WT human CD86 coding sequence

<400> SEQUENCE: 176

```
atggatcccc agtgcactat gggactgagt aacattctct tgtgatggc cttcctgctc    60
tctggtgctg ctcctctgaa gattcaagct tatttcaatg agactgcaga cctgccatgc   120
caatttgcaa actctcaaaa ccaaagcctg agtgagctag tagtattttg gcaggaccag   180
gaaaacttgg ttctgaatga ggtatactta ggcaaagaga aatttgacag tgttcattcc   240
aagtatatgg gccgcacaag ttttgattcg gacagttgga ccctgagact tcacaatctt   300
cagatcaagg acaagggctt gtatcaatgt atcatccatc acaaaaagcc cacaggaatg   360
attcgcatcc accagatgaa ttctgaactg tcagtgcttg ctaacttcag tcaacctgaa   420
atagtaccaa tttctaatat aacagaaaat gtgtacataa atttgacctg ctcatctata   480
cacggttacc cagaacctaa gaagatgagt gttttgctaa gaaccaagaa ttcaactatc   540
gagtatgatg gtattatgca gaaatctcaa gataatgtca gaactgta  cgacgtttcc   600
atcagcttgt ctgtttcatt ccctgatgtt acgagcaata tgaccatctt ctgtattctg   660
gaaactgaca agacgcggct tttatcttca cctttctcta tagagcttga ggaccctcag   720
cctcccccag accacattcc ttggattaca gctgtacttc aacagttat tatatgtgtg    780
atggttttct gtctaattct atggaaatgg aagaagaaga agcggcctcg caactcttat   840
aaatgtggaa ccaacacaat ggagagggaa gagagtgaac agaccaagaa agagaaaaa    900
atccatatac ctgaaagatc tgatgaagcc agcgtgtttt ttaaaagttc gaagacatct   960
tcatgcgaca aaagtgatac atgtttt                                       987
```

<210> SEQ ID NO 177
<211> LENGTH: 477
<212> TYPE: PRT
<213> ORGANISM: Artificial Sequence
<220> FEATURE:
<223> OTHER INFORMATION: Predicted WT human CD86-human IgG1 fusion protein

<400> SEQUENCE: 177

```
Met Asp Pro Gln Cys Thr Met Gly Leu Ser Asn Ile Leu Phe Val Met
  1               5                  10                  15

Ala Phe Leu Leu Ser Gly Ala Ala Pro Leu Lys Ile Gln Ala Tyr Phe
             20                  25                  30

Asn Glu Thr Ala Asp Leu Pro Cys Gln Phe Ala Asn Ser Gln Asn Gln
         35                  40                  45

Ser Leu Ser Glu Leu Val Val Phe Trp Gln Asp Gln Glu Asn Leu Val
     50                  55                  60

Leu Asn Glu Val Tyr Leu Gly Lys Glu Lys Phe Asp Ser Val His Ser
 65                  70                  75                  80

Lys Tyr Met Gly Arg Thr Ser Phe Asp Ser Asp Ser Trp Thr Leu Arg
                 85                  90                  95

Leu His Asn Leu Gln Ile Lys Asp Lys Gly Leu Tyr Gln Cys Ile Ile
            100                 105                 110

His His Lys Lys Pro Thr Gly Met Ile Arg Ile His Gln Met Asn Ser
        115                 120                 125

Glu Leu Ser Val Leu Ala Asn Phe Ser Gln Pro Glu Ile Val Pro Ile
    130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175
```

Asn Ser Thr Ile Glu Tyr Asp Gly Ile Met Gln Lys Ser Gln Asp Asn
            180                 185                 190

Val Thr Glu Leu Tyr Asp Val Ser Ile Ser Leu Ser Val Ser Phe Pro
        195                 200                 205

Asp Val Thr Ser Asn Met Thr Ile Phe Cys Ile Leu Glu Thr Asp Lys
    210                 215                 220

Thr Arg Leu Leu Ser Ser Pro Phe Ser Ile Glu Leu Glu Asp Pro Gln
225                 230                 235                 240

Pro Pro Pro Gly Val Thr Pro Lys Ser Cys Asp Lys Thr His Thr Cys
            245                 250                 255

Pro Pro Cys Pro Ala Pro Glu Leu Leu Gly Gly Pro Ser Val Phe Leu
        260                 265                 270

Phe Pro Pro Lys Pro Lys Asp Thr Leu Met Ile Ser Arg Thr Pro Glu
    275                 280                 285

Val Thr Cys Val Val Val Asp Val Ser His Glu Asp Pro Glu Val Lys
290                 295                 300

Phe Asn Trp Tyr Val Asp Gly Val Glu Val His Asn Ala Lys Thr Lys
305                 310                 315                 320

Pro Arg Glu Glu Gln Tyr Asn Ser Thr Tyr Arg Val Val Ser Val Leu
            325                 330                 335

Thr Val Leu His Gln Asp Trp Leu Asn Gly Lys Glu Tyr Lys Cys Lys
        340                 345                 350

Val Ser Asn Lys Ala Leu Pro Ala Pro Ile Glu Lys Thr Ile Ser Lys
    355                 360                 365

Ala Lys Gly Gln Pro Arg Glu Pro Gln Val Tyr Thr Leu Pro Pro Ser
370                 375                 380

Arg Asp Glu Leu Thr Lys Asn Gln Val Ser Leu Thr Cys Leu Val Lys
385                 390                 395                 400

Gly Phe Tyr Pro Ser Asp Ile Ala Val Glu Trp Glu Ser Asn Gly Gln
            405                 410                 415

Pro Glu Asn Asn Tyr Lys Thr Thr Pro Pro Val Leu Asp Ser Asp Gly
        420                 425                 430

Ser Phe Phe Leu Tyr Ser Lys Leu Thr Val Asp Lys Ser Arg Trp Gln
    435                 440                 445

Gln Gly Asn Val Phe Ser Cys Ser Val Met His Glu Ala Leu His Asn
450                 455                 460

His Tyr Thr Gln Lys Ser Leu Ser Leu Ser Pro Gly Lys
465                 470                 475

<210> SEQ ID NO 178
<211> LENGTH: 454
<212> TYPE: PRT
<213> ORGANISM: Artificial Sequence
<220> FEATURE:
<223> OTHER INFORMATION: Mature WT human CD86-human IgG1 fusion protein

<400> SEQUENCE: 178

Ala Pro Leu Lys Ile Gln Ala Tyr Phe Asn Glu Thr Ala Asp Leu Pro
1               5                   10                  15

Cys Gln Phe Ala Asn Ser Gln Asn Gln Ser Leu Ser Glu Leu Val Val
            20                  25                  30

Phe Trp Gln Asp Gln Glu Asn Leu Val Leu Asn Glu Val Tyr Leu Gly
        35                  40                  45

Lys Glu Lys Phe Asp Ser Val His Ser Lys Tyr Met Gly Arg Thr Ser
    50                  55                  60

```
Phe Asp Ser Asp Ser Trp Thr Leu Arg Leu His Asn Leu Gln Ile Lys
 65                  70                  75                  80

Asp Lys Gly Leu Tyr Gln Cys Ile Ile His Lys Lys Pro Thr Gly
             85                  90                  95

Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Gly Val Thr Pro
210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 179
<211> LENGTH: 1431
<212> TYPE: DNA
<213> ORGANISM: Artificial Sequence
```

```
<220> FEATURE:
<223> OTHER INFORMATION: WT human CD86-human IgG1 fusion protein coding
      sequence

<400> SEQUENCE: 179
atggatcccc agtgcactat gggactgagt aacattctct tgtgatggc cttcctgctc      60 tctggtgctg ctcctctgaa gattcaagct tatttcaatg agactgcaga cctgccatgc    120
caatttgcaa actctcaaaa ccaaagcctg agtgagctag tagtattttg gcaggaccag    180
gaaaacttgg ttctgaatga ggtatactta ggcaaagaga aatttgacag tgttcattcc    240
aagtatatgg gccgcacaag ttttgattcg gacagttgga ccctgagact tcacaatctt    300
cagatcaagg acaagggctt gtatcaatgt atcatccatc acaaaaagcc cacaggaatg    360
attcgcatcc accagatgaa ttctgaactg tcagtgcttg ctaacttcag tcaacctgaa    420
atagtaccaa tttctaatat aacagaaaat gtgtacataa atttgacctg ctcatctata    480
cacggctacc agaacctaa gaagatgagt gttttgctaa gaaccaagaa ttcaactatc    540
gagtatgatg gtattatgca gaaatctcaa gataatgtca gaactgta cgacgtttcc    600 atcagcttgt ctgtttcatt ccctgatgtt acgagcaata tgaccatctt ctgtattctg    660
gaaactgaca agacgcggct tttatcttca cctttctcta tagagcttga ggaccctcag    720
cctcccccag gggtgacccc aaagagctgc gacaaaactc acacatgccc accgtgccca    780
gcacctgaac tcctgggggg accgtcagtc ttcctcttcc ccccaaaacc caaggacacc    840
ctcatgatct cccggacccc tgaggtcaca tgcgtggtgg tggacgtgag ccacgaagac    900
cctgaggtca agttcaactg gtacgtggac ggcgtggagg tgcataatgc caagacaaag    960
ccgcgggagg agcagtacaa cagcacgtac cgtgtggtca gcgtcctcac cgtcctgcac   1020
caggactggc tgaatggcaa ggagtacaag tgcaaggtct ccaacaaagc cctcccagcc   1080
cccatcgaga aaaccatctc caaagccaaa gggcagcccc gagaaccaca ggtgtacacc   1140
ctgcccccat cccgggatga gctgaccaag aaccaggtca gcctgacctg cctggtcaaa   1200
ggcttctatc ccagcgacat cgccgtggag tgggagagca atgggcagcc ggagaacaac   1260
tacaagacca cgcctcccgt gctggactcc gacggctcct tcttcctcta cagcaagctc   1320
accgtggaca gagcaggtg gcagcagggg aacgtcttct catgctccgt gatgcatgag   1380
gctctgcaca accactacac gcagaagagc ctctccctgt ctccgggtaa a           1431

<210> SEQ ID NO 180
<211> LENGTH: 220
<212> TYPE: PRT
<213> ORGANISM: Homo Sapiens
<220> FEATURE:
<223> OTHER INFORMATION: WT human CD86 ECD

<400> SEQUENCE: 180

Ala Pro Leu Lys Ile Gln Ala Tyr Phe Asn Glu Thr Ala Asp Leu Pro
 1               5                  10                  15

Cys Gln Phe Ala Asn Ser Gln Asn Gln Ser Leu Ser Glu Leu Val Val
                20                  25                  30

Phe Trp Gln Asp Gln Glu Asn Leu Val Leu Asn Glu Val Tyr Leu Gly
            35                  40                  45

Lys Glu Lys Phe Asp Ser Val His Ser Lys Tyr Met Gly Arg Thr Ser
        50                  55                  60

Phe Asp Ser Asp Ser Trp Thr Leu Arg Leu His Asn Leu Gln Ile Lys
65                  70                  75                  80

Asp Lys Gly Leu Tyr Gln Cys Ile Ile His His Lys Lys Pro Thr Gly
```

```
                    85                  90                  95
Met Ile Arg Ile His Gln Met Asn Ser Glu Leu Ser Val Leu Ala Asn
            100                 105                 110

Phe Ser Gln Pro Glu Ile Val Pro Ile Ser Asn Ile Thr Glu Asn Val
        115                 120                 125

Tyr Ile Asn Leu Thr Cys Ser Ser Ile His Gly Tyr Pro Glu Pro Lys
    130                 135                 140

Lys Met Ser Val Leu Leu Arg Thr Lys Asn Ser Thr Ile Glu Tyr Asp
145                 150                 155                 160

Gly Ile Met Gln Lys Ser Gln Asp Asn Val Thr Glu Leu Tyr Asp Val
                165                 170                 175

Ser Ile Ser Leu Ser Val Ser Phe Pro Asp Val Thr Ser Asn Met Thr
            180                 185                 190

Ile Phe Cys Ile Leu Glu Thr Asp Lys Thr Arg Leu Leu Ser Ser Pro
        195                 200                 205

Phe Ser Ile Glu Leu Glu Asp Pro Gln Pro Pro Pro
    210                 215                 220

<210> SEQ ID NO 181
<211> LENGTH: 105
<212> TYPE: DNA
<213> ORGANISM: Artificial Sequence
<220> FEATURE:
<223> OTHER INFORMATION: WT human CTLA-4 signal peptide coding sequence

<400> SEQUENCE: 181
atggcttgtc ttggatttca acgccacaaa gctcaactca atctcgctac ccgaacatgg      60
ccttgtactc ttctcttttt tctcctcttc ataccggttt tttgt                    105

<210> SEQ ID NO 182
<211> LENGTH: 35
<212> TYPE: PRT
<213> ORGANISM: Homo Sapiens
<220> FEATURE:
<223> OTHER INFORMATION: WT human CTLA-4 signal peptide

<400> SEQUENCE: 182

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys
        35

<210> SEQ ID NO 183
<211> LENGTH: 684
<212> TYPE: DNA
<213> ORGANISM: Artificial Sequence
<220> FEATURE:
<223> OTHER INFORMATION: Coding sequence of human IgG2 Fc polypeptide
      (with C-terminal lysine)

<400> SEQUENCE: 183
gagcgcaaat gttgtgtcga gtgcccaccg tgcccagcac cacctgtggc aggaccgtca      60
gtcttcctct tccccccaaa acccaaggac accctcatga tctcccggac ccctgaggtc     120
acgtgcgtgg tggtggacgt gagccacgaa gaccccgagg tccagttcaa ctggtacgtg     180
gacggcgtgg aggtgcataa tgccaagaca aagccacggg aggagcagtt caacagcacg     240
ttccgtgtgt cagcgtcct caccgttgtg caccaggact ggctgaacgg caaggagtac     300
```

```
aagtgcaagg tctccaacaa aggcctccca gccccatcg agaaaaccat ctccaaaacc    360
aaagggcagc cccgagaacc acaggtgtac accctgcccc catcccggga ggagatgacc    420
aagaaccagg tcagcctgac ctgcctggtc aaaggcttct accccagcga catcgccgtg    480
gagtgggaga gcaatgggca gccggagaac aactacaaga ccacacctcc catgctggac    540
tccgacggct ccttcttcct ctacagcaag ctcaccgtgg acaagagcag gtggcagcag    600
gggaacgtct tctcatgctc cgtgatgcat gaggctctgc acaaccacta cacgcagaag    660
agcctctccc tgtctccggg taaa    684
```

<210> SEQ ID NO 184
<211> LENGTH: 228
<212> TYPE: PRT
<213> ORGANISM: Homo Sapiens
<220> FEATURE:
<223> OTHER INFORMATION: Human IgG2 Fc polypeptide (with C-terminal lysine)

<400> SEQUENCE: 184

```
Glu Arg Lys Cys Cys Val Glu Cys Pro Pro Cys Pro Ala Pro Pro Val
 1               5                  10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly Lys
225
```

<210> SEQ ID NO 185
<211> LENGTH: 231
<212> TYPE: PRT
<213> ORGANISM: Homo Sapiens
<220> FEATURE:
<223> OTHER INFORMATION: Human IgG1 Fc polypeptide

<400> SEQUENCE: 185

```
Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys
            20                  25                  30

Asp Thr Leu Met Ile Ser Arg Thr Pro Glu Val Thr Cys Val Val Val
        35                  40                  45

Asp Val Ser His Glu Asp Pro Glu Val Lys Phe Asn Trp Tyr Val Asp
    50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
        115                 120                 125

Glu Pro Gln Val Tyr Thr Leu Pro Pro Ser Arg Asp Glu Leu Thr Lys
    130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
                165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
        195                 200                 205

Cys Ser Val Met His Glu Ala Leu His Asn His Tyr Thr Gln Lys Ser
    210                 215                 220

Leu Ser Leu Ser Pro Gly Lys
225                 230

<210> SEQ ID NO 186
<211> LENGTH: 232
<212> TYPE: PRT
<213> ORGANISM: Artificial Sequence
<220> FEATURE:
<223> OTHER INFORMATION: Mutant IgG1 Fc polypeptide

<400> SEQUENCE: 186

Glu Pro Lys Ser Ser Asp Lys Thr His Thr Ser Pro Pro Ser Pro Ala
1               5                   10                  15

Pro Glu Leu Leu Gly Gly Ser Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
```

```
            130                 135                 140
Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230

<210> SEQ ID NO 187
<211> LENGTH: 59
<212> TYPE: DNA
<213> ORGANISM: Artificial Sequence
<220> FEATURE:
<223> OTHER INFORMATION: primer

<400> SEQUENCE: 187
ctattgctac ggccgctatg gccmtkcacg tcgctcaacc agccgtcgta ctcgcgtcc      59

<210> SEQ ID NO 188
<211> LENGTH: 30
<212> TYPE: DNA
<213> ORGANISM: Artificial Sequence
<220> FEATURE:
<223> OTHER INFORMATION: primer

<400> SEQUENCE: 188
gtgatggtga tggtgtgcgg ccgcatcaga                                      30

<210> SEQ ID NO 189
<211> LENGTH: 77
<212> TYPE: DNA
<213> ORGANISM: Artificial Sequence
<220> FEATURE:
<223> OTHER INFORMATION: primer

<400> SEQUENCE: 189
aagctgtcac cggtggatcg atcccgaacc ctgccctgat tctgatgagc gcaaatgttg     60
tgtcgagtgc ccaccgt                                                    77

<210> SEQ ID NO 190
<211> LENGTH: 42
<212> TYPE: DNA
<213> ORGANISM: Artificial Sequence
<220> FEATURE:
<223> OTHER INFORMATION: primer

<400> SEQUENCE: 190
cagaattcat tatttacccg gagacaggga gaggctcttc tg                        42

<210> SEQ ID NO 191
<211> LENGTH: 54
<212> TYPE: DNA
<213> ORGANISM: Artificial Sequence
<220> FEATURE:
<223> OTHER INFORMATION: primer

<400> SEQUENCE: 191
```

```
ggaataccgg ttttttgtaa agccatgcac gtcgctcaac cagccgtcgt actc              54
```

<210> SEQ ID NO 192
<211> LENGTH: 30
<212> TYPE: DNA
<213> ORGANISM: Artificial Sequence
<220> FEATURE:
<223> OTHER INFORMATION: primer

<400> SEQUENCE: 192

```
ggcactcaga tctacgtcat cgatcccgaa                                          30
```

<210> SEQ ID NO 193
<211> LENGTH: 372
<212> TYPE: DNA
<213> ORGANISM: Artificial Sequence
<220> FEATURE:
<223> OTHER INFORMATION: human CTLA-4 ECD coding sequence

<400> SEQUENCE: 193

```
atgcacgtgg cccagcctgc tgtggtactg gccagcagcc gaggcatcgc cagctttgtg         60
tgtgagtatg catctccagg caaagccact gaggtccggg tgacagtgct tcggcaggct        120
gacagccagg tgactgaagt ctgtgcggca acctacatga tggggaatga gttgaccttc        180
ctagatgatt ccatctgcac gggcacctcc agtggaaatc aagtgaacct cactatccaa        240
ggactgaggg ccatggacac gggactctac atctgcaagg tggagctcat gtacccaccg        300
ccatactacc tgggcatagg caacggaacc cagatttatg taattgatcc agaaccgtgc        360
ccagattctg ac                                                            372
```

<210> SEQ ID NO 194
<211> LENGTH: 672
<212> TYPE: DNA
<213> ORGANISM: Artificial Sequence
<220> FEATURE:
<223> OTHER INFORMATION: full-length human CTLA-4 coding sequence

<400> SEQUENCE: 194

```
atggcttgcc ttggatttca gcggcacaag gctcagctga acctggctac caggacctgg         60
ccctgcactc tcctgttttt tcttctcttc atccctgtct ctgcaaagc aatgcacgtg        120 gcccagcctg ctgtggtact ggccagcagc cgaggcatcg ccagctttgt gtgtgagtat        180
gcatctccag gcaaagccac tgaggtccgg gtgacagtgc ttcggcaggc tgacagccag        240
gtgactgaag tctgtgcggc aacctacatg atggggaatg agttgacctt cctagatgat        300
tccatctgca cgggcacctc cagtggaaat caagtgaacc tcactatcca aggactgagg        360
gccatggaca cgggactcta catctgcaag gtggagctca tgtacccacc gccatactac        420
ctgggcatag gcaacggaac ccagatttat gtaattgatc cagaaccgtg cccagattct        480
gacttcctcc tctggatcct tgcagcagtt agttcgggt tgttttttta tagctttctc        540
ctcacagctg tttctttgag caaaatgcta agaaaagaa gccctcttac aacagggtc        600 tatgtgaaaa tgccccaac agagccagaa tgtgaaaagc aatttcagcc ttatttatt        660 cccatcaatt ga                                                            672
```

<210> SEQ ID NO 195
<211> LENGTH: 288
<212> TYPE: PRT
<213> ORGANISM: Homo Sapiens
<220> FEATURE:
<223> OTHER INFORMATION: Predicted full-length human CD80

-continued

```
<400> SEQUENCE: 195

Met Gly His Thr Arg Arg Gln Gly Thr Ser Pro Ser Lys Cys Pro Tyr
 1               5                  10                  15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
        50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
                100                 105                 110

Thr Tyr Glu Cys Val Val Leu Lys Tyr Glu Lys Asp Ala Phe Lys Arg
            115                 120                 125

Glu His Leu Ala Glu Val Thr Leu Ser Val Lys Ala Asp Phe Pro Thr
        130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
                180                 185                 190

Pro Glu Thr Glu Leu Tyr Ala Val Ser Ser Lys Leu Asp Phe Asn Met
            195                 200                 205

Thr Thr Asn His Ser Phe Met Cys Leu Ile Lys Tyr Gly His Leu Arg
        210                 215                 220

Val Asn Gln Thr Phe Asn Trp Asn Thr Thr Lys Gln Glu His Phe Pro
225                 230                 235                 240

Asp Asn Leu Leu Pro Ser Trp Ala Ile Thr Leu Ile Ser Val Asn Gly
                245                 250                 255

Ile Phe Val Ile Cys Cys Leu Thr Tyr Cys Phe Ala Pro Arg Cys Arg
                260                 265                 270

Glu Arg Arg Arg Asn Glu Arg Leu Arg Arg Glu Ser Val Arg Pro Val
            275                 280                 285

<210> SEQ ID NO 196
<211> LENGTH: 867
<212> TYPE: DNA
<213> ORGANISM: Artificial Sequence
<220> FEATURE:
<223> OTHER INFORMATION: full-length human CD80 coding sequence

<400> SEQUENCE: 196
atgggccaca cacggaggca gggaacatca ccatccaagt gtccatacct caatttcttt      60
cagctcttgg tgctggctgg tctttctcac ttctgttcag gtgttatcca cgtgaccaag     120
gaagtgaaag aagtggcaac gctgtcctgt ggtcacaatg tttctgttga agagctggca     180
caaactcgca tctactggca aaaggagaag aaaatggtgc tgactatgat gtctggggac     240
atgaatatat ggcccgagta caagaaccgg accatctttg atatcactaa taacctctcc     300
attgtgatcc tggctctgcg cccatctgac gagggcacat acgagtgtgt tgttctgaag     360
tatgaaaaag acgctttcaa gcgggaacac ctggctgaag tgacgttatc agtcaaagct     420
```

```
gacttcccta cacctagtat atctgacttt gaaattccaa cttctaatat tagaaggata    480
atttgctcaa cctctggagg ttttccagag cctcacctct cctggttgga aaatggagaa    540
gaattaaatg ccatcaacac aacagtttcc caagatcctg aaactgagct ctatgctgtt    600
agcagcaaac tggatttcaa tatgacaacc aaccacagct tcatgtgtct catcaagtat    660
ggacatttaa gagtgaatca gaccttcaac tggaatacaa ccaagcaaga gcatttcct     720 gataacctgc tcccatcctg gccattacc ttaatctcag taaatggaat ttttgtgata    780
tgctgcctga cctactgctt tgccccaaga tgcagagaga aaggaggaa tgagagattg     840 agaagggaaa gtgtacgccc tgtataa                                        867
```

<210> SEQ ID NO 197
<211> LENGTH: 352
<212> TYPE: PRT
<213> ORGANISM: Artificial Sequence
<220> FEATURE:
<223> OTHER INFORMATION: D3-54-IgG2 fusion protein (with C-terminal lysine)

<400> SEQUENCE: 197

```
Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Glu Asn Glu Leu Thr Phe Leu Asp Asp Pro
    50                  55                  60

Ile Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Glu Arg Lys Cys
        115                 120                 125

Cys Val Glu Cys Pro Pro Cys Pro Ala Pro Pro Val Ala Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
    210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285
```

Asn Gly Gln Pro Glu Asn Asn Tyr Lys Thr Thr Pro Pro Met Leu Asp
            290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 198
<211> LENGTH: 352
<212> TYPE: PRT
<213> ORGANISM: Artificial Sequence
<220> FEATURE:
<223> OTHER INFORMATION: D3-56-IgG2 fusion protein (with C-terminal
      lysine)

<400> SEQUENCE: 198

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Glu Asn Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Glu Arg Lys Cys
        115                 120                 125

Cys Val Glu Cys Pro Pro Cys Pro Ala Pro Pro Val Ala Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
    210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Met Leu Asp
    290                 295                 300

```
Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 199
<211> LENGTH: 352
<212> TYPE: PRT
<213> ORGANISM: Artificial Sequence
<220> FEATURE:
<223> OTHER INFORMATION: D3-69-IgG2 fusion protein (with C-terminal
      lysine)

<400> SEQUENCE: 199

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
                20                  25                  30

Arg Val Thr Val Leu Arg Gln Ala Asp Ser Gln Val Thr Glu Val Cys
            35                  40                  45

Ala Met Thr Tyr Met Lys Gly Asp Glu Leu Thr Phe Leu Asp Asp Pro
        50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Glu Arg Lys Cys
        115                 120                 125

Cys Val Glu Cys Pro Pro Cys Pro Ala Pro Pro Val Ala Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Met Leu Asp
290                 295                 300

Ser Asp Gly Ser Phe Phe Leu Tyr Ser Lys Leu Thr Val Asp Lys Ser
305                 310                 315                 320
```

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
                340                 345                 350

<210> SEQ ID NO 200
<211> LENGTH: 352
<212> TYPE: PRT
<213> ORGANISM: Artificial Sequence
<220> FEATURE:
<223> OTHER INFORMATION: D3-75-IgG2 fusion protein (with C-terminal
      lysine)

<400> SEQUENCE: 200

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Val
                20                  25                  30

Arg Val Thr Val Leu Arg Gln Ala Asp Ser Gln Val Thr Glu Val Cys
            35                  40                  45

Ala Met Thr Tyr Met Lys Glu Asn Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Glu Arg Lys Cys
            115                 120                 125

Cys Val Glu Cys Pro Pro Cys Pro Ala Pro Pro Val Ala Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
                180                 185                 190

Lys Thr Lys Pro Arg Glu Glu Gln Phe Asn Ser Thr Phe Arg Val Val
            195                 200                 205

Ser Val Leu Thr Val Val His Gln Asp Trp Leu Asn Gly Lys Glu Tyr
    210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
                260                 265                 270

Leu Val Lys Gly Phe Tyr Pro Ser Asp Ile Ala Val Glu Trp Glu Ser
            275                 280                 285

Asn Gly Gln Pro Glu Asn Asn Tyr Lys Thr Thr Pro Pro Met Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
        340                 345                 350

<210> SEQ ID NO 201
<211> LENGTH: 1170
<212> TYPE: DNA
<213> ORGANISM: Artificial Sequence
<220> FEATURE:
<223> OTHER INFORMATION: D3-54-IgG2 fusion protein coding sequence

<400> SEQUENCE: 201

```
atggcttgtc ttggatttca acgccacaaa gctcaactca atctcgctac ccgaacatgg    60
ccttgtactc ttctcttttt tctcctcttc ataccggttt tttgtaaagc catgcacgtc   120
gctcaaccag ccgtcgtact cgcgtcctct agaggtatcg cttccttcgt gtgtgaatat   180
gcgtcacccg gcaaagccaa cgaagttaga gtcacagtgc tccgccaagc cgatagtcaa   240
gttacagaag tctgcgctat gacatacatg aaggaaaatg aactaacctt ccttgacgat   300
cccatctgca caggtacctt ttccggaaat caagttaatc ttactattca aggacttcga   360
gccatggata ccggactcta tatttgtaaa gtcgaactca tgtacccccc cccttactac   420
ttgggtattg gtaatggcac tcagatctac gtcatcgatc ccgaaccctg ccctgattct   480
gatgagcgca atgttgtgt cgagtgccca ccgtgcccag caccacctgt ggcaggaccg   540
tcagtcttcc tcttcccccc aaaacccaag gacacactca tgatctcccg gaccctgag    600
gtcacgtgcg tggtggtgga cgtgagccac gaagacccg aggtccagtt caactggtac    660
gtggacggcg tggaggtgca taatgccaag acaaagccac gggaggagca gttcaacagc   720
acgttccgtg tggtcagcgt cctcaccgtt gtgcaccagg actggctgaa cggcaaggag   780
tacaagtgca aggtctccaa caaaggcctc ccagcccca tcgagaaaac catctccaaa    840
accaaagggc agccccgaga accacaggtg tacaccctgc ccccatcccg ggaggagatg   900
accaagaacc aggtcagcct gacctgcctg gtcaaaggct tctacccag cgacatcgcc   960
gtggagtggg agagcaatgg gcagccggag aacaactaca agaccacacc tcccatgctg   1020
gactccgacg gctccttctt cctctacagc aagctcaccg tggacaagag caggtggcag   1080
caggggaacg tcttctcatg ctccgtgatg catgaggctc tgcacaacca ctacacgcag   1140
aagagcctct ccctgtctcc gggtaaataa                                    1170
```

<210> SEQ ID NO 202
<211> LENGTH: 1170
<212> TYPE: DNA
<213> ORGANISM: Artificial Sequence
<220> FEATURE:
<223> OTHER INFORMATION: D3-56-IgG2 fusion protein coding sequence

<400> SEQUENCE: 202

```
atggcttgtc ttggatttca acgccacaaa gctcaactca atctcgctac ccgaacatgg    60
ccttgtactc ttctcttttt tctcctcttc ataccggttt tttgtaaagc catgcacgtc   120
gctcaaccag ccgtcgtact cgcgtcctct agaggtatcg cttccttcgt gtgtgaatat   180
gcgtcacccg gcaaagccaa cgaagttaga gtcacagtgc tccgccaagc cgatagtcaa   240
gttacagaag tctgcgctat gacatacatg aaggaaaatg aactaacctt ccttgacgat   300
cccagctgca caggtacctt ttccggaaat caagttaatc ttactattca aggacttcga   360
gccatggata ccggactcta tatttgtaaa gtcgaactca tgtacccccc cccttactac   420
ttgggtattg gtaatggcac tcagatctac gtcatcgatc ccgaaccctg ccctgattct   480
```

```
gatgagcgca aatgttgtgt cgagtgccca ccgtgcccag caccacctgt ggcaggaccg      540
tcagtcttcc tcttcccccc aaaacccaag acacccctca tgatctcccg accccctgag      600
gtcacgtgcg tggtggtgga cgtgagccac gaagacccccg aggtccagtt caactggtac     660
gtggacggcg tggaggtgca taatgccaag acaaagccac gggaggagca gttcaacagc      720
acgttccgtg tggtcagcgt cctcaccgtt gtgcaccagg actggctgaa cggcaaggag      780
tacaagtgca aggtctccaa caaaggcctc ccagccccca tcgagaaaac catctccaaa      840 accaagggc agcccgaga ccacaggtg tacaccctgc ccccatcccg ggaggagatg         900
accaagaacc aggtcagcct gacctgcctg gtcaaaggct tctaccccag cgacatcgcc      960
gtggagtggg agagcaatgg gcagccggag aacaactaca agaccacacc tcccatgctg    1020
gactccgacg gctccttctt cctctacagc aagctcaccg tggacaagag caggtggcag    1080
caggggaacg tcttctcatg ctccgtgatg catgaggctc tgcacaacca ctacacgcag    1140
aagagcctct ccctgtctcc gggtaaataa                                     1170

<210> SEQ ID NO 203
<211> LENGTH: 1170
<212> TYPE: DNA
<213> ORGANISM: Artificial Sequence
<220> FEATURE:
<223> OTHER INFORMATION: D3-69-IgG2 fusion protein coding sequence

<400> SEQUENCE: 203
atggcttgtc ttggatttca acgccacaaa gctcaactca atctcgctac ccgaacatgg       60
ccttgtactc ttctcttttt tctcctcttc ataccggttt tttgtaaagc catgcacgtc      120
gctcaaccag ccgtcgtact cgcgtcctct agaggtatcg cttccttcgt gtgtgaatat      180
gagtcacccg gcaaagccaa cgaaattaga gtcacagtgc tccgccaagc cgatagtcaa      240
gttacagaag tctgcgctat gacatacatg aagggagatg aactaacctt ccttgacgat      300
cccagctgca caggtacctt ttccggaaat caagttaatc ttactattca aggacttcga      360
gccatggata ccggactcta tatttgtaaa gtcgaactca tgtacccccc cccttactac      420
gagggtatag gtaatggcac tcagatctac gtcatcgatc ccgaaccctg ccctgattct      480
gatgagcgca aatgttgtgt cgagtgccca ccgtgcccag caccacctgt ggcaggaccg      540
tcagtcttcc tcttcccccc aaaacccaag acacccctca tgatctcccg accccctgag      600
gtcacgtgcg tggtggtgga cgtgagccac gaagacccccg aggtccagtt caactggtac     660
gtggacggcg tggaggtgca taatgccaag acaaagccac gggaggagca gttcaacagc      720
acgttccgtg tggtcagcgt cctcaccgtt gtgcaccagg actggctgaa cggcaaggag      780
tacaagtgca aggtctccaa caaaggcctc ccagccccca tcgagaaaac catctccaaa      840 accaagggc agcccgaga ccacaggtg tacaccctgc ccccatcccg ggaggagatg         900
accaagaacc aggtcagcct gacctgcctg gtcaaaggct tctaccccag cgacatcgcc      960
gtggagtggg agagcaatgg gcagccggag aacaactaca agaccacacc tcccatgctg    1020
gactccgacg gctccttctt cctctacagc aagctcaccg tggacaagag caggtggcag    1080
caggggaacg tcttctcatg ctccgtgatg catgaggctc tgcacaacca ctacacgcag    1140
aagagcctct ccctgtctcc gggtaaataa                                     1170

<210> SEQ ID NO 204
<211> LENGTH: 1170
<212> TYPE: DNA
<213> ORGANISM: Artificial Sequence
<220> FEATURE:
```

-continued

<223> OTHER INFORMATION: D3-75-IgG2 fusion protein coding sequence

<400> SEQUENCE: 204

```
atggcttgtc ttggatttca acgccacaaa gctcaactca atctcgctac ccgaacatgg    60
ccttgtactc ttctcttttt tctcctcttc ataccggttt tttgtaaagc catgcacgtc   120
gctcaaccag ccgtcgtact cgcgtcctct agaggtatcg cttccttcgt gtgtgaatat   180
gagtcacccg gcaaagccaa cgaagttaga gtcacagtgc tccgccaagc cgatagtcaa   240
gttacagaag tctgcgctat gacatacatg aaggaaaatg aactaacctt ccttgacgat   300
cccagctgca caggtacctt ttccggaaat caagttaatc ttactattca aggacttcga   360
gccatggata ccggactcta tatttgtaaa gtcgaactca tgtacccccc cccttactac   420
ttgggtattg gtaatggcac tcagatctac gtcatcgatc ccgaaccctg ccctgattct   480
gatgagcgca aatgttgtgt cgagtgccca ccgtgcccag caccacctgt ggcaggaccg   540
tcagtcttcc tcttcccccc aaaacccaag gacaccctca tgatctcccg gacccctgag   600
gtcacgtgcg tggtggtgga cgtgagccac gaagaccccg aggtccagtt caactggtac   660
gtggacggcg tggaggtgca taatgccaag acaaagccac gggaggagca gttcaacagc   720
acgttccgtg tggtcagcgt cctcaccgtt gtgcaccagg actggctgaa cggcaaggag   780
tacaagtgca aggtctccaa caaaggcctc ccagccccca tcgagaaaac catctccaaa   840
accaaagggc agccccgaga ccacaggtg tacaccctgc ccccatcccg ggaggagatg   900
accaagaacc aggtcagcct gacctgcctg gtcaaaggct tctacccag cgacatcgcc   960
gtggagtggg agagcaatgg gcagccggag aacaactaca agaccacacc tcccatgctg   1020
gactccgacg gctccttctt cctctacagc aagctcaccg tggacaagag caggtggcag   1080
caggggaacg tcttctcatg ctccgtgatg catgaggctc tgcacaacca ctacacgcag   1140
aagagcctct ccctgtctcc gggtaaataa                                    1170
```

<210> SEQ ID NO 205
<211> LENGTH: 351
<212> TYPE: PRT
<213> ORGANISM: Artificial Sequence
<220> FEATURE:
<223> OTHER INFORMATION: D3-12-IgG2 fusion protein (without C-terminal lysine)

<400> SEQUENCE: 205

```
Met His Val Ala Gln Pro Ala Val Val Leu Ala Ser Ser Arg Gly Ile
  1               5                  10                  15

Ala Ser Phe Val Cys Glu Tyr Glu Ser Pro Gly Lys Ala Asn Glu Ile
             20                  25                  30

Arg Val Thr Val Leu Arg Gln Ala Gly Ser Gln Val Thr Glu Val Cys
         35                  40                  45

Ala Met Thr Tyr Met Lys Gly Asp Glu Leu Thr Phe Leu Asp Asp Pro
     50                  55                  60

Ser Cys Thr Gly Thr Phe Ser Gly Asn Gln Val Asn Leu Thr Ile Gln
 65                  70                  75                  80

Gly Leu Arg Ala Ala Asp Thr Gly Leu Tyr Ile Cys Lys Val Glu Leu
                 85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Glu Arg Lys Cys
        115                 120                 125

Cys Val Glu Cys Pro Pro Cys Pro Ala Pro Pro Val Ala Gly Pro Ser
```

```
              130                 135                 140
Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
                180                 185                 190

Lys Thr Lys Pro Arg Glu Glu Gln Phe Asn Ser Thr Phe Arg Val Val
                195                 200                 205

Ser Val Leu Thr Val Val His Gln Asp Trp Leu Asn Gly Lys Glu Tyr
                210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
                260                 265                 270

Leu Val Lys Gly Phe Tyr Pro Ser Asp Ile Ala Val Glu Trp Glu Ser
                275                 280                 285

Asn Gly Gln Pro Glu Asn Asn Tyr Lys Thr Thr Pro Pro Met Leu Asp
                290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly
                340                 345                 350

<210> SEQ ID NO 206
<211> LENGTH: 351
<212> TYPE: PRT
<213> ORGANISM: Artificial Sequence
<220> FEATURE:
<223> OTHER INFORMATION: D3-14-IgG2 fusion protein (without C-terminal
      lysine)

<400> SEQUENCE: 206

Met His Val Ala Gln Pro Ala Val Val Leu Ala Ser Ser Arg Gly Ile
 1               5                  10                  15

Ala Ser Phe Val Cys Glu Tyr Glu Ser Pro Gly Lys Ala Asn Glu Ile
                20                  25                  30

Arg Val Thr Val Leu Arg Gln Ala Asp Ser Gln Val Thr Glu Val Cys
                35                  40                  45

Ala Met Thr Tyr Met Lys Gly Asp Glu Leu Thr Phe Leu Asp Asp Pro
                50                  55                  60

Ser Cys Thr Gly Thr Phe Ser Gly Asn Gln Val Asn Leu Thr Ile Gln
65                  70                  75                  80

Gly Leu Arg Ala Ala Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
                100                 105                 110

Tyr Val Ile Asp Pro Glu Pro Cys Pro Asp Ser Asp Glu Arg Lys Cys
                115                 120                 125

Cys Val Glu Cys Pro Pro Cys Pro Ala Pro Val Ala Gly Pro Ser
                130                 135                 140

Val Phe Leu Phe Pro Pro Lys Pro Lys Asp Thr Leu Met Ile Ser Arg
```

```
                145                 150                 155                 160
Thr Pro Glu Val Thr Cys Val Val Asp Val Ser His Glu Asp Pro
                165                 170                 175
Glu Val Gln Phe Asn Trp Tyr Val Asp Gly Val Glu Val His Asn Ala
                180                 185                 190
Lys Thr Lys Pro Arg Glu Glu Gln Phe Asn Ser Thr Phe Arg Val Val
                195                 200                 205
Ser Val Leu Thr Val Val His Gln Asp Trp Leu Asn Gly Lys Glu Tyr
    210                 215                 220
Lys Cys Lys Val Ser Asn Lys Gly Leu Pro Ala Pro Ile Glu Lys Thr
225                 230                 235                 240
Ile Ser Lys Thr Lys Gly Gln Pro Arg Glu Pro Gln Val Tyr Thr Leu
                245                 250                 255
Pro Pro Ser Arg Glu Glu Met Thr Lys Asn Gln Val Ser Leu Thr Cys
                260                 265                 270
Leu Val Lys Gly Phe Tyr Pro Ser Asp Ile Ala Val Glu Trp Glu Ser
                275                 280                 285
Asn Gly Gln Pro Glu Asn Asn Tyr Lys Thr Thr Pro Pro Met Leu Asp
    290                 295                 300
Ser Asp Gly Ser Phe Phe Leu Tyr Ser Lys Leu Thr Val Asp Lys Ser
305                 310                 315                 320
Arg Trp Gln Gln Gly Asn Val Phe Ser Cys Ser Val Met His Glu Ala
                325                 330                 335
Leu His Asn His Tyr Thr Gln Lys Ser Leu Ser Leu Ser Pro Gly
                340                 345                 350

<210> SEQ ID NO 207
<211> LENGTH: 351
<212> TYPE: PRT
<213> ORGANISM: Artificial Sequence
<220> FEATURE:
<223> OTHER INFORMATION: D3-17-IgG2 fusion protein (without C-terminal
      lysine)

<400> SEQUENCE: 207

Met His Val Ala Gln Pro Ala Val Val Leu Ala Ser Ser Arg Gly Ile
1               5                   10                  15
Ala Ser Phe Val Cys Glu Tyr Glu Ser Pro Gly Lys Ala Asn Glu Ile
                20                  25                  30
Arg Val Thr Val Leu Arg Gln Ala Asp Ser Gln Val Thr Glu Val Cys
            35                  40                  45
Ala Met Thr Tyr Met Lys Gly Asp Glu Leu Thr Phe Leu Asp Asp Pro
    50                  55                  60
Ser Cys Thr Gly Thr Phe Ser Gly Asn Gln Val Asn Leu Thr Ile Gln
65                  70                  75                  80
Gly Leu Arg Ala Met Asp Thr Gly Leu Tyr Ile Cys Lys Val Glu Leu
                85                  90                  95
Met Tyr Pro Pro Pro Tyr Tyr Leu Gly Ile Gly Asn Gly Thr Gln Ile
                100                 105                 110
Tyr Val Ile Asp Pro Glu Pro Cys Pro Asp Ser Asp Glu Arg Lys Cys
            115                 120                 125
Cys Val Glu Cys Pro Pro Cys Pro Ala Pro Pro Val Ala Gly Pro Ser
    130                 135                 140
Val Phe Leu Phe Pro Pro Lys Pro Lys Asp Thr Leu Met Ile Ser Arg
145                 150                 155                 160
Thr Pro Glu Val Thr Cys Val Val Val Asp Val Ser His Glu Asp Pro
```

```
                165                 170                 175
Glu Val Gln Phe Asn Trp Tyr Val Asp Gly Val Glu Val His Asn Ala
            180                 185                 190
Lys Thr Lys Pro Arg Glu Glu Gln Phe Asn Ser Thr Phe Arg Val Val
        195                 200                 205
Ser Val Leu Thr Val Val His Gln Asp Trp Leu Asn Gly Lys Glu Tyr
    210                 215                 220
Lys Cys Lys Val Ser Asn Lys Gly Leu Pro Ala Pro Ile Glu Lys Thr
225                 230                 235                 240
Ile Ser Lys Thr Lys Gly Gln Pro Arg Glu Pro Gln Val Tyr Thr Leu
                245                 250                 255
Pro Pro Ser Arg Glu Glu Met Thr Lys Asn Gln Val Ser Leu Thr Cys
            260                 265                 270
Leu Val Lys Gly Phe Tyr Pro Ser Asp Ile Ala Val Glu Trp Glu Ser
        275                 280                 285
Asn Gly Gln Pro Glu Asn Asn Tyr Lys Thr Thr Pro Pro Met Leu Asp
    290                 295                 300
Ser Asp Gly Ser Phe Phe Leu Tyr Ser Lys Leu Thr Val Asp Lys Ser
305                 310                 315                 320
Arg Trp Gln Gln Gly Asn Val Phe Ser Cys Ser Val Met His Glu Ala
                325                 330                 335
Leu His Asn His Tyr Thr Gln Lys Ser Leu Ser Leu Ser Pro Gly
            340                 345                 350

<210> SEQ ID NO 208
<211> LENGTH: 351
<212> TYPE: PRT
<213> ORGANISM: Artificial Sequence
<220> FEATURE:
<223> OTHER INFORMATION: D3-20-IgG2 fusion protein (without C-terminal
      lysine)

<400> SEQUENCE: 208

Met His Val Ala Gln Pro Ala Val Val Leu Ala Ser Ser Arg Gly Ile
1               5                   10                  15
Ala Ser Phe Val Cys Glu Tyr Glu Ser Pro Gly Lys Ala Asn Glu Ile
            20                  25                  30
Arg Val Thr Val Leu Arg Gln Ala Asp Ser Gln Val Thr Glu Val Cys
        35                  40                  45
Ala Met Thr Tyr Met Lys Gly Asn Glu Leu Thr Phe Leu Asp Asp Pro
    50                  55                  60
Ser Cys Thr Gly Thr Phe Ser Gly Asn Gln Val Asn Leu Thr Ile Gln
65                  70                  75                  80
Gly Leu Arg Ala Met Asp Thr Gly Leu Tyr Ile Cys Lys Val Glu Leu
                85                  90                  95
Met Tyr Pro Pro Pro Tyr Tyr Leu Gly Ile Gly Asn Gly Thr Gln Ile
            100                 105                 110
Tyr Val Ile Asp Pro Glu Pro Cys Pro Asp Ser Asp Glu Arg Lys Cys
        115                 120                 125
Cys Val Glu Cys Pro Pro Cys Pro Ala Pro Pro Val Ala Gly Pro Ser
    130                 135                 140
Val Phe Leu Phe Pro Pro Lys Pro Lys Asp Thr Leu Met Ile Ser Arg
145                 150                 155                 160
Thr Pro Glu Val Thr Cys Val Val Val Asp Val Ser His Glu Asp Pro
                165                 170                 175
Glu Val Gln Phe Asn Trp Tyr Val Asp Gly Val Glu Val His Asn Ala
```

```
                180             185              190
Lys Thr Lys Pro Arg Glu Glu Gln Phe Asn Ser Thr Phe Arg Val Val
            195                 200                 205
Ser Val Leu Thr Val Val His Gln Asp Trp Leu Asn Gly Lys Glu Tyr
        210                 215                 220
Lys Cys Lys Val Ser Asn Lys Gly Leu Pro Ala Pro Ile Glu Lys Thr
225                 230                 235                 240
Ile Ser Lys Thr Lys Gly Gln Pro Arg Glu Pro Gln Val Tyr Thr Leu
                245                 250                 255
Pro Pro Ser Arg Glu Glu Met Thr Lys Asn Gln Val Ser Leu Thr Cys
            260                 265                 270
Leu Val Lys Gly Phe Tyr Pro Ser Asp Ile Ala Val Glu Trp Glu Ser
        275                 280                 285
Asn Gly Gln Pro Glu Asn Asn Tyr Lys Thr Thr Pro Pro Met Leu Asp
    290                 295                 300
Ser Asp Gly Ser Phe Phe Leu Tyr Ser Lys Leu Thr Val Asp Lys Ser
305                 310                 315                 320
Arg Trp Gln Gln Gly Asn Val Phe Ser Cys Ser Val Met His Glu Ala
                325                 330                 335
Leu His Asn His Tyr Thr Gln Lys Ser Leu Ser Leu Ser Pro Gly
            340                 345                 350

<210> SEQ ID NO 209
<211> LENGTH: 351
<212> TYPE: PRT
<213> ORGANISM: Artificial Sequence
<220> FEATURE:
<223> OTHER INFORMATION: D3-27-IgG2 fusion protein (without C-terminal
      lysine)

<400> SEQUENCE: 209

Met His Val Ala Gln Pro Ala Val Val Leu Ala Ser Ser Arg Gly Ile
1               5                   10                  15
Ala Ser Phe Val Cys Glu Tyr Glu Ser Pro Gly Lys Ala Asn Glu Val
            20                  25                  30
Arg Val Thr Val Leu Arg Gln Ala Asp Ser Gln Val Thr Glu Val Cys
        35                  40                  45
Ala Met Thr Tyr Met Lys Gly Asn Glu Leu Thr Phe Leu Asp Asp Pro
    50                  55                  60
Ser Cys Thr Gly Thr Phe Ser Gly Asn Gln Val Asn Leu Thr Ile Gln
65                  70                  75                  80
Gly Leu Arg Ala Met Asp Thr Gly Leu Tyr Ile Cys Lys Val Glu Leu
                85                  90                  95
Met Tyr Pro Pro Pro Tyr Tyr Leu Gly Ile Gly Asn Gly Thr Gln Ile
            100                 105                 110
Tyr Val Ile Asp Pro Glu Pro Cys Pro Asp Ser Asp Glu Arg Lys Cys
        115                 120                 125
Cys Val Glu Cys Pro Pro Cys Pro Ala Pro Pro Val Ala Gly Pro Ser
    130                 135                 140
Val Phe Leu Phe Pro Pro Lys Pro Lys Asp Thr Leu Met Ile Ser Arg
145                 150                 155                 160
Thr Pro Glu Val Thr Cys Val Val Val Asp Val Ser His Glu Asp Pro
                165                 170                 175
Glu Val Gln Phe Asn Trp Tyr Val Asp Gly Val Glu Val His Asn Ala
            180                 185                 190
Lys Thr Lys Pro Arg Glu Glu Gln Phe Asn Ser Thr Phe Arg Val Val
```

```
              195                 200                 205

Ser Val Leu Thr Val Val His Gln Asp Trp Leu Asn Gly Lys Glu Tyr
210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
            245                 250                 255

Pro Pro Ser Arg Glu Glu Met Thr Lys Asn Gln Val Ser Leu Thr Cys
                260                 265                 270

Leu Val Lys Gly Phe Tyr Pro Ser Asp Ile Ala Val Glu Trp Glu Ser
            275                 280                 285

Asn Gly Gln Pro Glu Asn Asn Tyr Lys Thr Thr Pro Pro Met Leu Asp
        290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly
            340                 345                 350

<210> SEQ ID NO 210
<211> LENGTH: 351
<212> TYPE: PRT
<213> ORGANISM: Artificial Sequence
<220> FEATURE:
<223> OTHER INFORMATION: D3-29-IgG2 fusion protein (without C-terminal
      lysine)

<400> SEQUENCE: 210

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asn Glu Ile
            20                  25                  30

Arg Val Thr Val Leu Arg Gln Ala Asp Ser Gln Val Thr Glu Val Cys
        35                  40                  45

Ala Met Thr Tyr Met Lys Gly Asp Glu Leu Thr Phe Leu Asp Asp Pro
50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Glu Arg Lys Cys
        115                 120                 125

Cys Val Glu Cys Pro Pro Cys Pro Ala Pro Val Ala Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
```

```
                210                 215                 220
Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
                260                 265                 270

Leu Val Lys Gly Phe Tyr Pro Ser Asp Ile Ala Val Glu Trp Glu Ser
                275                 280                 285

Asn Gly Gln Pro Glu Asn Asn Tyr Lys Thr Thr Pro Pro Met Leu Asp
                290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly
                340                 345                 350

<210> SEQ ID NO 211
<211> LENGTH: 351
<212> TYPE: PRT
<213> ORGANISM: Artificial Sequence
<220> FEATURE:
<223> OTHER INFORMATION: D3-54-IgG2 fusion protein (without C-terminal
      lysine)

<400> SEQUENCE: 211

Met His Val Ala Gln Pro Ala Val Val Leu Ala Ser Ser Arg Gly Ile
 1                  5                  10                  15

Ala Ser Phe Val Cys Glu Tyr Ala Ser Pro Gly Lys Ala Asn Glu Val
                20                  25                  30

Arg Val Thr Val Leu Arg Gln Ala Asp Ser Gln Val Thr Glu Val Cys
            35                  40                  45

Ala Met Thr Tyr Met Lys Glu Asn Glu Leu Thr Phe Leu Asp Asp Pro
        50                  55                  60

Ile Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Glu Arg Lys Cys
        115                 120                 125

Cys Val Glu Cys Pro Pro Cys Pro Ala Pro Pro Val Ala Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
210                 215                 220

Lys Cys Lys Val Ser Asn Lys Gly Leu Pro Ala Pro Ile Glu Lys Thr
```

-continued

```
                225                 230                 235                 240
Ile Ser Lys Thr Lys Gly Gln Pro Arg Glu Pro Gln Val Tyr Thr Leu
            245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
            275                 280                 285

Asn Gly Gln Pro Glu Asn Tyr Lys Thr Thr Pro Pro Met Leu Asp
            290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
            325                 330                 335

Leu His Asn His Tyr Thr Gln Lys Ser Leu Ser Leu Ser Pro Gly
            340                 345                 350

<210> SEQ ID NO 212
<211> LENGTH: 351
<212> TYPE: PRT
<213> ORGANISM: Artificial Sequence
<220> FEATURE:
<223> OTHER INFORMATION: D3-56-IgG2 fusion protein (without C-terminal
      lysine)

<400> SEQUENCE: 212

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
            35                  40                  45

Ala Met Thr Tyr Met Lys Glu Asn Glu Leu Thr Phe Leu Asp Asp Pro
50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
            85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Glu Arg Lys Cys
            115                 120                 125

Cys Val Glu Cys Pro Pro Cys Pro Ala Pro Pro Val Ala Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
            165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
            195                 200                 205

Ser Val Leu Thr Val Val His Gln Asp Trp Leu Asn Gly Lys Glu Tyr
            210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
```

```
                    245                 250                 255
Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Met Leu Asp
    290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly
            340                 345                 350

<210> SEQ ID NO 213
<211> LENGTH: 351
<212> TYPE: PRT
<213> ORGANISM: Artificial Sequence
<220> FEATURE:
<223> OTHER INFORMATION: D3-69-IgG2 fusion protein (without C-terminal
      lysine)

<400> SEQUENCE: 213

Met His Val Ala Gln Pro Ala Val Val Leu Ala Ser Ser Arg Gly Ile
1               5                   10                  15

Ala Ser Phe Val Cys Glu Tyr Glu Ser Pro Gly Lys Ala Asn Glu Ile
            20                  25                  30

Arg Val Thr Val Leu Arg Gln Ala Asp Ser Gln Val Thr Glu Val Cys
        35                  40                  45

Ala Met Thr Tyr Met Lys Gly Asp Glu Leu Thr Phe Leu Asp Asp Pro
    50                  55                  60

Ser Cys Thr Gly Thr Phe Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Glu Arg Lys Cys
        115                 120                 125

Cys Val Glu Cys Pro Pro Cys Pro Ala Pro Pro Val Ala Gly Pro Ser
    130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
    210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
```

Leu Val Lys Gly Phe Tyr Pro Ser Asp Ile Ala Val Glu Trp Glu Ser
            260             265                 270
                275
Asn Gly Gln Pro Glu Asn Asn Tyr Lys Thr Thr Pro Pro Met Leu Asp
            290             295                 300
Ser Asp Gly Ser Phe Phe Leu Tyr Ser Lys Leu Thr Val Asp Lys Ser
305                 310             315                 320
Arg Trp Gln Gln Gly Asn Val Phe Ser Cys Ser Val Met His Glu Ala
                325             330                 335
Leu His Asn His Tyr Thr Gln Lys Ser Leu Ser Leu Ser Pro Gly
            340             345                 350

<210> SEQ ID NO 214
<211> LENGTH: 351
<212> TYPE: PRT
<213> ORGANISM: Artificial Sequence
<220> FEATURE:
<223> OTHER INFORMATION: D3-75-IgG2 fusion protein (without C-terminal
      lysine)

<400> SEQUENCE: 214

Met His Val Ala Gln Pro Ala Val Val Leu Ala Ser Ser Arg Gly Ile
1               5                   10                  15
Ala Ser Phe Val Cys Glu Tyr Glu Ser Pro Gly Lys Ala Asn Glu Val
            20                  25                  30
Arg Val Thr Val Leu Arg Gln Ala Asp Ser Gln Val Thr Glu Val Cys
        35                  40                  45
Ala Met Thr Tyr Met Lys Glu Asn Glu Leu Thr Phe Leu Asp Asp Pro
    50                  55                  60
Ser Cys Thr Gly Thr Phe Ser Gly Asn Gln Val Asn Leu Thr Ile Gln
65                  70                  75                  80
Gly Leu Arg Ala Met Asp Thr Gly Leu Tyr Ile Cys Lys Val Glu Leu
                85                  90                  95
Met Tyr Pro Pro Pro Tyr Tyr Leu Gly Ile Gly Asn Gly Thr Gln Ile
            100                 105                 110
Tyr Val Ile Asp Pro Glu Pro Cys Pro Asp Ser Asp Glu Arg Lys Cys
        115                 120                 125
Cys Val Glu Cys Pro Pro Cys Pro Ala Pro Pro Val Ala Gly Pro Ser
    130                 135                 140
Val Phe Leu Phe Pro Pro Lys Pro Lys Asp Thr Leu Met Ile Ser Arg
145                 150                 155                 160
Thr Pro Glu Val Thr Cys Val Val Val Asp Val Ser His Glu Asp Pro
                165                 170                 175
Glu Val Gln Phe Asn Trp Tyr Val Asp Gly Val Glu Val His Asn Ala
            180                 185                 190
Lys Thr Lys Pro Arg Glu Glu Gln Phe Asn Ser Thr Phe Arg Val Val
        195                 200                 205
Ser Val Leu Thr Val Val His Gln Asp Trp Leu Asn Gly Lys Glu Tyr
    210                 215                 220
Lys Cys Lys Val Ser Asn Lys Gly Leu Pro Ala Pro Ile Glu Lys Thr
225                 230                 235                 240
Ile Ser Lys Thr Lys Gly Gln Pro Arg Glu Pro Gln Val Tyr Thr Leu
                245                 250                 255
Pro Pro Ser Arg Glu Glu Met Thr Lys Asn Gln Val Ser Leu Thr Cys
            260                 265                 270
Leu Val Lys Gly Phe Tyr Pro Ser Asp Ile Ala Val Glu Trp Glu Ser

```
                    275                 280                 285
Asn Gly Gln Pro Glu Asn Asn Tyr Lys Thr Thr Pro Pro Met Leu Asp
            290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly
            340                 345                 350

<210> SEQ ID NO 215
<211> LENGTH: 111
<212> TYPE: DNA
<213> ORGANISM: Artificial Sequence
<220> FEATURE:
<223> OTHER INFORMATION: Coding sequence of WT hCTLA-4 signal peptide
      sequence comprising amino acid residues 1-37 of full-length
      hCTLA-4 protein

<400> SEQUENCE: 215
atggcttgtc ttggatttca acgccacaaa gctcaactca atctcgctac ccgaacatgg     60
ccttgtactc ttctcttttt tctcctcttc ataccggttt tttgtaaagc c            111

<210> SEQ ID NO 216
<211> LENGTH: 37
<212> TYPE: PRT
<213> ORGANISM: Homo sapiens
<220> FEATURE:
<223> OTHER INFORMATION: WT hCTLA-4 signal peptide sequence comprising
      amino acid residues 1-37 of full-length hCTLA-4 protein

<400> SEQUENCE: 216

Met Ala Cys Leu Gly Phe Gln Arg His Lys Ala Gln Leu Asn Leu Ala
1               5                   10                  15

Thr Arg Thr Trp Pro Cys Thr Leu Leu Phe Phe Leu Leu Phe Ile Pro
            20                  25                  30

Val Phe Cys Lys Ala
        35

<210> SEQ ID NO 217
<211> LENGTH: 684
<212> TYPE: DNA
<213> ORGANISM: Artificial Sequence
<220> FEATURE:
<223> OTHER INFORMATION: Coding sequence of human IgG2 Fc polypeptide

<400> SEQUENCE: 217
gagcgcaaat gttgtgtcga gtgcccaccg tgcccagcac cacctgtggc aggaccgtca     60
gtcttcctct tccccccaaa acccaaggac accctcatga tctcccggac ccctgaggtc    120
acgtgcgtgg tggtggacgt gagccacgaa gaccccgagg tccagttcaa ctggtacgtg    180
gacggcgtgg aggtgcataa tgccaagaca aagccacggg aggagcagtt caacagcacg    240
ttccgtgtgg tcagcgtcct caccgttgtg caccaggact ggctgaacgg caaggagtac    300
aagtgcaagg tctccaacaa aggcctccca gcccccatcg agaaaaccat ctccaaaacc    360
aaagggcagc cccgagaacc acaggtgtac accctgcccc catcccggga ggagatgacc    420
aagaaccagg tcagcctgac ctgcctggtc aaaggcttct accccagcga catcgccgtg    480
gagtgggaga gcaatgggca gccggagaac aactacaaga ccacacctcc catgctggac    540
tccgacggct ccttcttcct ctacagcaag ctcaccgtgg acaagagcag gtggcagcag    600
```

-continued

```
gggaacgtct tctcatgctc cgtgatgcat gaggctctgc acaaccacta cacgcagaag    660
agcctctccc tgtctccggg taaa                                           684
```

<210> SEQ ID NO 218
<211> LENGTH: 227
<212> TYPE: PRT
<213> ORGANISM: Artificial Sequence
<220> FEATURE:
<223> OTHER INFORMATION: Human IgG2 Fc polypeptide (without C-terminal
      lysine)

<400> SEQUENCE: 218

```
Glu Arg Lys Cys Cys Val Glu Cys Pro Pro Cys Pro Ala Pro Pro Val
1               5                   10                  15

Ala Gly Pro Ser Val Phe Leu Phe Pro Pro Lys Pro Lys Asp Thr Leu
            20                  25                  30

Met Ile Ser Arg Thr Pro Glu Val Thr Cys Val Val Val Asp Val Ser
        35                  40                  45

His Glu Asp Pro Glu Val Gln Phe Asn Trp Tyr Val Asp Gly Val Glu
    50                  55                  60

Val His Asn Ala Lys Thr Lys Pro Arg Glu Glu Gln Phe Asn Ser Thr
65                  70                  75                  80

Phe Arg Val Val Ser Val Leu Thr Val Val His Gln Asp Trp Leu Asn
                85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220

Ser Pro Gly
225
```

<210> SEQ ID NO 219
<211> LENGTH: 351
<212> TYPE: PRT
<213> ORGANISM: Artificial Sequence
<220> FEATURE:
<223> OTHER INFORMATION: D3-71-IgG2 fusion protein (without C-terminal
      lysine)

<400> SEQUENCE: 219

```
Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Asn Glu Ile
            20                  25                  30

Arg Val Thr Val Leu Arg Gln Ala Asp Ser Gln Val Thr Glu Val Cys
        35                  40                  45
```

```
Ala Met Thr Tyr Met Lys Gly Asp Glu Leu Thr Phe Leu Asp Asp Pro
 50                  55                  60

Ser Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Glu Arg Lys Cys
            115                 120                 125

Cys Val Glu Cys Pro Pro Cys Pro Ala Pro Pro Val Ala Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
            195                 200                 205

Ser Val Leu Thr Val Val His Gln Asp Trp Leu Asn Gly Lys Glu Tyr
210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
            275                 280                 285

Asn Gly Gln Pro Glu Asn Asn Tyr Lys Thr Thr Pro Pro Met Leu Asp
290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly
            340                 345                 350

<210> SEQ ID NO 220
<211> LENGTH: 352
<212> TYPE: PRT
<213> ORGANISM: Artificial Sequence
<220> FEATURE:
<223> OTHER INFORMATION: D3-71-IgG2 fusion protein (with C-terminal
      lysine)

<400> SEQUENCE: 220

Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Ala Asn Glu Ile
                20                  25                  30

Arg Val Thr Val Leu Arg Gln Ala Asp Ser Gln Val Thr Glu Val Cys
             35                  40                  45

Ala Met Thr Tyr Met Lys Gly Asp Glu Leu Thr Phe Leu Asp Asp Pro
 50                  55                  60
```

-continued

Ser Cys Thr Gly Thr Phe Ser Gly Asn Gln Val Asn Leu Thr Ile Gln
 65                  70                  75                  80

Gly Leu Arg Ala Met Asp Thr Gly Leu Tyr Ile Cys Lys Val Glu Leu
                 85                  90                  95

Met Tyr Pro Pro Pro Tyr Tyr Glu Gly Ile Gly Asn Gly Thr Gln Ile
            100                 105                 110

Tyr Val Ile Asp Pro Glu Pro Cys Pro Asp Ser Asp Glu Arg Lys Cys
        115                 120                 125

Cys Val Glu Cys Pro Pro Cys Pro Ala Pro Pro Val Ala Gly Pro Ser
130                 135                 140

Val Phe Leu Phe Pro Pro Lys Pro Lys Asp Thr Leu Met Ile Ser Arg
145                 150                 155                 160

Thr Pro Glu Val Thr Cys Val Val Val Asp Val Ser His Glu Asp Pro
                165                 170                 175

Glu Val Gln Phe Asn Trp Tyr Val Asp Gly Val Glu Val His Asn Ala
            180                 185                 190

Lys Thr Lys Pro Arg Glu Glu Gln Phe Asn Ser Thr Phe Arg Val Val
        195                 200                 205

Ser Val Leu Thr Val Val His Gln Asp Trp Leu Asn Gly Lys Glu Tyr
210                 215                 220

Lys Cys Lys Val Ser Asn Lys Gly Leu Pro Ala Pro Ile Glu Lys Thr
225                 230                 235                 240

Ile Ser Lys Thr Lys Gly Gln Pro Arg Glu Pro Gln Val Tyr Thr Leu
                245                 250                 255

Pro Pro Ser Arg Glu Glu Met Thr Lys Asn Gln Val Ser Leu Thr Cys
            260                 265                 270

Leu Val Lys Gly Phe Tyr Pro Ser Asp Ile Ala Val Glu Trp Glu Ser
        275                 280                 285

Asn Gly Gln Pro Glu Asn Asn Tyr Lys Thr Thr Pro Pro Met Leu Asp
290                 295                 300

Ser Asp Gly Ser Phe Phe Leu Tyr Ser Lys Leu Thr Val Asp Lys Ser
305                 310                 315                 320

Arg Trp Gln Gln Gly Asn Val Phe Ser Cys Ser Val Met His Glu Ala
                325                 330                 335

Leu His Asn His Tyr Thr Gln Lys Ser Leu Ser Leu Ser Pro Gly Lys
            340                 345                 350

<210> SEQ ID NO 221
<211> LENGTH: 351
<212> TYPE: PRT
<213> ORGANISM: Artificial Sequence
<220> FEATURE:
<223> OTHER INFORMATION: D3-76-IgG2 fusion protein (without C-terminal
      lysine)

<400> SEQUENCE: 221

Met His Val Ala Gln Pro Ala Val Val Leu Ala Ser Ser Arg Gly Ile
 1               5                  10                  15

Ala Ser Phe Val Cys Glu Tyr Ala Ser Pro Gly Lys Ala Asn Glu Val
            20                  25                  30

Arg Val Thr Val Leu Arg Gln Ala Asp Ser Gln Val Thr Glu Val Cys
        35                  40                  45

Ala Met Thr Tyr Met Lys Glu Asp Glu Leu Thr Phe Leu Asp Asp Pro
    50                  55                  60

Ile Cys Thr Gly Thr Phe Ser Gly Asn Gln Val Asn Leu Thr Ile Gln
 65                  70                  75                  80

-continued

```
Gly Leu Arg Ala Met Asp Thr Gly Leu Tyr Ile Cys Lys Val Glu Leu
                85                  90                  95
Met Tyr Pro Pro Pro Tyr Leu Gly Ile Gly Asn Gly Thr Gln Ile
            100                 105                 110
Tyr Val Ile Asp Pro Glu Pro Cys Pro Asp Ser Asp Glu Arg Lys Cys
            115                 120                 125
Cys Val Glu Cys Pro Pro Cys Pro Ala Pro Pro Val Ala Gly Pro Ser
    130                 135                 140
Val Phe Leu Phe Pro Pro Lys Pro Lys Asp Thr Leu Met Ile Ser Arg
145                 150                 155                 160
Thr Pro Glu Val Thr Cys Val Val Val Asp Val Ser His Glu Asp Pro
                165                 170                 175
Glu Val Gln Phe Asn Trp Tyr Val Asp Gly Val Glu Val His Asn Ala
            180                 185                 190
Lys Thr Lys Pro Arg Glu Glu Gln Phe Asn Ser Thr Phe Arg Val Val
        195                 200                 205
Ser Val Leu Thr Val Val His Gln Asp Trp Leu Asn Gly Lys Glu Tyr
    210                 215                 220
Lys Cys Lys Val Ser Asn Lys Gly Leu Pro Ala Pro Ile Glu Lys Thr
225                 230                 235                 240
Ile Ser Lys Thr Lys Gly Gln Pro Arg Glu Pro Gln Val Tyr Thr Leu
                245                 250                 255
Pro Pro Ser Arg Glu Glu Met Thr Lys Asn Gln Val Ser Leu Thr Cys
            260                 265                 270
Leu Val Lys Gly Phe Tyr Pro Ser Asp Ile Ala Val Glu Trp Glu Ser
        275                 280                 285
Asn Gly Gln Pro Glu Asn Asn Tyr Lys Thr Thr Pro Pro Met Leu Asp
    290                 295                 300
Ser Asp Gly Ser Phe Phe Leu Tyr Ser Lys Leu Thr Val Asp Lys Ser
305                 310                 315                 320
Arg Trp Gln Gln Gly Asn Val Phe Ser Cys Ser Val Met His Glu Ala
                325                 330                 335
Leu His Asn His Tyr Thr Gln Lys Ser Leu Ser Leu Ser Pro Gly
            340                 345                 350

<210> SEQ ID NO 222
<211> LENGTH: 352
<212> TYPE: PRT
<213> ORGANISM: Artificial Sequence
<220> FEATURE:
<223> OTHER INFORMATION: D3-76-IgG2 fusion protein (with C-terminal
      lysine)

<400> SEQUENCE: 222

Met His Val Ala Gln Pro Ala Val Val Leu Ala Ser Ser Arg Gly Ile
1               5                   10                  15
Ala Ser Phe Val Cys Glu Tyr Ala Ser Pro Gly Lys Ala Asn Glu Val
            20                  25                  30
Arg Val Thr Val Leu Arg Gln Ala Asp Ser Gln Val Thr Glu Val Cys
        35                  40                  45
Ala Met Thr Tyr Met Lys Glu Asp Glu Leu Thr Phe Leu Asp Asp Pro
    50                  55                  60
Ile Cys Thr Gly Thr Phe Ser Gly Asn Gln Val Asn Leu Thr Ile Gln
65                  70                  75                  80
Gly Leu Arg Ala Met Asp Thr Gly Leu Tyr Ile Cys Lys Val Glu Leu
                85                  90                  95
```

```
Met Tyr Pro Pro Pro Tyr Tyr Leu Gly Ile Gly Asn Gly Thr Gln Ile
            100                 105                 110
Tyr Val Ile Asp Pro Glu Pro Cys Pro Asp Ser Asp Glu Arg Lys Cys
            115                 120                 125
Cys Val Glu Cys Pro Pro Cys Pro Ala Pro Pro Val Ala Gly Pro Ser
130                 135                 140
Val Phe Leu Phe Pro Pro Lys Pro Lys Asp Thr Leu Met Ile Ser Arg
145                 150                 155                 160
Thr Pro Glu Val Thr Cys Val Val Val Asp Val Ser His Glu Asp Pro
                165                 170                 175
Glu Val Gln Phe Asn Trp Tyr Val Asp Gly Val Glu Val His Asn Ala
            180                 185                 190
Lys Thr Lys Pro Arg Glu Glu Gln Phe Asn Ser Thr Phe Arg Val Val
            195                 200                 205
Ser Val Leu Thr Val Val His Gln Asp Trp Leu Asn Gly Lys Glu Tyr
            210                 215                 220
Lys Cys Lys Val Ser Asn Lys Gly Leu Pro Ala Pro Ile Glu Lys Thr
225                 230                 235                 240
Ile Ser Lys Thr Lys Gly Gln Pro Arg Glu Pro Gln Val Tyr Thr Leu
                245                 250                 255
Pro Pro Ser Arg Glu Glu Met Thr Lys Asn Gln Val Ser Leu Thr Cys
            260                 265                 270
Leu Val Lys Gly Phe Tyr Pro Ser Asp Ile Ala Val Glu Trp Glu Ser
            275                 280                 285
Asn Gly Gln Pro Glu Asn Asn Tyr Lys Thr Thr Pro Pro Met Leu Asp
290                 295                 300
Ser Asp Gly Ser Phe Phe Leu Tyr Ser Lys Leu Thr Val Asp Lys Ser
305                 310                 315                 320
Arg Trp Gln Gln Gly Asn Val Phe Ser Cys Ser Val Met His Glu Ala
                325                 330                 335
Leu His Asn His Tyr Thr Gln Lys Ser Leu Ser Leu Ser Pro Gly Lys
            340                 345                 350

<210> SEQ ID NO 223
<211> LENGTH: 1170
<212> TYPE: DNA
<213> ORGANISM: Artificial Sequence
<220> FEATURE:
<223> OTHER INFORMATION: D3-71-IgG2 fusion protein coding sequence

<400> SEQUENCE: 223
atggcttgtc ttggatttca acgccacaaa gctcaactca atctcgctac ccgaacatgg      60
ccttgtactc ttctcttttt tctcctcttc ataccggttt tttgtaaagc catgcacgtc     120
gctcaaccag ccgtcgtact cgcgtcctct agaggtatcg cttccttcgt gtgtgaatat     180
gcgtcacccg gcaaagccaa cgaaattaga gtcacagtgc tccgccaagc cgatagtcaa     240
gttacagaag tctgcgctat gacatacatg aagggagatg aactaacctt ccttgacgat     300
cccagctgca caggtaccct tccggaaat caagttaatc ttactattca aggacttcga     360
gccatggata ccggactcta tatttgtaaa gtcgaactca tgtaccccc ccttactac      420
gagggtatag gtaatggcac tcagatctac gtcatcgatc ccgaaccctg ccctgattct     480
gatgagcgca atgttgtgt cgagtgccca ccgtgcccag caccacctgt ggcaggaccg     540
tcagtcttcc tcttcccccc aaaacccaag gacacccctca tgatctcccg gacccctgag     600
gtcacgtgcg tggtggtgga cgtgagccac gaagacccg aggtccagtt caactggtac     660
```

```
gtggacggcg tggaggtgca taatgccaag acaaagccac gggaggagca gttcaacagc     720
acgttccgtg tggtcagcgt cctcaccgtt gtgcaccagg actggctgaa cggcaaggag     780
tacaagtgca aggtctccaa caaaggcctc ccagccccca tcgagaaaac catctccaaa     840
accaaagggc agccccgaga accacaggtg tacaccctgc ccccatcccg ggaggagatg     900
accaagaacc aggtcagcct gacctgcctg gtcaaaggct tctaccccag cgacatcgcc     960
gtggagtggg agagcaatgg gcagccggag aacaactaca agaccacacc tcccatgctg    1020
gactccgacg gctccttctt cctctacagc aagctcaccg tggacaagag caggtggcag    1080
caggggaacg tcttctcatg ctccgtgatg catgaggctc tgcacaacca ctacacgcag    1140
aagagcctct ccctgtctcc gggtaaataa                                     1170
```

<210> SEQ ID NO 224
<211> LENGTH: 1170
<212> TYPE: DNA
<213> ORGANISM: Artificial Sequence
<220> FEATURE:
<223> OTHER INFORMATION: D3-76-IgG2 fusion protein coding sequence

<400> SEQUENCE: 224

```
atggcttgtc ttggatttca acgccacaaa gctcaactca atctcgctac ccgaacatgg      60
ccttgtactc ttctcttttt tctcctcttc ataccggttt tttgtaaagc catgcacgtc     120
gctcaaccag ccgtcgtact cgcgtcctct agaggtatcg cttccttcgt gtgtgaatat     180
gcgtcacccg gcaaagccaa cgaagttaga gtcacagtgc tccgccaagc cgatagtcaa     240
gttacagaag tctgcgctat gacatacatg aaggaagatg aactaacctt ccttgacgat     300
cccatctgca caggtacctt ttccggaaat caagttaatc ttactattca aggacttcga     360
gccatggata ccggactcta tatttgtaaa gtcgaactca tgtaccccccc cccttactac     420 ttgggtattg gtaatggcac tcagatctac gtcatcgatc ccgaaccctg ccctgattct     480
gatgagcgca atgttgtgt cgagtgccca ccgtgcccag caccacctgt ggcaggaccg     540
tcagtcttcc tcttcccccc aaaacccaag gacaccctca tgatctcccg gacccctgag     600
gtcacgtgcg tggtggtgga cgtgagccac gaagaccccg aggtccagtt caactggtac     660
gtggacggcg tggaggtgca taatgccaag acaaagccac gggaggagca gttcaacagc     720
acgttccgtg tggtcagcgt cctcaccgtt gtgcaccagg actggctgaa cggcaaggag     780
tacaagtgca aggtctccaa caaaggcctc ccagccccca tcgagaaaac catctccaaa     840
accaaagggc agccccgaga accacaggtg tacaccctgc ccccatcccg ggaggagatg     900
accaagaacc aggtcagcct gacctgcctg gtcaaaggct tctaccccag cgacatcgcc     960
gtggagtggg agagcaatgg gcagccggag aacaactaca agaccacacc tcccatgctg    1020
gactccgacg gctccttctt cctctacagc aagctcaccg tggacaagag caggtggcag    1080
caggggaacg tcttctcatg ctccgtgatg catgaggctc tgcacaacca ctacacgcag    1140
aagagcctct ccctgtctcc gggtaaataa                                     1170
```

<210> SEQ ID NO 225
<211> LENGTH: 485
<212> TYPE: PRT
<213> ORGANISM: Artificial Sequence
<220> FEATURE:
<223> OTHER INFORMATION: Human CD86-murine Ig fusion protein

<400> SEQUENCE: 225

```
Met Asp Pro Gln Cys Thr Met Gly Leu Ser Asn Ile Leu Phe Val Met
1               5                   10                  15
```

```
Ala Phe Leu Leu Ser Gly Ala Ala Pro Leu Lys Ile Gln Ala Tyr Phe
            20                  25                  30

Asn Glu Thr Ala Asp Leu Pro Cys Gln Phe Ala Asn Ser Gln Asn Gln
            35                  40                  45

Ser Leu Ser Glu Leu Val Val Phe Trp Gln Asp Glu Asn Leu Val
 50                  55                  60

Leu Asn Glu Val Tyr Leu Gly Lys Glu Lys Phe Asp Ser Val His Ser
 65                  70                  75                  80

Lys Tyr Met Gly Arg Thr Ser Phe Asp Ser Asp Ser Trp Thr Leu Arg
                85                  90                  95

Leu His Asn Leu Gln Ile Lys Asp Lys Gly Leu Tyr Gln Cys Ile Ile
                100                 105                 110

His His Lys Lys Pro Thr Gly Met Ile Arg Ile His Gln Met Asn Ser
                115                 120                 125

Glu Leu Ser Val Leu Ala Asn Phe Ser Gln Pro Glu Ile Val Pro Ile
                130                 135                 140

Ser Asn Ile Thr Glu Asn Val Tyr Ile Asn Leu Thr Cys Ser Ser Ile
145                 150                 155                 160

His Gly Tyr Pro Glu Pro Lys Lys Met Ser Val Leu Leu Arg Thr Lys
                165                 170                 175

Asn Ser Thr Ile Glu Tyr Asp Gly Ile Met Gln Lys Ser Gln Asp Asn
                180                 185                 190

Val Thr Glu Leu Tyr Asp Val Ser Ile Ser Leu Ser Val Ser Phe Pro
                195                 200                 205

Asp Val Thr Ser Asn Met Thr Ile Phe Cys Ile Leu Glu Thr Asp Lys
                210                 215                 220

Thr Arg Leu Leu Ser Ser Pro Phe Ser Ile Glu Leu Glu Asp Pro Gln
225                 230                 235                 240

Pro Pro Pro Gly Val Thr Pro Arg Val Pro Ile Thr Gln Asn Pro Cys
                245                 250                 255

Pro Pro Leu Lys Glu Cys Pro Pro Cys Ala Ala Pro Asp Leu Leu Gly
                260                 265                 270

Gly Pro Ser Val Phe Ile Phe Pro Pro Lys Ile Lys Asp Val Leu Met
                275                 280                 285

Ile Ser Leu Ser Pro Met Val Thr Cys Val Val Val Asp Val Ser Glu
                290                 295                 300

Asp Asp Pro Asp Val Gln Ile Ser Trp Phe Val Asn Asn Val Glu Val
305                 310                 315                 320

His Thr Ala Gln Thr Gln Thr His Arg Glu Asp Tyr Asn Ser Thr Leu
                325                 330                 335

Arg Val Val Ser Ala Leu Pro Ile Gln His Gln Asp Trp Met Ser Gly
                340                 345                 350

Lys Glu Phe Lys Cys Lys Val Asn Asn Arg Ala Leu Pro Ser Pro Ile
                355                 360                 365

Glu Lys Thr Ile Ser Lys Pro Arg Gly Pro Val Arg Ala Pro Gln Val
                370                 375                 380

Tyr Val Leu Pro Pro Pro Ala Glu Glu Met Thr Lys Lys Glu Phe Ser
385                 390                 395                 400

Leu Thr Cys Met Ile Thr Gly Phe Leu Pro Ala Glu Ile Ala Val Asp
                405                 410                 415

Trp Thr Ser Asn Gly Arg Thr Glu Gln Asn Tyr Lys Asn Thr Ala Thr
                420                 425                 430

Val Leu Asp Ser Asp Gly Ser Tyr Phe Met Tyr Ser Lys Leu Arg Val
```

```
                    435                 440                 445
Gln Lys Ser Thr Trp Glu Arg Gly Ser Leu Phe Ala Cys Ser Val Val
450                 455                 460

His Glu Gly Leu His Asn His Leu Thr Thr Lys Thr Ile Ser Arg Ser
465                 470                 475                 480

Leu Gly Lys Ser Gly
              485

<210> SEQ ID NO 226
<211> LENGTH: 484
<212> TYPE: PRT
<213> ORGANISM: Artificial Sequence
<220> FEATURE:
<223> OTHER INFORMATION: Human CD80-murine Ig fusion protein

<400> SEQUENCE: 226

Met Gly His Thr Arg Arg Gln Gly Thr Ser Pro Ser Lys Cys Pro Tyr
1               5                   10                  15

Leu Asn Phe Phe Gln Leu Leu Val Leu Ala Gly Leu Ser His Phe Cys
                20                  25                  30

Ser Gly Val Ile His Val Thr Lys Glu Val Lys Glu Val Ala Thr Leu
            35                  40                  45

Ser Cys Gly His Asn Val Ser Val Glu Glu Leu Ala Gln Thr Arg Ile
        50                  55                  60

Tyr Trp Gln Lys Glu Lys Lys Met Val Leu Thr Met Met Ser Gly Asp
65                  70                  75                  80

Met Asn Ile Trp Pro Glu Tyr Lys Asn Arg Thr Ile Phe Asp Ile Thr
                85                  90                  95

Asn Asn Leu Ser Ile Val Ile Leu Ala Leu Arg Pro Ser Asp Glu Gly
            100                 105                 110

Thr Tyr Glu Cys Val Val Leu Lys Tyr Glu Lys Asp Ala Phe Lys Arg
        115                 120                 125

Glu His Leu Ala Glu Val Thr Leu Ser Val Lys Ala Asp Phe Pro Thr
130                 135                 140

Pro Ser Ile Ser Asp Phe Glu Ile Pro Thr Ser Asn Ile Arg Arg Ile
145                 150                 155                 160

Ile Cys Ser Thr Ser Gly Gly Phe Pro Glu Pro His Leu Ser Trp Leu
                165                 170                 175

Glu Asn Gly Glu Glu Leu Asn Ala Ile Asn Thr Thr Val Ser Gln Asp
            180                 185                 190

Pro Glu Thr Glu Leu Tyr Ala Val Ser Ser Lys Leu Asp Phe Asn Met
        195                 200                 205

Thr Thr Asn His Ser Phe Met Cys Leu Ile Lys Tyr Gly His Leu Arg
210                 215                 220

Val Asn Gln Thr Phe Asn Trp Asn Thr Thr Lys Gln Glu His Phe Pro
225                 230                 235                 240

Asp Asn Gly Val Thr Pro Arg Val Pro Ile Thr Gln Asn Pro Cys Pro
                245                 250                 255

Pro Leu Lys Glu Cys Pro Pro Cys Ala Ala Pro Asp Leu Leu Gly Gly
            260                 265                 270

Pro Ser Val Phe Ile Phe Pro Pro Lys Ile Lys Asp Val Leu Met Ile
        275                 280                 285

Ser Leu Ser Pro Met Val Thr Cys Val Val Val Asp Val Ser Glu Asp
290                 295                 300

Asp Pro Asp Val Gln Ile Ser Trp Phe Val Asn Asn Val Glu Val His
305                 310                 315                 320
```

Thr Ala Gln Thr Gln Thr His Arg Glu Asp Tyr Asn Ser Thr Leu Arg
            325                 330                 335

Val Val Ser Ala Leu Pro Ile Gln His Gln Asp Trp Met Ser Gly Lys
            340                 345                 350

Glu Phe Lys Cys Lys Val Asn Asn Arg Ala Leu Pro Ser Pro Ile Glu
            355                 360                 365

Lys Thr Ile Ser Lys Pro Arg Gly Pro Val Arg Ala Pro Gln Val Tyr
370                 375                 380

Val Leu Pro Pro Pro Ala Glu Glu Met Thr Lys Lys Glu Phe Ser Leu
385                 390                 395                 400

Thr Cys Met Ile Thr Gly Phe Leu Pro Ala Glu Ile Ala Val Asp Trp
            405                 410                 415

Thr Ser Asn Gly Arg Thr Glu Gln Asn Tyr Lys Asn Thr Ala Thr Val
            420                 425                 430

Leu Asp Ser Asp Gly Ser Tyr Phe Met Tyr Ser Lys Leu Arg Val Gln
            435                 440                 445

Lys Ser Thr Trp Glu Arg Gly Ser Leu Phe Ala Cys Ser Val Val His
            450                 455                 460

Glu Gly Leu His Asn His Leu Thr Thr Lys Thr Ile Ser Arg Ser Leu
465                 470                 475                 480

Gly Lys Ser Gly

<210> SEQ ID NO 227
<211> LENGTH: 1458
<212> TYPE: DNA
<213> ORGANISM: Artificial Sequence
<220> FEATURE:
<223> OTHER INFORMATION: Human CD86-murine Ig fusion protein coding
      sequence

<400> SEQUENCE: 227

| | |
|---|---|
| atggatcccc agtgcactat gggactgagt aacattctct tgtgatggc cttcctgctc | 60 |
| tctggtgctg ctcctctgaa gattcaagct tatttcaatg agactgcaga cctgccatgc | 120 |
| caatttgcaa actctcaaaa ccaaagcctg agtgagctag tagtattttg gcaggaccag | 180 |
| gaaaacttgg ttctgaatga ggtatactta ggcaaagaga aatttgacag tgttcattcc | 240 |
| aagtatatgg gccgcacaag ttttgattcg gacagttgga ccctgagact tcacaatctt | 300 |
| cagatcaagg acaagggctt gtatcaatgt atcatccatc acaaaaagcc cacaggaatg | 360 |
| attcgcatcc accagatgaa ttctgaactg tcagtgcttg ctaacttcag tcaacctgaa | 420 |
| atagtaccaa tttctaatat aacagaaaat gtgtacataa atttgacctg ctcatctata | 480 |
| cacggctacc agaacctaa gagatgagt gttttgctaa gaaccaagaa ttcaactatc | 540 |
| gagtatgatg gtattatgca gaaatctcaa gataatgtca gaactgta cgacgtttcc | 600 |
| atcagcttgt ctgtttcatt ccctgatgtt acgagcaata tgaccatctt ctgtattctg | 660 |
| gaaactgaca gaacgcggct tttatcttca cctttctcta tagagcttga ggaccctcag | 720 |
| cctccccag gggtgacccc cagagtgccc ataacacaga cccctgtcc tccactcaaa | 780 |
| gagtgtcccc catgcgcagc tccagacctc ttgggtggac catccgtctt catcttccct | 840 |
| ccaaagatca aggatgtact catgatctcc ctgagcccca tggtcacatg tgtggtggtg | 900 |
| gatgtgagcg aggatgaccc agacgtccag atcagctggt ttgtgaacaa cgtggaagta | 960 |
| cacacagctc agacacaaac ccatagagag gattacaaca gtactctccg ggtggtcagt | 1020 |
| gccctcccca tccagcacca ggactggatg agtggcaagg agttcaaatg caaggtcaac | 1080 |

```
aacagagccc tcccatcccc catcgagaaa accatctcaa aacccagagg gccagtaaga    1140
gctccacagg tatatgtctt gcctccacca gcagaagaga tgactaagaa agagttcagt    1200
ctgacctgca tgatcacagg cttcttacct gccgaaattg ctgtggactg gaccagcaat    1260
gggcgtacag agcaaaacta caagaacacc gcaacagtcc tggactctga tggttcttac    1320
ttcatgtaca gcaagctcag agtacaaaag agcacttggg aaagaggaag tcttttcgcc    1380
tgctcagtgg tccacgaggg tctgcacaat caccttacga ctaagaccat ctcccggtct    1440
ctgggtaaat ccggataa                                                  1458
```

<210> SEQ ID NO 228
<211> LENGTH: 1455
<212> TYPE: DNA
<213> ORGANISM: Artificial Sequence
<220> FEATURE:
<223> OTHER INFORMATION: Human CD80-murine Ig fusion protein coding
      sequence

<400> SEQUENCE: 228

```
atgggccaca cacggaggca gggaacatca ccatccaagt gtccataccct caatttctttt    60 cagctcttgg tgctggctgg tctttctcac ttctgttcag gtgttatcca cgtgaccaag    120
gaagtgaaag aagtggcaac gctgtcctgt ggtcacaatg tttctgttga agagctggca    180
caaactcgca tctactgcta aaaggagaag aaaatggtgc tgactatgat gtctggggac    240
atgaatatat ggcccgagta caagaaccgg accatctttg atatcactaa taacctctcc    300
atcgtgatcc tggctctgcg cccatctgac gagggcacat acgagtgtgt tgttctgaag    360
tatgaaaaag acgctttcaa gcgggaacac ctggctgaag tgacgttatc agtcaaagct    420
gacttcccta cacctagtat atctgacttt gaaattccaa cttctaatat tagaaggata    480
atttgctcaa cctctggagg ttttcctgag cctcacctct cctggctgga aaatggagaa    540
gaattaaatg ccatcaacac aacagtttcc caagatcctg aaactgagct ctatgctgtt    600
agcagcaaac tggatttcaa tatgacaacc aaccacagct tcatgtgtct catcaagtat    660
ggacatttaa gagtgaatca gaccttcaac tggaatacaa ccaagcaaga gcattttcct    720
gataacgggg tgaccccccag agtgcccata acacagaacc cctgtcctcc actcaaagag    780 tgtccccat gcgcagctcc agacctcttg ggtggaccat ccgtcttcat cttccctcca    840
aagatcaagg atgtactcat gatctccctg agccccatgg tcacatgtgt ggtggtggat    900
gtgagcgagg atgacccaga cgtccagatc agctggtttg tgaacaacgt ggaagtacac    960
acagctcaga cacaaacccca tagagaggat tacaacagta ctctccgggt ggtcagtgcc    1020
ctccccatcc agcaccagga ctggatgagt ggcaaggagt tcaaatgcaa ggtcaacaac    1080
agagccctcc catcccccat cgagaaaacc atctcaaaac ccagagggcc agtaagagct    1140
ccacaggtat atgtcttgcc tccaccagca gaagagatga ctaagaaaga gttcagtctg    1200
acctgcatga tcacaggctt cttacctgcc gaaattgctg tggactggac cagcaatggg    1260
cgtacagagc aaaactacaa gaacaccgca acagtcctgg actctgatgg ttcttacttc    1320
atgtacagca agctcagagt acaaaagagc acttgggaaa gaggaagtct tttcgcctgc    1380
tcagtggtcc acgagggtct gcacaatcac cttacgacta agaccatctc ccggtctctg    1440
ggtaaatccg gataa                                                     1455
```